(12) United States Patent
Pouzet et al.

(10) Patent No.: US 8,754,073 B2
(45) Date of Patent: Jun. 17, 2014

(54) SUBSTITUTED PIPERAZINO-DIHYDROTHIENOPYRIMIDINES

(75) Inventors: Pascale Pouzet, Biberach (DE); Ralf Anderskewitz, Laupheim (DE); Horst Dollinger, Schemmerhofen (DE); Dennis Fiegen, Biberach (DE); Thomas Fox, Biberach (DE); Rolf Goeggel, Ulm (DE); Christoph Hoenke, Ingelheim am Rhein (DE); Domnic Martyres, Biberach (DE); Peter Nickolaus, Warthausen (DE); Klaus Klinder, Oggelshausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 406 days.

(21) Appl. No.: 12/738,344

(22) PCT Filed: Oct. 16, 2008

(86) PCT No.: PCT/EP2008/063999
§ 371 (c)(1),
(2), (4) Date: Jul. 13, 2010

(87) PCT Pub. No.: WO2009/050248
PCT Pub. Date: Apr. 23, 2009

(65) Prior Publication Data
US 2011/0021501 A1    Jan. 27, 2011

(30) Foreign Application Priority Data

Oct. 19, 2007   (EP) .................................. 07118901

(51) Int. Cl.
| | | |
|---|---|---|
| C07D 495/04 | (2006.01) | |
| A61K 31/519 | (2006.01) | |
| A61P 29/00 | (2006.01) | |
| A61P 11/06 | (2006.01) | |
| A61P 25/28 | (2006.01) | |

(52) U.S. Cl.
USPC ... 514/217.02; 540/595; 514/267; 514/229.8; 514/260.1; 544/231; 544/71; 544/278

(58) Field of Classification Search
USPC ........................................ 544/278; 514/260.1
See application file for complete search history.

(56) References Cited

U.S. PATENT DOCUMENTS

| | | | |
|---|---|---|---|
| 3,318,881 A | 5/1967 | Ohnacker et al. | |
| 3,318,883 A | 5/1967 | Ohnacker et al. | |
| 3,763,156 A | 10/1973 | Horch et al. | |
| 3,838,121 A | 9/1974 | Woitun et al. | |
| 4,256,737 A | 3/1981 | Nestor et al. | |
| 4,256,738 A | 3/1981 | Woitun et al. | |
| 5,187,168 A | 2/1993 | Primeau et al. | |
| 7,019,013 B2 | 3/2006 | Eggenweiler et al. | |
| 7,511,045 B2 | 3/2009 | Hoenke et al. | |
| 7,723,341 B2 | 5/2010 | Hoenke et al. | |
| 7,960,422 B2 | 6/2011 | Arzel et al. | |
| 8,114,878 B2 | 2/2012 | Pouzet et al. | |
| 8,354,531 B2 | 1/2013 | Hoenke et al. | |
| 8,609,670 B2 | 12/2013 | Pouzet et al. | |
| 2003/0016795 A1 | 1/2003 | Brandenberger | |
| 2007/0259846 A1 | 11/2007 | Hoenke et al. | |
| 2008/0032358 A1 | 2/2008 | Behrens et al. | |
| 2008/0096882 A1 | 4/2008 | Pouzet et al. | |
| 2009/0131454 A1 | 5/2009 | Arzel et al. | |
| 2010/0137282 A1 | 6/2010 | Davies et al. | |
| 2010/0197656 A1 | 8/2010 | Hoenke et al. | |
| 2010/0222585 A1 | 9/2010 | Frutos et al. | |
| 2010/0273793 A1 | 10/2010 | Nemecek et al. | |
| 2010/0305102 A1 | 12/2010 | Pouzet et al. | |
| 2011/0021501 A1 | 1/2011 | Pouzet et al. | |
| 2011/0028441 A1 | 2/2011 | Pouzet et al. | |
| 2011/0046096 A1 | 2/2011 | Pouzet et al. | |
| 2011/0123435 A1 | 5/2011 | Siddiqui et al. | |
| 2012/0028932 A1 | 2/2012 | Nickolaus et al. | |
| 2012/0035143 A1 | 2/2012 | Nickolaus et al. | |
| 2012/0108534 A1 | 5/2012 | Pouzet et al. | |

FOREIGN PATENT DOCUMENTS

| | | |
|---|---|---|
| AR | 053235 | 4/2006 |
| AU | 2006237354 A1 | 10/2006 |

(Continued)

OTHER PUBLICATIONS

DiGirolamo et al. (Br. J. Pharmacol., 2003, 139(6), pp. 1164-1170).*
Chakraborti et al.; 3D-QSAR Studies on Thieno[3,2-d]pyrimidines as Phosphodiesterase IV Inhibitors; Bioorganic & Medicinal Chemistry Letters; 2003; vol. 13; pp. 1403-1408.

(Continued)

*Primary Examiner* — Susanna Moore
(74) *Attorney, Agent, or Firm* — Michael P. Morris; Timothy X. Witkowski

(57) ABSTRACT

Piperidinodihydrothienopyrimidines of formula 1

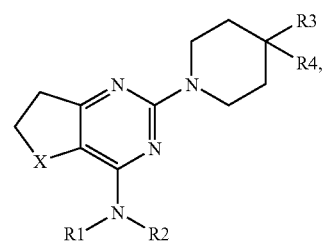

wherein X is SO or $SO_2$ (preferably SO), and $R^1$, $R^2$, $R^3$, and $R^4$ may have the meanings given in the disclosure and claims, pharmacologically acceptable salts thereof, and pharmaceutical compositions containing these compounds. These piperidinodihydrothienopyrimidines are suitable for the treatment of respiratory or gastrointestinal complaints or diseases, inflammatory diseases of the joints, skin, or eyes, diseases of the peripheral or central nervous system, or cancers.

34 Claims, No Drawings

(56) References Cited

FOREIGN PATENT DOCUMENTS

| | | |
|---|---|---|
| CA | 2605161 A1 | 10/2006 |
| CA | 2647243 A1 | 10/2007 |
| CA | 2705414 A1 | 4/2009 |
| DE | 1940572 A1 | 2/1971 |
| DE | 2112950 A1 | 10/1971 |
| DE | 2032687 A1 | 1/1972 |
| DE | 2121950 A1 | 11/1972 |
| DE | 102005019201 A1 | 11/2006 |
| EP | 0806418 A2 | 11/1997 |
| EP | 0899263 A2 | 3/1999 |
| EP | 1847543 A1 | 10/2007 |
| FR | 1603313 A | 4/1971 |
| GB | 1072414 A | 6/1967 |
| JP | 07330777 A | 12/1995 |
| JP | 2004516329 A | 6/2004 |
| JP | 200503345 | 2/2005 |
| WO | 02088138 A1 | 11/2002 |
| WO | 03055890 | 7/2003 |
| WO | 03059913 | 7/2003 |
| WO | 200496810 A1 | 11/2004 |
| WO | 2005049033 A1 | 6/2005 |
| WO | 2005082865 A1 | 9/2005 |
| WO | 2006111549 A1 | 10/2006 |
| WO | 2007118793 A1 | 10/2007 |
| WO | 2008128942 A1 | 10/2008 |
| WO | 2009050236 A1 | 4/2009 |
| WO | 2009050242 A2 | 4/2009 |
| WO | 2009050248 A1 | 4/2009 |
| WO | 2009051556 A1 | 4/2009 |
| WO | 2009052138 A1 | 4/2009 |
| WO | 2009052288 A1 | 4/2009 |
| WO | 2009053268 A1 | 4/2009 |
| WO | 2009087305 A1 | 7/2009 |
| WO | 2010097332 A1 | 9/2010 |
| WO | 2010097334 A1 | 9/2010 |

OTHER PUBLICATIONS

International Search Report, Form PCT/ISA/210, for corresponding PCT/EP2008/063999; date of mailing: Apr. 1, 2009.

Brown, W.M., "Treating COPD with PDE 4 Inhibitors", International Journal of COPD, 2007, vol. 2 (4), pp. 517-533.

Crespo, Maria, I., et al; Design, Synthesis, and Biological Activities of New Thieno[3,2-d]pyrimidines as Selective Type 4 Phosphodiesterase Inhibitors; J. Medicinal Chemistry (1998) vol. 41 pp. 4021-4035.

Digirolamo, G, et al; Effects of Cyclooxygenase Inhitor Pretreatment on Nitric Oxide production, nNOS and iNOS Expression in Rat Cerebellum; British Journal of Pharmacology (2003) vol. 139, No. 6 pp. 1164-1170.

Gavezzoti, A., "Are Crystal Structures Predicatable?" Accounts of Chemical Research. v. 27, 1994, p. 309-314.

Inernational Search Report, Form PCT/ISR/210, for corresponding application PCT/EP2008/063747 date of mailing Mar. 4, 2009.

International Search Report for PCT/EP2008/063970 mailed Apr. 1, 2009.

International Search Report for PCT/EP2012/066104, date of mailing Jan. 30, 2013.

International Search Report Form PCT/ISA/210, for corresponding application PCT/EP2007/053255 date of mailing Jul. 9, 2007.

International Search Report PCT/EP2007/053255, mailed Jun. 29, 2007.

International Search Report, Form PCT/ISA/210, and written opinion, form PCT/ISA/237, corresponding application PCT/EP2008/063983 mailing date Jun. 2, 2009.

Kolosionek, E. et al., "Expression and Activity of Phosphodiesterase Isoforms during Epithelial Mesenchymal Transition: The Role of Phosphodiesterase 4 ", Molecular Biology of the Cell, 2009, vol. 20, pp. 4751-4765.

Kumar, N., et al., "Phosphodiesterase 4-Targeted treatments for autoimmune diseases", BMC Medicine, 2013. vol. 20, pp. 4751-4765.

Odingo, Joshua; Inhibitors of PDE4: A Review of Recent Patent Literature; Expert Opinion (2005) vol. 15; No. 7 pp. 773-787.

Salari-Sharif, P., et al., "Phosphodiesterase 4 Inhibitors in Inflammatory Bowel Disease: A Comprehensive Review", Current Pharmaceutical Design, 2010, vol. 16, pp. 3661-3667.

Vippagunta, et al., "Crystalline Solids", Advanced Drug Delivery Reviews, V. 48, 2001, p. 3-26.

* cited by examiner

SUBSTITUTED PIPERAZINO-DIHYDROTHIENOPYRIMIDINES

RELATED APPLICATIONS

This application is a 371 of International Application No. PCT/EP2008/063999, filed Oct. 16, 2008, which claims priority to European Patent Application No. 07118901.3, filed Oct. 19, 2007, the contents of which are incorporated herein by reference in their entirety.

The invention relates to new piperidino-dihydrothienopyrimidinesulphoxides of formula 1, as well as pharmacologically acceptable salts, diastereomers, enantiomers, racemates, hydrates or solvates thereof,

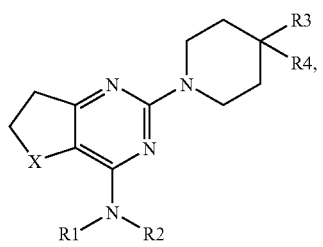

wherein X is SO or $SO_2$, but preferably SO, and wherein $R^1$, $R^2$, $R^3$ and $R^4$ have the meanings stated in claim 1, as well as pharmaceutical compositions which contain these compounds.

These new piperidino-dihydrothienopyrimidinesulphoxides are suitable for the treatment of respiratory or gastrointestinal complaints or diseases, inflammatory diseases of the joints, skin or eyes, diseases of the peripheral or central nervous system or cancers.

PRIOR ART

U.S. Pat. No. 3,318,881 and BE 663693 disclose the preparation of piperazino-dihydrothieno-[3,2-d]pyrimidines which have cardiovascular and sedative properties. WO 2006/111549 and EP06112779.1 (EP1847543) each disclose dihydrothieno-pyrimidinesulphoxides which are substituted by piperazine instead of piperidine.

DESCRIPTION OF THE INVENTION

Surprisingly it has been found that, besides piperazino-dihydrothienopyrimidine-sulphoxides, piperidino-dihydrothienopyrimidinesulphoxides of formula 1, wherein $R^3$ and $R^4$ have the meanings stated in claim 1, particularly those wherein X denotes SO, are particularly suitable for the treatment of inflammatory diseases and are superior to the corresponding piperazino-dihydrothienopyrimidinesulphoxides from the prior art.

The present invention therefore relates to compounds of formula 1

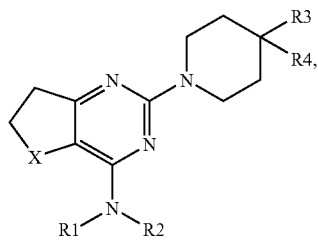

wherein
X denotes SO or $SO_2$,
$R^1$ denotes H, $C_{1-6}$-alkyl,
$R^2$ is H or a group selected from among $C_{1-10}$-alkyl and $C_{2-6}$-alkenyl, which may optionally be substituted by one or more groups selected from halogen and $C_{1-3}$-fluoroalkyl or which may optionally be substituted by one or more groups selected from among $OR^{2.1}$, $COOR^{2.1}$, $CONR^{2.2}R^{2.3}$, $SR^{2.1}$, $SO-R^{2.1}$, $SO_2-R^{2.1}$, $C_{6-10}$-aryl, -het, hetaryl, a mono- or bicyclic $-C_{3-10}$-cycloalkyl, $CH_2-NR^{2.2}R^{2.3}$ and $NR^{2.2}R^{2.3}$,
  which in turn may optionally be substituted by one or more groups selected from among OH, halogen, $OR^{2.1}$, oxo, $CF_3$, $CHF_2$, $CH_2F$, $C_{1-6}$-alkanol, $C_{6-10}$-aryl, $COOR^{2.1}$, $CH_2-NR^{2.2}R^{2.3}$ and $NR^{2.2}R^{2.3}$,
wherein
het denotes a three- to eleven-membered, mono- or bicyclic, saturated or partially saturated, optionally anellated or optionally bridged heterocycle is, which contains 1, 2, 3 or 4 heteroatoms selected independently of one another from among N, S or O contains,
and wherein
hetaryl is a five- to ten-membered, mono- or bicyclic, optionally anellated heteroaryl, which contains 1, 2, 3 or 4 heteroatoms selected independently of one another from among N, S or O,
and wherein
cycloalkyl may be saturated or partially saturated,
wherein $R^{2.1}$ is H or is a group selected from among $C_{1-6}$-alkyl, $C_{1-6}$-alkanol, $C_{1-3}$-haloalkyl, mono- or bicyclic, $-C_{3-10}$-cycloalkyl, $C_{6-10}$-aryl-$C_{1-6}$-alkylene, hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, heteroaryl and a -het,
  which may optionally be substituted by one or more groups selected from among OH, O—($C_{1-3}$-alkyl), halogen, $C_{1-6}$-alkyl and $C_{6-10}$-aryl,
wherein $R^{2.2}$ and $R^{2.3}$ independently of one another denote H or a group selected from among $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, $CO-NH_2$, $CO-NHCH_3$, $-CO-N(CH_3)_2$, $SO_2-(C_1-C_2$-alkyl), $CO-R^{2.1}$ and $COOR^{2.1}$, which may optionally be substituted by one or more groups selected from among OH, halogen, $C_{1-6}$-alkyl, $C_{6-10}$-aryl and $COOR^{2.1}$,
or
$R^2$ denotes a mono- or polycyclic $C_{3-10}$ cycloalkyl, which may optionally be bridged one or more times via $C_{1-3}$-alkyl groups and which may optionally be substituted by a group selected from among branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $-SO_2-NR^{2.2}R^{2.3}$, het, $-NH-CO-O-(C_{1-6}$-alkyl), $-NH-CO-(C_{1-6}$-alkyl), $-NH-CO-O-(C_{6-10}$-aryl), $-NH-CO-(C_{6-10}$-aryl), $-NH-CO-O$-hetaryl, $-NH-CO$-hetaryl, $-NH-CO-O-(C_{1-3}$-alkylene)-($C_{6-10}$-aryl), $-NH-CO-(C_{1-3}$-alkylene)-($C_{6-10}$-aryl), $-N(C_{1-3}$-alkyl)-CO-($C_{1-6}$-alkyl), $-N(C_{1-3}$-alkyl)-CO-O-($C_{6-10}$-aryl), $-N(C_{1-3}$-alkyl)-CO-($C_{6-10}$-aryl), $-N(C_{1-3}$-alkyl)-CO-O-hetaryl, $-N(C_{1-3}$-alkyl)-CO-hetaryl, $-N(C_{1-3}$-alkyl)-CO-O-($C_{1-3}$-alkylene)-($C_{6-10}$-aryl), $-N(C_{1-3}$-alkyl)-CO-($C_{1-3}$-alkylene)-($C_{6-10}$-aryl), $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl and $NR^{2.2}R^{2.3}$,
  which may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$,
or
$R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2-NR^{2.2}R^{2.3}$, $C_{3-10}$-cycloalkyl, het, $C_{1-6}$-alkyl, $C_{1-3}$-fluoroalkyl, $CF_3$, $CHF_2$, $CH_2F$, $C_{6-10}$-aryl-$C_{1-6}$-alkylene, het-$C_{1-6}$-alkylene, hetaryl-$C_{1-6}$-alkylene, $C_{6-10}$-aryl, $SO_2-CH_3$, $SO_2-CH_2CH_3$ and $SO_2-NR^{2.2}R^{2.3}$, which may in turn optionally be substituted by one or more groups selected from among OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a group selected from among het and hetaryl, which may optionally be substituted by one or more groups selected from among halogen, OH, oxo, $CF_3$, $CHF_2$ and $CH_2F$ or by one or more groups selected from among $OR^{2.1}$, $C_{1-3}$-alkylene-$OR^{2.1}$, $SR^{2.1}$, $SO-R^{2.1}$, $SO_2-R^{2.1}$, $COOR^{2.1}$, $COR^{2.1}$, $C_{1-6}$-alkanol, mono- or bicyclic $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$ and $NR^{2.2}R^{2.3}$, which may in turn optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or wherein $NR^1R^2$ together denotes a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-3}$-alkylene-$O^{R.1}$, oxo, halogen, $C_{1-6}$-alkyl, $C_{6-10}$-aryl, $COOR^{2.1}$, $CH_2-NR^{2.2}-COO-R^{2.1}$, $CH_2-NR^{2.2}-CO-R^{2.1}$, $CH_2-NR^{2.2}-CO-CH_2-NR^{2.2}R^{2.3}$, $CH_2-NR^{2.2}-SO_2-C_{1-3}$-alkyl, $CH_2-NR^{2.2}-SO_2-NR^{2.2}R^{2.3}$, $CH_2-NR^{2.2}-CO-NR^{2.2}R^{2.3}$, $CO-NR^{2.2}R^{2.3}$, $CH_2-NR^{2.2}R^{2.3}$ and $NR^{2.2}R^{2.3}$, and wherein $R^3$ is a $C_{6-10}$-aryl, which may optionally be substituted by in the ortho, para or meta position by one, two or three groups selected independently of one another from among fluorine, chlorine, bromine, hydroxy, CN, $C_{1-6}$-alkyl, $C_{1-3}$-fluoroalkyl, $-C_{1-3}$-alkylene-$OR^{2.1}$, $-C_{1-3}$-alkylene-$NR^{2.2}R^{2.3}$, $-NR^{2.2}R^{2.3}$, $O-R^{2.1}$; $SO-R^{2.1}$, $SO_2-R^{2.1}$, $COOR^{2.1}$, $-CO-NH-(C_{1-6}$-alkylene)-hetaryl, $-CO-N(CH_3)$-het, $-CO-N(CH_3)-(C_{1-3}$-alkylene)-het, $-CO-N(CH_3)-(C_{1-3}$-alkylene)-hetaryl, $-CO-N(C_{3-7}$-cycloalkyl)-het, $-CO-NR^{2.2}R^{2.3}$, $-CO-NH-(C_{1-6}$-alkylene)-het, $NR^{2.2}-CO-R^{2.1}$, $C_{6-10}$-aryl, $C_{6-10}$-aryl-$C_{1-2}$-alkylene, het-$C_{1-2}$-alkylene, -het, $-CO$-het, $CO-N(CH_3)-C_{3-7}$-cycloalkyl, $C_{3-7}$-cycloalkyl, $C_{3-7}$-cycloalkyl-$C_{1-2}$-alkylene, hetaryl-$C_{1-2}$-alkylene and hetaryl, while this groups may optionally be substituted by one or more groups selected from among OH, halogen, $-C_{1-3}$-fluoroalkyl, oxo, methyl and phenyl, or wherein $R^3$ is a group selected from among het and hetaryl, which may optionally be substituted by one or more groups selected from among halogen, $C_{1-3}$-fluoroalkyl, ON, OH, oxo, $-C_{1-6}$-alkyl, $-C_{1-3}$-alkylene-$NR^{2.2}R^{2.3}$, $-NR^{2.2}R^{2.3}$, $SO-R^{2.1}$, $SO_2-R^{2.1}$, $-O-R^{2.1}$, $-COOR^{2.1}$, $SO_2-(CH_3)$, $SO_2-(CH_2-CH_3)$, $C_{6-10}$-aryl het, $C_{3-7}$-cycloalkyl and hetaryl, which may in turn optionally be substituted by one or more groups selected from among OH, halogen, $-C_{1-3}$-fluoroalkyl, $C_{1-6}$-alkyl, $C_{6-10}$-aryl, $-COO(C_{1-3}$-alkyl) and $O-(C_{1-3}$-alkyl), or wherein $R^3$ denotes $-O-R^{3.1}$, wherein $R^{3.1}$ is a group selected from among $-C_{1-6}$-alkyl, $-C_{6-10}$-aryl, $-C_{1-3}$-alkylene-$C_{6-10}$-aryl, hetaryl and het, which may optionally be substituted in the ortho, para or meta position by one, two or three groups selected independently of one another from among fluorine, chlorine, bromine, hydroxy, CN, $C_{1-6}$-alkyl, $C_{1-3}$-fluoroalkyl, $CO-(C_{1-5}$-alkyl), $-CO-(C_{1-3}$-fluoroalkyl), $-CO-NH-(C_{1-6}$-alkylene)-hetaryl, $-CO-N(C_{1-3}$-alkyl)-(C_{1-6}$-alkylene)-hetaryl, $-CO-N(C_{1-3}$-alkyl)-het, $-CO-N(C_{3-7}$-cycloalkyl)-het, $-C_{1-3}$-alkylene-$OR^{2.1}$, $-C_{1-3}$-alkylene-$NR^{2.2}R^{2.3}$, $-NR^{2.2}R^{2.3}$, $O-R^{2.1}$; $SO-R^{2.1}$, $SO_2-R^{2.1}$, COOH, $COO-(C_{1-4}$-alkyl), $-O-C_{1-3}$-alkylene-$N(C_{1-3}$-alkyl)$_2$, $CO-NR^{2.2}R^{2.3}$, $NR^{2.2}-CO-R^{2.1}$, $C_{6-10}$-aryl, $C_{6-10}$-aryl-$C_{1-2}$-alkylene, het-$C_{1-2}$-alkylene, $-CO$-het, het, $-CO-C_{3-7}$-cycloalkyl, $-CO-N(C_{1-3}$-alkyl)-$C_{3-7}$-cycloalkyl, $C_{3-7}$-cycloalkyl, $C_{3-7}$-cycloalkyl-$C_{1-2}$-alkylene, hetaryl-$C_{1-2}$-alkylene and hetaryl, which may in turn optionally be substituted by 1, 2, 3 or 4 groups selected independently of one another from among F, Cl, Br, methyl, O-methyl, ethyl, O-ethyl, OH, oxo and $CF_3$.

and wherein $R^4$ denotes H, ON, OH, $CF_3$, $CHF_2$, $CH_2F$, F, methyl, ethyl, $-O-(C_{1-3}$-alkyl), $-C_{1-3}$-alkylene-OH, $-COO(C_{1-3}$-alkyl), $-CO$-het, $-(C_{1-2}$-alkylene)-NH-$SO_2-(C_{1-2}$-alkyl), $-(C_{1-2}$-alkylene)-$N(C_{1-3}$-alkyl)-$SO_2-(C_{1-2}$-alkyl), $-(C_{1-2}$-alkylene)-$O-(C_{1-2}$-alkylene)-$C_{6-10}$-aryl, $-C_{1-3}$-alkylene-$O-C_{1-3}$-alkyl, $-(C_{1-2}$-alkylene)-$N(C_{1-3}$-alkyl)-$CO-(C_{1-2}$-alkyl), $-NH-CO-(C_{1-3}$-alkylene)-$O-(C_{1-3}$-alkyl), $-C_{1-3}$-alkylene-$NH-CO-(C_{1-3}$-alkyl), $-C_{1-3}$-alkylene-$NH-CO-(C_{1-3}$-alkylene)-$N(C_{1-3}$-alkyl)$_2$, $-O-(C_{1-2}$-alkylene)-$(C_{6-10}$-aryl), $-C_{1-3}$-alkylene-$NH-CO-(C_{1-3}$-alkylene)-$O-(C_{1-3}$-alkyl), $-CO-(C_{6-10}$-aryl), $-(C_{1-2}$-alkylene)-$N(C_{1-3}$-alkyl)-$CO-(C_{1-2}$-alkylene)-$O-(C_{1-3}$-alkyl), wherein the aryl in the above groups may in turn optionally be substituted by one or more other groups selected from among F, Cl, Br, methyl, ethyl, propyl, isopropyl, cyclopropyl, $-O$-methyl, $-O$-ethyl, $-O$-propyl, $-O$-isopropyl, $-O$-cyclopropyl, $-OH$ and $CF_3$ or wherein $R^3$ and $R^4$ together form a mono- or bicyclic, unsaturated, saturated or partially saturated heterocycle, which contains 1, 2 or 3 heteroatoms selected from among N, O and S contains and which may optionally be substituted by one or more groups selected from among halogen, OH, oxo, $C_{1-3}$-fluoroalkyl, CN, $C_{1-6}$-alkyl, $-O-R^{2.1}$, $-COOR^{2.1}$, $SO-R^{2.1}$, $SO_2-R^{2.1}$, $-C_{1-3}$-alkylene-$NR^{2.2}R^{2.3}$, $-NR^{2.2}R^{2.3}$, $C_{6-10}$-aryl, $C_{3-7}$-cycloalkyl, het and hetaryl, as well as pharmacologically acceptable salts, diastereomers, enantiomers, racemates, hydrates or solvates thereof.

The present invention expressly relates to both the R-enantiomers of formula A and the S-enantiomers of formula A' with respect to the stereocentre at the sulphoxide-sulphur atom of the compounds of formula 1,

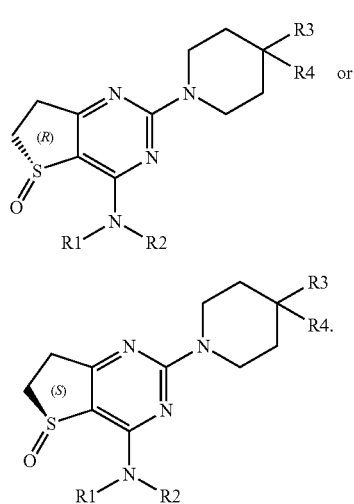

Also preferred are the above mentioned compounds of formula 1, wherein
X denotes SO or $SO_2$,
$R^1$ denotes H
$R^2$ denotes H or $C_{1-10}$-alkyl, which may optionally be substituted by one or more groups selected from halogen and $C_{1-3}$-fluoroalkyl or which may optionally be substituted by one or more groups selected from among $OR^{2.1}$, $COOR^{2.1}$, $CONR^{2.2}R^{2.3}$, $SR^{2.1}$, $SO$—$R^{2.1}$, $SO_2$—$R^{2.1}$, phenyl, het, hetaryl, a monocyclic $C_{3-7}$-cycloalkyl, $CH_2$—$NR^{2.2}R^{2.3}$ and $NR^{2.2}R^{2.3}$, which in turn may optionally be substituted by one or more groups selected from among OH, F, Cl, Br, $OR^{2.1}$, oxo, $CF_3$, $CHF_2$, $CH_2F$, $C_{1-6}$-alkyl, $C_{1-6}$-alkanol, phenyl, $COOR^{2.1}$, $CH_2$—$NR^{2.2}R^{2.3}$ and $NR^{2.2}R^{2.3}$,
wherein
het is a three- to seven-membered, monocyclic, saturated or partially saturated heterocycle or a seven- to eleven-membered, bicyclic, saturated or partially saturated heterocycle, which contains 1, 2, 3 or 4 heteroatoms selected independently of one another from among N, S or O, and wherein
hetaryl is a five- to six-membered, monocyclic, aromatic heteroaryl or a seven- to eleven-membered, bicyclic, aromatic heteroaryl, which contains in each case 1, 2, 3 or 4 heteroatoms selected independently of one another from among N, S or O,
and wherein
cycloalkyl may be saturated or partially saturated,
wherein $R^{2.1}$ is H or a group selected from among $C_{1-6}$-alkyl, $C_{1-6}$-alkanol, $C_{1-3}$-haloalkyl, monocyclic $C_{3-7}$ cycloalkyl, phenyl-$C_{1-6}$-alkylene, hetaryl-$C_{1-6}$-alkylene, het -$C_{1-6}$-alkylene, —$C_{3-7}$-cycloalkyl-$C_{1-6}$-alkylene, phenyl, hetaryl and a het, which may optionally be substituted by one or more groups selected from among OH, F, Cl, $C_{1-6}$-alkyl, —O—($C_{1-3}$-alkyl) and phenyl,
wherein $R^{2.2}$ and $R^{2.3}$ independently of one another denote H or a group selected from among $C_{1-6}$-alkyl, monocyclic $C_{3-7}$ cycloalkyl, phenyl-$C_{1-3}$-alkylene, hetaryl-$C_{1-3}$-alkylene, phenyl, het, hetaryl, CO—$NH_2$, —CO—$NHCH_3$, —$CON(CH_3)_2$, $SO_2$—($C_{1-2}$-alkyl), CO—$R^{2.1}$ and $COOR^{2.1}$,
which may optionally be substituted by one or more groups selected from among OH, F, Cl, $C_{1-6}$-alkyl, phenyl and $COOR^{2.1}$,
or
$R^2$ denotes a monocyclic $C_{3-7}$ cycloalkyl, which may optionally be substituted by a group selected from among branched or unbranched $C_{1-6}$-alkanol, $C_{1-3}$-fluoroalkyl, $OR^{2.1}$, $C_{1-3}$-alkylene-$OR^{2.1}$, $OR^{2.1}$, $COOR^{2.1}$, $SO_2$—$NR^{2.2}R^{2.3}$, -het, —NH—CO—O-(phenyl), phenyl, $C_{1-6}$-alkyl, phenyl-$C_{1-6}$-alkylene, -hetaryl-$C_{1-6}$-alkylene, monocyclic $C_{3-7}$ cycloalkyl and $NR^{2.2}R^{2.3}$,
which may optionally be substituted by one or more groups selected from among OH, $OR^{2.1}$, oxo, F, Cl, $CF_3$, $CHF_2$, $CH_2F$, $C_{1-6}$-alkyl, phenyl and —$NR^{2.2}R^{2.3}$,
or
$R^2$ denotes a phenyl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-7}$-cycloalkyl, $C_{3-7}$ heterocycle, $C_{1-6}$-alkyl, $C_{1-3}$-fluoroalkyl, phenyl-$C_{1-6}$-alkylene, -het-$C_{1-6}$-alkylene, -hetaryl-$C_{1-6}$-alkylene, phenyl, $SO_2$—$CH_3$, $SO_2$—$CH_2CH_3$ and $SO_2$—$NR^{2.2}R^{2.3}$,
which may in turn optionally be substituted by one or more groups selected from among OH, $OR^{2.1}$, oxo, F, Cl, $CF_3$, $CHF_2$, $CH_2F$, $C_{1-6}$-alkyl, phenyl and $NR^{2.2}R^{2.3}$,
or
$R^2$ denotes a group selected from among het and hetaryl, which may optionally be substituted by one or more groups selected from among F, Cl, OH, oxo, $CF_3$, $CHF_2$ and $CH_2F$ or by one or more groups selected from among $OR^{2.1}$, —$C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, monocyclic $C_{3-7}$-cycloalkyl, phenyl, $C_{1-6}$-alkyl, phenyl-$C_{1-6}$-alkylene, -hetaryl-$C_{1-6}$-alkylene, -het, -hetaryl, and $NR^{2.2}R^{2.3}$,
which may in turn optionally be substituted by one or more groups selected from among OH, $OR^{2.1}$, oxo, F, Cl, $CF_3$, $CHF_2$, $CH_2F$, $C_{1-6}$-alkyl, phenyl and $NR^{2.2}R^{2.3}$,
or wherein
$NR^1R^2$ together denotes a heterocyclic $C_{4-7}$ ring which may optionally be bridged, which contains 1, 2 or 3 heteroatoms selected from among N, O and S and which may optionally be substituted by one or more groups selected from among OH, $OR^{2.1}$, $C_{1-3}$-alkylene-$O^{R.1}$, oxo, F, Cl, $C_{1-6}$-alkyl, phenyl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$ and $NR^{2.2}R^{2.3}$,
and wherein
$R^3$ is a naphthalene or phenyl,
which may optionally be substituted in the ortho, para or meta position by one or two groups selected independently of one another from among fluorine, chlorine, bromine, hydroxy, CN, $C_{1-6}$-alkyl, $C_{1-3}$-fluoroalkyl, —$C_{1-3}$-alkylene-$OR^{2.1}$, —$C_{1-3}$-alkylene-$NR^{2.2}R^{2.3}$, —$NR^{2.2}R^{2.3}$, O—$R^{2.1}$; SO—$R^{2.1}$, $SO_2$—$R^{2.1}$, $COOR^{2.1}$, —CO—NH—($C_{1-6}$-alkylene)-hetaryl, —CO—NH-hetaryl, —CO—$N(CH_3)$-het, —CO—N$(CH_3)$—($C_{1-3}$-alkylene)-het, —CO—$N(CH_3)$—($C_{1-3}$-alkylene)-hetaryl, —CO—$N(C_{3-7}$-cycloalkyl)-het, CO—$NR^{2.2}R^{2.3}$,
—CO—NH—($C_{1-6}$-alkylene)-het, —$NR^{2.2}$—CO—$R^{2.1}$, phenyl, phenyl-$C_{1-2}$-alkylene, -het-$C_{1-2}$-alkylene, -het, —CO-het, —CO—$N(CH_3)$-het, CO—$N(CH_3)$—$C_{3-7}$-cycloalkyl, $C_{3-7}$-cycloalkyl, $C_{3-7}$-cycloalkyl-$C_{1-2}$-alkylene, -hetaryl-$C_{1-2}$-alkylene and -hetaryl,
while these groups may optionally be substituted by one or more groups selected from among OH, F, Cl, —$C_{1-3}$-fluoroalkyl, oxo, methyl and phenyl,
or wherein
$R^3$ denotes a group selected from among het and hetaryl, which may optionally be substituted by one or more groups selected from among F, Cl, Br, $C_{1-3}$-fluoroalkyl, CN, OH, oxo, —$C_{1-6}$-alkyl, —$C_{1-3}$-alkylene-$NR^{2.2}R^{2.3}$, —$NR^{2.2}R^{2.3}$, SO—$R^{2.1}$, $SO_2$—$R^{2.1}$, —O—$R^{2.1}$, —$COOR^{2.1}$, $SO_2$—$(CH_3)$, $SO_2$—$(CH_2$—$CH_3)$, phenyl, het, $C_{3-7}$-cycloalkyl and hetaryl, which may in turn optionally be substituted by one or more groups selected from among OH, F, Cl, Br, —$C_{1-3}$-fluoroalkyl, $C_{1-6}$-alkyl, phenyl, —$COO(C_{1-3}$-alkyl) and O—$(C_{1-3}$-alkyl), or wherein $R^3$ denotes —O—$R^{3.1}$, wherein $R^{3.1}$ is a group selected from among —$C_{1-6}$-alkyl, -phenyl, —$C_{1-3}$-alkylene-phenyl, hetaryl and het, which is optionally substituted in the ortho, para or meta position by one, two or three groups selected independently of one another from among fluorine, chlorine, bromine, hydroxy, CN, $C_{1-6}$-alkyl, $C_{1-3}$-fluoroalkyl, CO—$(C_{1-5}$-alkyl), —CO—$(C_{1-3}$-fluoroalkyl), —CO—NH—$(C_{1-6}$-alkylene)-hetaryl, —CO—$N(CH_3)$—$(C_{1-6}$-alkylene)-hetaryl, —CO—$N(CH_3)$-het, —CO—$N(C_{3-7}$-cycloalkyl)-het, —$C_{1-3}$-alkylene-$OR^{2.1}$, —$C_{1-3}$-alkylene-$NR^{2.2}R^{2.3}$, —$NR^{2.2}R^{2.3}$, O—$R^{2.1}$; SO—$R^{2.1}$, $SO_2$—$R^{2.1}$, COOH, COO—$(C_{1-4}$-alkyl), —O—$C_{1-3}$-alkylene-$N(C_{1-3}$-alkyl)$_2$, CO—$NR^{2.2}R^{2.3}$, $NR^{2.2}$—CO—$R^{2.1}$, phenyl, phenyl-$C_{1-2}$-alkylene, het-$C_{1-2}$-alkylene, —CO-het, het, —CO—$C_{3-7}$-cycloalkyl, —CO—$N(CH_3)$—$C_{3-7}$-cycloalkyl, $C_{3-7}$-cycloalkyl, $C_{3-7}$-cycloalkyl-$C_{1-2}$-alkylene, hetaryl-$C_{1-2}$-alkylene and hetaryl which may in turn optionally be substituted by 1, 2, 3 or 4 groups selected independently of one another from among F, Cl, Br, methyl, O-methyl, ethyl, O-ethyl, OH, oxo and $CF_3$, and wherein $R^4$ denotes H, CN, OH, $CF_3$, $CHF_2$, $CH_2F$, F, methyl, ethyl, O-methyl, O-ethyl, O-propyl, O-isopropyl, —$C_{1-3}$-alkylene-OH, —$COO(C_{1-3}$-alkyl), —CO-het, —$(C_{1-2}$-alkylene)-NH—$SO_2$—$(C_{1-2}$-alkyl),
—$(C_{1-2}$-alkylene)-$N(CH_3)$—$SO_2$—$(C_{1-2}$-alkyl),
—$(C_{1-2}$-alkylene)-O—$(C_{1-2}$-alkylene)-phenyl,
—$C_{1-3}$-alkylene-O—$C_{1-3}$-alkyl, —$(C_{1-2}$-alkylene)-$N(CH_3)$—CO—$(C_{1-2}$-alkyl), —NH—CO—$(C_{1-3}$-alkylene)-O—$(C_{1-3}$-alkyl), —$C_{1-3}$-alkylene-NH—CO—$(C_{1-3}$-alkyl), —$C_{1-3}$-alkylene-NH—CO—$(C_{1-3}$-alkylene)-$N(C_{1-3}$-alkyl)$_2$, —O—$(C_{1-2}$-alkylene)-phenyl —$C_{1-3}$-alkylene-NH—CO—$(C_{1-3}$-alkylene)-O—$(C_{1-3}$-alkyl), —CO-phenyl, —$(C_{1-2}$-alkylene)-$N(CH_3)$—CO—$(C_{1-2}$-alkylene)-O—$(C_{1-3}$-alkyl), wherein the phenyl in the above groups may optionally be substituted by one or more other groups selected from among F, Cl, Br, methyl, ethyl, propyl, —O-methyl, —O-ethyl, —O-propyl, —OH and $CF_3$ or wherein $R^3$ and $R^4$ together form a mono- or bicyclic, unsaturated, saturated or partially saturated heterocycle, which contains 1, 2 or 3 heteroatoms selected from among N, O and S contains and which may optionally be substituted by one or more groups selected from among F, Cl, Br, OH, oxo, $C_{1-3}$-fluoroalkyl, CN, $C_{1-6}$-alkyl, —O—$R^{2.1}$, —$COOR^{2.1}$, SO—$R^{2.1}$, $SO_2$—$R^{2.1}$, —$C_{1-3}$-alkylene-$NR^{2.2}R^{2.3}$, —$NR^{2.2}R^{2.3}$, phenyl, $C_{3-7}$-cycloalkyl, het and hetaryl, as well as pharmacologically acceptable salts, diastereomers, enantiomers, racemates, hydrates or solvates thereof.

Also more preferred are the above compounds of formula 1, wherein

X denotes SO, $R^1$ denotes H $R^2$ denotes H or $C_{1-6}$-alkyl, which may optionally be substituted by one or more groups selected from F, Cl, $CF_3$, $CHF_2$ or $CH_2F$ or which may optionally be substituted by one or more groups selected from among $OR^{2.1}$, $COOR^{2.1}$, $CONR^{2.2}R^{2.3}$, $SR^{2.1}$, SO—$R^{2.1}$, $SO_2$—$R^{2.1}$, phenyl, het, hetaryl, a monocyclic $C_{3-7}$-cycloalkyl, $CH_2$—$NR^{2.2}R^{2.3}$ and $NR^{2.2}R^{2.3}$, which in turn may optionally be substituted by one or more groups selected from among OH, F, Cl, Br, $CF_3$, $CHF_2$, $CH_2F$, $OR^{2.1}$, oxo, methyl, ethyl, propyl, isopropyl, methanol, ethanol, phenyl, $COOR^{2.1}$, $CH_2$—$NR^{2.2}R^{2.3}$ and $NR^{2.2}R^{2.3}$, wherein het is a three- to seven-membered, monocyclic, saturated or partially saturated heterocycle, which contains 1, 2 or 3 heteroatoms selected independently of one another from among N, S or O, and wherein hetaryl is a five- to six-membered, monocyclic, aromatic heteroaryl which contains 1, 2 or 3 heteroatoms selected independently of one another from among N, S or O, and wherein cycloalkyl may be saturated or partially saturated, wherein $R^{2.1}$ is H or a group selected from among methyl, ethyl, propyl, isopropyl, methanol, ethanol, monocyclic $C_{3-7}$ cycloalkyl, phenyl-$C_{1-2}$-alkylene, -hetaryl -$C_{1-2}$-alkylene, -het-$C_{1-2}$-alkylene, $C_{3-7}$-cycloalkyl-$C_{1-2}$-alkylene, phenyl, hetaryl and a het, which may optionally be substituted by one or more groups selected from among OH, F, Cl, methyl, ethyl, propyl, isopropyl, O-methyl, O-ethyl, O-propyl, O-isopropyl and phenyl, wherein $R^{2.2}$ and $R^{2.3}$ independently of one another denote H or a group selected from among from among methyl, ethyl, propyl, isopropyl, monocyclic $C_{3-7}$ cycloalkyl, phenyl-$C_{1-3}$-alkylene, hetaryl-$C_{1-3}$-alkylene, phenyl, -het, -hetaryl, CO—$NH_2$, CO—$NHCH_3$, $CON(CH_3)_2$, $SO_2$—$(C_{1-2}$-alkyl), CO—$R^{2.1}$ and $COOR^{2.1}$, which may optionally be substituted by one or more groups selected from among OH, F, Cl, methyl, ethyl, propyl, isopropyl, phenyl and $COOR^{2.1}$, or $R^2$ denotes a monocyclic $C_{3-7}$ cycloalkyl, which may optionally be substituted by a group selected from among $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, -het, —NH—CO—O-(phenyl), methyl, ethyl, propyl, isopropyl, phenyl, phenyl-$C_{1-2}$-alkylene, -hetaryl-$C_{1-2}$-alkylene, monocyclic $C_{3-7}$ cycloalkyl and $NR^{2.2}R^{2.3}$, which may optionally be substituted by one or more groups selected from among OH, $OR^{2.1}$, oxo, F, Cl, $CF_3$, $CHF_2$, $CH_2F$, methyl, ethyl, propyl, isopropyl, phenyl and $NR^{2.2}R^{2.3}$, or $R^2$ denotes a phenyl, which may optionally be substituted by OH, SH, F, Cl or Br or by one or more groups selected from among $OR^{2.1}$, $COOR^{2.1}$, $NR^{2.2}R^{2.3}$, $CH_2$—$NR^{2.2}R^{2.3}$, monocyclic $C_{3-7}$-cycloalkyl, -het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, F, Cl, $CF_3$, $CHF_2$, $CH_2F$, methyl, ethyl, propyl, isopropyl, phenyl and $NR^{2.2}R^{2.3}$, or $R^2$ denotes a group selected from among het and hetaryl, which may optionally be substituted by one or more groups selected from among F, Cl, OH, oxo, $CF_3$, $CHF_2$ and $CH_2F$ or by one or more groups selected from among $OR^{2.1}$, $C_{1-3}$-alkylene-$OR^{2.1}$, $SR^{2.1}$, $SO-R^{2.1}$, $SO_2-R^{2.1}$, $COOR^{2.1}$, $COR^{2.1}$, methanol, ethanol, monocyclic $C_{3-7}$-cycloalkyl, phenyl, methyl, ethyl, propyl, isopropyl, phenyl-$C_{1-2}$-alkylene, hetaryl-$C_{1-2}$-alkylene, -het, -hetaryl and $NR^{2.2}R^{2.3}$, which may in turn optionally be substituted by one or more groups selected from among OH, $OR^{2.1}$, oxo, F, Cl, $CF_3$, $CHF_2$, $CH_2F$, methyl, ethyl, propyl, isopropyl, butyl, isobutyl, phenyl and $NR^{2.2}R^{2.3}$, and wherein $R^3$ is a naphthalene or phenyl, which may optionally be substituted in the ortho, para or meta position by one or two groups selected independently of one another from among fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, SO—$CH_3$, $COOCH_3$, $COOCH_2CH_3$, —CO—NH-(methylene)-hetaryl, —CO—NH-(ethylene)-hetaryl, —CO—NH-hetaryl, —CO—N($CH_3$)-het, —CO—N($CH_3$)-(methylene)-het, —CO—N($CH_3$)-(ethylene)-het, —CO—N($CH_3$)-(methylene)-hetaryl, —CO—N($CH_3$)-(ethylene)-hetaryl, —CO—N(cyclopropyl)-het, CO—$NH_2$, $CONH(CH_3)$, $CON(CH_3)_2$, —CO—NH-(methylene)-het, —CO—NH-(ethylene)-het, —NH—CO-methyl, $NCH_3$—CO-methyl, —NH—CO-ethyl, $NCH_3$—CO-ethyl, —NH—CO-propyl, $NCH_3$—CO-propyl, —NH—CO-isopropyl, $NCH_3$—CO-isopropyl, phenyl, phenyl-methylene, phenyl-ethylene, het-methylene, het-ethylene, -het, —CO-het, —CO—N($CH_3$)-het, CO—N($CH_3$)-cyclopropyl, $C_{3-7}$-cycloalkyl, $C_{3-7}$-cycloalkyl-methylene, $C_{3-7}$-cycloalkyl-ethylene, hetaryl-methylene, hetaryl-ethylene, -hetaryl, $CH_2$—$NH_2$, $CH_2$—$NH(CH_3)$, $CH_2$—$N(CH_3)_2$, —$NH_2$, —$NH(CH_3)$ and —$N(CH_3)_2$, while these groups may optionally be substituted by one or more groups selected from among OH, F, Cl, —$CF_3$, $CHF_2$, $CH_2F$, oxo, methyl and phenyl or wherein $R^3$ denotes a group selected from among a het and hetaryl, which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, SO—($CH_3$), SO—($CH_2$—$CH_3$), $SO_2$—($CH_3$), $SO_2$—($CH_2$—$CH_3$), phenyl, $CH_2$—$NH_2$, $CH_2$—$NH(CH_3)$, $CH_2$—$N(CH_3)_2$, —$NH_2$, —$NH(CH_3)$, —$N(CH_3)_2$, het and hetaryl, which may in turn optionally be substituted by one or more groups selected from among OH, F, Cl, $CF_3$, $CHF_2$, $CH_2F$, methyl, ethyl, propyl, isopropyl, phenyl, —COO-methyl, —COO-ethyl and O-methyl, O-ethyl, or wherein $R^3$ denotes —O—$R^{3.1}$, wherein $R^{3.1}$ denotes a group selected from among —$C_{1-3}$-alkyl, -phenyl, —$C_{1-3}$-alkylene-phenyl, hetaryl and het, which may optionally be substituted in the ortho, para or meta position by one, two or three groups selected independently of one another from among fluorine, chlorine, bromine, hydroxy, CN, methyl, ethyl, propyl, isopropyl, butyl, isobutyl, $CF_3$, $CHF_2$, $CH_2F$, CO-(methyl), CO-(ethyl), CO-(propyl), CO-(isopropyl), —CO—($CF_3$), —CO—NH-(methylene)-hetaryl, —CO—NH-(ethylene)-hetaryl, —CO—N($CH_3$)-(methylene)-hetaryl, —CO—N($CH_3$)-(ethylene)-hetaryl, —CO—N($CH_3$)-(propylene)-hetaryl, —CO—N($CH_3$)-(isopropylene)-hetaryl —CO—N($CH_3$)-het, —CO—N(cyclopropyl)-het, —CO—N($C_{5-7}$-cycloalkyl)-het, -methylene-O-methyl, -ethylene-O-methyl, -propylen-O-methyl, -methylene-O-ethyl, -ethylene-O-ethyl, -propylen-O-ethyl, -methylene-$NH_2$, -methylene-$NHCH_3$, -methylene-$N(CH_3)_2$, -ethylene-$NH_2$, -ethylene-$NHCH_3$, -ethylene-$N(CH_3)_2$, $NH_2$, $N(CH_3)_2$, $NHCH_3$, —O-methyl, O-ethyl, O-propyl, O-isopropyl, O-butyl, O-isobutyl, —SO—$CH_3$, SO-ethyl, —SO-propyl, —SO-isopropyl, $SO_2$-methyl, —$SO_2$-ethyl, $SO_2$-propyl, $SO_2$-isopropyl, COOH, COO-(methyl), COO-(ethyl), COO-(propyl), COO-(isopropyl), —O-methylene-N(methyl)$_2$, —O-ethylene-N(methyl)$_2$, —O-methylene-N(ethyl)$_2$, —O-ethylene-N(ethyl)$_2$, CO—$NH_2$, CO—$NH(CH_3)$, CO—$N(CH_3)_2$, —NH—CO-methyl, —$NCH_3$—CO-methyl, —NH—CO-ethyl, $NCH_3$—CO-ethyl, phenyl, phenyl-methylene, phenyl-ethylene, het-methylene, het-ethylene, —CO-het, het, —CO—$C_{5-7}$-cycloalkyl, —CO-cyclopropyl, —CO—N($CH_3$)—$C_{5-7}$-cycloalkyl, —CO—N($CH_3$)-cyclopropyl, $C_{5-7}$-cycloalkyl, cyclopropyl, $C_{5-7}$-cycloalkyl-methylene, $C_{5-7}$-cycloalkyl-ethylene, cyclopropyl-methylene, cyclopropyl-ethylene, hetaryl-methylene, hetaryl-ethylene and hetaryl, which may in turn optionally be substituted by 1, 2, 3 or 4 groups selected independently of one another from among F, Cl, Br, methyl, O-methyl, ethyl, O-ethyl, OH, oxo and $CF_3$, and wherein $R^4$ denotes H, CN, OH, $CF_3$, $CHF_2$, $CH_2F$, F, methyl, ethyl, O-methyl or O-ethyl, -methylene-OH, -ethylene-OH, -propylene-OH, isopropylene-OH, —COO(methyl), —COO (ethyl), —COO(propyl), —COO(isopropyl), —CO-het, -(methylene)-NH—$SO_2$-(methyl), -(methylene)-NH—$SO_2$-(ethyl), -(ethylene)-NH—$SO_2$-(methyl), -(ethylene)-NH—$SO_2$-(ethyl), -(methylene)-N($CH_3$)—$SO_2$-(methyl), -(methylene)-N($CH_3$)—$SO_2$-(ethyl), -(ethylene)-N($CH_3$)—$SO_2$-(methyl), -(ethylene)-N($CH_3$)—$SO_2$-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl -ethylene-O-ethyl, -(methylene)-N($CH_3$)—CO-(methyl), -(methylene)-N($CH_3$)—CO-(ethyl) -(ethylene)-N($CH_3$)—CO-(methyl), -(ethylene)-N($CH_3$)—CO-(ethyl), —NH—CO—(methylene)-O-(methyl), —NH—CO—(methylene)-O-(ethyl), —NH—CO—(ethylene)-O-(methyl), —NH—CO—(ethylene)-O-(ethyl), -methylene-NH—CO-(methyl), -methylene-NH—CO—(ethyl), -ethylene-NH—CO-(methyl), -ethylene-NH—CO-(ethyl), -methylene-NH—CO-(methylene)-N(methyl)$_2$, -methylene-NH—CO-(ethylene)-N(methyl)$_2$, -ethylene-NH—CO-(methylene)-N(methyl)$_2$, -ethylene-NH—CO-(ethylene)-N(methyl)$_2$, -methylene-NH—CO- (methylene)-O-(methyl), -methylene-NH—CO-(ethylene)-O-(methyl), -ethylene-NH—CO-(methylene)-O-(methyl), -methylene-NH—CO-(methylene)-O-(ethyl), -methylene-NH—CO-(ethylene)-O-(ethyl), -ethylene-NH—CO-(methylene)-O-(ethyl), -(methylene)-N(CH$_3$)—CO-(methylene)-O-(methyl), -(methylene)-N(CH$_3$)—CO-(ethylene)-O-(methyl), -(ethylene)-N(CH$_3$)—CO-(methylene)-O-(methyl), -(methylene)-N(CH$_3$)—CO-(methylene)-O-(ethyl), -(methylene)-N(CH$_3$)—CO-(ethylene)-O-(ethyl), -(ethylene)-N(CH$_3$)—CO-(methylene)-O-(ethyl), —O-(methylene)-phenyl, —O-(ethylene)-phenyl, —CO-phenyl, wherein the phenyl in the above groups may optionally be substituted by one or more other groups selected from among F, Cl, Br, methyl, ethyl, propyl, —O-methyl, —O-ethyl, —O-propyl, —OH and CF$_3$ or wherein R$^3$ and R$^4$ together form a mono- or bicyclic, unsaturated, saturated or partially saturated heterocycle, which contains 1, 2 or 3 heteroatoms selected from among N, O and S and which may optionally be substituted by one or more groups selected from among F, Cl, Br, OH, oxo, CF$_3$, CHF$_2$, CH$_2$F, CN, methyl, ethyl, propyl, isopropyl, cyclopropyl, COO-methyl, —COO-ethyl, O-methyl, O-ethyl, SO$_2$—(CH$_3$), SO$_2$—(CH$_2$CH$_3$), SO—(CH$_3$), SO—(CH$_2$CH$_3$), CH$_2$—NH$_2$, CH$_2$—NH(CH$_3$), CH$_2$—N(CH$_3$)$_2$, —NH$_2$, —NH(CH$_3$), —N(CH$_3$)$_2$, phenyl, C$_{5-7}$-cycloalkyl, het and hetaryl, as well as pharmacologically acceptable salts, diastereomers, enantiomers, racemates, hydrates or solvates thereof.

More preferably, also, the present invention relates to the above compounds of formula 1, wherein R$^2$ denotes a group according to formula 2

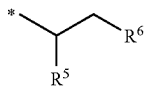

2 and wherein R$^6$ is OH or NH$_2$ and wherein R$^5$ is a group selected from among C$_{1-4}$-alkyl, a five- to six-membered heteroaryl with 1, 2 or 3 heteroatoms selected from among S, O and N and phenyl, which may optionally be substituted by one or more groups selected from among OH, F, Br, OR$^{2.1}$, oxo, methyl, ethyl, methanol, ethanol, phenyl, COOR$^{2.1}$, CH$_2$—NR$^{2.2}$R$^{2.3}$ and NR$^{2.2}$R$^{2.3}$ as well as pharmacologically acceptable salts, diastereomers, enantiomers, racemates, hydrates or solvates thereof.

Preferably, also, the present invention relates to the above compounds of formula 1, wherein R$^2$ is a group according to formula 2

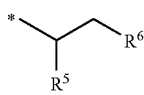

2 wherein R$^6$ is OH or NH$_2$ and wherein R$^5$ is methyl, ethyl, propyl, isopropyl as well as pharmacologically acceptable salts, diastereomers, enantiomers, racemates, hydrates or solvates thereof.

Preferably, also, the present invention relates to the above compounds of formula 1, wherein R$^2$ is a monocyclic three-, four-, five-, six- or seven-membered cycloalkyl ring which may optionally be substituted in the spiro position by a group selected from among —CH$_2$—OR$^{2.1}$, branched or unbranched C$_{2-6}$-alkylene-OR$^{2.1}$, methyl, ethyl, propyl, isopropyl, butyl, isobutyl, cyclopropyl, —CF$_3$, CHF$_2$, CH$_2$F and C$_{2-4}$-fluoroalkyl, wherein R$^{2.1}$ is selected from among methyl, ethyl, propyl, isopropyl, butyl, isobutyl, as well as pharmacologically acceptable salts, diastereomers, enantiomers, racemates, hydrates or solvates thereof.

Also preferred are the above mentioned compounds of formula 1, wherein

R$^2$ is a cyclopropyl which may optionally be substituted by another group selected from among —NH$_2$, CH2—NH$_2$, —NH(CH$_3$), —N(CH$_3$)$_2$, methyl, ethyl, propyl, isopropyl, —NH—CO-(tert-butyl), —NH—CO—O-(tert-butyl), —N(CH$_3$)—CO-(tert-butyl), —N(CH$_3$)—CO—O-(tert-butyl), —CF$_3$, —CHF$_2$, CH$_2$F, F, Cl and Br, as well as pharmacologically acceptable salts, diastereomers, enantiomers, racemates, hydrates or solvates thereof.

Also preferred are the above mentioned compounds of formula 1, wherein

R$^2$ denotes a phenyl which may optionally be substituted in one or both meta positions by one or more groups selected from among methyl, ethyl, propyl, isopropyl, cyclopropyl, F, Cl, Br, OH, OR$^{2.1}$, COOR$^{2.1}$, CF$_3$, CHF$_2$, CH$_2$F, NH$_2$, NH(CH$_3$) and N(CH$_3$)$_2$, wherein R$^{2.1}$ may be H, methyl or ethyl, as well as pharmacologically acceptable salts, diastereomers, enantiomers, racemates, hydrates or solvates thereof.

Also preferred are the above mentioned compounds of formula 1, wherein

R$^2$ is a group selected from among monocyclic, saturated three-, four-, five-, six- or seven-membered heterocycles with 1, 2 or 3 heteroatoms selected in each case from among N, O and S, which may optionally be substituted by one or more groups selected from among fluorine, chlorine, bromine, CF$_3$, CHF$_2$, CH$_2$F, OH and oxo or by one or more groups selected from among OR$^{2.1}$, C$_{1-3}$-alkylene-OR$^{2.1}$, SR$^{2.1}$, SO—R$^{2.1}$, COOR$^{2.1}$, COR$^{2.1}$, C$_{1-6}$-alkanol, C$_{3-10}$-cycloalkyl, phenyl, C$_{1-6}$-alkyl, phenyl-C$_{1-6}$-alkylene, C$_{5-10}$-heteroaryl-C$_{1-6}$-alkylene, C$_{5-10}$ heterocycle, C$_{5-10}$-heteroaryl and NR$^{2.2}$R$^{2.3}$, which may in turn optionally be substituted by one or more groups selected from among OH, OR$^{2.1}$, oxo, F, Cl, CF$_3$, CHF$_2$, CH$_2$F, C$_{1-6}$-alkyl, phenyl and NR$^{2.2}$R$^{2.3}$, and wherein R$^{2.1}$, R$^{2.2}$ and R$^{2.3}$ are as hereinbefore defined, as well as pharmacologically acceptable salts, diastereomers, enantiomers, racemates, hydrates or solvates thereof.

The present invention preferably also relates to the compounds of formula 1, wherein R$^2$ denotes a group selected from among a monocyclic, saturated six-membered heterocycle with a heteroatom selected from among N, O and S, which may optionally be substituted by one or more groups selected from among F, Cl, Br, CF$_3$, CHF$_2$, CH$_2$F, OH, oxo, NH$_2$, NHCH$_3$ and N(CH$_3$)$_2$, methyl, ethyl, propyl, isopropyl, cyclopropyl, methoxy and ethoxy, as well as pharmacologically acceptable salts, diastereomers, enantiomers, racemates, hydrates or solvates thereof.

The present invention preferably also relates to the above compounds of formula 1, wherein R$^2$ denotes a group selected from among piperidine or tetrahydropyran, which may optionally be substituted by one or more groups selected from among F, Cl, Br, OH, $CF_3$, $CHF_2$, $CH_2F$, $NH_2$, $NHCH_3$, $N(CH_3)_2$, oxo, methyl and methoxy, as well as pharmacologically acceptable salts, diastereomers, enantiomers, racemates, hydrates or solvates thereof.

The present invention preferably also relates to the above compounds of formula 1, wherein $R^3$ is a naphthalene or phenyl,
which may optionally be substituted in any position by one, two or three groups selected independently of one another from among fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, $SO_2$—$CH_2CH_3$, $COOCH_3$ and CO—O—$CH_2CH_3$, as well as pharmacologically acceptable salts, diastereomers, enantiomers, racemates, hydrates or solvates thereof.

The present invention preferably also relates to the above compounds of formula 1, wherein $R^3$ denotes a group selected from among het and hetaryl, which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, $C_{5-7}$-cycloalkyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, het and hetaryl, which may in turn optionally be substituted by one or more groups selected from among OH, F, Cl, Br, $CF_3$, $CHF_2$, $CH_2F$, methyl, ethyl, propyl, isopropyl, phenyl, —COO-methyl, —COO-ethyl, —COO-propyl, —COO-isopropyl and O-methyl, O-ethyl, O-propyl and O-isopropyl,
and wherein
$R^4$ denotes H, CN, OH, $CF_3$, $CHF_2$, $CH_2F$, F, methyl, ethyl, O-methyl or O-ethyl,
wherein
het is a three- to seven-membered, monocyclic, saturated or partially saturated heterocycle or a seven- to eleven-membered, bicyclic, anellated, saturated or partially saturated heterocycle which contains 1, 2 or 3 heteroatoms selected independently of one another from among N, S or O,
and wherein
hetaryl is a five- to six-membered, monocyclic, aromatic heteroaryl or a seven- to eleven-membered, bicyclic, anellated, aromatic heteroaryl, which contains in each case 1, 2 or 3 heteroatoms selected independently of one another from among N, S or O,
and wherein
cycloalkyl may be saturated or partially saturated, as well as pharmacologically acceptable salts, diastereomers, enantiomers, racemates, hydrates or solvates thereof.

The present invention particularly preferably also relates to the above compounds of formula 1, wherein $R^3$ denotes a group selected from a bicyclic, seven- to eleven-membered, saturated or partially saturated heterocycle or a bicyclic, seven- to eleven-membered heteroaryl, which is selected from among indole, dihydroindole, quinazoline, dihydroquinazoline, tetrahydroquinazoline, benzoisoxazole, dihydrobenzoisoxazole, benzoxazine, dihydrobenzoxazine, benzothiazole, dihydrobenzothiazole, triazolopyridine, dihydrotriazolopyridine, benzofuran, dihydrobenzofuran, isobenzofuran and dihydroisobenzofuran,
which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, furanyl and pyridinyl, which in turn may be substituted by one or more groups selected from among OH, F, Cl, Br, $CF_3$, $CHF_2$, $CH_2F$, methyl, ethyl, propyl, isopropyl, phenyl, —COO-methyl, —COO-ethyl and O-methyl, O-ethyl, as well as pharmacologically acceptable salts, diastereomers, enantiomers, racemates, hydrates or solvates thereof.

The present invention particularly preferably also relates to the above compounds of formula 1, wherein $R^3$ denotes a group selected from a monocyclic, saturated or partially saturated, three- to seven-membered heterocycle or a monocyclic five- to six-membered heteroaryl, which is selected from among imidazole, dihydroimidazole, oxadiazole, oxadiazolidine, pyrazole, pyridine and dihydropyrazole, which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, furanyl and pyridinyl, which may in turn optionally be substituted by one or more groups selected from among OH, F, Cl, Br, $CF_3$, $CHF_2$, $CH_2F$, methyl, ethyl, propyl, isopropyl, phenyl, —COO-methyl, —COO-ethyl and O-methyl, O-ethyl, as well as pharmacologically acceptable salts, diastereomers, enantiomers, racemates, hydrates or solvates thereof.

The present invention particularly preferably also relates to the above compounds of formula 1, wherein $R^3$ and $R^4$ together form a mono- or bicyclic, unsaturated or partially saturated, three- to eleven-membered heterocycle which contains 1, 2 or 3 heteroatoms selected from among N, O and S and which may optionally be substituted by one or more groups selected from among F, Cl, Br, OH, oxo, $CF_3$, $CHF_2$, $CH_2F$, CN, methyl, ethyl, propyl, isopropyl, cyclopropyl, COO-methyl, —COO-ethyl, O-methyl, O-ethyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2NHCH_3$, —$CH_2$—$N(CH_3)_2$, $NH_2$, $NHCH_3$, $N(CH_3)_2$, a saturated or partially saturated, five- to six-membered heterocycle and a five- to six-membered heteroaryl, as well as pharmacologically acceptable salts, diastereomers, enantiomers, racemates, hydrates or solvates thereof.

The present invention particularly preferably also relates to the above compounds of formula 1, wherein $R^3$ and $R^4$ together form a bicyclic heterocycle selected from among tetrahydroquinazoline, tetrahydrobenzoxazine and dihydroindole, dihydroisobenzofuran, which may optionally be substituted by one or more groups selected from among F, Cl, Br, OH, oxo, $CF_3$, $CHF_2$, $CH_2F$, CN, methyl, ethyl, propyl, isopropyl, cyclopropyl, COO-methyl, —COO-ethyl, O-methyl, O-ethyl, $SO_2$—$(CH_3)$, $SO_2$—$(CH_2$—$CH_3)$, phenyl, —$CH_2$—$NH_2$, —$CH_2NHCH_3$, —$CH_2$—$N(CH_3)_2$, $NH_2$, $NHCH_3$, $N(CH_3)_2$, a saturated or partially saturated, five- to six-membered heterocycle and a five- to six-membered heteroaryl, as well as pharmacologically acceptable salts, diastereomers, enantiomers, racemates, hydrates or solvates thereof.

The invention preferably further relates to those compounds according to formula 1, wherein
$R^3$ is —O—$R^{3.1}$,
wherein $R^{3.1}$ is a group selected from among methyl, ethyl, propyl, isopropyl, butyl, isobutyl, pentyl, isopentyl, -phenyl, -methylene-phenyl, -ethylene-phenyl, -propylene-phenyl, -isopropylene-phenyl, hetaryl and het, which may optionally be substituted in the ortho, para or meta position by one, two or three groups selected independently of one another from among fluorine, chlorine, bromine, hydroxy, CN, methyl, ethyl, propyl, isopropyl, butyl, isobutyl, —$CF_3$, $CHF_2$, $CH_2F$, CO-(methyl), CO-(ethyl), CO-(propyl), CO-(isopropyl), CO-(butyl), CO-(isobutyl), —CO—($CF_3$), —CO—($CH_2F$), —CO—($CHF_2$), —CO—NH-(methylene)-hetaryl, —CO—NH-(ethylene)-hetaryl, —CO—NH-(propylene)-hetaryl, —CO—NH-(isopropylene)-hetaryl,
—CO—N($CH_3$)-(methylene)-hetaryl, —CO—N($CH_3$)-(ethylene)-hetaryl, —CO—N($CH_3$)-(propylene)-hetaryl, —CO—N($CH_3$)-(isopropylene)-hetaryl, —CO—N($CH_3$)-het, —CO—N($C_{3-7}$-cycloalkyl)-het, -methylene-O-methyl, -ethylene-O-methyl, -methylene-O-ethyl, -ethylene-O-ethyl, -methylene-$NH_2$, -ethylene-$NH_2$, -methylene-$NHCH_3$, -ethylene-$NHCH_3$, -methylene-N($CH_3$)$_2$, -ethylene-N($CH_3$)$_2$, —$NH_2$, —$NHCH_3$, —N($CH_3$)$_2$, —O-methyl, —O-ethyl, —O-propyl, —O-isopropyl, —SO—$CH_3$, —SO—($CH_2CH_3$), —$SO_2$—$CH_3$, —$SO_2$—($CH_2CH_3$), COOH, COO-(methyl), COO-(ethyl), COO-(propyl), COO-(isopropyl), —O-methylene-N(methyl)$_2$, —O-ethylene-N(methyl)$_2$, —O-methylene-N(ethyl)$_2$, —O-ethylene-N(ethyl)$_2$, CO—$NH_2$, CO—$NHCH_3$, CO—N($CH_3$)$_2$, NH—CO-methyl, $NCH_3$—CO-methyl, NH—CO-ethyl, N($CH_3$)—CO-ethyl,
phenyl, phenyl-methylene, phenyl-ethylene, het-methylene, het-ethylene, —CO-het, het, —CO—$C_{4-7}$-cycloalkyl, —CO-cyclopropyl,
—CO—N($CH_3$)-cyclopropyl, —CO—N($CH_3$)—$C_{4-7}$-cycloalkyl,
$C_{4-7}$-cycloalkyl, cyclopropyl, $C_{4-7}$-cycloalkyl-methylene, cyclopropyl-methylene, $C_{4-7}$-cycloalkyl-ethylene, cyclopropyl-ethylene, hetaryl-methylene, hetaryl-ethylene and hetaryl,
which may in turn optionally be substituted by 1, 2, 3 or 4 groups selected independently of one another from among F, Cl, Br, methyl, O-methyl, ethyl, O-ethyl, OH, oxo and $CF_3$, and wherein the other variables are as hereinbefore defined,
as well as pharmacologically acceptable salts, diastereomers, enantiomers, racemates, hydrates or solvates thereof.

Also preferred within the scope of the invention are the compounds of formula 1,
wherein
$R^4$ denotes H, CN, OH, $CF_3$, $CHF_2$, $CH_2F$, F, methyl, ethyl, O-methyl or O-ethyl, -methylene-OH, -ethylene-OH, -propylene-OH, isopropylene-OH, —COO(methyl), —COO(ethyl), —COO(propyl), —COO(isopropyl), —CO-het, -(methylene)-NH—$SO_2$-(methyl), -(methylene)-NH—$SO_2$-(ethyl), -(ethylene)-NH—$SO_2$-(methyl), -(ethylene)-NH—$SO_2$-(ethyl), -(methylene)-N($CH_3$)—$SO_2$-(methyl), -(methylene)-N($CH_3$)—$SO_2$-(ethyl), -(ethylene)-N($CH_3$)—$SO_2$-(methyl), -(ethylene)-N($CH_3$)—$SO_2$-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl -ethylene-O-ethyl, -(methylene)-N($CH_3$)—CO-(methyl), -(methylene)-N($CH_3$)—CO-(ethyl) -(ethylene)-N($CH_3$)—CO-(methyl), -(ethylene)-N($CH_3$)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO-(methyl), -methylene-NH—CO-(ethyl), -ethylene-NH—CO-(methyl), -ethylene-NH—CO-(ethyl), -methylene-NH—CO-(methylene)-N(methyl)$_2$, -methylene-NH—CO-(ethylene)-N(methyl)$_2$, -ethylene-NH—CO-(methylene)-N(methyl)$_2$, -ethylene-NH—CO-(ethylene)-N(methyl)$_2$, -methylene-NH—CO-(methylene)-O-(methyl), -methylene-NH—CO-(ethylene)-O-(methyl), -ethylene-NH—CO-(methylene)-O-(methyl), -methylene-NH—CO-(methylene)-O-(ethyl), -methylene-NH—CO-(ethylene)-O-(ethyl), -ethylene-NH—CO-(methylene)-O-(ethyl), -(methylene)-N($CH_3$)—CO-(methylene)-O-(methyl), -(methylene)-N($CH_3$)—CO-(ethylene)-O-(methyl), -(ethylene)-N($CH_3$)—CO-(methylene)-O-(methyl), -(methylene)-N($CH_3$)—CO-(methylene)-O-(ethyl), (methylene)-N($CH_3$)—CO-(ethylene)-O-(ethyl), -(ethylene)-N($CH_3$)—CO-(methylene)-O-(ethyl), —O-(methylene)-phenyl, —O-(ethylene)-phenyl, —CO-phenyl,
while the phenyl in the above groups may optionally be substituted by one or more other groups selected from among F, Cl, Br, methyl, ethyl, propyl, —O-methyl, —O-ethyl, —O-propyl, —OH and $CF_3$, and wherein the other variables are as hereinbefore defined,
as well as pharmacologically acceptable salts, diastereomers, enantiomers, racemates, hydrates or solvates thereof.

Also preferred within the scope of the invention are those compounds of formula 1 wherein
$R^3$ is a group selected from among oxazole, imidazole and thiazole, while these groups may optionally be substituted by one, two or three further groups selected independently of one another from among methyl, ethyl, propyl, isopropyl, O-methyl, O-ethyl, O-propyl, O-isopropyl, OH, F, Cl, Br, $CF_3$, phenyl, hetaryl and $C_{3-6}$-cycloalkyl, and wherein the other variables are as hereinbefore defined,
as well as pharmacologically acceptable salts, diastereomers, enantiomers, racemates, hydrates or solvates thereof.

The present invention preferably also relates to the above compounds of formula 1,
wherein X is $SO_2$,
and wherein the other variables are as hereinbefore defined,
as well as pharmacologically acceptable salts, diastereomers, enantiomers, racemates, hydrates or solvates thereof.

The invention particularly relates to compounds according to formula 1, which are selected from among

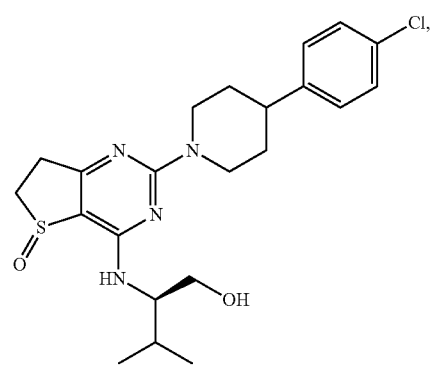

17
-continued
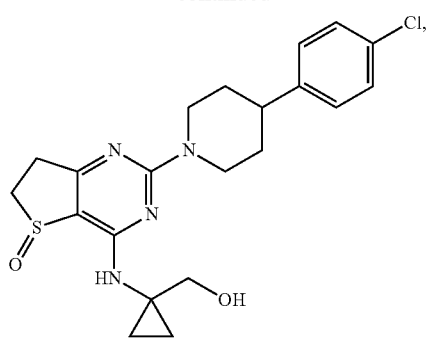
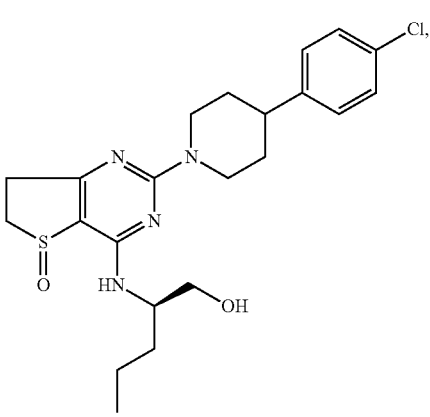
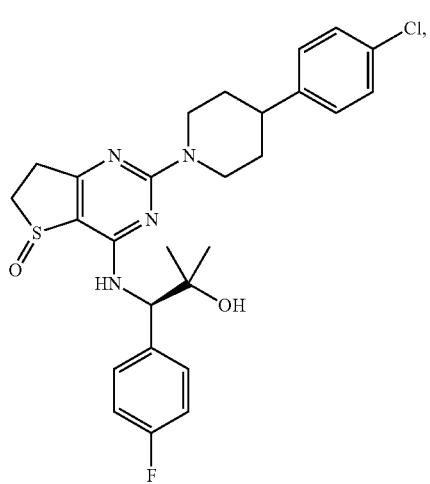
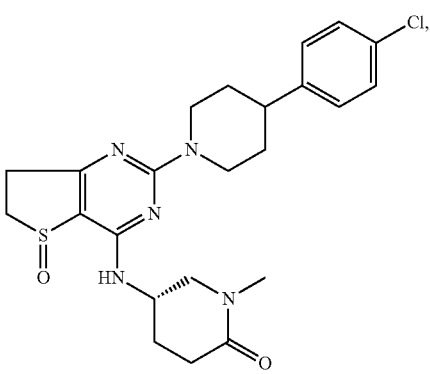
18
-continued
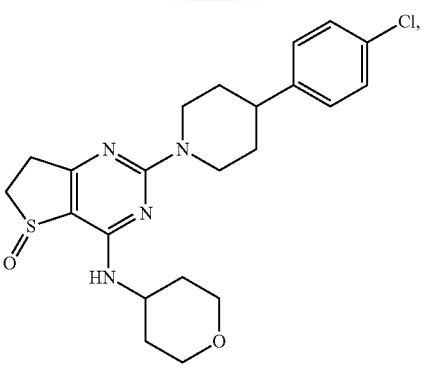
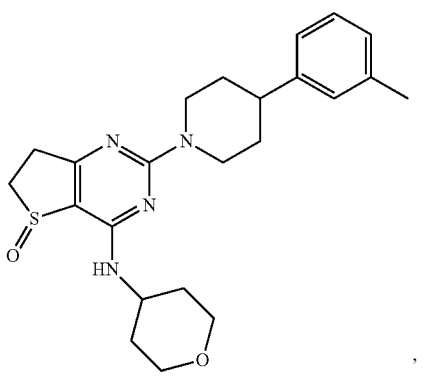
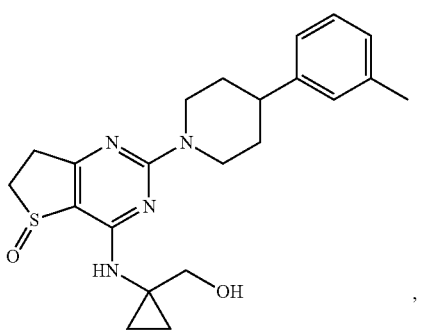
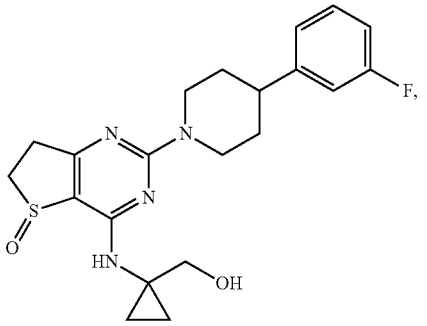

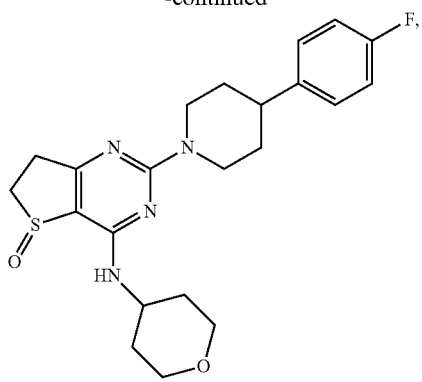
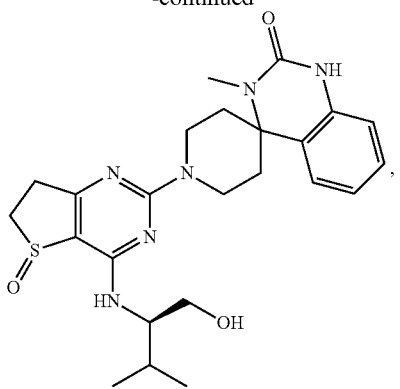
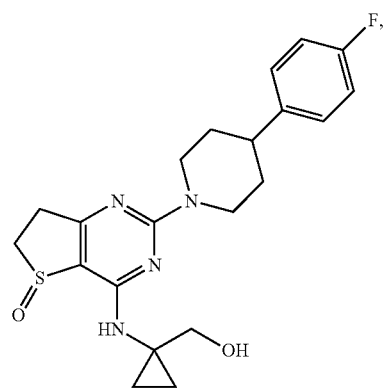
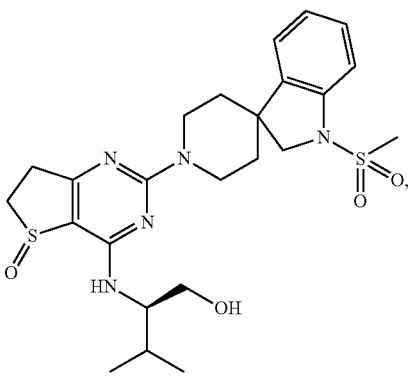
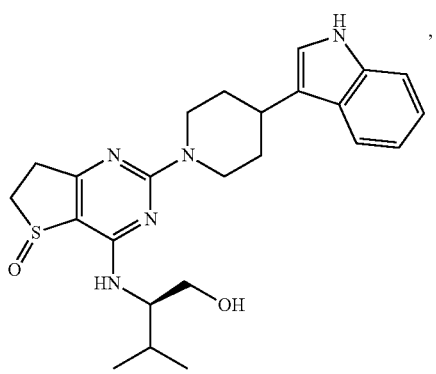
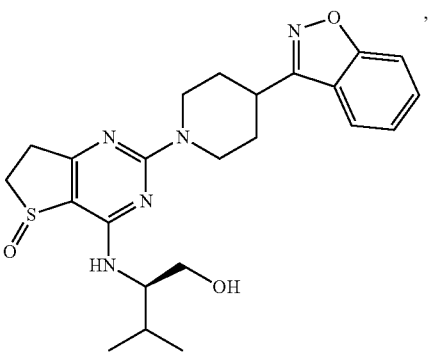
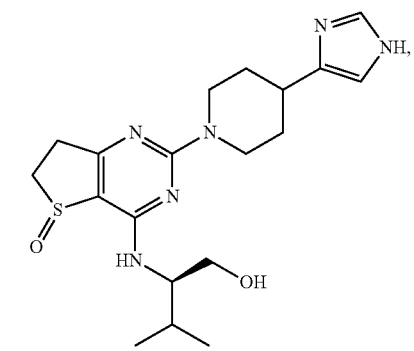
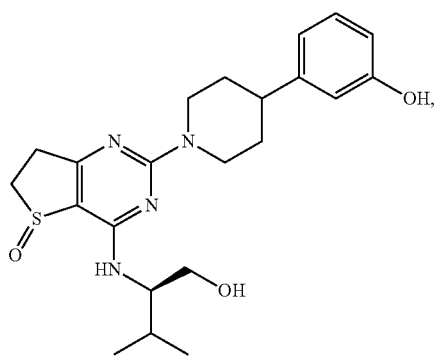

-continued
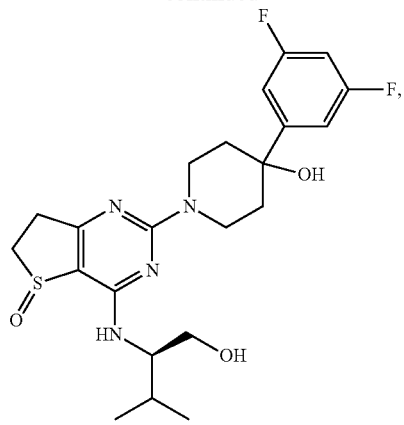
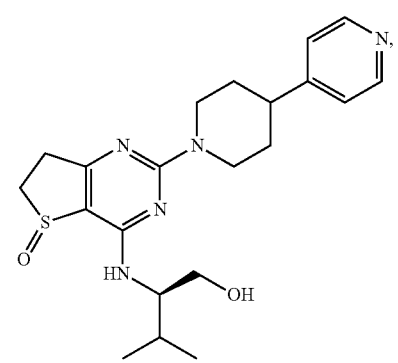
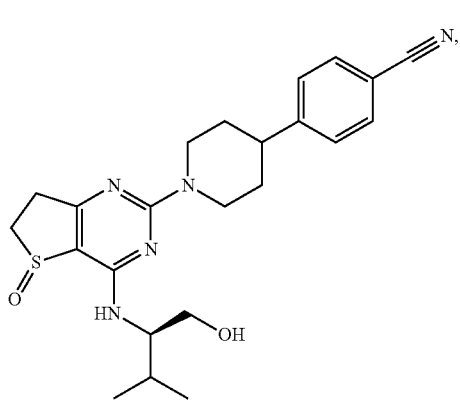
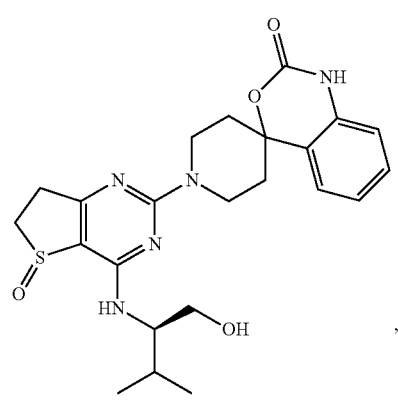
-continued
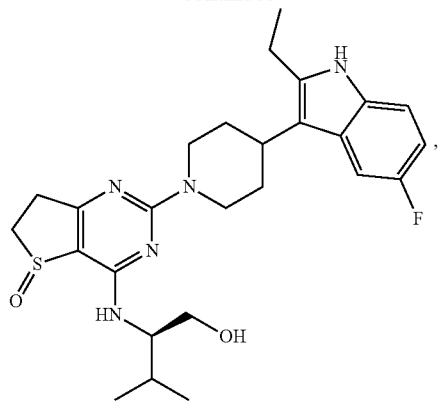
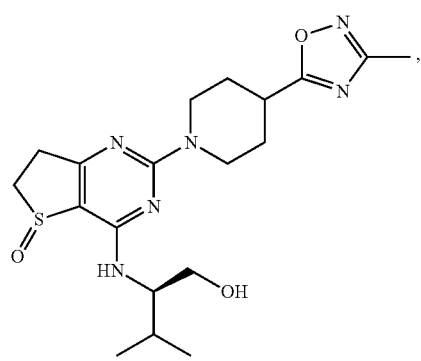
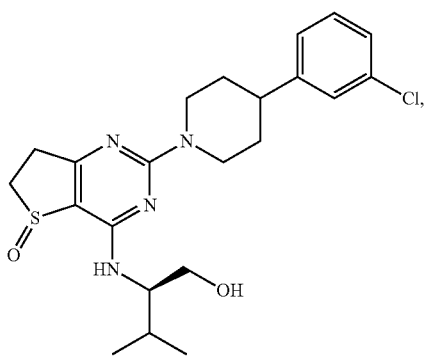
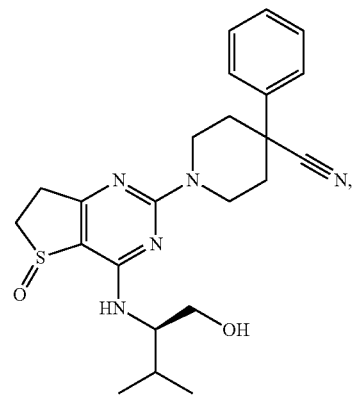

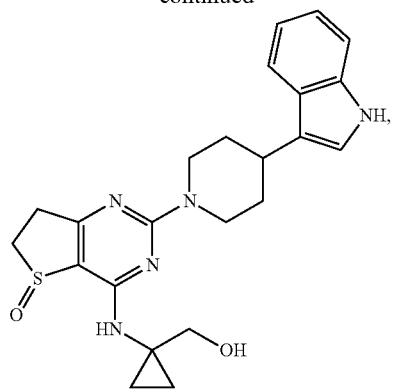
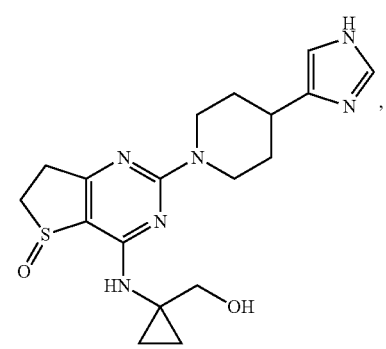
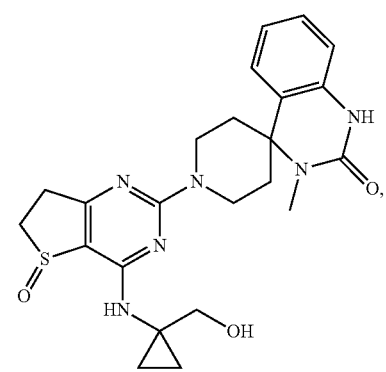
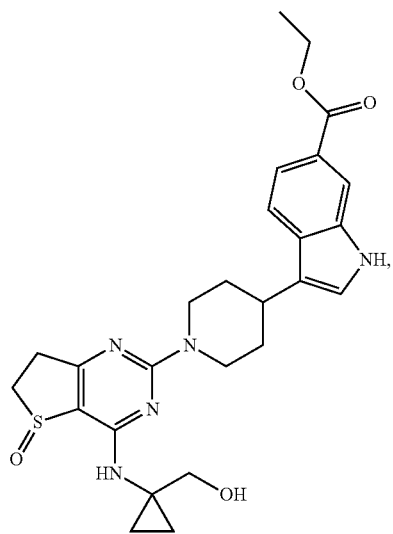
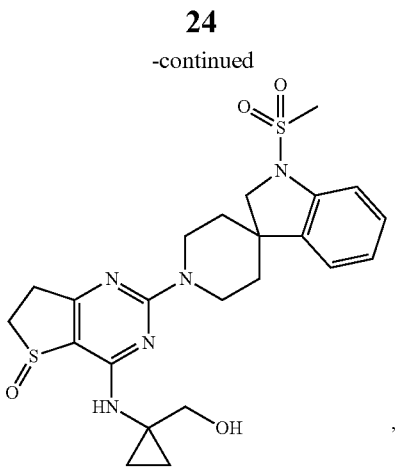
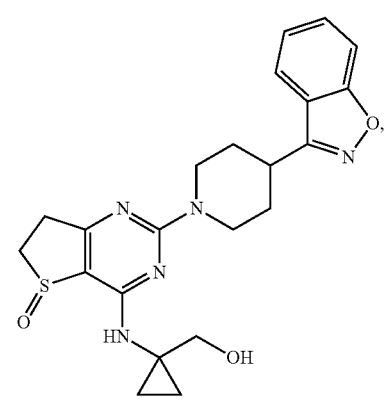
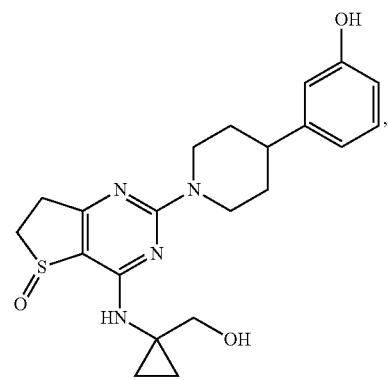
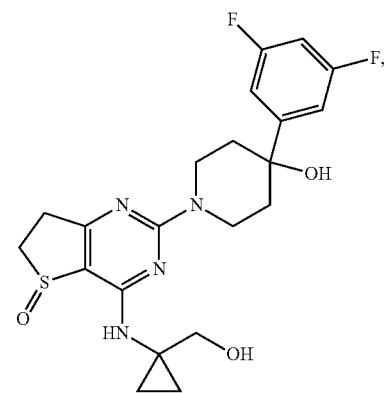

25
-continued
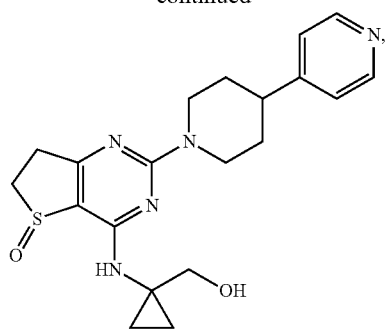
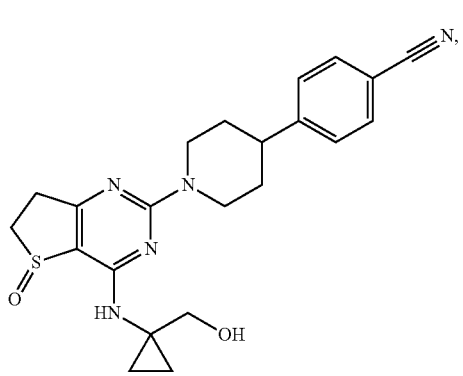
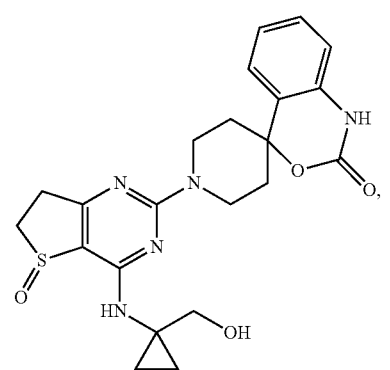
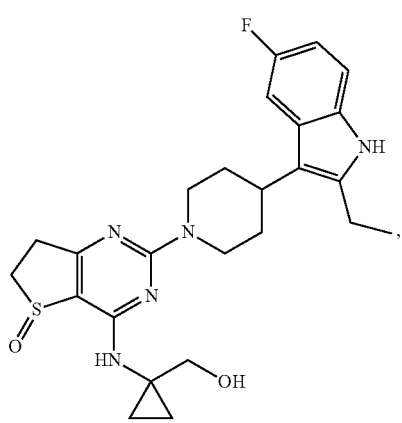
26
-continued
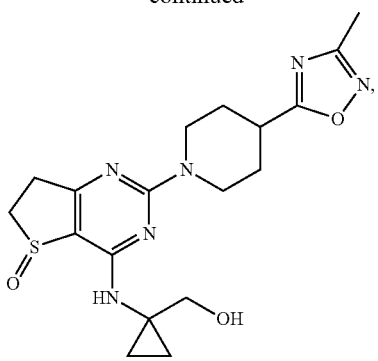
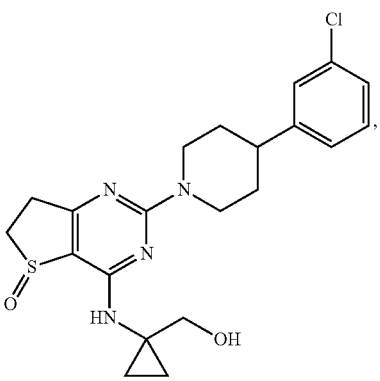
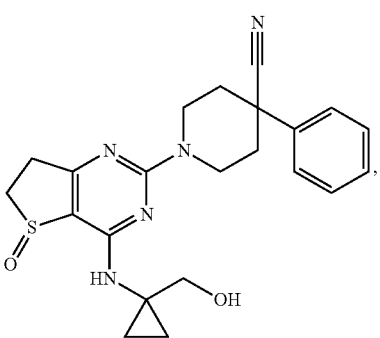
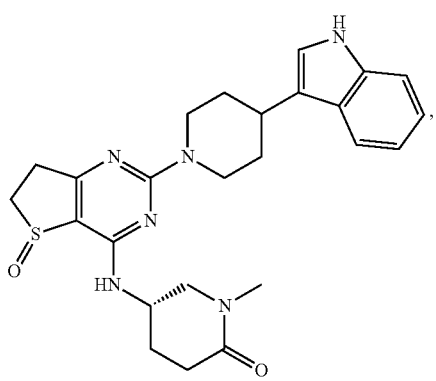

27
-continued
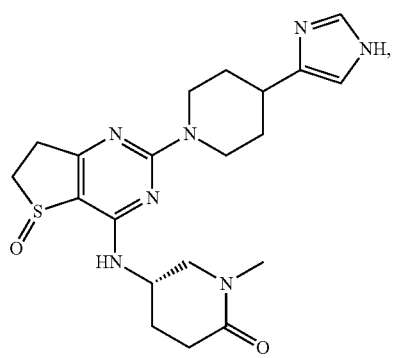
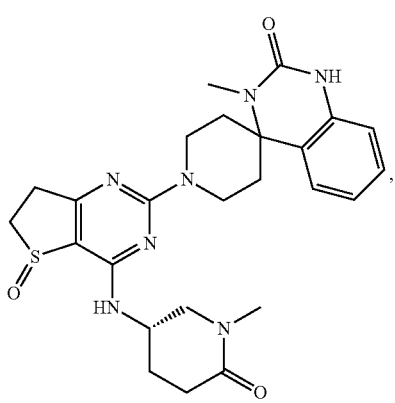
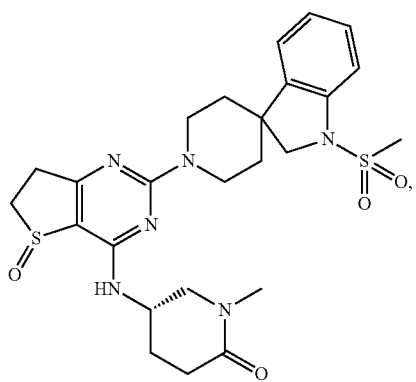
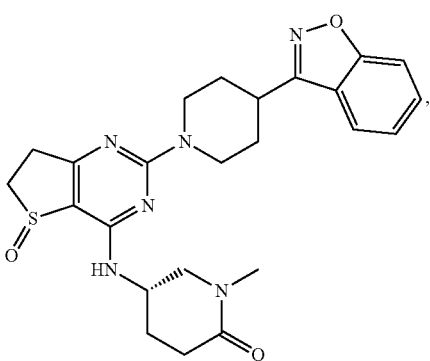
28
-continued
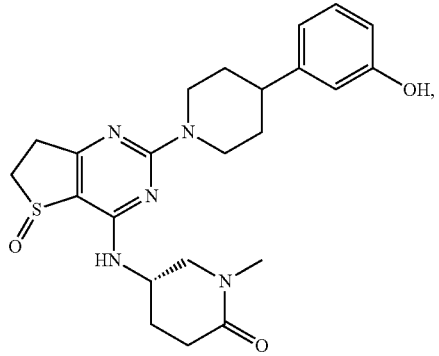
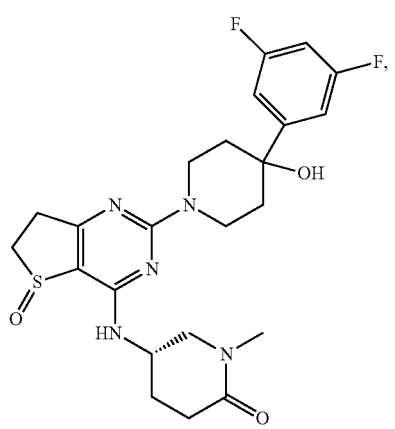
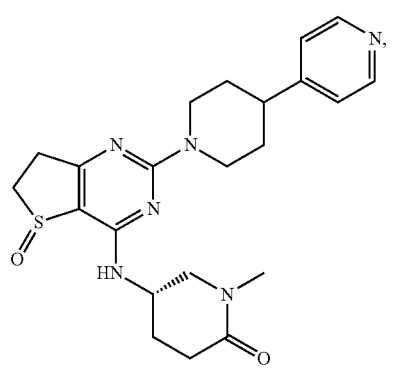
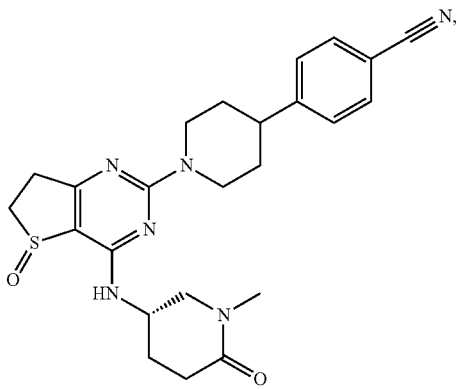

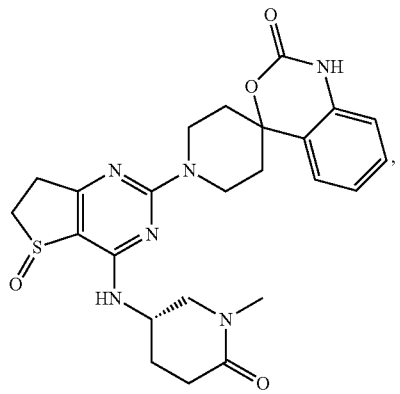
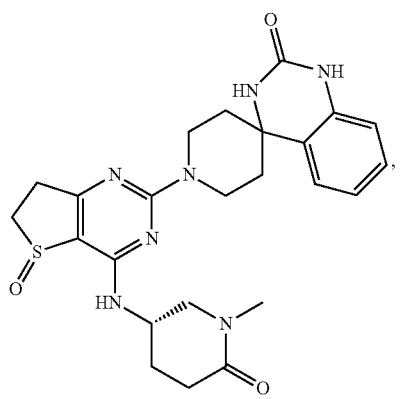
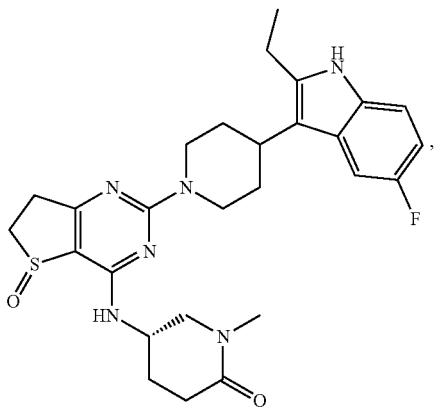
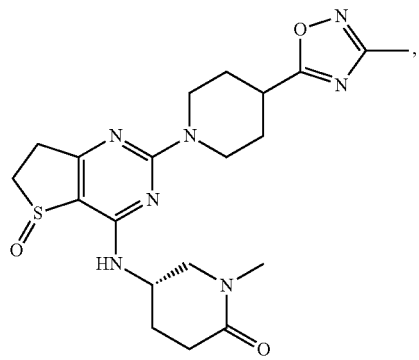
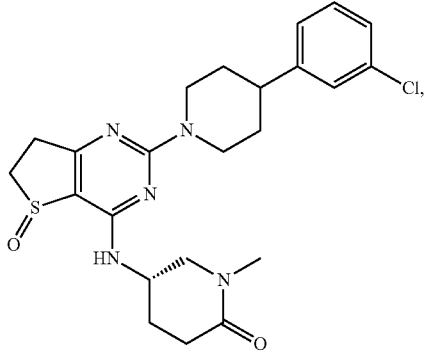
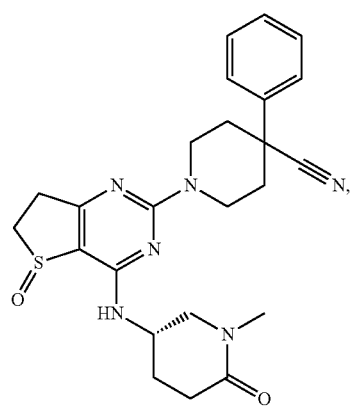
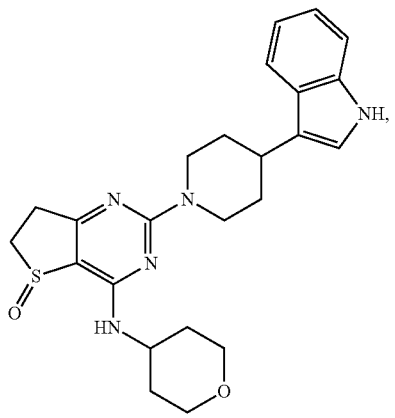
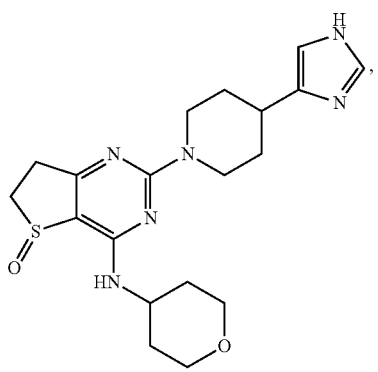

31
-continued
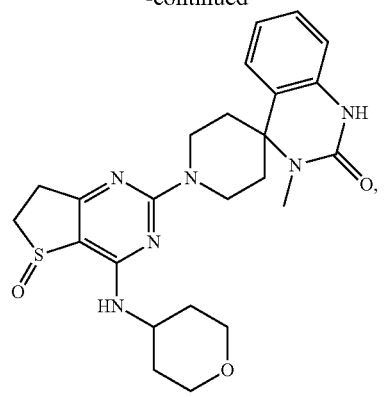
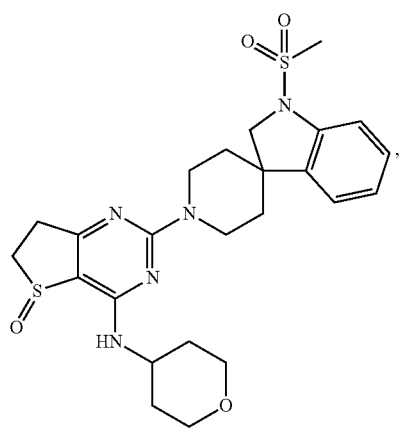
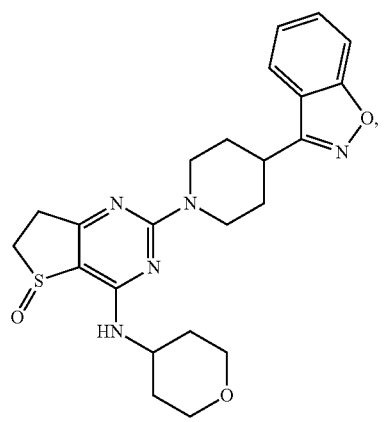
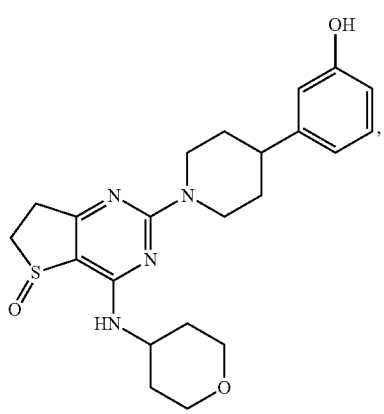
32
-continued
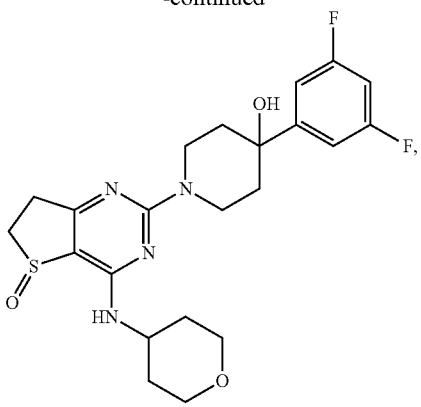
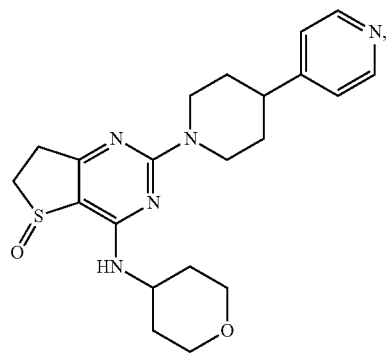
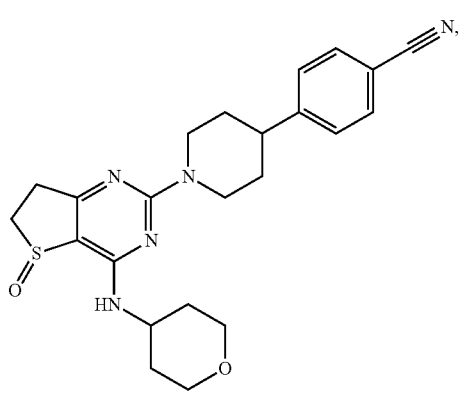
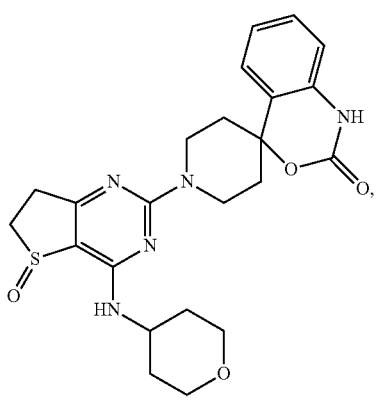

33
-continued
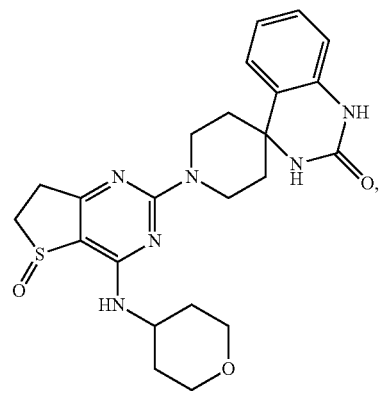
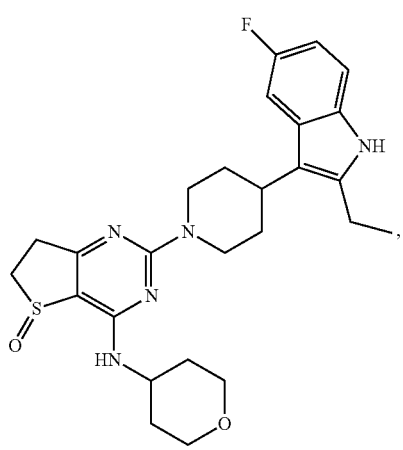
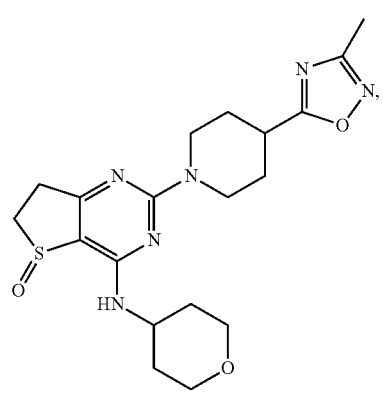
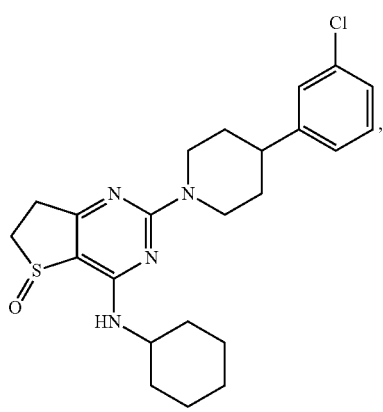
34
-continued
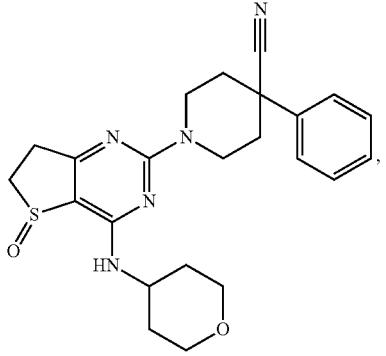
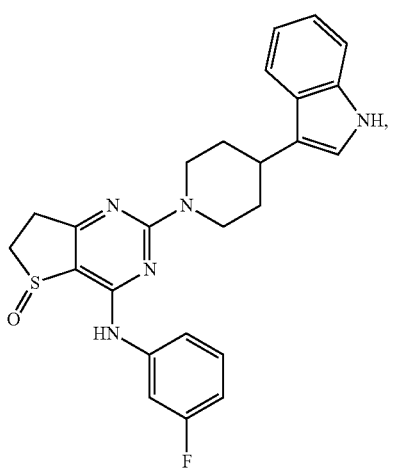
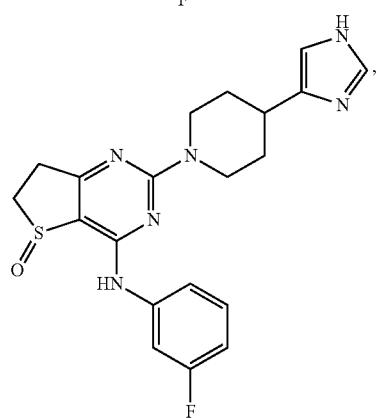
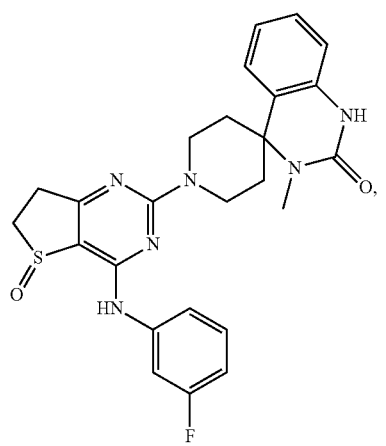

35
-continued
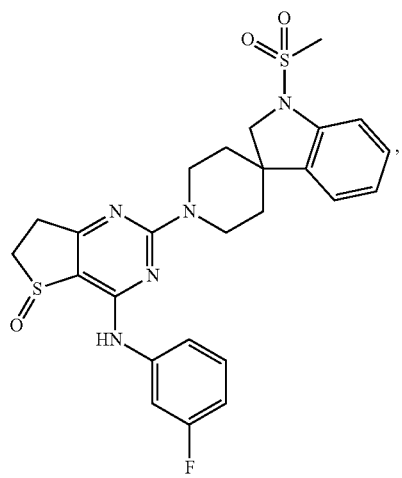
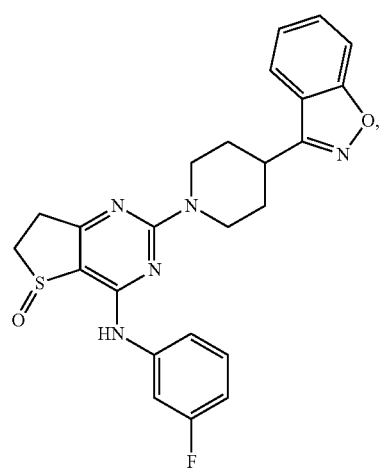
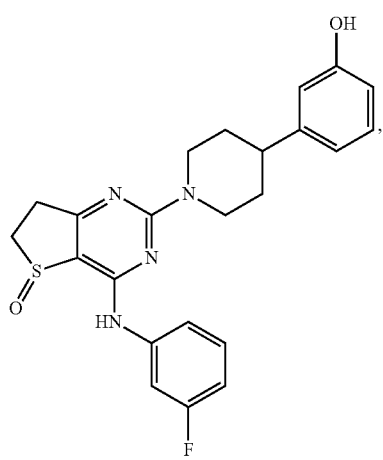
36
-continued
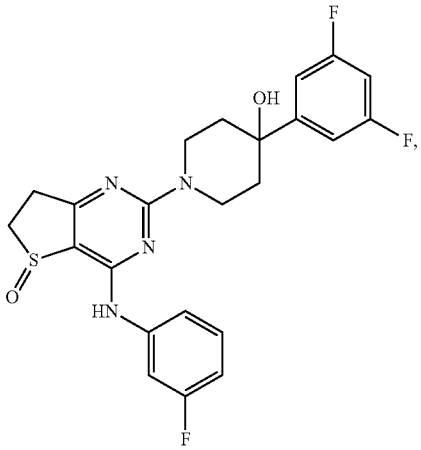
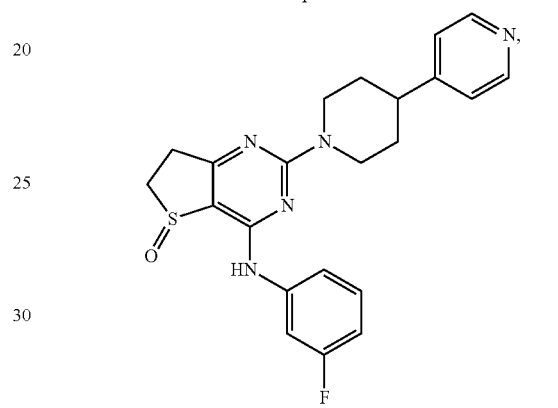
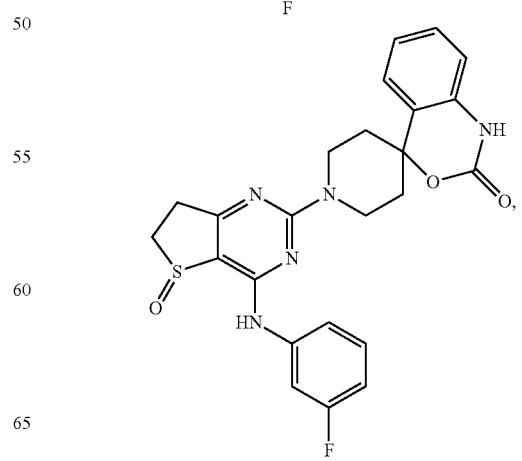

37
-continued
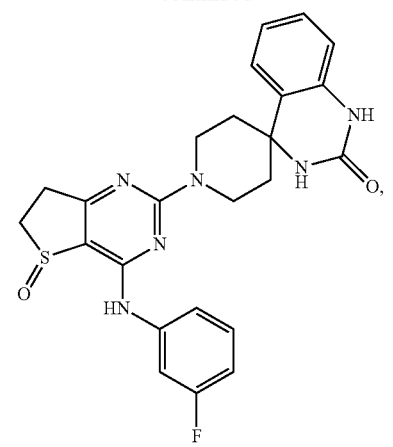
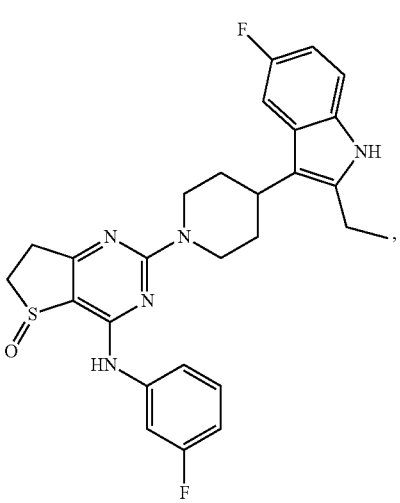
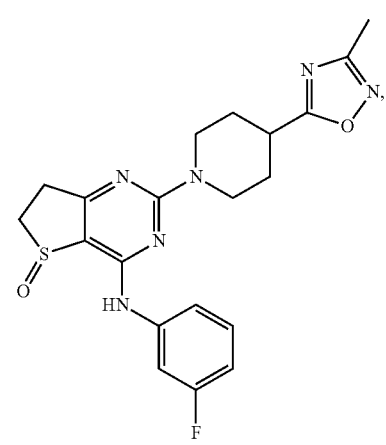
38
-continued
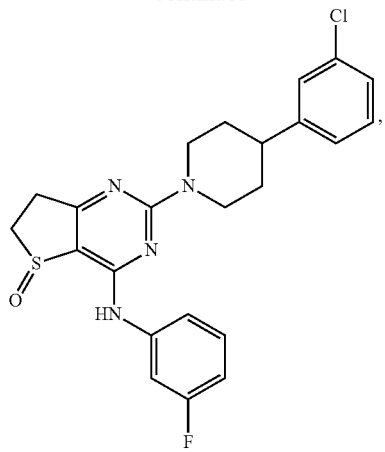
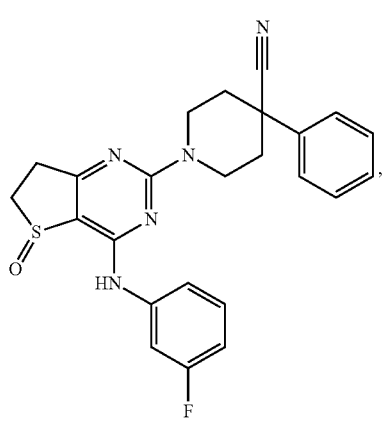
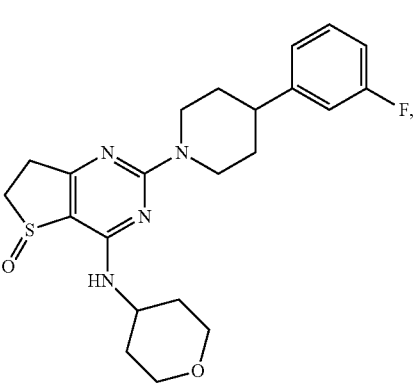
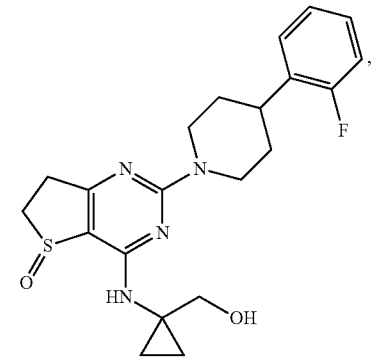

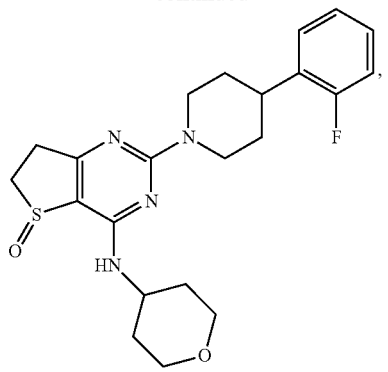
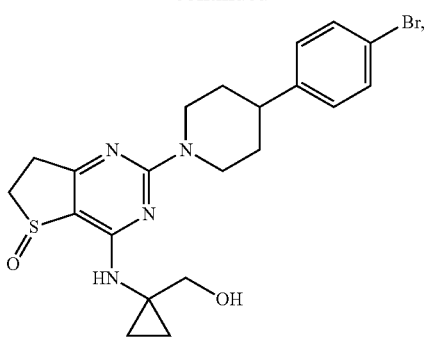
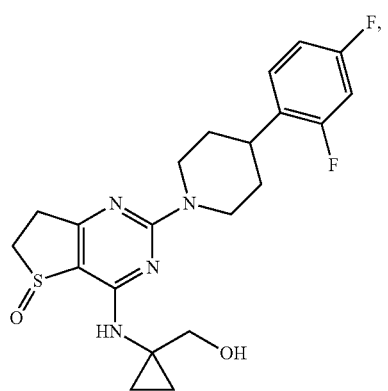
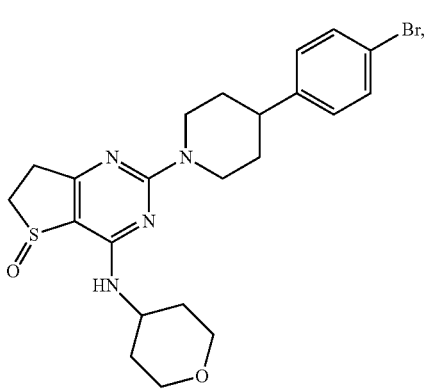
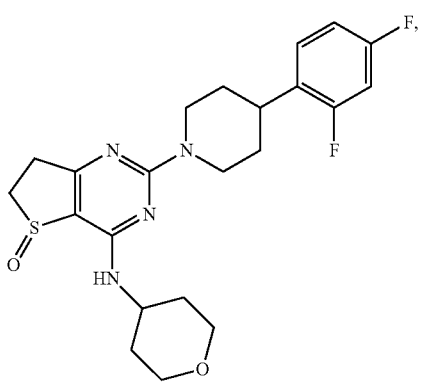
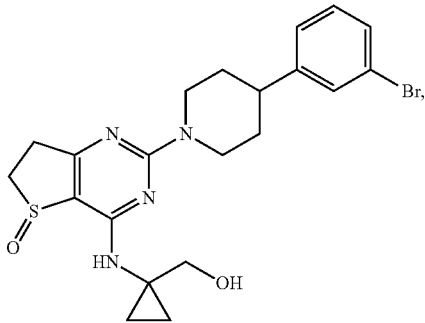
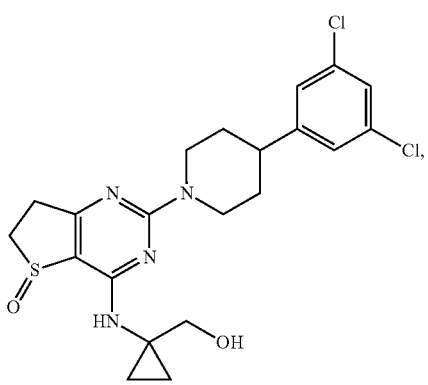
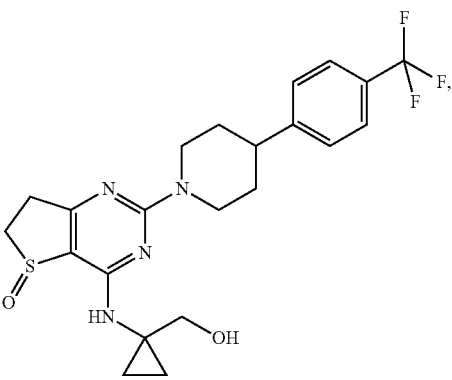

41
-continued
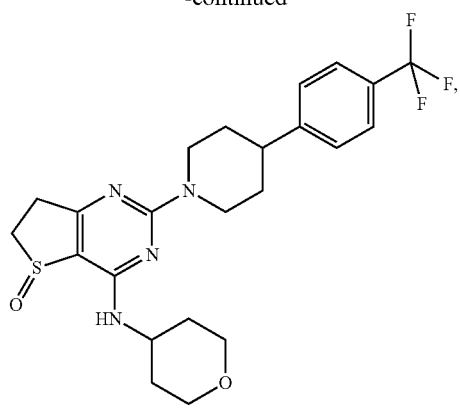
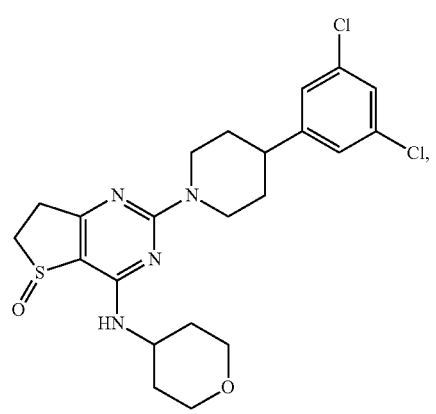
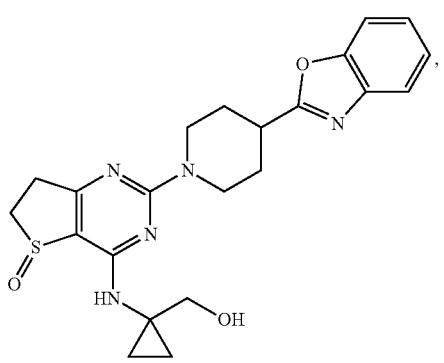
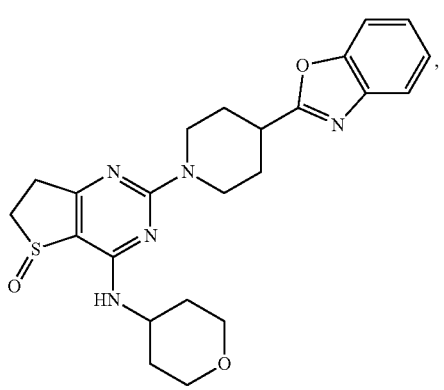
42
-continued
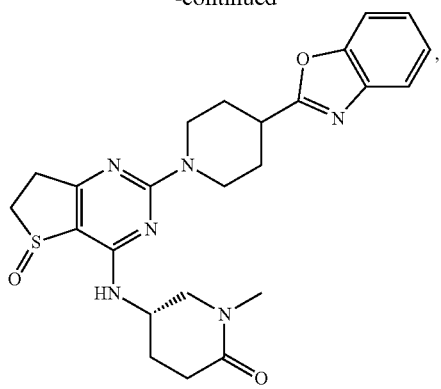
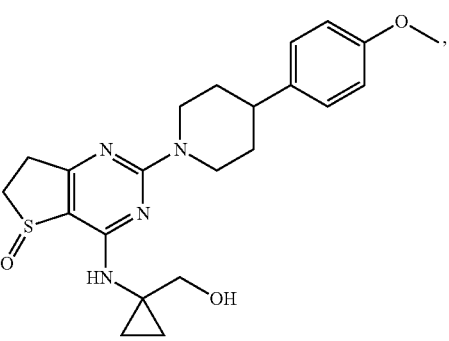
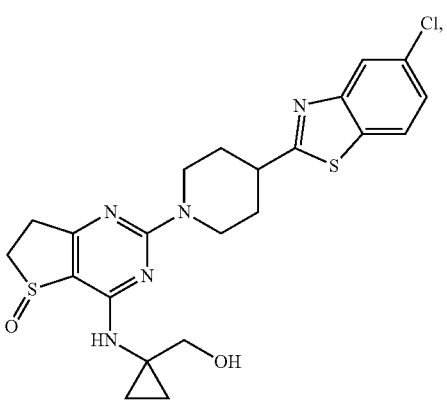
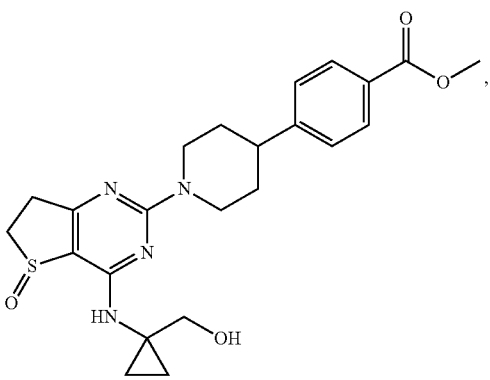

-continued
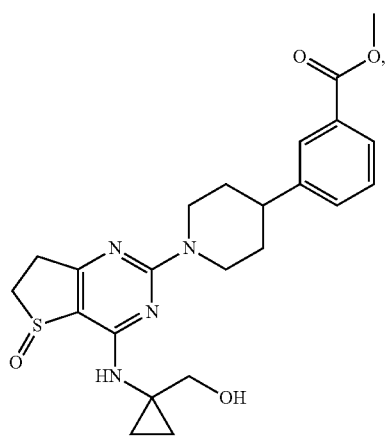
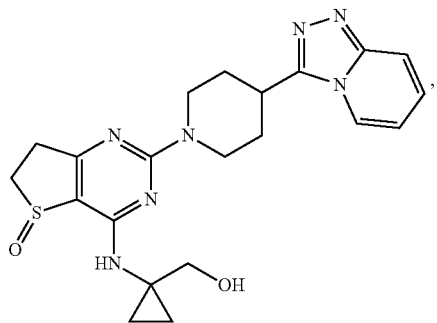
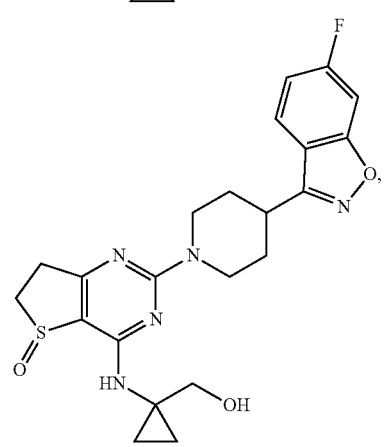
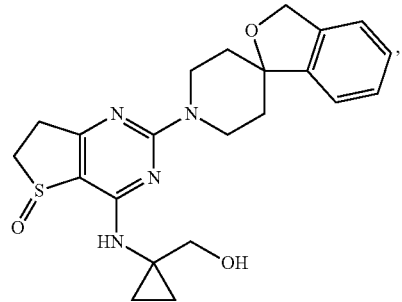
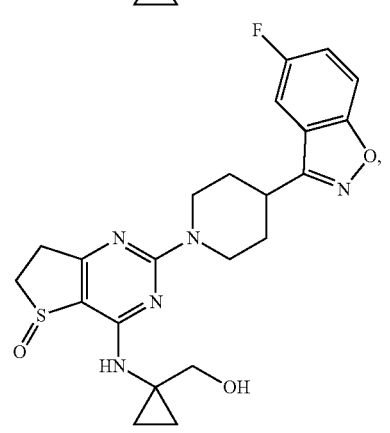
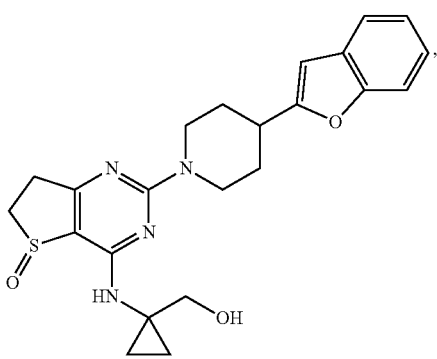
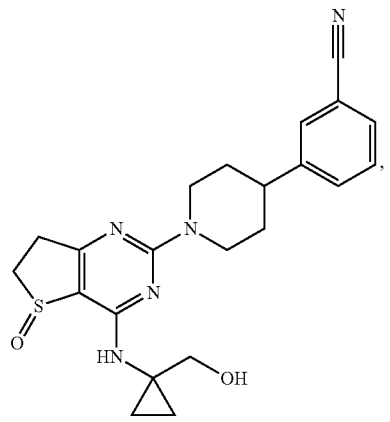
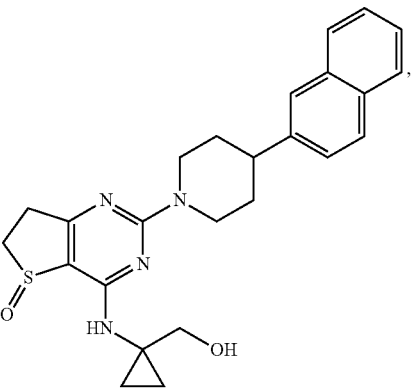

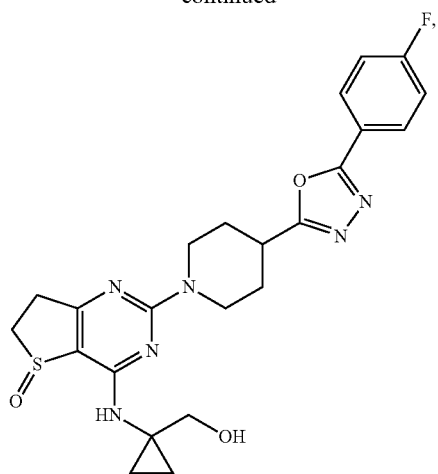
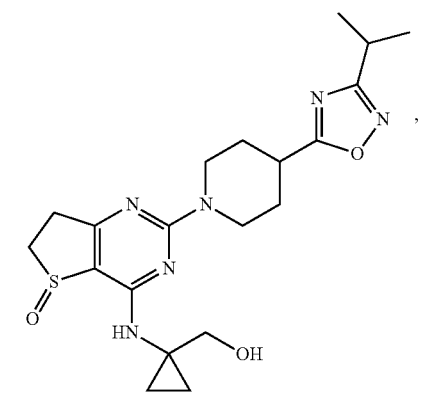
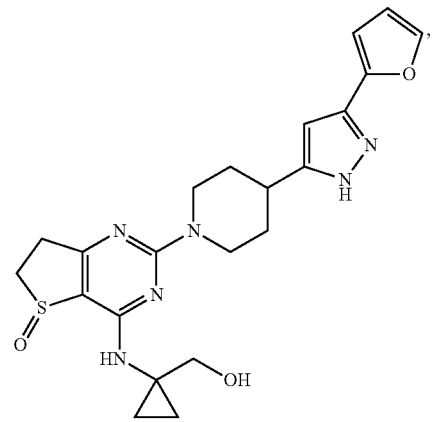
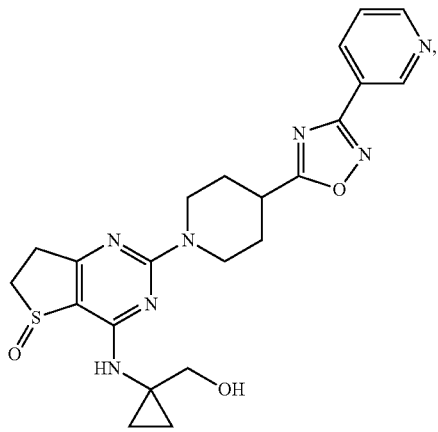
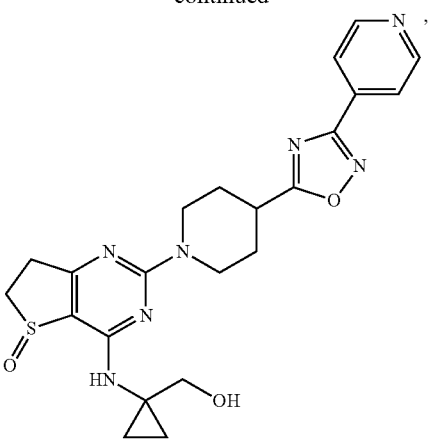
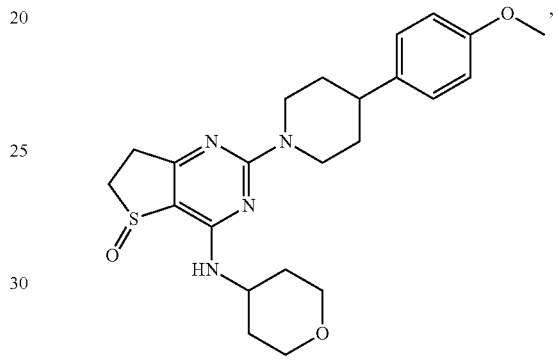
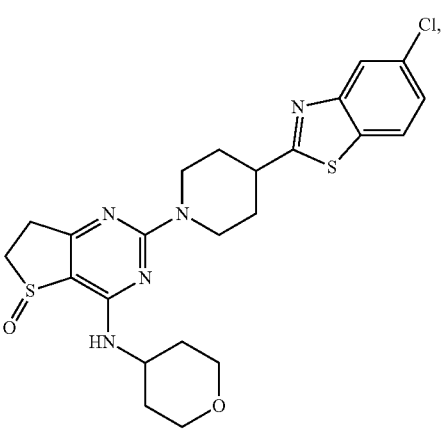
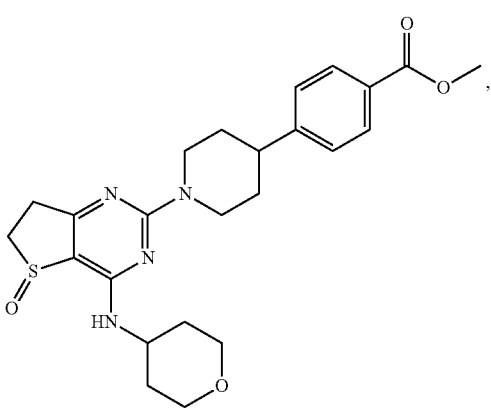

47
-continued
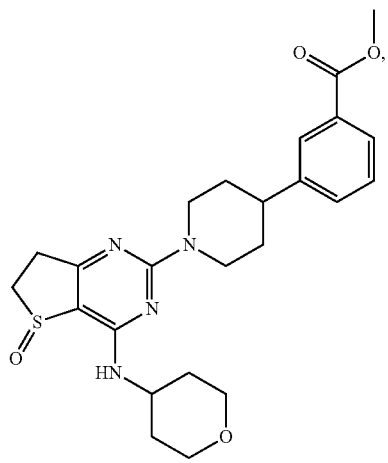
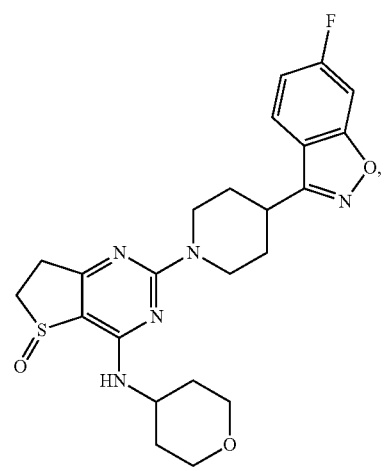
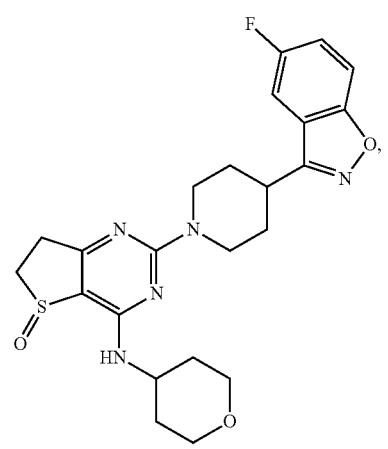
48
-continued
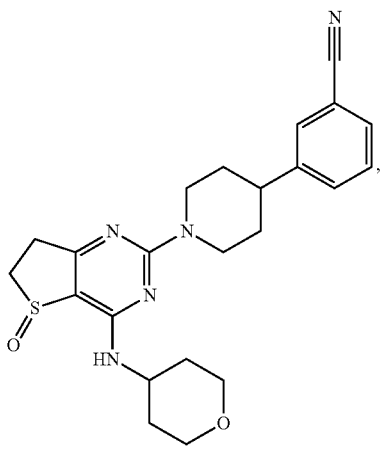
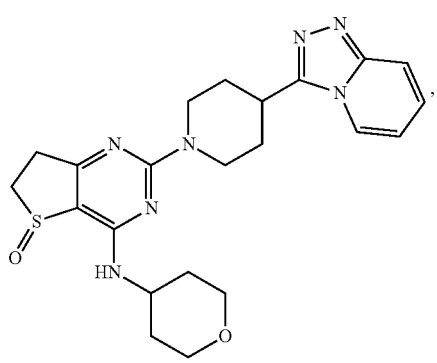
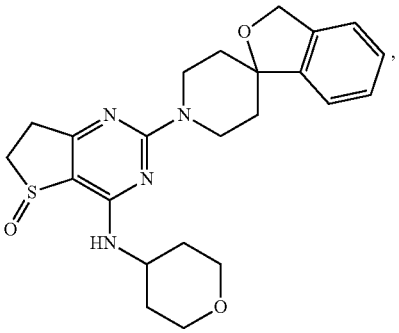
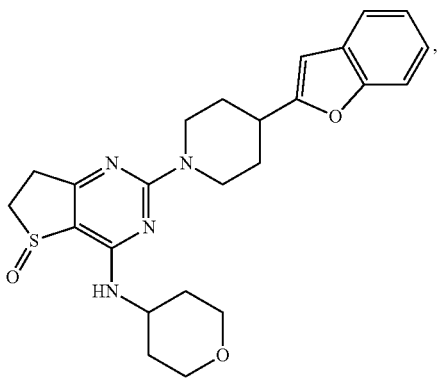

49
-continued
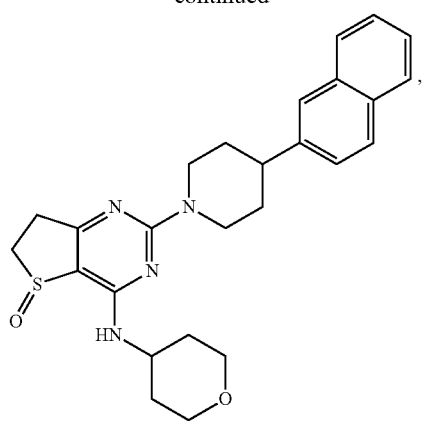
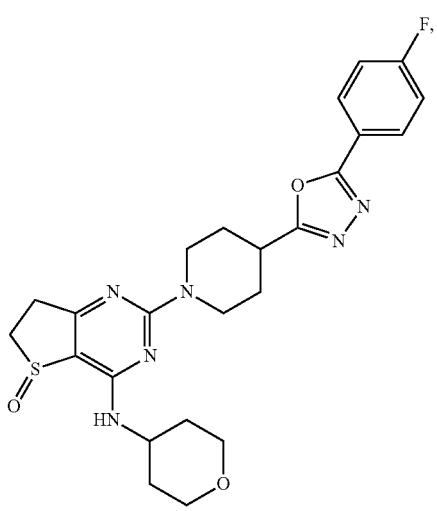
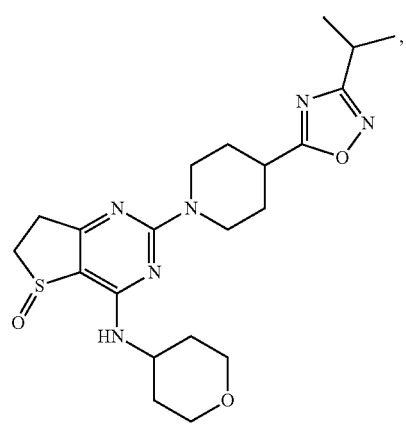
50
-continued
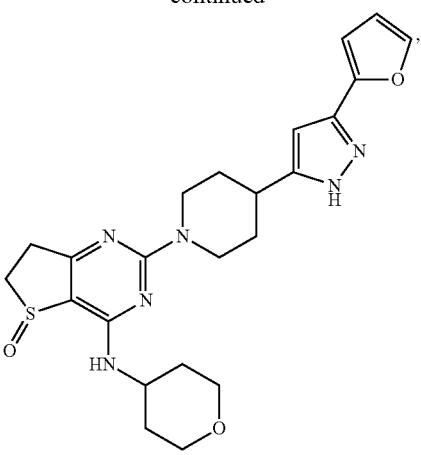
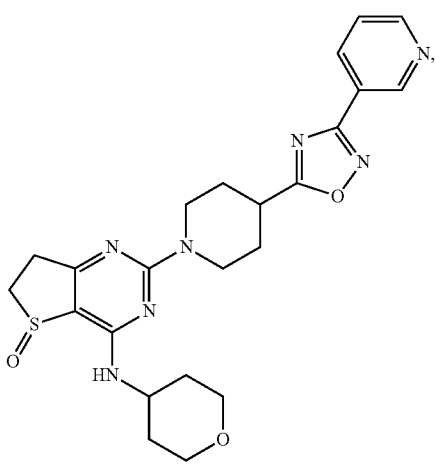
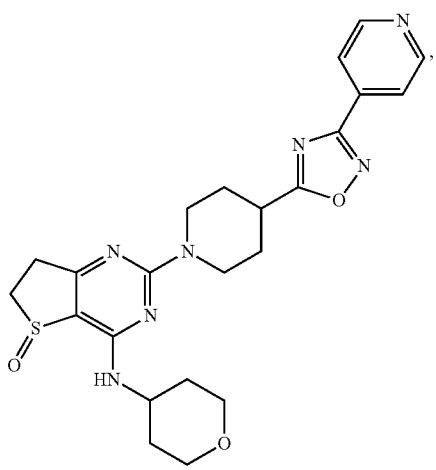

51
-continued
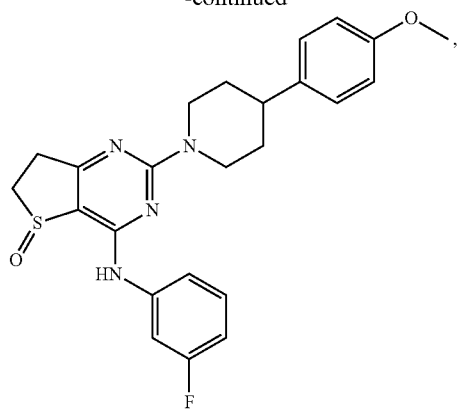
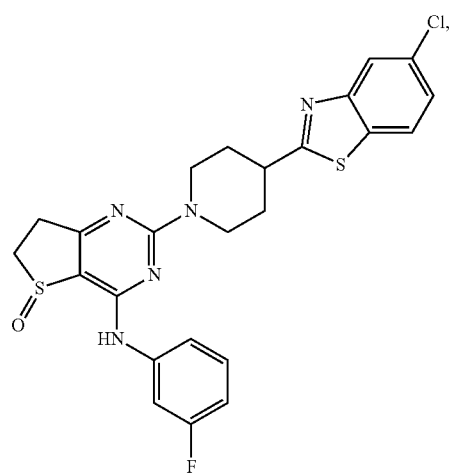
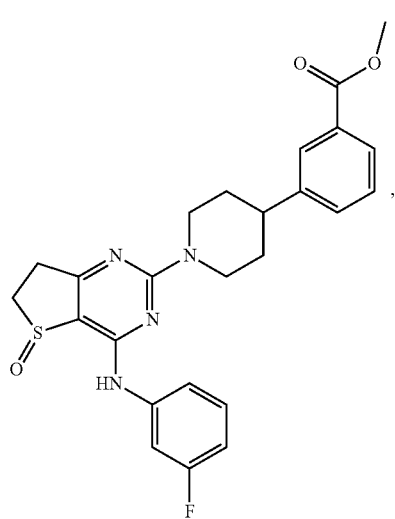
52
-continued
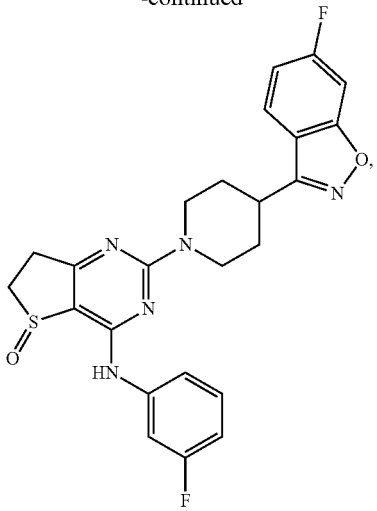
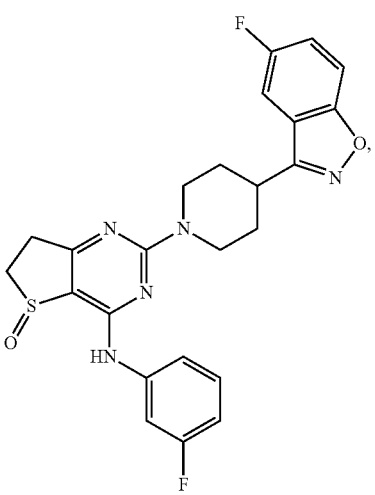
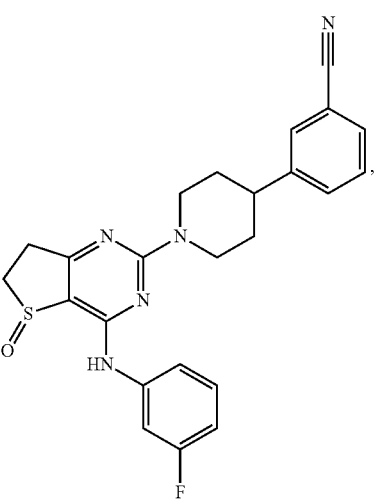

53
-continued
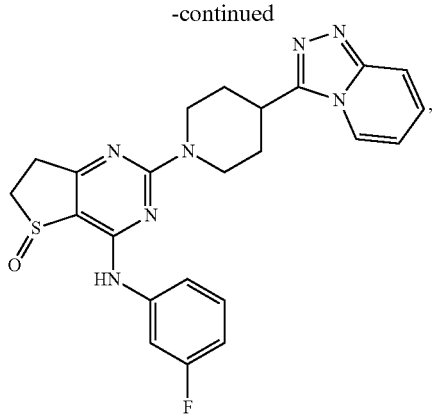
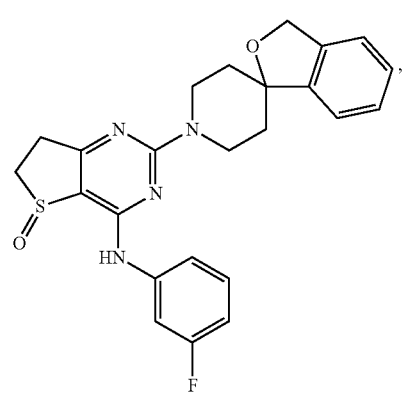
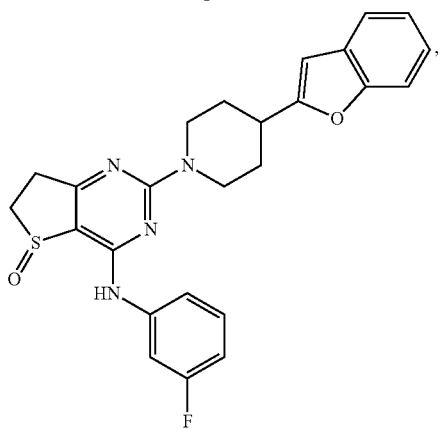
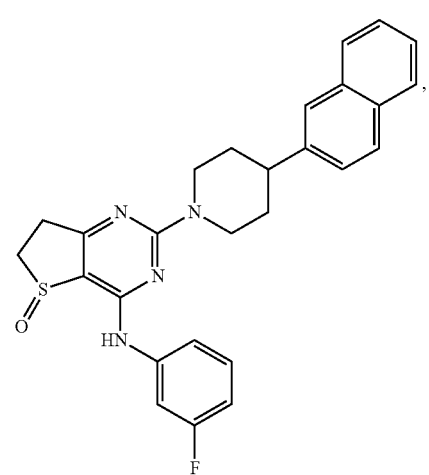
54
-continued
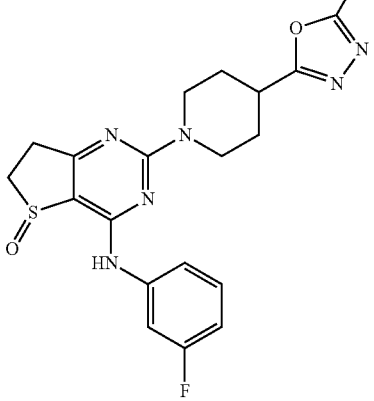
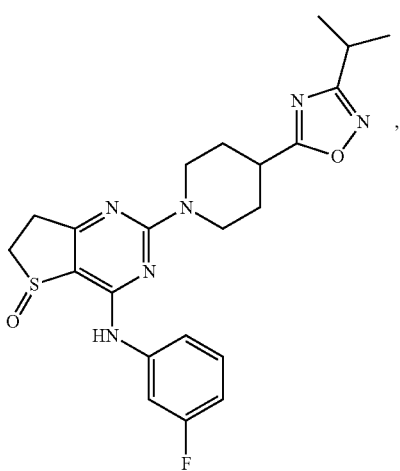
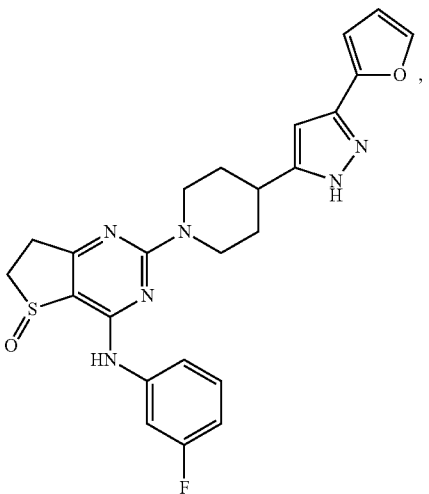

55
-continued
56
-continued
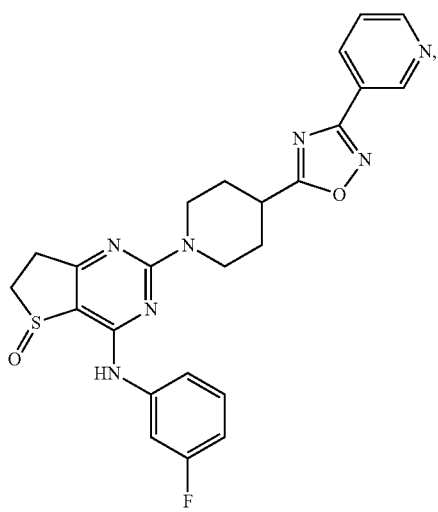
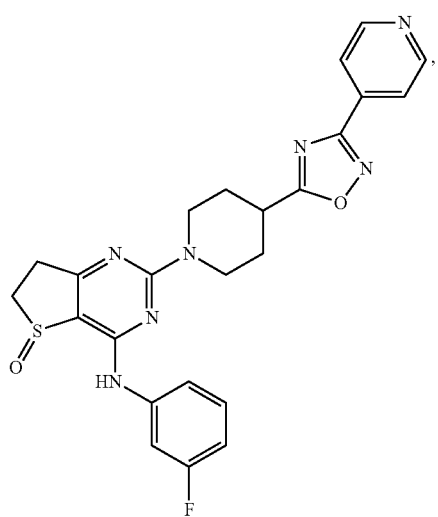
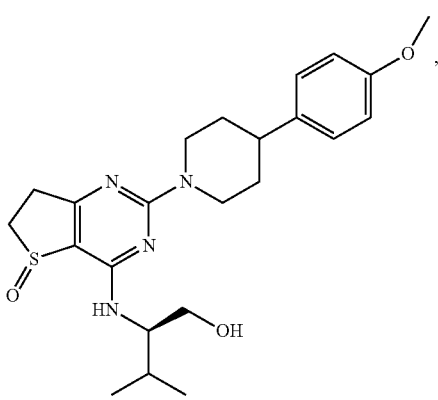
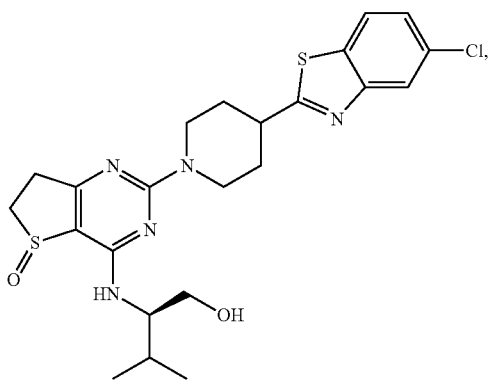
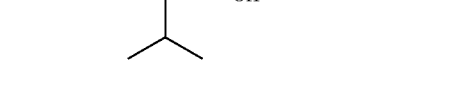
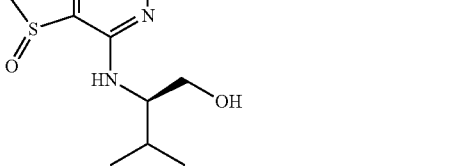
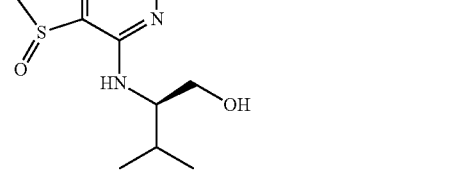

57
-continued
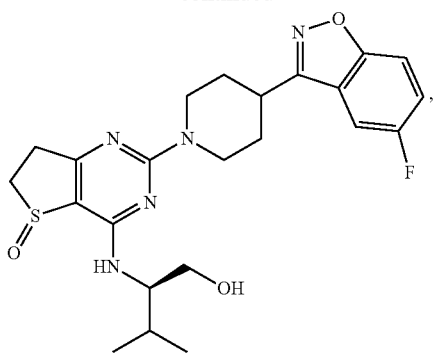
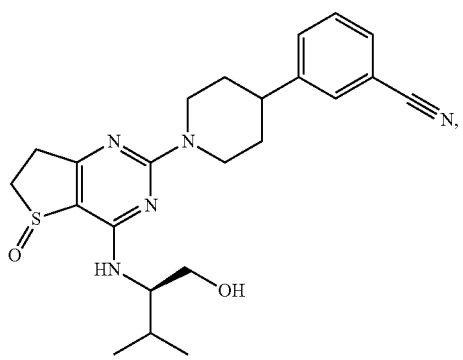
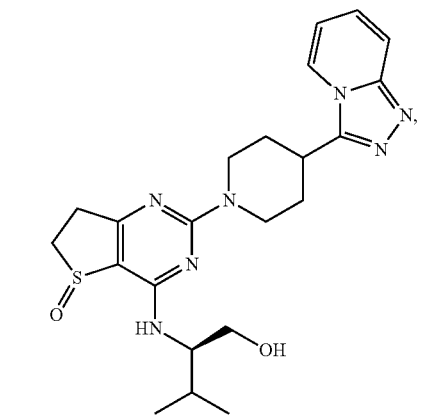
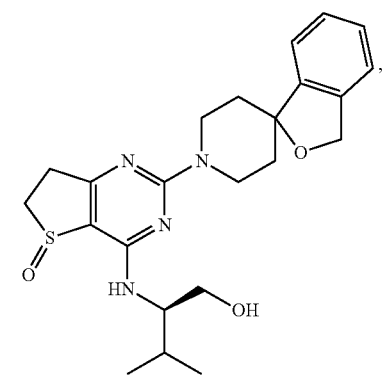
58
-continued
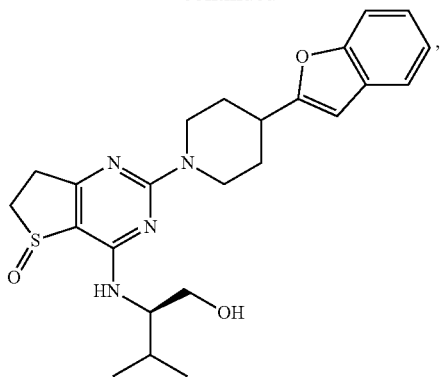
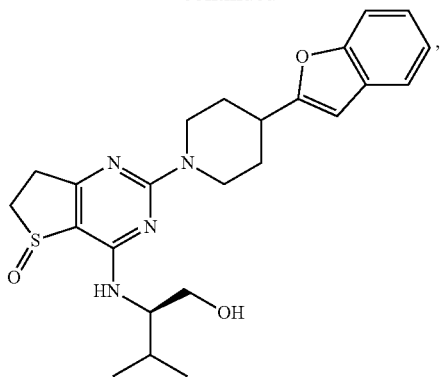
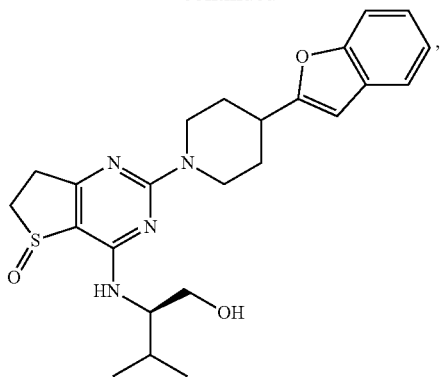
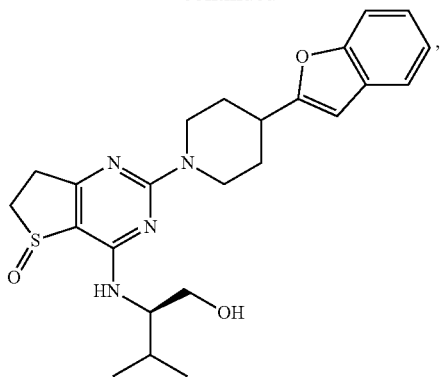

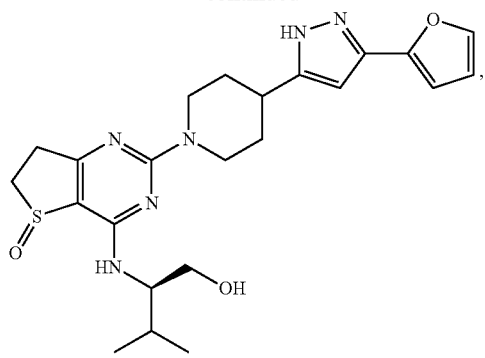
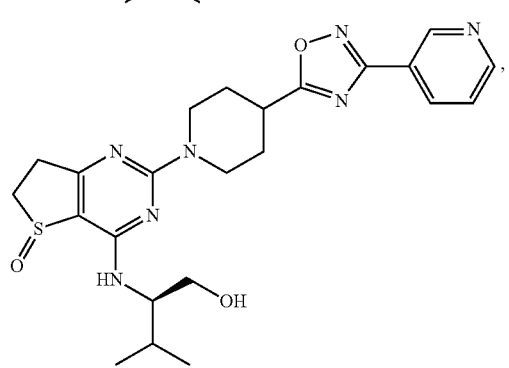
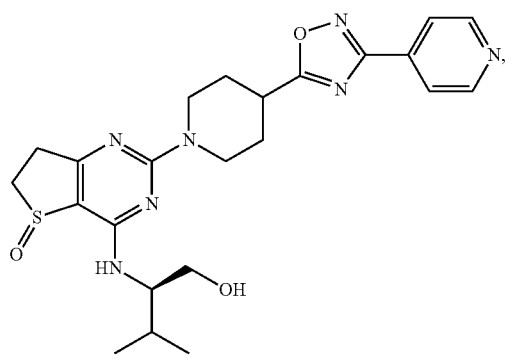
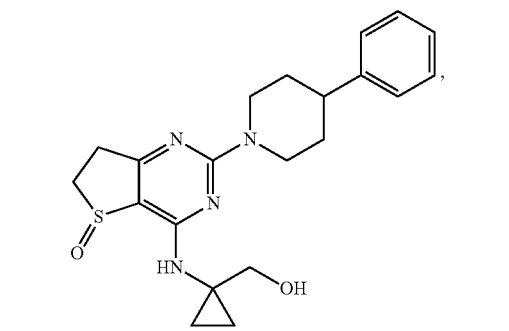
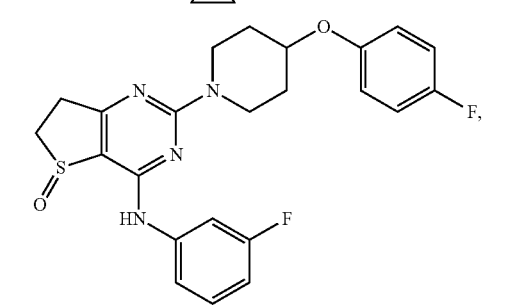
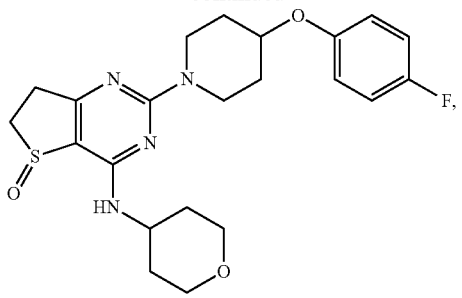
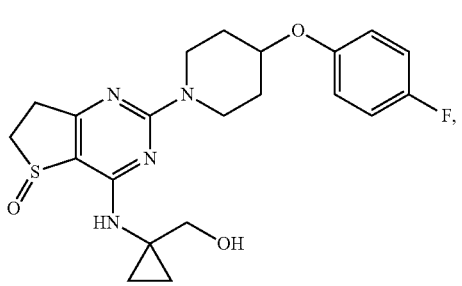
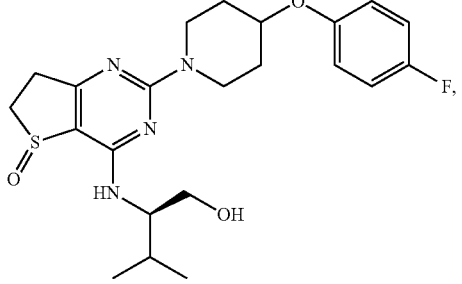
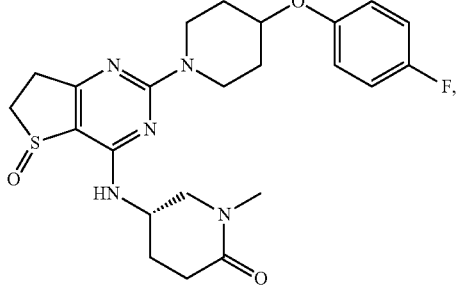
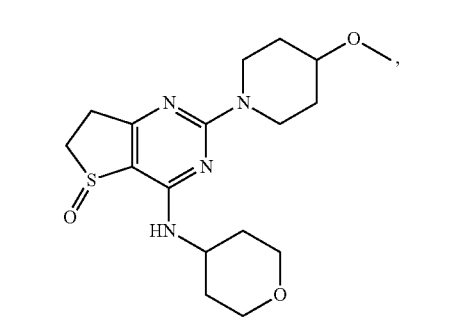

61
-continued
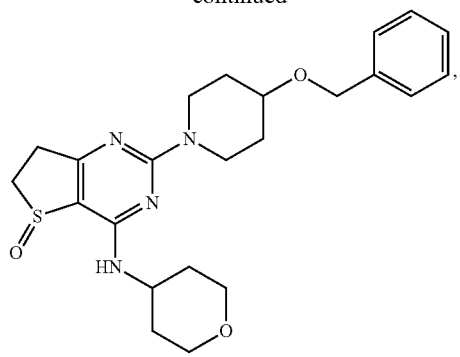
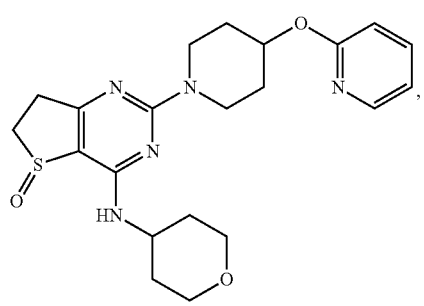
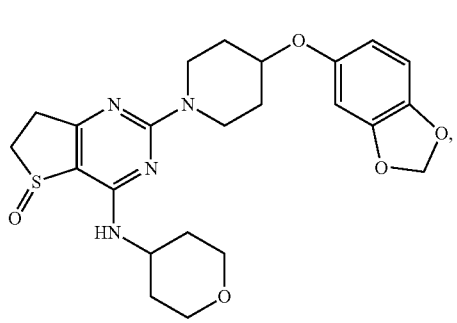
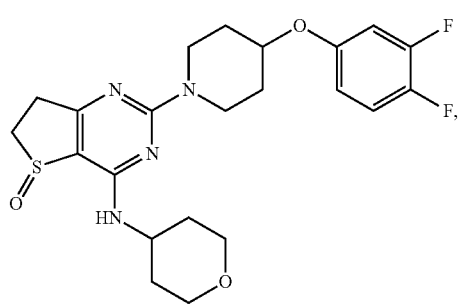
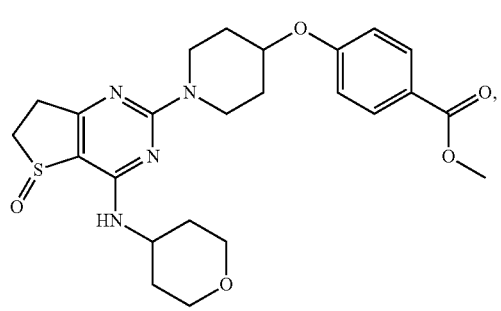
62
-continued
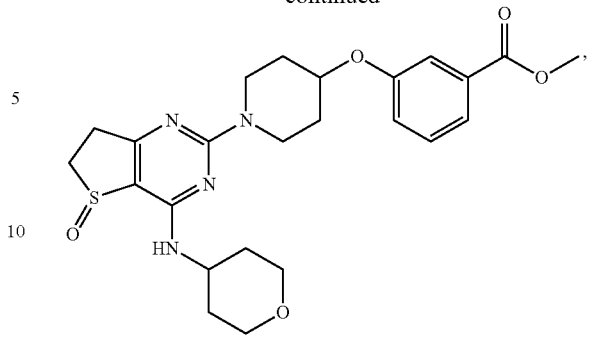
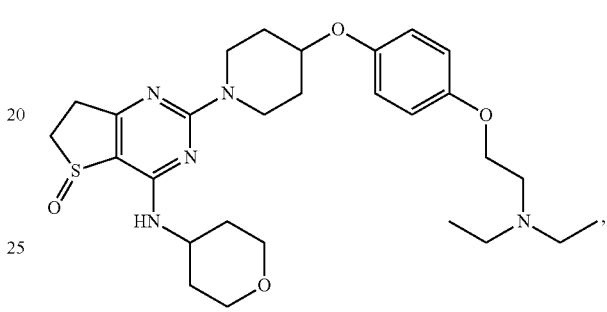
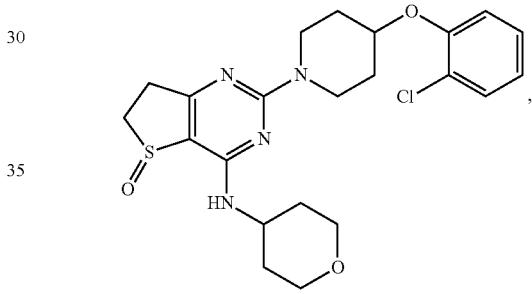
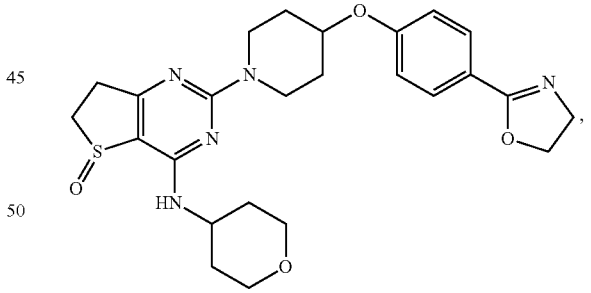
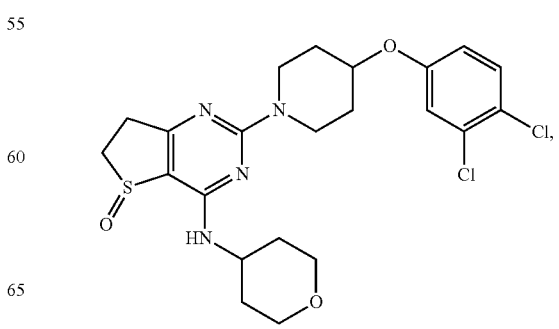

63
-continued
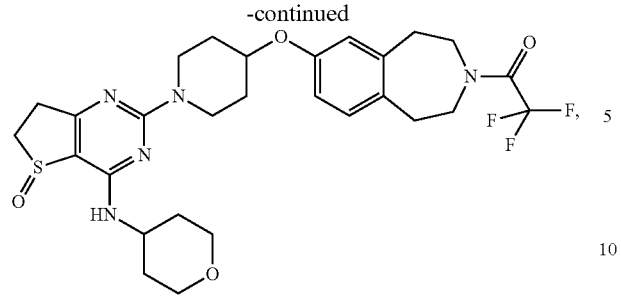
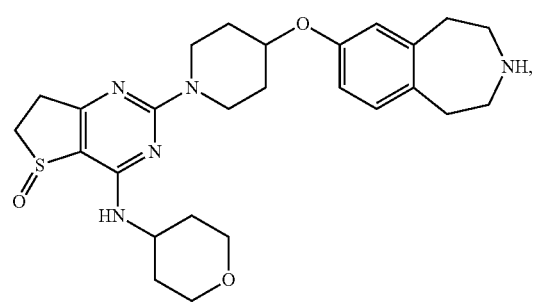
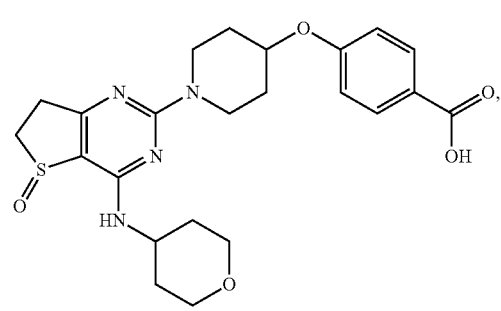
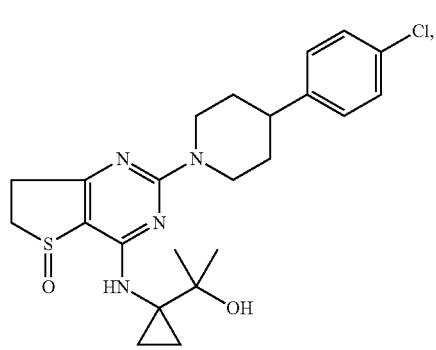
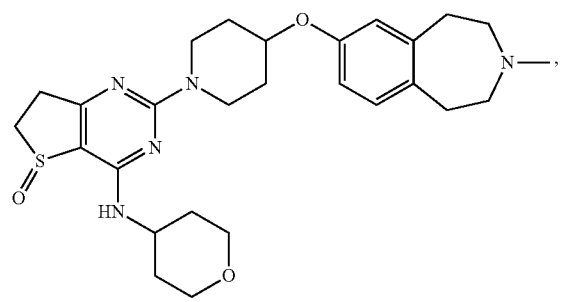
64
-continued
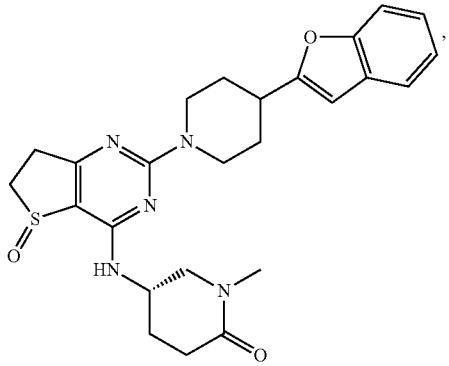
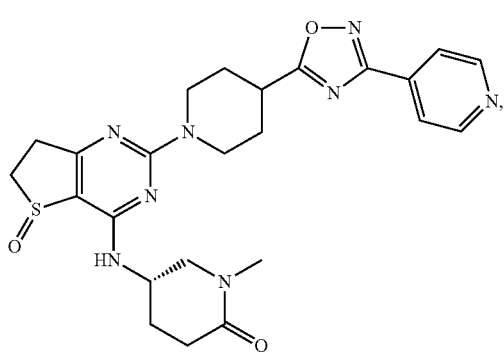
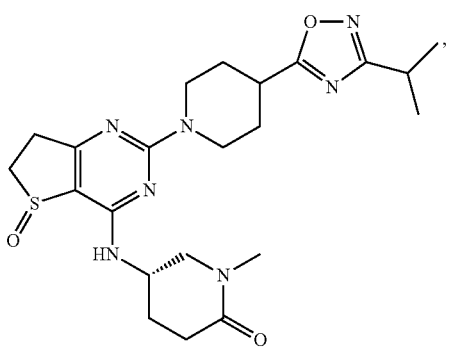
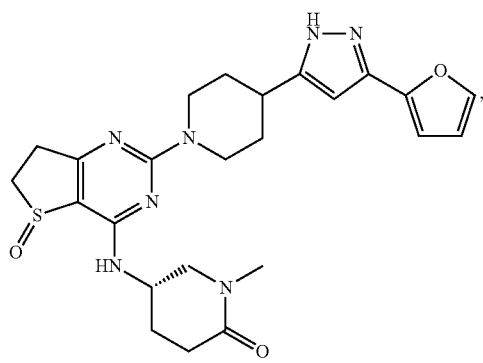

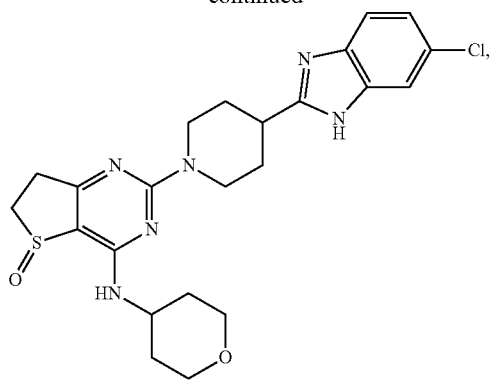
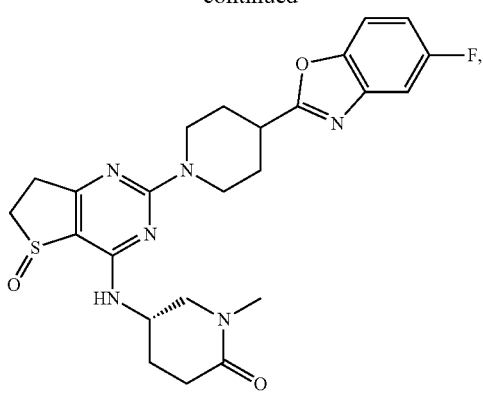
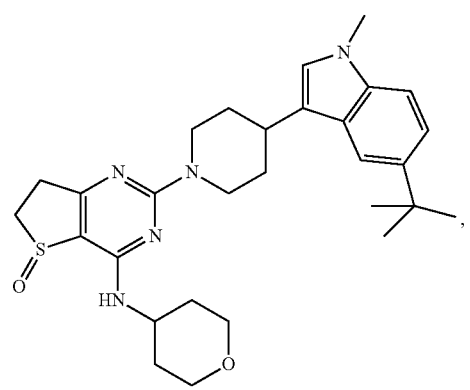
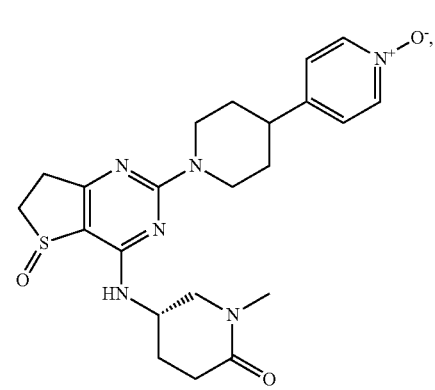
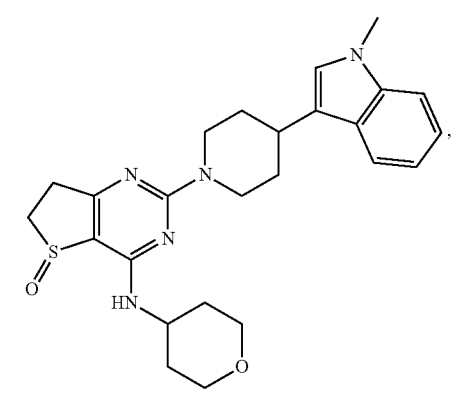
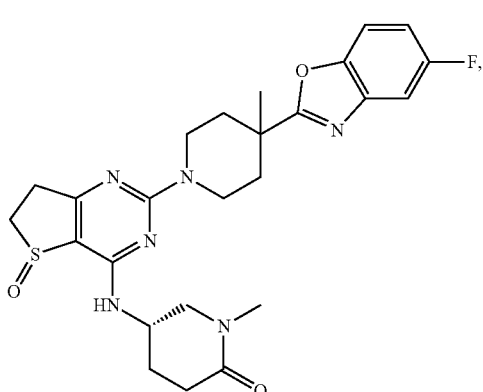
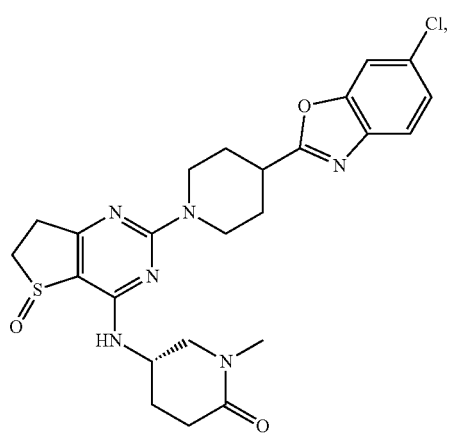
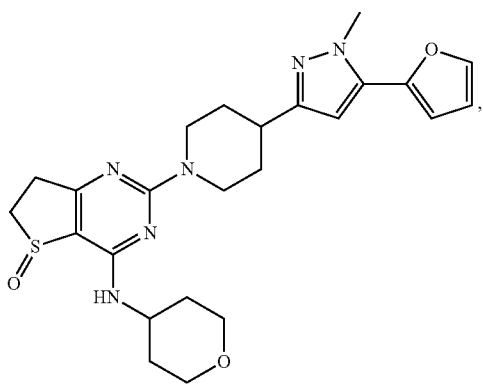

67
-continued
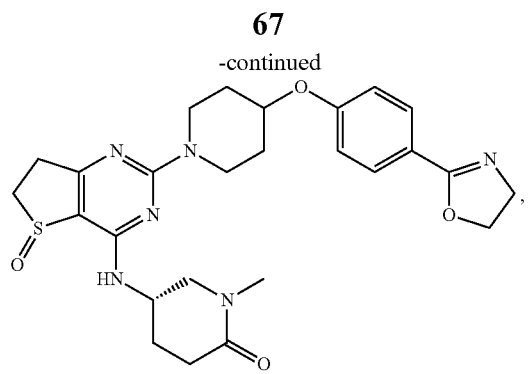
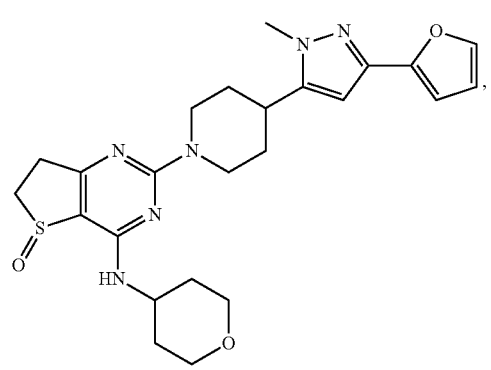
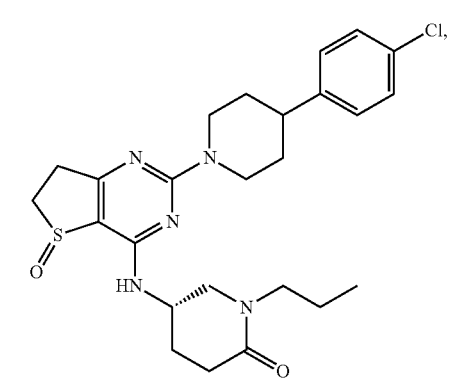
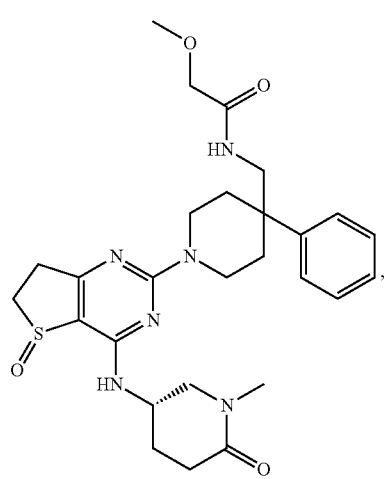
68
-continued
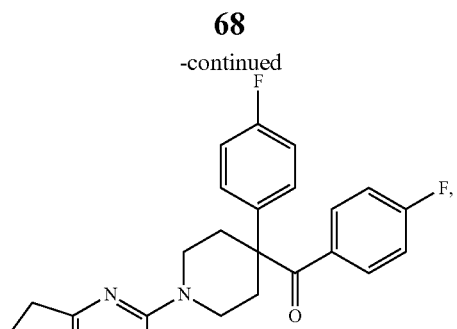
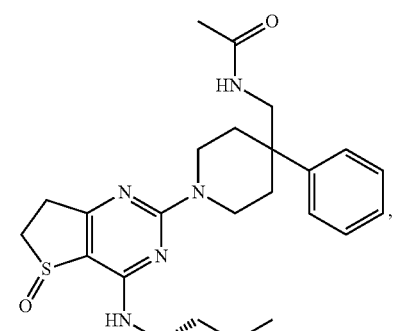
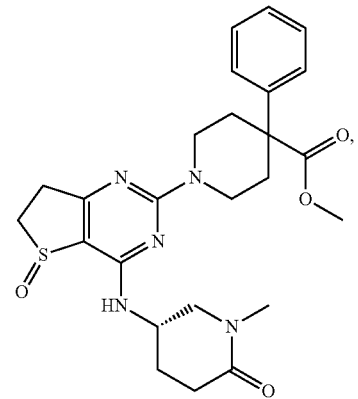
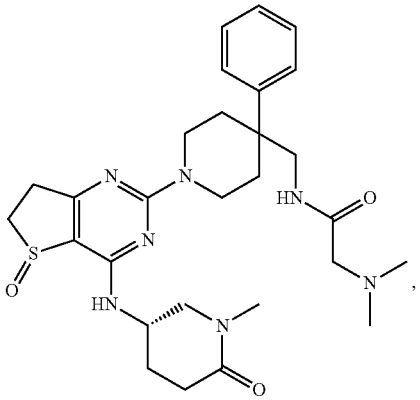

69
-continued
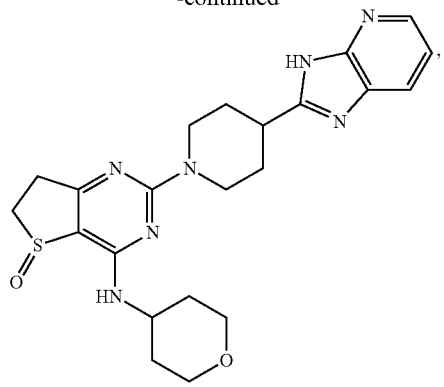
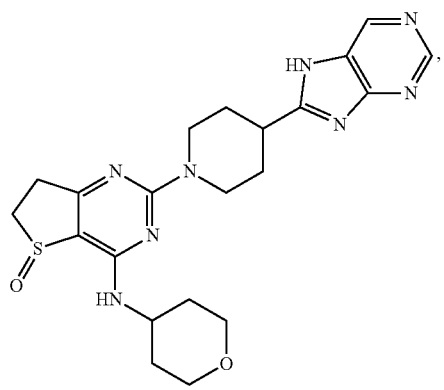
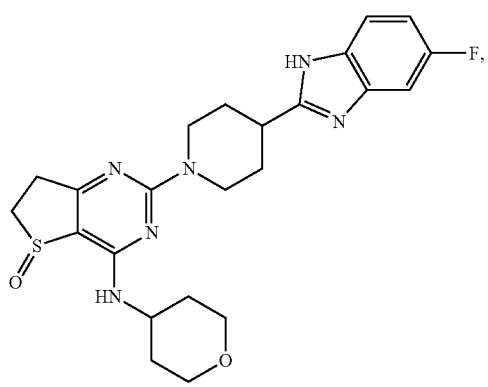
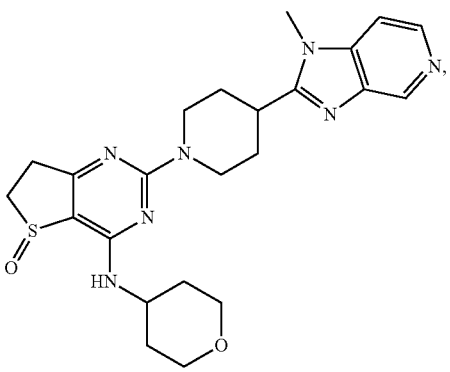
70
-continued
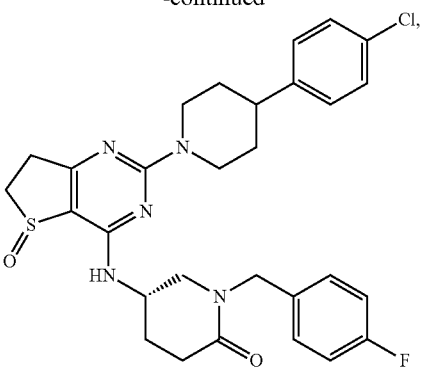
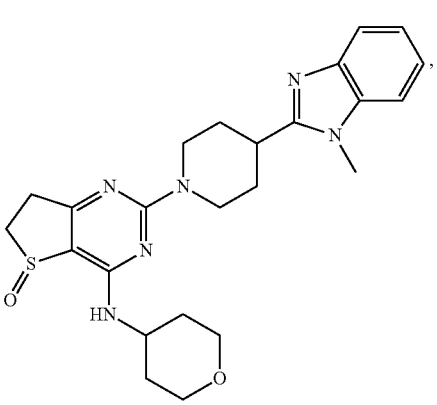
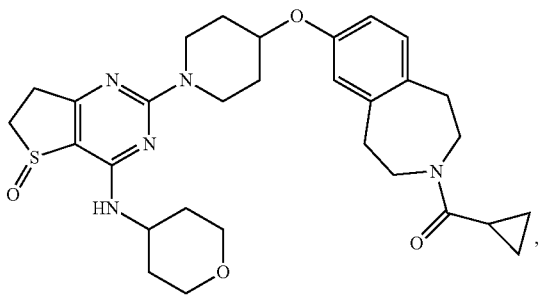
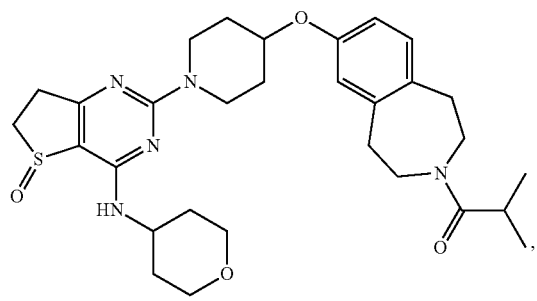

71
-continued
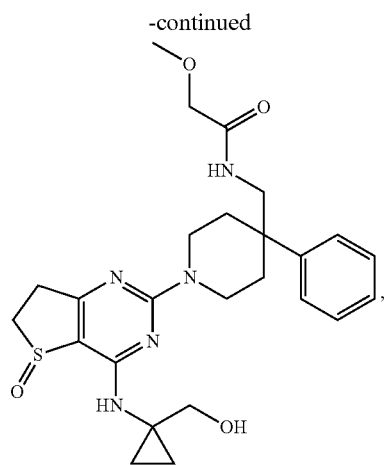
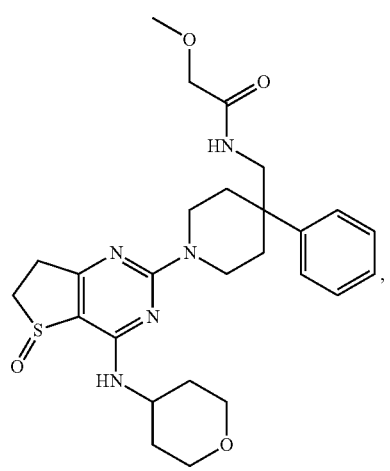
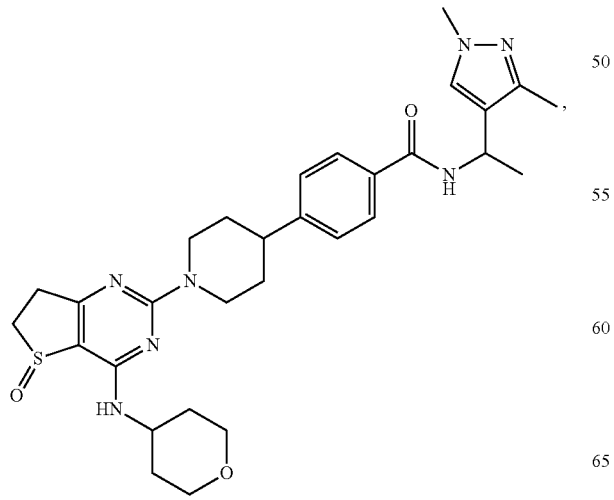
72
-continued
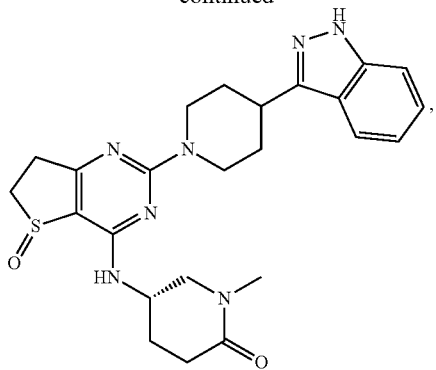
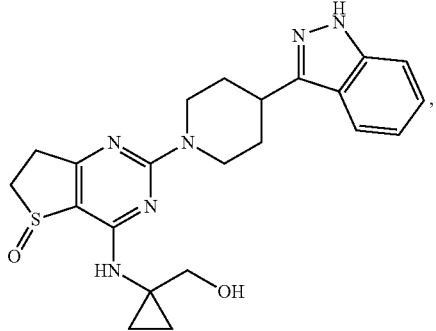
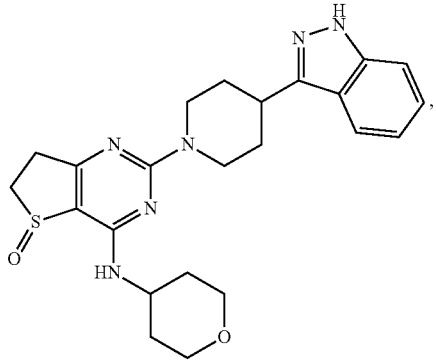
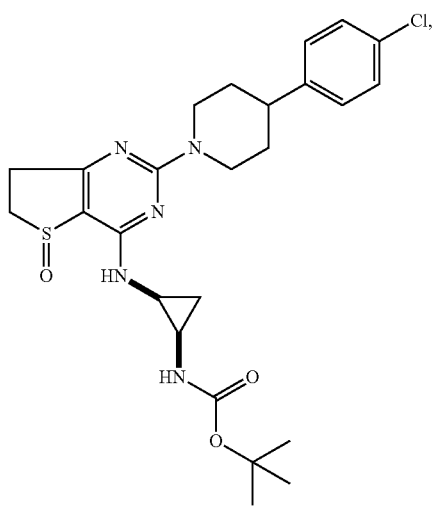

73
-continued
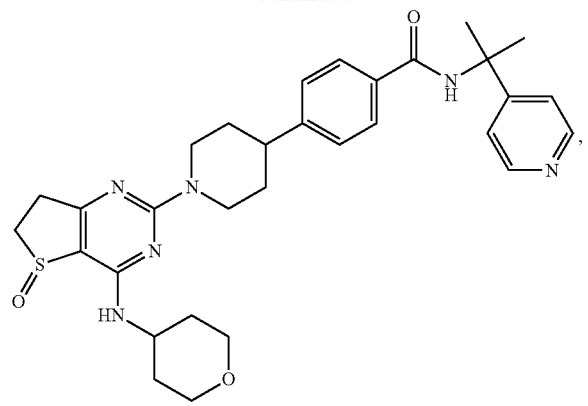
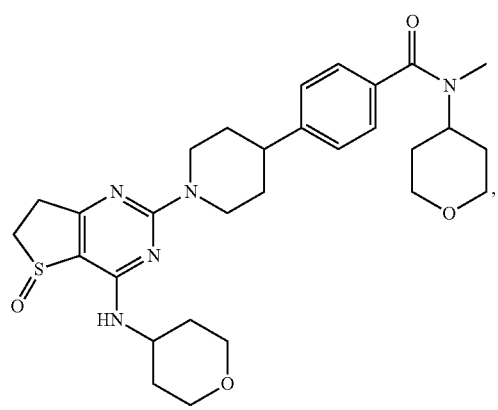
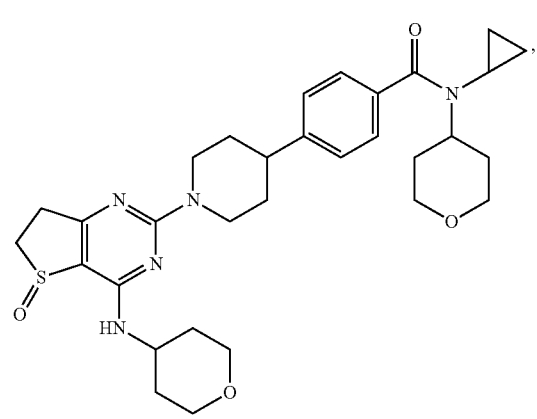
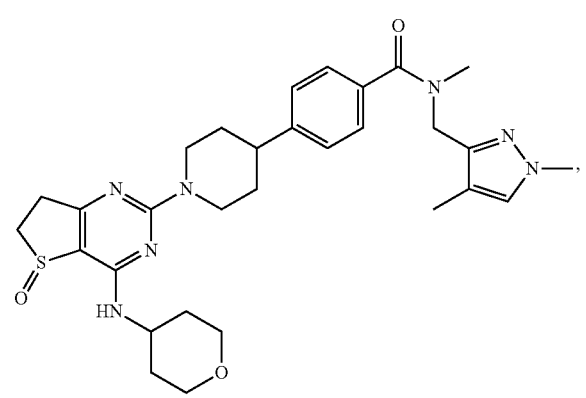 [SMILES: Cc1cn(C)nc1CN(C)C(=O)c1ccc(C2CCN(c3nc4c(c(NC5CCOCC5)n3)S(=O)CC4)CC2)cc1 ; ","]
74
-continued
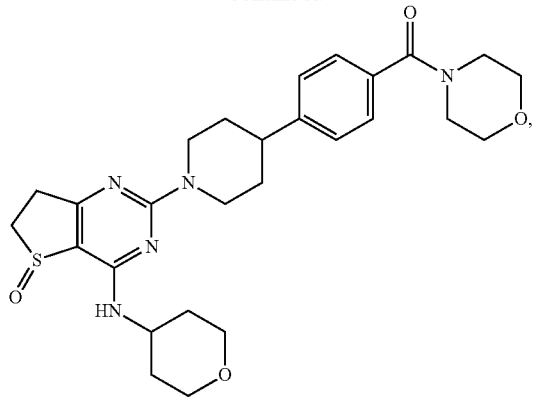
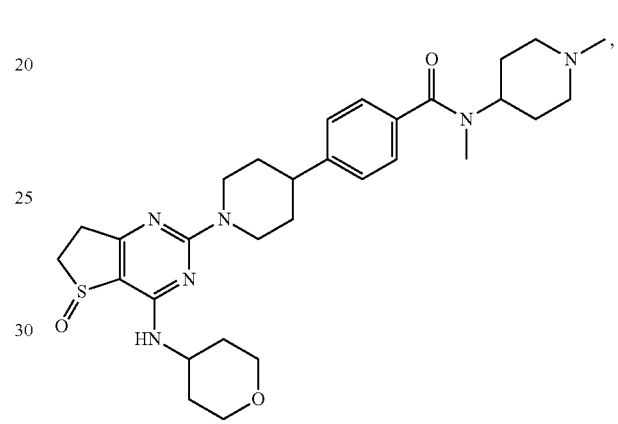
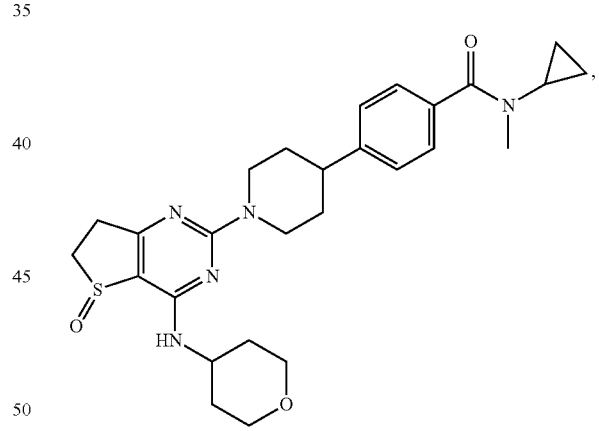
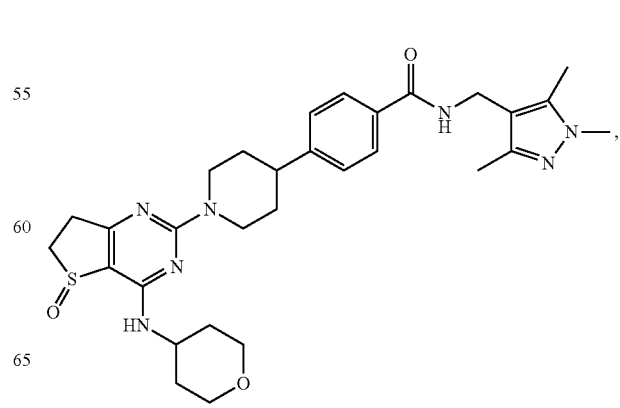

75
-continued
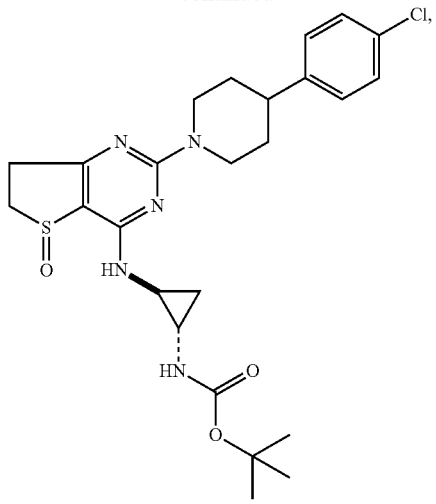
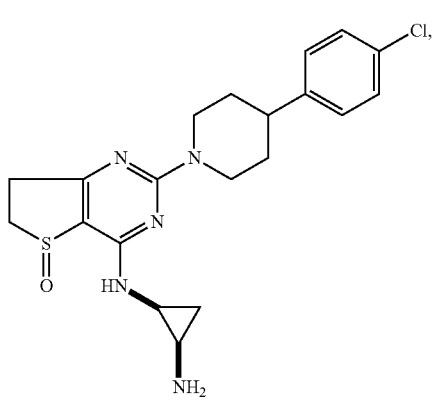
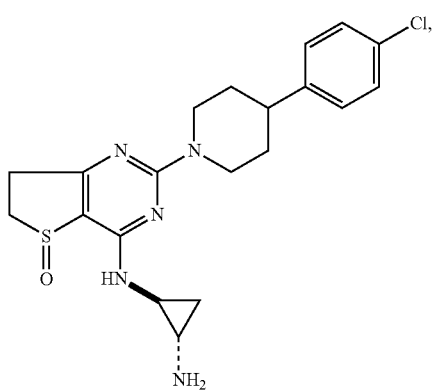
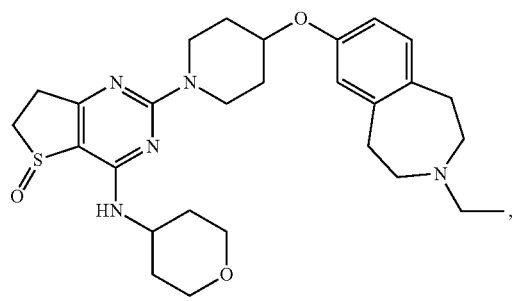
76
-continued
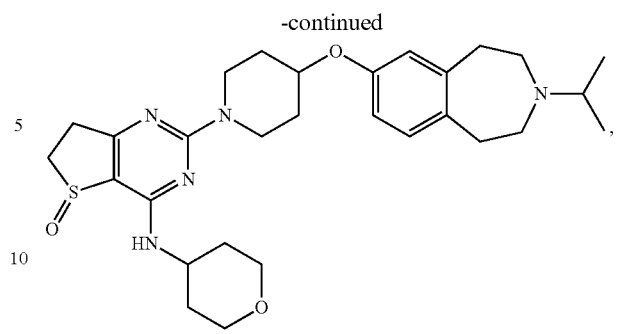
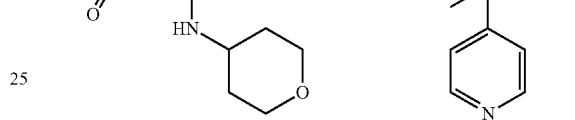
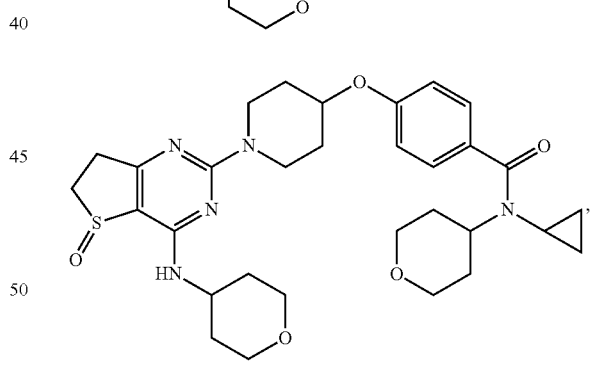
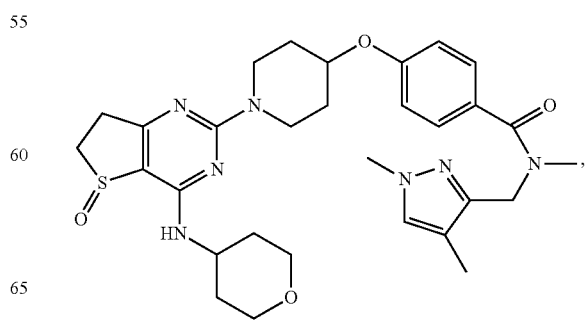

77
-continued
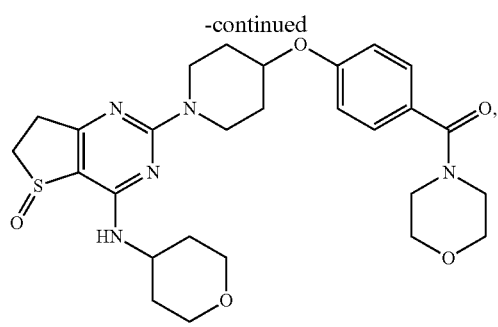
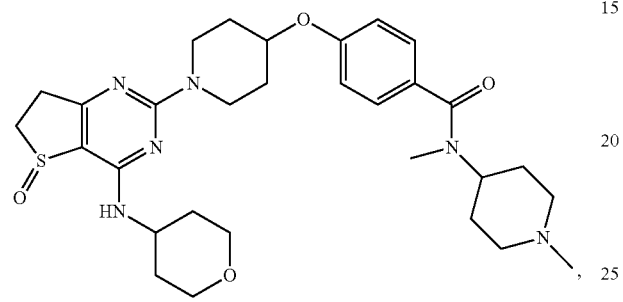
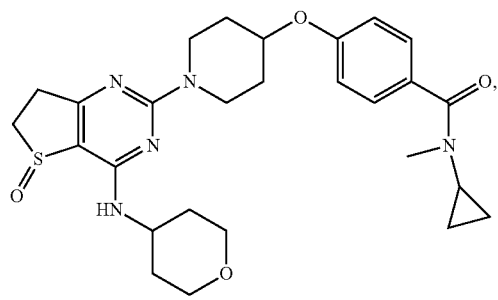
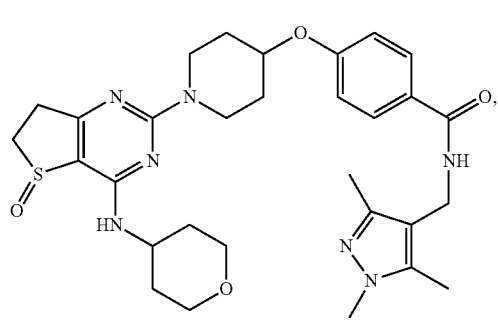
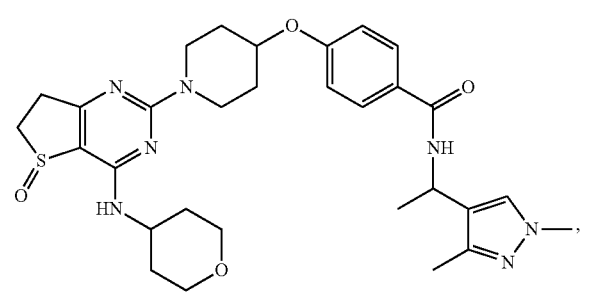
78
-continued
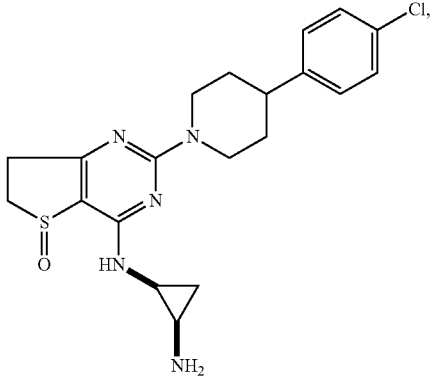
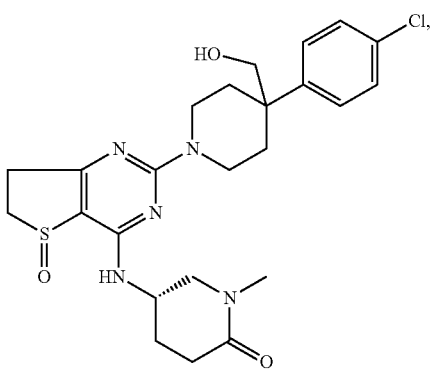

79
-continued
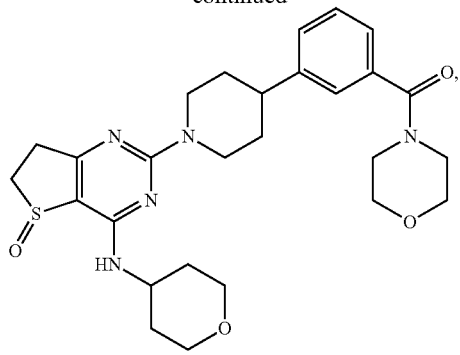
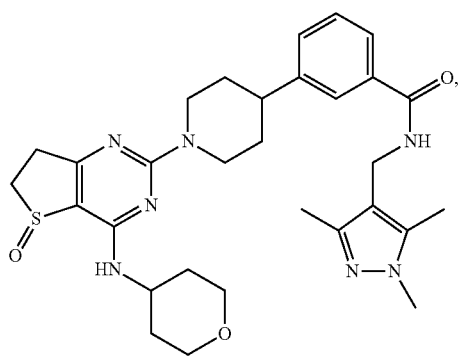
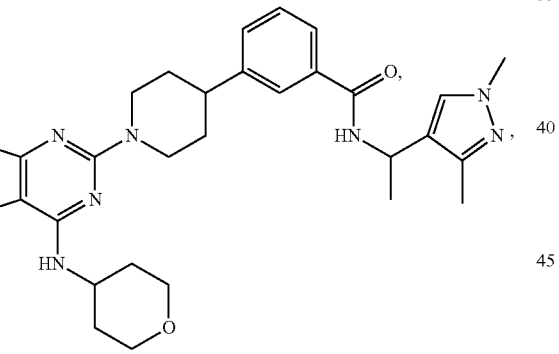
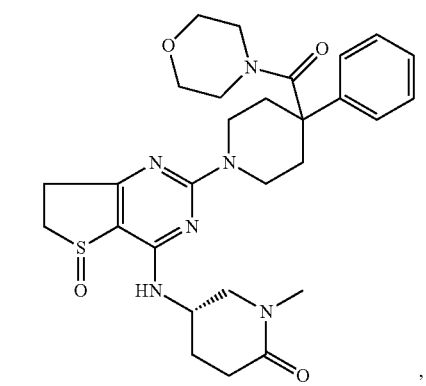
80
-continued
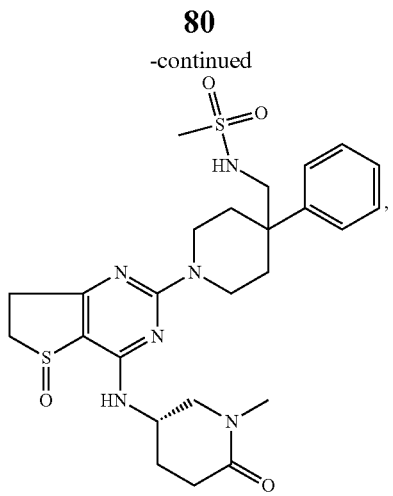
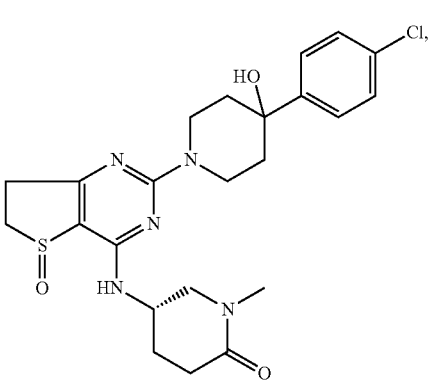
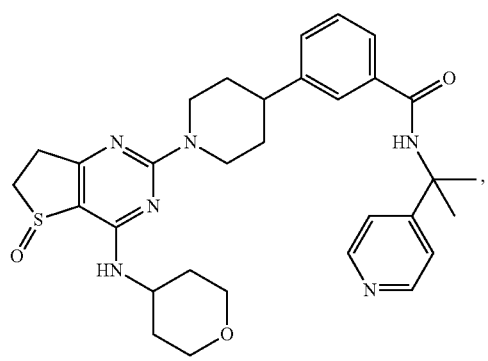
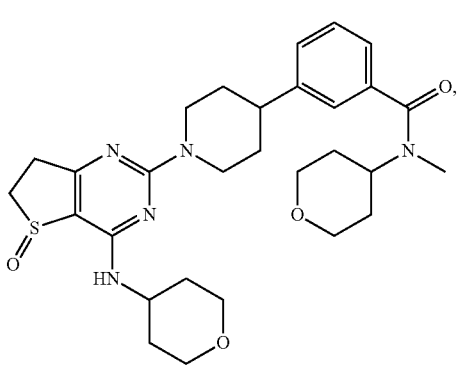

81
-continued
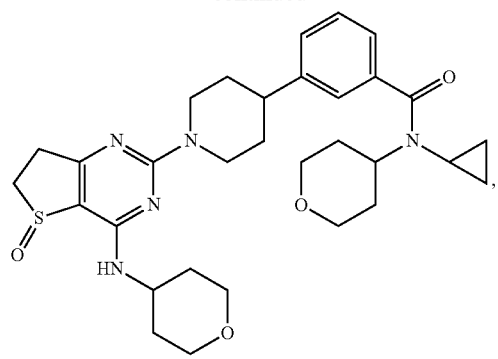
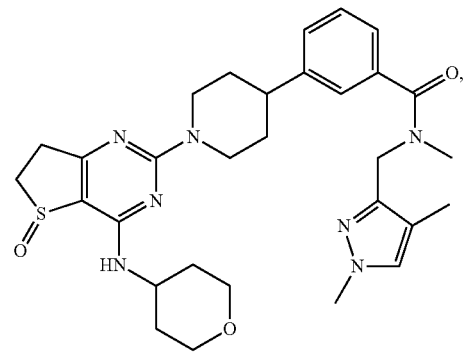
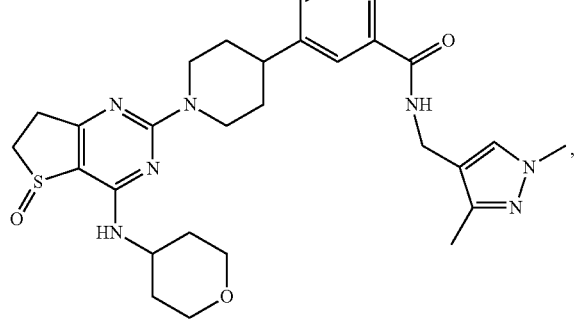
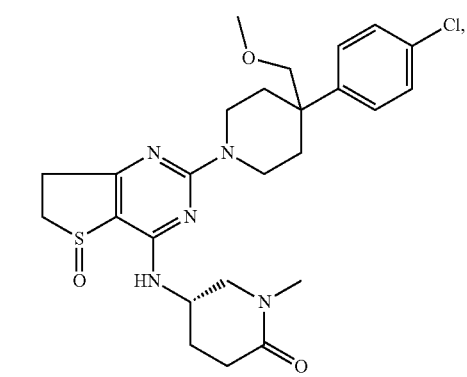
82
-continued
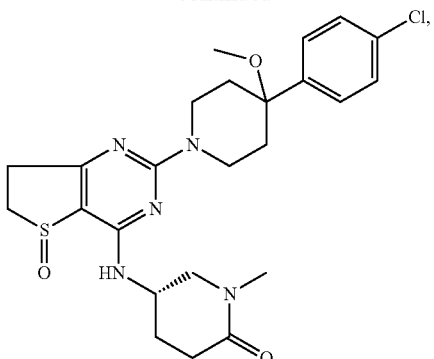
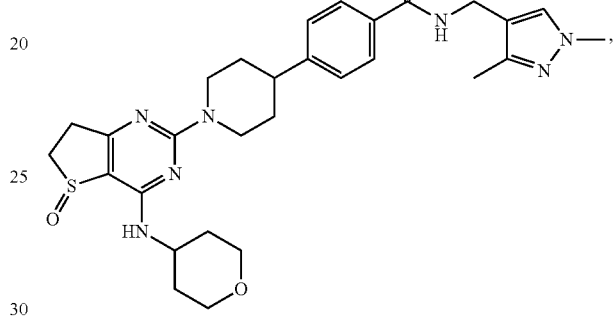
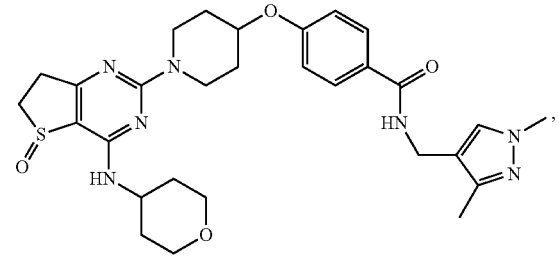
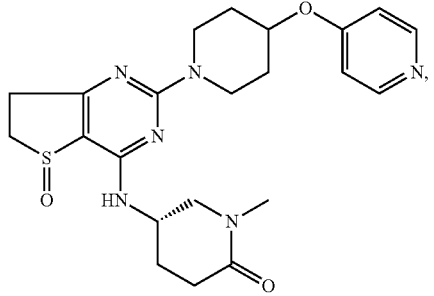
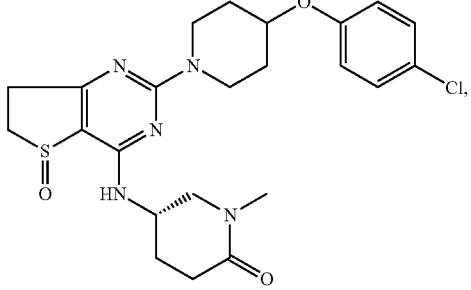

83
-continued
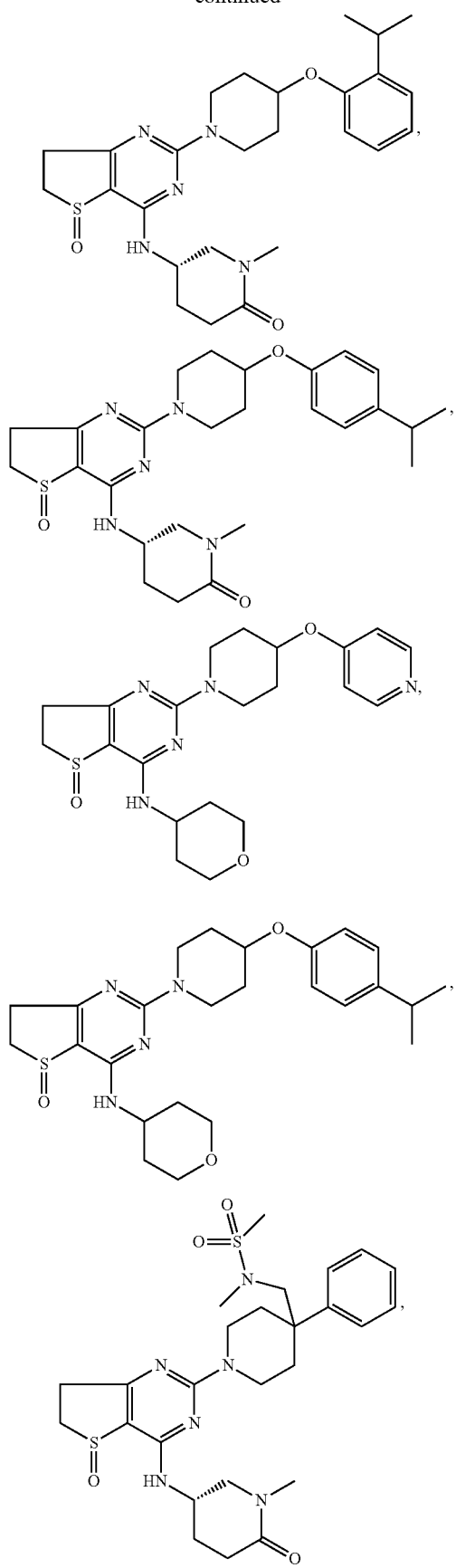
84
-continued
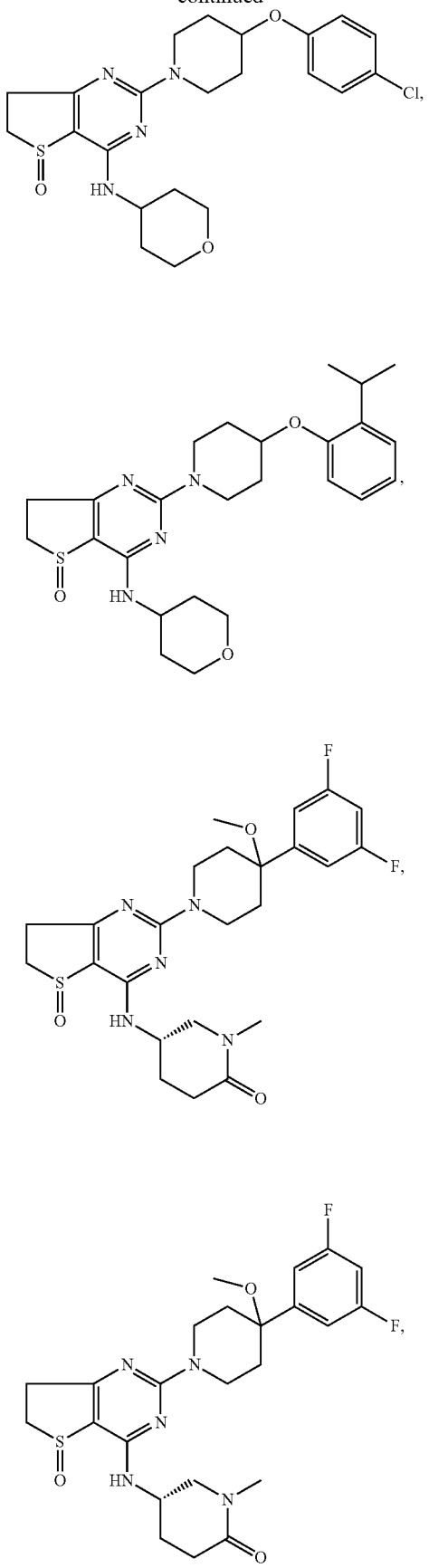

85
-continued
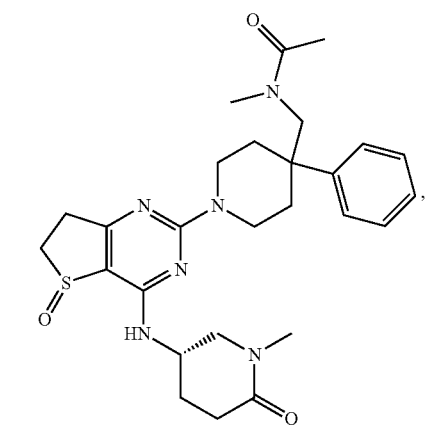
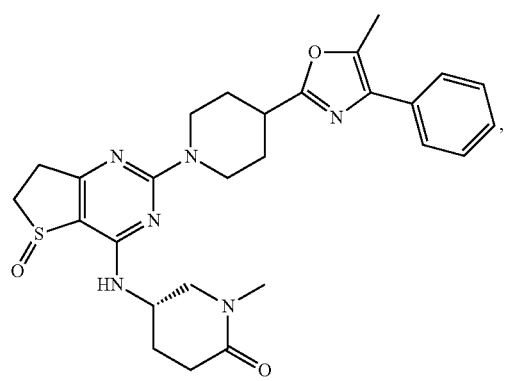
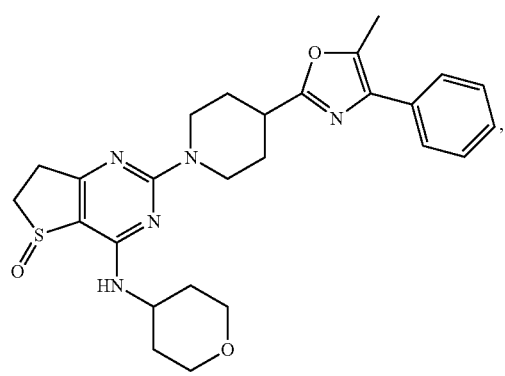
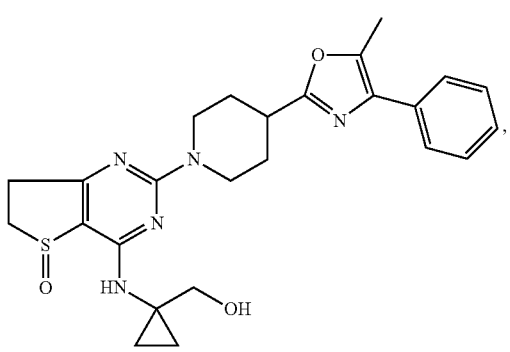
86
-continued
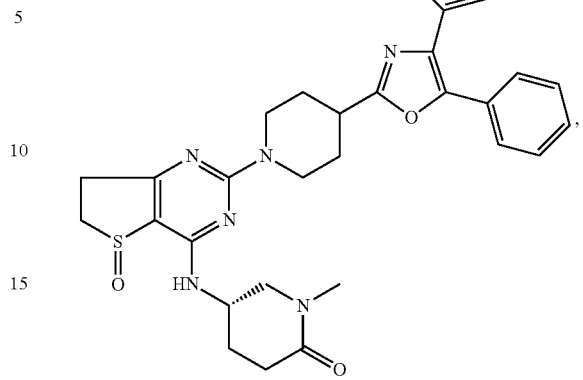
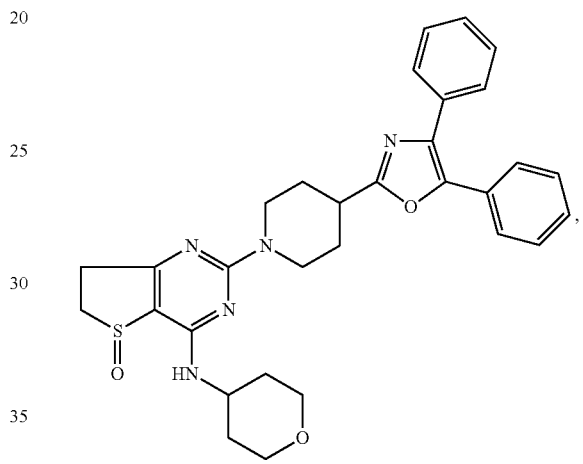

87
-continued
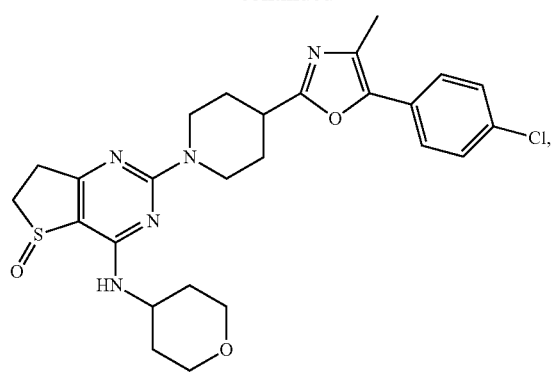
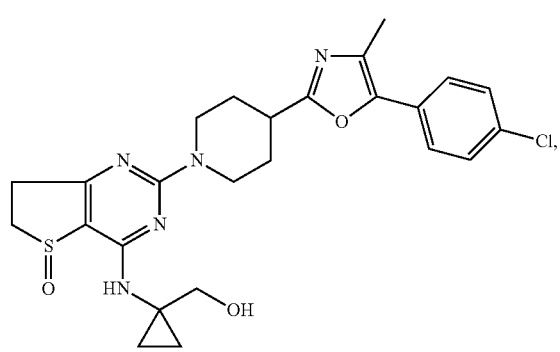
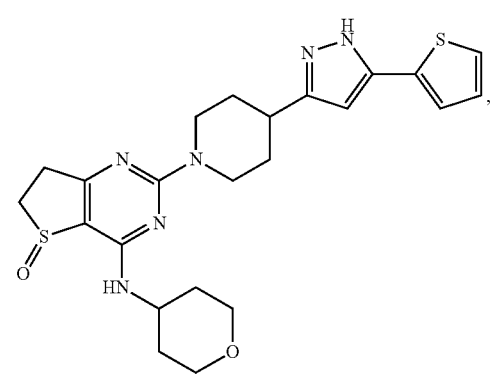
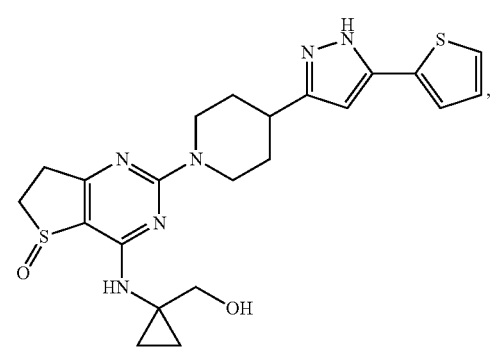
88
-continued
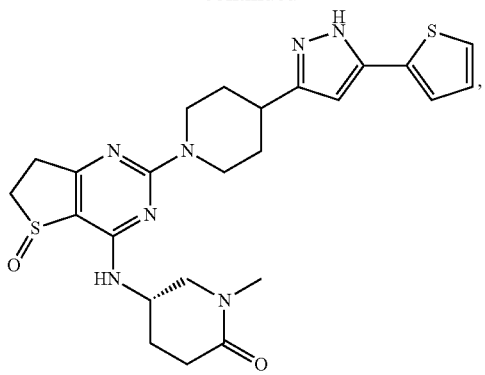
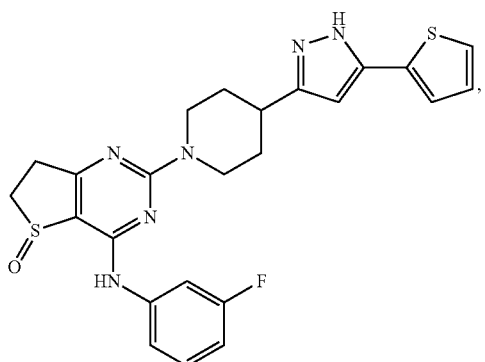
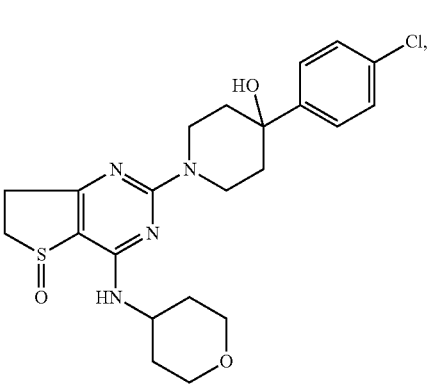
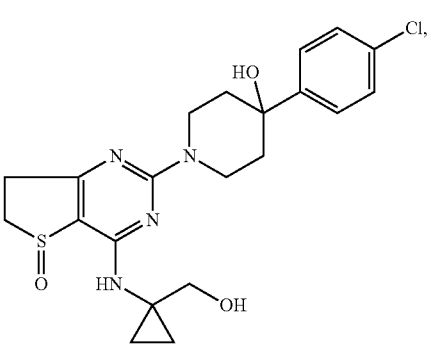

89
-continued
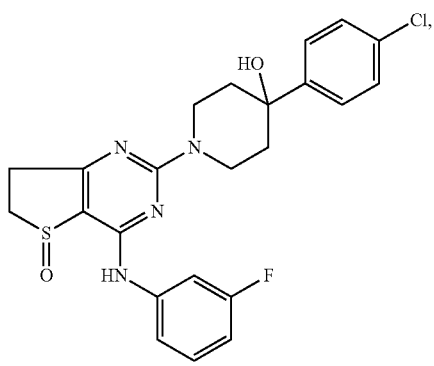
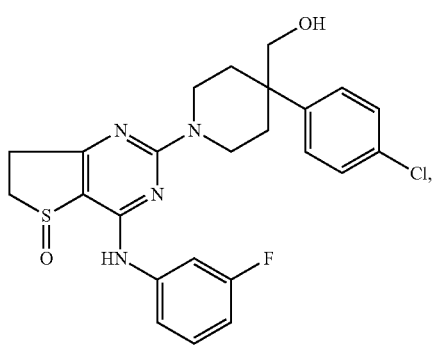
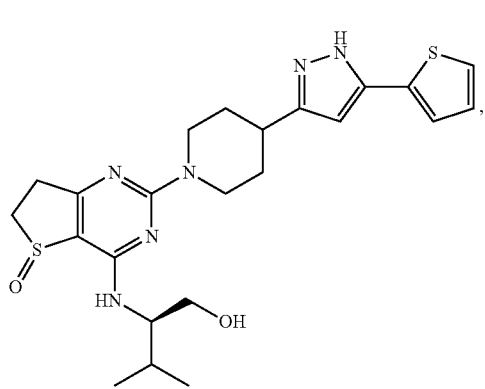
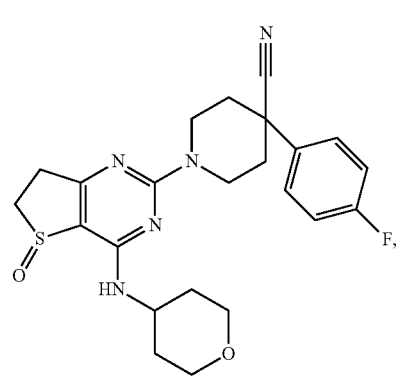
90
-continued
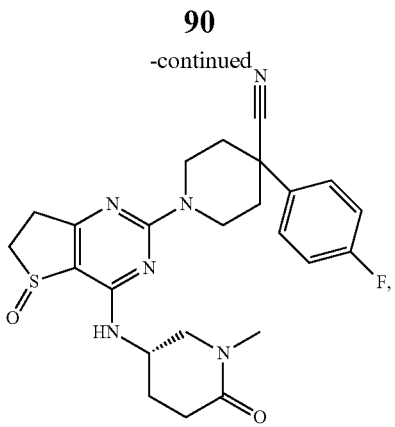
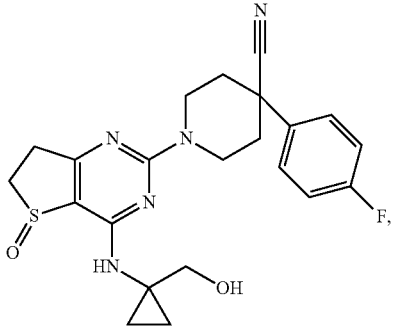
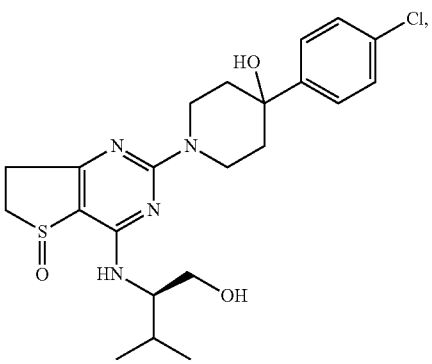

91
-continued
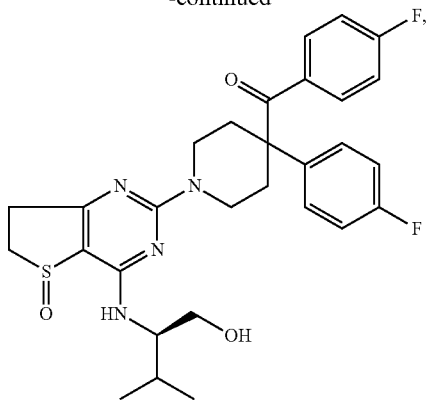
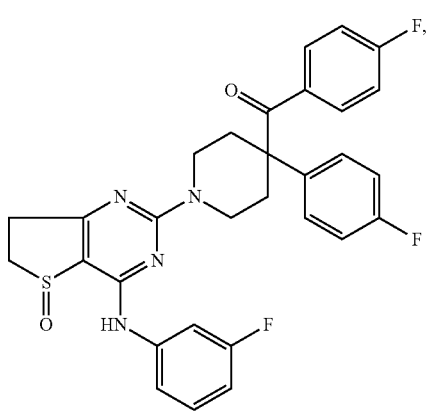
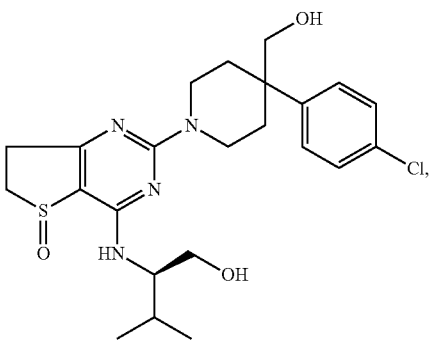
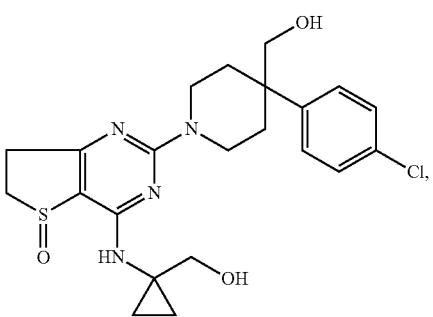
92
-continued
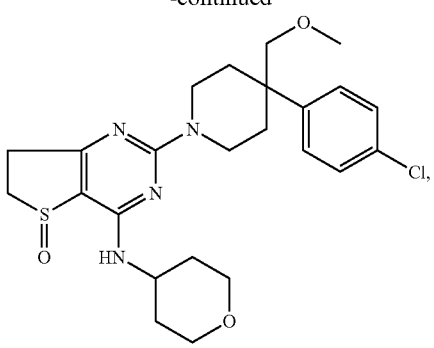
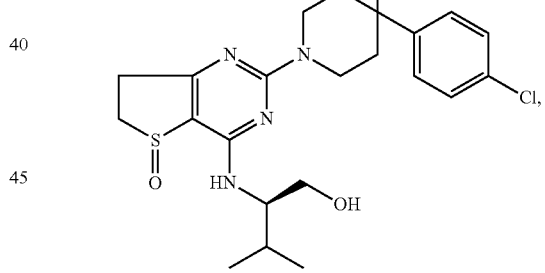
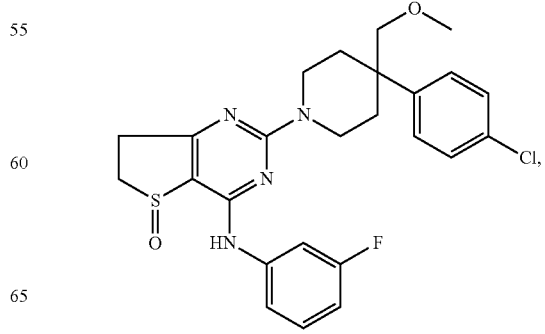

93
-continued
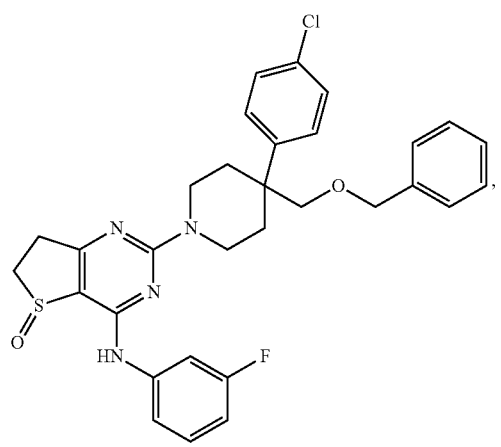
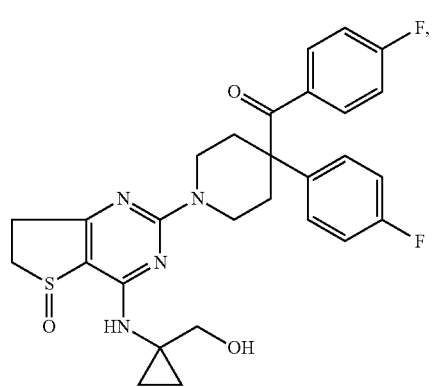
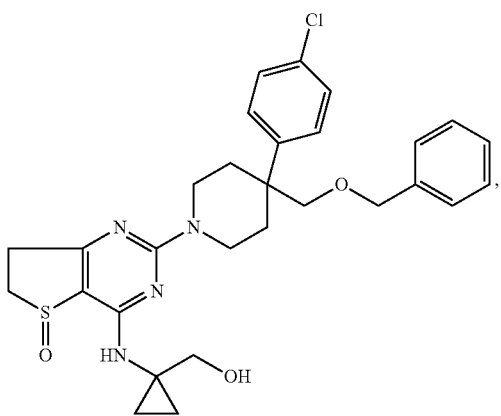
94
-continued
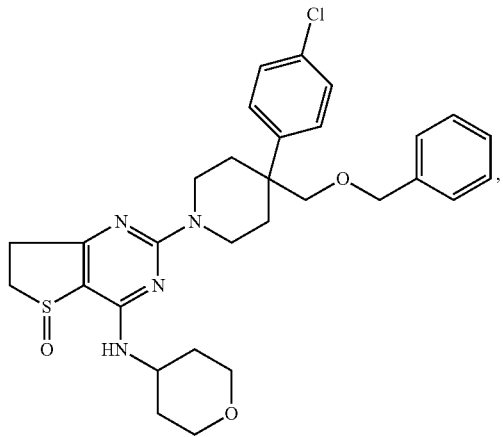
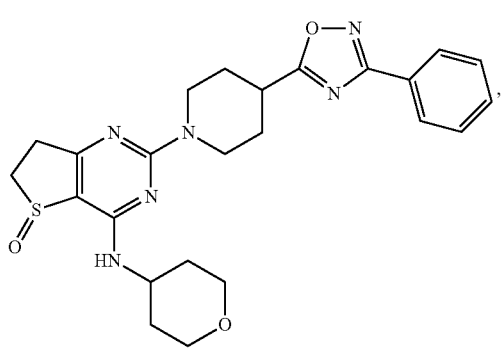
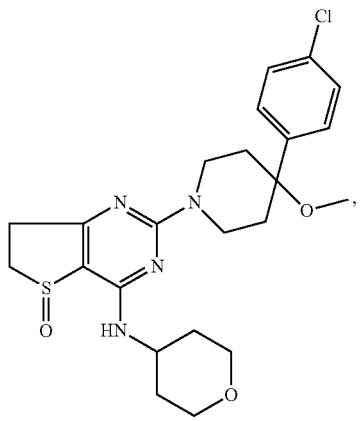

95
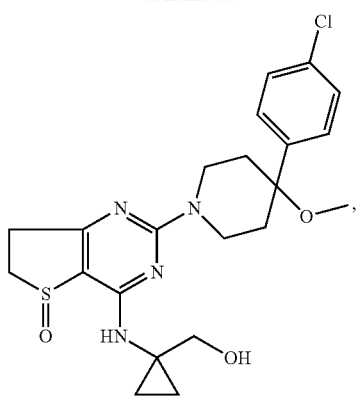
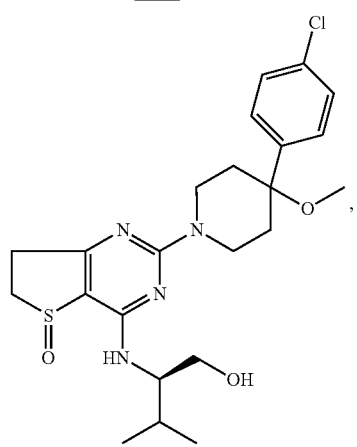
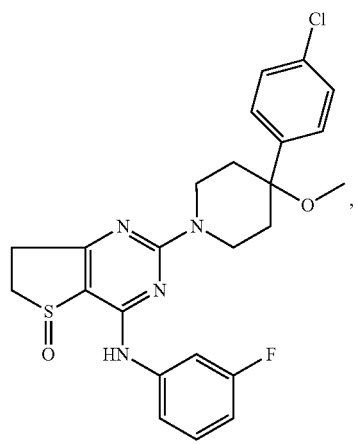
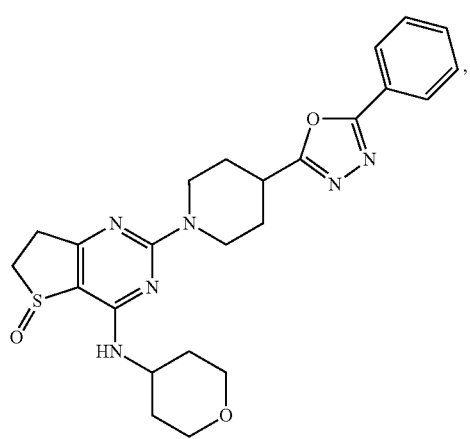
96
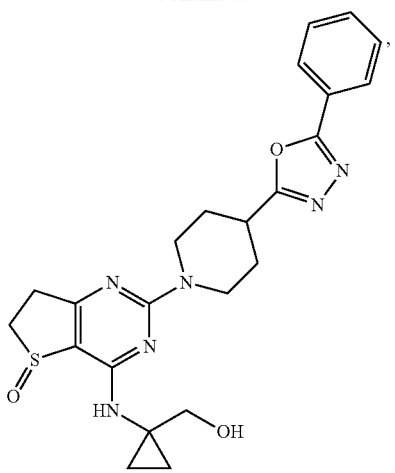
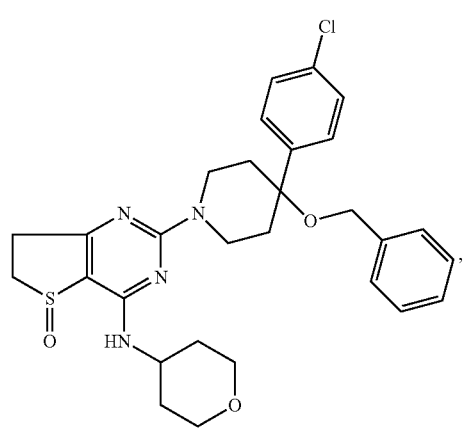
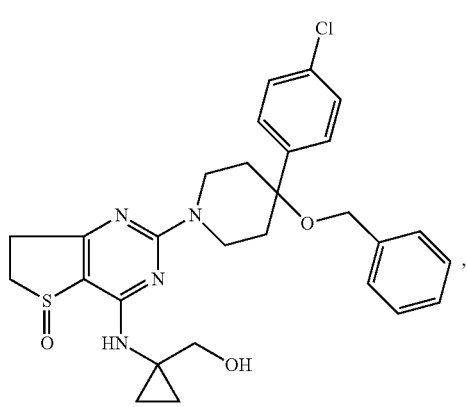
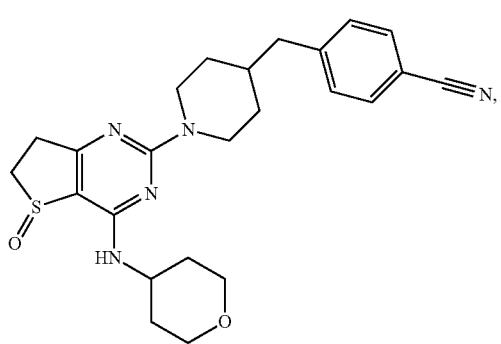

97
-continued
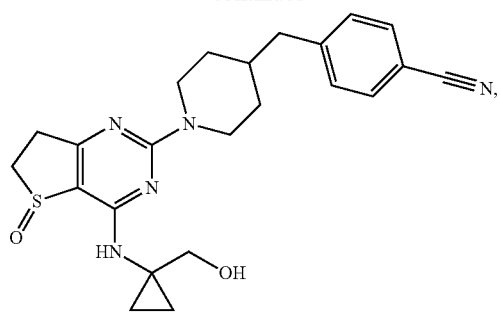
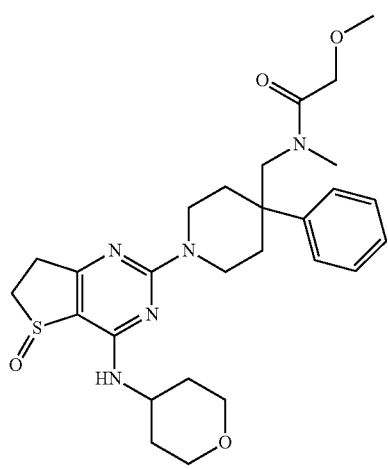
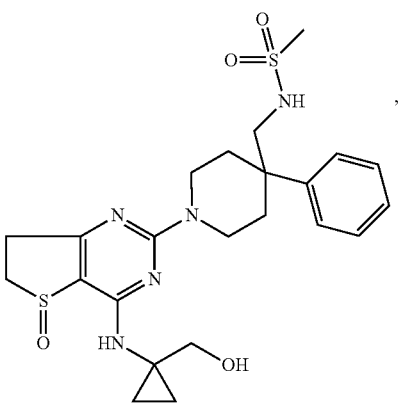
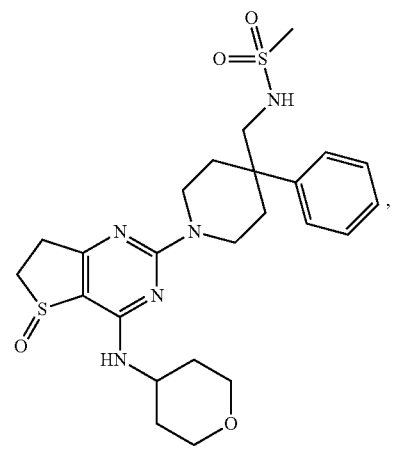
98
-continued
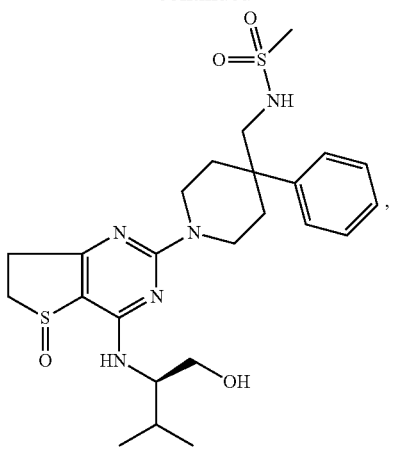
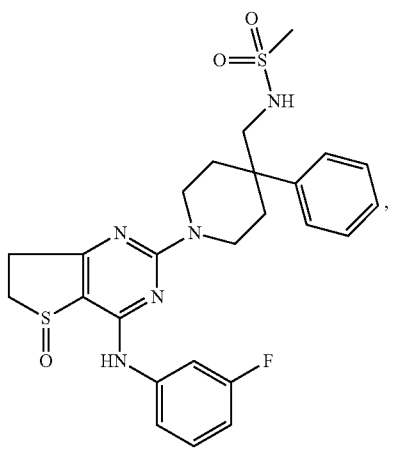
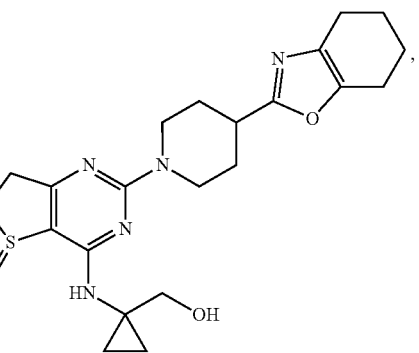
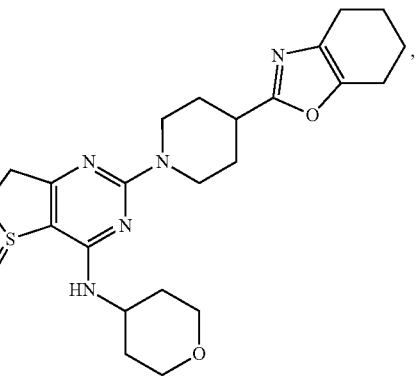

-continued

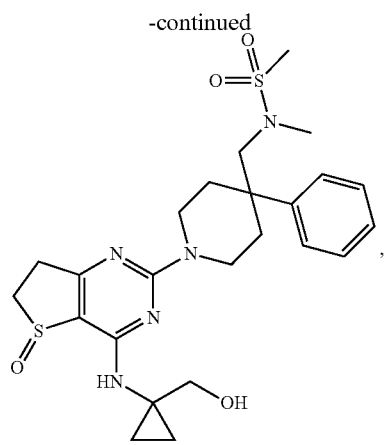

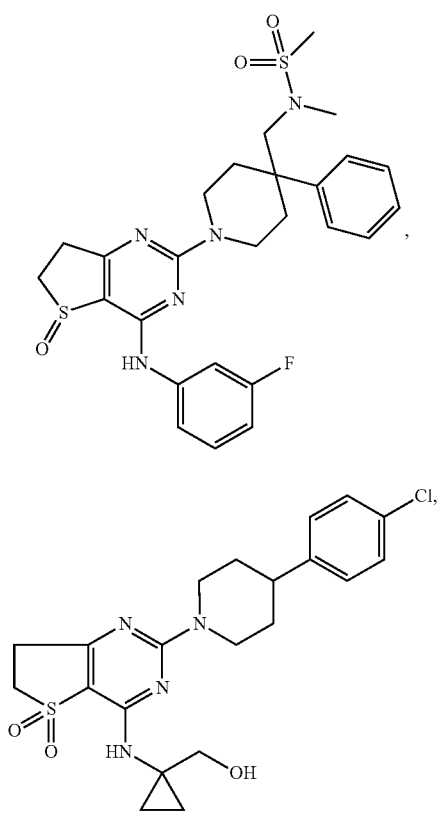

-continued

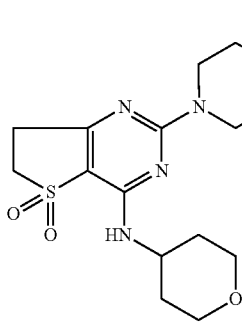

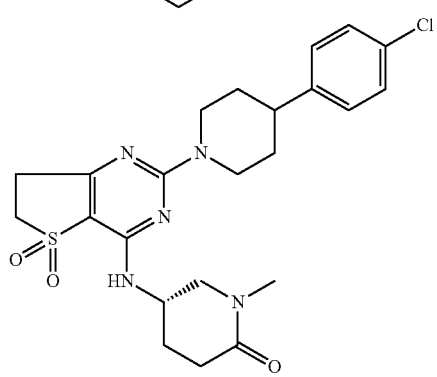

as well as pharmacologically acceptable salts, diastereomers, enantiomers, racemates, hydrates or solvates thereof, particularly the R-enantiomers and the S-enantiomers with respect to the stereocentre at the sulphoxide sulphur atom of the above compounds.

The invention further relates to the above compounds of formula 1 as pharmaceutical compositions.

The invention further relates to the use of the above compounds according to formula 1 for preparing a medicament for the treatment of diseases which can be treated by inhibition of the PDE4 enzyme.

The invention further relates to the use of the above compounds according to formula 1 for preparing a medicament for the treatment of respiratory or gastrointestinal diseases or complaints, as well as inflammatory diseases of the joints, skin or eyes, cancers, and diseases of the peripheral or central nervous system.

The invention further relates to the use of the above compounds according to formula 1 for preparing a medicament for the prevention and/or treatment of respiratory or pulmonary diseases which are accompanied by increased mucus production, inflammations and/or obstructive diseases of the respiratory tract.

The invention further relates to the use of the above compounds according to formula 1 for preparing a medicament for the treatment of inflammatory and/or obstructive diseases such as COPD, chronic sinusitis, asthma, Crohn's disease and ulcerative colitis.

The invention further relates to the use of the above compounds according to formula 1 for preparing a medicament for the treatment of inflammatory diseases of the gastrointestinal tract.

The invention further relates to the use of the above compounds according to formula 1 for preparing a medicament for the prevention and treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain and brain damage caused by stroke, hypoxia or cranio-cerebral trauma.

The invention further relates to pharmaceutical formulations which contain one or more of the above compounds according to formula 1.

The invention further relates to pharmaceutical formulations containing one or more compounds of formula 1 in combination with one or more active substances selected from among betamimetics, corticosteroids, other PDE4-inhibitors, EGFR-inhibitors and LTD4-antagonists, CCR3-inhibitors, iNOS-inhibitors and SYK-inhibitors.

Terms and Definitions Used

Unless otherwise stated, all the substituents are independent of one another. If for example a plurality of $C_{1-6}$-alkyl groups are possible substituents in one group, in the case of three substituents $C_{1-6}$-alkyl, for example, one may represent methyl, one n-propyl and one tert-butyl, for example.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus for example the groups N-piperidinyl (I), 4-piperidinyl (II), 2-tolyl (III), 3-tolyl (IV) and 4-tolyl (V) are shown as follows:

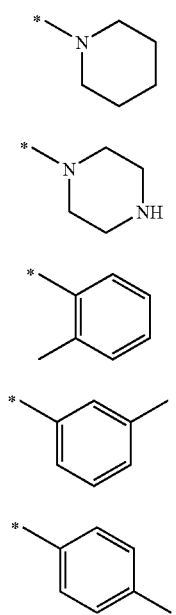

If there is no asterisk (*) in the structural formula of the substituent, each hydrogen atom may be removed at the substituent and the valency thus freed may serve as a binding site to the rest of a molecule, unless the linking point to the remainder of the molecule is otherwise designated or defined. Thus, for example, VI may represent 2-tolyl, 3-tolyl, 4-tolyl and benzyl.

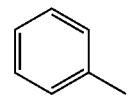

VI

By the term "$C_{1-10}$-alkyl" (including those which are part of other groups) are meant branched and unbranched alkyl groups with 1 to 10 carbon atoms and by the term "$C_{1-6}$-alkyl" are meant, accordingly, branched and unbranched alkyl groups with 1 to 6 carbon atoms. "$C_{1-4}$-Alkyl" accordingly denotes branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or hexyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Preferred are alkylene groups with 1 to 4 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, the following examples of rings are also included:

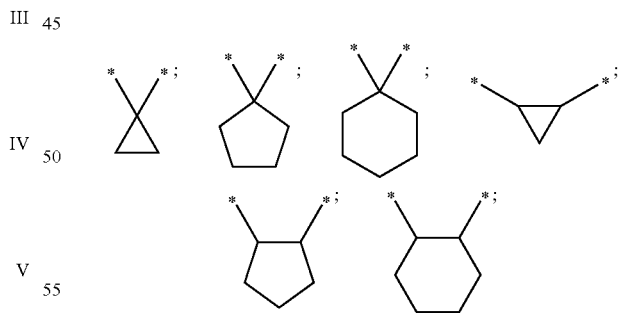

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question.

Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"-branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two or three heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

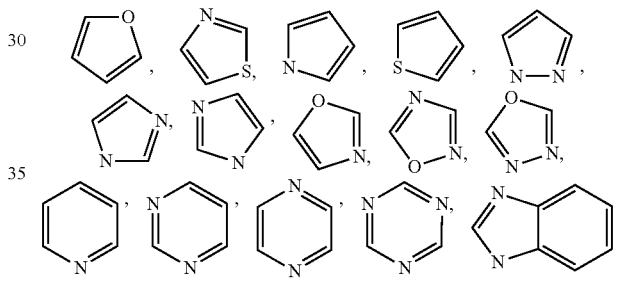

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

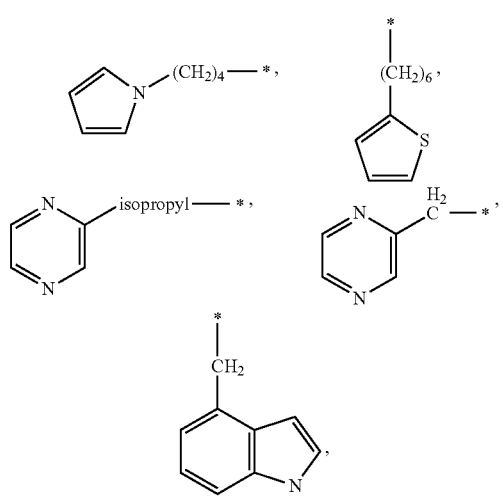

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant five-, six- or seven-membered, saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "heterocyclic non-aromatic rings" refers to five-, six- or seven-membered unsaturated rings. Examples include:

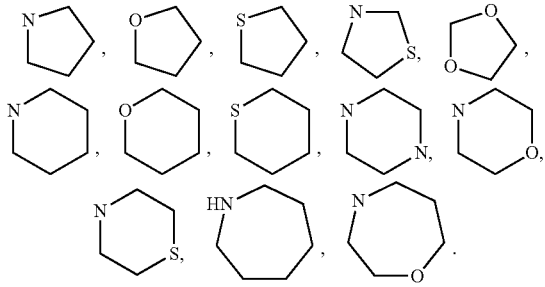

Although included by the term "heterocyclic rings" or "heterocycles", the term "heterocyclic aromatic rings" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

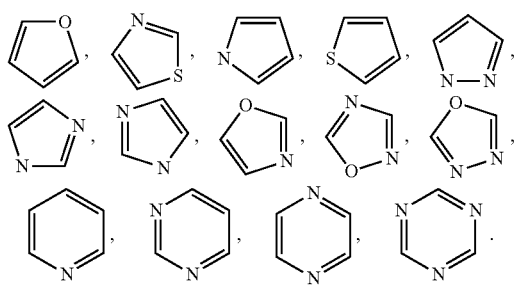

Unless otherwise mentioned, a heterocyclic ring (or heterocycle) may be provided with a keto group. Examples include:

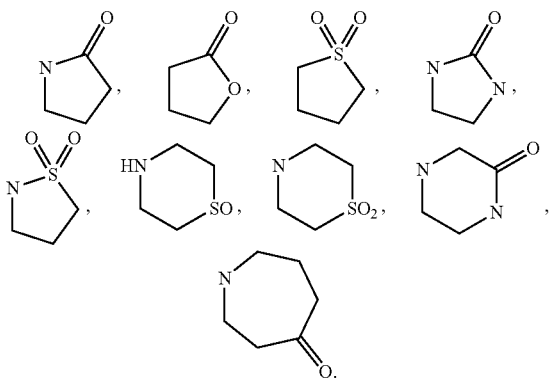

Although covered by the term "cycloalkyl", the term "bicyclic cycloalkyls" generally denotes eight-, nine- or ten-membered bicyclic carbon rings. Examples include

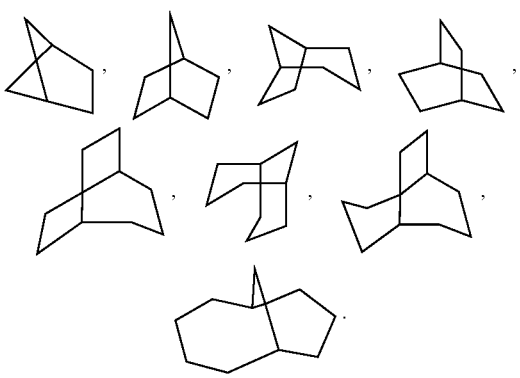

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one. Examples include:

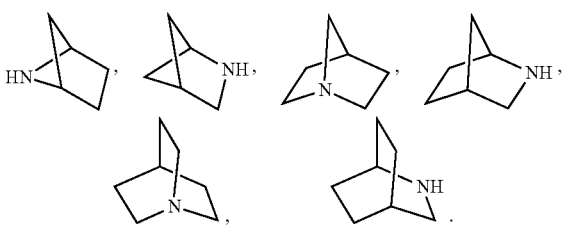

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

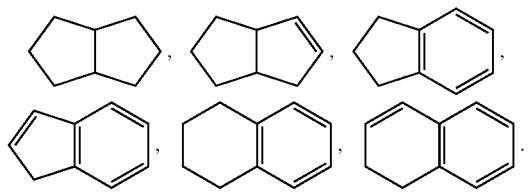

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two or three heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

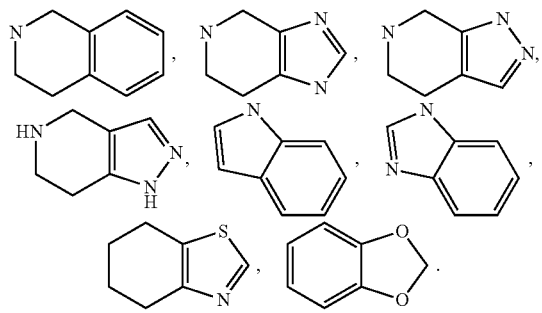

By the term "heterocyclic spiro rings" (spiro) are meant 5-10 membered, spirocyclic rings which may optionally contain one, two or three heteroatoms, selected from among oxygen, sulphur and nitrogen, while the ring may be linked to the molecule through a carbon atom or if available through a nitrogen atom. Unless otherwise mentioned, a spirocyclic ring may be provided with an oxo, methyl or ethyl group. Examples of this include:

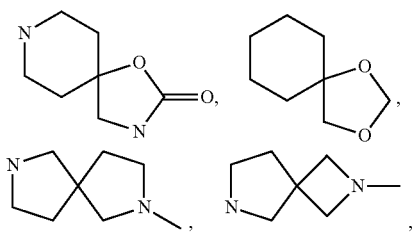

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1 wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula 1 may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers, i.e. in the (R) or (S) form.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof as hereinbefore described. These pharmacologically acceptable salts of the compounds of formula 1 may also be present in the form of their respective hydrates (e.g. monohydrated, dihydrates, etc.) as well as in the form of their respective solvates.

By a hydrate of the compound according to the formula 1 is meant, for the purposes of the invention, a crystalline salt of the compound according to formula 1, containing water of crystallisation.

By a solvate of the compound according to the formula 1 is meant, for the purposes of the invention, a crystalline salt of the compound according to formula 1, which contains solvent molecules (e.g. ethanol, methanol etc) in the crystal lattice.

The skilled man will be familiar with the standard methods of obtaining hydrates and solvates (e.g. recrystallisation from the corresponding solvent in the case of solvates or from water in the case of hydrates).

METHODS OF SYNTHESIS

The compounds of general formula (I) may be prepared according to the following general synthesis scheme, wherein the substituents of general formula (I) have the meanings given hereinbefore. These methods are to be understood as being an illustration of the invention without restricting it to the subject-matter thereof.

GENERAL SYNTHESIS SCHEME

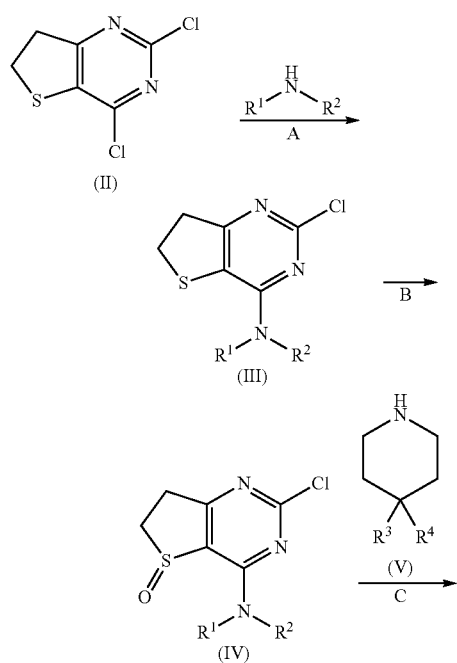

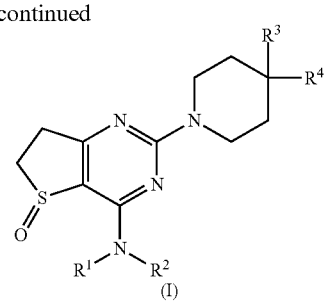

For the preparation of (II) see WO06111549

1. Synthesis of (R)-2-{2-[4-(4-Chlorophenyl)-Piperidin-1-Yl]-5-Oxo-6,7-Dihydro-5H-5λ⁴-Thieno[3,2-d]Pyrimidin-4-Ylamino}-3-Methylbutan-1-Ol (Example 1)

1.1 (R)-2-(2-chloro-6,7-dihydrothieno[3,2-d]pyrimidin-4-ylamino)-3-methylbutan-1-ol (III-1)

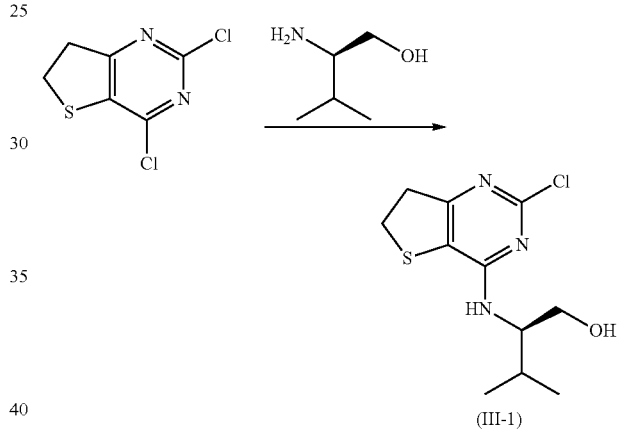

7.2 g of 2,4-dichloro-6,7-dihydrothieno[3,2-d]pyrimidin (II) are in 36 ml dioxane placed, and then first 18 ml diisopropylethylamine, then 6.1 g (R)-(−)-2-amino-3-methyl-1-butanol are added. The reaction mixture is heated to 100° C., until there is no further reaction and cooled, then evaporated down. The residue is treated with petroleum ether/ethyl acetate (9:1) in the ultrasound bath and the solid is suction filtered and dried. 8.3 g (III-1) are obtained as a solid. Analytical HPLC (method A): RT=2.75 min 1.2 (R)-2-(2-chloro-5-oxo-6,7-dihydro-5H-5λ⁴-thieno[3,2-d]pyrimidin-4-ylamino)-3-methylbutan-1-ol (IV-1)

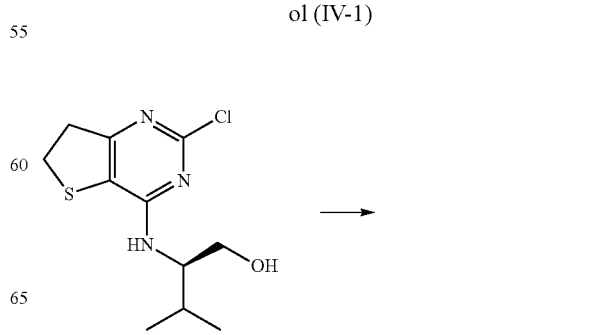

-continued

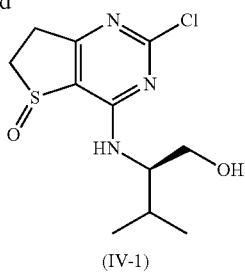

(IV-1)

4.1 g S-(−)-1,1′-bi-2-naphthol are placed in 15 ml chloroform under argon, then 0.44 ml titanium(IV)-isopropoxide and 0.54 ml of water are added. The reaction mixture is stirred for 1 hour at ambient temperature. Then a suspension of 4.1 g (III-1) in 107 ml dichloromethane is added. The reaction mixture is cooled to −2° C. and after 30 minutes 2.7 ml tert-butylhydroperoxide 5-6 M in decane are added dropwise. The reaction mixture is stirred further at −2° C., until there is no further reaction, and made basic with NH$_4$OH. The product is extracted with dichloromethane and purified by chromatography (silica gel, ethyl acetate/methanol 100/0 to 86/14). 2.45 g (IV-1) are obtained as a solid.

Analytical HPLC (method A): RT=2.37 min

1.3 (R)-2-{2-[4-(4-chlorophenyl)-piperidin-1-yl]-5-oxo-6,7-dihydro-5H-5λ$^4$-thieno[3,2-d]pyrimidin-4-ylamino}-3-methylbutan-1-ol (Example 1)

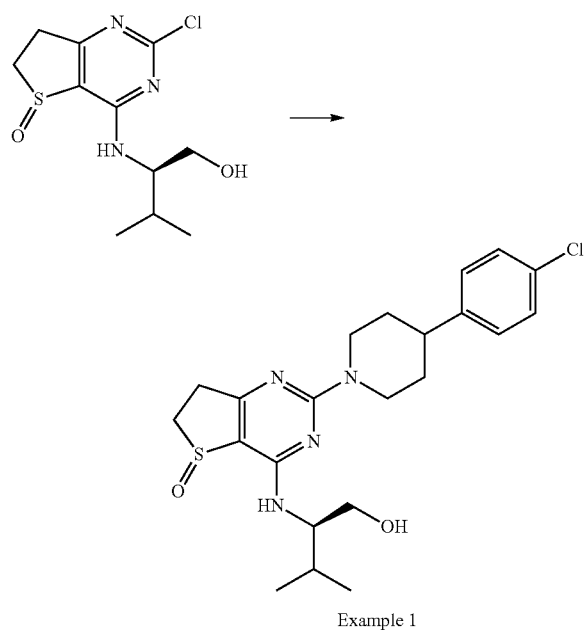

Example 1

0.2 g (IV-1) is placed in 3 ml dioxane and 360 µl diisopropylethylamine, combined with 0.16 g 4-(4-chlorophenyl)-piperidine and heated in the microwave at 120° C., until there is no further reaction. The reaction mixture is mixed with water, extracted with dichloromethane and the product is purified by chromatography (silica gel, dichloromethane/methanol 100/0 to 92/8). 0.33 g Example 1 are obtained as a solid.

Analytical HPLC-MS (method A): RT=1.24 min.

2. Synthesis of (1-{2-[4-(4-Chlorophenyl)-Piperidin-1-Yl]-5-Oxo-6,7-Dihydro-5H-5λ$^4$-Thieno[3,2-d]Pyrimidin-4-Ylamino}-Cyclopropyl)-Methanol (Example 2)

2.1 tert-butyl (1-hydroxymethylcyclopropyl)-carbamidate

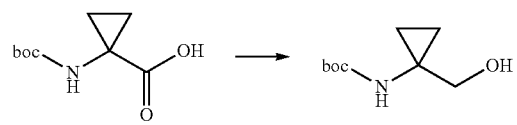

1 g 1-(BOC-amino)-cyclopropanecarboxylic acid is dissolved in 20 ml dimethoxyethane and cooled to −70° C. Then 0.65 ml N-methylmorpholine are added and 0.71 ml isobutylchloroformate in 5 ml dimethoxyethane are added dropwise. The reaction mixture is heated to −5° C. The precipitate is suction filtered. The eluate is cooled to −15° C. and 0.303 g sodiumborohydride are slowly added. The reaction mixture is then stirred for 30 minutes at ambient temperature, mixed with water and the product is extracted with dichloromethane. The organic phase is dried and evaporated to dryness. 1.04 g product are obtained as a solid. $^1$H NMR (400 MHz, DMSO): 1.36 (9H, s); 0.61 (2H, t); 0.52 (2H, t).

2.2 1-aminocyclopropanemethanol

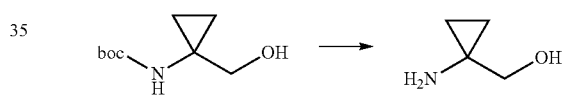

1.04 g tert-butyl (1-hydroxymethylcyclopropyl)-carbamidate are placed in 5 ml dioxane. 2.5 ml HCl in dioxane (4 mol/l) are added dropwise. The reaction mixture is stirred for 15 h at ambient temperature. The solvent is evaporated down by half and the precipitated solid is suction filtered. 0.5 g product are obtained as the hydrochloride.

$^1$H NMR (400 MHz, DMSO): 5.27 (1H, t); 0.91 (2H, t); 0.71 (2H, t).

2.3 [1-(2-chloro-6,7-dihydrothieno[3,2-d]pyrimidin-4-ylamino)-cyclopropyl]-methanol (III-2)

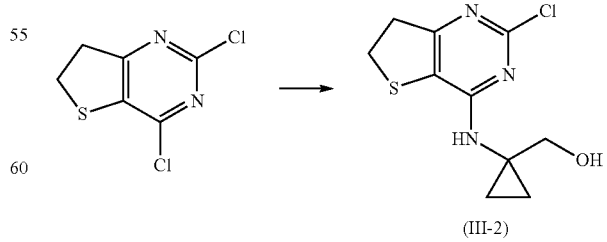

(III-2)

1.4 g (II) are placed in 10 ml dioxane, then 3.6 ml diisopropylethylamine and then 1 g of 1-aminocyclopropanemethanol (see 2.2) are added. The reaction mixture is heated to 160° C., until there is no further reaction, and cooled, then evaporated down. The residue is treated with cyclohexane/ethyl acetate (4:1) in the ultrasound bath, the solid is suction filtered and dried. 1.24 g (III-2) are obtained as a solid. Analytical HPLC-MS (method A): RT=1.01 min.

2.4 [1-(2-chloro-5-oxo-6,7-dihydro-5H-5λ⁴-thieno[3,2-d]pyrimidin-4-ylamino)-cyclopropyl]-methanol (IV-2)

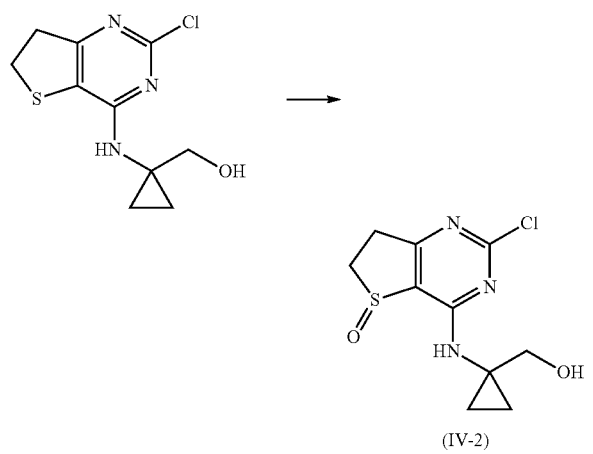

0.28 g S-(−)-1,1'-bi-2-naphthol are placed in 20 ml chloroform under argon, then 0.14 ml titanium(IV)-isopropoxide and 0.17 ml of water are added. The reaction mixture is stirred for 1 hour at ambient temperature. Then a suspension of 1.2 g (III-2) in 40 ml dichloromethane and 2 ml of methanol is added. The reaction mixture is cooled to −5° C. and after 30 minutes 0.91 ml tert-butylhydroperoxide 5-6 M in decane are added dropwise. The reaction mixture is stirred further at −5° C., until there is no further reaction, and made basic with NH₄OH. The aqueous phase is washed with dichloromethane and freeze-dried. 1 g (IV-2) is obtained as a solid. Analytical HPLC-MS (method A) RT=0.85 min 2.5 (1-{2-[4-(4-chlorophenyl)-piperidin-1-yl]-5-oxo-6,7-dihydro-5H-5λ⁴-thieno[3,2-c]pyrimidin-4-ylamino}-cyclopropyl)-methanol (Example 2)

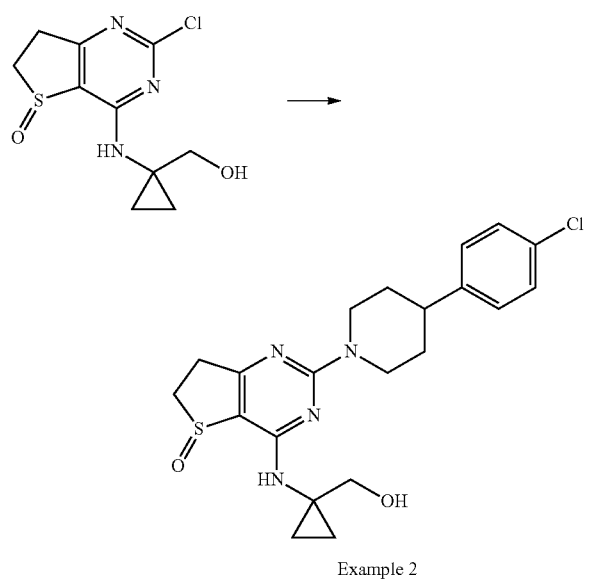

Example 2

Starting from 0.17 g (IV-2) and 0.15 g 4-(4-chlorophenyl)-piperidine 0.14 g Example 2 are prepared and purified analogously to Example 1 (see 1.3).
Analytical HPLC-MS (method B): RT=1.32 min.

3. Synthesis of (R)-2-{2-[4-(4-Chlorophenyl)-Piperidin-1-Yl]-5-Oxo-6,7-Dihydro-5H-5λ⁴-Thieno[3,2-d]Pyrimidin-4-Ylamino}-Pentan-1-Ol (Example 3)

3.1 (R)-2-(2-chloro-6,7-dihydrothieno[3,2-d]pyrimidin-4-ylamino)-pentan-1-ol (III-3)

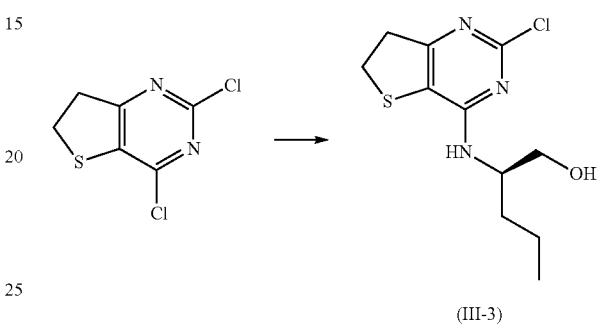

(III-3)

1.4 g 2,4-dichloro-6,7-dihydrothieno[3,2-d]pyrimidine (II) are placed in 9 ml dioxane, then first 3.5 ml diisopropylethylamine, then 0.9 g D-norvalinol are added. The reaction mixture is heated in the microwave at 120° C., until there is no further reaction, and cooled, then evaporated down. The residue is treated with petroleum ether/ethyl acetate 9:1 in the ultrasound bath, the solid is suction filtered and dried. 1.5 g (III-3) are obtained as a solid.
¹H NMR (400 MHz, DMSO): 4.67 (1H, t); 0.86 (3H, t).

3.2 (R)-2-(2-chloro-5-oxo-6,7-dihydro-5H-5λ⁴-thieno[3,2-d]pyrimidin-4-ylamino)-pentan-1-ol (IV-3)

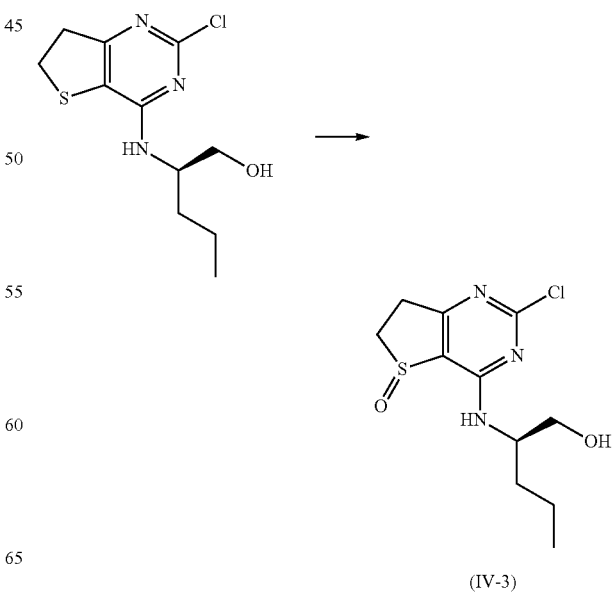

(IV-3)

0.3 g S-(−)-1,1'-bi-2-naphthol are placed in 5 ml chloroform under argon, then 0.15 ml titanium(IV)-isopropoxide and 0.19 ml of water are added. The reaction mixture is stirred for 1 hour at ambient temperature. Then a suspension of 1.4 g (III-3) in 20 ml dichloromethane is added. The reaction mixture is cooled to −5° C. and after 30 minutes 0.95 ml tert-butylhydroperoxide 5-6 M in decane are added dropwise. The reaction mixture is stirred further at −5° C., until there is no further reaction, and made basic with NH₄OH. The product is extracted with dichloromethane and purified by chromatography (ethyl acetate/methanol 100/0 to 80/20). 1.17 g (IV-3) are obtained as a solid.

Analytical HPLC (method A): RT=2.41 min 3.3 (R)-2-{2-[4-(4-chlorophenyl)-piperidin-1-yl]-5-oxo-6,7-dihydro-5H-5λ⁴-thieno[3,2-d]pyrimidin-4-ylamino}-pentan-1-ol (Example 3)

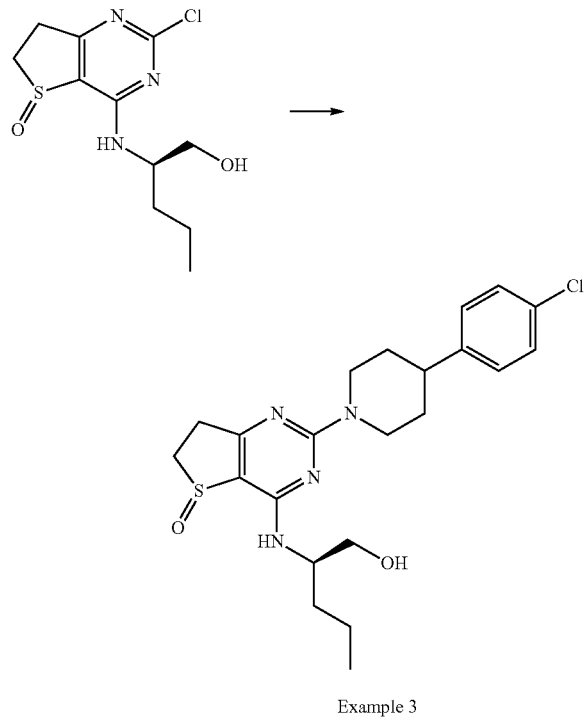

Example 3

0.2 g (IV-3) are placed in 4 ml dioxane and 237 µl diisopropylethylamine, combined with 0.149 g 4-(4-chlorophenyl)-piperidine and heated to 130° C. in the microwave for 30 min. The reaction mixture is mixed with water and the product is extracted with dichloromethane. The residue is treated with acetonitrile in the ultrasound bath and the solid is suction filtered. 0.104 g Example 3 are obtained as a solid. Analytical HPLC-MS (method A): RT=1.29 min.

4. Synthesis of (R)-1-{2-[4-(4-Chlorophenyl)-Piperidin-1-Yl]-5-Oxo-6,7-Dihydro-5H-5λ⁴-thieno[3,2-d]Pyrimidin-4-Ylamino}-1-(4-Fluorophenyl)-2-Methylpropan-2-Ol (Example 4)

4.1 methyl(R)-amino-(4-fluorophenyl)-acetate

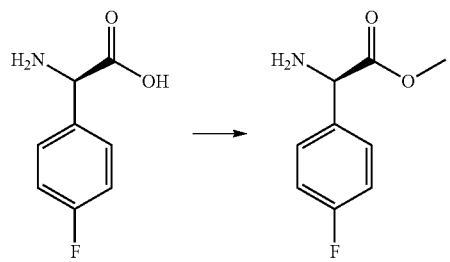

4 g (R)-4-fluorophenylglycine are suspended in 80 ml of methanol. While cooling with the ice bath 3.28 ml of thionyl chloride are slowly added dropwise, so that the temperature is maintained between 15° C. and 20° C. The reaction mixture is stirred for 12 hours at ambient temperature and then evaporated to dryness. 5.1 g of the product are obtained as the hydrochloride. Analytical HPLC-MS (method A): RT=0.8 min.

4.2 methyl(R)-(4-fluorophenyl)-(2,2,2-trifluoroacetylamino)-acetate

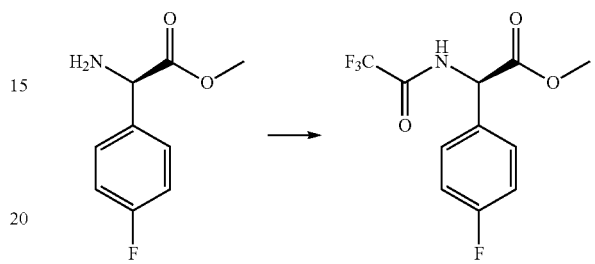

5.1 g methyl(R)-amino-(4-fluorophenyl)-acetate are placed in 36.5 ml abs. Tetrahydrofuran, then 3.9 ml triethylamine added. The reaction mixture is cooled to −70° C. 3.9 ml trifluoroacetic anhydride are then slowly added dropwise, so that the temperature does not exceed −60° C. The reaction mixture is stirred for 12 hours at ambient temperature and then mixed with water. Then potassium hydrogen carbonate is added until no further foaming can be observed and the product is extracted with ethyl acetate. 6.2 g of the product are obtained as an oil. Analytical HPLC-MS (method A): RT=1.28 min.

4.3 2,2,2-trifluoro-N-[(R)-1-(4-fluorophenyl)-2-hydroxy-2-methylpropyl]-acetamide

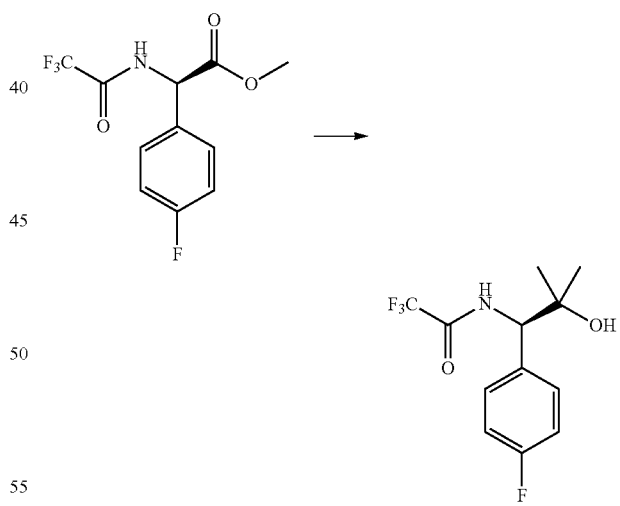

6.2 g methyl(R)-(4-fluorophenyl)-(2,2,2-trifluoroacetylamino)-acetate are placed in 195 ml abs. Tetrahydrofuran and the reaction mixture is cooled to +3° C. 37.2 ml of a methylmagnesium iodide solution (3 M) are slowly added dropwise, so that the temperature does not exceed +10° C. The reaction mixture is stirred for 12 hours at ambient temperature and then stirred into ice water. Ammonium chloride is added until the precipitate has dissolved and the product is extracted with ethyl acetate. 5.6 g of the product are obtained as an oil.

Analytical HPLC-MS (method A): RT=1.19 min

4.4 (R)-1-amino-1-(4-fluorophenyl)-2-methylpropan-2-ol

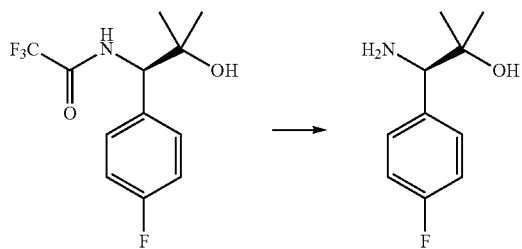 [SMILES: CC(C)(O)[C@H](NC(=O)C(F)(F)F)c1ccc(F)cc1 ; CC(C)(O)[C@H](N)c1ccc(F)cc1]

5.6 g 2,2,2-trifluoro-N-[(R)-1-(4-fluorophenyl)-2-hydroxy-2-methylpropyl]-acetamide and 2.27 g KOH are suspended in 60 ml of methanol. The reaction mixture is stirred for 20 hours at 60° C., then mixed with water and the product is extracted with dichloromethane. 3.2 g product are obtained as an oil. Analytical HPLC-MS (method A): RT=0.79 min.

4.5 (R)-1-(2-chloro-6,7-dihydrothieno[3,2-d]pyrimidin-4-ylamino)-1-(4-fluorophenyl)-2-methylpropan-2-ol (III-4)

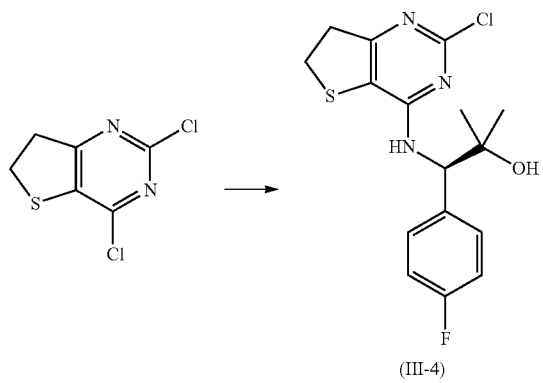 [SMILES: Clc1nc(Cl)c2c(n1)CCS2 ; CC(C)(O)[C@H](Nc1nc(Cl)nc2c1SCC2)c1ccc(F)cc1 ; "(III-4)"]

0.533 g (II), 0.850 g (R)-1-amino-1-(4-fluorophenyl)-2-methylpropan-2-ol and 1.3 ml diisopropylethylamine are suspended in 9.8 ml dioxane. The reaction mixture is heated to 80° C. in the microwave for 2 hours and then evaporated to dryness. The residue is mixed with water. The precipitate formed is suction filtered and purified by chromatography (silica gel, petroleum ether/ethyl acetate 100/0 to 60/40). 0.260 g (III-4) are obtained as a solid. Analytical HPLC-MS (method A): 1.39 min.

4.6 (R)-1-(2-chloro-5-oxo-6,7-dihydro-5H-5λ⁴-thieno[3,2-d]pyrimidin-4-ylamino)-1-(4-fluorophenyl)-2-methylpropan-2-ol (IV-4)

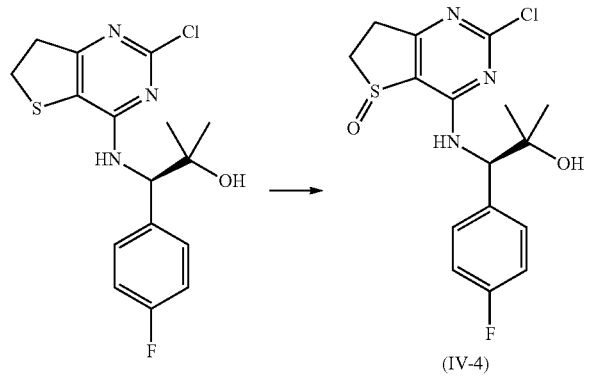 [SMILES: CC(C)(O)[C@H](Nc1nc(Cl)nc2c1SCC2)c1ccc(F)cc1 ; CC(C)(O)[C@H](Nc1nc(Cl)nc2c1S(=O)CC2)c1ccc(F)cc1 ; "(IV-4)"]

0.24 g S-(−)-1,1'-bi-2-naphthol are placed in 4 ml chloroform under argon, then 0.125 ml titanium(IV)-isopropoxide and 0.15 ml of water are added. The reaction mixture is stirred for 1 hour at ambient temperature. Then a suspension of 1.51 g (III-4) in 26 ml chloroform is added. The reaction mixture is cooled to −6° C. and after 30 minutes 0.78 ml tert-butylhydroperoxide 5-6 M in decane are added dropwise. The reaction mixture is stirred further at −6° C. until there is no further reaction, and made basic with NH₄OH. The product is extracted with dichloromethane and purified by chromatography (dichloromethane/methanol 100/0 to 95/5). 0.62 g (IV-4) are obtained as a solid.

Analytical HPLC-MS (method A): RT=1.19 min.

4.7 (R)-1-{2-[4-(4-chlorophenyl)-piperidin-1-yl]-5-oxo-6,7-dihydro-5H-5λ⁴-thieno[3,2-d]pyrimidin-4-ylamino}-1-(4-fluorophenyl)-2-methylpropan-2-ol (Example 4)

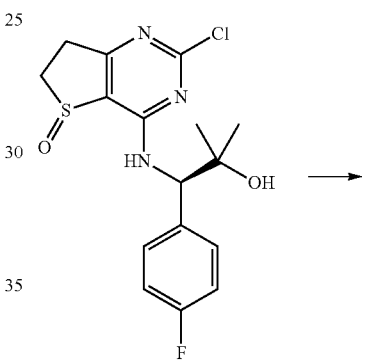

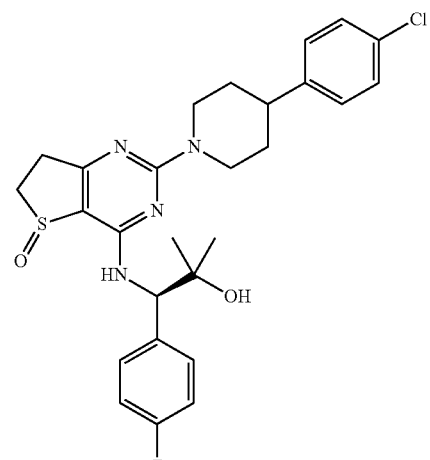

Example 4

Starting from 0.24 g (IV-4) and 0.15 g 4-(4-chlorophenyl)-piperidine 0.19 g Example 4 are prepared analogously to Example 1 (see 1.3). The product is purified by chromatography (dichloromethane/methanol 100/0 to 96/4). Analytical HPLC-MS (method A): RT=1.36 min.

5. Synthesis of (S)-5-{2-[4-(4-Chlorophenyl)-Piperidin-1-Yl]-5-Oxo-6,7-Dihydro-5H-5λ⁴-Thieno[3,2-d]Pyrimidin-4-Ylamino}-1-Methylpiperidin-2-One (Example 5)

5.1 (S)-5-dibenzylaminopiperidin-2-one

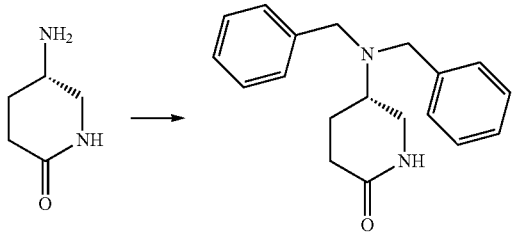 [SMILES: N[C@H]1CCC(=O)NC1 ; O=C1CC[C@H](N(Cc2ccccc2)Cc2ccccc2)CN1]

0.600 g 4-(S)-amino-delta-valerolactam hydrochloride, 0.970 ml benzylbromide and 1.5 g sodium hydrogen carbonate are suspended in 30 ml of ethanol. The reaction mixture is then stirred for 8 hours at 80° C. and then evaporated to dryness. The residue is suspended in water and the product is extracted with dichloromethane and purified by chromatography (silica gel, dichloromethane/methanol 100/0 to 95/5). 0.500 g product are obtained as an oil. Analytical HPLC-MS (method A): RT=1.01 min.

5.2 (S)-5-dibenzylamino-1-methylpiperidin-2-one

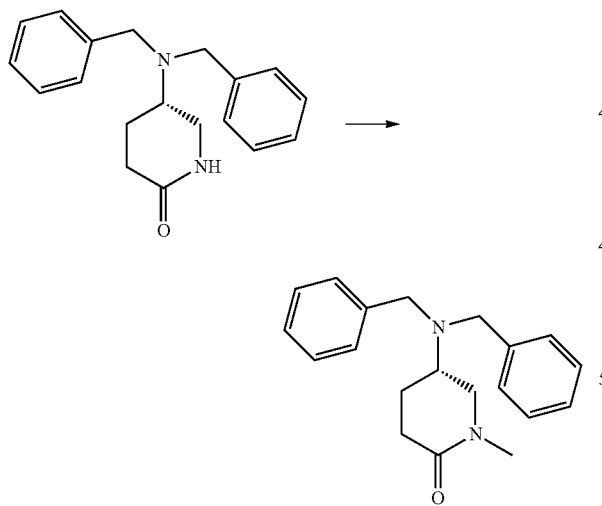

0.500 g (S)-5-dibenzylaminopiperidin-2-one are suspended in 15 ml of tetrahydrofuran. While cooling with the ice bath 0.175 g potassium-tert-butoxide are added. The reaction mixture is then stirred for 30 minutes at ambient temperature. While cooling with the ice bath 0.095 ml methyl iodide are added. The reaction mixture is then stirred for 48 hours at ambient temperature and then combined with a saturated NaCl solution. The product is extracted with ethyl acetate. 0.450 g product are obtained as an oil.

Analytical HPLC-MS (method A): RT=1.07 min.

5.3 (S)-5-amino-1-methylpiperidin-2-one

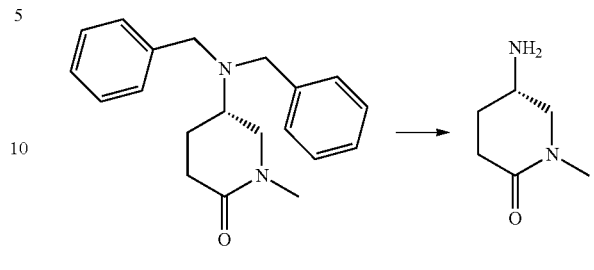

0.450 g (S)-5-dibenzylamino-1-methylpiperidin-2-one are suspended in 25 ml of methanol and hydrogenated with 0.150 g Pd/C 10% at a pressure of 3 bar and a temperature of 60° C. After 16 hours the catalyst is suction filtered and the filtrate is evaporated to dryness. 0.190 g of the product are obtained as an oil. ¹H NMR (400 MHz, DMSO): 2.76 (3H, s). 5.4 (S)-5-(2-chloro-6,7-dihydrothieno[3,2-d]pyrimidin-4-ylamino)-1-methylpiperidin-2-one (III-5):

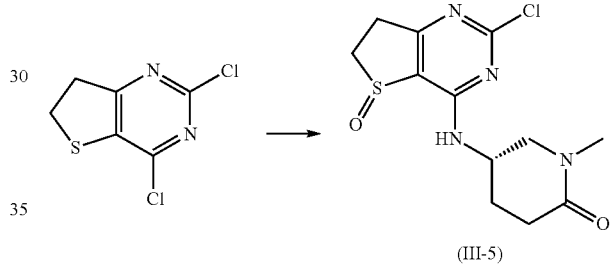

(III-5)

0.27 g (II) are placed in 3 ml dioxane, then first 0.45 ml diisopropylethylamine, then 0.25 g (S)-5-amino-1-methylpiperidin-2-one are added. The reaction mixture is heated to 130° C., until there is no further reaction, and cooled, then evaporated down. The product is extracted with dichloromethane and purified by chromatography (preparative HPLC, method A). 0.26 g (III-5) are obtained as a solid. Analytical HPLC-MS (method A): RT=1.06 min.

5.5 (S)-5-(2-chloro-5-oxo-6,7-dihydro-5H-5λ⁴-thieno[3,2-d]pyrimidin-4-ylamino)-1-methylpiperidin-2-one (IV-5)

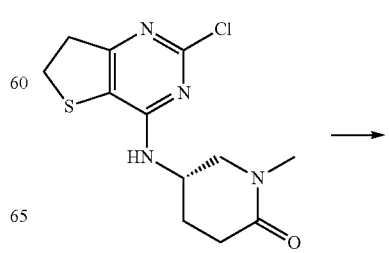

-continued

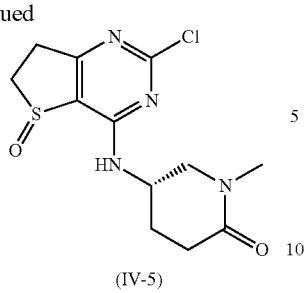

(IV-5)

0.04 g S-(−)-1,1'-bi-2-naphthol are placed in 5 ml chloroform under argon, then 0.02 ml titanium(IV)-isopropoxide and 0.025 ml of water are added. The reaction mixture is stirred for 1 hour at ambient temperature. Then a suspension of 0.2 g (III-5) in 4 ml dichloromethane is added. The reaction mixture is cooled to −5° C. and after 20 minutes 0.12 ml tert-butylhydroperoxide 5-6 M in decane are added dropwise. The reaction mixture is stirred further at −5° C., until there is no further reaction, and made basic with NH$_4$OH. The product is purified by chromatography (silica gel, ethyl acetate/methanol 100/0 to 60/40). 0.09 g (IV-5) are obtained as a solid. Analytical HPLC-MS (method A): RT=0.83 min.

5.6 (S)-5-{2-[4-(4-chlorophenyl)-piperidin-1-yl]-5-oxo-6,7-dihydro-5H-5λ$^4$-thieno[3,2-d]pyrimidin-4-ylamino}-1-methylpiperidin-2-one (Example 5)

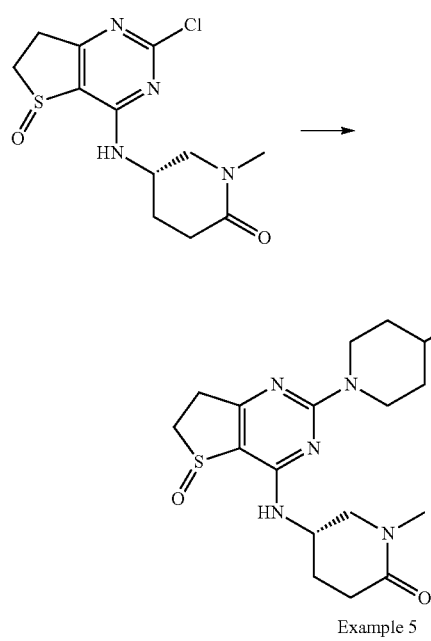

Example 5

Starting from 0.2 g (IV-5) and 0.18 g 4-(4-chlorophenyl)-piperidine 0.17 g Example 5 are prepared analogously to Example 1 (see 1.3). The product is purified by chromatography (preparative HPLC, method A). The product fractions are made basic with ammonia and freeze-dried. Analytical HPLC-MS (method A): RT=1.18 min 6. Synthesis of {2-[4-(4-Chlorophenyl)-Piperidin-1-Yl]-5-Oxo-6,7-Dihydro-5H-5λ$^4$-Thieno[3,2-d]Pyrimidin-4-Yl}-(Tetrahydropyran-4-Yl)-Amine (Example 6)

6.1 (2-chloro-6,7-dihydrothieno[3,2-d]pyrimidin-4-yl)-(tetrahydropyran-4-yl)-amine (III-6)

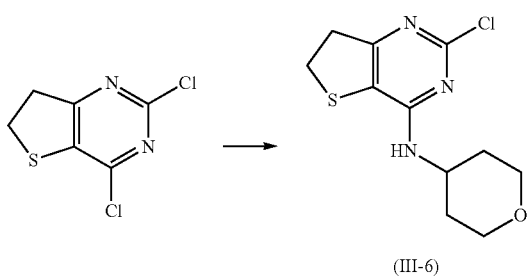 [SMILES: Clc1nc(Cl)c2c(n1)CCS2 ; Clc1nc2c(c(NC3CCOCC3)n1)SCC2 ; "(III-6)"]

(III-6)

0.68 g (II) are placed in 6 ml dioxane, then first 1.72 ml diisopropylethylamine, then 0.6 g 4-aminotetrahydropyran are added. The reaction mixture is heated to 130° C., until there is no further reaction, and cooled, then evaporated down. The product is treated with water in the ultrasound bath, then suction filtered and dried. 0.66 g (III-6) are obtained as a solid. Analytical HPLC-MS (method C): RT=1.08 min.

6.2 (2-chloro-5-oxo-6,7-dihydro-5H-5λ$^4$-thieno[3,2-d]pyrimidin-4-yl)-(tetrahydropyran-4-yl)-amine (IV-6)

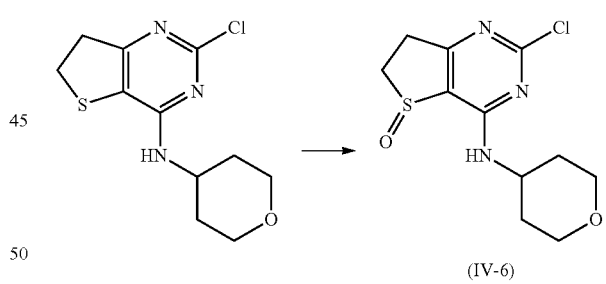

(IV-6)

0.14 g S-(−)-1,1'-bi-2-naphthol are placed in 5 ml chloroform under argon, then 0.072 ml titanium(IV)-isopropoxide and 0.087 ml of water are added. The reaction mixture is stirred for 45 minutes at ambient temperature. Then a suspension of 0.66 g (III-6) in 25 ml chloroform is added. The reaction mixture is cooled to −10° C. and after 60 minutes 0.444 ml tert-butylhydroperoxide 5-6 M in decane are added dropwise. The reaction mixture is stirred further at −10 to −4° C., until there is no further reaction, and mixed with water. The product is extracted with dichloromethane and purified by chromatography (silica gel, ethyl acetate/methanol 100/0 to 80/20). 0.42 g (IV-6) are obtained as a solid.

Analytical HPLC-MS (method A): RT=0.94 min.

6.3 {2-[4-(4-chlorophenyl)-piperidin-1-yl]-5-oxo-6,7-dihydro-5H-5λ⁴-thieno[3,2-d]pyrimidin-4-yl}-(tetrahydropyran-4-yl)-amine (Example 6)

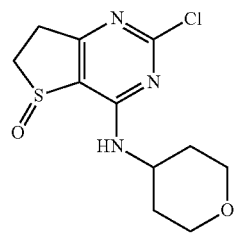

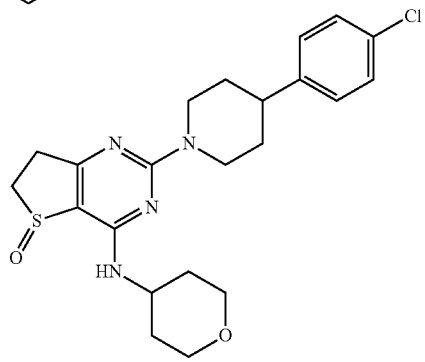

Example 6

Starting from 0.18 g (IV-6) and 0.17 g 4-(4-chlorophenyl)-piperidine 0.23 g Example 6 are prepared analogously to Example 1 (see 1.3). The product is treated with water in the ultrasound bath and the solid is suction filtered.
Analytical HPLC-MS (method A): RT=1.24 min 7 Synthesis of (R)-1-(4-(1-Hydroxy-3-Methylbutan-2-Ylamino)-5-Oxo-6,7-Dihydro-5H-5λ⁴-Thieno[3,2-d]Pyrimidin-2-Yl)-3'-Methyl-1'H-Spiro[Piperidin-4,4'-Quinazolin]-2'(3'H)-One (Example 14)

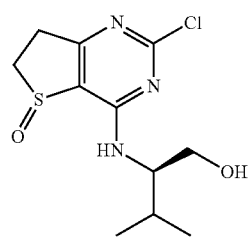

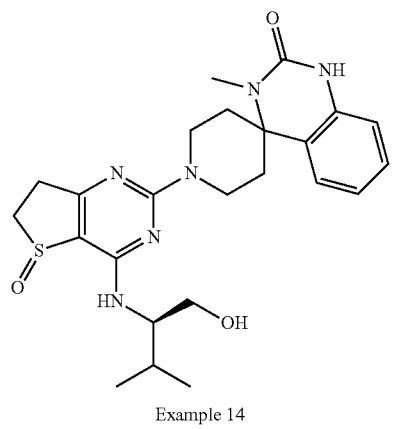

Example 14

(IV-1) (see 1.2, 0.1 mmol) is placed in 750 μl N-methyl-2-pyrrolidone (NMP) and 50 μl diisopropylethylamine, combined with a solution of 3'-methyl-1'H-spiro[piperidin-4,4'-quinazolin]-2'(3'H)-one (*Chem. Pharm. Bull.* 1988, 4659) (0.1 mmol) in 400 μl NMP and heated for 30 min at 120° C. in the microwave. Then 600 μl DMF are added, the reaction solution is purified by preparative HPLC-MS (method A) and the product fractions are freeze-dried. Analytical HPLC-MS (method C): RT=1.58 min.

8. Synthesis of (R)-2-[2-(4-Benzo[d]Isoxazol-3-Yl-Piperidin-1-Yl)-5-Oxo-6,7-Dihydro-5H-5λ⁴-Thieno[3,2-d]Pyrimidin-4-Ylamino]-3-Methylbutan-1-Ol (Example 16)

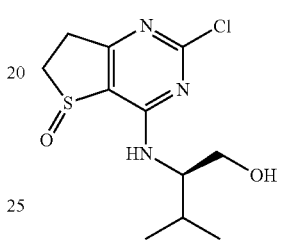

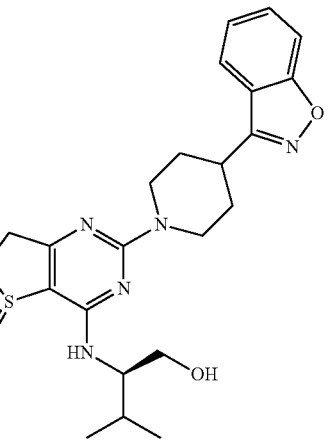

Example 16

Starting from (IV-1) (see 1.2) and 3-piperidin-4-yl-benzo[d]isoxazole Example 16 may be prepared and purified analogously to Example 14 (see 7.).
Analytical HPLC-MS (method C): RT=1.74 min.

9. Synthesis of (R)-3-Methyl-2-[5-Oxo-2-(3.4.5.6-Tetrahydro-2H-[4,4']Bipyridinyl-1-Yl)-6,7-Dihydro-5H-5λ⁴-Thieno[3,2-d]Pyrimidin-4-Ylamino]-Butan-1-Ol (Example 19)

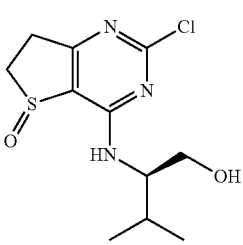

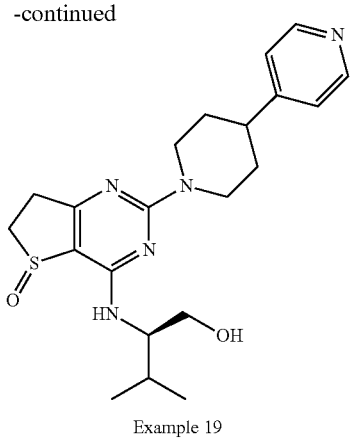

Example 19

Starting from (IV-1) (see 1.2) and 4-piperidin-4-yl-pyridin Example 19 may be prepared and purified analogously to Example 14 (see 7). Analytical HPLC-MS (method C): RT=1.33 min.

10. Synthesis of (R)-2-{2-[4-(2-Ethyl-5-Fluoro-1H-Indol-3-Yl)-Piperidin-1-Yl]-5-Oxo-6,7-Dihydro-5H-5λ⁴-Thieno[3,2-d]Pyrimidin-4-Ylamino}-3-Methylbutan-1-Ol (Example 22)

10.1 2-but-1-ynyl-4-fluorophenylamine

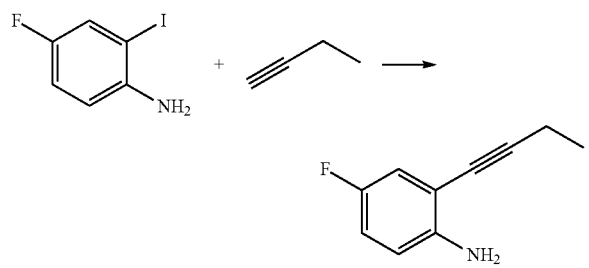

80 ml of tetrahydrofuran is placed under argon. 5 g of 4-fluoro-2-iodophenylamine, 0.74 g dichlorobis(triphenylphosphine) palladium(II), 0.2 g copper iodide and 8.8 ml triethylamine are added. 4 g of gaseous 1-butyne are passed through the suspension. The reaction mixture is stirred under argon for 15 hours at ambient temperature, then filtered through Celite and evaporated to dryness. 3.4 g product are obtained as a solid.
¹H NMR (400 MHz, DMSO): 2.45 (2H, q); 1.18 (3H, t).

10.2 2-ethyl-5-fluoro-1H-indole

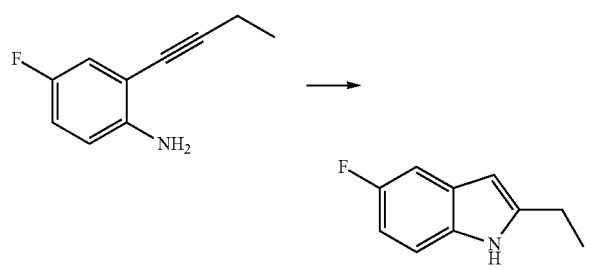

Under argon 4.9 g potassium-tert-butoxide are suspended in 25 ml N-methyl-2-pyrrolidinone and a suspension of 3.4 g 2-but-1-ynyl-4-fluorophenylamine in 25 ml N-methyl-2-pyrrolidinone is added dropwise thereto. The reaction mixture is stirred for 3 hours at ambient temperature and mixed with water. The product is extracted with diethyl ether and purified by chromatography (silica gel, cyclohexane/ethyl acetate 100/0-90/10). 2.83 g product are obtained as a solid. ¹H NMR (400 MHz, DMSO): 2.72 (2H, q); 1.27 (3H, t).

10.3 2-ethyl-5-fluoro-3-(1,2,3,6-tetrahydropyridin-4-yl)-1H-indole

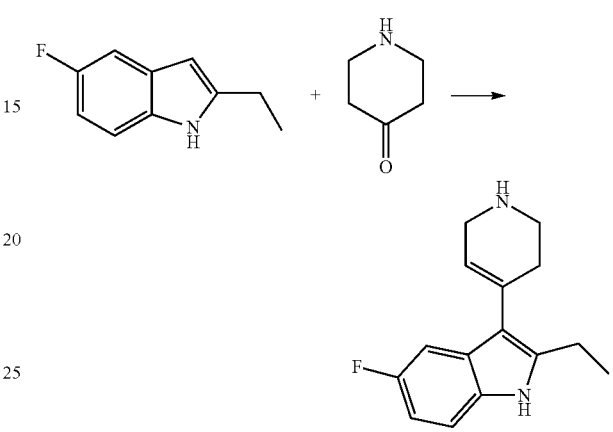

2.83 g 2-ethyl-5-fluoro-1H-indole are suspended in 50 ml acetic acid and heated to 90° C. A suspension of 6.66 g 4-piperidone in 15 ml phosphoric acid 2N is added. The reaction mixture is stirred for 3 hours at 90° C., combined with sodium hydroxide solution and the product is extracted with ethyl acetate. 2.85 g product are obtained as a solid.
¹H NMR (400 MHz, DMSO): 5.63 (1H, s); 2.73 (2H, q); 1.23 (3H, t).

10.4 2-ethyl-5-fluoro-3-piperidin-4-yl-1H-indole (V-1)

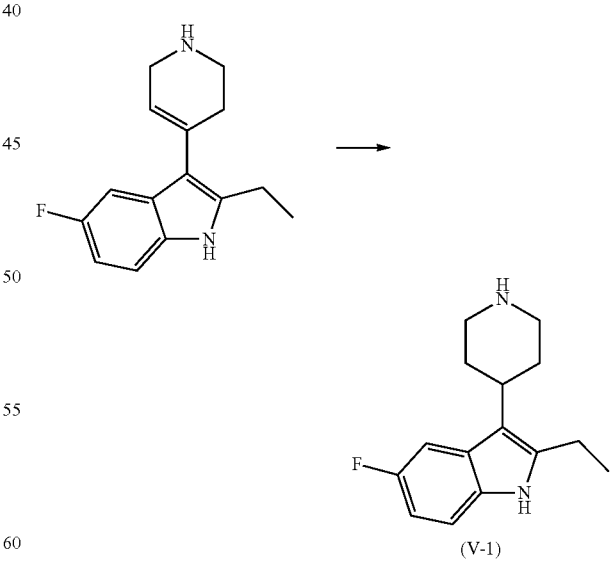

2.83 g 2-ethyl-5-fluoro-3-(1,2,3,6-tetrahydropyridin-4-yl)-1H-indole are suspended in 50 ml of methanol and hydrogenated with 0.3 g Pd/C 10% at normal pressure and ambient temperature. The catalyst is suction filtered and the filtrate is evaporated to dryness. 2.3 g (V-1) are obtained as a solid. ¹H NMR (400 MHz, DMSO): 2.70 (2H, q); 1.19 (3H, t).

10.5 (R)-2-{2-[4-(2-ethyl-5-fluoro-1H-indol-3-yl)-piperidin-1-yl]-5-oxo-6,7-dihydro-5H-5λ⁴-thieno[3,2-d]pyrimidin-4-ylamino}-3-methylbutan-1-ol (Example 22)

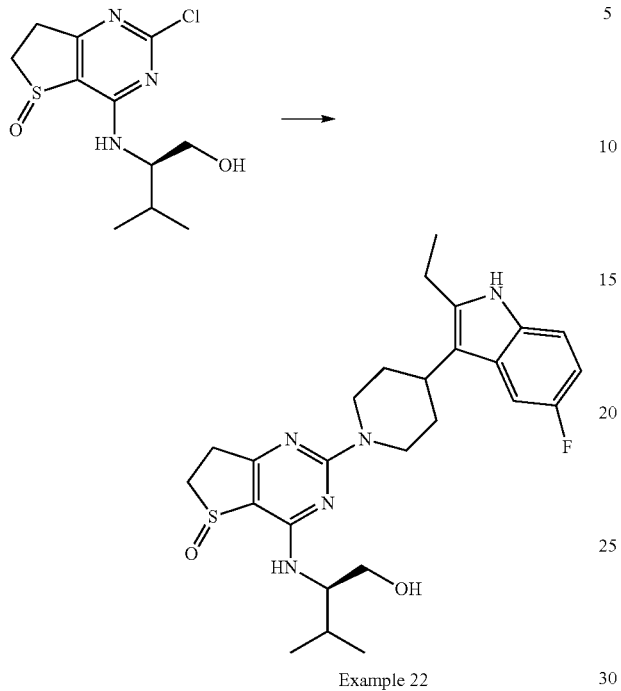

Example 22

Starting from (IV-1) (see 1.2) and (V-1) Example 22 may be prepared and purified analogously to Example 14 (see 7.). Analytical HPLC-MS (method C): RT=1.83 min.

11. Synthesis of 1-(4-(1-Hydroxymethylcyclopropylamino)-5-Oxo-6,7-Dihydro-5H-5λ⁴-Thieno[3,2-d]Pyrimidin-2-Yl)-3'-Methyl-1'H-Spiro[Piperidin-4,4'-Quinazolin]-2'(3'H)-One (Example 28)

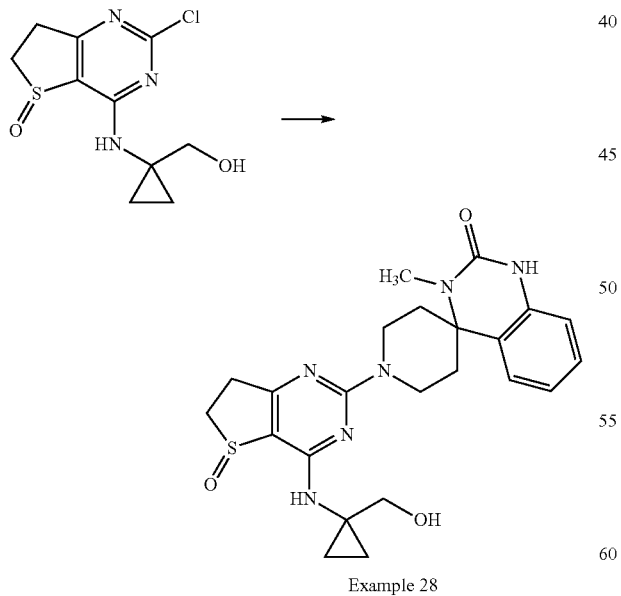

Example 28

Starting from (IV-2) (see 2.4) and 3'-methyl-1'H-spiro[piperidin-4,4'-quinazolin]-2'(3'H)-one (*Chem. Pharm. Bull.* 1988, 4659) Example 28 may be prepared and purified analogously to Example 14 (see 7.). Analytical HPLC-MS (method C): RT=1.52 min.

12. Synthesis of Ethyl 3-{1-[4-(1-Hydroxymethylcyclopropylamino)-5-Oxo-6,7-Dihydro-5H-5λ⁴-Thieno[3,2-d]Pyrimidin-2-Yl]-Piperidin-4-Yl}-1H-Indol-6-Carboxylate (Example 29)

12.1 3-(1-benzyl-1,2,3,6-tetrahydropyridin-4-yl)-1H-indole-6-carboxylic acid

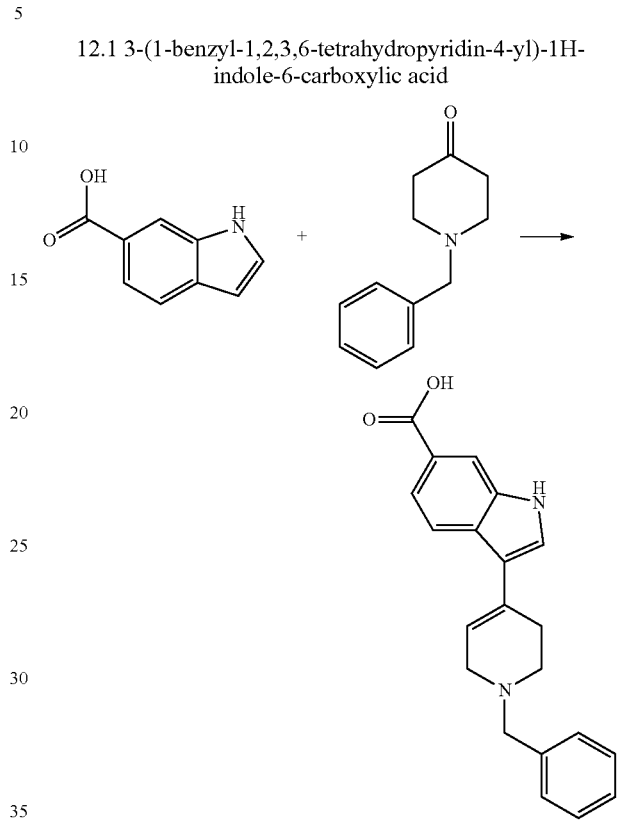

2.6 g potassium hydroxide are suspended in 25 ml of methanol and 2.5 g 1H-indole-6-carboxylic acid and 5.5 g 1-benzyl-piperidin-4-one are added. The reaction mixture is stirred for 15 hours at reflux temperature and then evaporated to dryness. The residue is combined with hydrochloric acid (1 M) and evaporated to dryness. The residue is treated with methanol and diethyl ether and the solid is suction filtered. 12.4 g product are obtained as a solid.

¹H NMR (400 MHz, DMSO): 6.2 (1H, s).

12.2 ethyl 3-(1-benzyl-1,2,3,6-tetrahydropyridin-4-yl)-1H-indole-6-carboxylate

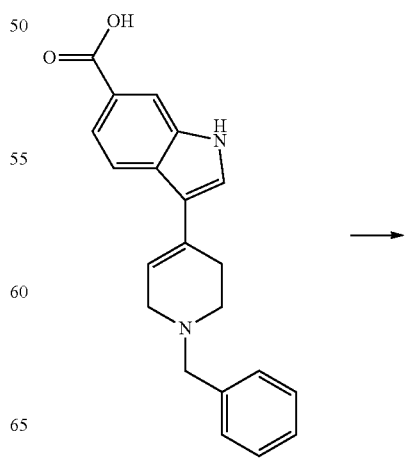

-continued

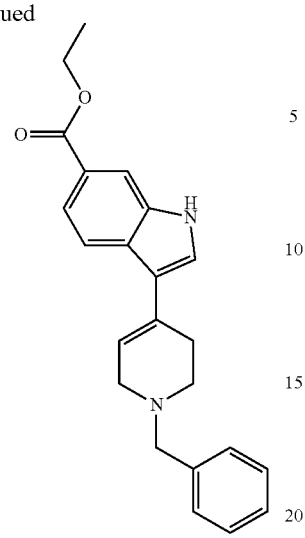

12.4 g 3-(1-benzyl-1,2,3,6-tetrahydropyridin-4-yl)-1H-indole-6-carboxylic acid are suspended in 80 ml of ethanol and 1.6 ml conc. Sulphuric acid are added. The reaction mixture is stirred for 96 hours at reflux temperature. The solid is suction filtered, dissolved in ethanol and made basic with sodium hydroxide solution. 5.3 g product are obtained as a solid.

$^1$H NMR (400 MHz, DMSO): 6.2 (1H, s); 4.3 (2H, q); 1.35 (3H, s).

12.3 ethyl 3-(1,2,3,6-tetrahydropyridin-4-yl)-1H-indole-6-carboxylate (V-2)

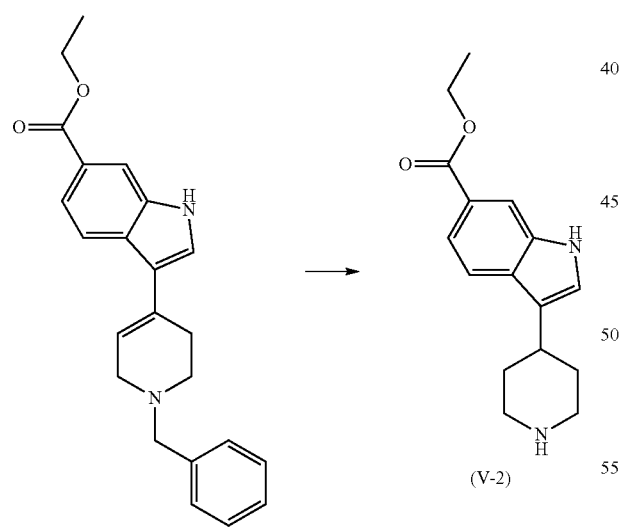

5 g ethyl 3-(1-benzyl-1,2,3,6-tetrahydropyridin-4-yl)-1H-indole-6-carboxylate and 2.3 g palladium hydroxide are suspended in 180 ml of methanol and hydrogenated at 50 psi for 2 hours at ambient temperature. The catalyst is suction filtered and the mother liquor is evaporated to dryness. 3.6 g (V-2) are obtained as a solid.

$^1$H NMR (400 MHz, DMSO): 4.3 (2H, q); 2.95-2.80 (1H, m); 1.35 (3H, s).

12.4 ethyl 3-{1-[4-(1-hydroxymethylcyclopropylamino)-5-oxo-6,7-dihydro-5H-5$\lambda^4$-thieno[3,2-d]pyrimidin-2-yl]-piperidin-4-yl}-1H-indole-6-carboxylate (Example 29)

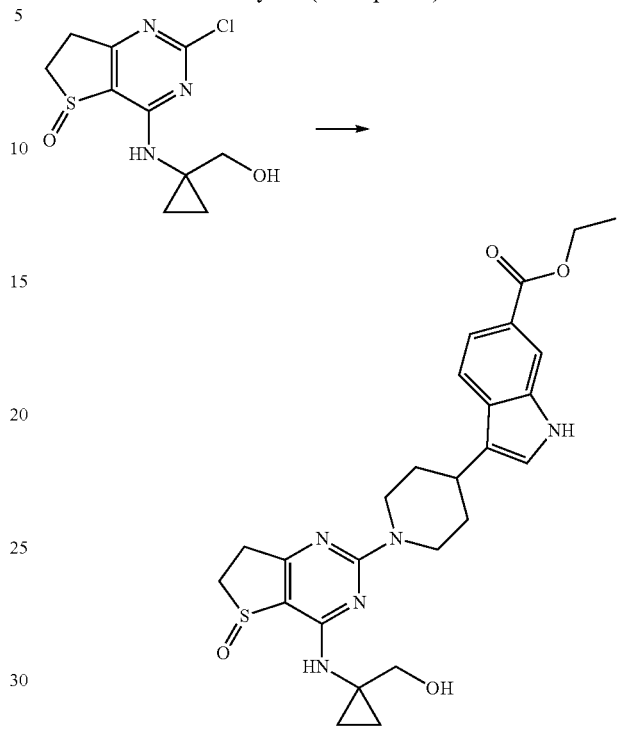

Example 29

Starting from (IV-2) (see 2.4) and (V-2) (see 12.3) Example 29 may be prepared and purified analogously to Example 14 (see 7.). Analytical HPLC-MS (method C): RT=1.77 min.

13. Synthesis of (1-{2-[4-(2-Ethyl-5-Fluoro-1H-Indol-3-Yl)-Piperidin-1-Yl]-5-Oxo-6,7-Dihydro-5H-5$\lambda^4$-Thieno[3,2-d]Pyrimidin-4-Ylamino}-Cyclopropyl)-Methanol (Example 37)

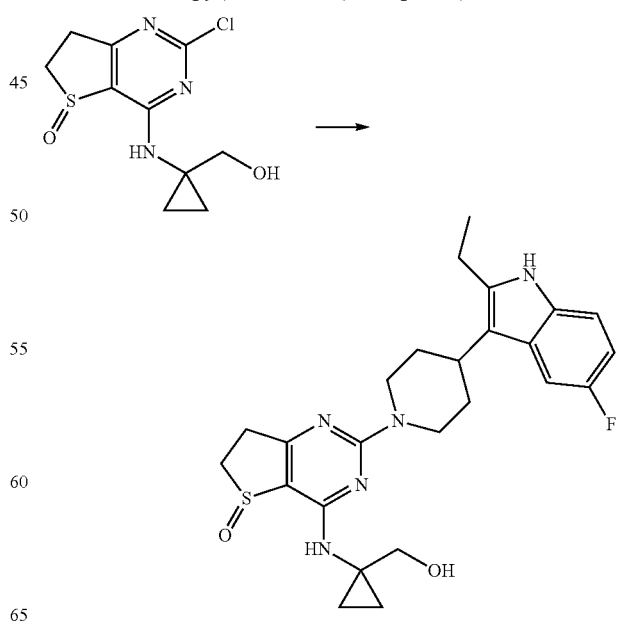

Example 37

Starting from (IV-2) (see 2.4) and (V-1) (see 10.4) Example 37 may be prepared and purified analogously to Example 14 (see 7.). Analytical HPLC-MS (method C): RT=1.78 min.

14. Synthesis of (S)-3'-Methyl-1-(4-(1-Methyl-6-Oxopiperidin-3-Ylamino)-5-Oxo-6,7-Dihydro-5H-5λ⁴-Thieno[3,2-d]Pyrimidin-2-YL)-3'-Methyl-1'H-Spiro[Piperidin-4,4'-Quinazolin]-2'(3'H)-One (Example 43)

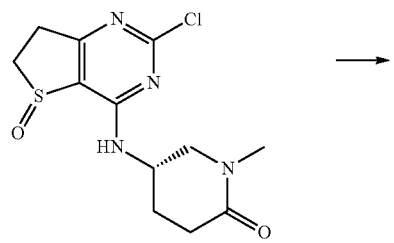

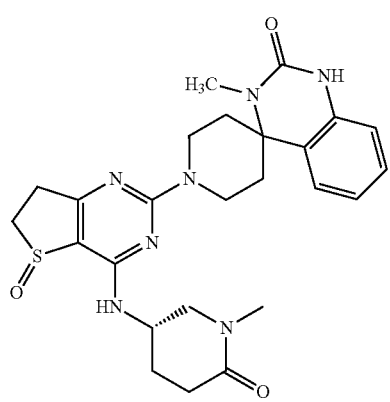

Example 43

Starting from (IV-5) (see 5.5) and 3'-methyl-1'H-spiro[piperidin-4,4'-quinazolin]-2'(3'-1)-one (*Chem. Pharm. Bull.* 1988, 4659) Example 43 may be prepared and purified analogously to Example 14 (see 7.). Analytical HPLC-MS (method C): RT=1.49 min.

15. Synthesis of 1-[4-((S)-1-Methyl-6-Oxopiperidin-3-Ylamino)-5-Oxo-6,7-Dihydro-5H-5λ⁴-Thieno[3,2-d]Pyrimidine-2-Yl]-4-Phenylpiperidine-4-Carbonitrile (Example 55)

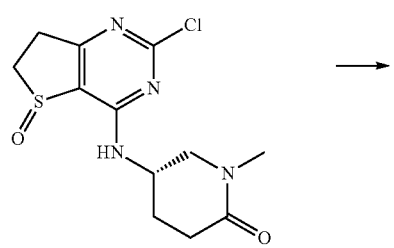

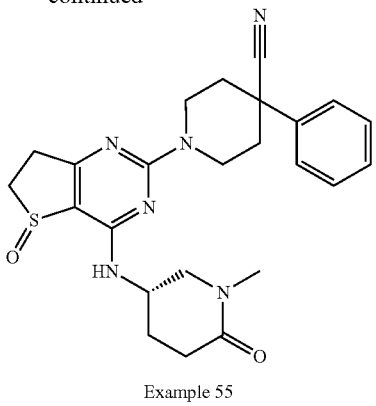

Example 55

Starting from (IV-5) (see 5.5) and 4-phenylpiperidine-4-carbonitrile Example 55 may be prepared and purified analogously to Example 14 (see 7).

Analytical HPLC-MS (method C): RT=1.71 min.

16. Synthesis of 3'-Methyl-1-(4-(Tetrahydro-2H-Pyran-4-Ylamino)-5-Oxo-6,7-Dihydro-5H-5λ⁴-Thieno[3,2-d]Pyrimidin-2-Yl)-1'H-Spiro[Piperidin-4,4'-Quinazolin]-2'(3'H)-One (Example 58)

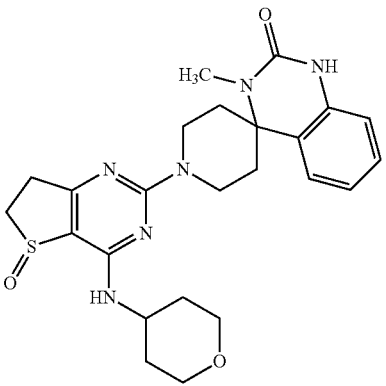

Example 58

Starting from (IV-6) (see 6.2) and 3'-methyl-1'H-spiro[piperidin-4,4'-quinazolin]-2'(3'H)-ONE (*Chem. Pharm. Bull.* 1988, 4659) Example 58 may be prepared and purified analogously to Example 14 (see 7.). Analytical HPLC-MS (method C): RT=1.56 min.

17. Synthesis of 1-(4-(3-Fluorophenylamino)-5-Oxo-6,7-Dihydro-5H-5λ⁴-Thieno[3,2-d]Pyrimidin-2-Yl)-3'-Methyl-1'H-Spiro[Piperidin-4,4'-Quinazolin]-2'(3'H)-One (Example 73)

17.1 (2-chloro-6,7-dihydrothieno[3,2-d]pyrimidin-4-yl)-(3-fluorophenyl)-amine (III-7)

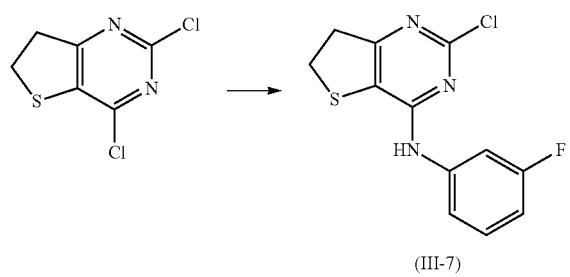 [SMILES: Clc1nc(Cl)c2c(n1)CCS2 ; Fc1cccc(Nc2nc(Cl)nc3c2SCC3)c1 ; "(III-7)"]

(III-7)

4 g (II) are placed in 15 ml dimethylformamide, then 4.5 ml diisopropylethylamine and then 2.5 ml 3-fluorophenylamine are added. The reaction mixture is heated to 120° C., until there is no further reaction, and cooled, then evaporated down. The residue is mixed with water. The product is extracted with dichloromethane and purified by chromatography (silica gel, petroleum ether/ethyl acetate 80/20 to 60/40). 2.6 g (III-7) are obtained as a solid.
Analytical HPLC (method A): RT=3.27 min 17.2 2-chloro-5-oxo-6,7-dihydro-5H-5λ⁴-thieno[3,2-d]pyrimidin-4-yl)-(3-fluorophenyl)-amine (IV-7)

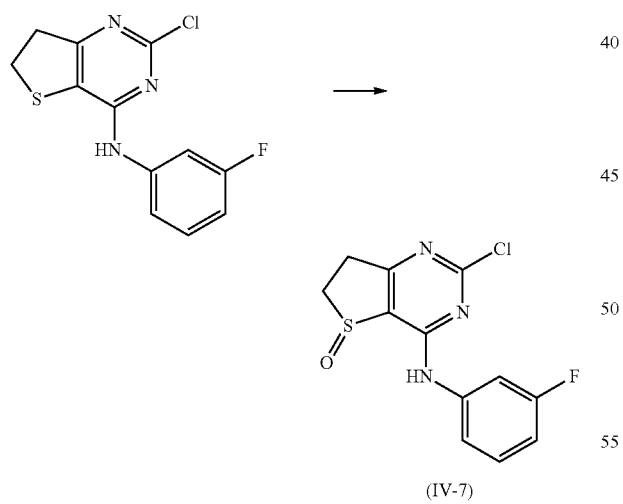

(IV-7)

0.102 g S-(−)-1,1'-bi-2-naphthol are placed in 0.5 ml chloroform under argon, then 0.052 ml titanium(IV)-isopropoxide and 0.064 ml of water are added. The reaction mixture is stirred for 45 minutes at ambient temperature. Then a suspension of 0.5 g (III-7) in 25 ml chloroform is added. The reaction mixture is cooled to −2°/−4° C. and after 20 minutes 0.323 ml tert-butylhydroperoxide 5-6 M in decane are added dropwise. The reaction mixture is stirred further at −2/−4° C., until there is no further reaction, and mixed with water. The product is extracted with dichloromethane and purified by chromatography (silica gel, dichloromethane/methanol 100/0 to 95/5). 0.47 g (IV-7) are obtained as a solid.
Analytical HPLC-MS (method A): RT=1.15 min.

17.3 1-(4-(3-fluorophenylamino)-5-oxo-6,7-dihydro-5H-5λ⁴-thieno[3,2-d]pyrimidin-2-yl)-3'-methyl-1'H-spiro[piperidin-4,4'-quinazolin]-2'(3'H)-one (Example 73)

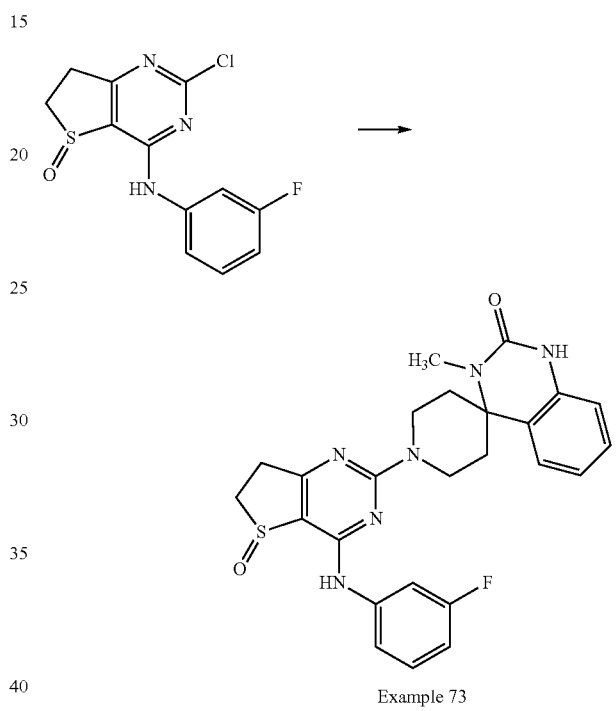

Example 73

Starting from (IV-7) (see 17.2) and 3'-methyl-1'H-spiro[piperidin-4,4'-quinazolin]-2'(3'H)-one (*Chem. Pharm. Bull.* 1988, 4659) Example 73 may be prepared and purified analogously to Example 14 (see 7.). Analytical HPLC-MS (method C): RT=1.81 min.

18. Synthesis of [2-(4-Benzo[d]Isoxazol-3-Yl-Piperidin-1-Yl)-5-Oxo-6,7-6,7-Dihydro-5H-5λ⁴-Thieno[3,2-d]Pyrimidin-4-Yl]-(3-Fluorophenyl)-Amine (Example 75)

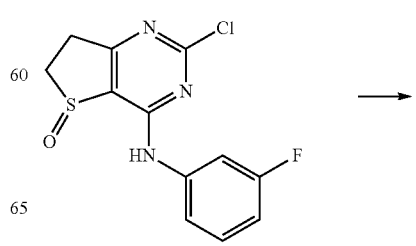

-continued

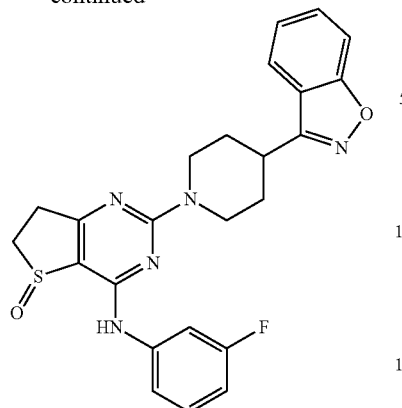

Example 75

Starting from (IV-7) (see 17.2) and 3-piperidin-4-yl-benzo[d]isoxazole Example 75 may be prepared and purified analogously to Example 14 (see 7.).

Analytical HPLC-MS (method C): RT=2.11 min.

19. Synthesis of (3-Fluorophenyl)-[5-Oxo-2-(3.4.5.6-Tetrahydro-2H-[4,4']Bipyridinyl-1-Yl)-6,7-Dihydro-5H-5λ⁴-Thieno[3,2-d]Pyrimidin-4-Yl]-Amine Trifluoroacetate (Example 78)

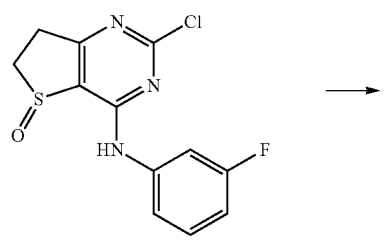

Example 78

Starting from (IV-7) (see 17.2) and 4-(4-chlorophenyl)-piperidine Example 78 may be prepared and purified as the trifluoroacetate analogously to Example 14 (see 7.).

Analytical HPLC-MS (method C): RT=1.55 min.

20. Synthesis of {2-[4-(2-Ethyl-5-Fluoro-1H-Indol-3-Yl)-Piperidin-1-Yl]-5-Oxo-6,7-Dihydro-5H-5λ⁴-Thieno[3,2-d]Pyrimidin-4-Yl}-(3-Fluorophenyl)-Amine (Example 82)

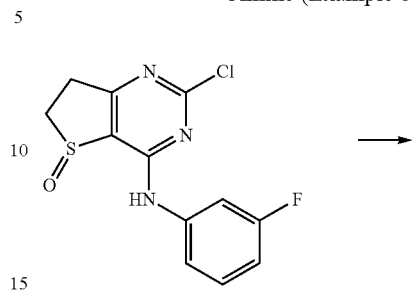

Example 82

Starting from (IV-7) (see 17.2) and (V-1) (see 10.4) Example 82 may be prepared and purified analogously to Example 14 (see 7.).

Analytical HPLC-MS (method C): RT=2.12 min.

21. Synthesis of (1-{2-[4-(2,4-Difluorophenyl)-Piperidin-1-Yl]-5-Oxo-6,7-Dihydro-5H-5λ⁴-Thieno[3,2-d]Pyrimidin-4-Ylamino}-Cyclopropyl)-Methanol (Example 89)

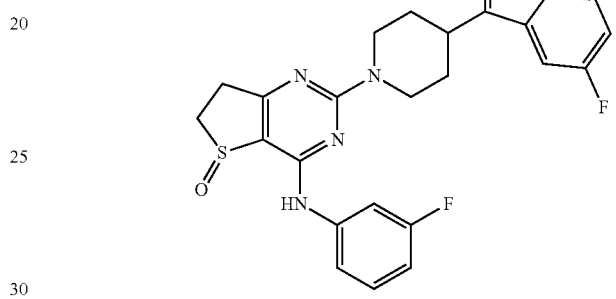

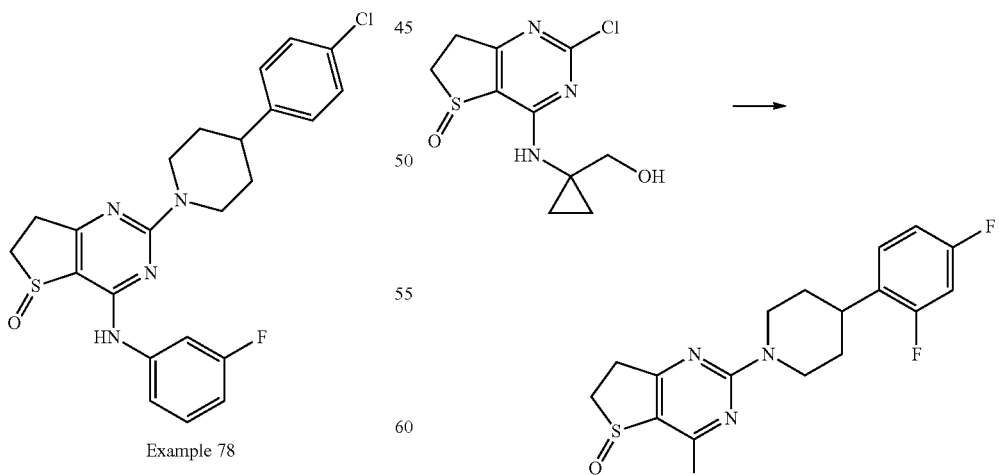

Example 89

Starting from (IV-2) (see 2.4) and 4-(2,4-difluorophenyl)-piperidine Example 89 may be prepared analogously to Example 14 (see 7.). The product may be purified by chromatography (preparative HPLC, method B).

Analytical HPLC-MS (method D): RT=1.18 min.

22. Synthesis of {2-[4-(2,4-Difluorophenyl)-Piperidin-1-Yl]-5-Oxo-6,7-Dihydro-5H-5λ⁴-Thieno[3,2-d]Pyrimidin-4-Yl}-(Tetrahydropyran-4-Yl)-Amine (Example 90)

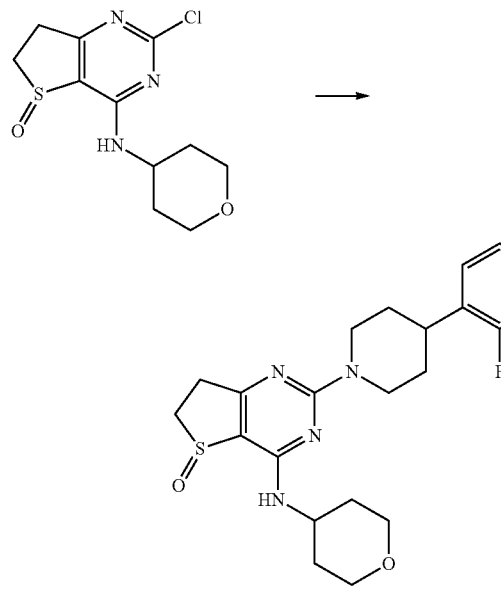

Example 90

Starting from (IV-6) (see 6.2) and 4-(2,4-difluorophenyl)-piperidine Example 90 may be prepared and purified analogously to Example 89 (see 21.).

Analytical HPLC-MS (method D): RT=1.23 min.

23. Synthesis of (1-{2-[4-(3,5-Dichlorophenyl)-Piperidin-1-Yl]-5-Oxo-6,7-Dihydro-5H-5λ⁴-Thieno[3,2-d]Pyrimidin-4-Ylamino}-Cyclopropyl)-Methanol (Example 91)

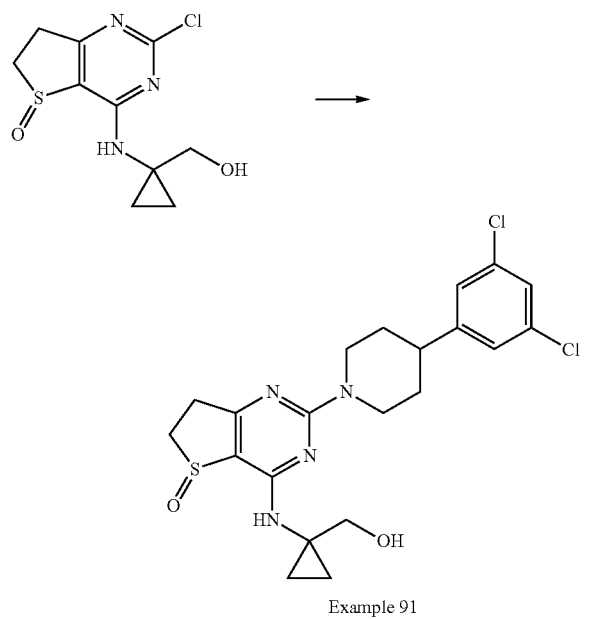

Example 91

Starting from (IV-2) (see 2.4) and 4-(3,5-dichlorophenyl)-piperidine Example 91 may be prepared and purified analogously to Example 89 (see 21.).

Analytical HPLC-MS (method D): RT=1.30 min.

24. Synthesis of (1-{2-[4-(4-Bromophenyl)-Piperidin-1-Yl]-5-Oxo-6,7-Dihydro-5H-5λ⁴-Thieno[3,2-d]Pyrimidin-4-Ylamino}-Cyclopropyl)-Methanol (Example 92)

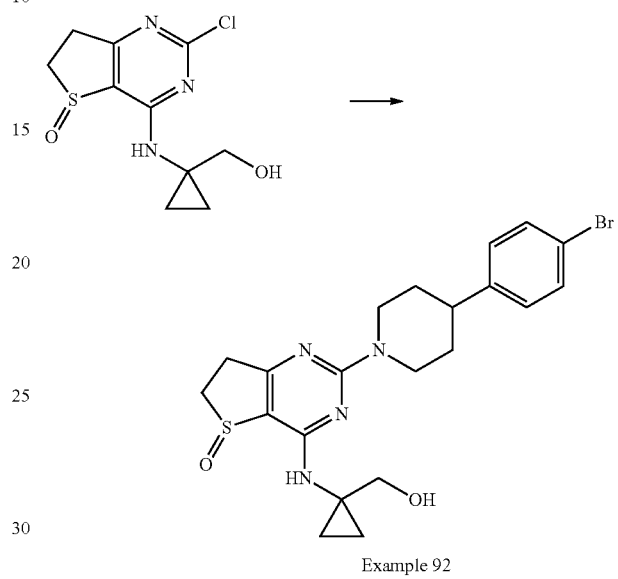

Example 92

Starting from (IV-2) (see 2.4) and 4-(4-bromophenyl)-piperidine Example 92 may be prepared and purified analogously to Example 89 (see 21.).

Analytical HPLC-MS (method D): RT=1.23 min.

25. Synthesis of {2-[4-(4-Bromophenyl)-Piperidin-1-Yl]-5-Oxo-6,7-Dihydro-5H-5λ⁴-Thieno[3,2-d]Pyrimidine-4-Yl}-(Tetrahydropyran-4-Yl)-Amine (Example 93)

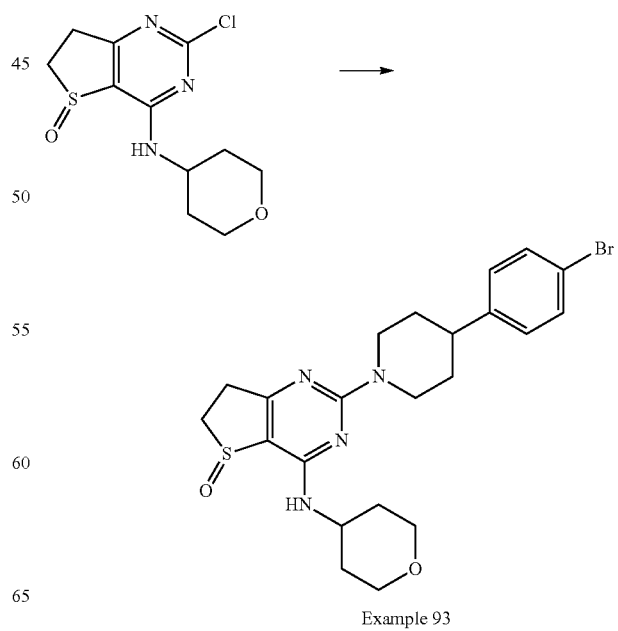

Example 93

Starting from (IV-6) (see 6.2) and 4-(4-bromophenyl)-piperidine Example 93 may be prepared and purified analogously to Example 89 (see 21).
Analytical HPLC-MS (method D): RT=1.28 min.

26. Synthesis of (1-{5-Oxo-2-[4-(4-Trifluoromethylphenyl)-Piperidin-1-Yl]-6,7-Dihydro-5H-5λ⁴-Thieno[3,2-d]Pyrimidin-4-Ylamino}-Cyclopropyl)-Methanol (Example 95)

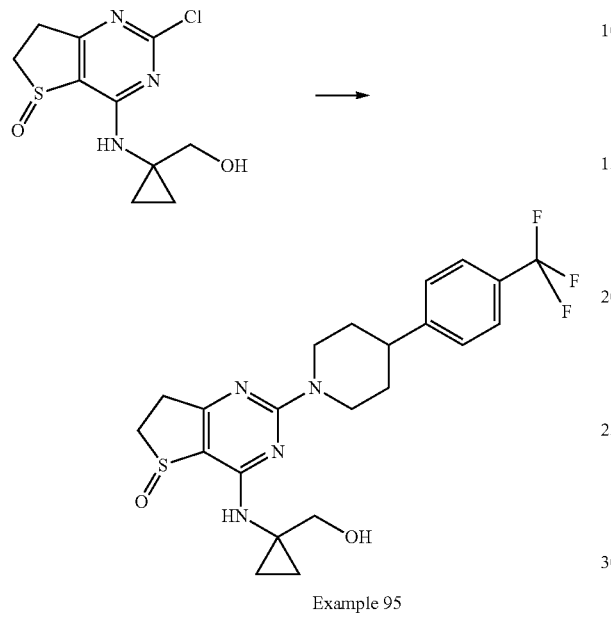

Example 95

Starting from (IV-2) (see 2.4) and 4-(4-trifluoromethylphenyl)-piperidine Example 95 may be prepared and purified analogously to Example 89 (see 21.).
Analytical HPLC-MS (method D): RT=1.25 min.

27. Synthesis of {5-Oxo-2-[4-(4-Trifluoromethylphenyl)-Piperidin-1-Yl]-6,7-Dihydro-5H-5λ⁴-Thieno[3,2-d]Pyrimidin-4-Yl}-(Tetrahydropyran-4-Yl)-Amine (Example 96)

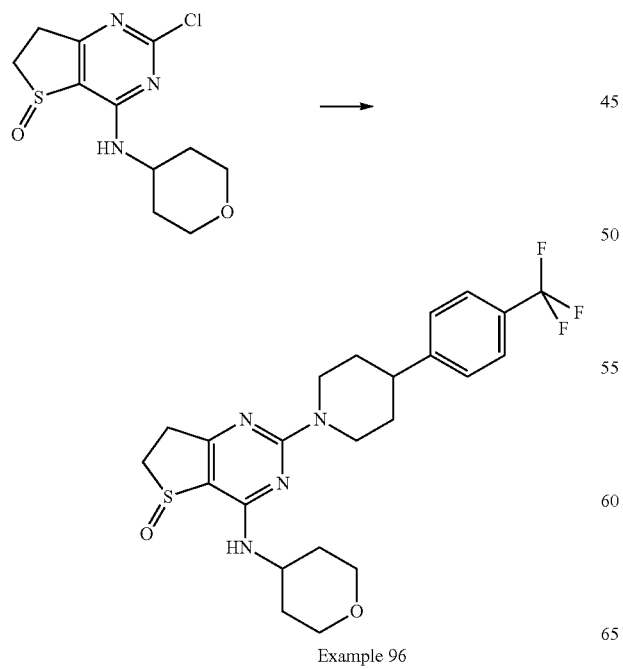

Example 96

Starting from (IV-6) (see 6.2) and 4-(4-trifluoromethylphenyl)-piperidine Example 96 may be prepared and purified analogously to Example 89 (see 21.).
Analytical HPLC-MS (method D): RT=1.29 min.

28. Synthesis of {2-[4-(3,5-Dichlorophenyl)-Piperidin-1-Yl]-5-Oxo-6,7-Dihydro-5H-5λ⁴-Thieno[3,2-d]Pyrimidin-4-Yl}-(Tetrahydropyran-4-Yl)-Amine (Example 97)

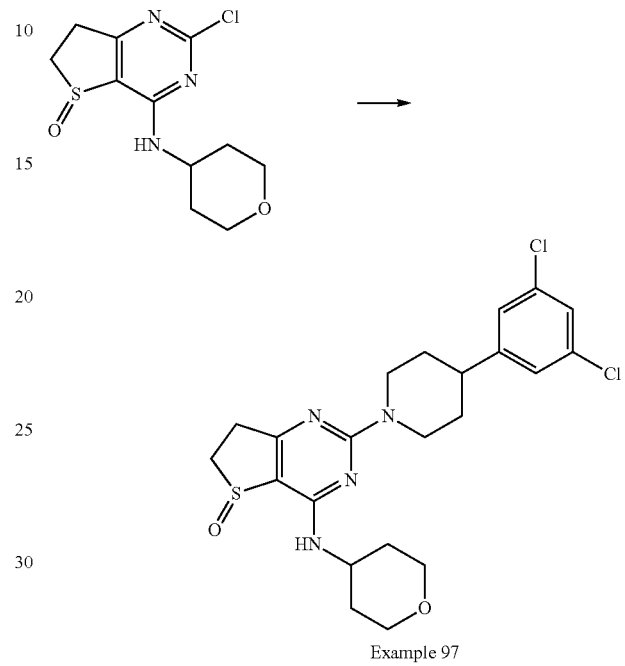

Example 97

Starting from (IV-6) (see 6.2) and 4-(3,5-dichlorophenyl)-piperidine Example 97 may be prepared and purified analogously to Example 89 (see 21.).
Analytical HPLC-MS (method A): RT=1.29 min.

29. Synthesis of {1-[2-(4-Benzoxazol-2-Yl-Piperidin-1-Yl)-5-Oxo-6,7-Dihydro-5H-5λ⁴-Thieno[3,2-d]Pyrimidin-4-Ylamino]-Cyclopropyl}-Methanol (Example 98)

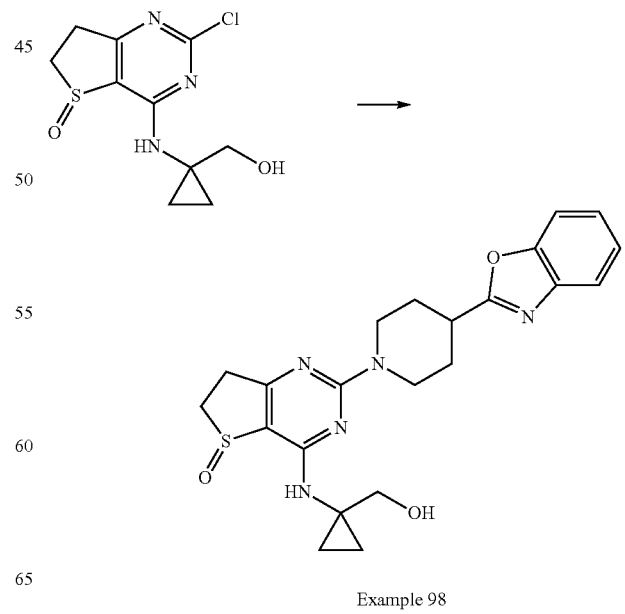

Example 98

Starting from (IV-2) (see 2.4) and 2-piperidin-4-yl-benzoxazole Example 98 may be prepared and purified analogously to Example 89 (see 21).

Analytical HPLC-MS (method B): RT=1.22 min.

30. Synthesis of [2-(4-Benzoxazol-2-Yl-Piperidin-1-Yl)-5-Oxo-6,7-Dihydro-5H-5λ$^4$-Thieno[3,2-d]Pyrimidin-4-Yl]-(Tetrahydropyran-4-Yl)-Amine (Example 99)

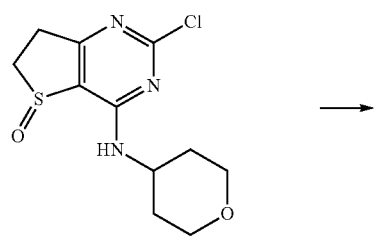

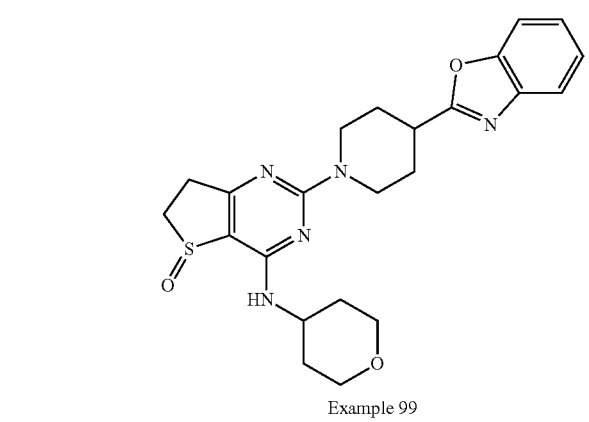

Example 99

Starting from (IV-6) (see 6.2) and 2-piperidin-4-yl-benzoxazole Example 99 may be prepared and purified analogously to Example 89 (see 21.).

Analytical HPLC-MS (method B): RT=1.23 min.

31. Synthesis of (S)-5-[2-(4-Benzoxazol-2-Yl-Piperidin-1-Yl)-5-Oxo-6,7-Dihydro-5H-5λ$^4$-Thieno[3,2-d]Pyrimidin-4-Ylamino]-1-Methylpiperidin-2-One (Example 100)

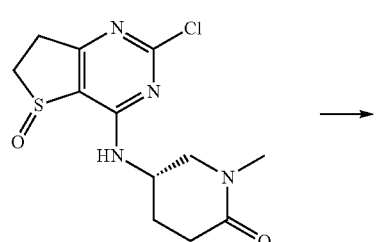
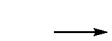

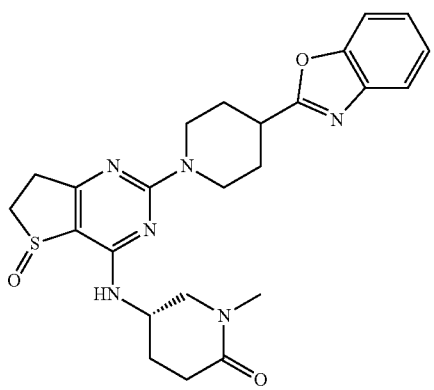

Example 100

Starting from (IV-5) (see 5.5) and 2-piperidin-4-yl-benzoxazole Example 100 may be prepared and purified analogously to Example 89 (see 21.).

Analytical HPLC-MS (method B): RT=1.18 min.

32. Synthesis of (3-Fluorophenyl)-{2-[4-(5-Furan-2-Yl-2H-Pyrazol-3-Yl)-Piperidin-1-Yl]-5-Oxo-6,7-Dihydro-5H-5λ$^4$-Thieno[3,2-d]Pyrimidin-4-Yl}-Amine Trifluoracetat (Example 145)

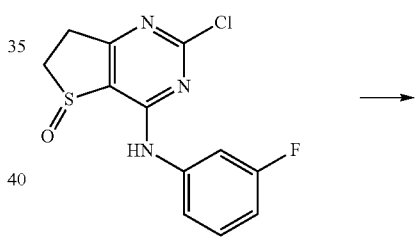

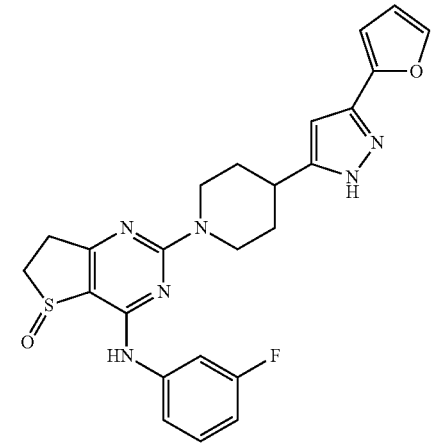

Example 145

Starting from (IV-7) (see 17.2) and 4-(5-furan-2-yl-2H-pyrazol-3-yl)-piperidine Example 145 may be prepared and purified as the trifluoroacetate analogously to Example 14 (see 7.). Analytical HPLC-MS (method C): RT=1.89 min.

33. Synthesis of (3-Fluorophenyl)-{5-Oxo-2-[4-(3-Pyridin-4-Yl-[1,2,4]Oxadiazol-5-Yl)-Piperidin-1-Yl]-6,7-Dihydro-5H-5λ⁴-Thieno[3,2-d]Pyrimidin-4-Yl}-Amine Trifluoroacetate (Example 147)

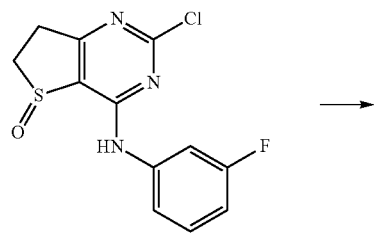

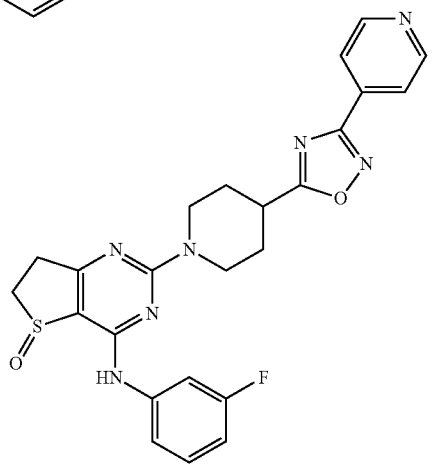

Example 147

Starting from (IV-7) (see 17.2) and 4-(5-piperidin-4-yl-[1,2,4]oxadiazol-3-yl)-pyridine Example 147 may be prepared and purified as the trifluoroacetate analogously to Example 14 (see 7.). Analytical HPLC-MS (method C): RT=1.72 min.

34. Synthesis of (R)-2-{2-[4-(5-Furan-2-Yl-2H-Pyrazol-3-Yl)-Piperidin-1-Yl]-5-Oxo-6,7-Dihydro-5H-5λ⁴-Thieno[3,2-d]Pyrimidin-4-Ylamino}-3-Methylbutan-1-Ol Trifluoroacetate (Example 161)

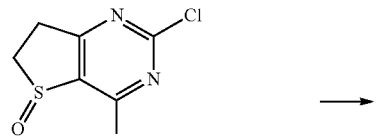

Example 161

Starting from (IV-1) (see 1.2) and 4-(5-furan-2-yl-2H-pyrazol-3-yl)-piperidine Example 161 may be prepared and purified as the trifluoroacetate analogously to Example 14 (see 7.). Analytical HPLC-MS (method C): RT=1.67 min.

35. Synthesis of (R)-3-Methyl-2-{5-Oxo-2-[4-(3-Pyridin-4-Yl-[1,2,4]Oxadiazol-5-Yl)-Piperidin-1-Yl]-6,7-Dihydro-5H-5λ⁴-Thieno[3,2-d]Pyrimidin-4-Ylamino}-Butan-1-Ol Trifluoroacetate (Example 163)

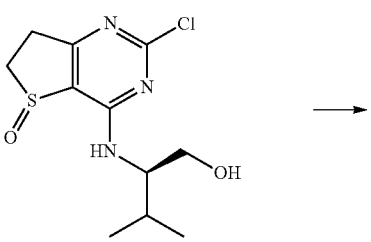

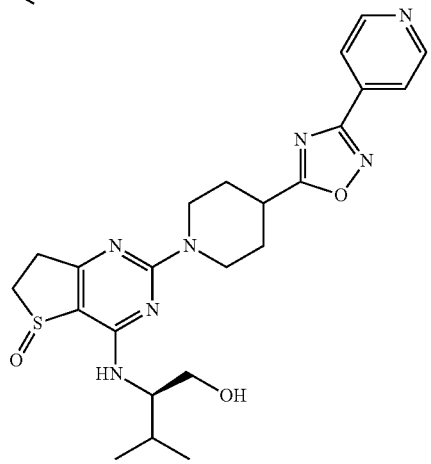

Example 163

Starting from (IV-1) (see 1.2) and 4-(5-piperidin-4-yl-[1,2,4]oxadiazol-3-yl)-pyridine Example 163 may be prepared and purified as the trifluoroacetate analogously to Example 14 (see 7.). Analytical HPLC-MS (method C): RT=1.48 min.

36. Synthesis of: (2-{4-[4-(2-Diethylaminoethoxy)-Phenoxy]-Piperidin-1-Yl}-5-Oxo-6,7-Dihydro-5H-5λ⁴-Thieno[3,2-d]Pyrimidin-4-Yl)-(Tetrahydro Pyran-4-Yl)-Amine (Example 178)

36.1 tert-butyl 4-[4-(2-diethylaminoethoxy)-phenoxy]-piperidine-1-carboxylate

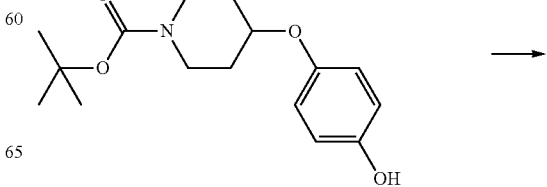

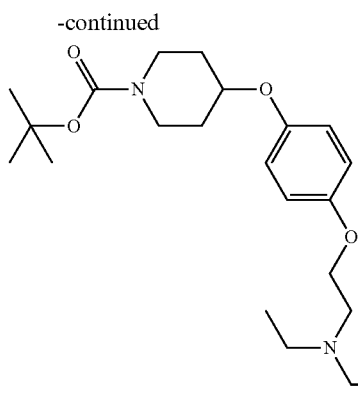

7.9 g tert-butyl 4-(4-hydroxyphenoxy)-piperidine-1-carboxylate (see WO2006/64218), 5.2 g (2-chloroethyl)-diethylamine hydrochloride and 16.6 g potassium carbonate are placed in 250 ml acetone. The reaction mixture is stirred at reflux temperature. After 4 hours the inorganic salts are suction filtered and the mixture is evaporated to dryness. The residue is combined with ethyl acetate. The organic phase is washed with a saturated NaHCO₃ solution, dried and evaporated to dryness. 10.1 g of the product are obtained as an oil.

36.2 diethyl-{2-[4-(piperidin-4-yloxy)-phenoxy]-ethyl}-amine (V-3)

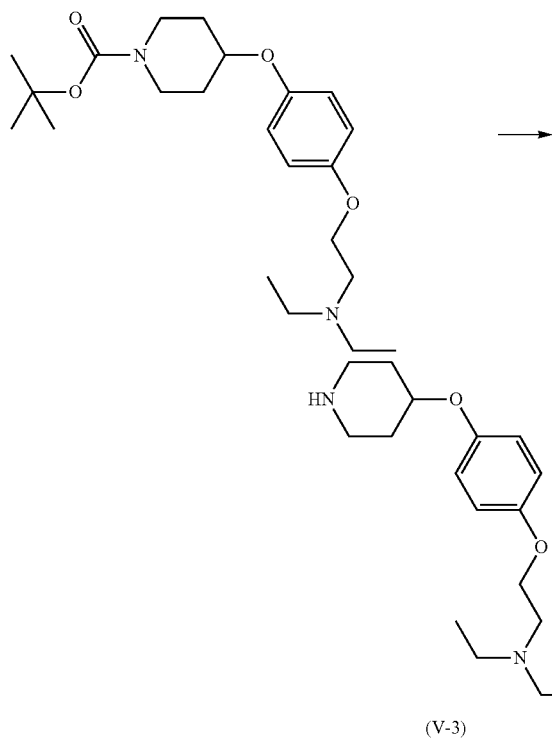

(V-3)

10.1 g tert-butyl 4-[4-(2-diethylaminoethoxy)-phenoxy]-piperidine-1-carboxylate are placed in 20 ml dichloromethane and combined with 30 ml trifluoroacetic acid while being cooled. The reaction mixture is stirred at ambient temperature. After 2 hours the reaction mixture is evaporated to dryness. The residue is combined with an NaOH solution (1M) and the product is extracted with dichloromethane. 5.6 g (V-3) are obtained.

36.3 (2-{4-[4-(2-diethylamino-ethoxy)-phenoxy]-piperidin-1-yl}-5-oxo-6,7-dihydro-5H-5λ⁴-thieno[3,2-d]pyrimidin-4-yl)-(tetrahydropyran-4-yl)-amine (Example 178)

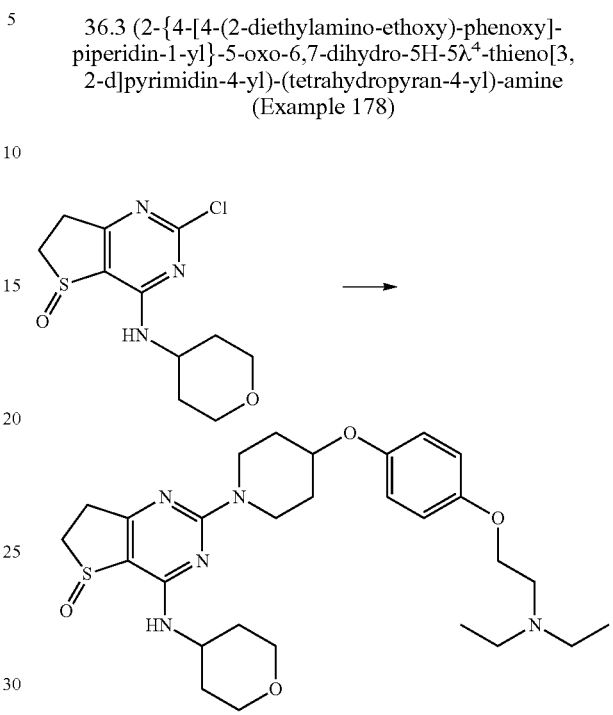

Example 178

Starting from (IV-6) (see 6.2) and (V-3) Example 178 may be prepared and purified analogously to Example 89 (see 21.). Analytical HPLC-MS (method A): RT=1.01 min.

37. Synthesis of: (2-{4-[4-(4,5-Dihydroxazol-2-Yl)-Phenoxy]-Piperidin-1-Yl}-5-Oxo-6,7-Dihydro-5H-5λ⁴-Thieno[3,2-d]Pyrimidin-4-Yl)-(Tetrahydro Pyran-4-Yl)-Amine (Example 180)

37.1 tert-butyl 4-(toluene-4-sulphonyloxy)-piperidine-1-carboxylate

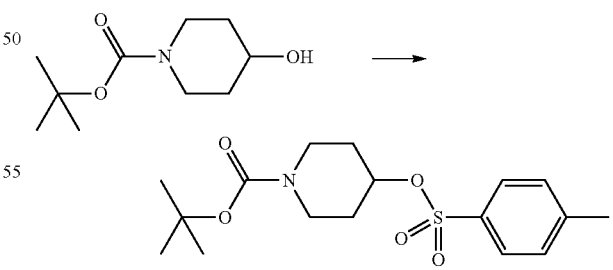

5 g tert-butyl 4-hydroxypiperidine-1-carboxylate are placed in 15 ml of pyridine, then 4.7 g p-toluenesulphonyl chloride are added batchwise. The reaction mixture is stirred at ambient temperature, after 12 hours it is poured onto ice water and the mixture obtained is stirred for a further hour at ambient temperature. The precipitated solid is suction filtered and dried. 7.5 g product are obtained.

37.2 tert-butyl 4-[4-(4,5-dihydroxazol-2-yl)-phenoxy]-piperidine-1-carboxylate

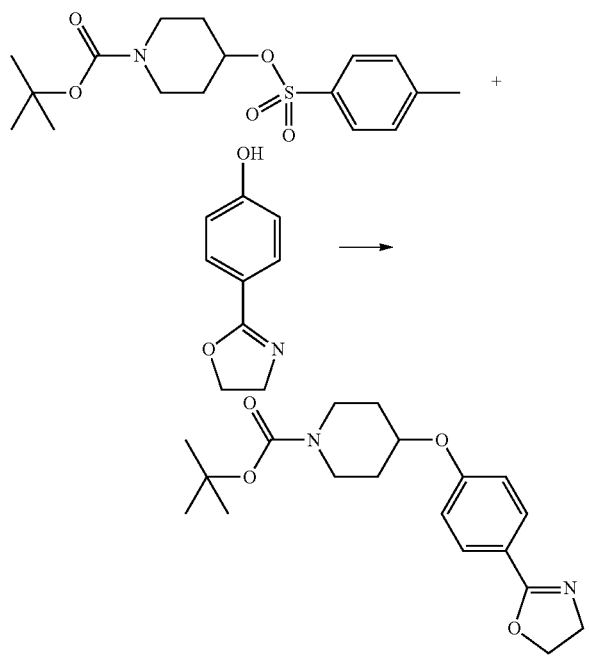

2.0 g 4-(4,5-dihydroxazol-2-yl)-phenol (see U.S. Pat. No. 5,491,201) are placed in 30 ml dimethylformamide, then 3.3 g potassium carbonate and 4.2 g tert-butyl 4-(toluene-4-sulphonyloxy)-piperidine-1-carboxylate are added. The reaction mixture is stirred at 75° C., after 12 hours it is mixed with water and the precipitated solid is suction filtered and dried. 2.8 g product are obtained.

37.3 4-[4-(4,5-dihydroxazol-2-yl)-phenoxy]-piperidine (V-4)

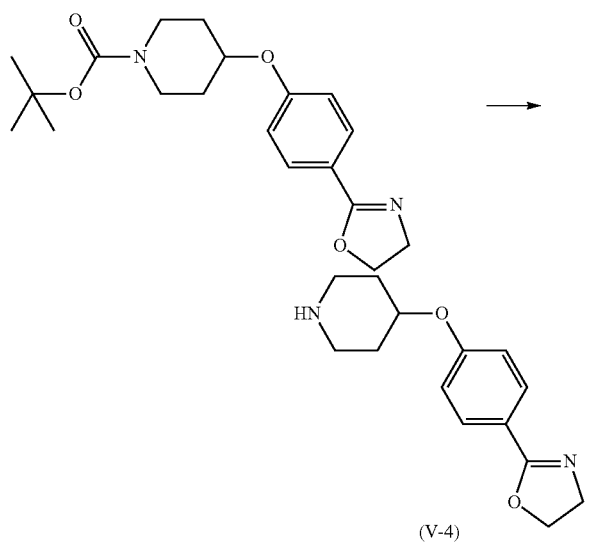

50 mg tert-butyl 4-[4-(4,5-dihydroxazol-2-yl)-phenoxy]-piperidine-1-carboxylate are taken and combined with 6 ml of a (5/1) dichloromethane/trifluoroacetic acid mixture. The reaction mixture is stirred at ambient temperature and after 15 min it is carefully combined with a saturated NaHCO$_3$ solution. The organic phase is dried and evaporated to dryness. 20 mg (V-4) are obtained.

37.4 (2-{4-[4-(4,5-dihydroxazol-2-yl)-phenoxy]-piperidin-1-yl}-5-oxo-6,7-dihydro-5H-5λ$^4$-thieno[3,2-d]pyrimidin-4-yl)-(tetrahydropyran-4-yl)-amine (Example 180)

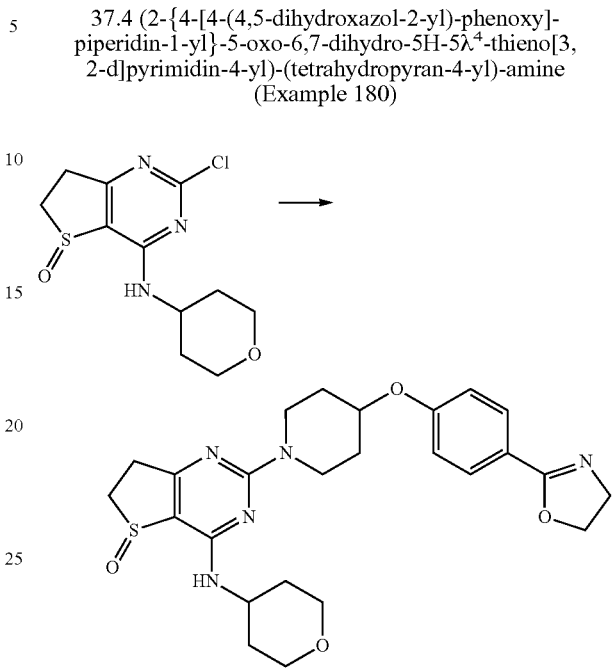

Example 180

Starting from (IV-6) (see 6.2) and (V-4) Example 180 may be prepared and purified analogously to Example 89 (see 21.). Analytical HPLC-MS (method A): RT=0.99 min.

38. Synthesis of: 2,2,2-Trifluoro-1-(7-{1-[5-Oxo-4-(Tetrahydropyran-4-Ylamino)-6,7-Dihydro-5H-5λ$^4$-Thieno[3,2-d]Pyrimidin-2-Yl]-Piperidin-4-Yloxy}-1,2,4,5-Tetrahydrobenzo[d]Azepin-3-Yl)-Ethanone (Example 182)

38.1 2,2,2-trifluoro-1-(7-hydroxy-1,2,4,5-tetrahydrobenzo[d]azepin-3-yl)-ethanone

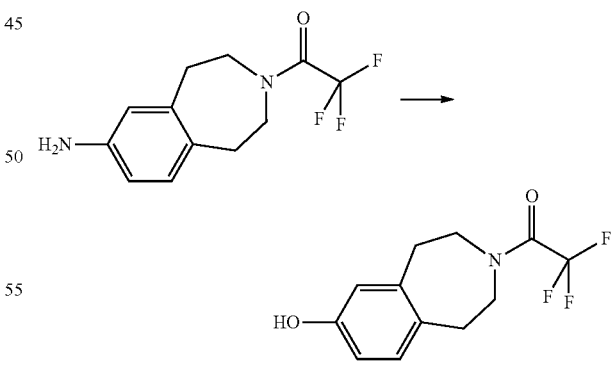

80 g 1-(7-amino-1,2,4,5-tetrahydrobenzo[d]azepin-3-yl)-2,2,2-trifluoro-ethanone (see US2005/137186) and 80 ml conc. Sulphuric acid are placed in 672 ml of water. The reaction mixture is cooled to 0° C., then a mixture of 21.6 g sodium nitrite in 128 ml of water is added dropwise within 10 min. The reaction mixture is stirred for 10 min. At 0°, then for 2 hours at reflux temperature, cooled and poured onto 4 liters of ice water. The precipitated solid is suction filtered and dried. 71.9 g product are obtained.

38.2 2,2,2-trifluoro-1-[7-(piperidin-4-yloxy)-1,2,4,5-tetrahydrobenzo[d]azepin-3-yl]-ethanone (V-5):

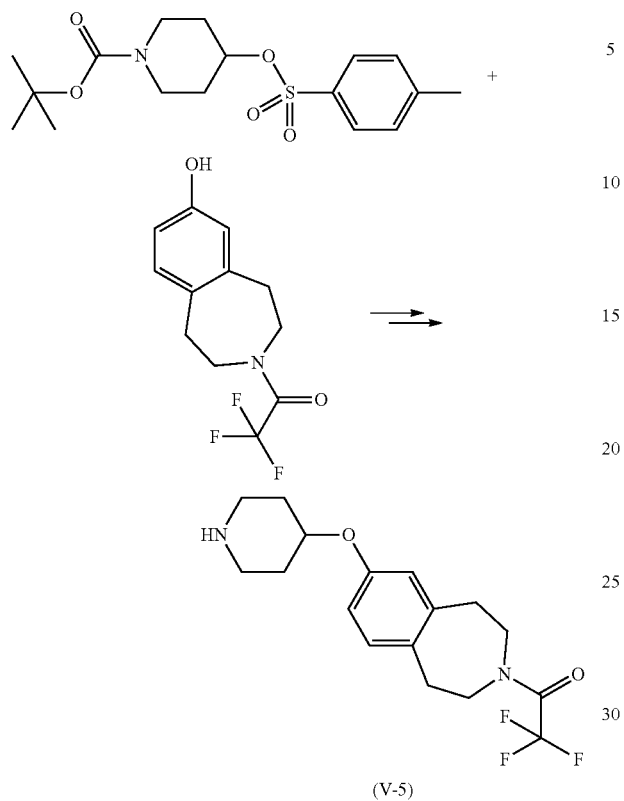

(V-5)

Starting from tert-butyl 4-(toluene-4-sulphonyloxy)-piperidine-1-carboxylate (see 37.1) and 2,2,2-trifluoro-1-(7-hydroxy-1,2,4,5-tetrahydrobenzo[d]azepin-3-yl)-ethanone (see 38.1) (V-5) may be prepared analogously to (V-4) (see 37.2 and 37.3).

38.3 (2-{4-[4-(4,5-dihydroxazol-2-yl)-phenoxy]-piperidin-1-yl}-5-oxo-6,7-dihydro-5H-5λ⁴-thieno[3,2-d]pyrimidin-4-yl)-(tetrahydropyran-4-yl)-amine (Example 182)

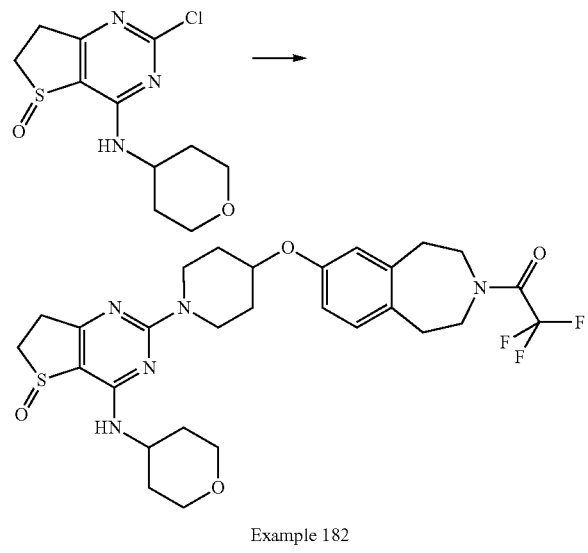

Example 182

Starting from (IV-6) (see 6.2) and (V-5) Example 182 may be prepared and purified analogously to Example 89 (see 21.). Analytical HPLC-MS (method A): RT=1.27 min.

39. Synthesis of: (5-Oxo-2-[4-(2,3,4,5-Tetrahydro-1H-Benzo[d]Azepin-7-Yloxy)-Piperidin-1-Yl]-6,7-Dihydro-5H-5λ⁴-Thieno[3,2-d]Pyrimidin-4-Yl)-(Tetrahydropyran-4-Yl)-Amine (Example 183)

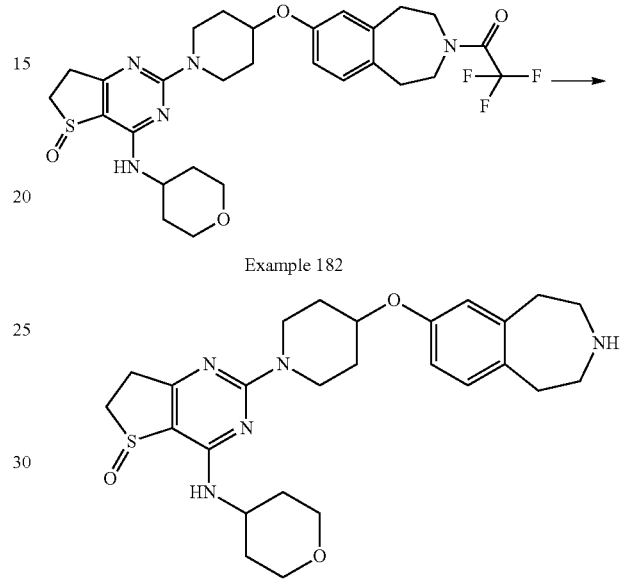

Example 182

Example 183

160 mg of Example 182 (see 38.3) are placed in 5 ml of methanol, then a mixture of 45 mg potassium carbonate in 1 ml of water is added. The reaction mixture is stirred at ambient temperature. After 24 hours the methanol is spun off. The residue is combined with dichloromethane and water. The organic phase is dried and evaporated to dryness. 130 mg Example 183 are obtained as a solid. Analytical HPLC-MS (method A): RT=0.99 min.

40. Synthesis of: 4-{1-[5-Oxo-4-(Tetrahydropyran-4-Ylamino)-6,7-Dihydro-5H-5λ⁴-Thieno[3,2-d]Pyrimidin-2-Yl]-Piperidin-4-Yloxy}-Benzoic Acid (Example 184)

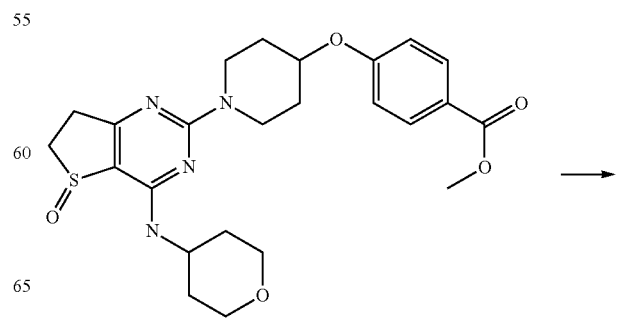

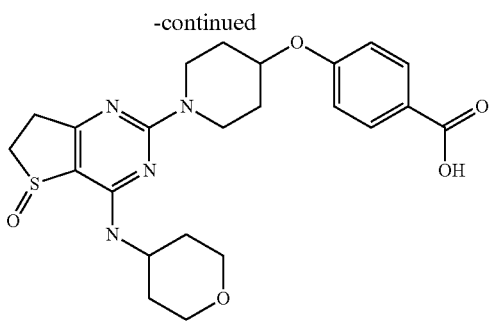

Example 184

80 mg of Example 176 (see Table D) are placed in 1.5 ml of methanol, then 560 l of a 1N NaOH solution are added. The reaction mixture is stirred at 50° C., until there is no further reaction, then combined with a 1 M HCl solution. The product is extracted with dichloromethane. 77 mg Example 184 are obtained as a solid. Analytical HPLC-MS (method B): RT=1.19 min.

41. Synthesis of 2-(1-{2-[4-(4-Chlorophenyl)-Piperidin-1-Yl]-5-Oxo-6,7-Dihydro-5H-5λ$^4$-Thieno[3,2-d]Pyrimidin-4-Ylamino}-Cyclopropyl)-Propan-2-Ol (Example 185)

41.1 2-[1-(2-chloro-6,7-dihydrothieno[3,2-d]pyrimidin-4-ylamino)-cyclopropyl]-propan-2-ol (III-8):

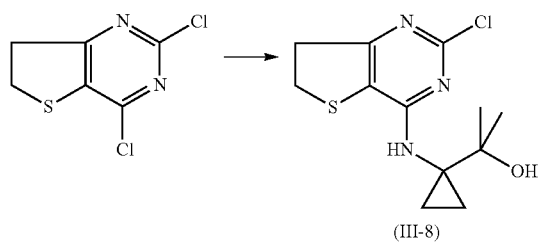 [SMILES: Clc1nc(Cl)c2c(n1)CCS2 ; CC(C)(O)C1(Nc2nc(Cl)nc3c2SCC3)CC1 ; "(III-8)"]

(III-8)

2.7 g (II) are placed in 30 ml dioxane, then 6.8 ml diisopropyl-ethylamine and 1.8 g 2-(1-aminocyclopropyl)-propan-2-ol (see *Liebigs Ann. Chem.* 1978.1194) are added. The reaction mixture is heated to 160° C., until there is no further reaction, and after cooling evaporated to dryness. The residue is combined with ice water. The product is extracted with dichloromethane and purified by chromatography. 125 mg (III-8) are obtained as a solid. Analytical HPLC-MS (method A): RT=1.08 min.

41.2 2-[1-(2-chloro-5-oxo-6,7-dihydro-5H-5λ$^4$-thieno[3,2-d]pyrimidin-4-ylamino)-cyclopropyl]-propan-2-ol (IV-8)

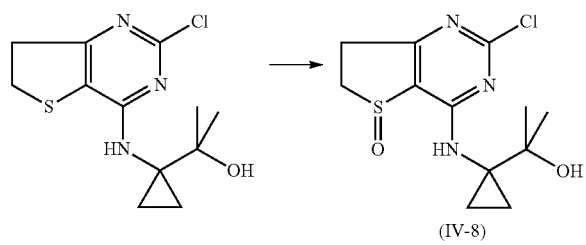

(IV-8)

21.6 mg S-(−)-1,1'-bi-2-naphthol are placed in 1 ml chloroform under argon, then 11 μl titanium(IV)-isopropoxide and 14 μl water are added. The reaction mixture is stirred for 1 hour at ambient temperature. Then a mixture of 120 mg (III-8) in 4 ml dichloromethane is added. The reaction mixture is cooled to −5° C. and after 30 minutes 69.5 μl tert-butylhydroperoxide 5-6 M in decane are added dropwise. The reaction mixture is stirred at −5° C. After 2 days are the same amounts again of S-(−)-1,1'-bi-2-naphthol, titanium(IV)-isopropoxide, water and tert-butylhydroperoxide are added. The reaction mixture is stirred further at −5° C. to 5° C. until there is no further reaction, mixed with water and made basic with NH$_4$OH. The organic phase is evaporated to dryness and the product is purified by chromatography (preparative HPLC, method B). 105 mg (IV-8) are obtained.

Analytical HPLC-MS (method A): RT=0.96 min.

41.3 2-(1-{2-[4-(4-chlorophenyl)-piperidin-1-yl]-5-oxo-6,7-dihydro-5H-5λ$^4$-thieno[3,2-d]pyrimidin-4-ylamino}-cyclopropyl)-propan-2-ol (Example 185)

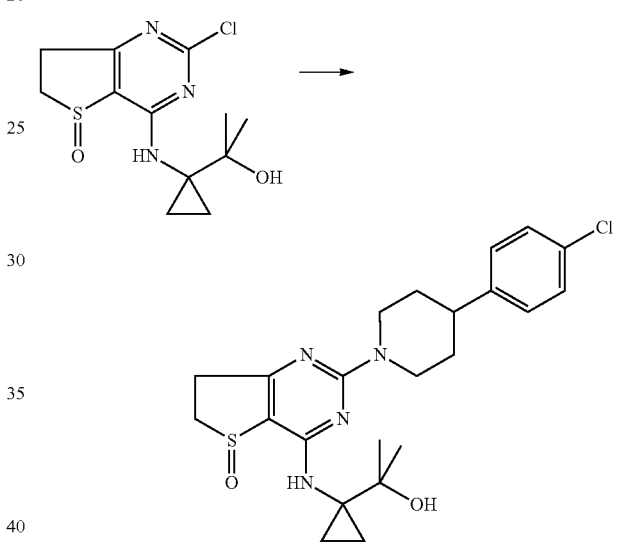

Example 185

Starting from (IV-8) and 4-(4-chlorophenyl)-piperidine hydrochloride Example 185 may be prepared and purified analogously to Example 89 (see 21.).

Analytical HPLC-MS (method B): RT=1.37 min.

42. Synthesis of: (2-[4-(3-Methyl-2,3,4,5-Tetrahydro-1H-Benzo[d]Azepin-7-Yloxy)-Piperidin-1-Yl]-5-Oxo-6,7-Dihydro-5H-5λ$^4$-Thieno[3,2-d]Pyrimidin-4-Yl)-(Tetrahydropyran-4-Yl)-Amine(Example 186)

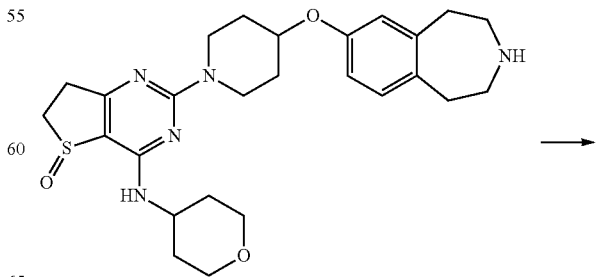

Example 183

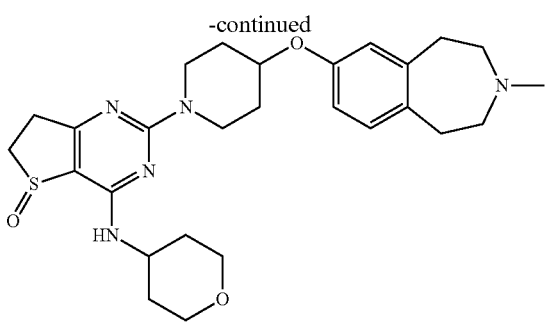

Example 186

100 mg of Example 183 (see 39.) are placed in 2 ml of methanol. The pH of the mixture is adjusted to 6 with acetic acid. 34 l of an aqueous formalin solution are then added. The reaction mixture is stirred for 20 min at ambient temperature, then 50 mg sodium triacetoxyborohydride are slowly added. The reaction mixture is stirred for a further hour at ambient temperature, then combined with an NaHCO$_3$ solution. The product is extracted with dichloromethane and purified by chromatography. 56 mg Example 186 are obtained. Analytical HPLC-MS (method B): RT=1.10 min.

43. Synthesis of: {2-[4-(5-Tert-Butyl-1-Methyl-1H-Indol-3-Yl)-Piperidin-1-Yl]-5-Oxo-6,7-Dihydro-5H-5λ$^4$-Thieno[3,2-d]Pyrimidin-4-Yl}-(Tetrahydro Pyran-4-Yl)-Amine (Example 192)

43.1 tert-butyl 4-(1H-indol-3-yl)-piperidine-1-carboxylate

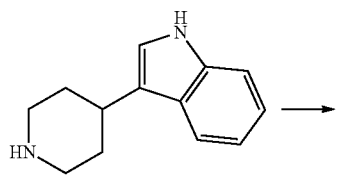

10 g 3-piperidin-4-yl-1H-indole are placed in 300 mL THF and 10.9 g di-tert-butyl-dicarbonate are added. The reaction mixture is stirred overnight at ambient temperature and evaporated to dryness. The residue is mixed with water and the product is extracted with diethyl ether and purified by chromatography. 9 g of the product are obtained as a solid.

43.2 tert-butyl 4-(1-methyl-1H-indol-3-yl)-piperidine-1-carboxylate

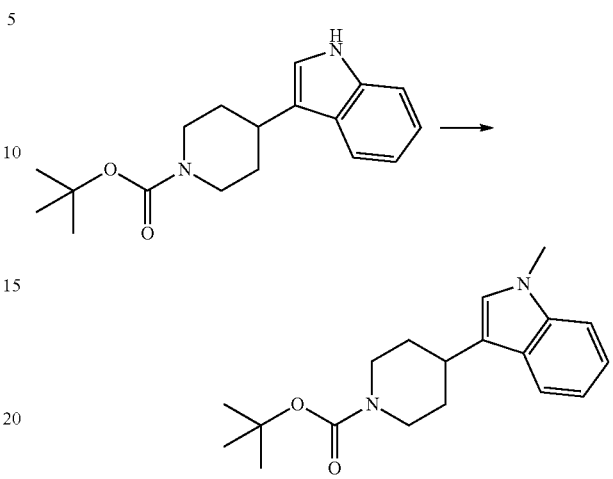

500 mg tert-butyl 4-(1H-indol-3-yl)-piperidine-1-carboxylate are placed in 8 ml dimethylformamide and 73.3 mg sodium hydride (60% in mineral oil) are added. After 15 min 175 µl methyl iodide are added. The reaction mixture is stirred at ambient temperature. After the reaction is complete the product is purified directly by preparative HPLC (method C). 302 mg of the product are obtained as an oil.

Analytical HPLC-MS (method A): RT=1.65 min.

43.3 5-tert-butyl-1-methyl-3-piperidin-4-yl-1H-indole (V-6)

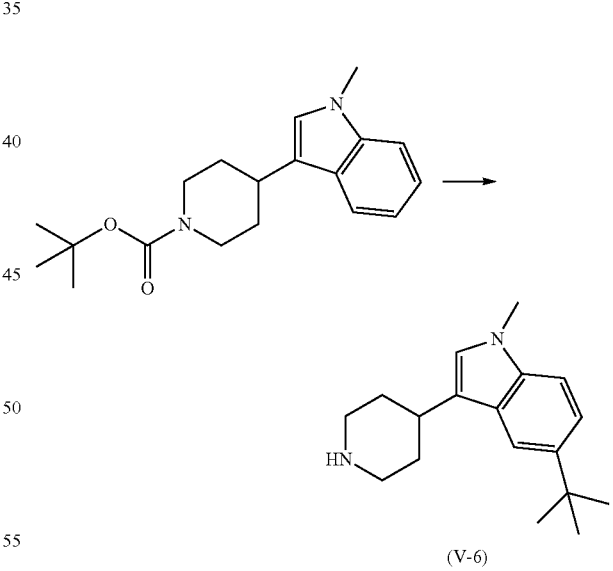

(V-6)

365 mg tert-butyl 4-(1-methyl-1H-indol-3-yl)-piperidine-1-carboxylate are placed in 1 ml dichloromethane and combined with 1.03 ml trifluoroacetic acid. The reaction mixture is stirred at ambient temperature. After 12 and 16 h another 1.03 ml trifluoroacetic acid are added. After another 12 h the reaction mixture is evaporated to dryness. The residue is combined with toluene and evaporated to dryness. The residue is triturated with diethyl ether, the precipitate is suction filtered and dried. 154 mg (V-6) are obtained as a solid.

Analytical HPLC-MS (method A): RT=1.34 min.

43.4 {2-[4-(5-tert-butyl-1-methyl-1H-indol-3-yl)-piperidin-1-yl]-5-oxo-6,7-dihydro-5H-5λ⁴-thieno[3,2-d]pyrimidin-4-yl}-(tetrahydropyran-4-yl)-amine (Example 192)

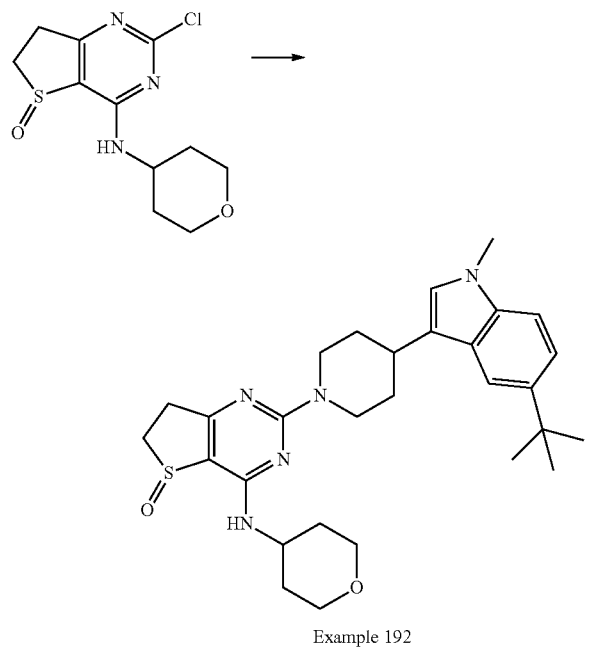

Example 192

Starting from (IV-6) (see 6.2) and (V-6) Example 192 may be prepared and purified analogously to Example 89 (see 21.). Analytical HPLC-MS (method B): RT=1.16 min.

44. Synthesis of: 5-{2-[4-(6-Chlorbenzoxazol-2-Yl)-Piperidin-1-Yl]-5-Oxo-6,7-Dihydro-5H-5λ⁴-Thieno[3,2-d]Pyrimidin-4-ylamino}-1-Methylpiperidin-2-One (Example 194)

44.1 6-chloro-2-piperidin-4-yl-benzoxazole (V-7)

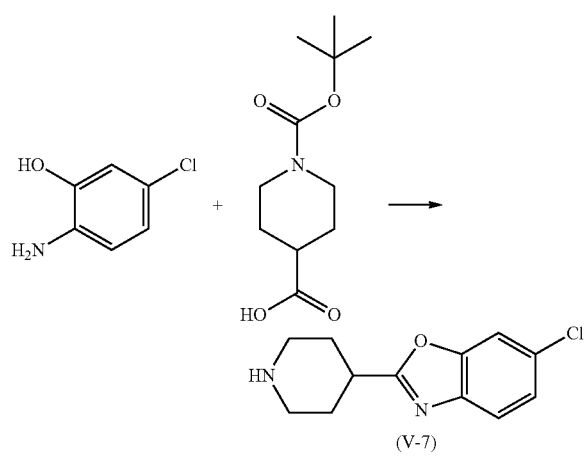

500 mg 2-amino-5-chlorophenol and 800 mg mono-tert-butyl piperidine-1,4-dicarboxylate are heated to 200° C. in 4 ml polyphosphoric acid for 4 h. After cooling the reaction mixture is combined with ice water and stirred for 30 min. The precipitate is suction filtered, washed with water and dried. 850 mg product are obtained as the phosphate.

Analytical HPLC-MS (method A): RT=1.05 min.

44.2 5-{2-[4-(6-Chlorbenzoxazol-2-yl)-piperidin-1-yl]-5-oxo-6,7-dihydro-5H-5λ⁴-thieno[3,2-d]pyrimidin-4-ylamino}-1-methylpiperidin-2-one (Example 194)

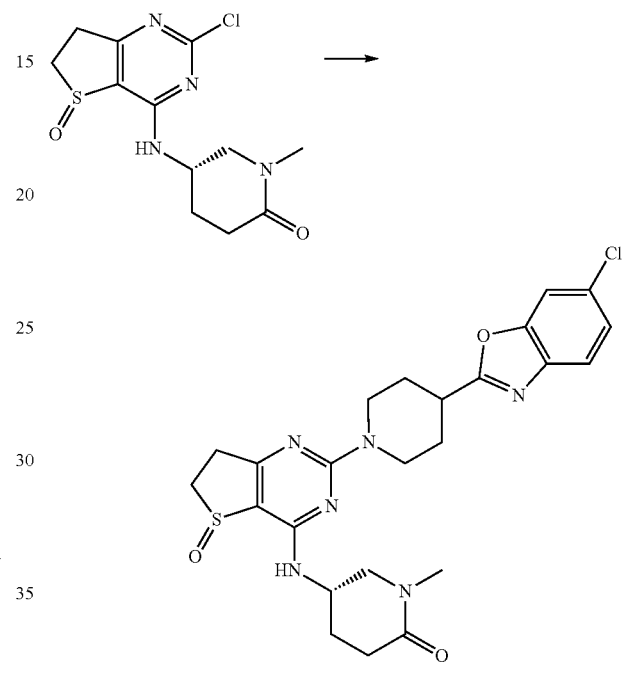

Example 194

Starting from (IV-5) (see 5.5) and (V-7) Example 194 may be prepared and purified analogously to Example 89 (see 21.). Analytical HPLC-MS (method B): RT=1.27 min.

45. Synthesis of: 5-{2-[4-(5-Fluorobenzoxazol-2-Yl)-Piperidin-1-Yl]-5-Oxo-6,7-Dihydro-5H-5λ⁴-Thieno[3,2-d]Pyrimidin-4-Ylamino}-1-Methylpiperidin-2-One (Example 195)

45.1 5-fluoro-2-piperidin-4-yl-benzoxazole (V-8)

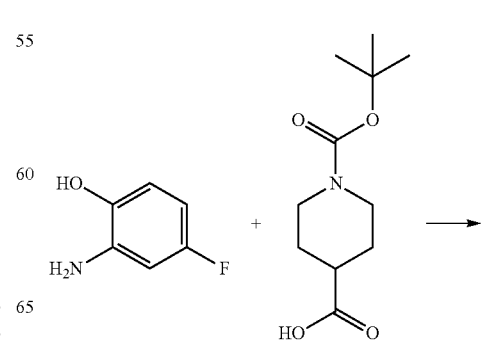

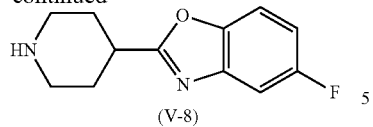

(V-8)

500 mg 2-amino-4-fluorophenol and 900 mg mono-tert-butyl piperidine-1,4-dicarboxylate are heated in 5 g polyphosphoric acid at 200° C. for 4 h. After cooling the reaction mixture is combined with ice water and made basic with 50% NaOH solution. The precipitate is suction filtered, washed with water and dried. 290 mg (V-8) are obtained as a solid.

45.2 5-{2-[4-(5-fluorobenzoxazol-2-yl)-piperidin-1-yl]-5-oxo-6,7-dihydro-5H-5λ$^4$-thieno[3,2-d]pyrimidin-4-ylamino}-1-methylpiperidin-2-one (Example 195)

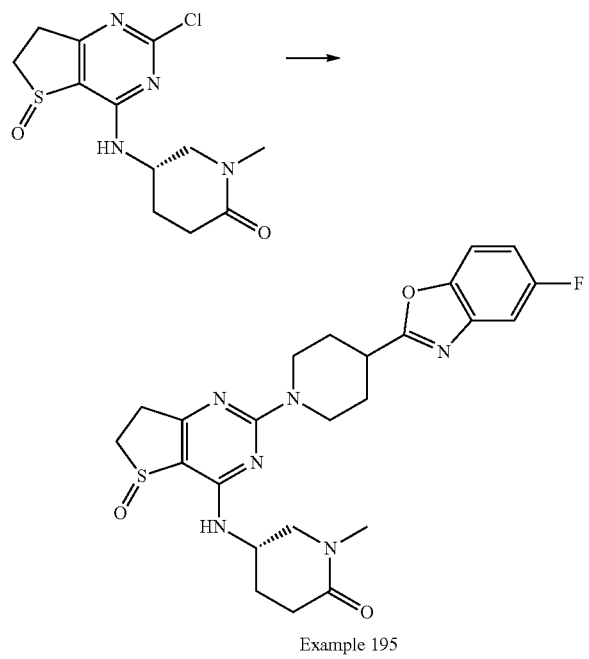

Example 195

Starting from (IV-5) (see 5.5) and (V-8) Example 195 may be prepared and purified analogously to Example 89 (see 21.). Analytical HPLC-MS (method B): RT=1.21 min.

46. Synthesis of: 5-{2-[4-(5-Fluorobenzoxazol-2-Yl)-4-Methylpiperidin-1-Yl]-5-Oxo-6,7-Dihydro-5H-5λ$^4$-Thieno[3,2-d]Pyrimidin-4-Ylamino}-1-Methyl Piperidin-2-One (Example 197)

46.1 5-fluoro-2-(4-methylpiperidin-4-yl)-benzoxazole (V-9)

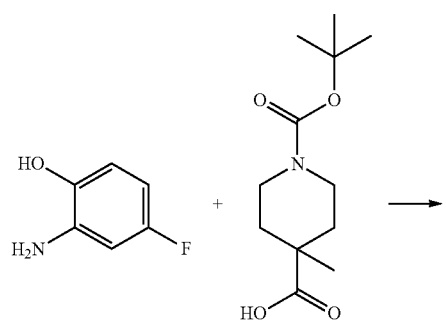

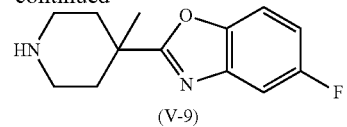

(V-9)

Starting from 2-amino-4-fluorophenol and mono-tert-butyl 4-methylpiperidine-1,4-dicarboxylate (V-9) may be prepared and purified analogously to (V-8) (see 45.1).

46.2 5-{2-[4-(5-fluorobenzoxazol-2-yl)-4-methylpiperidin-1-yl]-5-oxo-6,7-dihydro-5H-5λ$^4$-thieno[3,2-d]pyrimidin-4-ylamino}-1-methylpiperidin-2-one (Example 197)

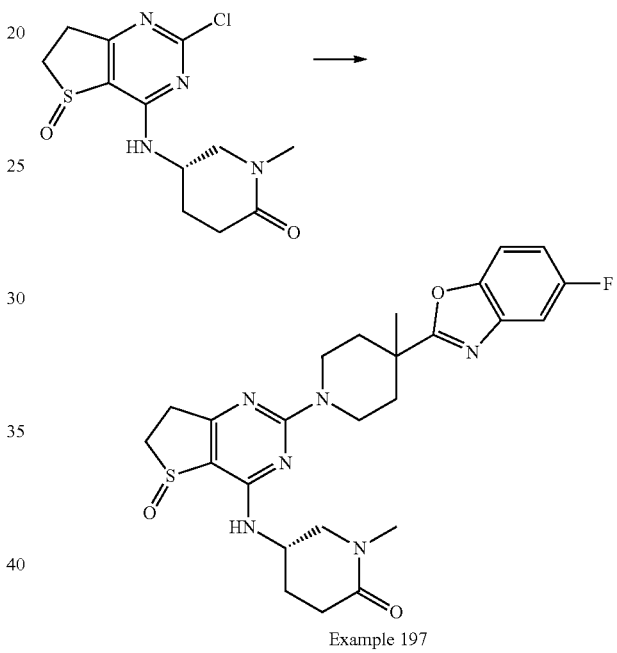

Example 197

Starting from (IV-5) (see 5.5) and (V-9) Example 197 may be prepared and purified analogously to Example 89 (see 21.). Analytical HPLC-MS (method B): RT=1.26 min.

47. Synthesis of: {2-[4-(5-Furan-2-Yl-1-Methyl-1H-Pyrazol-3-Yl)-Piperidin-1-Yl]-5-Oxo-6,7-Dihydro-5H-5λ$^4$-Thieno[3,2-d]Pyrimidin-4-Yl}-(Tetrahydropyran-4-Yl)-Amine (Example 198)

47.1 tert-butyl 14-(5-furan-2-yl-2H-pyrazol-3-yl)-piperidine-1-carboxylate

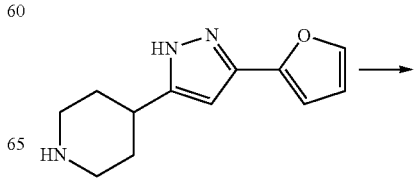

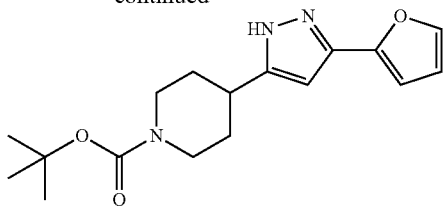

200 mg 4-(5-furan-2-yl-2H-pyrazol-3-yl)-piperidine are placed in 2 ml dioxane. Then 0.34 ml of water and 155 mg sodium carbonate are added. The reaction mixture is stirred at ambient temperature. After 5 min, 204 mg di-tert-butyl-dicarbonate are added. After 3 h the reaction mixture is mixed with water and the product is extracted with dichloromethane. 300 mg product are obtained as an oil. Analytical HPLC-MS (method B): RT=1.54 min.

47.2 tert-butyl 4-(5-furan-2-yl-2-methyl-2H-pyrazol-3-yl)-piperidine-1-carboxylate tert-butyl and 4-(5-furan-2-yl-1-methyl-1H-pyrazol-3-yl)-piperidine-1-carboxylate

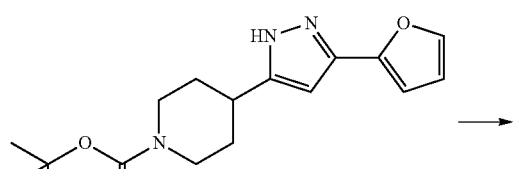

Isomer 1

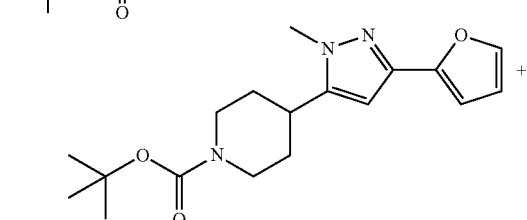

Isomer 2

250 mg tert-butyl 14-(5-furan-2-yl-2H-pyrazol-3-yl)-piperidine-1-carboxylate are placed in 1.5 ml dimethylformamide. The reaction mixture is cooled in the ice bath and 40 mg sodium hydride (60% in mineral oil) are added. After 10 min 60 µl methyl iodide are added. The reaction mixture is stirred for 30 min at 5° C. and then for 4 h at ambient temperature. The product is then purified directly by preparative HPLC (method D). 90 mg of isomer 1 and 50 mg of isomer 2 are obtained as a solid.

Analytical HPLC-MS (method D): RT=1.33 min (isomer 1); RT=1.28 (isomer 2).

47.3 4-(5-furan-2-yl-1-methyl-1H-pyrazol-3-yl)-piperidine (V-10)

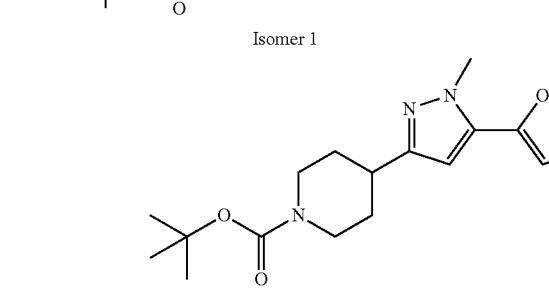

Isomer 2

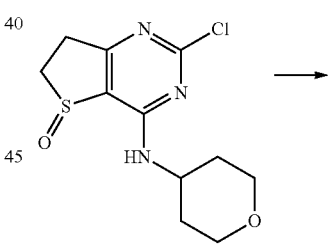

(V-10)

47 mg isomer 2 are placed in 1 ml dichloromethane and 120 µl trifluoroacetic acid are added. The reaction mixture is stirred for 2 h at ambient temperature, then evaporated to dryness. The residue is combined with toluene and evaporated to dryness. The residue is mixed with water, made basic with conc. Ammonia and the product is extracted with dichloromethane. 23 mg (V-10) are obtained as a solid.

Analytical HPLC-MS (method B): RT=0.85 min

47.4 {2-[4-(5-furan-2-yl-1-methyl-1H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine (Example 198)

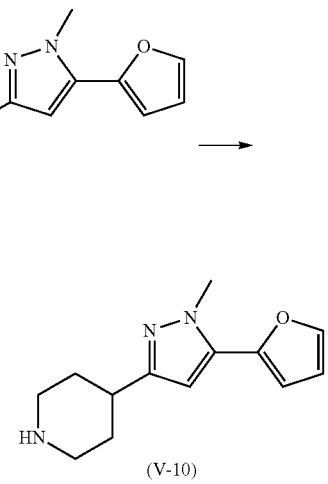

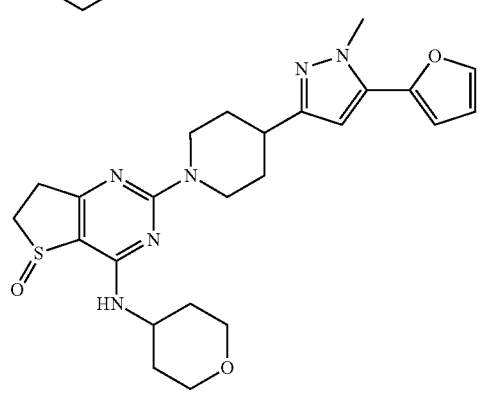

Example 198

Starting from (IV-6) (see 6.2) and (V-10) Example 198 may be prepared and purified analogously to Example 89 (see 21). Analytical HPLC-MS (method B): RT=1.21 min.

48. Synthesis of: {2-[4-(5-Furan-2-Yl-2-Methyl-2H-Pyrazol-3-Yl)-Piperidin-1-Yl]-5-Oxo-6,7-Dihydro-5H-5λ⁴-Thieno[3,2-d]Pyrimidin-4-Yl}-(Tetrahydropyran-4-Yl)-Amine (Example 200)

48.1 4-(5-furan-2-yl-2-methyl-2H-pyrazol-3-yl)-piperidine (V-11)

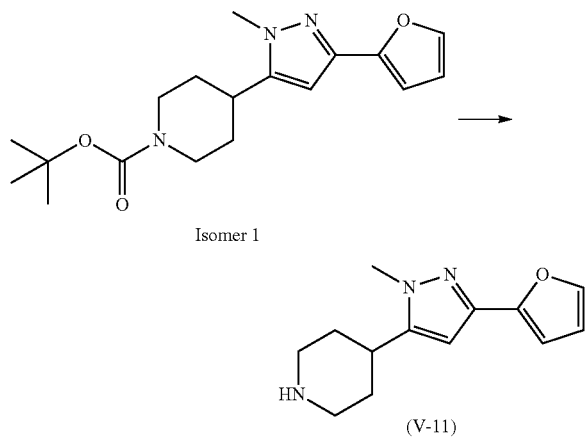

Isomer 1

(V-11)

Starting from isomer 1 (see 47.2), (V-11) may be prepared analogously to (V-10) (see 47.3). Analytical HPLC-MS (method D): RT=0.89 min.

48.2 Synthesis of: {2-[4-(5-furan-2-yl-2-methyl-2H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine (Example 200)

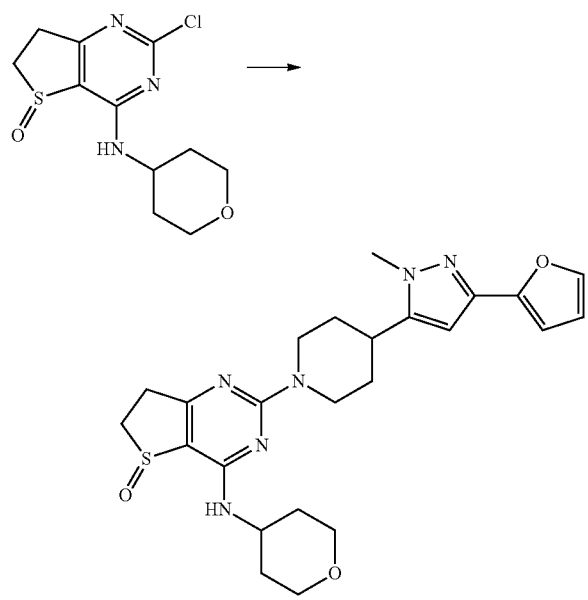

Example 200

Starting from (IV-6) (see 6.2) and (V-11) Example 200 may be prepared and purified analogously to Example 89 (see 21). Analytical HPLC-MS (method B): RT=1.26 min.

49. Synthesis of 5-{2-[4-(4-Chlorophenyl)-Piperidin-1-Yl]-5-Oxo-6,7-Dihydro-5H-5λ⁴-Thieno[3,2-d]Pyrimidin-4-Ylamino}-1-Propylpiperidin-2-One (Example 201)

49.1 (S)-5-dibenzylamino-1-propylpiperidin-2-one

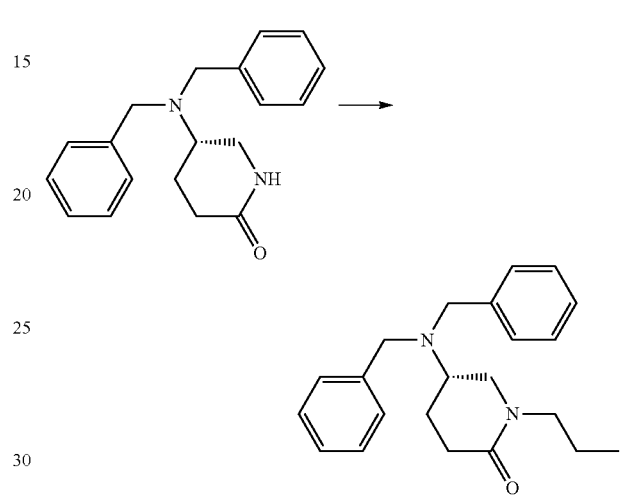

0.51 g (S)-5-dibenzylaminopiperidin-2-one (see 5.1) are placed in 5 ml dimethylformamide. While cooling with the ice bath 120 mg sodium hydride (60% in mineral oil) are added. The reaction mixture is then stirred for 30 minutes at ambient temperature. While cooling with the ice bath 0.289 ml 1-iodopropane are added. The reaction mixture is then stirred overnight at ambient temperature, then combined with a saturated NaCl solution. The product is extracted with ethyl acetate. 0.569 g product are obtained as an oil.

Analytical HPLC-MS (method A): RT=1.13 min.

49.2 (S)-5-amino-1-propylpiperidin-2-one

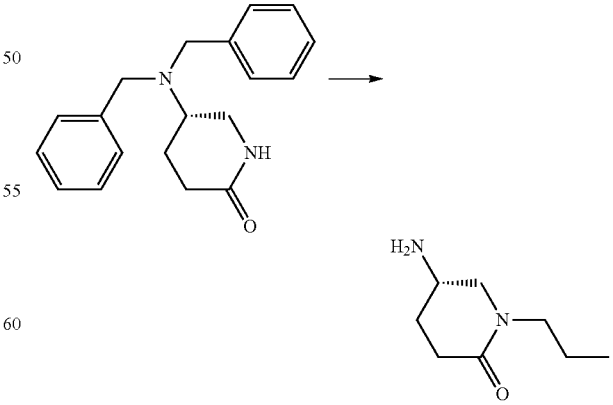

0.569 g (S)-5-dibenzylamino-1-propylpiperidin-2-one are placed in 25 ml of methanol and hydrogenated with 0.150 g Pd/C 10% at a pressure of 3 bar and a temperature of 60° C.

After 19 hours the catalyst is suction filtered and the filtrate is evaporated to dryness. 0.217 g of the product are obtained as an oil.

49.3 5-{2-[4-(4-chlorophenyl)-piperidin-1-yl]-5-oxo-6,7-dihydro-5H-5λ⁴-thieno[3,2-d]pyrimidin-4-ylamino}-1-propylpiperidin-2-one (Example 201)

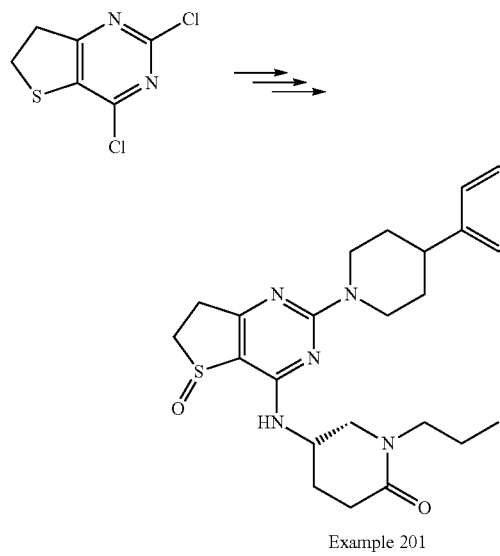

Example 201

Starting from (II), (S)-5-amino-1-propylpiperidin-2-one (see 49.2) and 4-(4-chlorophenyl)-piperidine hydrochloride Example 201 may be prepared analogously to Example 5 (see 5.4 to 5.6). The product may be purified by preparative HPLC (method B).

Analytical HPLC-MS (method B): RT=1.36 min.

50. Synthesis of: 2-Methoxy-N-{1-[4-(1-Methyl-6-Oxopiperidin-3-Ylamino)-5-Oxo-6,7-Dihydro-5H-5λ⁴-Thieno[3,2-d]Pyrimidin-2-Yl]-4-Phenyl Piperidin-4-Ylmethyl}-Acetamide (Example 202)

50.1 tert-butyl 4-[(2-methoxyacetylamino)-methyl]-4-phenylpiperidine-1-carboxylate

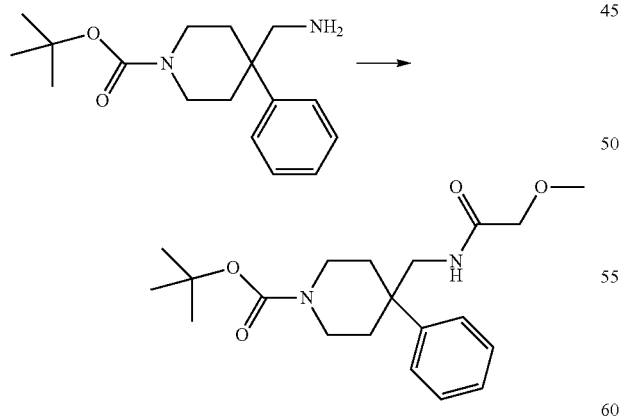

3.7 g of commercial tert-butyl 4-aminomethyl-4-phenylpiperidine-1-carboxylate and 3 ml diisopropylethylamine are placed in 30 ml dichloromethane. Then 2.25 ml methoxyacetyl chloride are slowly added. The reaction mixture is stirred at ambient temperature, until there is no further reaction, then mixed with water. The organic phase is evaporated to dryness. 4.7 g product are obtained as an oil.

50.2 2-methoxy-N-(4-phenylpiperidin-4-ylmethyl)-acetamide (V-12)

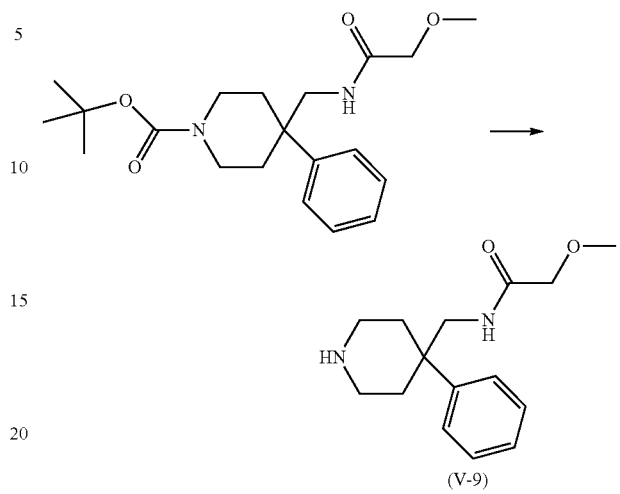

(V-9)

1 g tert-butyl 4-[(2-methoxyacetylamino)-methyl]-4-phenylpiperidine-1-carboxylate are placed in 4 ml dichloromethane. Then 1.7 ml trifluoroacetic acid are added and the mixture is stirred overnight at ambient temperature. The reaction mixture is made basic with potassium carbonate and the organic phase is evaporated to dryness. 610 mg (V-12) are obtained as an oil.

50.3 Synthesis of: 2-methoxy-N-{1-[4-(1-methyl-6-oxopiperidin-3-ylamino)-5-oxo-6,7-dihydro-5H-5λ⁴-thieno[3,2-d]pyrimidin-2-yl]-4-phenylpiperidin-4-ylmethyl}-acetamide (Example 202)

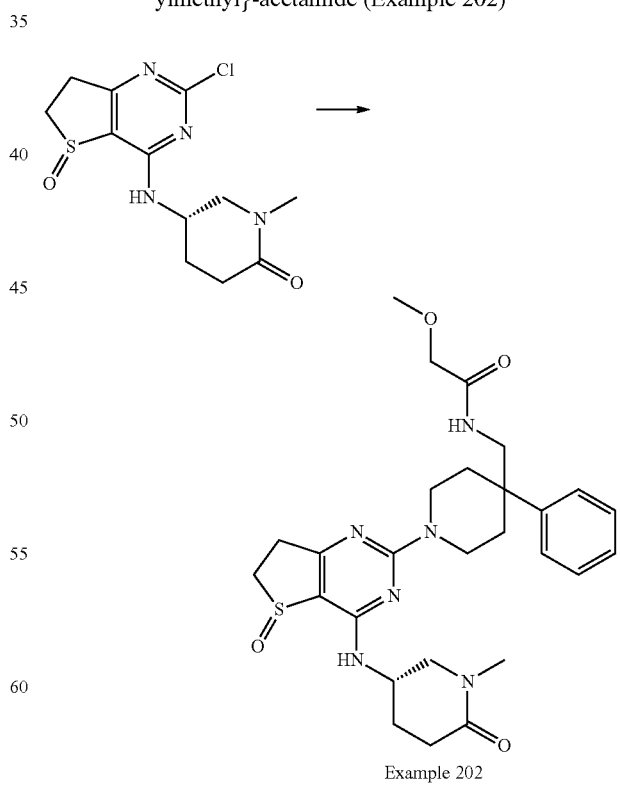

Example 202

Starting from (IV-5) (see 5.5) and (V-12) Example 202 may be prepared and purified analogously to Example 89 (see 21.).

Analytical HPLC-MS (method B): RT=1.16 min.

51. Synthesis of: 5-{2-[4-(4-Fluorobenzoyl)-4-(4-Fluorophenyl)-Piperidin-1-Yl]-5-Oxo-6,7-Dihydro-5H-5λ⁴-Thieno[3,2-d]Pyrimidin-4-Ylamino}-1-Methylpiperidin-2-One (Example 203)

51.1 1-benzyl-4-(4-fluorophenyl)-piperidine-4-carbonitrile

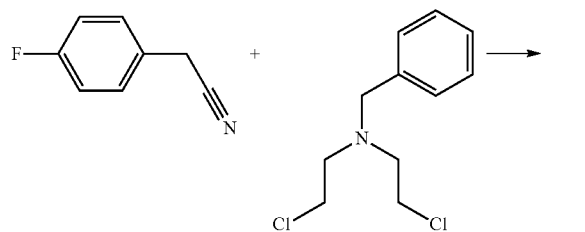

Under argon 16 ml 4-fluorobenzylcyanide and 35.1 g N-benzyl-N,N-di-(2-chloroethyl)amine hydrochloride are placed in 500 ml NMP and the mixture is cooled to 5° C. Then 18.9 g sodium hydride (55% in mineral oil) are added batchwise within 30 min. The reaction mixture is stirred for 30 min at 5-10° C. and for 6 h at ambient temperature and then poured onto ice water. The product is extracted with ethyl acetate and purified by chromatography (silica gel, dichloromethane/ethanol 100:1 to 50:1). 33 g product are obtained as an oil.

51.2 [1-benzyl-4-(4-fluorophenyl)-piperidin-4-yl]-(4-fluorophenyl)-methanone

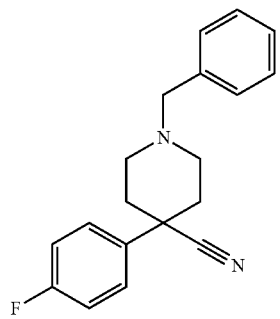

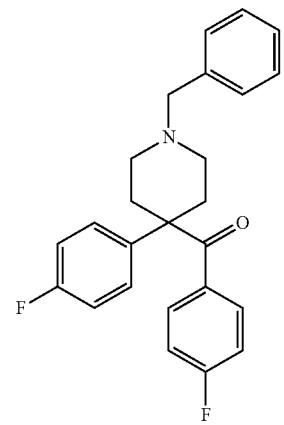

Under argon 11.86 g magnesium chips are placed in 50 ml anhydrous diethyl ether, then a solution of 85.4 g 4-bromofluorobenzene in 200 ml anhydrous diethyl ether is slowly added dropwise. The reaction mixture is stirred for 2 h at reflux temperature and then cooled to ambient temperature. A solution of 45.4 g 1-benzyl-4-(4-fluoro-phenyl)-piperidine-4-carbonitrile in 100 ml anhydrous toluene is added dropwise. The diethyl ether is distilled off and the remainder of the reaction mixture is stirred overnight at 80° C. After cooling the reaction mixture is combined with 500 ml ice water and 100 g NH₄Cl and the product is extracted with ethyl acetate. The organic phase is washed with water and sat. NaCl solution, dried and evaporated to dryness. 70 ml glacial acetic acid and 20 ml sulphuric acid 33% are added to the residue. The reaction mixture is heated to 100° C., then cooled, combined with ice water and adjusted to pH ~9 with 4N NaOH. Then 250 ml diisopropylether are added. The reaction mixture is then stirred overnight at ambient temperature. The precipitate formed is suction filtered, washed with diisopropylether and water and dried. 42.7 g product are obtained as a solid. M.p: 136-138.5° C.

51.3 (4-fluorophenyl)-[4-(4-fluorophenyl)-piperidin-4-yl]-methanone (V-13)

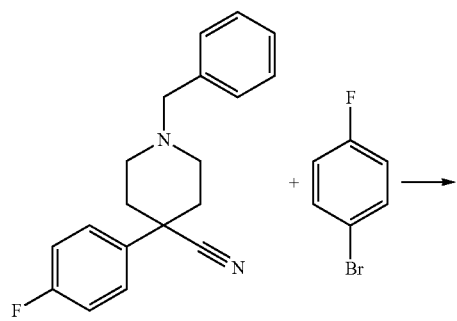

-continued

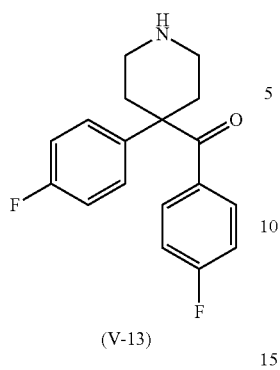

(V-13)

42.6 g [1-benzyl-4-(4-fluoro-phenyl)-piperidin-4-yl]-(4-fluoro-phenyl)-methanone are placed in 400 ml of methanol and 15 ml ethereal hydrochloric acid 10 mol/l and hydrogenated overnight with 8 g Pd/C 5% at 30° C. and 50 psi hydrogen pressure. The catalyst is filtered off and the filtrate is evaporated to dryness. The residue is stirred with tert-butylmethylether, the solid is suction filtered, washed with tert-butylmethylether and dried. 35.08 g (V-13) are obtained as the hydrochloride. M.p: 149-151° C.

51.4 5-{2-[4-(4-fluorobenzoyl)-4-(4-fluorophenyl)-piperidin-1-yl]-5-oxo-6,7-dihydro-5H-5λ$^4$-thieno[3,2-d]pyrimidin-4-ylamino}-1-methylpiperidin-2-one (Example 203)

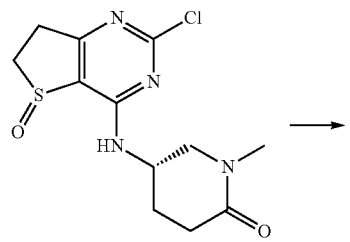

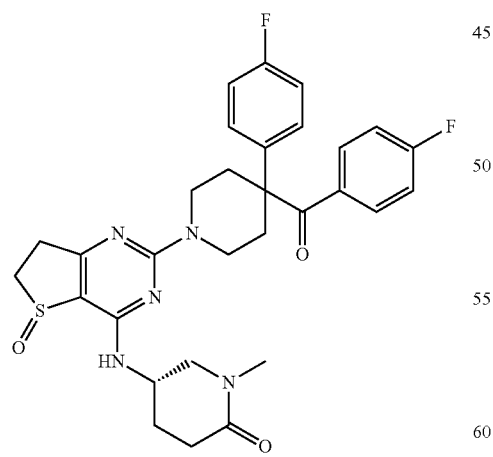

Example 203

Starting from (IV-5) (see 5.5) and (V-13) Example 203 may be prepared and purified analogously to Example 89 (see 21.). Analytical HPLC-MS (method B): RT=1.38 min.

52. Synthesis of: N-{1-[4-(1-Methyl-6-Oxopiperidin-3-Ylamino)-5-Oxo-6,7-Dihydro-5H-5λ$^4$-Thieno[3,2-d]Pyrimidin-2-Yl]-4-Phenylpiperidin-4-Ylmethyl}-Acetamide (Example 204)

52.1 tert-butyl 4-(acetylaminomethyl)-4-phenylpiperidine-1-carboxylate

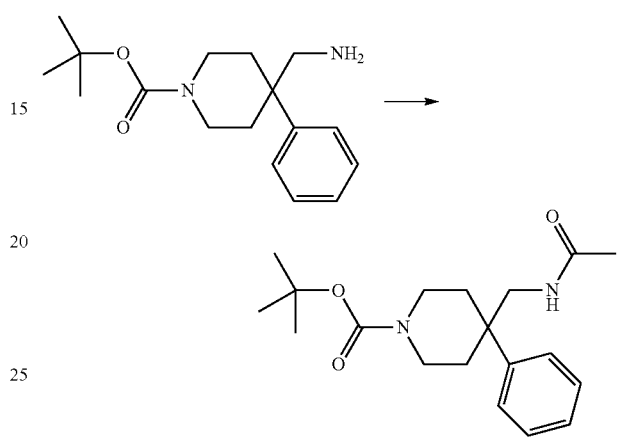

8 g tert-butyl 4-aminomethyl-4-phenylpiperidine-1-carboxylate and 2.9 ml acetic anhydride are stirred in 80 ml of ethanol overnight at ambient temperature and then evaporated to dryness. 10.4 g product are obtained.

52.2 N-(4-phenylpiperidin-4-ylmethyl)-acetamide (V-14)

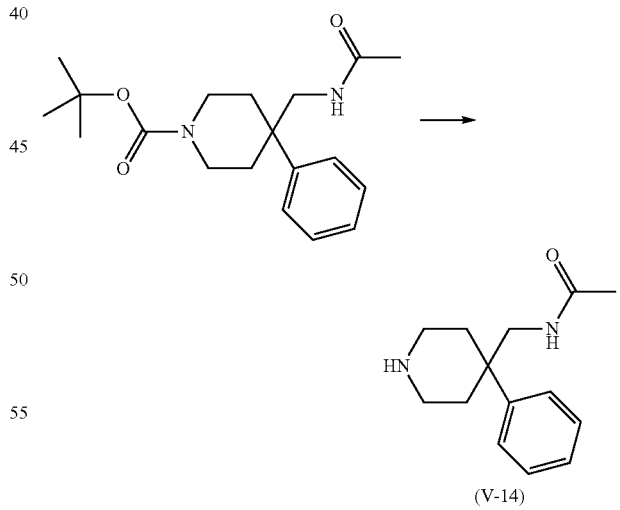

(V-14)

11.5 g tert-butyl 4-(acetylaminomethyl)-4-phenylpiperidine-1-carboxylate and 25 ml trifluoroacetic acid are stirred in 200 ml dichloromethane overnight at ambient temperature. The reaction mixture is evaporated to dryness and the residue is triturated with diethyl ether/diisopropylether. The precipitated solid is suction filtered and washed with diethyl ether. 10 g (V-14) are obtained as the trifluoroacetate.

52.3 N-{1-[4-(1-methyl-6-oxopiperidin-3-ylamino)-5-oxo-6,7-dihydro-5H-5λ⁴-thieno[3,2-d]pyrimidin-2-yl]-4-phenylpiperidin-4-ylmethyl}-acetamide (Example 204)

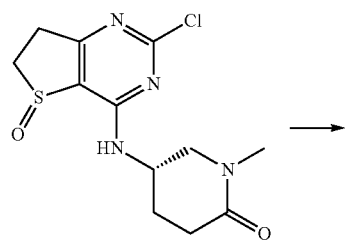

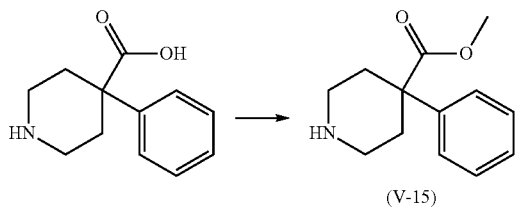

Example 204

Starting from (IV-5) (see 5.5) and (V-14) Example 204 may be prepared and purified analogously to Example 89 (see 21.). Analytical HPLC-MS (method B): RT=1.11 min.

53. Synthesis of: Methyl 1-[4-(1-Methyl-6-Oxopiperidin-3-Ylamino)-5-Oxo-6,7-Dihydro-5H-5λ⁴-Thieno[3,2-d]Pyrimidin-2-Yl]-4-Phenylpiperidine-4-Carboxylate (Example 205)

53.1 methyl 4-phenylpiperidine-4-carboxylate (V-15)

(V-15)

270 ml of methanol are taken. 10.6 ml sulphuric acid and 25 g 4-phenyl-4-piperidine-carboxylic acid p-toluenesulphonic acid are added with stirring. The reaction mixture is refluxed for 9 h, cooled and carefully poured onto a mixture of ice water and 10 M NaOH. The precipitated solid is suction filtered, washed with water and dried. 11.2 g (V-15) are obtained as a solid.

53.2 methyl 1-[4-(1-methyl-6-oxopiperidin-3-ylamino)-5-oxo-6,7-dihydro-5H-5λ⁴-thieno[3,2-d]pyrimidin-2-yl]-4-phenylpiperidine-4-carboxylate (Example 205)

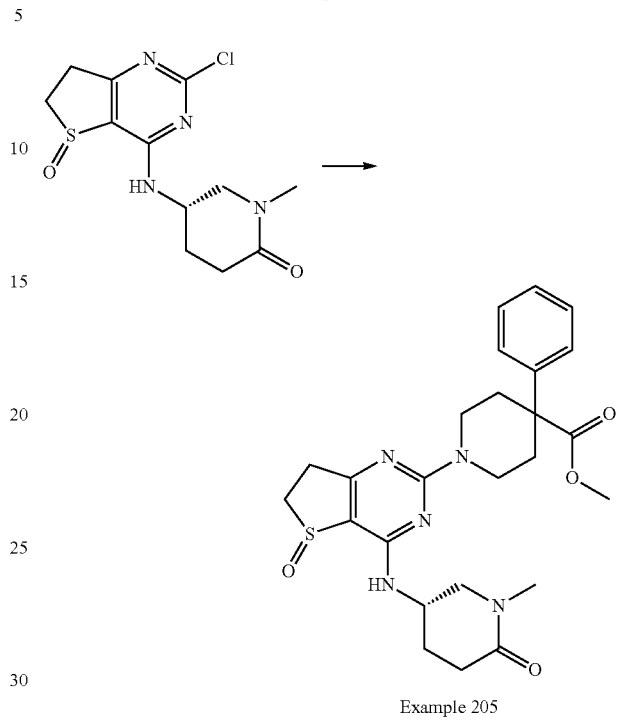

Example 205

Starting from (IV-5) (see 5.5) and (V-15) Example 205 may be prepared and purified analogously to Example 89 (see 21.). Analytical HPLC-MS (method B): RT=1.23 min.

54. Synthesis of: 2-Dimethylamino-N-{1-[4-(1-Methyl-6-Oxopiperidin-3-Ylamino)-5-Oxo-6,7-Dihydro-5H-5λ⁴-Thieno[3,2-d]Pyrimidin-2-Yl]-4-Phenyl Piperidin-4-Ylmethyl}-Acetamide (Example 206)

54.1 2-dimethylamino-N-[4-(1-propenylbuta-1,3-dienyl)-piperidin-4-ylmethyl]-acetamide (V-16)

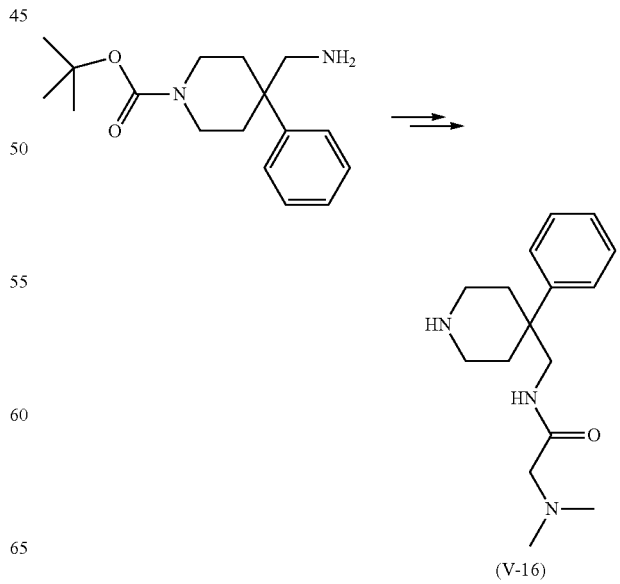

(V-16)

Starting from commercial tert-butyl 4-aminomethyl-4-phenyl-piperidine-1-carboxylate and dimethylaminoacetyl chloride hydrochloride (V-16) may be prepared analogously to (V-12) (see 50.1 and 50.2).

54.2 2-dimethylamino-N-{1-[4-(1-methyl-6-oxopiperidin-3-ylamino)-5-oxo-6,7-dihydro-5H-5λ⁴-thieno[3,2-d]pyrimidin-2-yl]-4-phenylpiperidin-4-ylmethyl}-acetamide (Example 206)

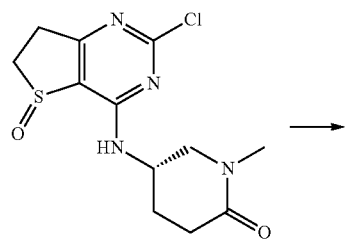

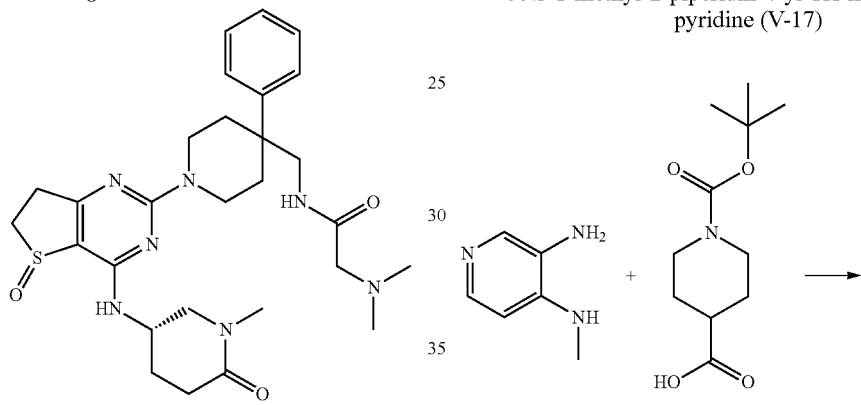

Example 206

Starting from (IV-5) (see 5.5) and (V-16) Example 206 may be prepared and purified analogously to Example 89 (see 21.). Analytical HPLC-MS (method B): RT=1.08 min.

55. Synthesis of: {2-[4-(1-Methyl-1H-Imidazo[4,5-c]Pyridin-2-Yl)-Piperidin-1-Yl]-5-Oxo-6,7-Dihydro-5H-5λ⁴-Thieno[3,2-d]Pyrimidin-4-Yl}-(Tetrahydro Pyran-4-Yl)-Amine (Example 210)

55.1 methyl-(3-nitropyridin-4-yl)-amine

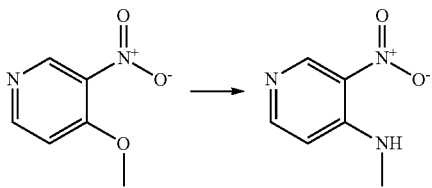

2.36 g 4-methoxy-3-nitro-pyridine and 2.33 ml methylamine (40% in water) are refluxed in 25 ml of ethanol for 3 h. Then the reaction mixture is evaporated to dryness. 2.3 g product are obtained as a solid.

55.2 N⁴-methylpyridin-3,4-diamine

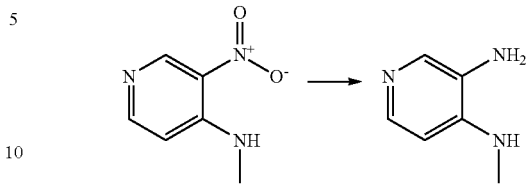

2.3 g methyl-(3-nitropyridin-4-yl)-amine are hydrogenated in 50 ml of methanol for and with 0.8 g Raney nickel for 2.5 h at 50° C. and 50 psi hydrogen pressure. The catalyst is filtered off and the filtrate is evaporated to dryness. The product is purified by chromatography (Alox, dichloromethane/methanol from 99/1 to 19/1). 1.55 g product are obtained as a solid.

M.p: 163-165° C.

55.3 1-methyl-2-piperidin-4-yl-1H-imidazo[4,5-c]pyridine (V-17)

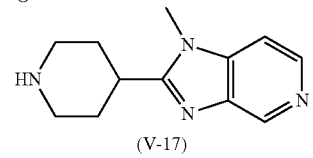

(V-17)

450 mg N⁴-methylpyridin-3,4-diamine and 838 mg mono-tert-butyl piperidine-1,4-dicarboxylate are heated for 4 h in 8.6 g polyphosphoric acid at 200° C. After cooling the mixture is made basic with 4 N NaOH and acidified with trifluoroacetic acid. The mixture is purified by preparative HPLC (method C). 3.37 g (50%) (V-17) are obtained as the trifluoroacetate. Analytical HPLC-MS (method B): RT=0.30 min.

55.4 {2-[4-(1-methyl-1H-imidazo[4,5-c]pyridin-2-yl)-piperidin-1-yl]-5-oxo-6,7-dihydro-5H-5λ⁴-thieno[3,2-d]pyrimidin-4-yl}-(tetrahydropyran-4-yl)-amine (Example 210)

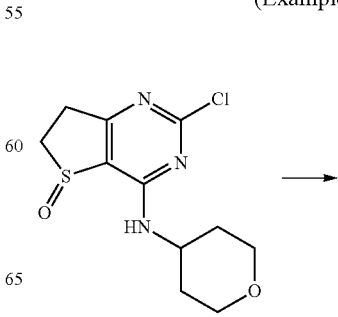

-continued

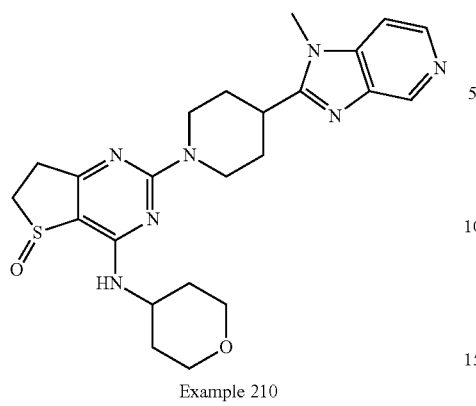

Example 210

Starting from (IV-6) (see 6.2) and (V-17) Example 210 may be prepared and purified analogously to Example 89 (see 21.). Analytical HPLC-MS (method D): RT=0.86 min.

56. Synthesis of 5-{2-[4-(4-Chlorophenyl)-Piperidin-1-Yl]-5-Oxo-6,7-Dihydro-5H-5λ⁴-Thieno[3,2-d]Pyrimidin-4-Ylamino}-1-(4-Fluorobenzyl)-Piperidin-2-One (Example 211)

56.1 (S)-5-dibenzylamino-1-(4-fluorobenzyl)-piperidin-2-one

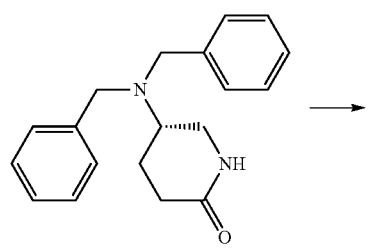

0.8 g (S)-5-dibenzylaminopiperidin-2-one (see 5.1) are placed in 8 ml dimethylformamide, then 200 mg sodium hydride (60% in mineral oil) and 0.4 ml 4-fluorobenzylbromide are added. The reaction mixture is stirred overnight at 70° C. and then combined with ice water. The precipitate is filtered off and washed with water. The product is purified by chromatography (silica gel, petroleum ether/ethyl acetate and ethyl acetate/methanol). 0.5 g product are obtained as an oil. Analytical HPLC-MS (method A): RT=1.21 min.

56.2 (S)-5-amino-1-(4-fluoro-benzyl)-piperidin-2-one

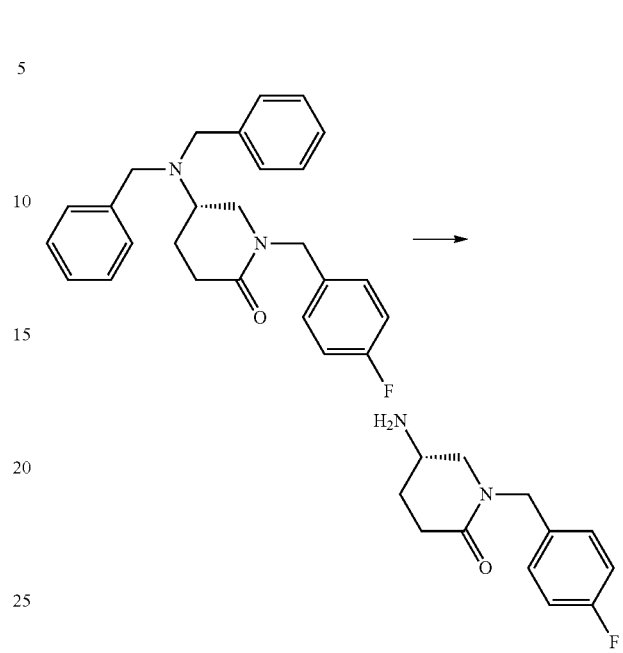

0.5 g (S)-5-dibenzylamino-1-(4-fluorobenzyl)-piperidin-2-one are placed in 20 ml of methanol and hydrogenated with 0.150 g Pd/C 10% at a pressure of 3 bar and a temperature of 60° C. After 5 hours the catalyst is suction filtered and the filtrate is evaporated to dryness. 0.21 g of the product are obtained as an oil. Analytical HPLC-MS (method A): RT=0.68 min.

56.3 5-{2-[4-(4-chlorophenyl)-piperidin-1-yl]-5-oxo-6,7-dihydro-5H-5λ⁴-thieno[3,2-d]pyrimidin-4-ylamino}-1-(4-fluorobenzyl)-piperidin-2-one (Example 211)

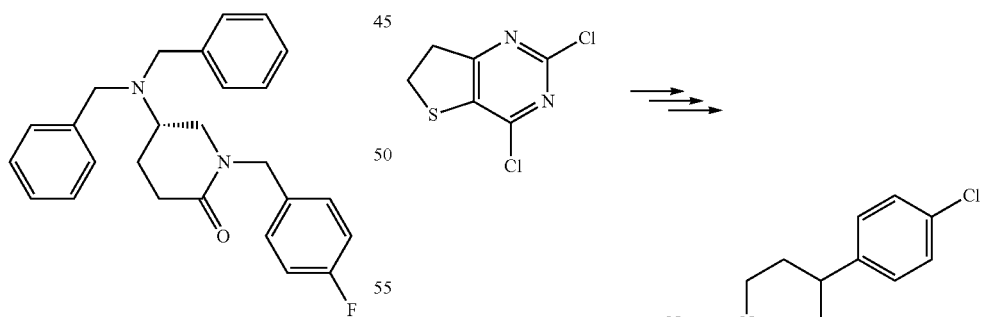

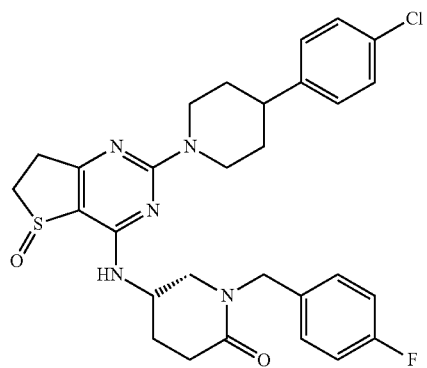

Example 211

Starting from (II), (S)-5-amino-1-(4-fluorobenzyl)-piperidin-2-one (see 56.2) and 4-(4-chlorophenyl)-piperidine hydrochloride Example 211 may be prepared analogously to Example 5 (see 5.4 to 5.6). The product may be purified by preparative HPLC (method A). Analytical HPLC-MS (method B): RT=1.45 min.

57. Synthesis of: Cyclopropyl-(7-{1-[5-Oxo-4-(Tetrahydropyran-4-Ylamino)-6,7-Dihydro-5H-5λ⁴-Thieno[3,2-d]Pyrimidin-2-Yl]-Piperidin-4-Yloxy}-1,2,4,5-Tetrahydrobenzo[d]Azepin-3-Yl)-Methanone (Example 214)

57.1 tert-butyl 4-(2,3,4,5-tetrahydro-1H-benzo[d]azepin-7-yloxy)-piperidine-1-carboxylate

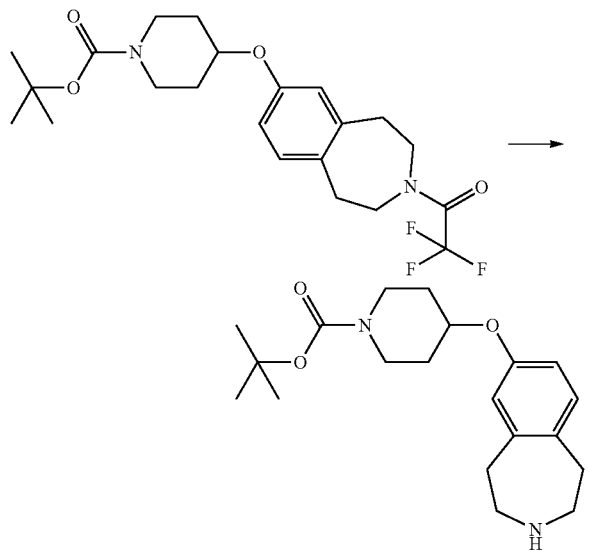

400 mg tert-butyl 4-[3-(2,2,2-trifluoracetyl)-2,3,4,5-tetrahydro-1H-benzo[d]azepin-7-yloxy]-piperidine-1-carboxylate (see 38.2) are placed in 17 ml of methanol, then a mixture of 151.2 mg potassium carbonate in 3.3 ml of water is added. The reaction mixture is stirred at ambient temperature, until there is no further reaction. The methanol is then spun off. The residue is combined with dichloromethane and water. The organic phase is dried and evaporated to dryness. 310 mg are obtained as an oil.

Analytical HPLC-MS (method D): RT=1.25 min.

57.2 tert-butyl 4-(3-cyclopropanecarbonyl-2,3,4,5-tetrahydro-1H-benzo[d]azepin-7-yloxy)-piperidine-1-carboxylate

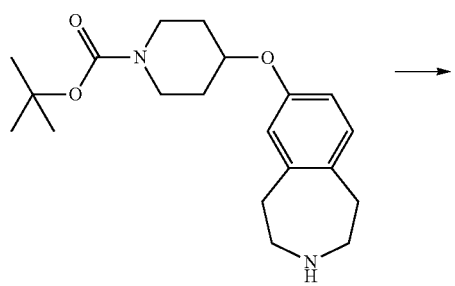

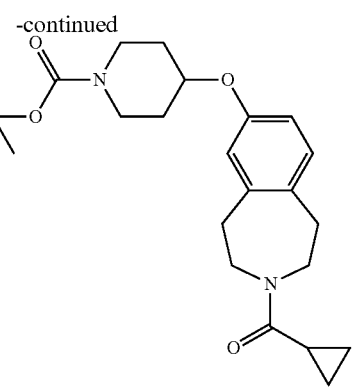

16 l cyclopropylcarboxylic acid are placed in 3 ml dimethylformamide, then 174 l diisopropylethylamine and 93.1 mg O-(7-azabenzotriazol-1-yl-)-N,N,N',N'-tetramethyluronium hexafluorophosphate (HATU) are added. After 15 min 77.5 mg tert-butyl 4-(2,3,4,5-tetrahydro-1H-benzo[d]azepin-7-yloxy)-piperidine-1-carboxylate are added. The reaction mixture is stirred at ambient temperature until there is no further reaction and the product is purified directly by preparative HPLC (method B). 70 mg of the product are obtained as a solid. Analytical HPLC-MS (method D): RT=1.37 min.

57.3 cyclopropyl-[7-(piperidin-4-yloxy)-1,2,4,5-tetrahydro-benzo[d]azepin-3-yl]-methanone (V-18)

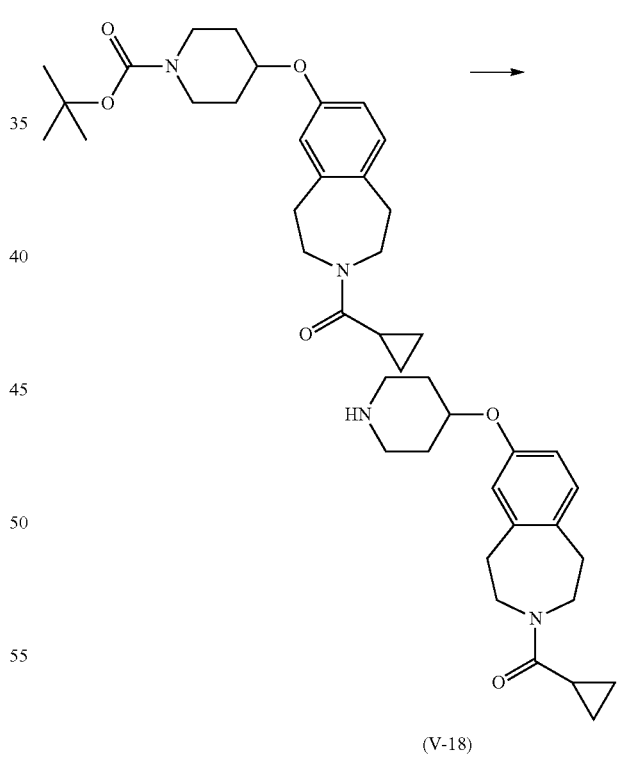

(V-18)

70 mg tert-butyl 4-(3-cyclopropanecarbonyl-2,3,4,5-tetrahydro-1H-benzo[d]azepin-7-yloxy)-piperidine-1-carboxylate are placed in 1.4 ml dichloromethane and combined with 224 l trifluoroacetic acid. The reaction mixture is stirred for 3 hours at ambient temperature, then evaporated to dryness. The residue is combined with toluene and evaporated to dryness. 77 mg (V-18) are obtained as an oil. Analytical HPLC-MS (method B): RT=1.18 min.

57.4 cyclopropyl-(7-{1-[5-oxo-4-(tetrahydropyran-4-ylamino)-6,7-dihydro-5H-5λ⁴-thieno[3,2-d]pyrimidin-2-yl]-piperidin-4-yloxy}-1,2,4,5-tetrahydrobenzo[d]azepin-3-yl)-methanone (Example 214)

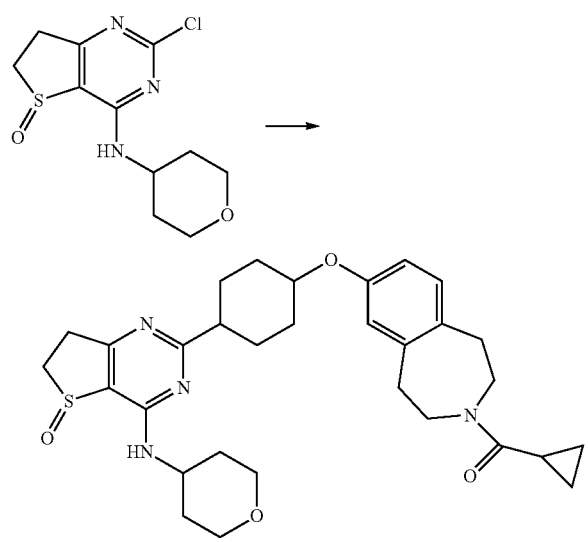

Example 214

Starting from (IV-6) (see 6.2) and (V-18) Example 214 may be prepared and purified analogously to Example 89 (see 21.). Analytical HPLC-MS (method D): RT=1.10 min.

58. Synthesis of Tert-Butyl (2-{2-[4-(4-Chlorophenyl)-Piperidin-1-Yl]-5-Oxo-6,7-Dihydro-5H-5λ⁴-Thieno[3,2-d]Pyrimidin-4-Ylamino}-Cyclopropyl)-Carbamidate (Example 222)

58.1 dihydrazide cis-1,2-cyclopropanedicarboxylic acid

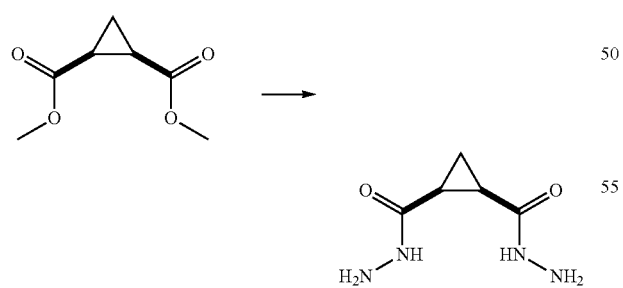

10 g dimethyl cis-1,2-cyclopropanedicarboxylate are placed in 100 ml of ethanol and 12.7 ml hydrazine monohydrate are added. The reaction mixture is stirred for 12 h at reflux temperature. After cooling the precipitated solid is filtered, washed with petroleum ether and diethyl ether and dried. 8 g (80%) product are obtained as a solid.

58.2 cis-1,2-cyclopropanediamine

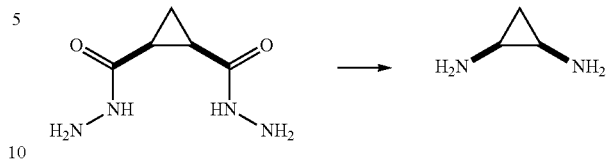

2 g dihydrazide cis-1,2-cyclopropanedicarboxylic acid are placed in 35 ml diethyl ether, then 14.2 ml conc. Hydrochloric acid in 28 g ice are added. The reaction mixture is cooled to 0-5° C. and then a solution of 5.45 g sodium nitrite in water is slowly added dropwise. After 20 min the organic phase is separated off and dried. 50 ml of toluene are added and the ether is distilled off. The toluene solution remaining is heated at 80-90° C. until the development of nitrogen ceases. The hot toluene solution is carefully poured onto hot (60° C.) conc. Hydrochloric acid and the toluene is distilled off. Anhydrous ethanol is added and distilled off again until a solid is obtained. The solid is combined with cold ethanol and filtered off. 1.25 g product are obtained as the dihydrochloride. M.p: 225° C. (decomposition).

58.3 tert-butyl cis-(2-tert-butoxycarbonylaminocyclopropyl)-carbamidate

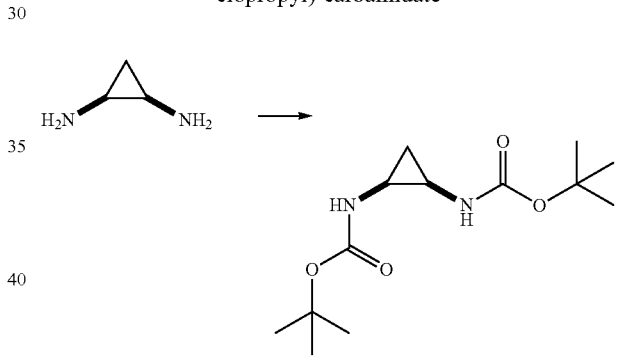

5 g cis-1,2-cyclopropanediamine dihydrochloride is placed in 50 ml dioxane, cooled to 0° C. and then combined with 13.8 g 5 N sodium hydroxide solution and 22.55 g di-tert-butyl-dicarbonate. The reaction mixture is stirred for 3 h at ambient temperature and the product is extracted with dichloromethane. 6.3 g product are obtained as a solid. M.p: 131-132° C.

58.4 cis-N-tert-butyloxycarbonyl-1,2-cyclopropanediamine

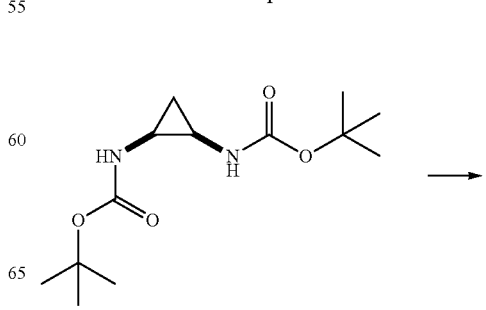

-continued

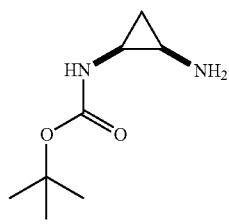

5 g tert-butyl cis-(2-tert-butoxycarbonylaminocyclopropyl)-carbamidate are placed in 50 ml of ethyl acetate and cooled to 0° C. A solution of 0.87 g hydrochloric acid in 9.5 ml of ethyl acetate is added dropwise. Then the reaction mixture is stirred overnight at ambient temperature. The precipitated solid is filtered off and washed with ethyl acetate. 0.76 g product are obtained as the hydrochloride. M.p: 208-209° C.

58.5 tert-butyl[2-(2-chloro-6,7-dihydrothieno[3,2-d]pyrimidin-4-ylamino)-cyclopropyl]-carbamidate (III-9)

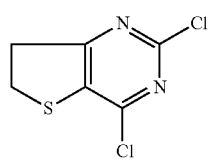 

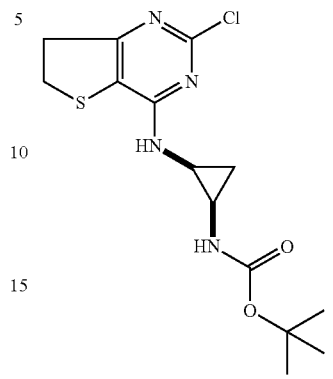

0.55 g (II) are placed in 9 ml dioxane, then 1.4 ml diisopropyl ethylamine and 0.6 g cis-N-tent-butyloxycarbonyl-1,2-cyclopropanediamin hydrochloride (see 58.4) are added. The reaction mixture is heated in the microwave at 110° C. until there is no further reaction and after cooling it is evaporated to dryness. The residue is treated with water in the ultrasound bath, the precipitate is suction filtered and washed with water. The solid is treated with 10 ml petroleum ether/ethyl acetate=7/3 and suction filtered. 520 mg (III-9) are obtained as a solid. Analytical HPLC-MS (method B): RT=1.42 min.

58.6 tert-butyl[2-(2-chloro-5-oxo-6,7-dihydro-5H-5λ⁴-thieno[3,2-d]pyrimidin-4-ylamino)-cyclopropyl]-carbamidate (IV-9)

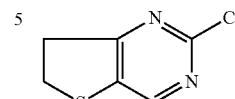

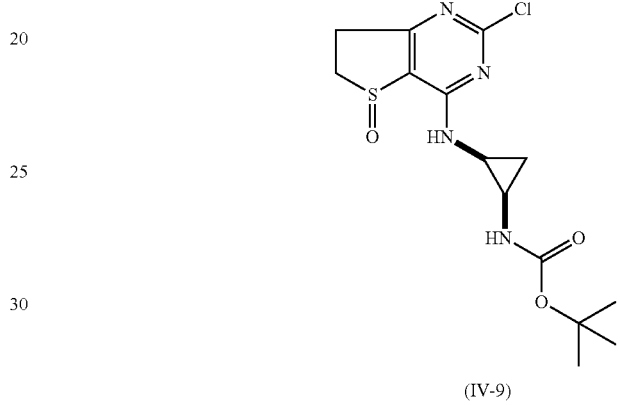

73 mg S-(−)-1,1'-bi-2-naphthol are placed in 2 ml chloroform under argon, then 38 μl titanium(IV)-isopropoxide and 47 μl water are added. The reaction mixture is stirred for 1 hour at ambient temperature. Then a mixture of 480 mg (III-9) in 6 ml chloroform is added. The reaction mixture is cooled to −5° C. and after 60 minutes 232 μl tert-butylhydroperoxide 5-6 M in decane are added dropwise. The reaction mixture is stirred for 24 h at −5° C. and then combined with water and made basic with NH₄OH. The organic phase is evaporated to dryness and the product is purified by chromatography (silica gel, ethyl acetate/methanol+1% NH4OH). 460 mg (IV-9) are obtained as a mixture of diastereomers.

Analytical HPLC-MS (method B): RT=1.23 and 1.24 min.

58.7 Synthesis of tert-butyl (2-{2-[4-(4-chlorophenyl)-piperidin-1-yl]-5-oxo-6,7-dihydro-5H-5λ⁴-thieno[3,2-d]pyrimidin-4-ylamino}-cyclopropyl)-carbamidate (Example 222)

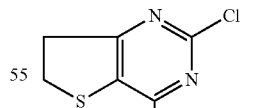
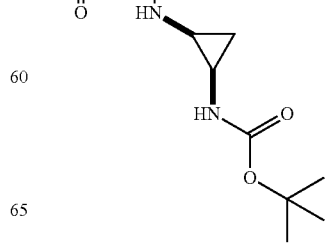

-continued

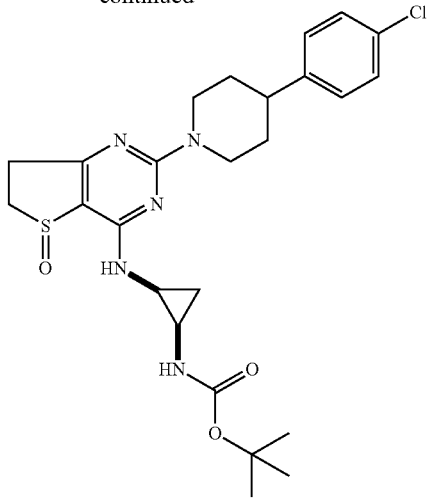

Example 222

380 mg (IV-9) and 266 mg 4-(4-chlorophenyl)-piperidine hydrochloride are placed in 3 ml dioxane, combined with 570 μl diisopropylethylamine and heated in the microwave for 25 min at 120° C. The reaction mixture is combined with ice water and the product is extracted with dichloromethane. The organic phase is evaporated to dryness and the residue is treated with water in the ultrasound bath. The precipitated solid is suction filtered, washed with water and dried. 485 mg product are obtained as a mixture of diastereomers.

Analytical HPLC-MS (method B): RT=1.46 min. Chiral HPLC (column: Diacel ADS-H, 250×4.6 mm, 5 μm, eluant: (hexane+diethylamine (0.2%)/isopropanol (75/25), 10° C., flow rate: 1 ml/min): RT=11.5 min and RT=13.7 min.

59. Synthesis of: N-Cyclopropyl-N-Methyl-4-{1-[5-Oxo-4-(Tetrahydro Pyran-4-Ylamino)-6,7-Dihydro-5H-5λ⁴-Thieno[3,2-d]Pyrimidin-2-Yl]-Piperidin-4-Yl}-Benzamide (Example 229)

59.1 tert-butyl 4-[4-(cyclopropylmethylcarbamoyl)-phenyl]-piperidine-1-carboxylate

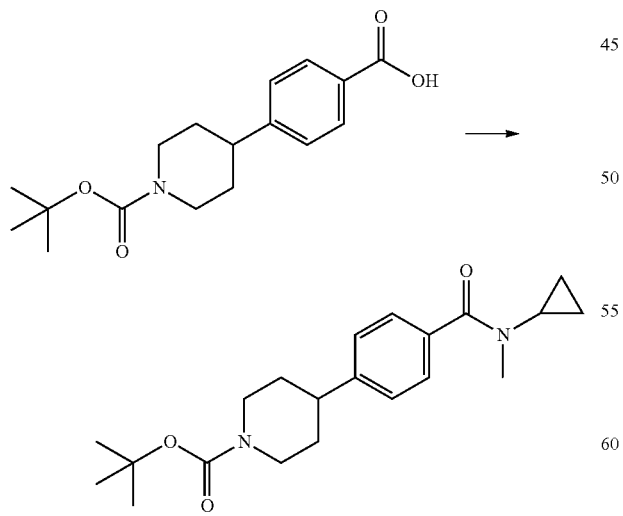

500 mg tert-butyl 4-(4-carboxyphenyl)-piperidine-1-carboxylate are placed in 28 ml dimethylformamide, then 1.14 ml diisopropylethylamine and 747 mg HATU are added. The reaction mixture is stirred for 15 min at ambient temperature, then 194 mg cyclopropylmethylamin hydrochloride are added. The reaction mixture is stirred overnight at ambient temperature. Then the product is purified by preparative HPLC (method A). 480 mg product are obtained as an oil. Analytical HPLC-MS (method B): RT=1.64 min.

59.2 N-cyclopropyl-N-methyl-4-piperidin-4-yl-benzamide (V-19)

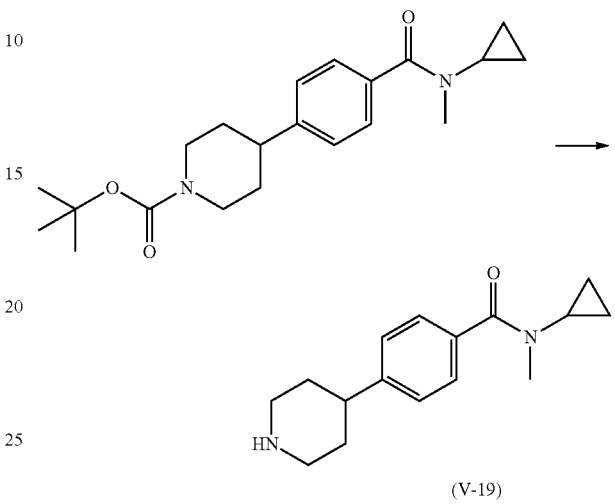

(V-19)

480 mg tert-butyl 4-[4-(cyclopropylmethylcarbamoyl)-phenyl]-piperidine-1-carboxylate are placed in 7.8 ml dichloromethane and combined with 1.09 ml trifluoroacetic acid. The reaction mixture is stirred for 1.5 h at ambient temperature and then evaporated to dryness. The residue is combined with toluene and evaporated to dryness again. 444 mg (V-19) are obtained as the trifluoroacetate. Analytical HPLC-MS (method B): RT=1.11 min.

59.3 N-cyclopropyl-N-methyl-4-{1-[5-oxo-4-(tetrahydropyran-4-ylamino)-6,7-dihydro-5H-5λ⁴-thieno[3,2-d]pyrimidin-2-yl]-piperidin-4-yl}-benzamide (Example 229)

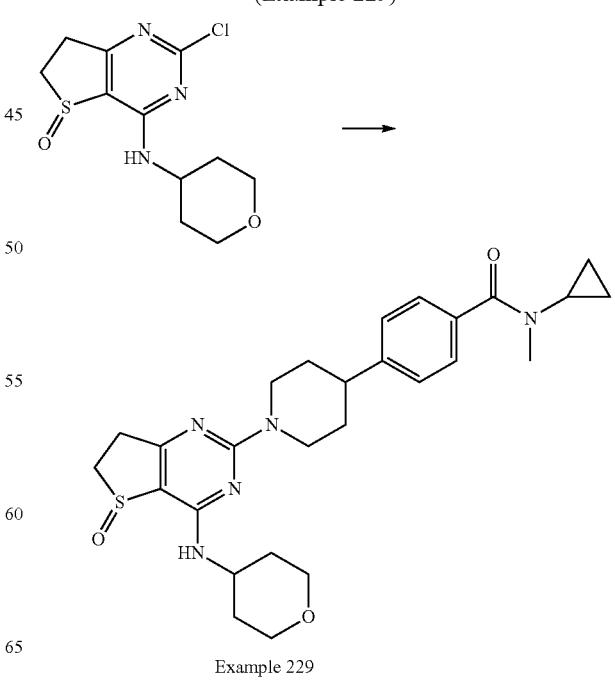

Example 229

Starting from (IV-6) (see 6.2) and (V-19) Example 229 may be prepared and purified analogously to Example 89 (see 21). Analytical HPLC-MS (method D): RT=1.05 min.

60. Synthesis of Tert-Butyl (2-{2-[4-(4-Chlorophenyl)-Piperidin-1-Yl]-5-Oxo-6,7-Dihydro-5H-5λ$^4$-Thieno[3,2-d]Pyrimidin-4-Ylamino}-Cyclopropyl)-Carbamidate (Example 231)

60.1 trans-N-tert-butyloxycarbonyl-1,2-cyclopropanediamine

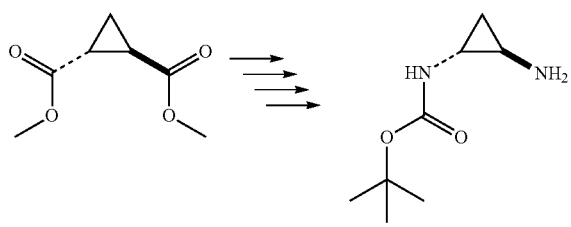

Starting from dimethyl trans-1,2-cyclopropanedicarboxylate, trans-N-tert-butyloxycarbonyl-1,2-cyclopropanediamin hydrochloride may be prepared and purified analogously to cis-N-tert-butyloxycarbonyl-1,2-cyclopropanediamin hydrochloride (see 58.4). M.p: 200-202° C.

60.2 tert-butyl[2-(2-chloro-6,7-dihydrothieno[3,2-d]pyrimidin-4-ylamino)-cyclopropyl]-carbamidate (III-10)

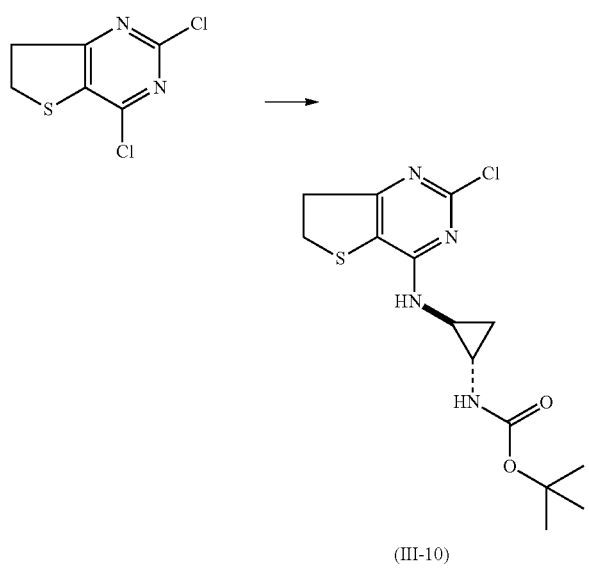

(III-10)

Starting from (II) and trans-N-tert-butyloxycarbonyl-1,2-cyclopropanediamin hydrochloride (III-10) may be prepared and purified analogously to Example (III-9) (see 58.5).

Analytical HPLC-MS (method B): RT=1.46 min.

60.3 tert-butyl 2-(2-chloro-5-oxo-6,7-dihydro-5H-5λ$^4$-thieno[3,2-d]pyrimidin-4-ylamino)-cyclopropyl]-carbamidate (IV-10)

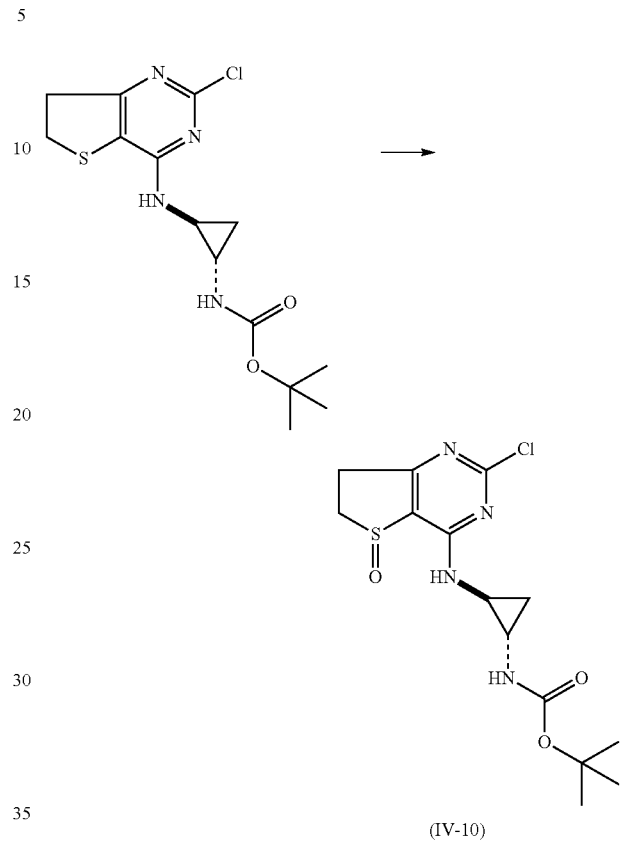

(IV-10)

Starting from (III-10) (IV-10) is prepared and purified as a mixture of diastereomers analogously to Example (IV-9).

Analytical HPLC-MS (method B): RT=1.27 min. Chiral HPLC (column: Diacel ADS-H, 250×4.6 mm, 5 μm, eluant: ((9/1) hexane+diethylamine (0.2%)/methanol/ethanol (1/1), 10° C., flow rate: 1 ml/min): RT=6.7 min and RT=8.3 min.

60.4 tert-butyl (2-{2-[4-(4-chlorophenyl)-piperidin-1-yl]-5-oxo-6,7-dihydro-5H-5λ$^4$-thieno[3,2-d]pyrimidin-4-ylamino}-cyclopropyl)-carbamidate (Example 231)

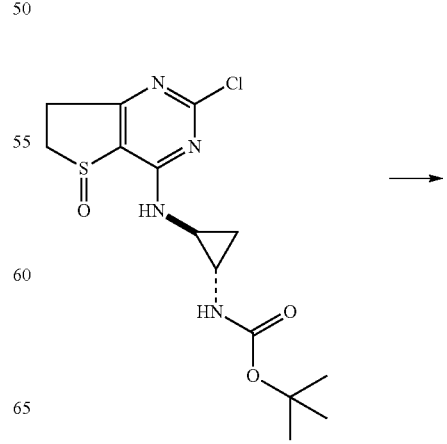

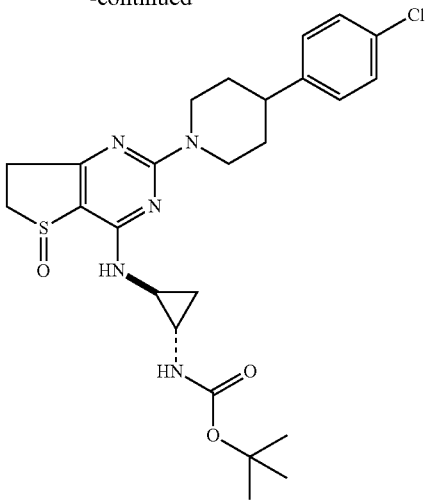

Example 231

Starting from (IV-10) Example 231 is prepared and purified as a mixture of diastereoisomers analogously to Example 222 (see 58.7). Analytical HPLC-MS (method B): RT=1.48 min. Chiral HPLC (column: Diacel ADS-H, 250×4.6 mm, 5 µm, eluant: (hexane+diethylamine (0.2%)/isopropanol (8/2), 10° C., flow rate: 1 ml/min): RT=15.17 min and RT=18.1 min.

61. Synthesis of: N-{2-[4-(4-Chlorophenyl)-Piperidin-1-Yl]-5-Oxo-6,7-Dihydro-5H-5$\lambda^4$-Thieno[3,2-d]Pyrimidin-4-Yl}-Cyclopropan-1,2-Diamine (Examples 232 and 245)

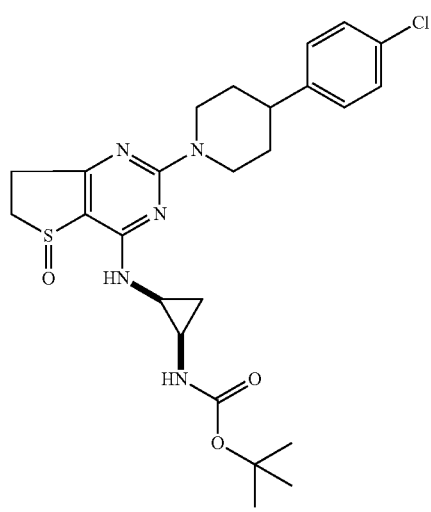

Examples 232 and 245

150 mg of Example 222 (see 58.7) are placed in 0.5 ml dichloromethane and 0.25 ml trifluoroacetic acid are added. The reaction mixture is stirred for 1 h in the ice bath and 2 h at ambient temperature, then cooled in the ice bath, mixed with water and made basic with conc. Ammonia. The product is extracted with dichloromethane and purified by chromatography (preparative HPLC, method B). 57 mg of Example 232 and 27 mg of Example 245 are obtained. Analytical HPLC-MS (method E): RT=2.73 min (Example 232); RT=2.85 min (Example 245).

62. Synthesis of: N-{2-[4-(4-Chlorophenyl)-Piperidin-1-Yl]-5-Oxo-6,7-Dihydro-5H-5$\lambda^4$-Thieno[3,2-d]Pyrimidin-4-Yl}-Cyclopropan-1,2-Diamine (Example 233)

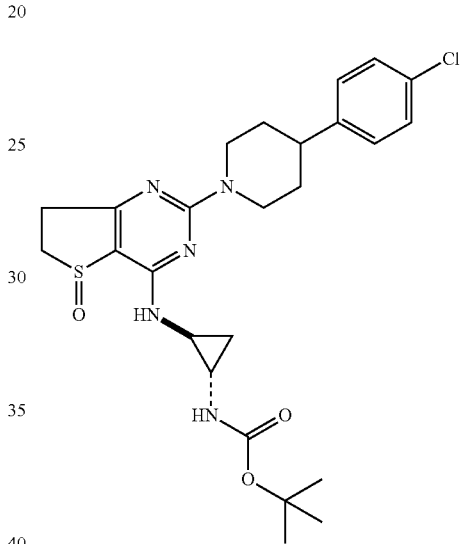

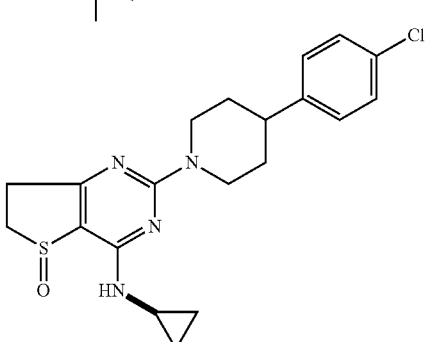

Example 233

Starting from Example 231 (see 60.4) Example 233 is prepared and purified as a mixture of diastereomers analogously to Examples 232/245 (see 61).

Analytical HPLC-MS (method B): RT=1.24 min.

62. Synthesis of: N-Cyclopropyl-N-Methyl-4-{1-[5-Oxo-4-(Tetrahydropyran-4-Ylamino)-6,7-Dihydro-5H-5λ⁴-Thieno[3,2-d]Pyrimidin-2-Yl]-Piperidin-4-Yloxy}-Benzamide (Example 242)

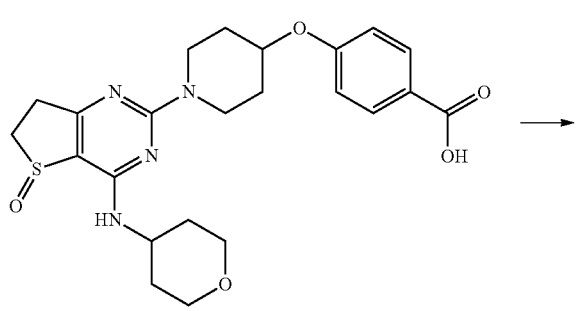

Example 184

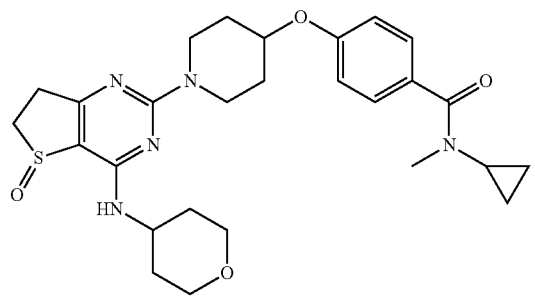

Example 242

55 mg of Example 184 (see 40.) are placed in 2 ml dimethylformamide, then 81 l diisopropylethylamine and 53.1 mg O-(7-azabenzotriazol-1-yl-)-N,N,N',N'-tetramethyluronium hexafluorophosphate (HATU) are added. After 15 min 13.8 mg cyclopropylmethylamine hydrochloride are added. The reaction mixture is stirred at ambient temperature until there is no further reaction and the product is purified directly by preparative HPLC (method B). 30 mg of Example 242 are obtained as a solid.

Analytical HPLC-MS (method D): RT=1.03 min.

63. Synthesis of: 5-{2-[4-(4-Chlorophenyl)-4-Hydroxymethylpiperidin-1-Yl]-5-Oxo-6,7-Dihydro-5H-5λ⁴-Thieno[3,2-d]Pyrimidin-4-Ylamino}-1-Methyl Piperidin-2-One (Example 246)

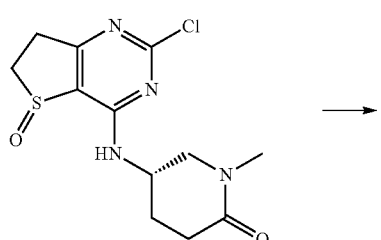

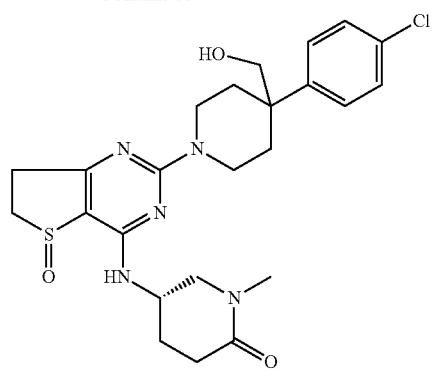

Example 246

Starting from (IV-5) (see 5.5) and [4-(4-chlorophenyl)-piperidin-4-yl]-methanol (see *J. Med. Chem.* 2004, 497) Example 246 may be prepared and purified analogously to Example 89 (see 21.). Analytical HPLC-MS (method B): RT=1.21 min.

64. Synthesis of: N-Cyclopropyl-N-Methyl-3-{1-[5-Oxo-4-(Tetrahydro Pyran-4-Ylamino)-6,7-Dihydro-5H-5λ⁴-Thieno[3,2-d]Pyrimidin-2-Yl]-Piperidin-4-Yl}-Benzamide (Example 249)

64.1 methyl 3-{1-[5-oxo-4-(tetrahydropyran-4-ylamino)-6,7-dihydro-5H-5λ⁴-thieno[3,2-d]pyrimidin-2-yl]-piperidin-4-yl}-benzoate

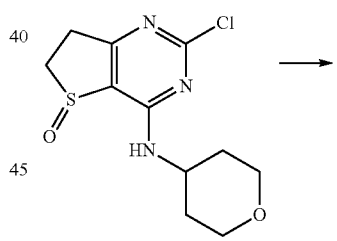

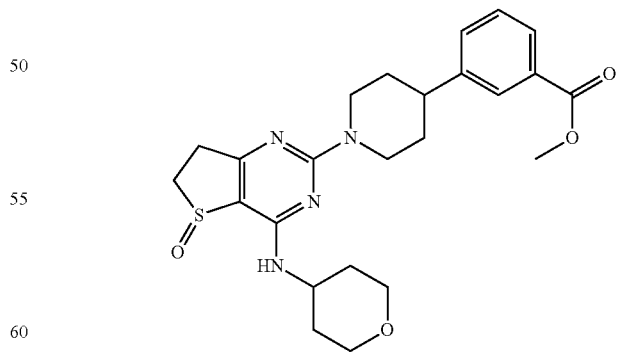

Starting from (IV-6) (see 6.2) and methyl 3-piperidin-4-yl-benzoate hydrochloride the product may be prepared and purified analogously to Example 89 (see 21.).

Analytical HPLC-MS (method D): RT=1.15 min.

64.2 3-{1-[5-oxo-4-(tetrahydropyran-4-ylamino)-6,7-dihydro-5H-5λ⁴-thieno[3,2-d]pyrimidin-2-yl]-piperidin-4-yl}-benzoic acid

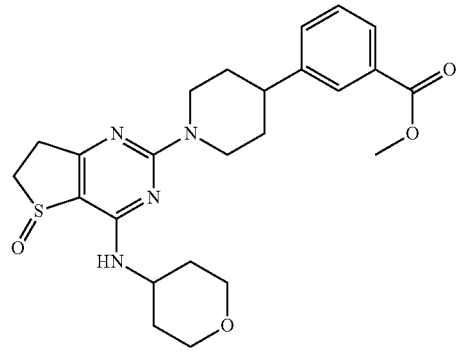

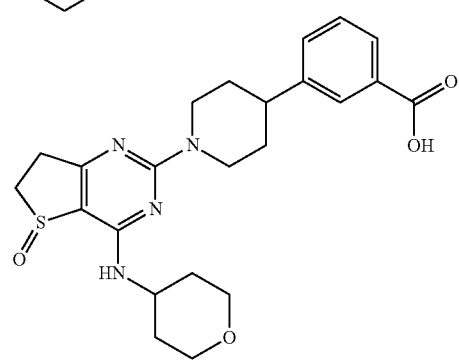

1.3 g methyl 3-{1-[5-oxo-4-(tetrahydropyran-4-ylamino)-6,7-dihydro-5H-5λ⁴-thieno[3,2-d]pyrimidin-2-yl]-piperidin-4-yl}-benzoate are placed in 24.6 ml of methanol, then 9.2 ml of a 1 N NaOH solution are added. The reaction mixture is stirred at ambient temperature until there is no further reaction, then combined with a 1 N HCl solution. The methanol is spun off and the precipitated solid is suction filtered. The product is purified by preparative HPLC (method B). 760 mg product are obtained as a solid.

Analytical HPLC-MS (method D): RT=0.80 min.

64.3 N-cyclopropyl-N-methyl-3-{1-[5-oxo-4-(tetrahydropyran-4-ylamino)-6,7-dihydro-5H-5λ⁴-thieno[3,2-d]pyrimidin-2-yl]-piperidin-4-yl}-benzamide (Example 249)

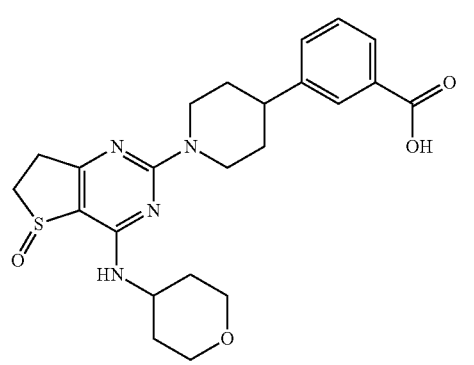

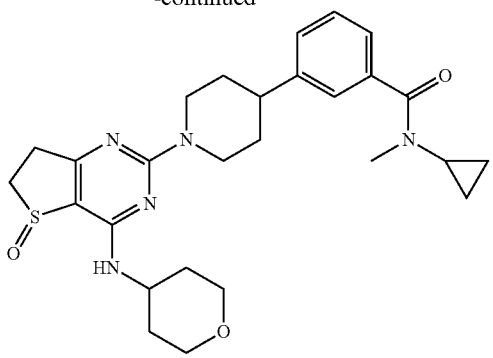

Example 249

59.8 mg 3-{1-[5-oxo-4-(tetrahydropyran-4-ylamino)-6,7-dihydro-5H-5λ⁴-thieno[3,2-d]pyrimidin-2-yl]-piperidin-4-yl}-benzoic acid are placed in 2.3 ml dimethylformamide, then 91 l diisopropylethylamine and 60 mg O-(7-azabenzotriazol-1-yl-)-N,N,N',N'-tetramethyluronium hexafluorophosphate (HATU) are added. After 15 min a mixture of 15.5 mg cyclopropylmethylamine hydrochloride in 300 l dimethylformamide is added. The reaction mixture is stirred at ambient temperature until there is no further reaction, and the product is purified directly by preparative HPLC (method B). 50 mg Example 249 are obtained as a solid. Analytical HPLC-MS (method D): RT=1.05 min.

65. Synthesis of: 1-Methyl-5-{2-[4-(Morpholine-4-Carbonyl)-4-Phenyl Piperidin-1-Yl]-5-Oxo-6,7-Dihydro-5H-5λ⁴-Thieno[3,2-d]Pyrimidin-4-Ylamino}-Piperidin-2-One (Example 252)

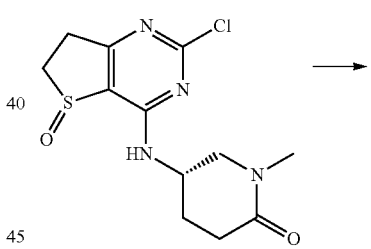

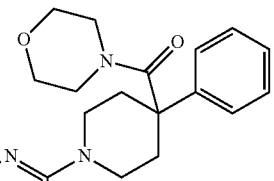

Example 252

Starting from (IV-5) (see 5.5) and morpholin-4-yl-(4-phenylpiperidin-4-yl)-methanone (see *bioorg. Med. Chem. Lett.* 1997, 2531) Example 252 may be prepared and purified analogously to Example 89 (see 21.). Analytical HPLC-MS (method B): RT=1.18 min.

66. Synthesis of: N-{1-[4-(1-Methyl-6-Oxo-Piperidin-3-Ylamino)-5-Oxo-6,7-Dihydro-5H-5λ⁴-Thieno[3,2-d]Pyrimidin-2-Yl]-4-Phenylpiperidin-4-Ylmethyl}-Methanesulphonamide (Example 253)

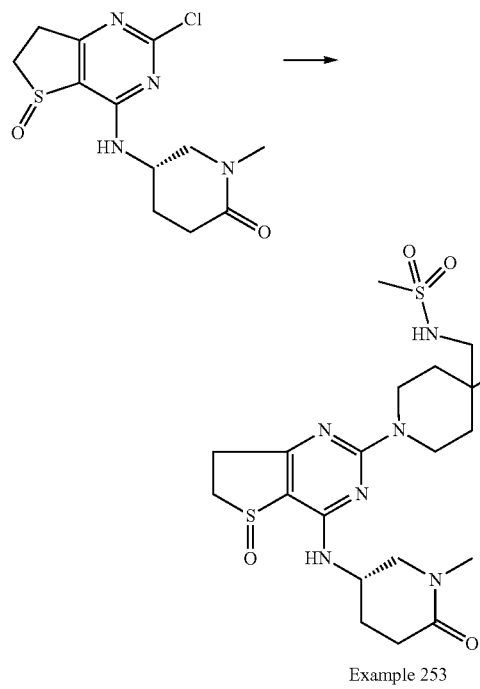

Example 253

Starting from (IV-5) (see 5.5) and N-(4-phenylpiperidin-4-ylmethyl)-methanesulphonamide (see *Bioorg. Med. Chem. Lett.*, 1998, 1851) Example 253 may be prepared and purified analogously to Example 89 (see 21.). Analytical HPLC-MS (method B): RT=1.15 min.

67. Synthesis of: 5-{2-[4-(4-Chlorophenyl)-4-Methoxymethylpiperidin-1-Yl]-5-Oxo-6,7-Dihydro-5H-5λ⁴-Thieno[3,2-d]Pyrimidin-4-Ylamino}-1-Methyl Piperidin-2-One (Example 260)

67.1 tert-butyl 4-(4-chlorophenyl)-4-hydroxymethylpiperidine-1-carboxylate

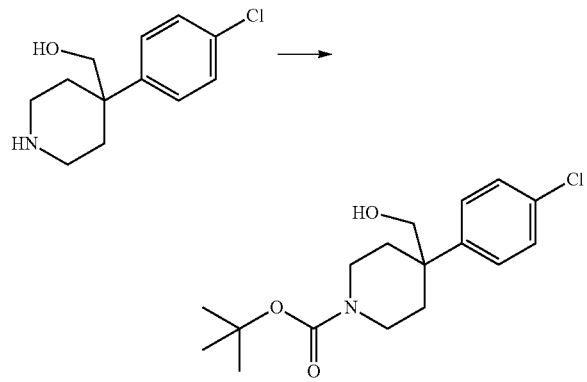

300 mg [4-(4-chlorophenyl)-piperidin-4-yl]-methanol (see *J. Med. Chem.* 2004, 497) are placed in 3 ml dioxane, then 0.5 ml of water and 0.224 g sodium carbonate are added. After 5 min 300 mg di-tert-butyl-dicarbonate are added. The reaction mixture is stirred for 3 h at ambient temperature, then mixed with water and the product is extracted with dichloromethane. 440 mg product are obtained as an oil.
Analytical HPLC-MS (method B): RT=1.65 min.

67.2 tert-butyl 4-(4-chlorophenyl)-4-methoxymethylpiperidine-1-carboxylate

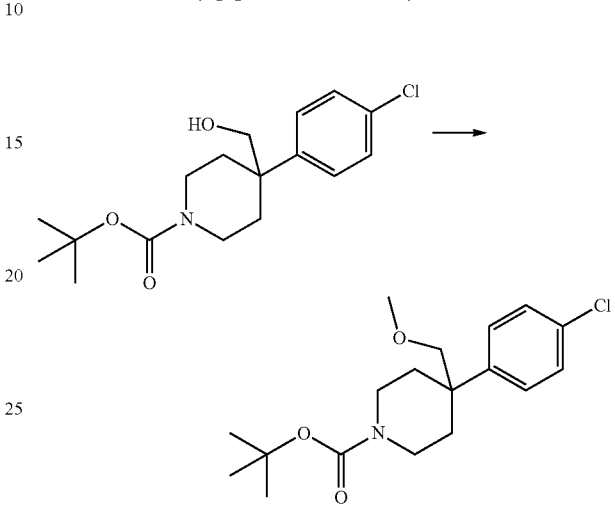

440 mg tert-butyl 4-(4-chlorophenyl)-4-hydroxymethylpiperidine-1-carboxylate are placed in 2.5 ml dimethylformamide and 92 mg sodium hydride (60% in mineral oil) are added. The reaction mixture is stirred for 30 min at ambient temperature, then 95 µl methyl iodide are added. After 1 h the reaction mixture is poured onto ice and the product is extracted with diethyl ether. 370 mg product are obtained as an oil.
Analytical HPLC-MS (method B): RT=1.87 min.

67.3 4-(4-chlorophenyl)-4-methoxymethylpiperidine (V-20)

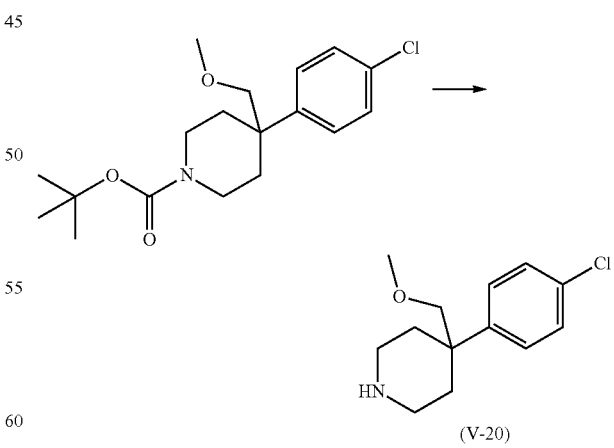

370 mg tert-butyl 4-(4-chlorophenyl)-4-methoxymethylpiperidine-1-carboxylate are placed in 1.5 ml dichloromethane, then 0.8 ml trifluoroacetic acid are added. The reaction mixture is stirred overnight at ambient temperature and evaporated to dryness. The residue is combined with toluene and evaporated to dryness again. The residue is triturated with diethyl ether and the solid is suction filtered. 284 mg (V-20) are obtained as the trifluoroacetate. Analytical HPLC-MS (method B): RT=1.23 min.

67.4 5-{2-[4-(4-chlorophenyl)-4-methoxymethylpiperidin-1-yl]-5-oxo-6,7-dihydro-5H-5μ⁴-thieno[3,2-d]pyrimidin-4-ylamino}-1-methylpiperidin-2-one (Example 260)

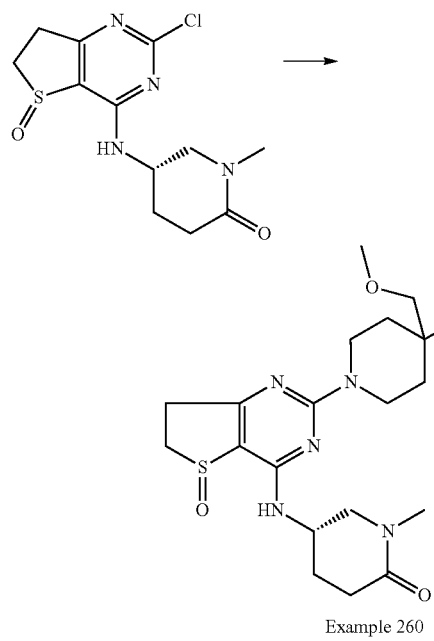

Example 260

Starting from (IV-5) (see 5.5) and (V-20) Example 260 may be prepared and purified analogously to Example 89 (see 21.). Analytical HPLC-MS (method B): RT=1.30 min.

68. Synthesis of: 5-{2-[4-(4-Chlorophenyl)-4-Methoxypiperidin-1-Yl]-5-Oxo-6,7-Dihydro-5H-5λ⁴-Thieno[3,2-d]Pyrimidin-4-Ylamino}-1-Methylpiperidin-2-One (Example 261)

68.1 4-(4-chlorophenyl)-4-methoxypiperidine (V-21)

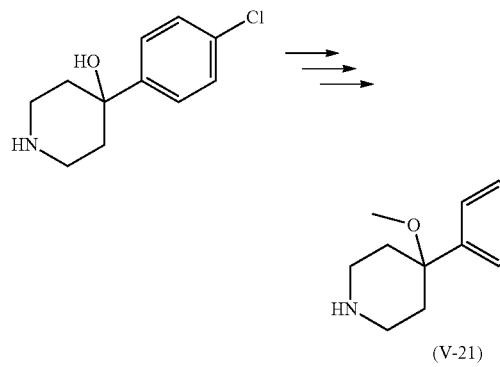

Starting from 4-(4-chlorophenyl)-piperidin-4-ol (V-21) may be prepared analogously to (V-20) (see 67.1 to 67.3). Analytical HPLC-MS (method B): RT=1.22 min.

68.2 5-{2-[4-(4-chlorophenyl)-4-methoxypiperidin-1-yl]-5-oxo-6,7-dihydro-5H-5λ⁴-thieno[3,2-d]pyrimidin-4-ylamino}-1-methylpiperidin-2-one (Example 261)

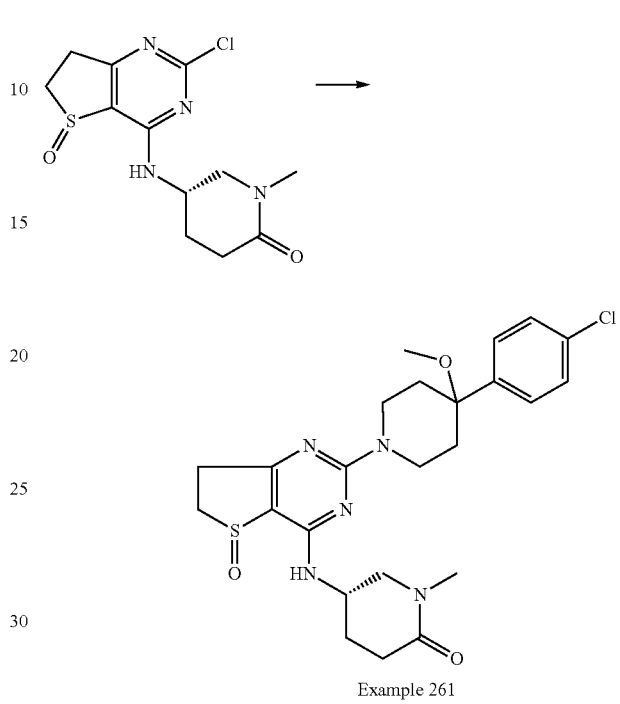

Example 261

Starting from (IV-5) (see 5.5) and (V-21) Example 261 may be prepared and purified analogously to Example 89 (see 21.). Analytical HPLC-MS (method B): RT=1.30 min.

69. Synthesis of: N-Methyl-N-{1-[4-(1-Methyl-6-Oxo-Piperidin-3-Ylamino)-5-Oxo-6,7-Dihydro-5H-5λ⁴-Thieno[3,2-d]Pyrimidin-2-Yl]-4-Phenylpiperidin-4-Ylmethyl}-Methanesulphonamide (Example 270)

69.1 N-methyl-N-(4-phenylpiperidin-4-ylmethyl)-methanesulphonamide (V-22)

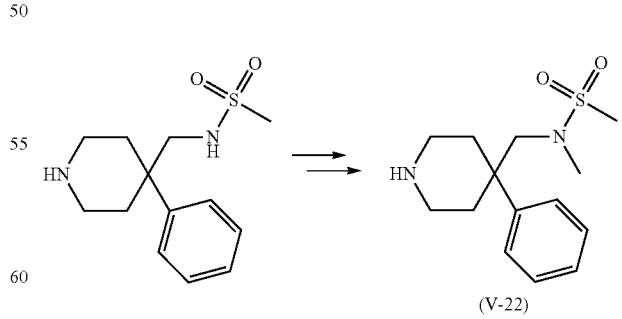

Starting from N-(4-phenylpiperidin-4-ylmethyl)-methanesulphonamide (see *Bioorg. Med. Chem. Lett.*, 1998, 1851) (V-22) may be prepared analogously to (V-20) (see 67.1 to 67.3). Analytical HPLC-MS (method B): RT=1.10 min.

69.2 N-methyl-N-{1-[4-(1-methyl-6-oxo-piperidin-3-ylamino)-5-oxo-6,7-dihydro-5H-5λ⁴-thieno[3,2-d]pyrimidin-2-yl]-4-phenylpiperidin-4-ylmethyl}-methanesulphonamide (Example 270)

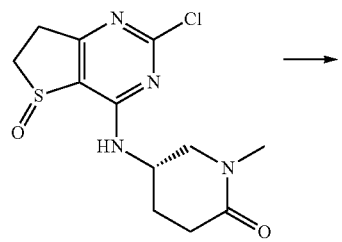

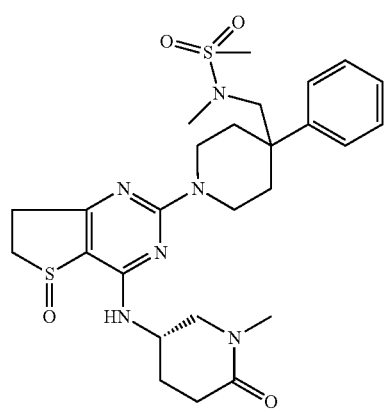

Example 270

Starting from (IV-5) (see 5.5) and (V-22) Example 270 may be prepared and purified analogously to Example 89 (see 21.). Analytical HPLC-MS (method B): RT=1.21 min.

70. Synthesis of: 5-{2-[4-(3,5-Difluorophenyl)-4-Methoxypiperidin-1-Yl]-5-Oxo-6,7-Dihydro-5H-5λ⁴-Thieno[3,2-d]Pyrimidin-4-Ylamino}-1-Methyl Piperidin-2-One (Example 273)

70.1 4-(3,5-difluorophenyl)-4-methoxypiperidine (V-23)

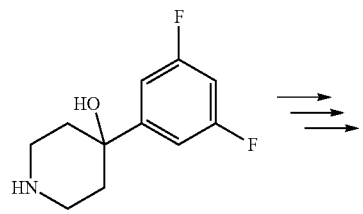

(V-23)

Starting from 4-(3,5-difluorophenyl)-piperidin-4-ol hydrochloride (V-23) may be prepared analogously to (V-20) (see 67.1 to 67.3). Analytical HPLC-MS (method B): RT=1.10 min.

70.2 5-{2-[4-(3,5-difluorophenyl)-4-methoxypiperidin-1-yl]-5-oxo-6,7-dihydro-5H-5λ⁴-thieno[3,2-d]pyrimidin-4-ylamino}-1-methylpiperidin-2-one (Example 273)

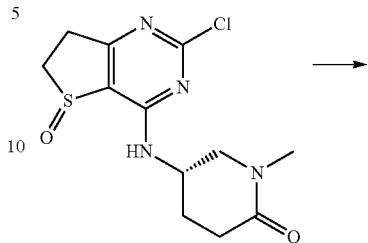

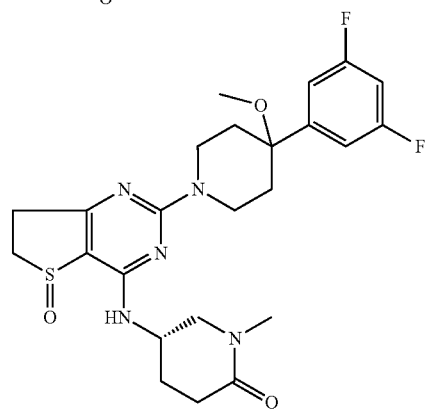

Example 273

Starting from (IV-5) (see 5.5) and (V-23) Example 273 may be prepared and purified analogously to Example 89 (see 21.). Analytical HPLC-MS (method B): RT=1.23 min.

71. Synthesis of: N-Methyl-N-{1-[4-(1-Methyl-6-Oxo-Piperidin-3-Ylamino)-5-Oxo-6,7-Dihydro-5H-5λ⁴-Thieno[3,2-d]Pyrimidin-2-Yl]-4-Phenylpiperidin-4-Ylmethyl}-Acetamide (Example 274)

71.1 N-methyl-N-(4-phenylpiperidin-4-ylmethyl)-acetamide (V-24)

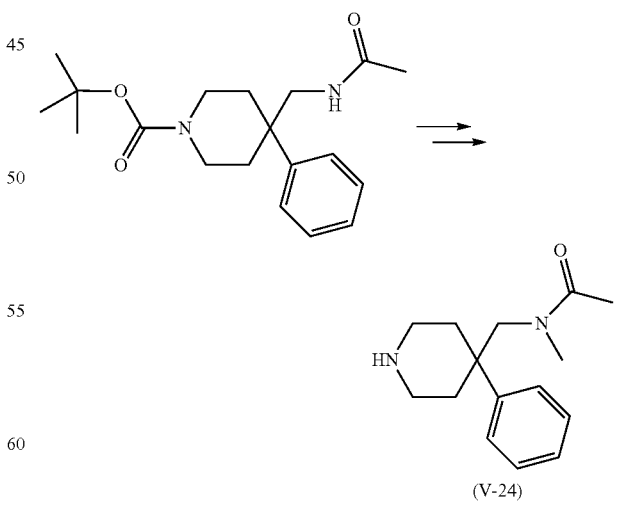

(V-24)

Starting from tert-butyl 4-(acetylaminomethyl)-4-phenylpiperidine-1-carboxylate (see 52.1) (V-24) may be prepared analogously to (V-20) (see 67.2 and 67.3).

Analytical HPLC-MS (method B): RT=1.12 min.

71.2 N-methyl-N-{1-[4-(1-methyl-6-oxo-piperidin-3-ylamino)-5-oxo-6,7-dihydro-5H-5λ⁴-thieno[3,2-d]pyrimidin-2-yl]-4-phenylpiperidin-4-ylmethyl}-acetamide (Example 274)

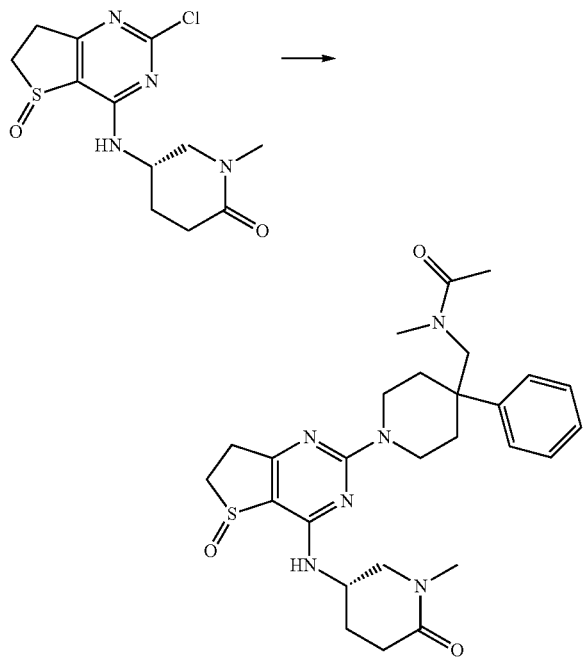

Example 274

Starting from (IV-5) (see 5.5) and (V-24) Example 274 may be prepared and purified analogously to Example 89 (see 21.). Analytical HPLC-MS (method D): RT=1.19 min.

72. Synthesis of: 1-Methyl-5-{2-[4-(5-Methyl-4-Phenyl-Oxazol-2-Yl)-Piperidin-1-Yl]-5-Oxo-6,7-Dihydro-5H-5λ⁴-Thieno[3,2-d]Pyrimidin-4-Ylamino}-Piperidin-2-One (Example 275)

72.1 4-(5-methyl-4-phenyloxazol-2-yl)-piperidine (V-25)

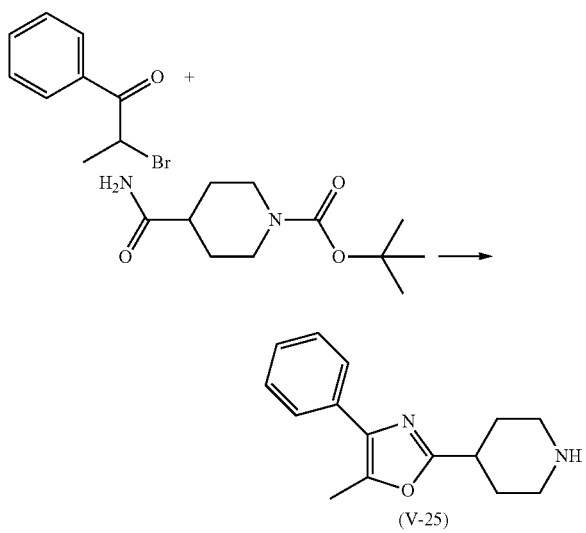

1.75 g 2-bromo-1-phenylpropan-1-one and 1.87 g tert-butyl 4-carbamoylpiperidine-1-carboxylate are placed in 0.5 ml NMP. The reaction mixture is heated to 160° C. for 20 min in the microwave and for 35 min in the oil bath, then after cooling it is taken up in methanol and evaporated to dryness. The residue is mixed with water, treated in the ultrasound bath and the insoluble oil is suction filtered. The mother liquor is purified by preparative HPLC (method C). 160 mg (V-25) are obtained as the trifluoroacetate.

Analytical HPLC-MS (method B): RT=1.24 min.

72.2 1-methyl-5-{2-[4-(5-methyl-4-phenyloxazol-2-yl)-piperidin-1-yl]-5-oxo-6,7-dihydro-5H-5λ⁴-thieno[3,2-d]pyrimidin-4-ylamino}-piperidin-2-one (Example 275)

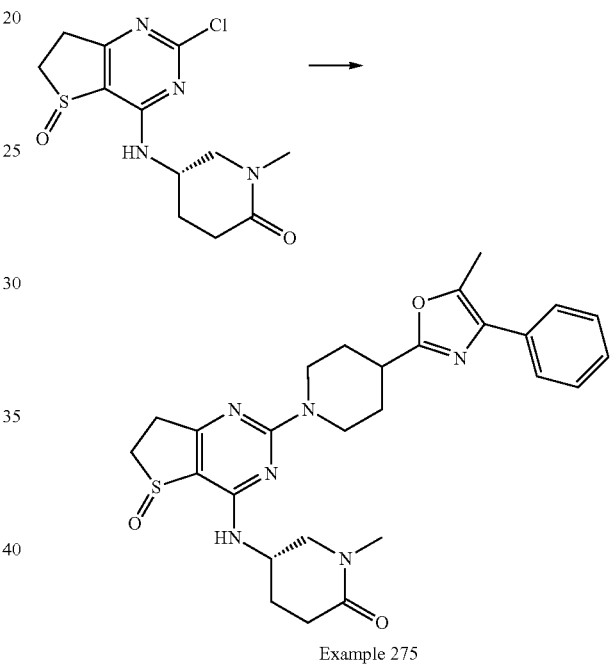

Example 275

Starting from (IV-5) (see 5.5) and (V-21) Example 275 may be prepared and purified analogously to Example 89 (see 21.). Analytical HPLC-MS (method D): RT=1.08 min.

73. Synthesis of: 5-{2-[4-(4,5-Diphenyloxazol-2-Yl)-Piperidin-1-Yl]-5-Oxo-6,7-DIHYDRO-5H-5λ⁴-Thieno[3,2-d]Pyrimidin-4-Ylamino}-1-Methylpiperidin-2-One (Example 278)

73.1 tert-butyl 4-(4,5-diphenyloxazol-2-yl)-piperidine-1-carboxylate

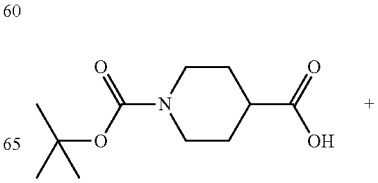

-continued

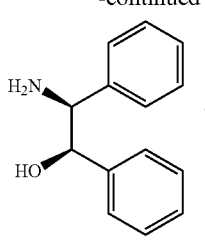

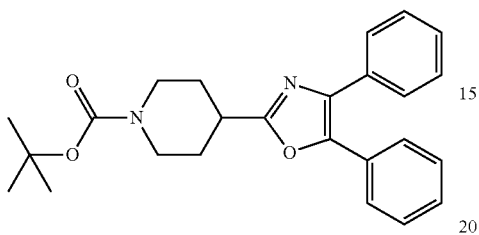

Starting from 1.08 g mono-tert-butyl piperidine-1,4-dicarboxylate and 1 g 2-amino-1,2-diphenyl-ethanol the product may be obtained as described in the literature (see *Tet.* 2001, 4867). The product is purified by chromatography (method B). 560 mg are obtained as an oil. Analytical HPLC-MS (method A): RT=1.72 min.

73.2 4-(4,5-diphenyloxazol-2-yl)-piperidine (V-26)

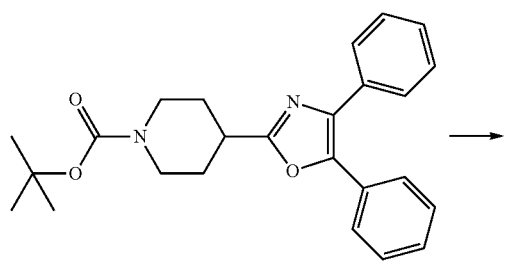

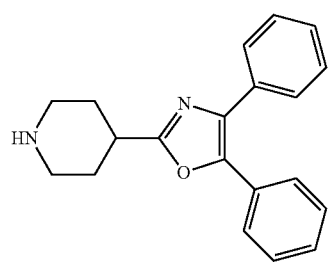

(V-26)

560 mg tert-butyl 4-(4,5-diphenyloxazol-2-yl)-piperidine-1-carboxylate are placed in 2 ml dichloromethane, then 1.1 ml trifluoroacetic acid are added. The reaction mixture is stirred for 15 hours at ambient temperature, then evaporated to dryness. The residue is combined with toluene and evaporated to dryness again. The residue is combined with diethyl ether and the precipitated solid is suction filtered and dried. 510 mg (V-26) are obtained.

Analytical HPLC-MS (method B): RT=1.38 min.

73.3 5-{2-[4-(4,5-diphenyloxazol-2-yl)-piperidin-1-yl]-5-oxo-6,7-dihydro-5H-5λ$^4$-thieno[3,2-d]pyrimidin-4-ylamino}-1-methylpiperidin-2-one (Example 278)

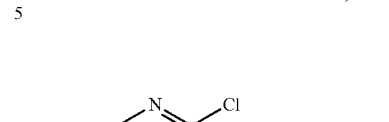

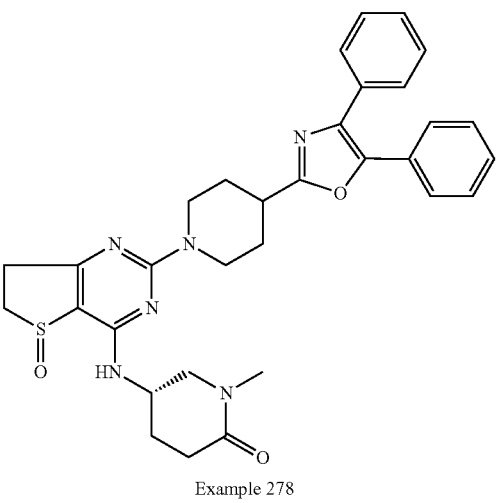

Example 278

Starting from (IV-5) (see 5.5) and (V-26) Example 278 may be prepared and purified analogously to Example 89 (see 21.). Analytical HPLC-MS (method B): RT=1.40 min.

74. Synthesis of: [1-(2-{4-[5-(4-Chlorophenyl)-4-Methyloxazol-2-Yl]-Piperidin-1-Yl}-5-Oxo-6,7-Dihydro-5H-5λ$^4$-Thieno[3,2-d]Pyrimidin-4-Ylamino)-Cyclopropyl]-Methanol (Example 283)

74.1 4-[5-(4-chlorophenyl)-4-methyloxazol-2-yl]-piperidine (V-27)

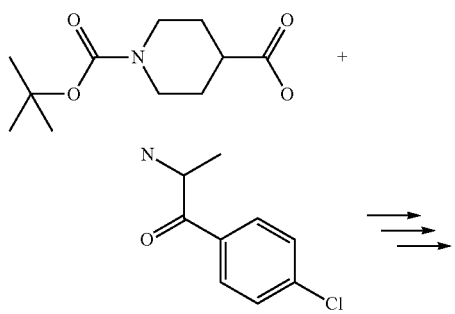

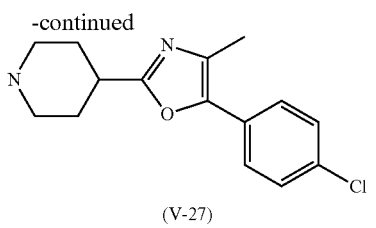

(V-27)

Starting from mono-tert-butyl piperidine-1,4-dicarboxylate and 2-amino-1-(4-chlorophenyl)-propane-1-one (see *J. Med. Chem.* 1974, 416) (V-27) may be prepared analogously to (V-26) (see 73.1 and 73.2). Analytical HPLC-MS (method B): RT=1.30 min.

74.2 [1-(2-{4-[5-(4-chlorophenyl)-4-methyloxazol-2-yl]-piperidin-1-yl}-5-oxo-6,7-dihydro-5H-5λ⁴-thieno[3,2-d]pyrimidin-4-ylamino)-cyclopropyl]-methanol (Example 283)

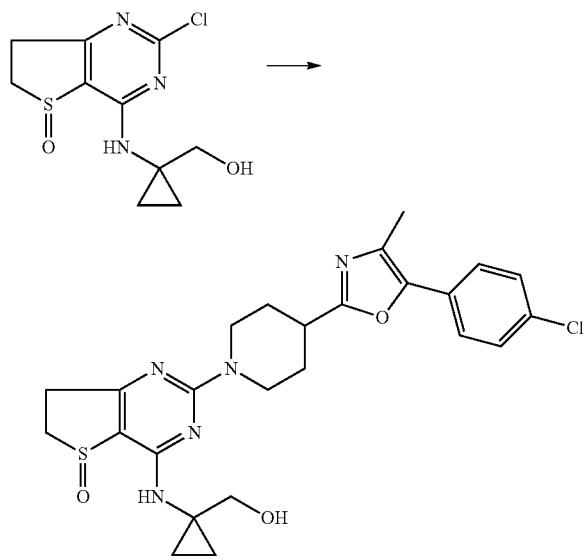

Example 283

Starting from (IV-2) (see 2.4) and (V-27) Example 283 may be prepared and purified analogously to Example 89 (see 21.). Analytical HPLC-MS (method B): RT=1.37 min.

75. Synthesis of: {2-[4-Benzyloxymethyl-4-(4-Chlorophenyl)-Piperidin-1-Yl]-5-Oxo-6,7-Dihydro-5H-5λ⁴-Thieno[3,2-d]Pyrimidin-4-Yl}-(3-Fluorophenyl)-Amine (Example 306)

75.1
4-benzyloxymethyl-4-(4-chlorophenyl)-piperidine
(V-28)

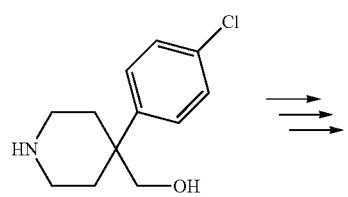

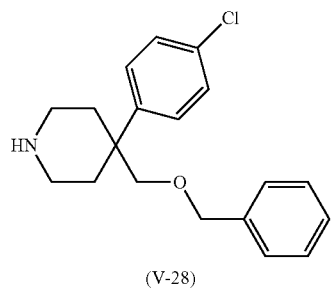

(V-28)

Starting from [4-(4-chlorophenyl)-piperidin-4-yl]-methanol (see *J. Med. Chem.* 2004, 497) (V-28) may be prepared analogously to (V-20) (see 67.1 to 67.3).

Analytical HPLC-MS (method B): RT=1.43 min 75.2 {2-[4-benzyloxymethyl-4-(4-chlorophenyl)-piperidin-1-yl]-5-oxo-6,7-dihydro-5H-5λ⁴-thieno[3,2-d]pyrimidin-4-yl}-(3-fluorophenyl)-amine (Example 306)

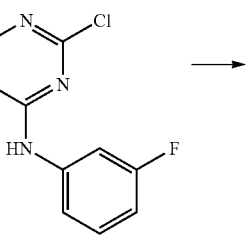

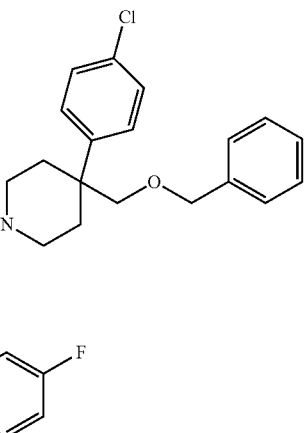

Example 306

Starting from (IV-7) (see 17.2) and (V-28) Example 306 may be prepared and purified analogously to Example 89 (see 21.). Analytical HPLC-MS (method B): RT=1.75 min.

76. Synthesis of: 2-Methoxy-N-Methyl-N-{1-[5-Oxo-4-(Tetrahydropyran-4-Ylamino)-6,7-Dihydro-5H-5λ⁴-Thieno[3,2-d]Pyrimidin-2-Yl]-4-Phenylpiperidin-4-Ylmethyl}-Acetamide (Example 323)

76.1 4-benzyloxymethyl-4-(4-chlorophenyl)-piperidine (V-29)

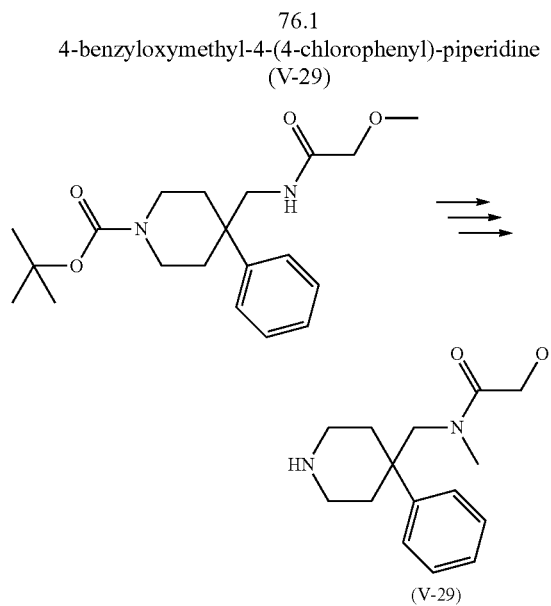

Starting from tert-butyl 4-[(2-methoxyacetylamino)-methyl]-4-phenylpiperidine-1-carboxylate (see 50.1) (V-28) may be prepared analogously to (V-20) (see 67.2 to 67.3).

76.2 2-methoxy-N-methyl-N-{1-[5-oxo-4-(tetrahydropyran-4-ylamino)-6,7-dihydro-5H-5λ⁴-thieno[3,2-d]pyrimidin-2-yl]-4-phenylpiperidin-4-ylmethyl}-acetamide (Example 323)

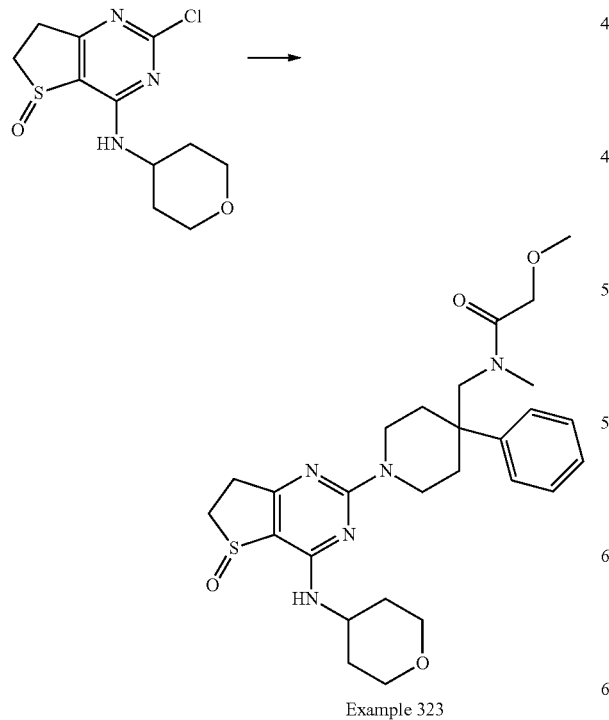

Starting from (IV-6) (see 6.2) and (V-29) Example 323 may be prepared and purified analogously to Example 89 (see 21.). Analytical HPLC-MS (method B): RT=1.24 min.

77. Synthesis of: 5-Oxo-2-[4-(4,5,6,7-Tetrahydrobenzoxazol-2-Yl)-Piperidin-1-Yl]-6,7-Dihydro-5H-5λ⁴-Thieno[3,2-d]Pyrimidin-4-Yl}-(Tetrahydro Pyran-4-Yl)-Amine (Example 329)

77.1 2-(1-benzylpiperidin-4-yl)-4,5,6,7-tetrahydrobenzoxazole

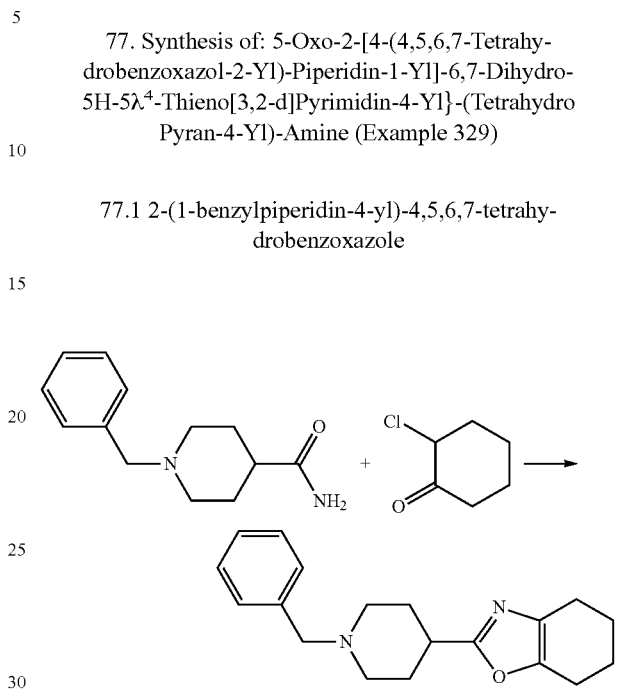

A mixture of 2.43 g 2-chlorocyclohexanone and 1 g 1-benzylpiperidine-4-carboxylic acid amide (see WO2005/61483) is heated to 160° C. in the microwave until there is no further reaction. The product is purified by chromatography. 963 mg of the product are obtained. Analytical HPLC-MS (method B): RT=1.28 min.

77.2 2-piperidin-4-yl-4,5,6,7-tetrahydrobenzoxazole (V-30)

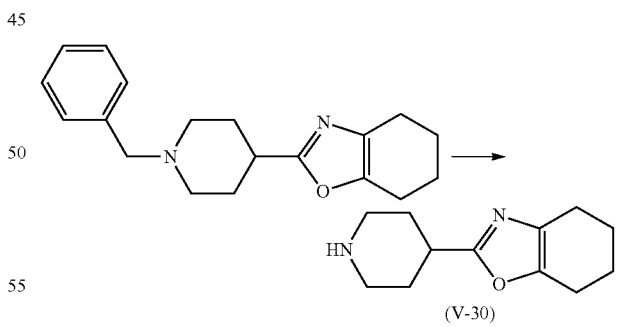

903 mg 2-(1-benzyl-piperidin-4-yl)-4,5,6,7-tetrahydrobenzoxazole are placed in 20 ml of methanol and hydrogenated with 450 mg Pd/C 10% at a pressure of 3 bar and at ambient temperature. After 12 hours the catalyst is suction filtered and the filtrate is evaporated to dryness. The product is purified by chromatography. 469 mg (V-30) are obtained as the trifluoroacetate. Analytical HPLC-MS (method B): RT=1.09 min.

77.3 5-oxo-2-[4-(4,5,6,7-tetrahydrobenzoxazol-2-yl)-piperidin-1-yl]-6,7-dihydro-5H-5λ⁴-thieno[3,2-d]pyrimidin-4-yl}-(tetrahydropyran-4-yl)-amine (Example 329)

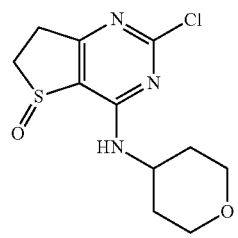
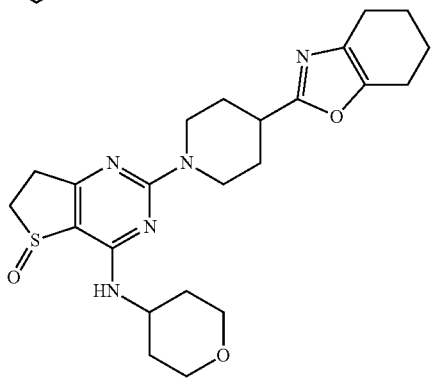

Example 329

Starting from (IV-2) (see 2.4) and (V-30) Example 329 may be prepared and purified analogously to Example 89 (see 21.). Analytical HPLC-MS (method B): RT=1.23 min.

Synthesis Scheme 2

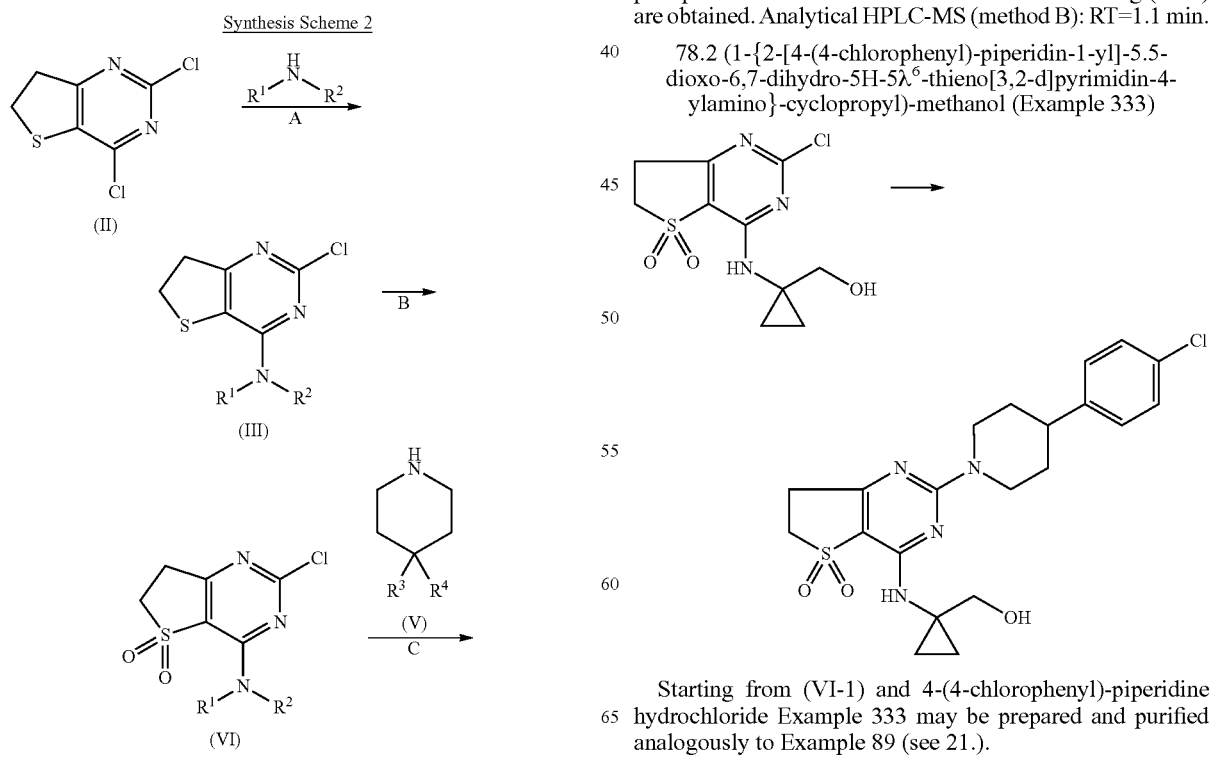

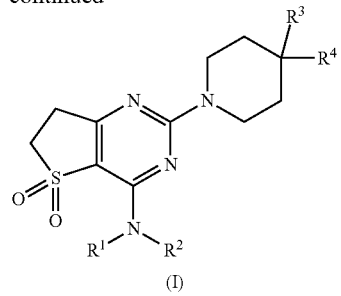

(I)

For the preparation of (II) see WO06111549

78. Synthesis of: (1-{2-[4-(4-Chlorophenyl)-Piperidin-1-Yl]-5.5-Dioxo-6,7-Dihydro-5H-5λ⁶-Thieno[3,2-d]Pyrimidin-4-Ylamino}-Cyclopropyl)-Methanol (Example 333)

78.1 [1-(2-chloro-5.5-dioxo-6,7-dihydro-5H-5λ⁶-thieno[3,2-d]pyrimidin-4-ylamino)-cyclopropyl]-methanol (VI-1)

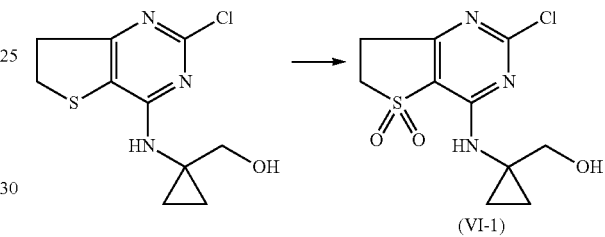

(VI-1)

200 mg (III-2) (see 2.2) are placed in 3 ml trifluoroacetic acid, then 180 l hydrogen peroxide (35%) are slowly added dropwise. An exothermic reaction takes place. The reaction mixture is stirred for 12 hours at ambient temperature, then combined with ice water and made basic with NH₄OH. The precipitated solid is suction filtered and dried. 80 mg (VI-1) are obtained. Analytical HPLC-MS (method B): RT=1.1 min.

78.2 (1-{2-[4-(4-chlorophenyl)-piperidin-1-yl]-5.5-dioxo-6,7-dihydro-5H-5λ⁶-thieno[3,2-d]pyrimidin-4-ylamino}-cyclopropyl)-methanol (Example 333)

Starting from (VI-1) and 4-(4-chlorophenyl)-piperidine hydrochloride Example 333 may be prepared and purified analogously to Example 89 (see 21.).
Analytical HPLC-MS (method B): RT=1.49 min.

79. Synthesis of: {2-[4-(4-Chlorophenyl)-Piperidin-1-Yl]-5.5-Dioxo-6,7-Dihydro-5H-5λ⁶-Thieno[3,2-d]Pyrimidine-4-Yl}-(Tetrahydropyran-4-Yl)-Amine (Example 334)

79.1 (2-chloro-5.5-dioxo-6,7-dihydro-5H-5λ⁶-thieno[3,2-d]pyrimidin-4-yl)-(tetrahydropyran-4-yl)-amine (VI-2)

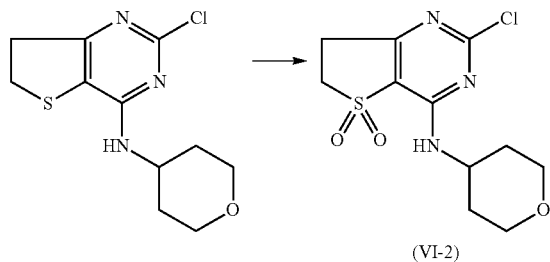 [SMILES: Clc1nc2c(c(NC3CCOCC3)n1)SCC2 ; O=S1(=O)CCc2nc(Cl)nc(NC3CCOCC3)c21 ; "(VI-2)"]

200 mg (III-2) (see 2.2) are placed in 3 ml trifluoroacetic acid, then 180 l hydrogen peroxide (35%) is slowly added dropwise. An exothermic reaction takes place. The reaction mixture is stirred for 12 hours at ambient temperature, then combined with ice water and made basic with NH₄OH. The precipitated solid is suction filtered and dried. 170 mg (VI-2) are obtained as a solid.

79.2 {2-[4-(4-chlorophenyl)-piperidin-1-yl]-5.5-dioxo-6,7-dihydro-5H-5λ⁶-thieno[3,2-d]pyrimidin-4-yl}-(tetrahydropyran-4-yl)-amine (Example 334)

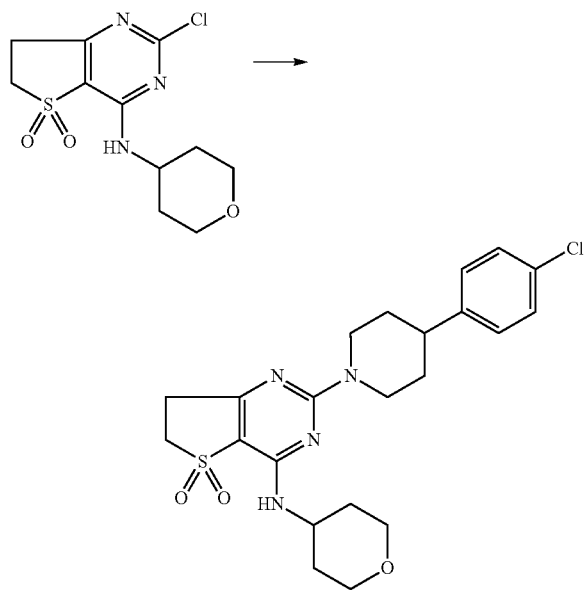

Starting from (VI-2) and 4-(4-chlorophenyl)-piperidine hydrochloride Example 334 may be prepared and purified analogously to Example 89 (see 21.).

Analytical HPLC-MS (method B): RT=1.55 min.

80. Synthesis of: 5-{2-[4-(4-Chlorophenyl)-Piperidin-1-Yl]-5.5-Dioxo-6,7-Dihydro-5H-5λ⁶-Thieno[3,2-d]Pyrimidin-4-Ylamino}-1-Methylpiperidin-2-One (Example 335)

80.1 5-(2-chloro-5.5-dioxo-6,7-dihydro-5H-5λ⁶-thieno[3,2-d]pyrimidin-4-ylamino)-1-methylpiperidin-2-one (VI-3)

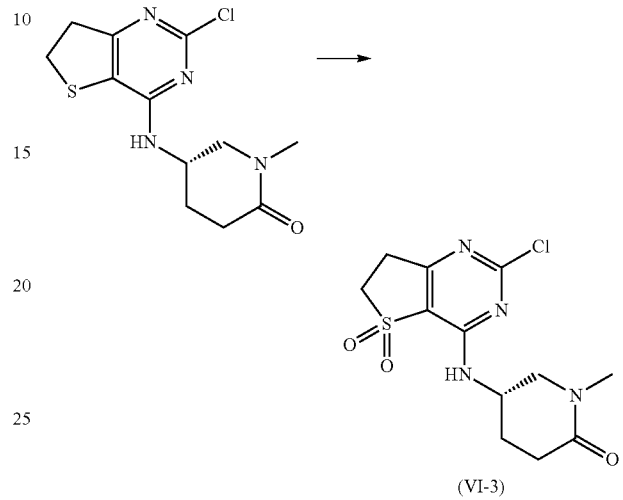

200 mg (III-5) (see 5.4) are placed in 3 ml trifluoroacetic acid, then 165 l hydrogen peroxide (35%) are slowly added dropwise. An exothermic reaction takes place. The reaction mixture is stirred for 12 hours at ambient temperature, then combined with ice water and made basic with NH₄OH. The product is extracted with dichloromethane. 150 mg (VI-3) are obtained as a solid.

80.2 5-{2-[4-(4-chlorophenyl)-piperidin-1-yl]-5.5-dioxo-6,7-dihydro-5H-5λ⁶-thieno[3,2-d]pyrimidin-4-ylamino}-1-methylpiperidin-2-one (Example 335)

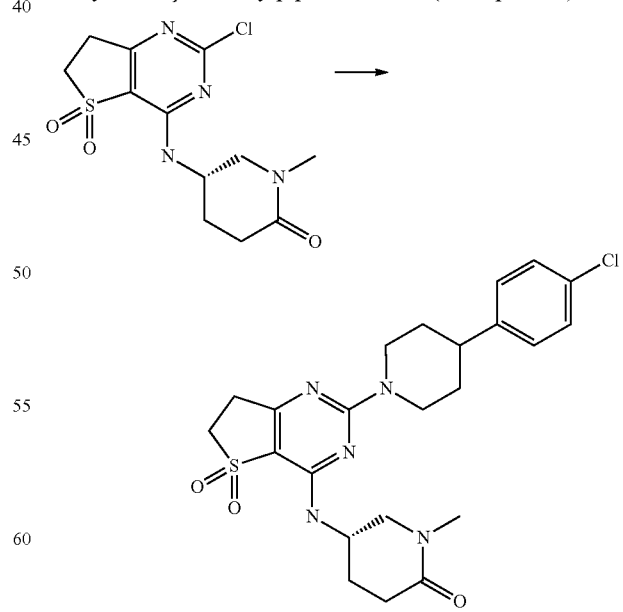

Starting from (VI-3) and 4-(4-chlorophenyl)-piperidine hydrochloride Example 335 may be prepared and purified analogously to Example 89 (see 21.).

Analytical HPLC-MS (method B): RT=1.48 min.

Chromatographical Methods

The Example compounds prepared by the synthesis schemes shown hereinbefore were characterised by the following chromatographical methods, which, if carried out, are shown specifically in Tables B, D and E.

Analytical HPLC-MS, Method A

Waters ZMD Mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

The stationary phase used is a Merck Chromolith™ Flash RP-18e column, 4.6 mm×25 mm (column temperature: constant at 25° C.).

Analytical HPLC-MS, Method B

Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

The stationary phase used is a Merck Chromolith™ Flash RP-18e column, 3 mm×100 mm (column temperature: constant at 25° C.).

Analytical HPLC-MS, Method C

Waters ZQ2000 mass spectrometer (positive ionisation (ESI+)), HP1100 HPLC (DAD, wavelength range: 210 to 500 nm), and Gilson 215 Autosampler.
A: water with 0.10% TFA
B: acetonitrile with 0.10% TFA

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

The stationary phase used is a Sunfire C18 column, 4.6×50 mm, 3.5 μm, column temperature 40° C.

Analytical HPLC-MS, Method D

Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% $NH_3$
B: acetonitrile with 0.10% $NH_3$

| time in min | % A | % B | flow rate in ml/min |
|---|---|---|---|
| 0.00 | 95 | 5 | 3.00 |
| 0.20 | 95 | 5 | 3.00 |
| 1.50 | 2 | 98 | 3.00 |
| 1.90 | 2 | 98 | 3.00 |
| 2.00 | 2 | 98 | 3.00 |

The stationary phase used is Waters, X-Bridge, C18, 3.5 nm, 4.6×20 mm. Ambient temperature.

Analytical HPLC-MS, Method E

Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 1.20 |
| 0.30 | 95 | 5 | 1.20 |
| 9.00 | 2 | 98 | 1.20 |
| 9.40 | 2 | 98 | 1.20 |
| 9.50 | 95 | 5 | 2.80 |
| 9.90 | 95 | 5 | 2.80 |
| 10.00 | 95 | 5 | 0.20 |

The stationary phase used is a Merck Chromolith™ Flash RP-18e column, 4.6 mm×25 mm (column temperature: constant at 25° C.).

Analytical HPLC, Method A

Agilent 1100 (diode array detection, wavelength range: 210-380 nm).
A: water with 0.10% TFA
B: acetonitrile with 0.13% TFA

| time in min | % A | % B | flow rate in ml/min |
|---|---|---|---|
| 0.00 | 95 | 5 | 1.50 |
| 0.60 | 95 | 5 | 1.50 |
| 3.40 | 2 | 98 | 1.50 |
| 3.90 | 2 | 98 | 1.50 |
| 4.20 | 95 | 5 | 1.50 |
| 4.90 | 95 | 5 | 1.50 |

The stationary phase used is a Varian Microsorb column, RP C18, 3 μm, 100 A, ambient temperature.

Preparative HPLC-MS, Method A

Waters ZQ2000 mass spectrometer (positive ionisation (ESI+)), HP1100 HPLC (DAD, wavelength range: 210-500 nm), and Gilson 215 Autosampler.
A: water with 0.10% TFA
B: acetonitrile

| time in min | % A | % B | flow rate in ml/min |
|---|---|---|---|
| 0.00 | 90 | 10 | 50 |
| 1.50 | 90 | 10 | 50 |
| 8.00 | 40 | 60 | 50 |
| 10.00 | 40 | 60 | 50 |
| 11.00 | 90 | 10 | 50 |

The stationary phase used is a Sunfire C18 column, 30×100 mm, 5 μm, ambient temperature.

Preparative HPLC, Method A

Gilson HPLC with Gilson UV-VIS-155 detector, Sampling injector 231 XL. The wavelength given is the substance-specific UV maximum.

A: water with 0.13% TFA
B: acetonitrile with 0.1% TFA

| time in min | % A | % B | flow rate in ml/min |
|---|---|---|---|
| 0.00 | 95 | 5 | 165 |
| 1.30 | 95 | 5 | 165 |
| 8.90 | 2 | 98 | 165 |
| 10.00 | 2 | 98 | 165 |
| 10.50 | 95 | 5 | 165 |
| 11.60 | 95 | 5 | 165 |

The stationary phase used is a Microsorb RP 18 column, 8 μm, 50×65 mm, ambient temperature.

Preparative HPLC, Method B

Gilson HPLC with Gilson UV-VIS-155 detector, Sampling injector 231 XL. The wavelength given is the substance-specific UV maximum.

A: water with 0.1% ammonia 35%
B: acetonitrile

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.-50 | 95 | 5 | 180 |

The stationary phase used is a Pursuit XRS RP 18 column, 10 μm, 50×150 mm, ambient temperature.

Preparative HPLC, Method C

Gilson HPLC with Gilson UV-VIS-155 detector, sampling injector 231 XL. The wavelength given is the substance-specific UV maximum.

A: water with 0.13% TFA
B: acetonitrile with 0.1% TFA

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.50 | 95 | 5 | 180 |

The stationary phase used is a Microsorb RP 18 column, 8 μm, 50×150 mm, ambient temperature.

Preparative HPLC, Method D

Gilson HPLC with Gilson UV-VIS-155 detector, sampling injector 231 XL. The wavelength given is the substance-specific UV maximum.

A: water with 0.1% ammonia 35%
B: acetonitrile

| time in min | % A | % B | flow rate in ml/min |
|---|---|---|---|
| 0.00 | 95 | 5 | 180 |
| 1.10 | 95 | 5 | 180 |
| 9.00 | 2 | 98 | 180 |
| 10.00 | 2 | 98 | 180 |
| 10.50 | 95 | 5 | 180 |
| 12.00 | 95 | 5 | 180 |

The stationary phase used is an X-Bridge C18 column, 5 μm, 50×65 mm, ambient temperature.

EXAMPLES

The following Examples were prepared analogously to the methods of synthesis described hereinbefore (as indicated in the Table). These compounds are suitable for use as PDE4-inhibitors and have $IC_{50}$ values of less than or equal to 1 μmol. The inhibitions (in %) at 1 μM of the individual Example substances are given in the following Table of Examples and were determined as follows:

The Scintillation Proximity Assay (SPA) (GE Healthcare, No. TRKQ7090) was carried out by using the different affinities of cyclic 3'-5'-adenosinemonophosphate (cAMP, low affinity) and linear 5'-adenosinemonophosphate (AMP, high affinity) for yttrium silicate scintillator beads. The cAMP specific phosphodiesterase (PDE) PDE4B cleaves the 3'-phosphoester bond of tritium-labelled [H3]-cAMP to form [H3]-5'-AMP. This [H3]-AMP accumulates on the scintillator beads because of its higher affinity for them and causes scintillation events (flashes of light) which are measured in a Wallac Microbeta Scintillation Counter.

The experiment starts with a one-hour incubation of [H3]-cAMP with the PDE4B enzyme in assay buffer at 30° C., in each case once with the Example substance to be tested (in a concentration of 1 μM) and once without the Example substance to be tested.

After this incubation, the reaction is stopped by the addition of the beads. The beads have an opportunity to settle in the next 45 minutes, then the measurement is carried out in the Scintillation Counter. If the substance is capable of inhibiting the enzymatic activity of the PDE4B, less [H3]-AMP is produced during the incubation phase and fewer scintillation events can be measured. These results are expressed as the percentage inhibition at a concentration of the test substance of 1 μM.

The Examples relate to compounds of the following formula 1,

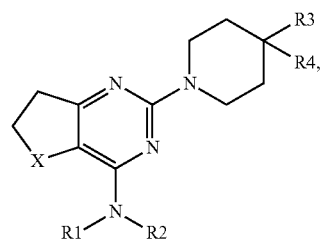

having the properties indicated in Tables A and B hereinafter:

TABLE A

Chemical structures of the Example substances 1-163

| # | Structure | R¹ | R² | R³ | R⁴ | % Inhibition PDE4B @ 1 μM |
|---|---|---|---|---|---|---|
| 1 | 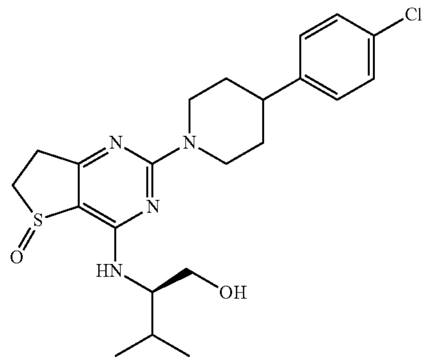 | H | | | H | 93 |
| 2 | 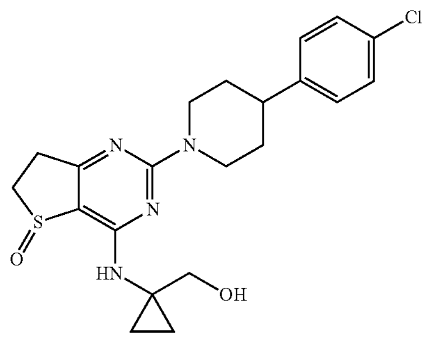 | H | | | H | 94 |
| 3 | 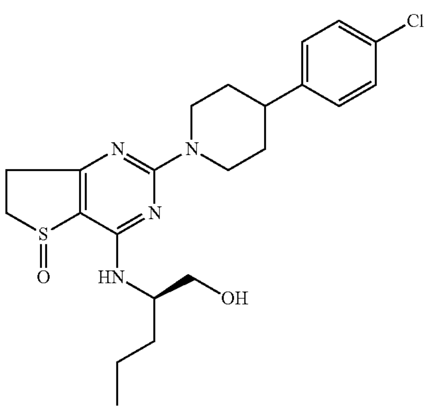 | H | | | H | 94 |
| 4 | 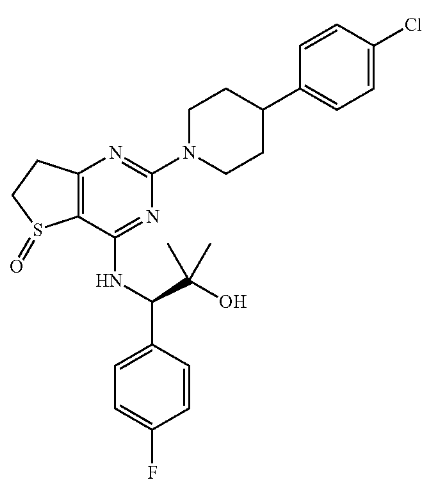 | H | | | H | 91 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 5 | 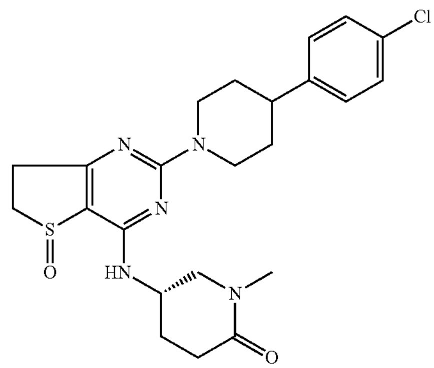 | H | * with (S)-5-methyl-2-oxopiperidin-5-yl | 4-chlorophenyl | H | 94 |
| 6 | 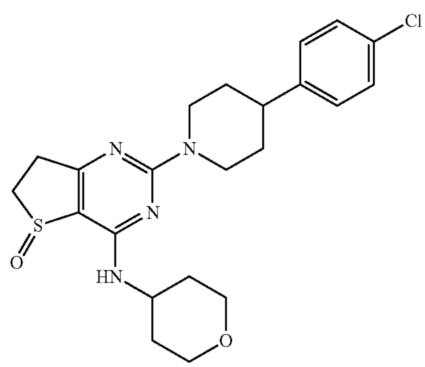 | H | * tetrahydropyran-4-yl | 4-chlorophenyl | H | 94 |
| 7 | 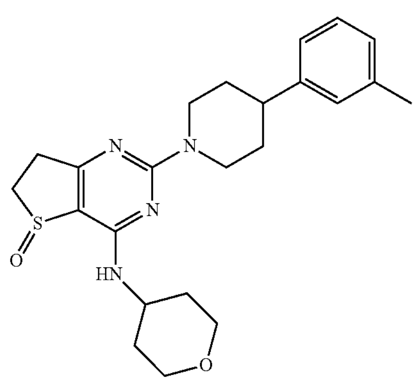 | H | * tetrahydropyran-4-yl | 3-methylphenyl | H | 93 |
| 8 | 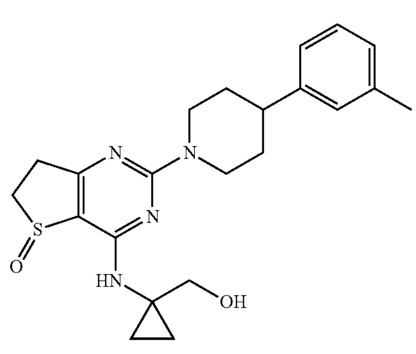 | H | * 1-(hydroxymethyl)cyclopropyl | 3-methylphenyl | H | 93 |

TABLE A-continued

Chemical structures of the Example substances 1-163

| # | Structure | R¹ | R² | R³ | R⁴ | % Inhibition PDE4B @ 1 μM |
|---|-----------|----|----|----|----|---------------------------|
| 9 | 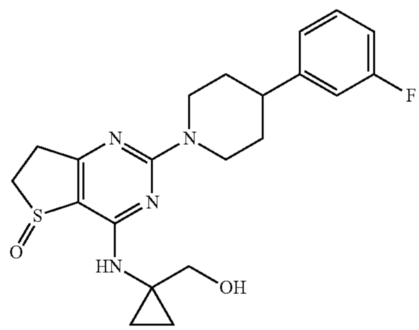 | H | *-C(cyclopropyl)(CH₂OH) | 3-F-C₆H₄-* | H | 95 |
| 10 | | F | H | *-tetrahydropyran-4-yl | 4-F-C₆H₄-* | H | 93 |
| 11 | | F | H | *-C(cyclopropyl)(CH₂OH) | 4-F-C₆H₄-* | H | 94 |
| 12 | 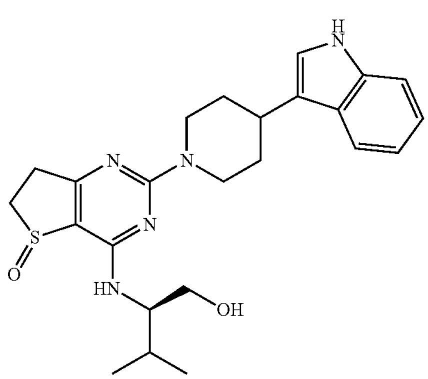 | H | *-CH(iPr)(CH₂OH) | 1H-indol-3-yl-* | H | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 13 | 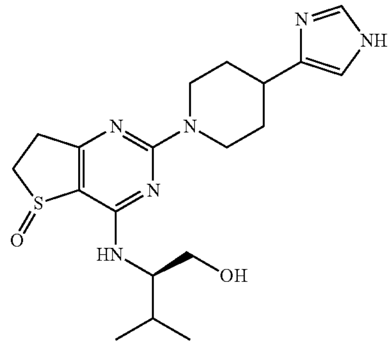 | H | *⟨OH (isobutyl) | imidazole | H | 71 |
| 14 | 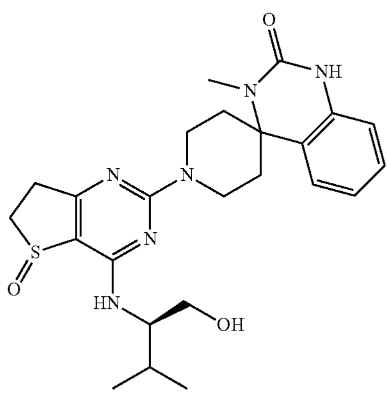 [SMILES: CC(C)[C@H](CO)Nc1nc(N2CCC3(CC2)c2ccccc2NC(=O)N3C)nc2c1S(=O)CC2] | H | *⟨OH (isobutyl) | N-methyl benzo-fused urea | | 60 |
| 15 | 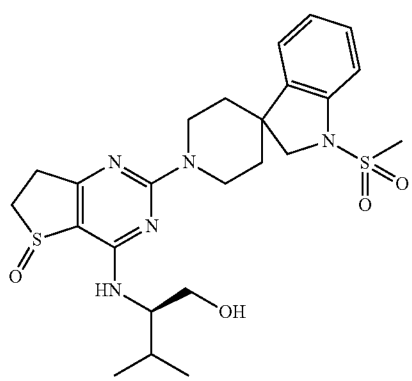 [SMILES: CC(C)[C@H](CO)Nc1nc(N2CCC3(CC2)CN(S(C)(=O)=O)c2ccccc23)nc2c1S(=O)CC2] | H | *⟨OH (isobutyl) | N-methylsulfonyl indoline | | 67 |
| 16 | 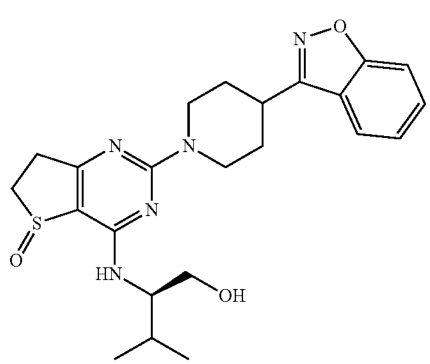 | H | *⟨OH (isobutyl) | benzisoxazole | H | 96 |

TABLE A-continued
Chemical structures of the Example substances 1-163
| # | Structure | R¹ | R² | R³ | R⁴ | % Inhibition PDE4B @ 1 μM |
|---|---|---|---|---|---|---|
| 17 | 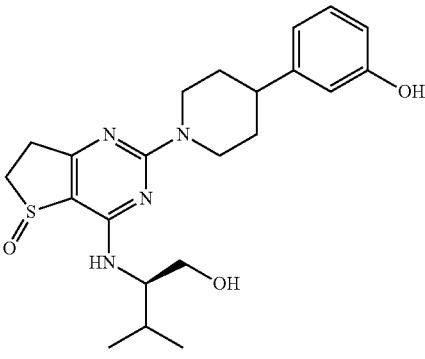 | H | 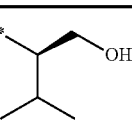 | 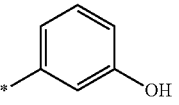 | H | 93 |
| 18 | 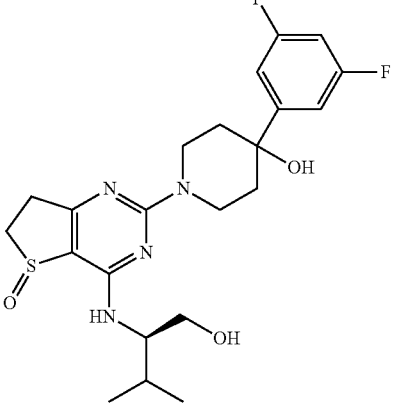 | H | 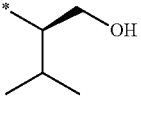 [SMILES: *[C@@H](CO)C(C)C] | 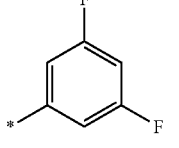 | OH | 92 |
| 19 | 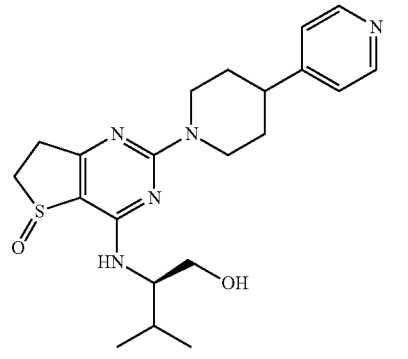 | H | 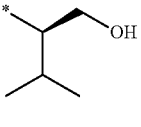 [SMILES: *[C@@H](CO)C(C)C] | 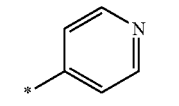 | H | 83 |
| 20 | 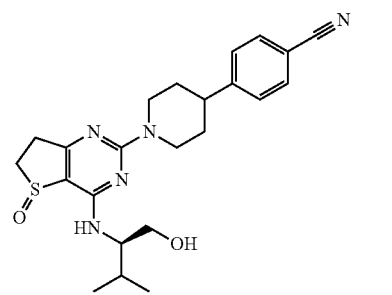 | H | 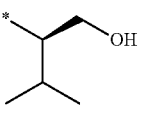 [SMILES: *[C@@H](CO)C(C)C] | 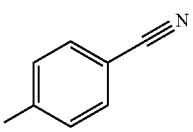 | H | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 21 | 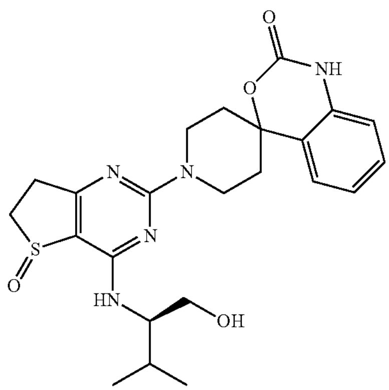 [SMILES: CC(C)[C@H](CO)Nc1nc(N2CCC3(CC2)OC(=O)Nc2ccccc23)nc2c1S(=O)CC2] | H | *∼isobutyl-CH₂OH | benzo-oxazinone | | 83 |
| 22 | 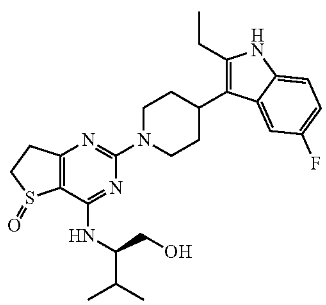 | H | *∼isobutyl-CH₂OH | 2-ethyl-5-fluoro-indol-3-yl | H | 86 |
| 23 | 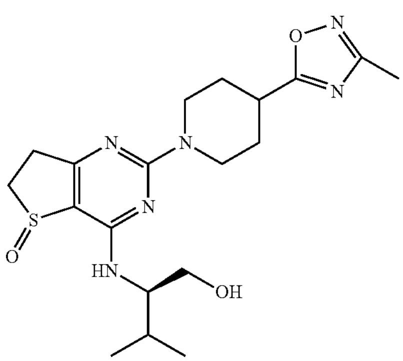 | H | *∼isobutyl-CH₂OH | 3-methyl-1,2,4-oxadiazol-5-yl | H | 85 |
| 24 | 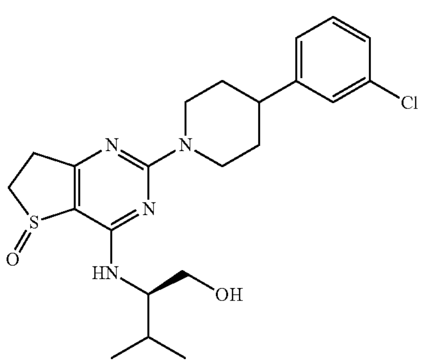 | H | *∼isobutyl-CH₂OH | 3-chlorophenyl | H | 94 |

TABLE A-continued

Chemical structures of the Example substances 1-163

| # | Structure | $R^1$ | $R^2$ | $R^3$ | $R^4$ | % Inhibition PDE4B @ 1 μM |
|---|---|---|---|---|---|---|
| 25 | 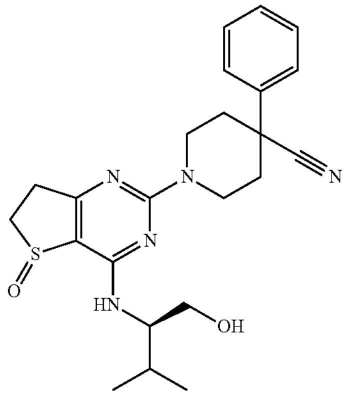 | H | *isobutyl-CH(CH2OH) | phenyl | CN | 90 |
| 26 | 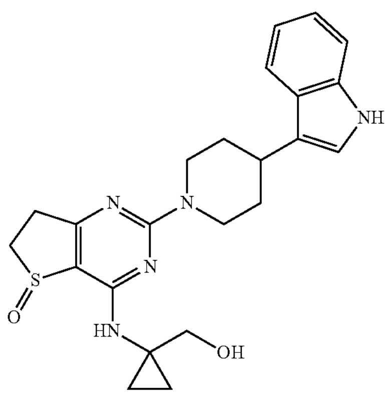 | H | 1-(hydroxymethyl)cyclopropyl | 1H-indol-3-yl | H | 96 |
| 27 | 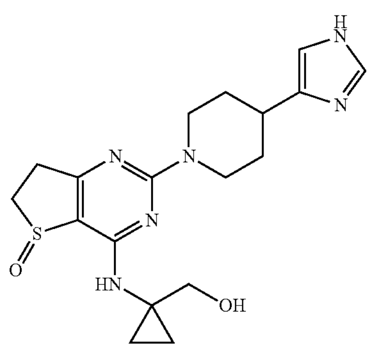 | H | 1-(hydroxymethyl)cyclopropyl | 1H-imidazol-4-yl | H | 87 |
| 28 | 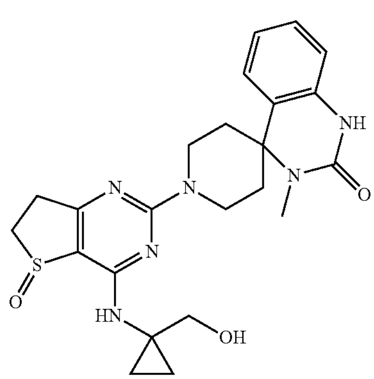 [SMILES: CN1C(=O)Nc2ccccc2C12CCN(c1nc3c(c(NC4(CO)CC4)n1)S(=O)CC3)CC2] | H | 1-(hydroxymethyl)cyclopropyl | 3-methyl-2-oxo-2,3-dihydroquinazolin-4(1H)-yl | | 85 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 29 | 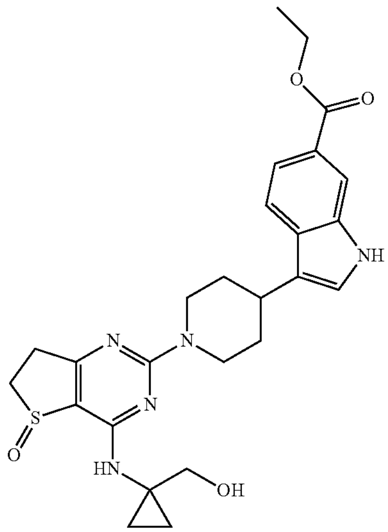 | H | *⟨cyclopropyl⟩CH₂OH | 3-methyl-1H-indole-6-carboxylic acid ethyl ester | H | 97 |
| 30 | 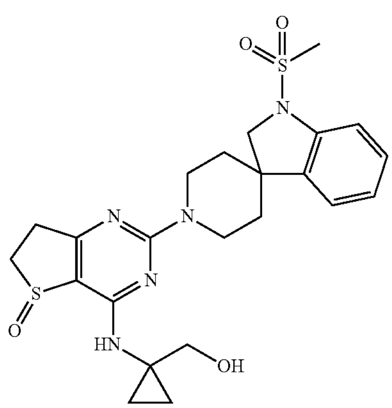 [SMILES: CS(=O)(=O)N1CC2(CCN(c3nc4c(c(NC5(CO)CC5)n3)S(=O)CC4)CC2)c2ccccc21] | H | *⟨cyclopropyl⟩CH₂OH | 1-(methylsulfonyl)-2,3-dihydro-1H-indole | | 89 |
| 31 | 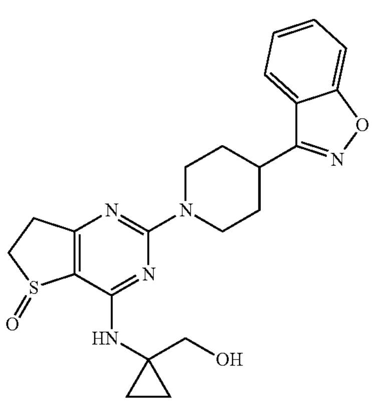 | H | *⟨cyclopropyl⟩CH₂OH | benzo[d]isoxazol-3-yl | H | 97 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 32 | 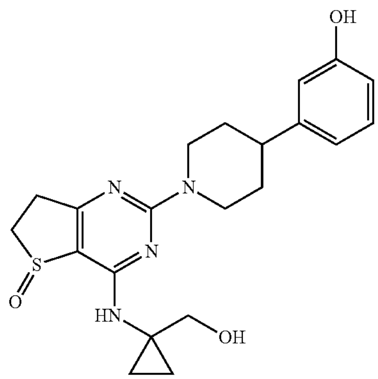 | H | *-C(cyclopropyl)-CH₂OH | 3-hydroxyphenyl | H | 96 |
| 33 | 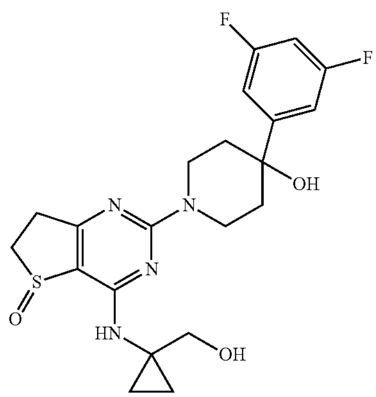 | H | *-C(cyclopropyl)-CH₂OH | 3,5-difluorophenyl | OH | 95 |
| 34 | 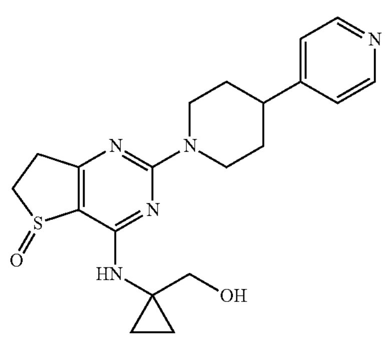 | H | *-C(cyclopropyl)-CH₂OH | 4-pyridyl | H | 92 |
| 35 | 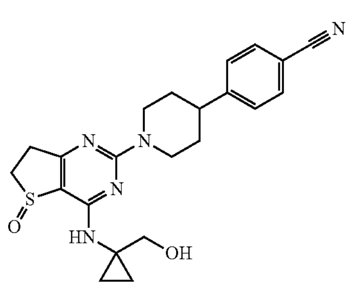 | H | *-C(cyclopropyl)-CH₂OH | 4-cyanophenyl | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 36 | 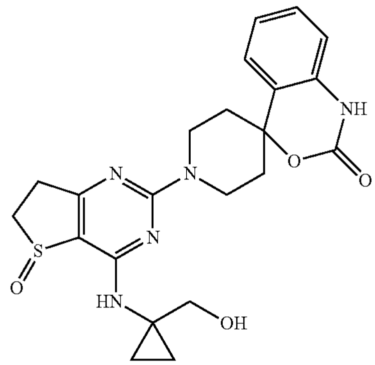 [SMILES: O=C1Nc2ccccc2C2(CCN(c3nc4c(c(NC5(CO)CC5)n3)S(=O)CC4)CC2)O1] | H | *⟨cyclopropyl⟩-CH₂OH | benzoxazinone | | 92 |
| 37 | 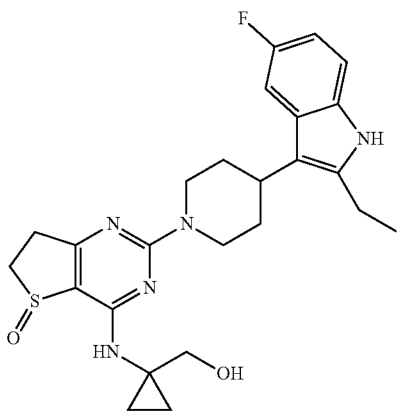 | H | *⟨cyclopropyl⟩-CH₂OH | 5-F-2-ethyl-indol-3-yl | H | 92 |
| 38 | 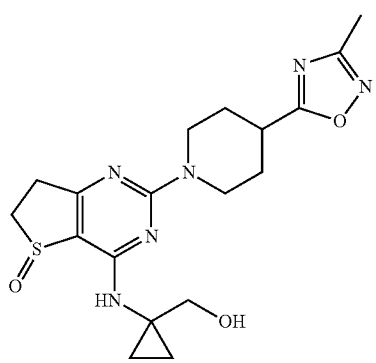 | H | *⟨cyclopropyl⟩-CH₂OH | 3-methyl-1,2,4-oxadiazol-5-yl | H | 92 |
| 39 | 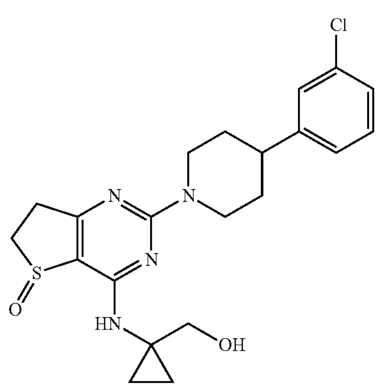 | H | *⟨cyclopropyl⟩-CH₂OH | 3-chlorophenyl | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 40 | 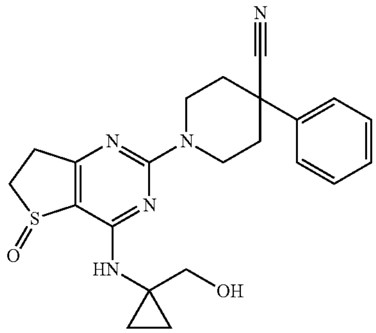 | H | *-C(cyclopropyl)(CH₂OH) | *-phenyl | OH | 94 |
| 41 | 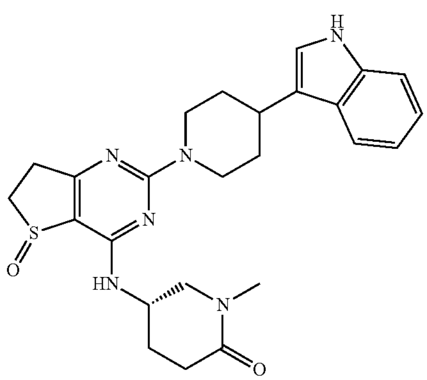 | H | *-(5S)-1-methyl-2-oxopiperidin-5-yl | *-1H-indol-3-yl | H | 97 |
| 42 | 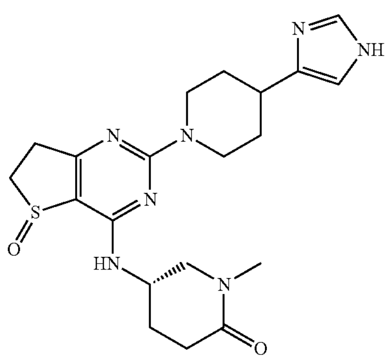 | H | *-(5S)-1-methyl-2-oxopiperidin-5-yl | *-1H-imidazol-4-yl | H | 95 |
| 43 | 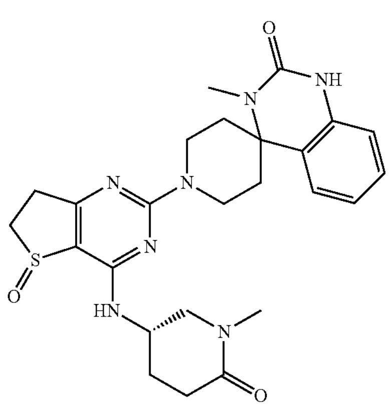 [SMILES: CN1C[C@@H](Nc2nc(N3CCC4(CC3)c3ccccc3NC(=O)N4C)nc3c2S(=O)CC3)CCC1=O] | H | *-(5S)-1-methyl-2-oxopiperidin-5-yl | *-3-methyl-2-oxo-1,2,3,4-tetrahydroquinazolin-4-yl | | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 44 | 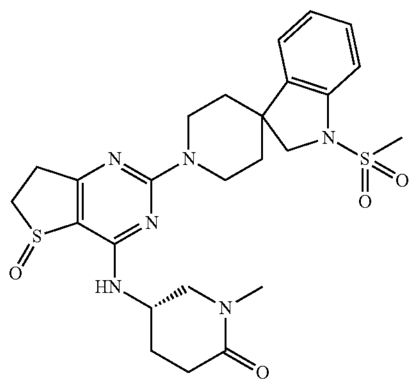 [SMILES: CN1C[C@@H](Nc2nc(N3CCC4(CC3)CN(S(C)(=O)=O)c3ccccc34)nc3c2S(=O)CC3)CCC1=O] | H | *piperidinone-N-methyl | methylsulfonyl-indoline | | 95 |
| 45 | 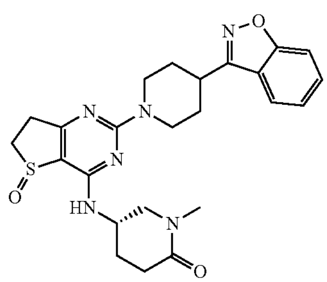 | H | *piperidinone-N-methyl | benzisoxazole | H | 97 |
| 46 | 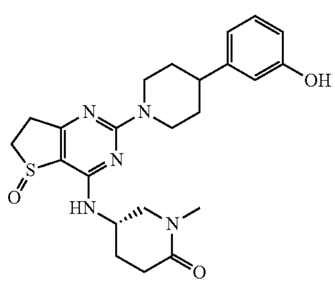 | H | *piperidinone-N-methyl | 3-hydroxyphenyl | H | 97 |
| 47 | 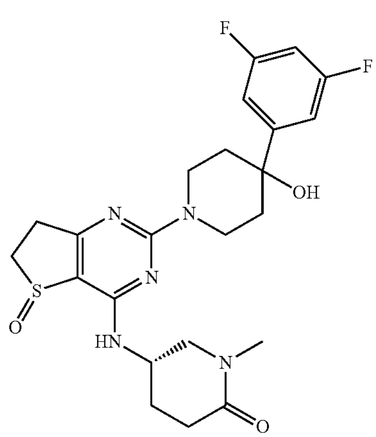 | H | *piperidinone-N-methyl | 3,5-difluorophenyl | OH | 97 |

TABLE A-continued

Chemical structures of the Example substances 1-163

| # | Structure | R¹ | R² | R³ | R⁴ | % Inhibition PDE4B @ 1 µM |
|---|---|---|---|---|---|---|
| 48 | 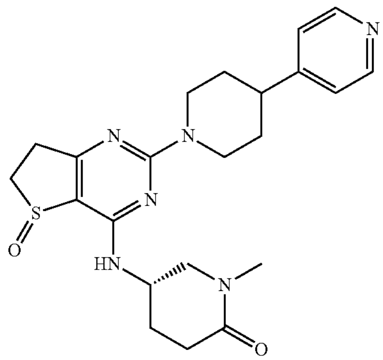 | H | *-piperidinone-N-Me | 4-pyridyl | H | 96 |
| 49 | 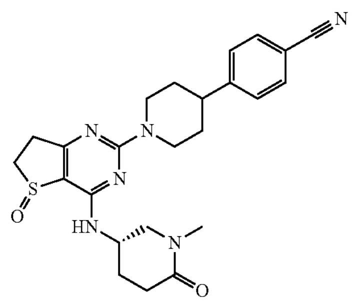 | H | *-piperidinone-N-Me | 4-cyanophenyl | H | 96 |
| 50 | 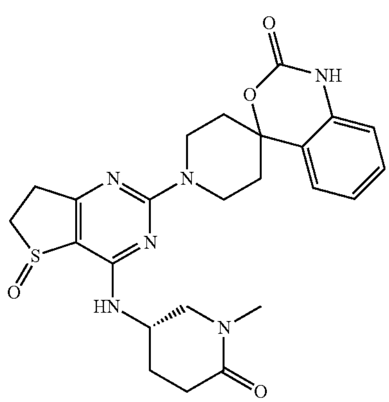 [SMILES: CN1C[C@@H](Nc2nc(N3CCC4(CC3)OC(=O)Nc3ccccc34)nc3c2S(=O)CC3)CCC1=O] | H | *-piperidinone-N-Me | benzoxazinone | | 95 |
| 51 | 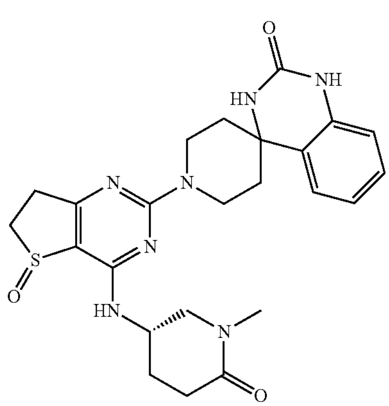 [SMILES: CN1C[C@@H](Nc2nc(N3CCC4(CC3)NC(=O)Nc3ccccc34)nc3c2S(=O)CC3)CCC1=O] | H | *-piperidinone-N-Me | benzodiazinone | | 83 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 52 | 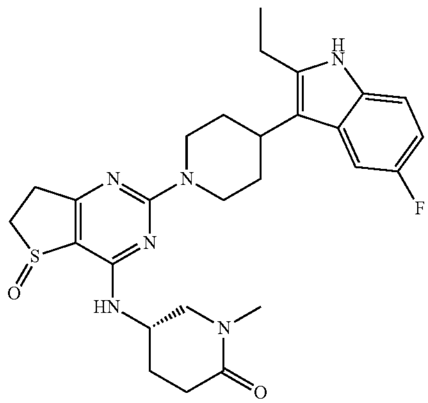 | H | | | H | 96 |
| 53 | 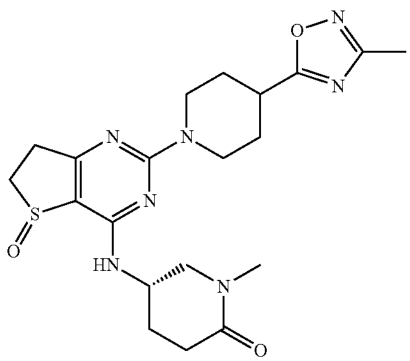 | H | | | H | 96 |
| 54 | 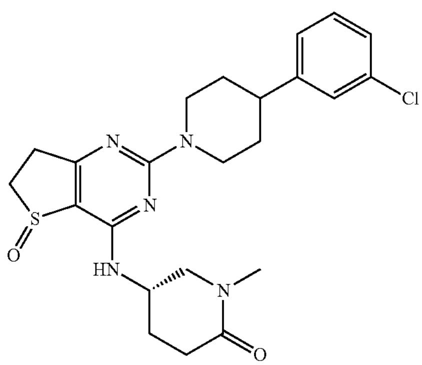 | H | | | H | 97 |
| 55 | 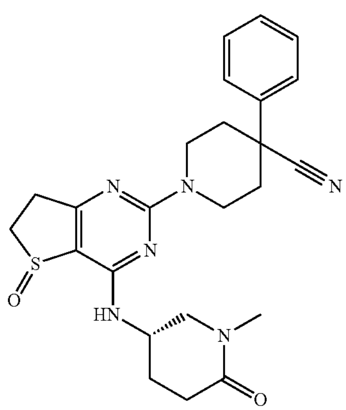 | H | | | CN | 96 |

TABLE A-continued

Chemical structures of the Example substances 1-163

| # | Structure | R¹ | R² | R³ | R⁴ | % Inhibition PDE4B @ 1 μM |
|---|-----------|----|----|----|----|---------------------------|
| 56 | 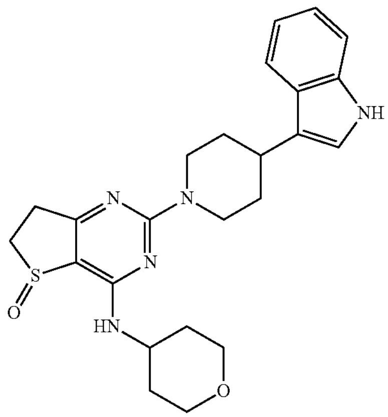 | H | *-tetrahydropyran-4-yl | *-(1H-indol-3-yl) | H | 96 |
| 57 | 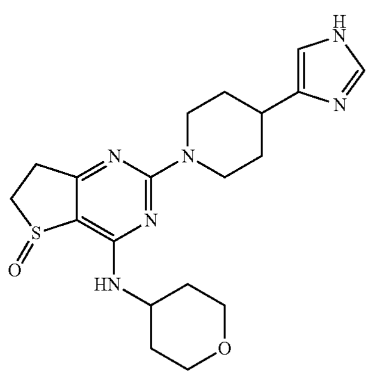 | H | *-tetrahydropyran-4-yl | *-(1H-imidazol-4-yl) | H | 86 |
| 58 | 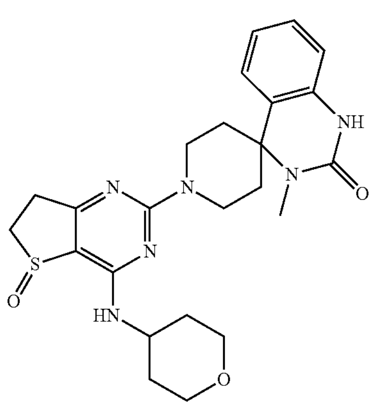 [SMILES: CN1C(=O)Nc2ccccc2C12CCN(c1nc3c(c(NC4CCOCC4)n1)S(=O)CC3)CC2] | H | *-tetrahydropyran-4-yl | *-(3-methyl-2-oxo-2,3-dihydro-1H-quinazolin-4-yl) | | 88 |

TABLE A-continued

Chemical structures of the Example substances 1-163

| # | Structure | R¹ | R² | R³ | R⁴ | % Inhibition PDE4B @ 1 µM |
|---|---|---|---|---|---|---|
| 59 | 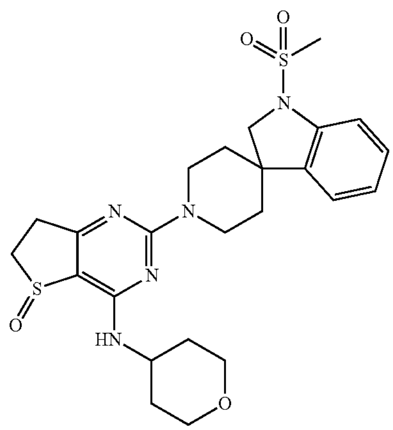 [SMILES: CS(=O)(=O)N1CC2(CCN(c3nc4c(c(NC5CCOCC5)n3)S(=O)CC4)CC2)c2ccccc21] | | H | * tetrahydropyran-4-yl | | 90 |
| 60 | | | H | * tetrahydropyran-4-yl | | H | 97 |
| 61 | | | H | * tetrahydropyran-4-yl | | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 62 | 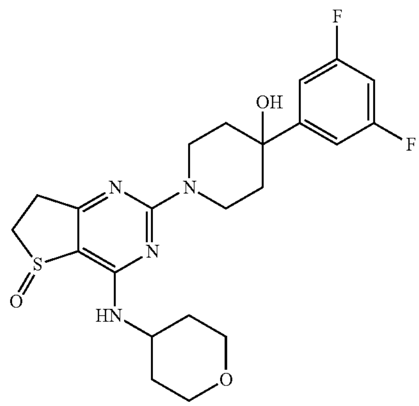 | H | 4-tetrahydropyranyl | 3,5-difluorophenyl | OH | 96 |
| 63 | 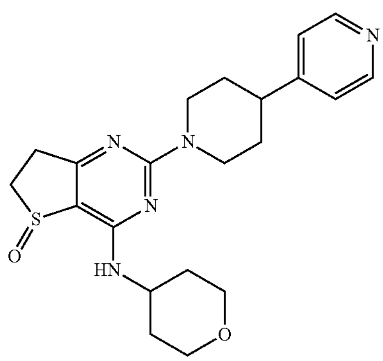 | H | 4-tetrahydropyranyl | 4-pyridyl | H | 92 |
| 64 | 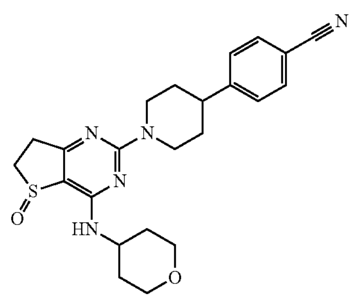 | H | 4-tetrahydropyranyl | 4-cyanophenyl | H | 96 |
| 65 | 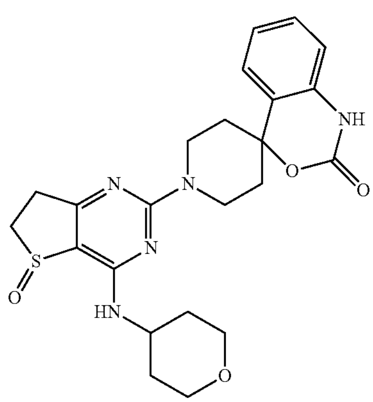 [SMILES: O=C1Nc2ccccc2C2(CCN(c3nc4c(c(NC5CCOCC5)n3)S(=O)CC4)CC2)O1] | H | 4-tetrahydropyranyl | benzoxazinone | | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 66 | 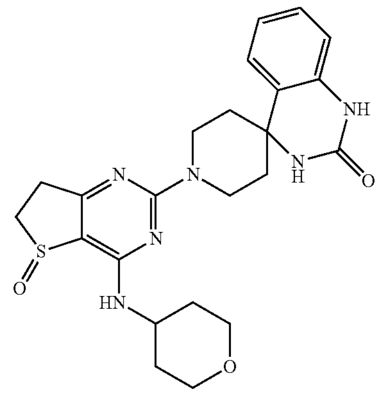 [SMILES: O=C1Nc2ccccc2C2(CCN(c3nc4c(c(NC5CCOCC5)n3)S(=O)CC4)CC2)N1] | H | *-tetrahydropyran-4-yl | benzo-fused cyclic urea | | 62 |
| 67 | 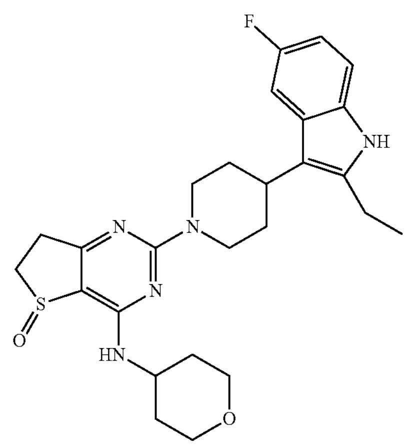 | H | *-tetrahydropyran-4-yl | 5-fluoro-2-ethyl-1H-indol-3-yl | H | 93 |
| 68 | 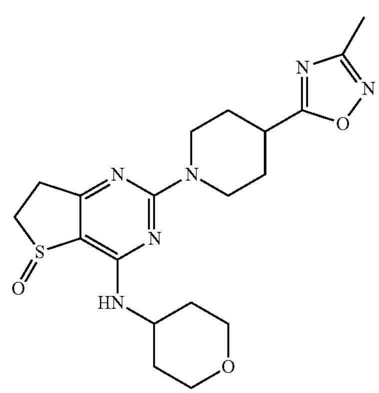 | H | *-tetrahydropyran-4-yl | 3,5-dimethyl-1,2,4-oxadiazol-yl | H | 93 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 69 | | Cl | H | *tetrahydropyran-4-yl | 3-Cl-phenyl | H | 93 |
| 70 | | CN | H | *tetrahydropyran-4-yl | phenyl | CN | 95 |
| 71 | | indol-3-yl | H | 3-F-phenyl | indol-3-yl | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 72 | 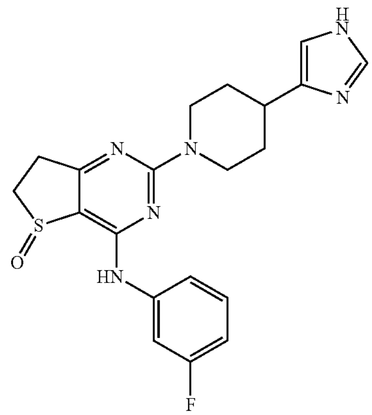 | H | F-phenyl (3-F) | imidazolyl | H | 95 |
| 73 | 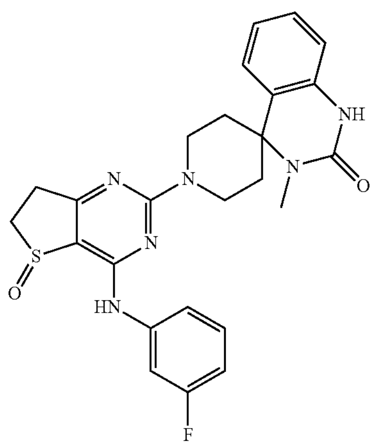 [SMILES: CN1C(=O)Nc2ccccc2C12CCN(c1nc3c(c(Nc4cccc(F)c4)n1)S(=O)CC3)CC2] | H | F-phenyl (3-F) | N-methyl benzo-fused urea | | 94 |
| 74 | 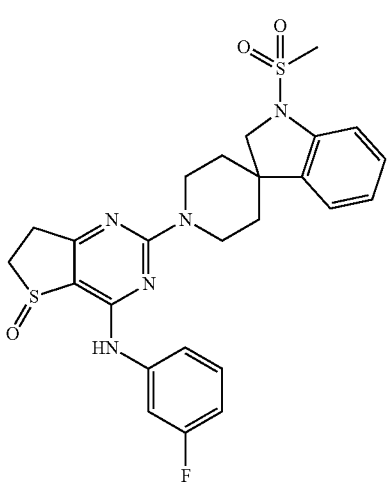 [SMILES: CS(=O)(=O)N1CC2(CCN(c3nc4c(c(Nc5cccc(F)c5)n3)S(=O)CC4)CC2)c2ccccc21] | H | F-phenyl (3-F) | N-methylsulfonyl indoline | | 95 |

TABLE A-continued
Chemical structures of the Example substances 1-163
| # | Structure | $R^1$ | $R^2$ | $R^3$ | $R^4$ | % Inhibition PDE4B @ 1 μM |
|---|---|---|---|---|---|---|
| 75 | 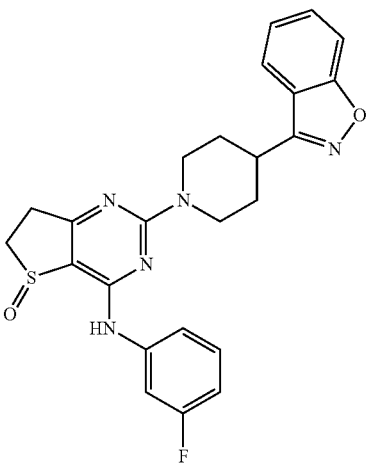 | H | 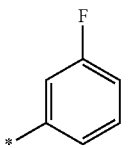 [SMILES: *c1cccc(F)c1] | 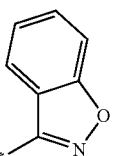 | H | 97 |
| 76 | 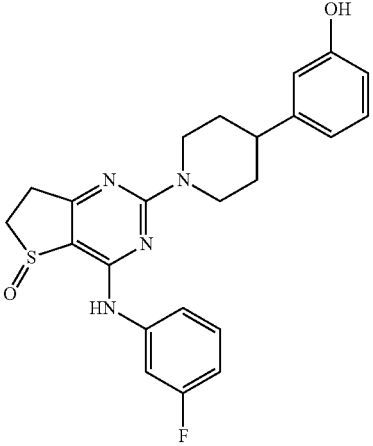 [SMILES: O=S1CCc2nc(N3CCC(c4cccc(O)c4)CC3)nc(Nc3cccc(F)c3)c21] | 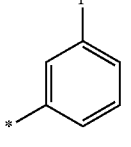 | 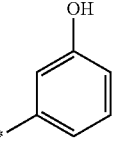 | 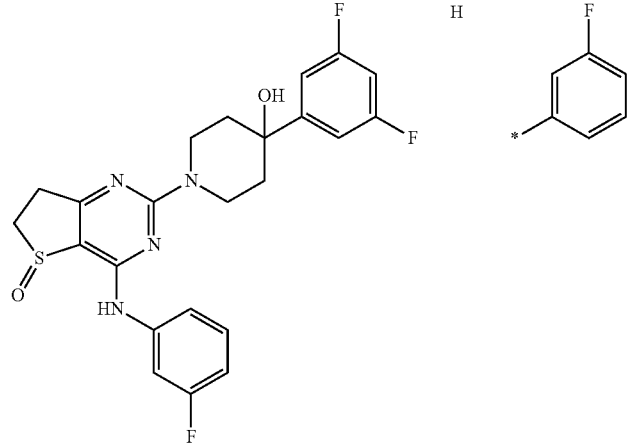 | H | 97 |
| 77 | 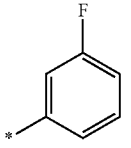 [SMILES: *c1cccc(F)c1] | 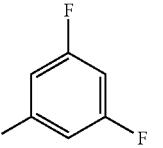 | (3-F-phenyl) | (3,5-diF-phenyl) | OH | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 78 | 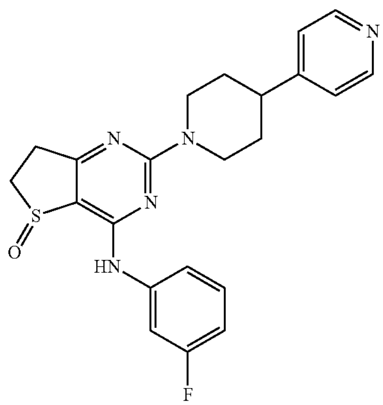 | H | 3-F-phenyl | 4-pyridyl | H | 96 |
| 79 | 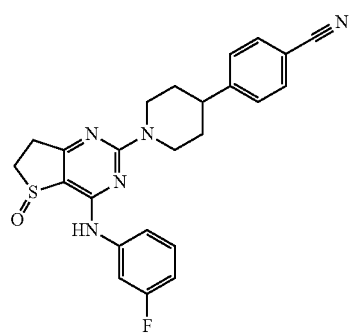 | H | 3-F-phenyl | 4-cyanophenyl | H | 96 |
| 80 | 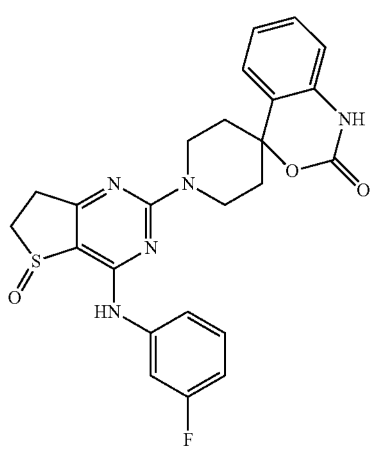 [SMILES: O=C1Nc2ccccc2C2(CCN(c3nc4c(c(Nc5cccc(F)c5)n3)S(=O)CC4)CC2)O1] | H | 3-F-phenyl | spiro-benzoxazinone | | 94 |

US 8,754,073 B2
TABLE A-continued
Chemical structures of the Example substances 1-163
| # | Structure | R¹ | R² | R³ | R⁴ | % Inhibition PDE4B @ 1 μM |
|---|---|---|---|---|---|---|
| 81 | 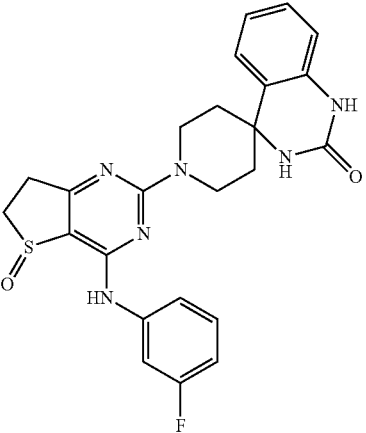 [SMILES: O=C1Nc2ccccc2C2(CCN(c3nc4c(c(Nc5cccc(F)c5)n3)S(=O)CC4)CC2)N1] | H | 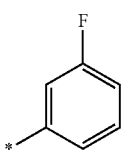 [SMILES: *c1cccc(F)c1] | 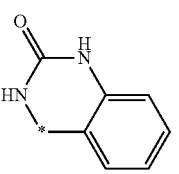 [SMILES: O=C1N*c2ccccc2N1] |  | 83 |
| 82 | 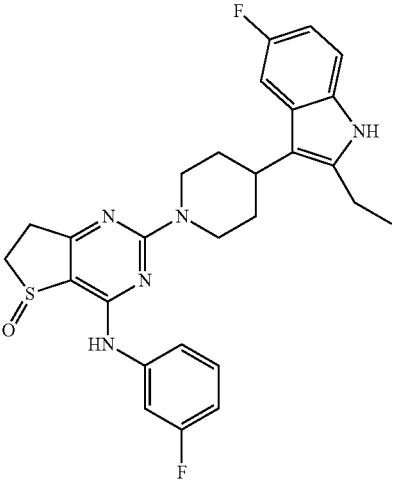 | H | 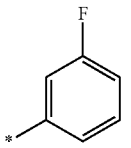 [SMILES: *c1cccc(F)c1] | 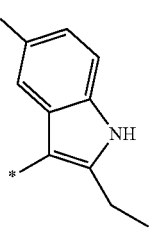 | H | 92 |
| 83 | 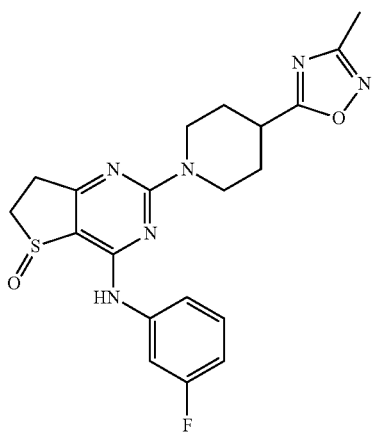 | H | 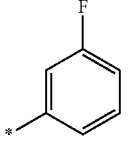 [SMILES: *c1cccc(F)c1] | 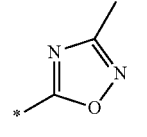 | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 84 | | Cl (3-Cl-phenyl) | H | F (3-F-phenyl) | Cl (3-Cl-phenyl) | H | 95 |
| 85 | | CN (4-CN-4-phenyl-piperidine) | H | F (3-F-phenyl) | phenyl | CN | 96 |
| 86 | | F (3-F-phenyl) | H | X₁-tetrahydropyran-4-yl | F (3-F-phenyl) | H | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 87 | 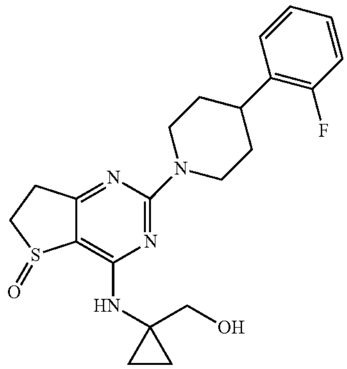 | H | *⟨△⟩—CH₂OH | *-(2-F-phenyl) | H | 92 |
| 88 | 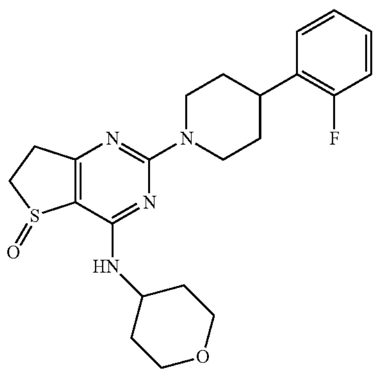 | H | *-(tetrahydropyran-4-yl) | *-(2-F-phenyl) | H | 92 |
| 89 | 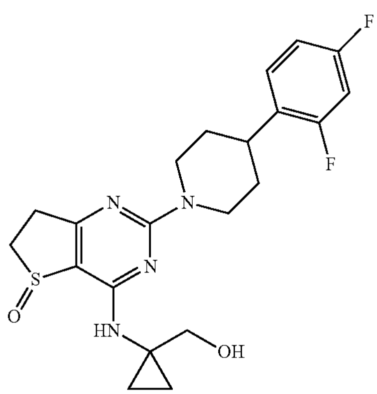 | H | *⟨△⟩—CH₂OH | *-(2,4-diF-phenyl) | H | 93 |
| 90 | 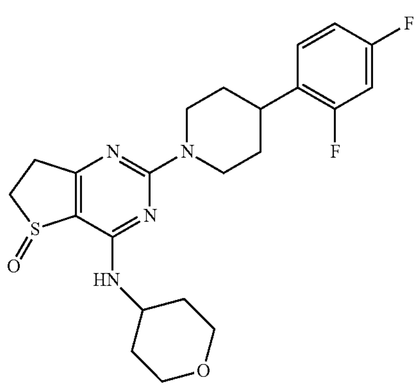 | H | *-(tetrahydropyran-4-yl) | *-(2,4-diF-phenyl) | H | 92 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 91 | | Cl, Cl (3,5-dichlorophenyl) | H | *-C(cyclopropyl)-CH₂OH | Cl, Cl (3,5-dichlorophenyl) | H | 94 |
| 92 | | 4-Br-phenyl | H | *-C(cyclopropyl)-CH₂OH | 4-Br-phenyl | H | 94 |
| 93 | | 4-Br-phenyl | H | *-tetrahydropyran-4-yl | 4-Br-phenyl | H | 94 |
| 94 | | 3-Br-phenyl | H | *-C(cyclopropyl)-CH₂OH | 3-Br-phenyl | H | 94 |

TABLE A-continued
Chemical structures of the Example substances 1-163
| # | Structure | R¹ | R² | R³ | R⁴ | % Inhibition PDE4B @ 1 µM |
|---|---|---|---|---|---|---|
| 95 | 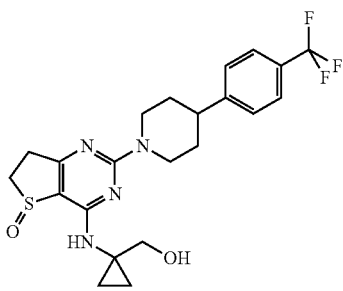 | H | 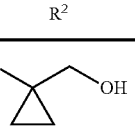 | 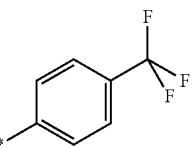 | H | 93 |
| 96 | 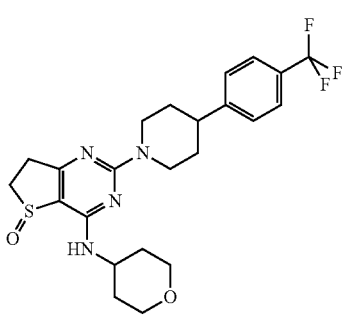 | H | 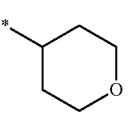 [SMILES: *C1CCOCC1] | 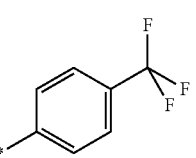 | H | 94 |
| 97 | 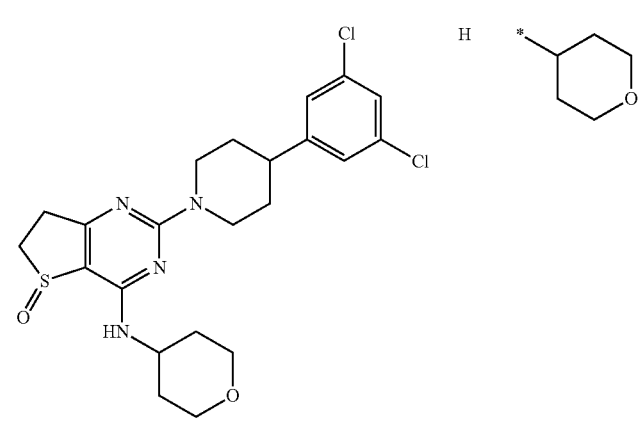 | H | 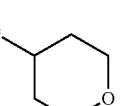 | 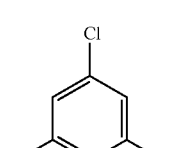 | H | 93 |
| 98 | 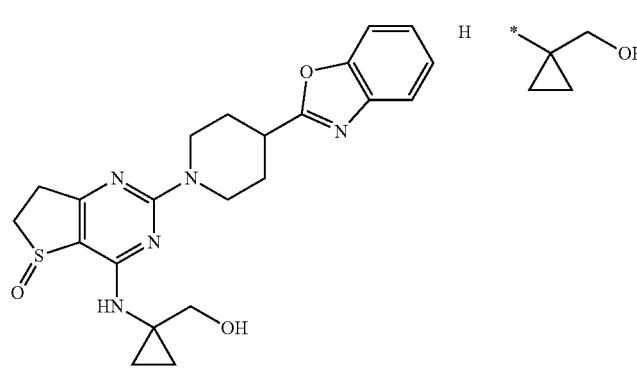 | H | 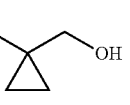 | 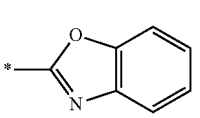 [SMILES: *c1nc2ccccc2o1] | H | 97 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 99 | 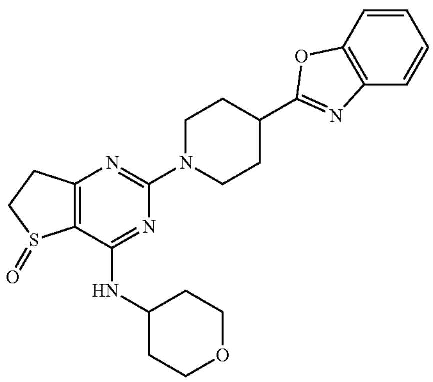 | H | *-tetrahydropyran-4-yl | *-benzoxazol-2-yl | H | 97 |
| 100 | 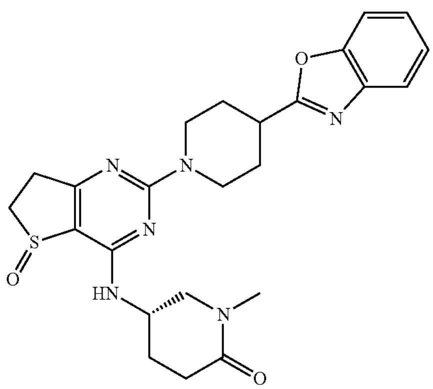 | H | *-(5S)-1-methyl-2-oxopiperidin-5-yl | *-benzoxazol-2-yl | H | 97 |
| 101 | 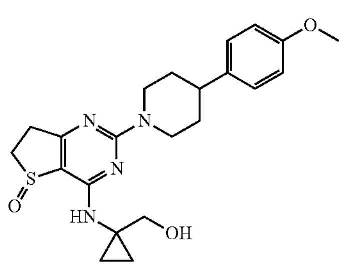 | H | *-1-(hydroxymethyl)cyclopropyl | *-4-methoxyphenyl | H | 94 |
| 102 | 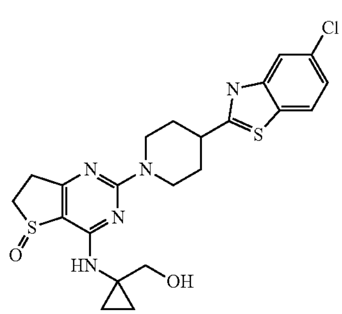 | H | *-1-(hydroxymethyl)cyclopropyl | *-5-chlorobenzothiazol-2-yl | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 103 | 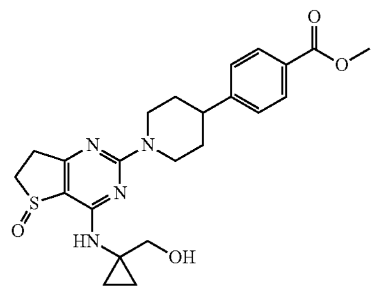 | H | *⟨cyclopropyl⟩CH₂OH | methyl 4-benzoate | H | 95 |
| 104 | 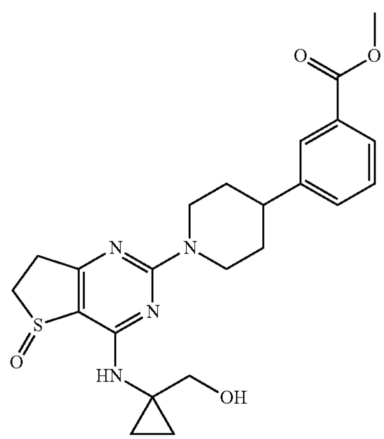 | H | *⟨cyclopropyl⟩CH₂OH | methyl 3-benzoate | H | 95 |
| 105 | 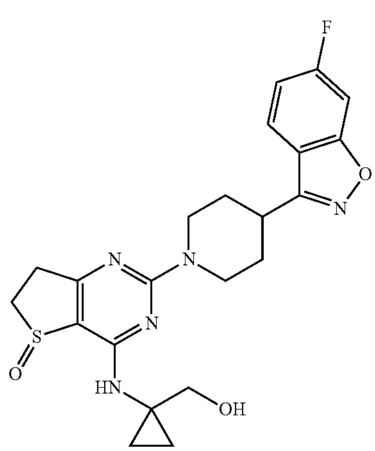 | H | *⟨cyclopropyl⟩CH₂OH | 6-fluorobenzo[d]isoxazol-3-yl | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 106 | 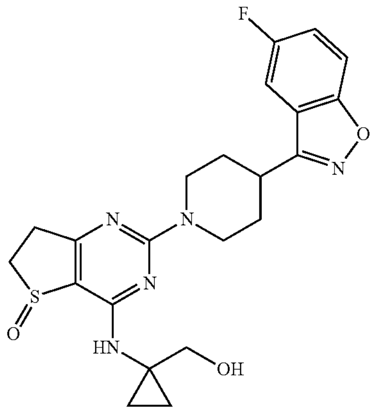 | H | *-C(cyclopropyl)(CH₂OH) | 5-fluoro-benzo[d]isoxazol-3-yl | H | 95 |
| 107 | 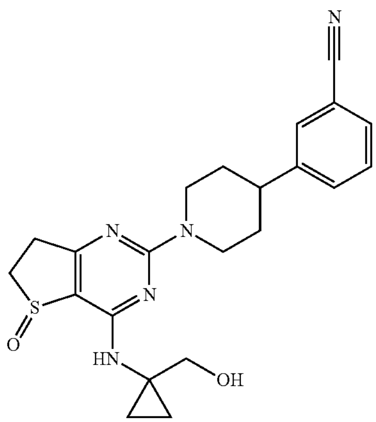 | H | *-C(cyclopropyl)(CH₂OH) | 3-cyanophenyl | H | 94 |
| 108 | 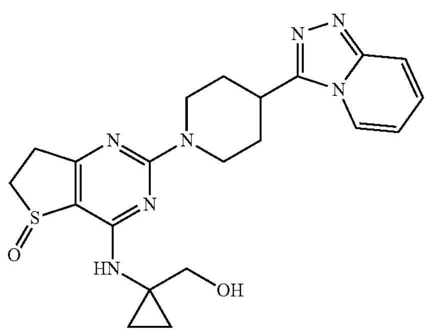 | H | *-C(cyclopropyl)(CH₂OH) | [1,2,4]triazolo[4,3-a]pyridin-3-yl | H | 88 |
| 109 | 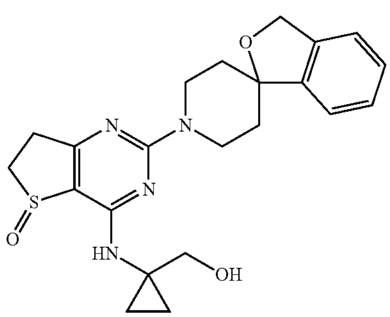 [SMILES: O=S1CCc2nc(N3CCC4(CC3)OCc3ccccc34)nc(NC3(CO)CC3)c21] | H | *-C(cyclopropyl)(CH₂OH) | spiro-isobenzofuran | | 75 |

US 8,754,073 B2
273 274
TABLE A-continued
Chemical structures of the Example substances 1-163
| # | Structure | R¹ | R² | R³ | R⁴ | % Inhibition PDE4B @ 1 µM |
|---|---|---|---|---|---|---|
| 110 | 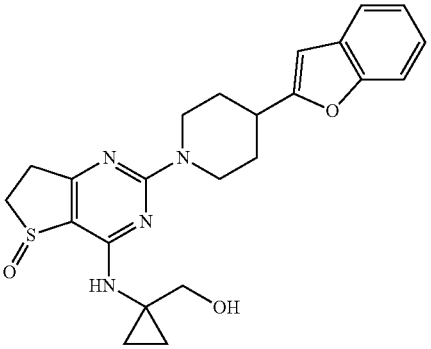 | H | 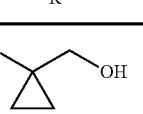 | 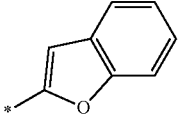 [SMILES: *c1cc2ccccc2o1] | H | 97 |
| 111 | 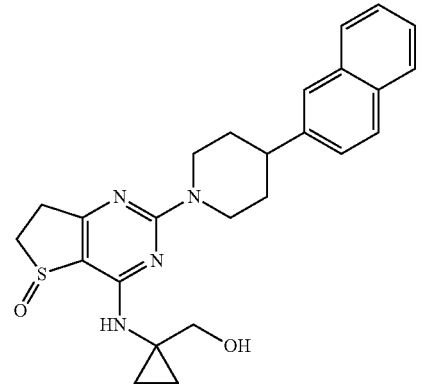 | H | 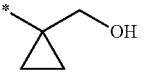 | 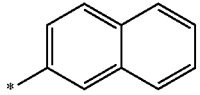 | H | 96 |
| 112 | 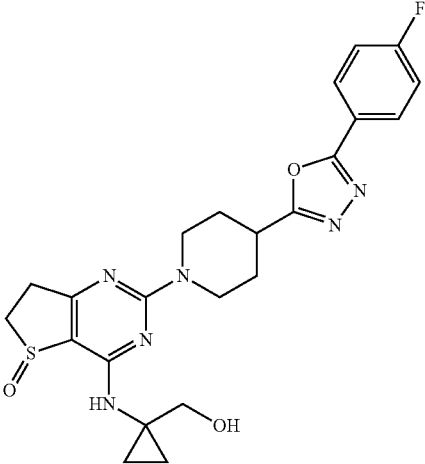 | H | 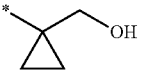 | 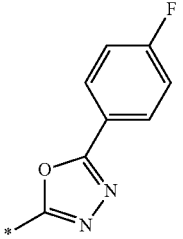 [SMILES: *c1nnc(-c2ccc(F)cc2)o1] | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 113 | 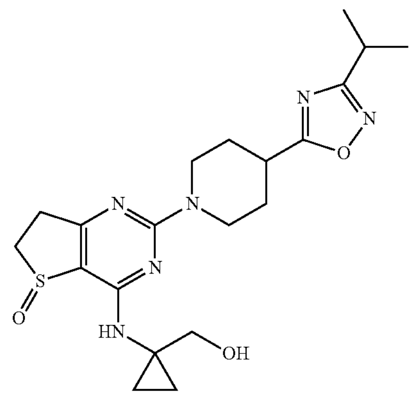 | H | *-C(cyclopropyl)(CH₂OH) | 3-isopropyl-1,2,4-oxadiazol-5-yl | H | 92 |
| 114 | 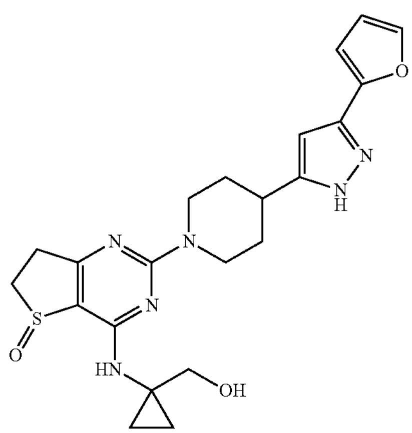 | H | *-C(cyclopropyl)(CH₂OH) | 3-(furan-2-yl)-1H-pyrazol-5-yl | H | 96 |
| 115 | 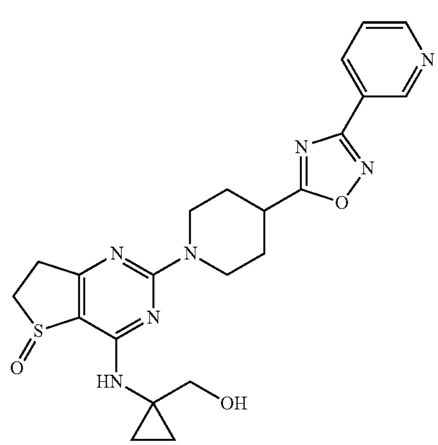 | H | *-C(cyclopropyl)(CH₂OH) | 3-(pyridin-3-yl)-1,2,4-oxadiazol-5-yl | H | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 116 | 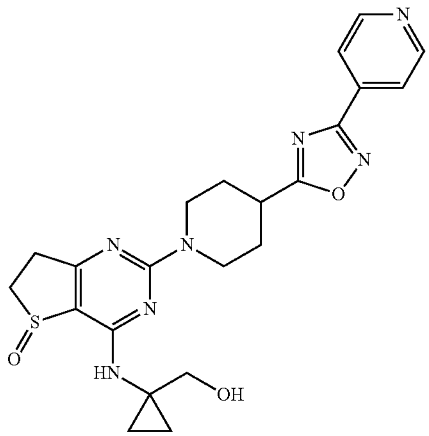 | H | *-C(cyclopropyl)(CH₂OH) | 3-(pyridin-4-yl)-1,2,4-oxadiazol-5-yl | H | 94 |
| 117 | 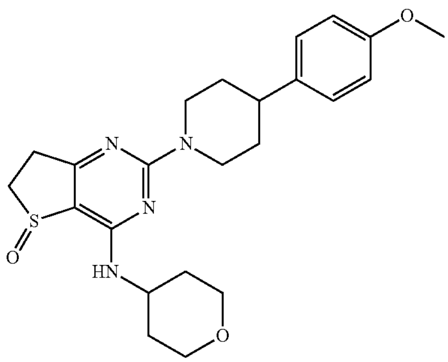 | H | *-tetrahydropyran-4-yl | 4-methoxyphenyl | H | 94 |
| 118 | 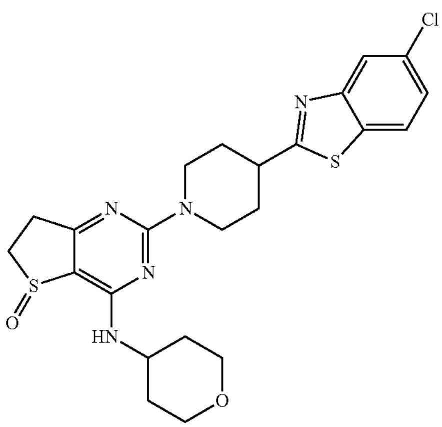 | Cl | *-tetrahydropyran-4-yl | 5-chlorobenzothiazol-2-yl | H | 96 |
| 119 | 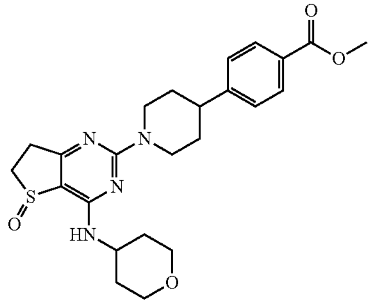 | H | *-tetrahydropyran-4-yl | 4-(methoxycarbonyl)phenyl | H | 95 |

TABLE A-continued
Chemical structures of the Example substances 1-163
| # | Structure | R¹ | R² | R³ | R⁴ | % Inhibition PDE4B @ 1 μM |
|---|---|---|---|---|---|---|
| 120 | 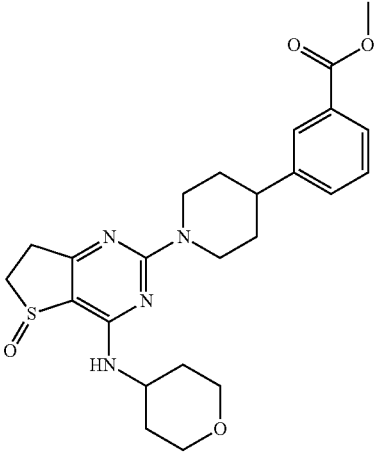 | H | 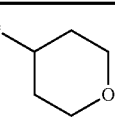 | 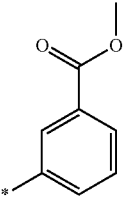 | H | 95 |
| 121 | 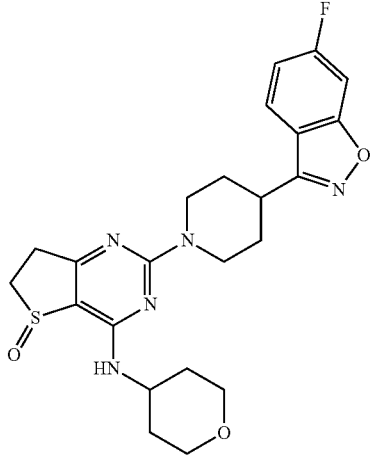 | H | 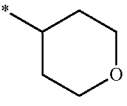 | 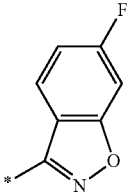 [SMILES: *c1noc2cc(F)ccc12] | H | 96 |
| 122 | 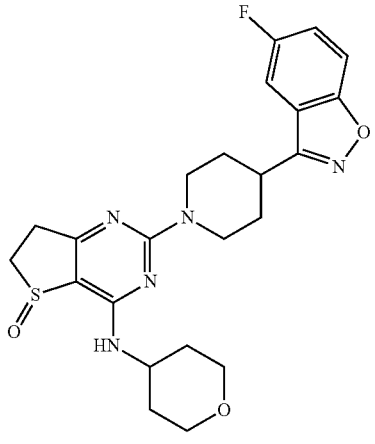 | H | 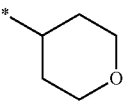 | 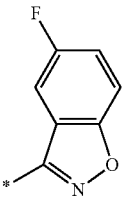 [SMILES: *c1noc2ccc(F)cc12] | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 123 | 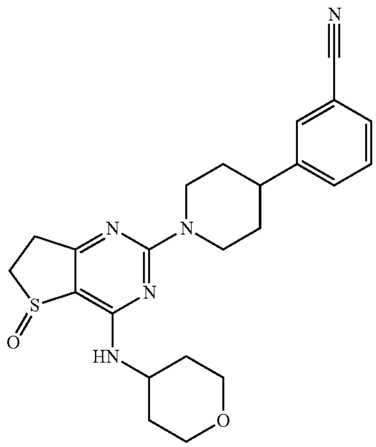 | H | *-tetrahydropyran-4-yl | 3-cyanophenyl | H | 94 |
| 124 | 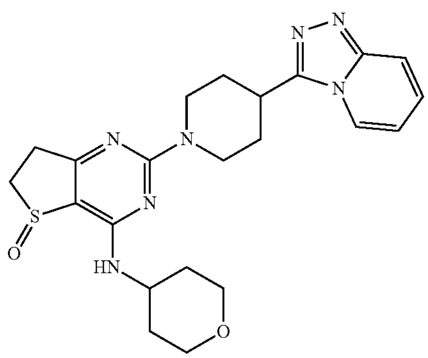 | H | *-tetrahydropyran-4-yl | [1,2,4]triazolo[4,3-a]pyridin-3-yl | H | 89 |
| 125 | 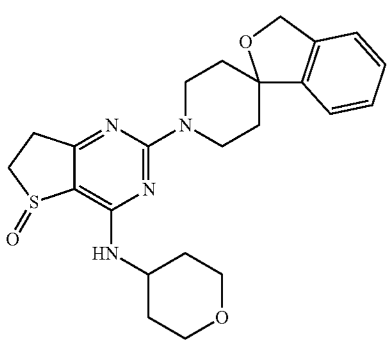 [SMILES: O=S1CCc2nc(N3CCC4(CC3)OCc3ccccc34)nc(NC3CCOCC3)c21] | H | *-tetrahydropyran-4-yl | 1,3-dihydroisobenzofuran-1-yl | | 74 |
| 126 | 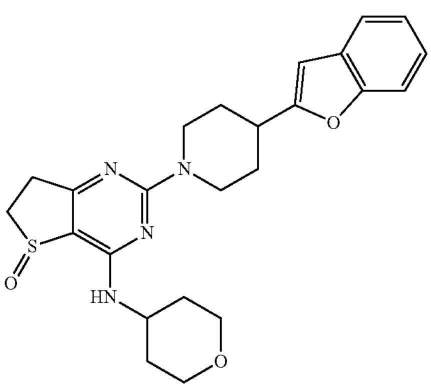 | H | *-tetrahydropyran-4-yl | benzofuran-2-yl | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 127 | 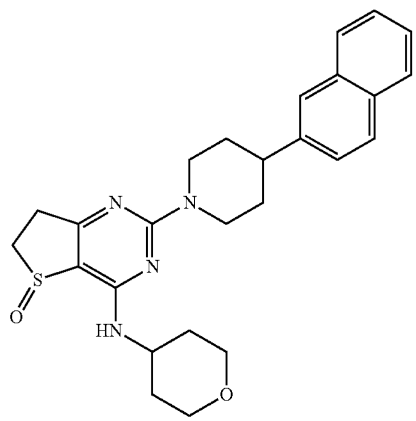 | H | * (tetrahydropyran-4-yl) | 2-naphthyl | H | 96 |
| 128 | 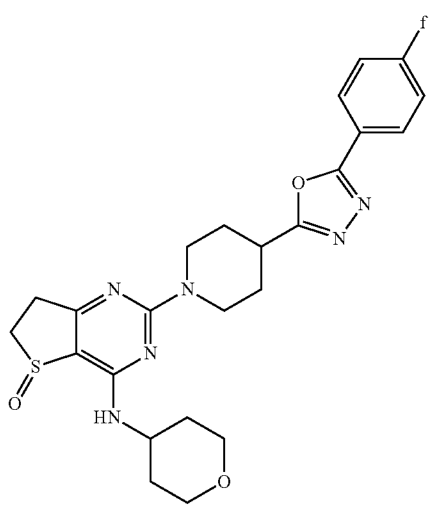 | H | * (tetrahydropyran-4-yl) | 5-(4-fluorophenyl)-1,3,4-oxadiazol-2-yl | H | 95 |
| 129 | 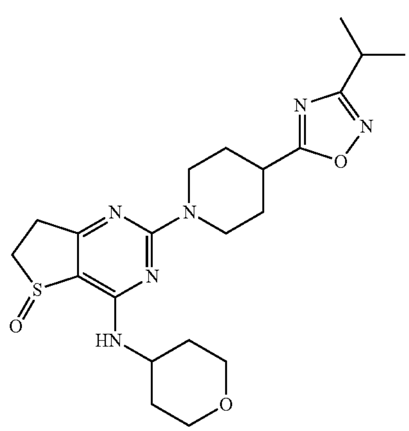 | H | * (tetrahydropyran-4-yl) | 3-isopropyl-1,2,4-oxadiazol-5-yl | H | 93 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 130 | 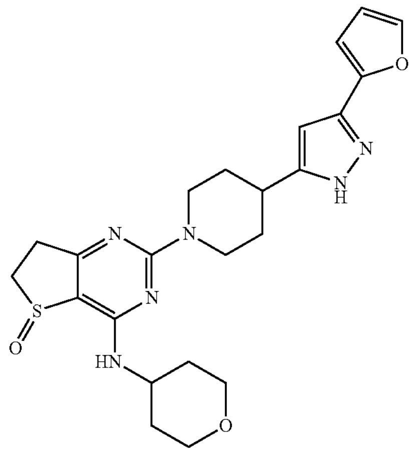 | H | *-tetrahydropyran-4-yl | furan-2-yl-pyrazol-3-yl | H | 96 |
| 131 | 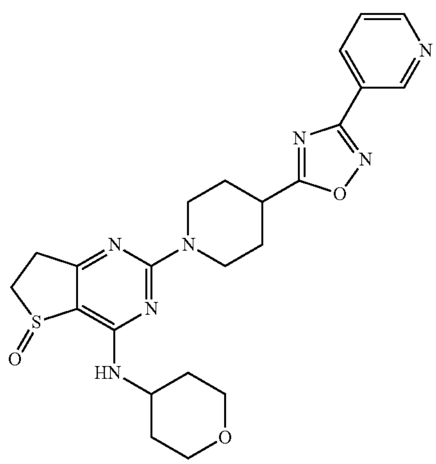 | H | *-tetrahydropyran-4-yl | pyridin-3-yl-1,2,4-oxadiazol-5-yl | H | 94 |
| 132 | 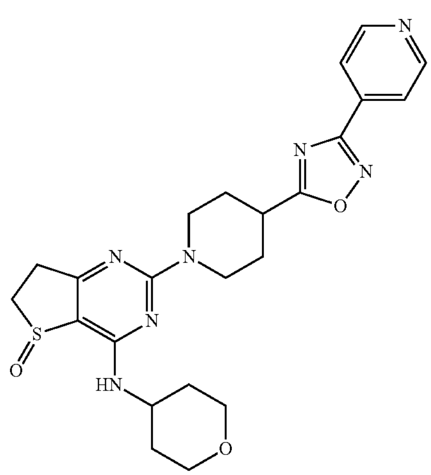 | H | *-tetrahydropyran-4-yl | pyridin-4-yl-1,2,4-oxadiazol-5-yl | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 133 | 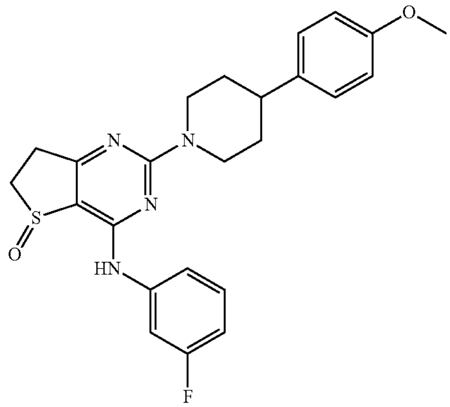 | H | 3-F-phenyl | 4-methoxyphenyl | H | 95 |
| 134 | 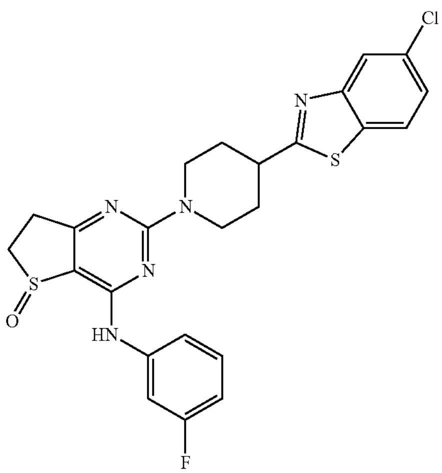 | H | 3-F-phenyl | 5-chlorobenzothiazol-2-yl | H | 95 |
| 135 | 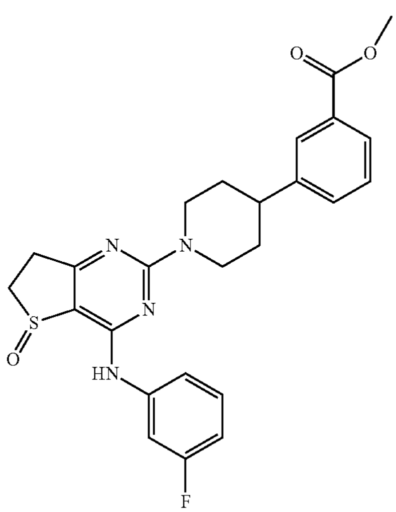 | H | 3-F-phenyl | 3-(methoxycarbonyl)phenyl | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 136 | 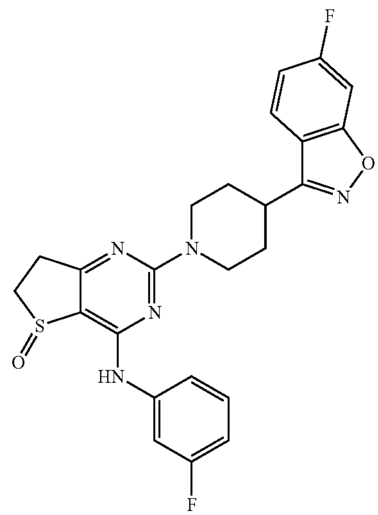 | H | | | H | 95 |
| 137 | 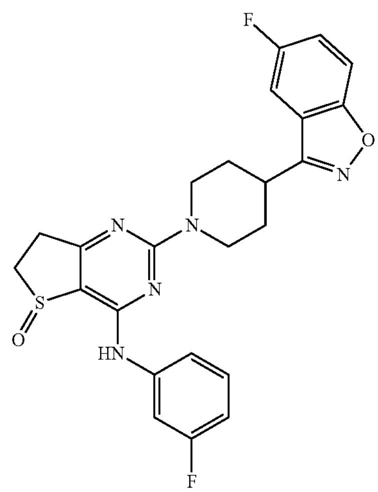 | H | | | H | 95 |
| 138 | 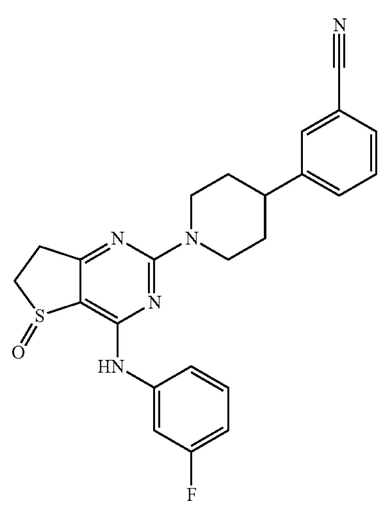 | H | | | H | 96 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 139 | 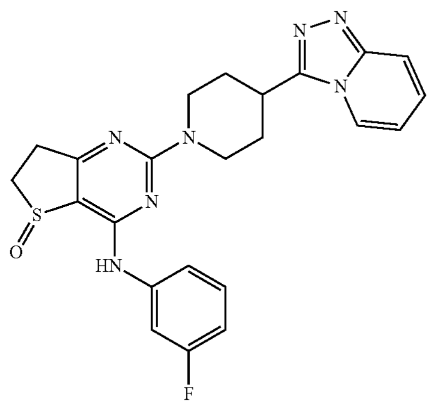 | H | 3-F-phenyl | [1,2,4]triazolo[4,3-a]pyridin-3-yl | H | 94 |
| 140 | 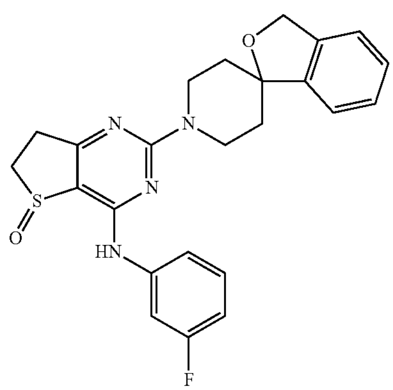 [SMILES: O=S1CCc2nc(N3CCC4(CC3)OCc3ccccc34)nc(Nc3cccc(F)c3)c21] | H | 3-F-phenyl | spiro-isobenzofuran | | 83 |
| 141 | 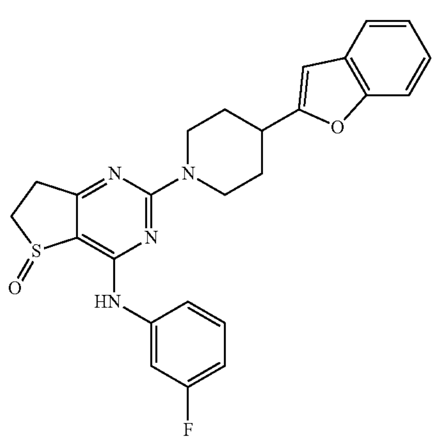 [SMILES: O=S1CCc2nc(N3CCC(c4cc5ccccc5o4)CC3)nc(Nc3cccc(F)c3)c21] | H | 3-F-phenyl | benzoxazol-2-yl | | 97 |

TABLE A-continued

Chemical structures of the Example substances 1-163

| # | Structure | R¹ | R² | R³ | R⁴ | % Inhibition PDE4B @ 1 µM |
|---|---|---|---|---|---|---|
| 142 | 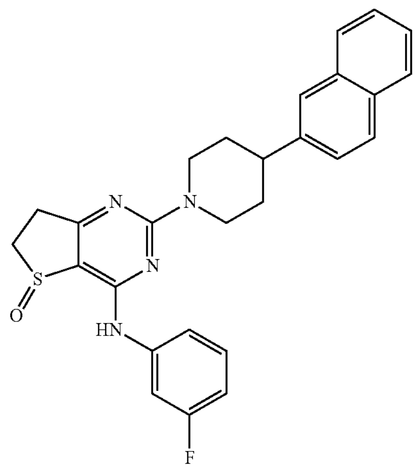 [SMILES: O=S1CCc2nc(N3CCC(c4ccc5ccccc5c4)CC3)nc(Nc3cccc(F)c3)c21] | H | F (3-fluorophenyl) | naphthalen-2-yl | | 94 |
| 143 | | F (4-fluorophenyl-oxadiazole) | H | F (3-fluorophenyl) | 5-(4-fluorophenyl)-1,3,4-oxadiazol-2-yl | H | 95 |
| 144 | | isopropyl-oxadiazole | H | F (3-fluorophenyl) | 3-isopropyl-1,2,4-oxadiazol-5-yl | H | 94 |

TABLE A-continued
Chemical structures of the Example substances 1-163
| # | Structure | R¹ | R² | R³ | R⁴ | % Inhibition PDE4B @ 1 μM |
|---|---|---|---|---|---|---|
| 145 | 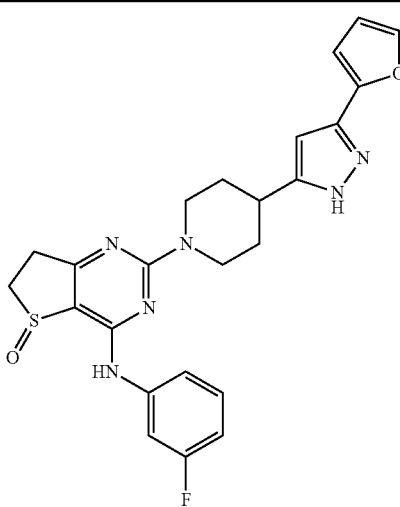 | H | 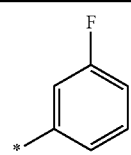 | 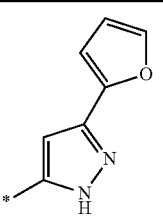 | H | 96 |
| 146 | 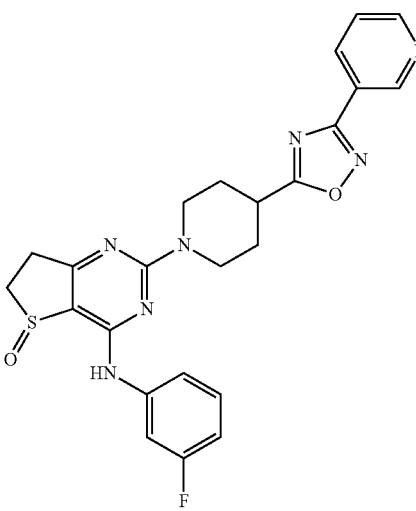 | H | 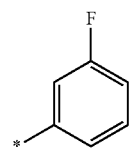 [SMILES: *c1cccc(F)c1] | 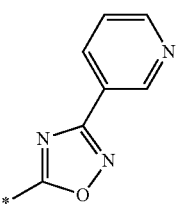 [SMILES: *c1nc(-c2cccnc2)no1] | H | 96 |
| 147 | 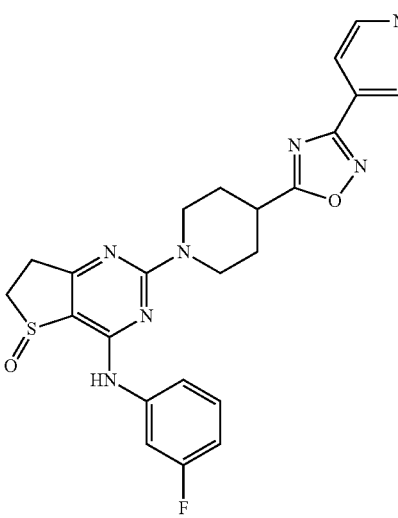 | H | 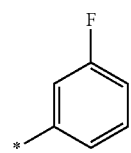 [SMILES: *c1cccc(F)c1] | 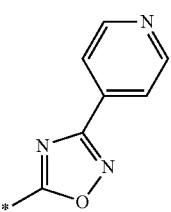 [SMILES: *c1nc(-c2ccncc2)no1] | H | 95 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 148 | 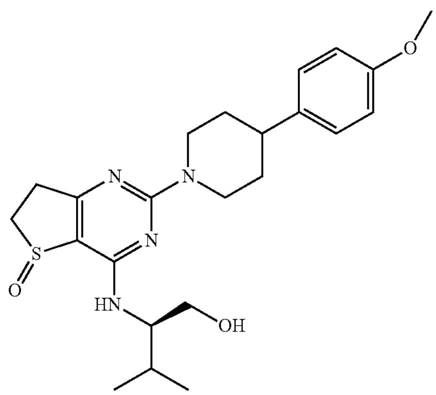 | H | *⟋⟍OH with isopropyl | 4-methoxyphenyl | H | 93 |
| 149 | 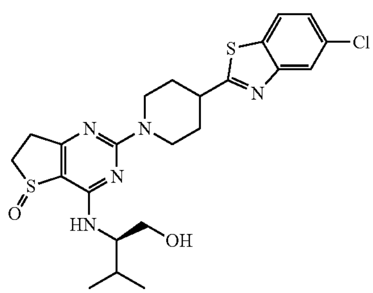 | H | *⟋⟍OH with isopropyl | 5-chloro-benzothiazol-2-yl | H | 94 |
| 150 | 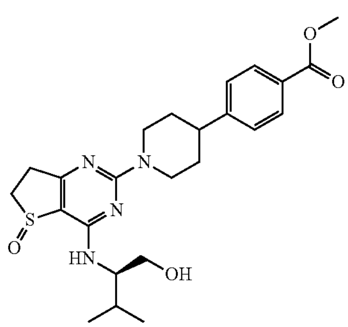 | H | *⟋⟍OH with isopropyl | 4-(methoxycarbonyl)phenyl | H | 94 |
| 151 | 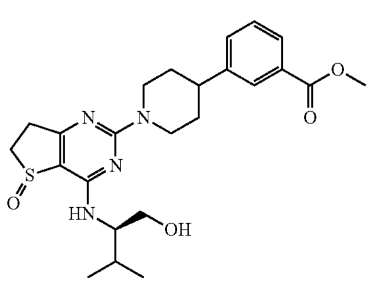 | H | *⟋⟍OH with isopropyl | 3-(methoxycarbonyl)phenyl | H | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 152 | 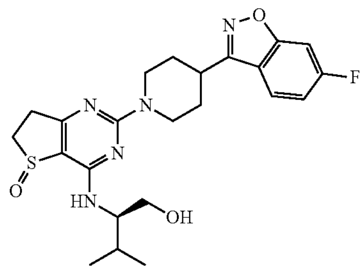 | H | *⟨CH(iPr)⟩CH₂OH | 6-fluoro-benzo[d]isoxazol-3-yl | H | 95 |
| 153 | 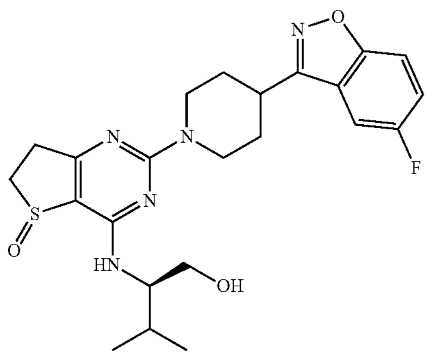 | H | *⟨CH(iPr)⟩CH₂OH | 5-fluoro-benzo[d]isoxazol-3-yl | H | 95 |
| 154 | 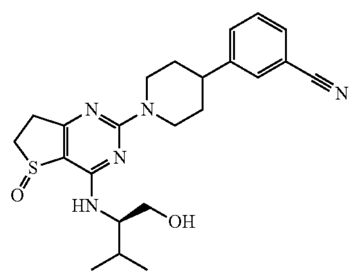 | H | *⟨CH(iPr)⟩CH₂OH | 3-cyanophenyl | H | 92 |
| 155 | 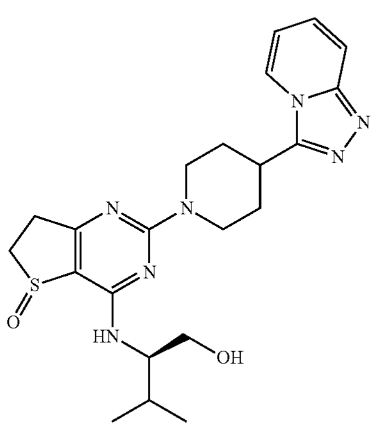 | H | *⟨CH(iPr)⟩CH₂OH | [1,2,4]triazolo[4,3-a]pyridin-3-yl | H | 83 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 156 | 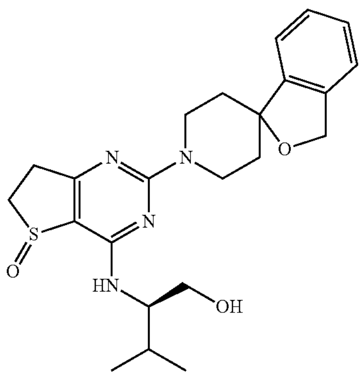 [SMILES: CC(C)[C@H](CO)Nc1nc(N2CCC3(CC2)OCc2ccccc23)nc2c1S(=O)CC2] | H | *⋏OH (with isopropyl) | benzofuran-spiro (1,3-dihydroisobenzofuran) | | 64 |
| 157 | 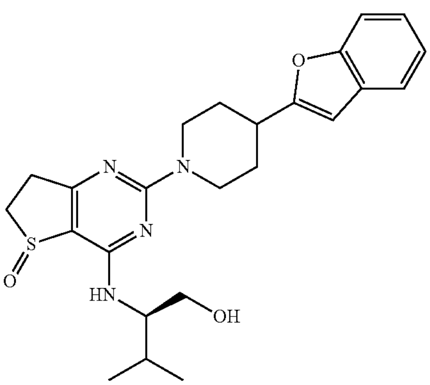 | H | *⋏OH (with isopropyl) | benzofuran-2-yl | H | 96 |
| 158 | 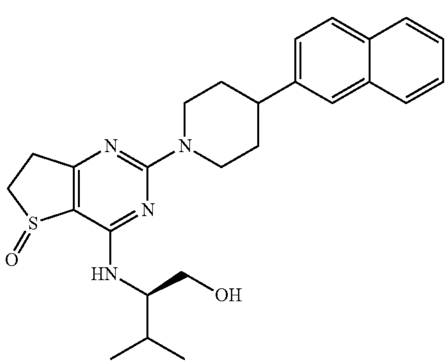 | H | *⋏OH (with isopropyl) | naphthalen-2-yl | H | 94 |
| 159 | 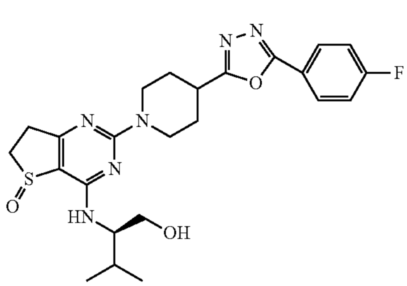 | H | *⋏OH (with isopropyl) | 5-(4-fluorophenyl)-1,3,4-oxadiazol-2-yl | H | 94 |

TABLE A-continued

Chemical structures of the Example substances 1-163

| # | Structure | R¹ | R² | R³ | R⁴ | % Inhibition PDE4B @ 1 μM |
|---|---|---|---|---|---|---|
| 160 | 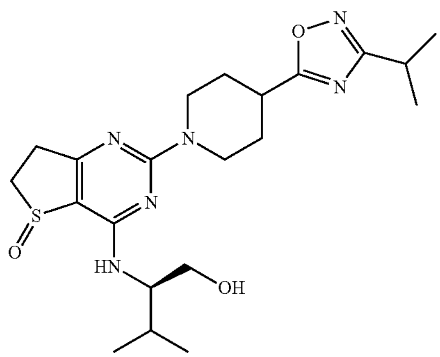 | H | *⟵CH(iPr)CH₂OH | 3-isopropyl-1,2,4-oxadiazol-5-yl | H | 86 |
| 161 | 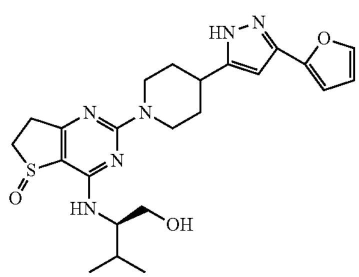 | H | *⟵CH(iPr)CH₂OH | 5-(furan-2-yl)-1H-pyrazol-3-yl | H | 94 |
| 162 | 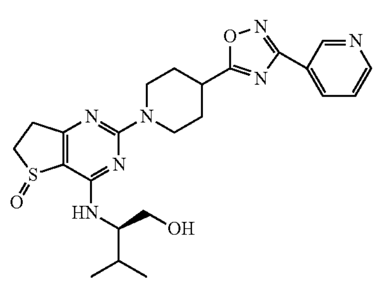 | H | *⟵CH(iPr)CH₂OH | 3-(pyridin-3-yl)-1,2,4-oxadiazol-5-yl | H | 92 |
| 163 | 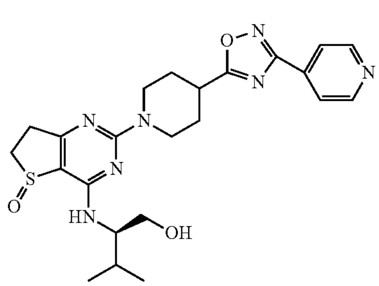 | H | *⟵CH(iPr)CH₂OH | 3-(pyridin-4-yl)-1,2,4-oxadiazol-5-yl | H | 92 |

Table B that follows gives detailed information on the chemical syntheses and the analysis of the individual Example substances 1-163.

TABLE B

Detailed information on the preparatino of the individual Example substances 1-163

| # | Prepared analogously to #* | non-commercial arylpiperidine component (V) | literature on the preperation of the non-commercial arylpiperidine component (V) | analytical HPLC-MS, RT [min], method |
|---|---|---|---|---|
| 1 | see experim. Section | | | 1.24 method A |
| 2 | see experim. Section | | | 1.32 method B |
| 3 | see experim. Section | | | 1.29 method A |
| 4 | see experim. Section | | | 1.36 method A |
| 5 | see experim. Section | | | 1.18 method A |
| 6 | see experim. Section | | | 1.24 method A |
| 7 | 6 | | | 1.25 method A |
| 8 | 2 | | | 1.21 method A |
| 9 | 2 | | | 1.15 method D |
| 10 | 6 | | | 1.20 method D |
| 11 | 2 | | | 1.14 method D |
| 12 | 14 | | | 1.77 method C |
| 13 | 14 | | | 1.32 method C |
| 14 | see experim. Section | | | 1.58 method C |
| 15 | 14 | | | 1.74 method C |
| 16 | see experim. Section | | | 1.74 method C |
| 17 | 14 | | | 1.65 method C |
| 18 | 14 | | | 1.64 method C |
| 19 | see experim. Section | | | 1.33 method C |
| 20 | 14 | | | 1.73 method C |
| 21 | 14 | (structure: spiro piperidine-benzoxazinone, HN-piperidine spiro fused to benzo[d][1,3]oxazin-2(1H)-one) | J. Med. Chem. 1983, 657 | 1.6 method C |
| 22 | see experim Section | | | 1.83 method C |
| 23 | 14 | | | 1.55 method C |
| 24 | 14 | | | 1.87 method C |
| 25 | 14 | | | 1.78 method C |
| 26 | 28 | | | 1.72 method C |
| 27 | 28 | | | 0.55 method C |
| 28 | see experim. Section | | | 1.52 method C |
| 29 | see experim. Section | | | 1.77 method C |

TABLE B-continued

Detailed information on the preparatino of the individual Example substances 1-163

| # | Prepared analogously to #* | non-commercial arylpiperidine component (V) | literature on the preperation of the non-commercial arylpiperidine component (V) | analytical HPLC-MS, RT [min], method |
|---|---|---|---|---|
| 30 | 28 | | | 1.69 method C |
| 31 | 28 | | | 1.7 method C |
| 32 | 28 | | | 1.59 method C |
| 33 | 28 | | | 1.58 method C |
| 34 | 28 | | | 0.56 method C |
| 35 | 28 | | | 1.68 method C |
| 36 | 28 | 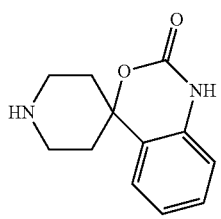 [SMILES: O=C1Nc2ccccc2C2(CCNCC2)O1] | J. Med. Chem. 1983, 657 | 1.54 method C |
| 37 | see experim. Section | | | 1.78 method C |
| 38 | 28 | | | 1.48 method C |
| 39 | 28 | | | 1.21 method D |
| 40 | 28 | | | 1.74 method C |
| 41 | 43 | | | 1.68 method C |
| 42 | 43 | | | 0.55 method C |
| 43 | see experim. Section | | | 1.49 method C |
| 44 | 43 | | | 1.66 method C |
| 45 | 43 | | | 1.66 method C |
| 46 | 43 | | | 1.55 method C |
| 47 | 43 | | | 1.54 method C |
| 48 | 43 | | | 0.56 method C |
| 49 | 43 | | | 1.64 method C |
| 50 | 43 | 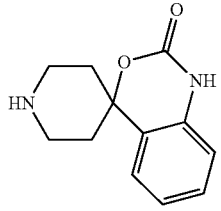 [SMILES: O=C1Nc2ccccc2C2(CCNCC2)O1] | J. Med. Chem. 1983, 657 | 1.5 method C |
| 51 | 43 | 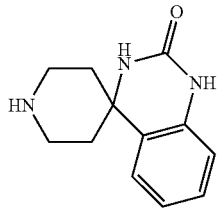 [SMILES: O=C1Nc2ccccc2C2(CCNCC2)N1] | WO2003/104236 | 1.49 method C |

TABLE B-continued

Detailed information on the preparatino of the individual Example substances 1-163

| # | Prepared analogously to #* | non-commercial arylpiperidine component (V) | literature on the preperation of the non-commercial arylpiperidine component (V) | analytical HPLC-MS, RT [min], method |
|---|---|---|---|---|
| 52 | 43 | ![structure: 5-fluoro-2-ethyl-3-(piperidin-4-yl)-1H-indole] | see experim. Section § 10.4, component (V-1) | 1.73 method C |
| 53 | 43 | | | 1.45 method C |
| 54 | 43 | | | 1.77 method C |
| 55 | see experim. Section | | | 1.71 method C |
| 56 | 58 | | | 1.76 method C |
| 57 | 58 | | | 1.3 method C |
| 58 | see experim. Section | | | 1.56 method C |
| 59 | 58 | | | 1.72 method C |
| 60 | 58 | | | 1.73 method C |
| 61 | 58 | | | 1.63 method C |
| 62 | 58 | | | 1.61 method C |
| 63 | 58 | | | 1.3 method C |
| 64 | 58 | | | 1.71 method C |
| 65 | 58 | ![structure: spiro piperidine benzoxazinone] | J. Med. Chem. 1983, 657 | 1.56 method C |
| 66 | 58 | ![structure: spiro piperidine quinazolinone] | WO2003/104236 | 1.55 method C |
| 67 | 58 | ![structure: 5-fluoro-2-ethyl-3-(piperidin-4-yl)-1H-indole] | see experim. Section § 10.4, compnent (V-1) | 1.81 method C |

TABLE B-continued

Detailed information on the preparatino of the individual Example substances 1-163

| # | Prepared analogously to #* | non-commercial arylpiperidine component (V) | literature on the preperation of the non-commercial arylpiperidine component (V) | analytical HPLC-MS, RT [min], method |
|---|---|---|---|---|
| 68 | 58 | | | 1.52 method C |
| 69 | 58 | | | 1.25 method D |
| 70 | 58 | | | 1.78 method C |
| 71 | 73 | | | 2.07 method C |
| 72 | 73 | | | 1.53 method C |
| 73 | see experim. Section | | | 1.81 method C |
| 74 | 73 | | | 2.07 method C |
| 75 | see experim. Section | | | 2.11 method C |
| 76 | 73 | | | 1.92 method C |
| 77 | 73 | | | 1.91 method C |
| 78 | see experim. Section | | | 1.55 method C |
| 79 | 73 | | | 2.09 method C |
| 80 | 73 | 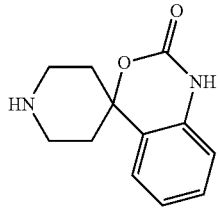 [SMILES: O=C1Nc2ccccc2C2(CCNCC2)O1] | J. Med. Chem. 1983, 657 | 1.86 method C |
| 81 | 73 | 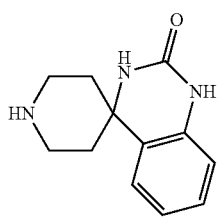 [SMILES: O=C1Nc2ccccc2C2(CCNCC2)N1] | WO2003/104236 | 1.81 method C |
| 82 | see experim. Section | | | 2.12 method C |
| 83 | 73 | | | 1.87 method C |
| 84 | 73 | | | 2.29 method C |
| 85 | 73 | | | 2.24 method C |
| 86 | 73 | | | 1.20 method D |
| 87 | 28 | | | 1.15 method D |
| 88 | 58 | | | 1.20 method D |
| 89 | see experim. Section | | | 1.18 method D |
| 90 | see experim. Section | | | 1.23 method D |
| 91 | see experim. Section | | | 1.30 method D |
| 92 | see experim. Section | | | 1.23 method D |
| 93 | see experim. Section | | | 1.28 method D |
| 94 | 28 | | | 1.22 method D |

TABLE B-continued

Detailed information on the preparatino of the individual Example substances 1-163

| # | Prepared analogously to #* | non-commercial arylpiperidine component (V) | literature on the preperation of the non-commercial arylpiperidine component (V) | analytical HPLC-MS, RT [min], method |
|---|---|---|---|---|
| 95 | see experim. Section | | | 1.25 method D |
| 96 | see experim. Section | | | 1.29 method D |
| 97 | see experim. Section | | | 1.29 method A |
| 98 | see experim. Section | | | 1.22 method B |
| 99 | see experim. Section | | | 1.23 method B |
| 100 | see experim. Section | | | 1.18 method B |
| 101 | 28 | | | 1.74 method C |
| 102 | 28 | | | 1.86 method C |
| 103 | 28 | | | 1.73 method C |
| 104 | 28 | | | 1.73 method C |
| 105 | 28 | | | 1.76 method C |
| 106 | 28 | | | 1.74 method C |
| 107 | 28 | | | 1.71 method C |
| 108 | 28 | | | 1.33 method C |
| 109 | 28 | | | 1.71 method C |
| 110 | 28 | | | 1.83 method C |
| 111 | 28 | | | 1.89 method C |
| 112 | 28 | | | 1.69 method C |
| 113 | 28 | | | 1.66 method C |
| 114 | 28 | | | 1.61 method C |
| 115 | 28 | | | 1.46 method C |
| 116 | 28 | | | 1.43 method C |
| 117 | 58 | | | 1.77 method C |
| 118 | 58 | | | 1.91 method C |
| 119 | 58 | | | 1.77 method C |
| 120 | 58 | | | 1.78 method C |
| 121 | 58 | | | 1.79 method C |
| 122 | 58 | | | 1.78 method C |
| 123 | 58 | | | 1.74 method C |
| 124 | 58 | | | 1.36 method C |
| 125 | 58 | | | 1.74 method C |
| 126 | 58 | | | 1.88 method C |
| 127 | 58 | | | 1.92 method C |
| 128 | 58 | | | 1.73 method C |
| 129 | 58 | | | 1.69 method C |
| 130 | 58 | | | 1.64 method C |

TABLE B-continued

Detailed information on the preparatino of the individual Example substances 1-163

| # | Prepared analogously to #* | non-commercial arylpiperidine component (V) | literature on the preperation of the non-commercial arylpiperidine component (V) | analytical HPLC-MS, RT [min], method |
|---|---|---|---|---|
| 131 | 58 | | | 1.5 method C |
| 132 | 58 | | | 1.45 method C |
| 133 | 73 | | | 2.14 method C |
| 134 | 73 | | | 2.44 method C |
| 135 | 73 | | | 2.14 method C |
| 136 | 73 | | | 2.17 method C |
| 137 | 73 | | | 2.16 method C |
| 138 | 73 | | | 2.09 method C |
| 139 | 73 | | | 1.6 method C |
| 140 | 73 | | | 2.12 method C |
| 141 | 73 | | | 2.31 method C |
| 142 | 73 | | | 2.34 method C |
| 143 | 73 | | | 2.07 method C |
| 144 | 73 | | | 2.08 method C |
| 145 | see experim. Section | | | 1.89 method C |
| 146 | 73 | | | 1.79 method C |
| 147 | see experim. Section | | | 1.72 method C |
| 148 | 14 | | | 1.8 method C |
| 149 | 14 | | | 1.9 method C |
| 150 | 14 | | | 1.78 method C |
| 151 | 14 | | | 1.79 method C |
| 152 | 14 | | | 1.81 method C |
| 153 | 14 | | | 1.8 method C |
| 154 | 14 | | | 1.76 method C |
| 155 | 14 | | | 1.39 method C |
| 156 | 14 | | | 1.76 method C |
| 157 | 14 | | | 1.88 method C |
| 158 | 14 | | | 1.94 method C |
| 159 | 14 | | | 1.74 method C |
| 160 | 14 | | | 1.71 method C |
| 161 | see experim. Section | | | 1.67 method C |
| 162 | 14 | | | 1.52 method C |
| 163 | see experim. Section | | | 1.48 method C |

*the Example may be prepared and purified analogously.

TABLE C

Chemical structures of the Example substances 164-332

| Ex. | Structure | R¹ | R² | R³ | R⁴ | % Inhibition PDE4B @ 1 μM |
|---|---|---|---|---|---|---|
| 164 | (structure) | H | cyclopropyl-CH₂OH | phenyl | H | 92 |
| 165 | (structure) | H | 3-fluorophenyl | 4-fluorophenoxy | H | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 166 | 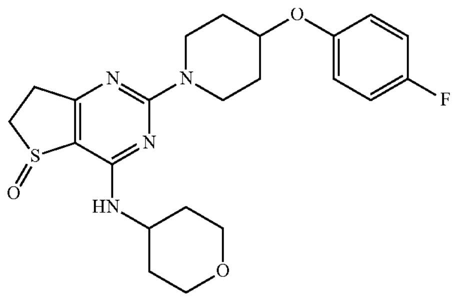 | H | 4-tetrahydropyranyl | 4-fluorophenoxy | H | 92 |
| 167 | 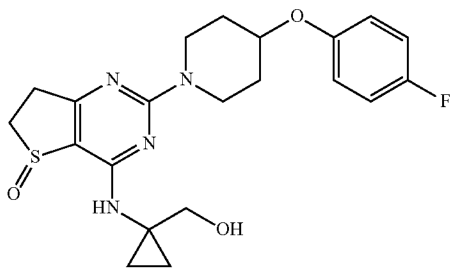 | H | 1-(hydroxymethyl)cyclopropyl | 4-fluorophenoxy | H | 91 |
| 168 | 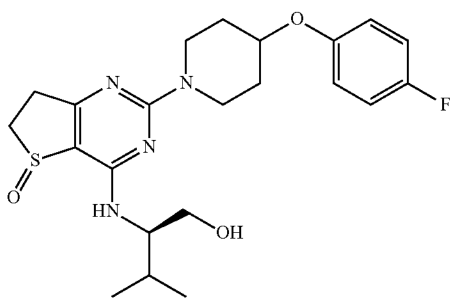 | H | (S)-1-hydroxy-3-methylbutan-2-yl | 4-fluorophenoxy | H | 89 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 169 | 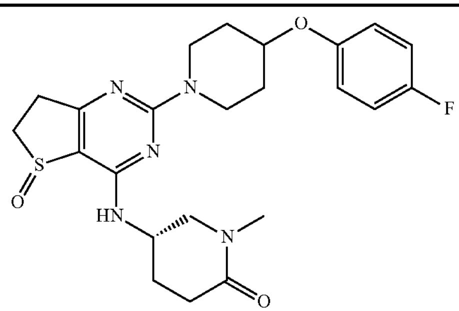 | H | | | H | 92 |
| 170 | 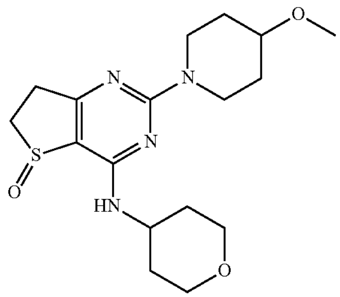 | H | | OCH₃ | H | 77 |
| 172 | 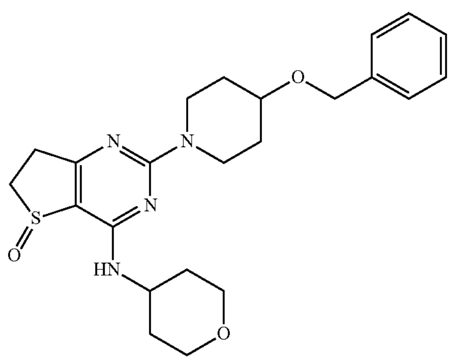 | H | | | H | 91 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 173 | 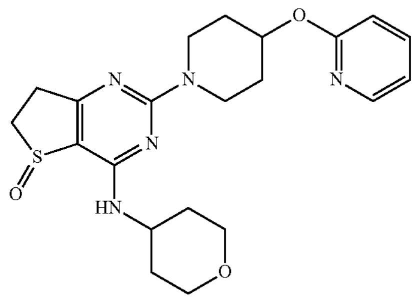 | H | *-tetrahydropyran-4-yl | *-O-(pyridin-2-yl) | H | 95 |
| 174 | 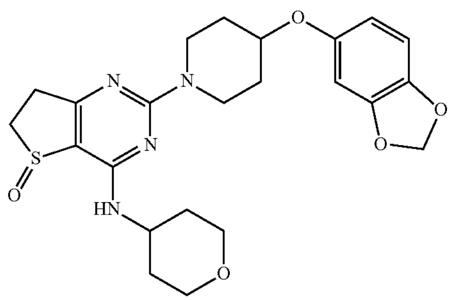 | H | *-tetrahydropyran-4-yl | *-O-(benzo[1,3]dioxol-5-yl) | H | 92 |
| 175 | 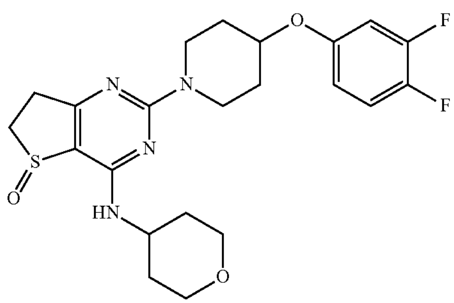 | H | *-tetrahydropyran-4-yl | *-O-(3,4-difluorophenyl) | H | 89 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 176 | 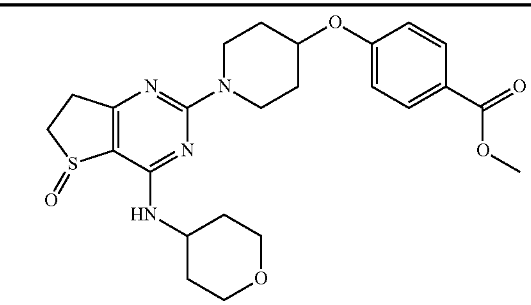 | H | tetrahydropyran-4-yl | 4-(methoxycarbonyl)phenoxy | H | 93 |
| 177 | 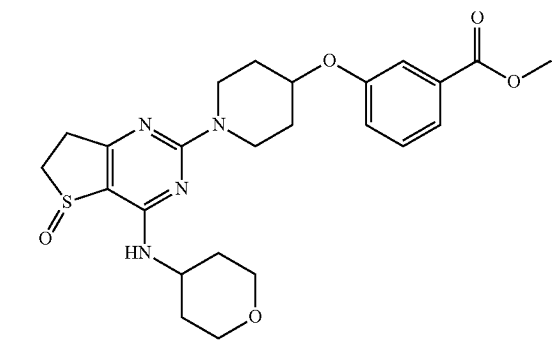 | H | tetrahydropyran-4-yl | 3-(methoxycarbonyl)phenoxy | H | 93 |
| 178 | 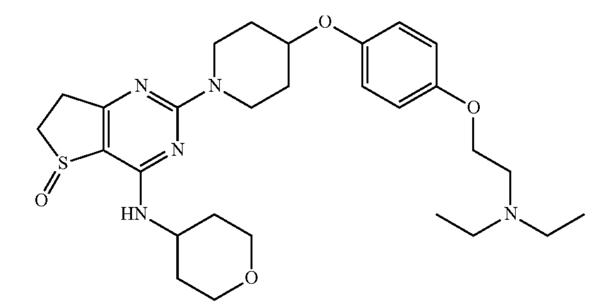 | H | tetrahydropyran-4-yl | 4-(2-(diethylamino)ethoxy)phenoxy | H | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 179 | 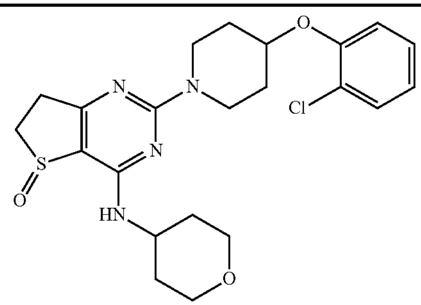 | H | 4-tetrahydropyranyl | 2-chlorophenoxy | H | 75 |
| 180 | 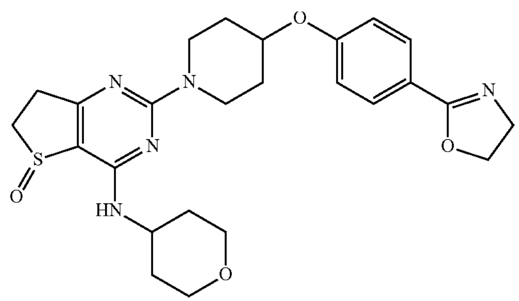 | H | 4-tetrahydropyranyl | 4-(4,5-dihydrooxazol-2-yl)phenoxy | H | 93 |
| 181 | 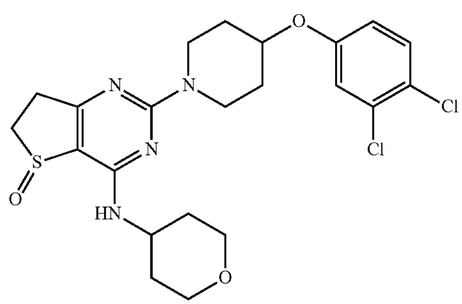 | H | 4-tetrahydropyranyl | 3,4-dichlorophenoxy | H | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 182 | 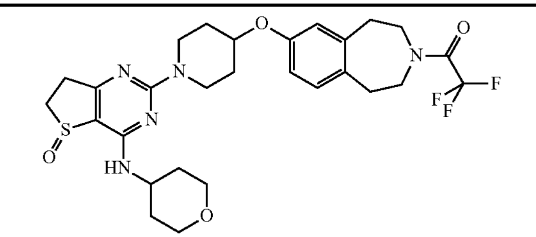 | H | tetrahydropyran-4-yl | 7-(2,2,2-trifluoroacetyl)-2,3,4,5-tetrahydro-1H-benzo[d]azepin-8-yloxy | H | 82 |
| 183 | 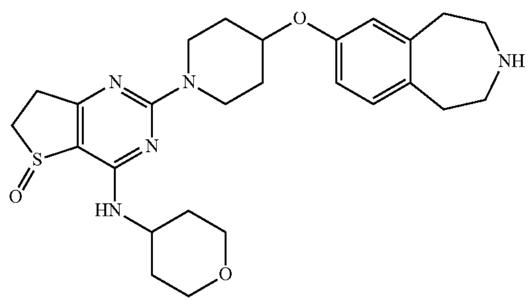 | H | tetrahydropyran-4-yl | 2,3,4,5-tetrahydro-1H-benzo[d]azepin-7-yloxy | H | 91 |
| 184 | 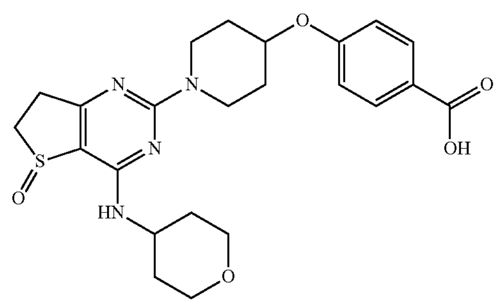 | H | tetrahydropyran-4-yl | 4-carboxyphenoxy | H | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 185 | 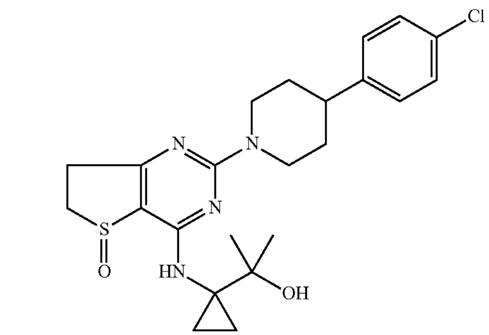 | H | | | H | 94 |
| 186 | 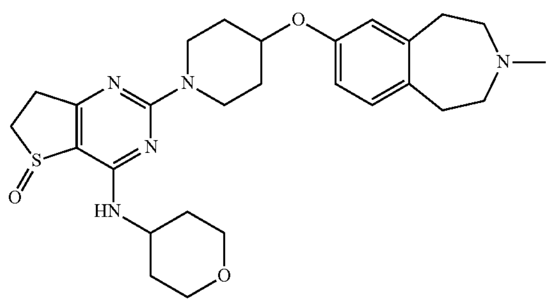 | H | | | H | 96 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 187 | 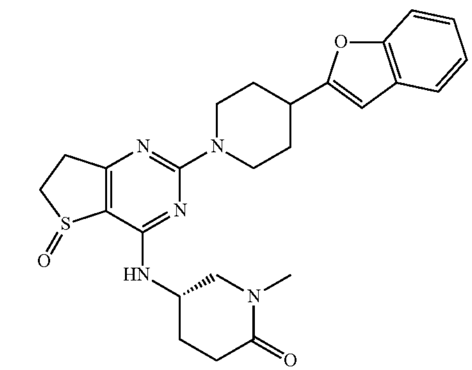 | H | | | H | 98 |
| 188 | 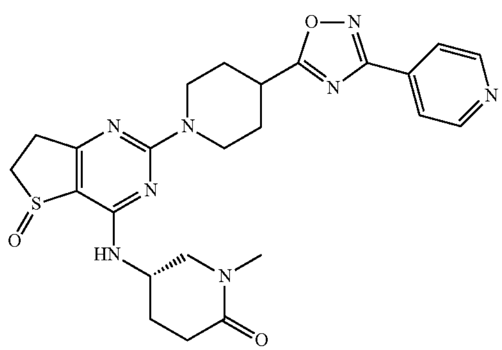 | H | | | H | 97 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 189 | 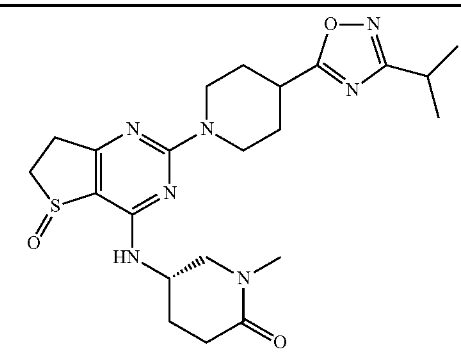 | H | N-methyl-piperidinone (*) | 3-isopropyl-1,2,4-oxadiazol-5-yl (*) | H | 97 |
| 190 | 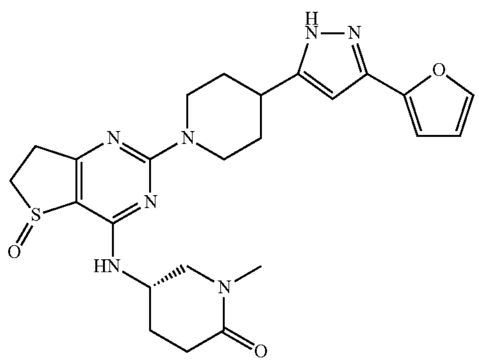 | H | N-methyl-piperidinone (*) | 5-(furan-2-yl)-1H-pyrazol-3-yl (*) | H | 97 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 191 | (structure) | H | tetrahydropyran-4-yl | 6-chloro-1H-benzimidazol-2-yl | H | 96 |
| 192 | (structure) | H | tetrahydropyran-4-yl | 5-tert-butyl-1-methyl-1H-indol-3-yl | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 193 | 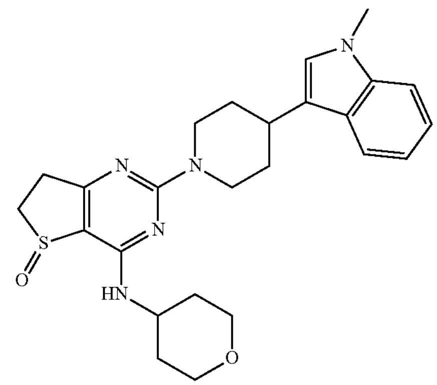 | H | tetrahydropyran-4-yl | 1-methyl-1H-indol-3-yl | H | 96 |
| 194 | 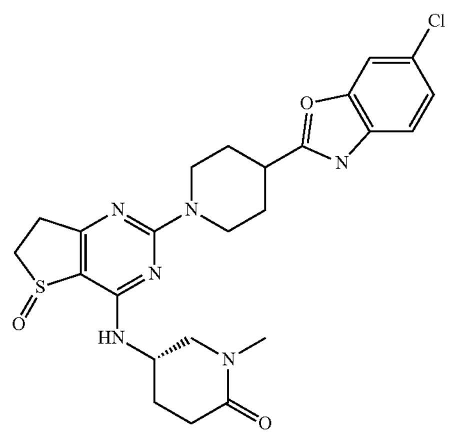 | H | (R)-1-methyl-6-oxopiperidin-3-yl | 6-chlorobenzo[d]oxazol-2-yl | H | 97 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 195 | 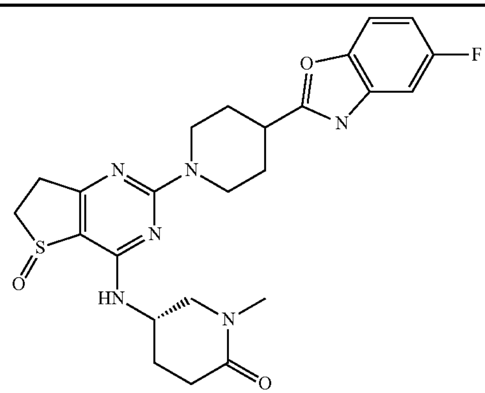 | H | | | H | 96 |
| 196 | 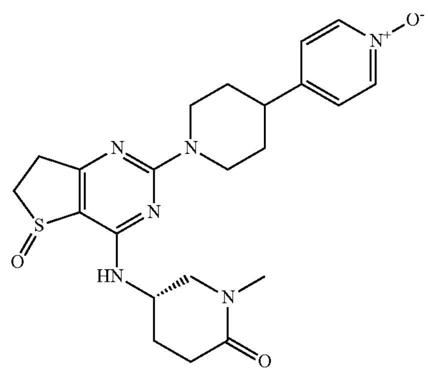 | H | | | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 197 | 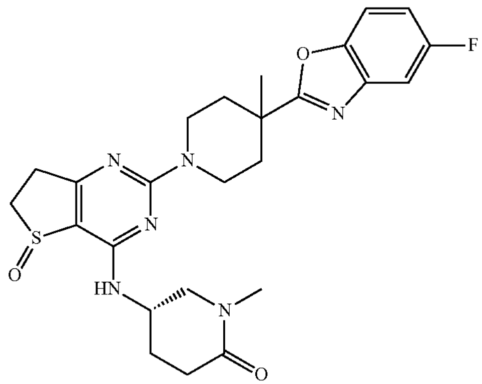 | H | (N-methyl-piperidinone, *) | (5-fluorobenzoxazol-2-yl, *) | CH₃ | 96 |
| 198 | 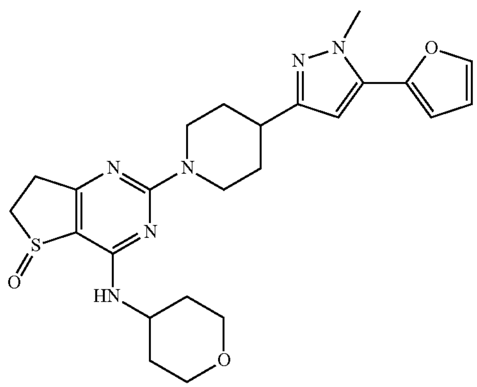 | H | (tetrahydropyran-4-yl, *) | (5-(furan-2-yl)-1-methyl-pyrazol-3-yl, *) | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 199 | 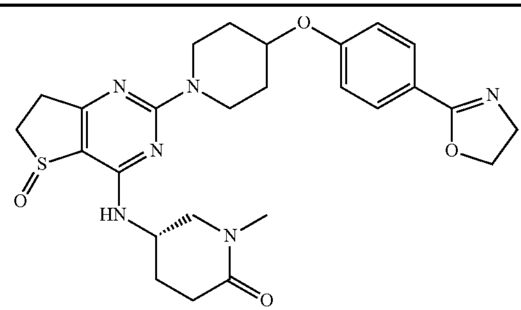 | H | | | H | 96 |
| 200 | 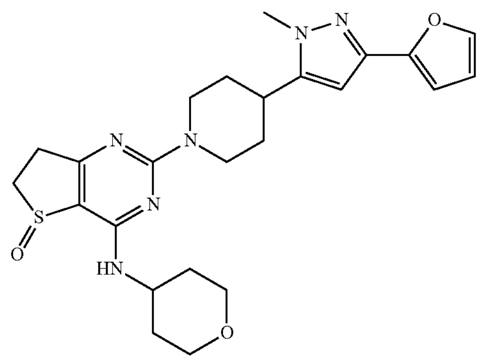 | H | | | H | 97 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 201 | 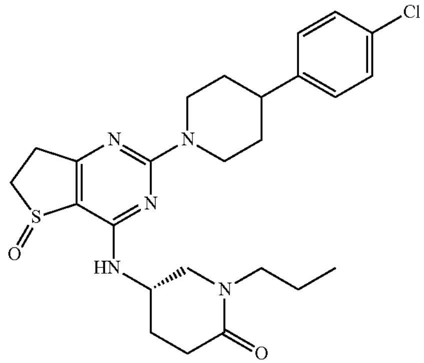 | H | | 4-Cl-phenyl | H | 95 |
| 202 | 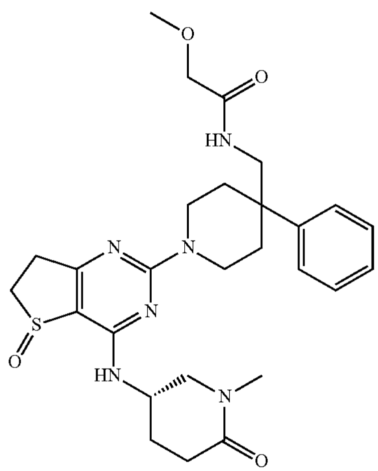 [SMILES: COCC(=O)NCC1(c2ccccc2)CCN(c2nc3c(c(N[C@H]4CCC(=O)N(C)C4)n2)S(=O)CC3)CC1] | H | | phenyl | | 96 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 203 | 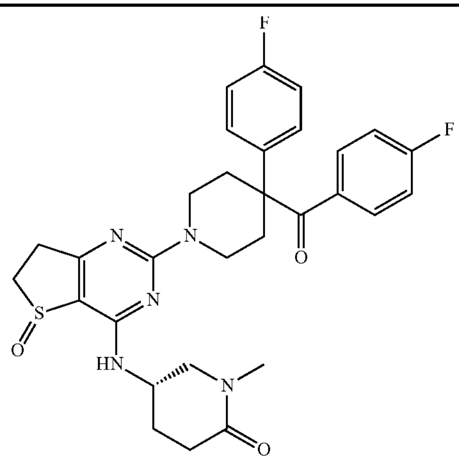 | H | N-methyl-piperidinone (*) | 4-fluorophenyl (*) | 4-fluorobenzoyl (*) | 96 |
| 204 | 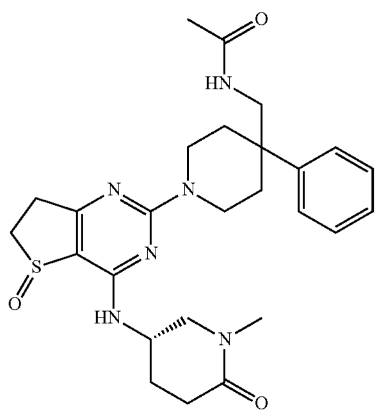 [SMILES: CC(=O)NCC1(c2ccccc2)CCN(c2nc3c(c(N[C@H]4CCC(=O)N(C)C4)n2)S(=O)CC3)CC1] | H | N-methyl-piperidinone (*) | phenyl (*) | acetamidomethyl (*) | 96 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 205 | 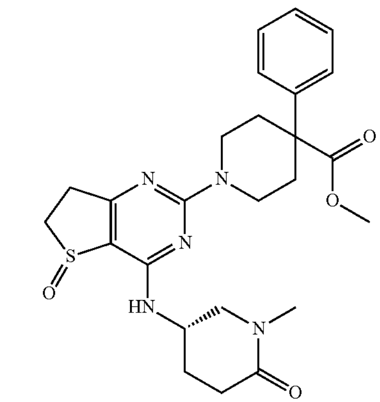 [SMILES: COC(=O)C1(c2ccccc2)CCN(c2nc3c(c(N[C@H]4CCC(=O)N(C)C4)n2)S(=O)CC3)CC1] | H | | | | 96 |
| 206 | 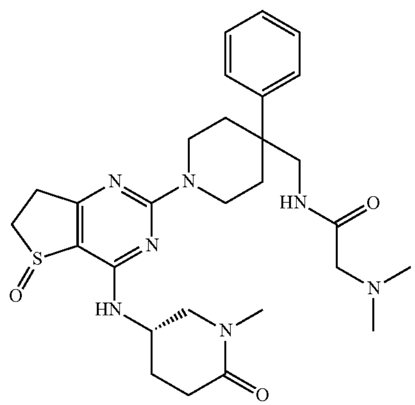 [SMILES: CN(C)CC(=O)NCC1(c2ccccc2)CCN(c2nc3c(c(N[C@H]4CCC(=O)N(C)C4)n2)S(=O)CC3)CC1] | H | | | | 95 |

TABLE C-continued
Chemical structures of the Example substances 164-332
| Ex. | Structure | R¹ | R² | R³ | R⁴ | % Inhibition PDE4B @ 1 μM |
|---|---|---|---|---|---|---|
| 207 | 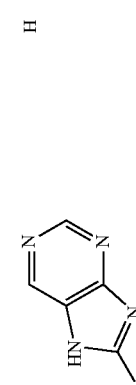 | H | *-tetrahydropyran-4-yl | *-(3H-imidazo[4,5-b]pyridin-2-yl) | H | 95 |
| 208 | 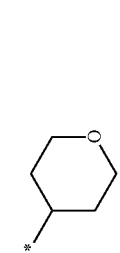 | H | *-tetrahydropyran-4-yl | *-(3H-imidazo[4,5-d]pyrimidin-2-yl) | H | 82 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 209 | 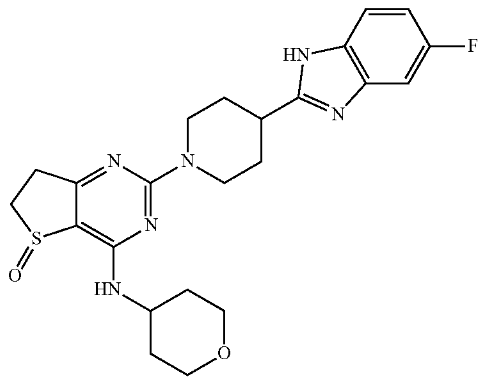 | H | tetrahydropyran-4-yl | 5-fluoro-1H-benzimidazol-2-yl | H | 95 |
| 210 | 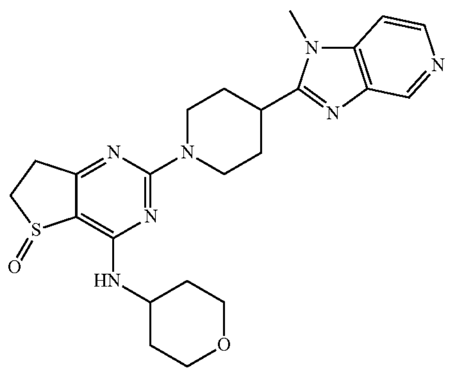 | H | tetrahydropyran-4-yl | 1-methyl-imidazo[4,5-b]pyridin-2-yl | H | 85 |

TABLE C-continued

Chemical structures of the Example substances 164-332

| Ex. | Structure | $R^1$ | $R^2$ | $R^3$ | $R^4$ | % Inhibition PDE4B @ 1 μM |
|---|---|---|---|---|---|---|
| 211 | 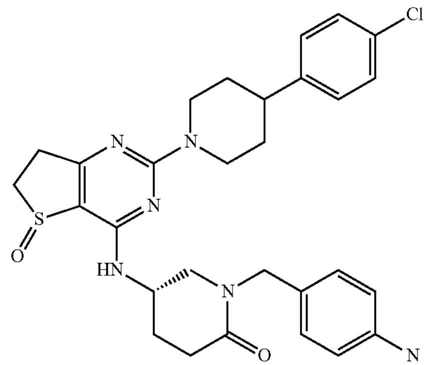 | H | | | H | 94 |
| 212 | 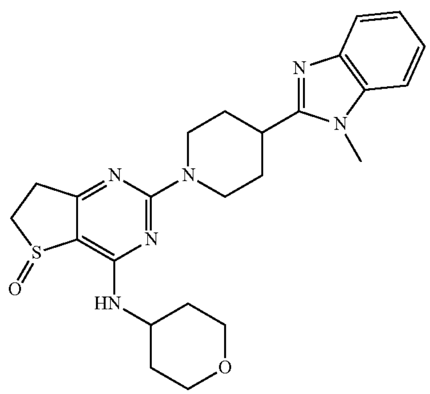 | H | | | H | 93 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 213 | (structure) | H | tetrahydropyran-4-yl | imidazo-pyridinyl | H | 88 |
| 214 | (structure) | H | tetrahydropyran-4-yl | cyclopropanoyl-benzazepine-O- | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 215 | 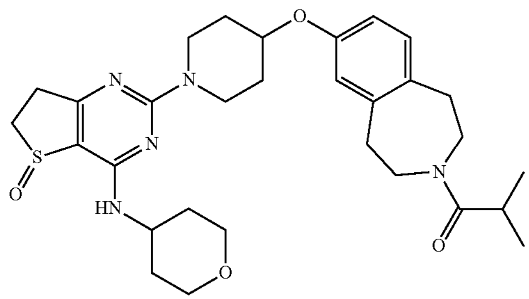 | H | | | H | 79 |
| 216 | 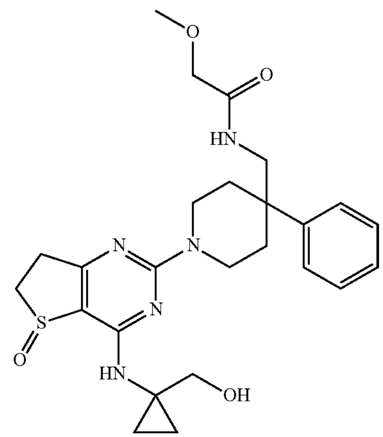 [SMILES: COCC(=O)NCC1(c2ccccc2)CCN(c2nc3c(c(NC4(CO)CC4)n2)S(=O)CC3)CC1] | H | | | | 80 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 217 | 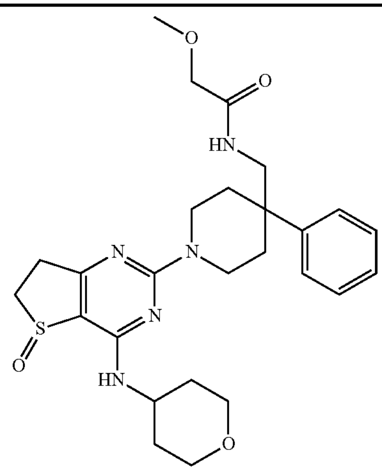 | H | tetrahydropyran-4-yl | phenyl | methoxyacetamidomethyl | 88 |
| 218 | 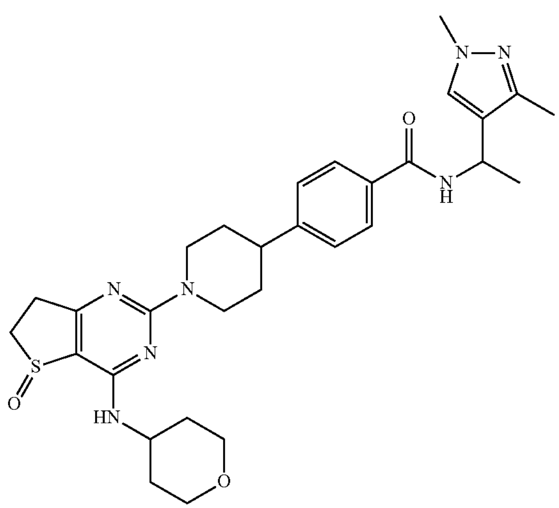 | H | tetrahydropyran-4-yl | 4-[N-(1-(1,3-dimethylpyrazol-4-yl)ethyl)carbamoyl]phenyl | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 219 | (structure) | H | (N-methyl-piperidinone, *) | (1H-indazol-3-yl, *) | H | 82 |
| 220 | (structure) | H | (hydroxymethyl-cyclopropyl, *) | (1H-indazol-3-yl, *) | H | 93 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 221 | 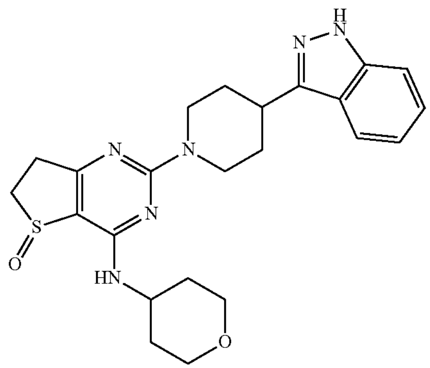 | H | tetrahydropyran-4-yl | 1H-indazol-3-yl | H | 94 |
| 222 | 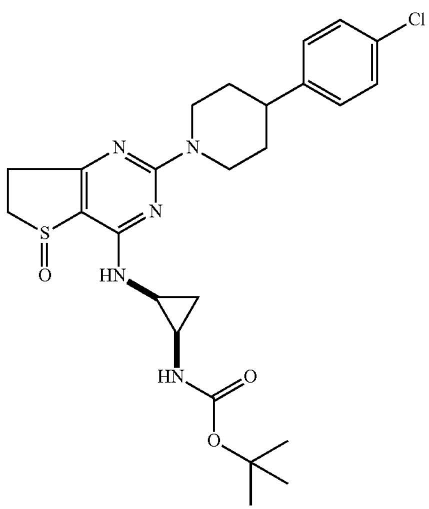 | H | trans-2-(Boc-amino)cyclopropyl | 4-chlorophenyl | H | 89 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 223 | (structure) | H | 4-tetrahydropyranyl | 4-[C(CH₃)₂-NH-C(O)-]-phenyl with pyridin-4-yl | H | 80 |
| 224 | (structure) | H | 4-tetrahydropyranyl | 4-[N-methyl-N-(tetrahydropyran-4-yl)carbamoyl]-phenyl | H | 93 |

TABLE C-continued
Chemical structures of the Example substances 164-332
| Ex. | Structure | R¹ | R² | R³ | R⁴ | % Inhibition PDE4B @ 1 μM |
|---|---|---|---|---|---|---|
| 225 | 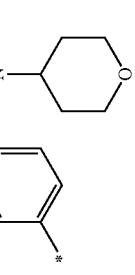 | H | tetrahydropyran-4-yl | N-cyclopropyl-N-(tetrahydropyran-4-yl)-4-methylbenzamide | H | 89 |
| 226 | 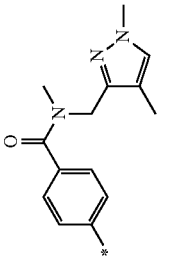 | H | tetrahydropyran-4-yl | N-methyl-N-((1,4-dimethyl-1H-pyrazol-3-yl)methyl)-4-methylbenzamide | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 227 | (structure) | H | tetrahydropyran-4-yl | 4-(morpholin-4-ylcarbonyl)phenyl | H | 83 |
| 228 | (structure) | H | tetrahydropyran-4-yl | 4-[methyl(1-methylpiperidin-4-yl)carbamoyl]phenyl | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 229 | 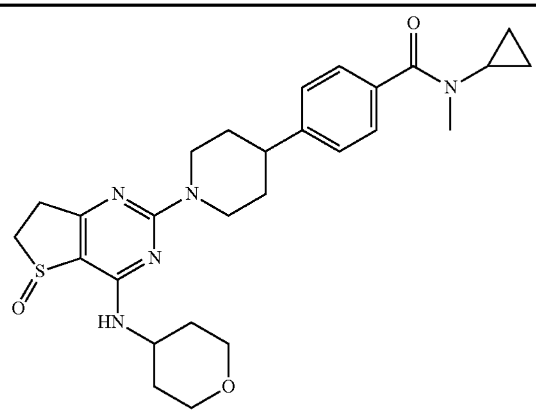 | H | tetrahydropyran-4-yl | N-cyclopropyl-N-methyl-4-methylbenzamide | H | 94 |
| 230 | 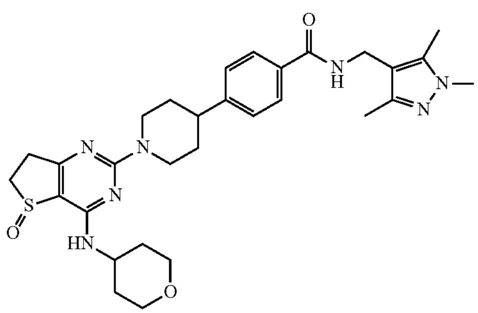 | H | tetrahydropyran-4-yl | N-((1,3,5-trimethyl-1H-pyrazol-4-yl)methyl)-4-methylbenzamide | H | 81 |

TABLE C-continued
Chemical structures of the Example substances 164-332
| Ex. | Structure | R¹ | R² | R³ | R⁴ | % Inhibition PDE4B @ 1 μM |
|---|---|---|---|---|---|---|
| 231 | 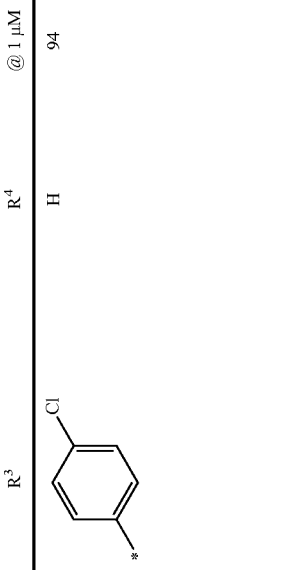 | H | 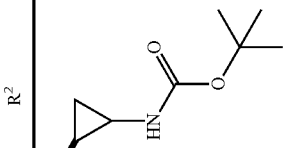 |  | H | 94 |
| 232[1)] | 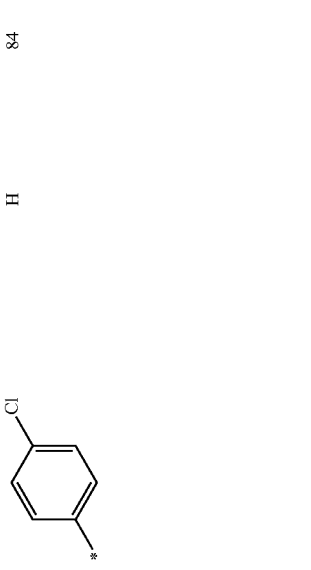 | H | 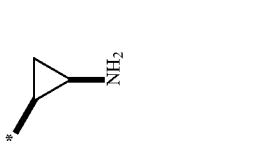 |  | H | 84 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 233 | 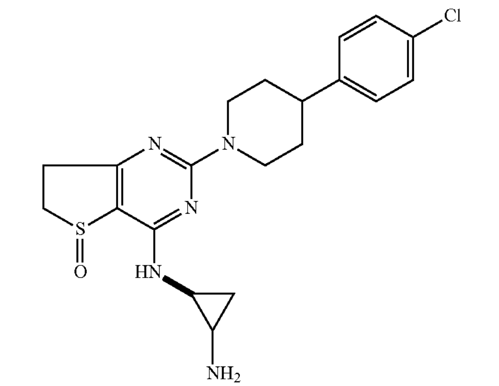 | H | cyclopropyl-NH₂ (*) | 4-chlorophenyl (*) | H | 93 |
| 234 | 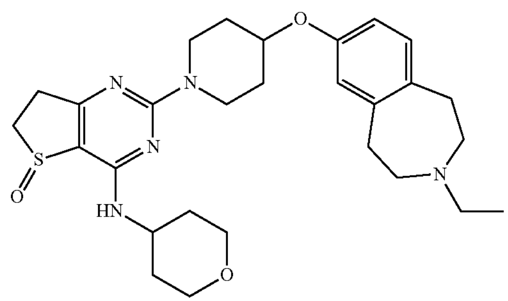 | H | tetrahydropyran-4-yl (*) | 3-ethyl-2,3,4,5-tetrahydro-1H-benzo[d]azepin-7-yloxy (*) | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 235 | 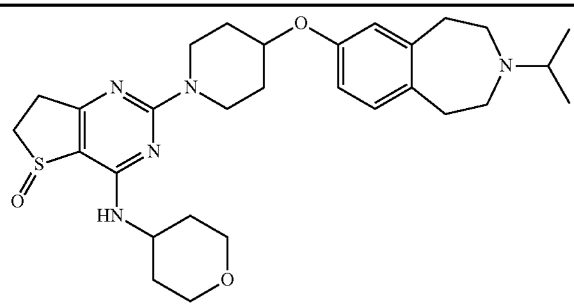 | H | tetrahydropyran-4-yl | isopropyl-benzazepine-methoxy | H | 87 |
| 236 | 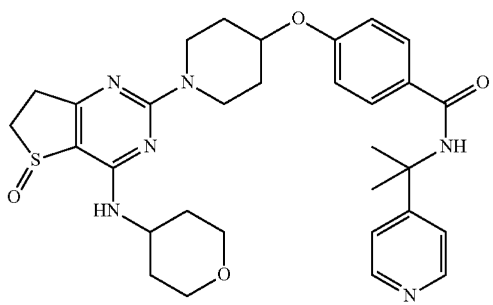 | H | tetrahydropyran-4-yl | 4-methoxy-N-(2-(pyridin-4-yl)propan-2-yl)benzamide | H | 95 |
| 237 | 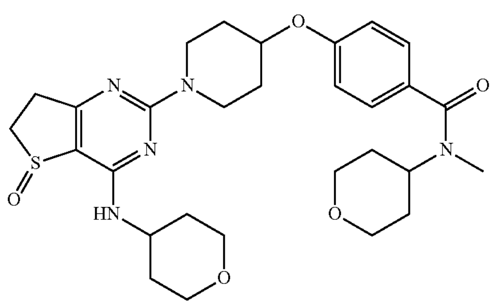 | H | tetrahydropyran-4-yl | 4-methoxy-N-methyl-N-(tetrahydropyran-4-yl)benzamide | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 238 | 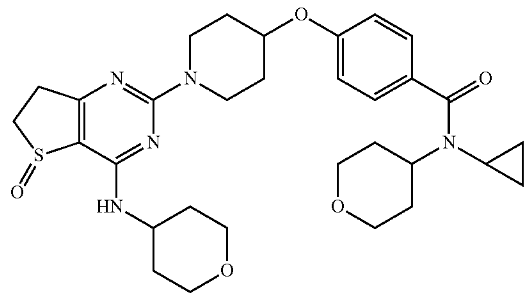 | H | tetrahydropyran-4-yl | 4-methoxy-N-cyclopropyl-N-(tetrahydropyran-4-yl)benzamide | H | 95 |
| 239 | 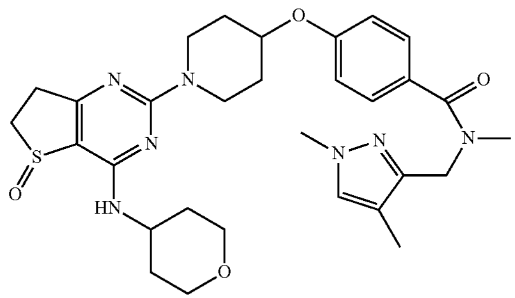 | H | tetrahydropyran-4-yl | 4-methoxy-N-methyl-N-((1,4-dimethyl-1H-pyrazol-3-yl)methyl)benzamide | H | 94 |
| 240 | 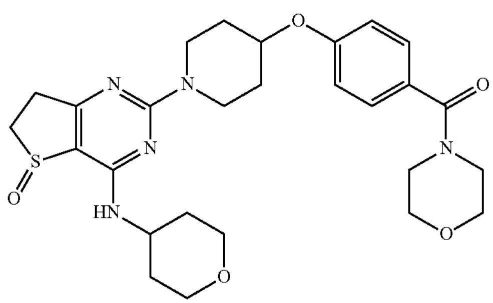 | H | tetrahydropyran-4-yl | (4-methoxyphenyl)(morpholino)methanone | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 241 | 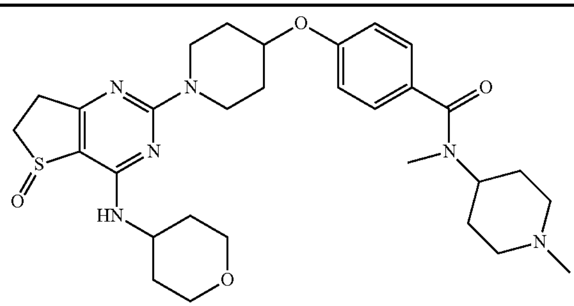 | H | tetrahydropyran-4-yl | 4-methoxy-N-methyl-N-(1-methylpiperidin-4-yl)benzamide | H | 93 |
| 242 | 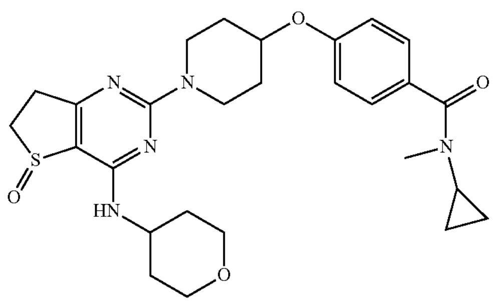 | H | tetrahydropyran-4-yl | N-cyclopropyl-4-methoxy-N-methylbenzamide | H | 94 |
| 243 | 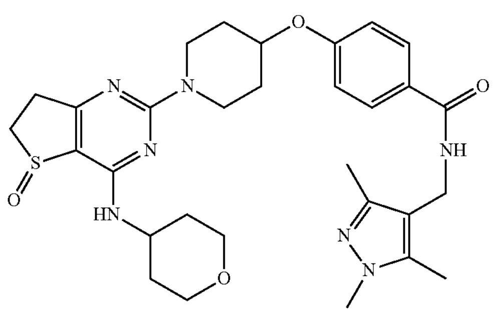 | H | tetrahydropyran-4-yl | 4-methoxy-N-((1,3,5-trimethyl-1H-pyrazol-4-yl)methyl)benzamide | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 244 | 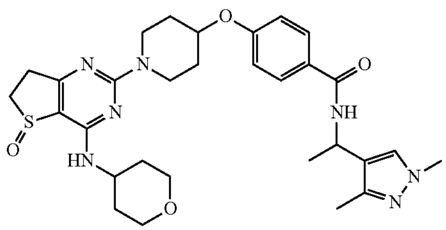 | H | *-tetrahydropyran-4-yl | *-O-C₆H₄-C(O)NH-CH(CH₃)-(1,3-dimethylpyrazol-4-yl) | H | 95 |
| 245[2)] | 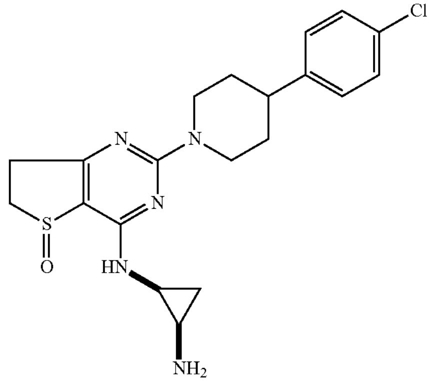 | H | *-(2-aminocyclopropyl) | *-(4-chlorophenyl) | H | 68 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 246 | 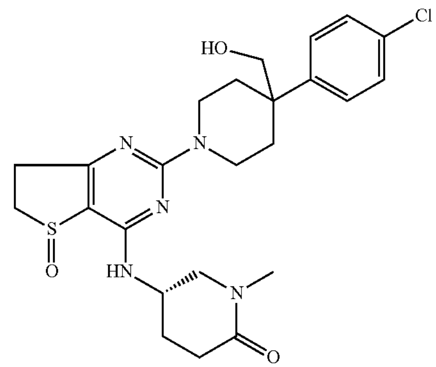 [SMILES: CN1C[C@@H](Nc2nc(N3CCC(CO)(c4ccc(Cl)cc4)CC3)nc3c2S(=O)CC3)CCC1=O] | H | (N-methyl-piperidinone) | 4-chlorophenyl | HOCH₂-* | 93 |
| 247 | 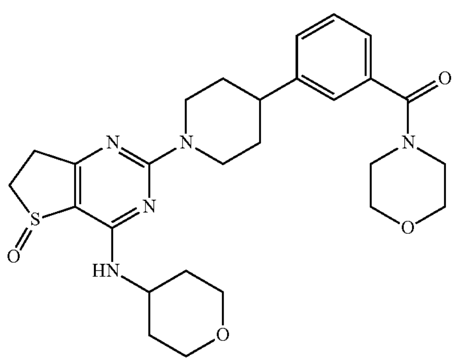 | H | (tetrahydropyran-4-yl) | 3-(morpholine-4-carbonyl)phenyl | H | 90 |

TABLE C-continued
Chemical structures of the Example substances 164-332
| Ex. | Structure | R¹ | R² | R³ | R⁴ | % Inhibition PDE4B @ 1 µM |
|---|---|---|---|---|---|---|
| 248 | 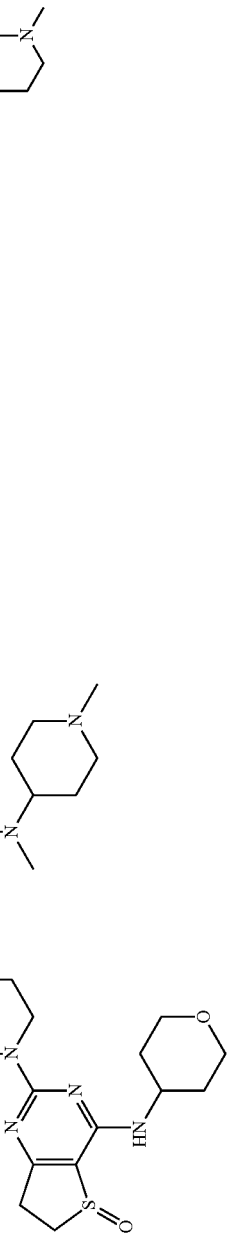 | H | 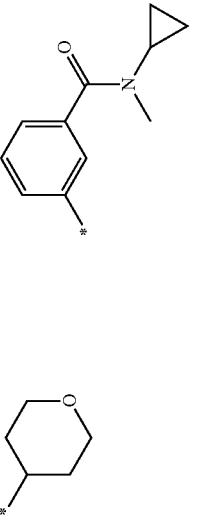 | 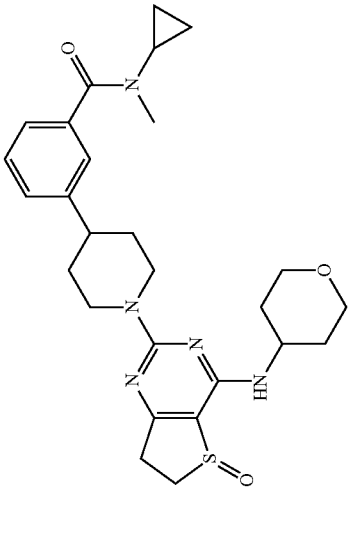 | H | 88 |
| 249 | 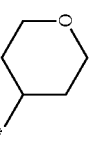 | H | 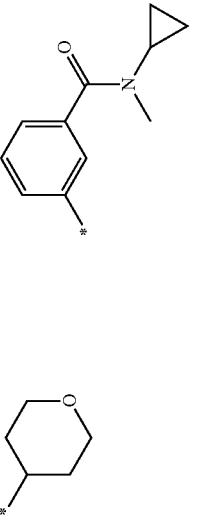 | 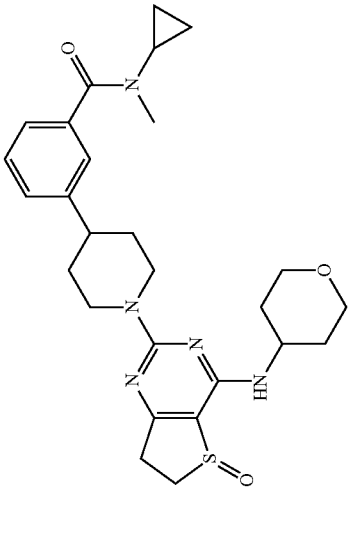 | H | 93 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 250 | 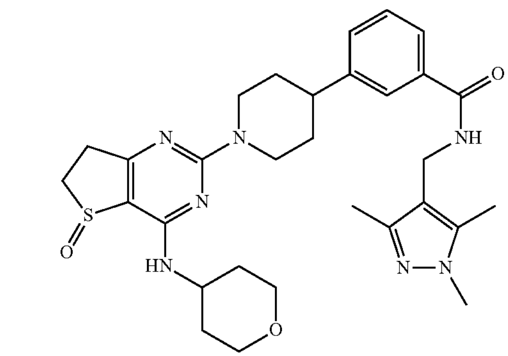 | H | tetrahydropyran-4-yl | | H | 92 |
| 251 | 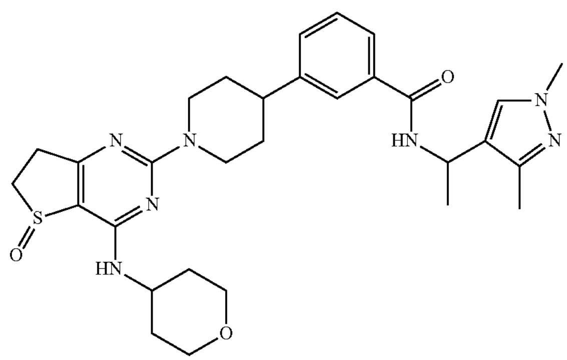 | H | tetrahydropyran-4-yl | | H | 90 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 252 | 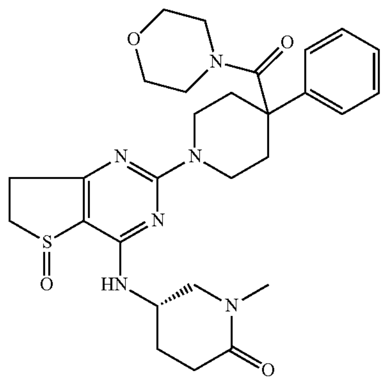 [SMILES: CN1C[C@@H](Nc2nc(N3CCC(C(=O)N4CCOCC4)(c4ccccc4)CC3)nc3c2S(=O)CC3)CCC1=O] | H | | | | 92 |
| 253 | 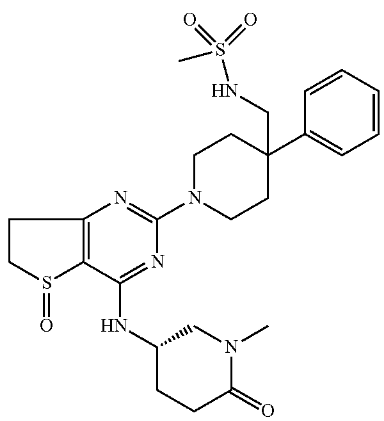 [SMILES: CN1C[C@@H](Nc2nc(N3CCC(CNS(C)(=O)=O)(c4ccccc4)CC3)nc3c2S(=O)CC3)CCC1=O] | H | | | | 92 |

TABLE C-continued

Chemical structures of the Example substances 164-332

| Ex. | Structure | R[1] | R[2] | R[3] | R[4] | % Inhibition PDE4B @ 1 µM |
|---|---|---|---|---|---|---|
| 254 | 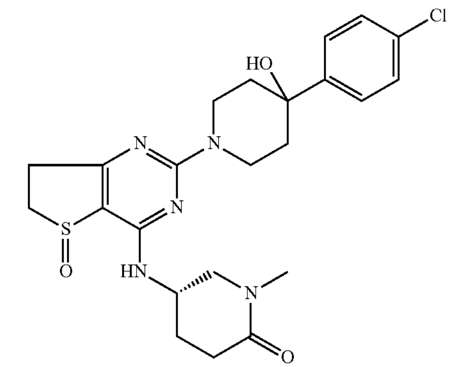 | H | N-methyl-6-oxopiperidin-3-yl (*) | 4-chlorophenyl (*) | OH | 92 |
| 255 | 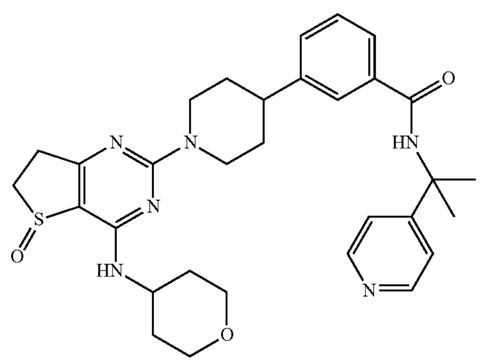 | H | tetrahydro-2H-pyran-4-yl (*) | 3-[(2-(pyridin-4-yl)propan-2-yl)carbamoyl]phenyl (*) | H | 93 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 256 | 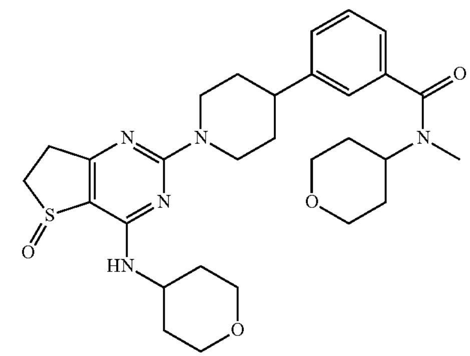 | H | tetrahydropyran-4-yl | 3-(N-methyl-N-(tetrahydropyran-4-yl)carbamoyl)phenyl | H | 91 |
| 257 | 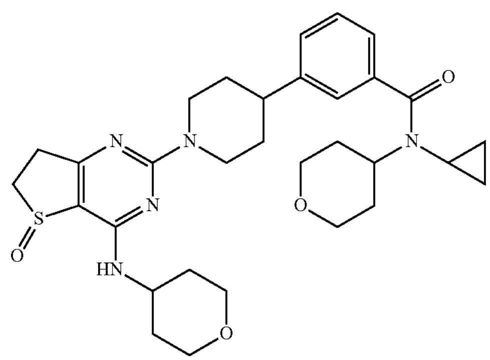 | H | tetrahydropyran-4-yl | 3-(N-cyclopropyl-N-(tetrahydropyran-4-yl)carbamoyl)phenyl | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 258 | 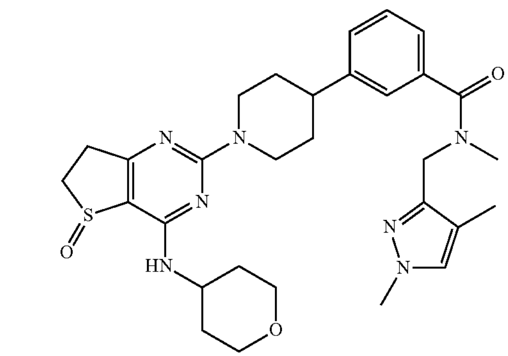 | H | *-tetrahydropyran-4-yl | 3-(N-methyl-N-((1,4-dimethylpyrazol-3-yl)methyl)carbamoyl)phenyl | H | 93 |
| 259 | 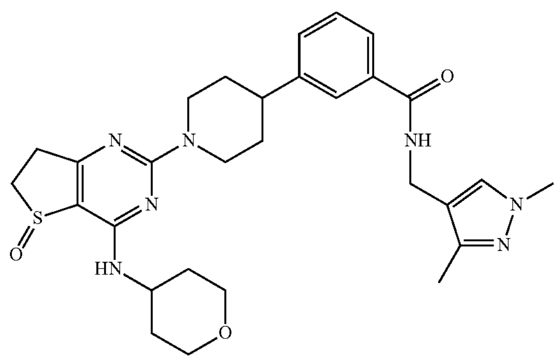 | H | *-tetrahydropyran-4-yl | 3-(N-((1,3-dimethylpyrazol-4-yl)methyl)carbamoyl)phenyl | H | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 260 | 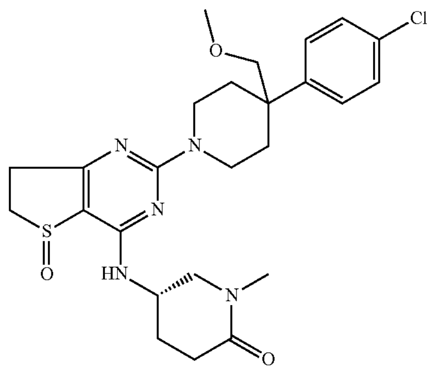 [SMILES: COCC1(c2ccc(Cl)cc2)CCN(c2nc3c(c(N[C@H]4CCC(=O)N(C)C4)n2)S(=O)CC3)CC1] | H | N-methyl-piperidinone (via *) | 4-Cl-phenyl | CH₂OCH₃ | 96 |
| 261 | 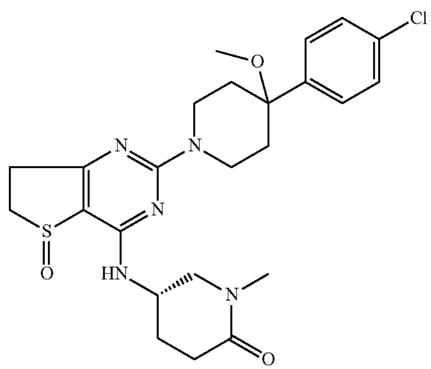 | H | N-methyl-piperidinone (via *) | 4-Cl-phenyl | OCH₃ | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 262 | 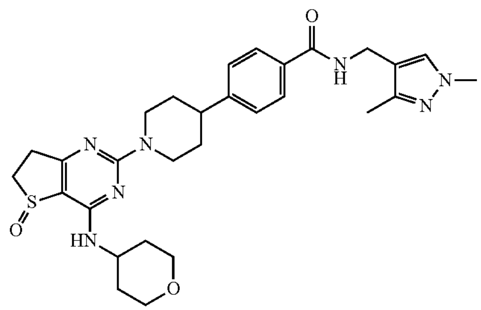 | H | tetrahydropyran-4-yl | 4-(N-((1,3-dimethylpyrazol-4-yl)methyl)carbamoyl)phenyl | H | 94 |
| 263 | 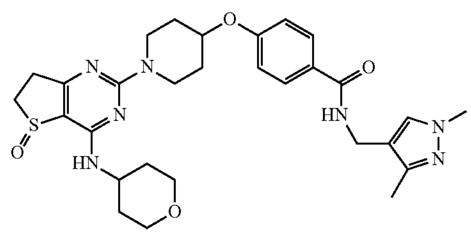 | H | tetrahydropyran-4-yl | 4-(N-((1,3-dimethylpyrazol-4-yl)methyl)carbamoyl)phenoxy | H | 94 |
| 264 | 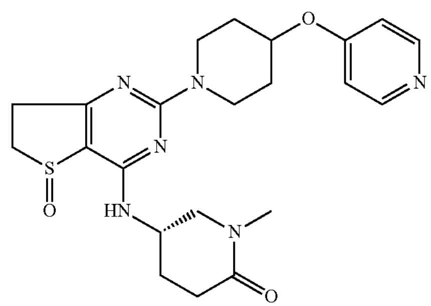 | H | 1-methyl-6-oxopiperidin-3-yl | pyridin-4-yloxy | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 265 | 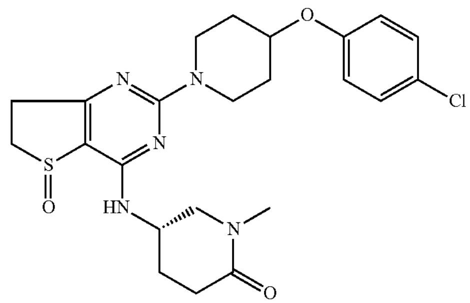 | H | | | H | 89 |
| 266 | 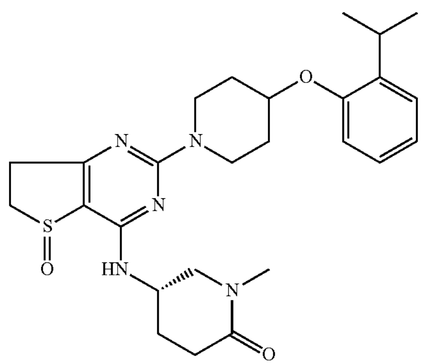 | H | | | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 267 | 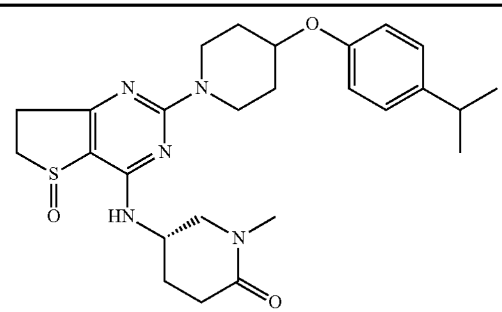 | H | (N-methyl-piperidinone, *-linked) | 4-isopropylphenoxy | H | 78 |
| 268 | 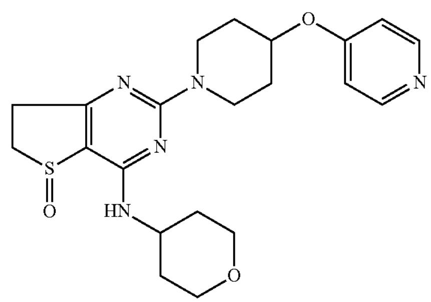 | H | tetrahydropyran-4-yl | pyridin-4-yloxy | H | 80 |
| 269 | 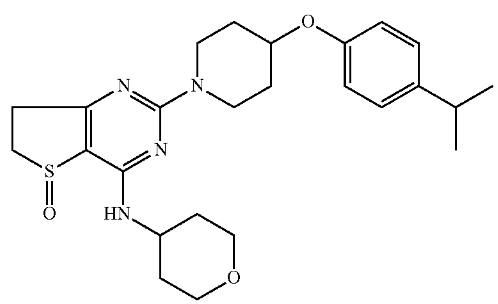 | H | tetrahydropyran-4-yl | 4-isopropylphenoxy | H | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 270 | 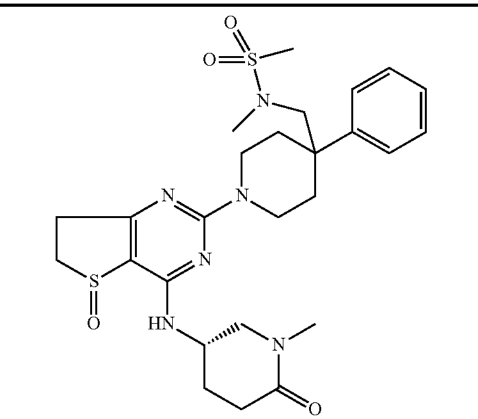 | H | 1-methyl-6-oxopiperidin-3-yl | phenyl | (N-methylmethanesulfonamido)methyl | 95 |
| 271 | 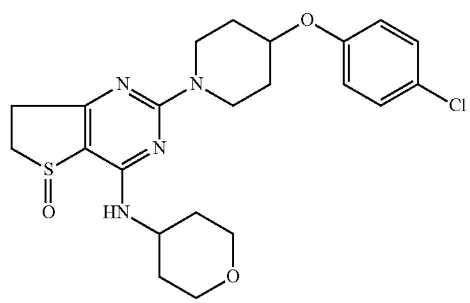 | H | tetrahydropyran-4-yl | 4-chlorophenoxy | H | 92 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 272 | 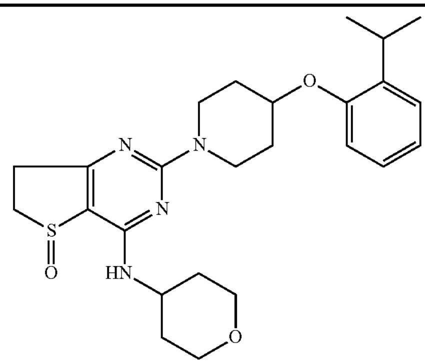 | H | tetrahydropyran-4-yl (*) | 2-isopropylphenoxy (*) | H | 95 |
| 273 | 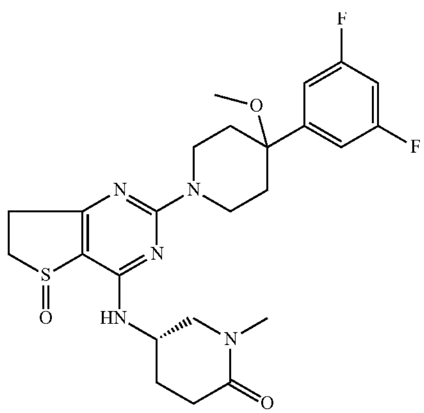 | H | 1-methyl-6-oxopiperidin-3-yl (*) | 3,5-difluorophenyl (*) | OCH₃ | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 274 | 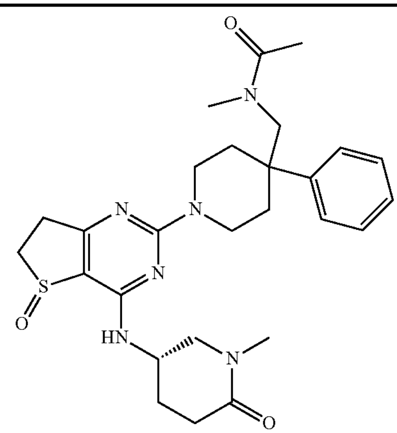 | H | N-methyl-piperidinone (*5-position) | phenyl (*) | N-methyl-N-acetyl-aminomethyl (*) | 94 |
| 275 | 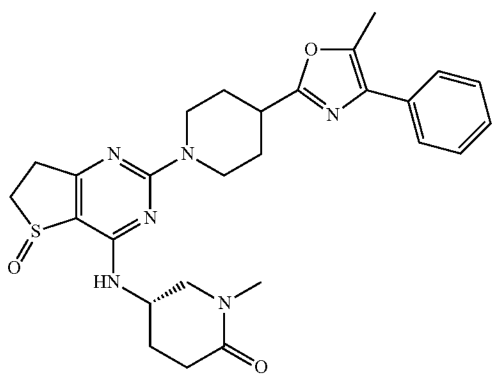 | H | N-methyl-piperidinone (*5-position) | 5-methyl-4-phenyl-oxazol-2-yl (*) | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 276 | 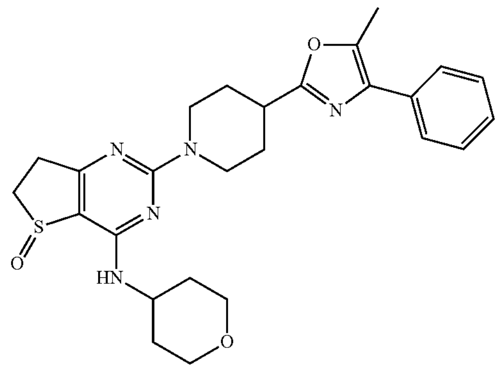 | H | tetrahydropyran-4-yl | 5-methyl-4-phenyloxazol-2-yl | H | 95 |
| 277 | 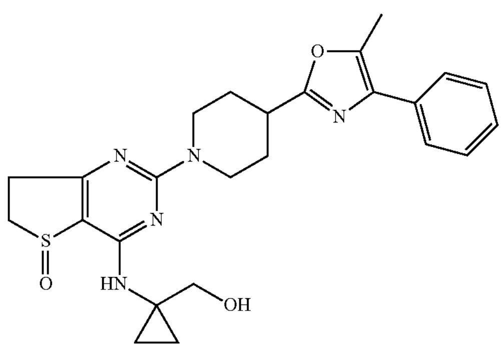 | H | (1-hydroxymethyl)cyclopropyl | 5-methyl-4-phenyloxazol-2-yl | H | 96 |

TABLE C-continued
Chemical structures of the Example substances 164-332
| Ex. | Structure | R¹ | R² | R³ | R⁴ | % Inhibition PDE4B @ 1 µM |
|---|---|---|---|---|---|---|
| 278 | 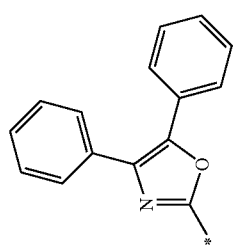 | H | 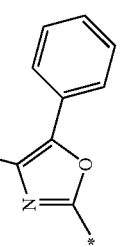 | 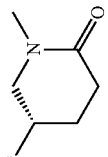 | H | 95 |
| 279 | 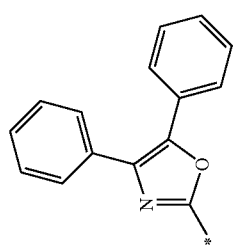 | H | 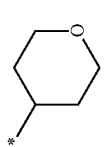 | 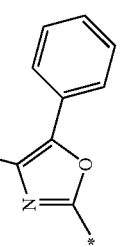 | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 280 | (structure with 4,5-diphenyloxazol-2-yl piperidine linked to pyrimidine-thiophene sulfoxide with hydroxymethyl-cyclopropyl-amino) | H | *-C(cyclopropyl)-CH₂OH | 4,5-diphenyloxazol-2-yl | H | 95 |
| 281 | (structure with 4-chlorophenyl/hydroxymethyl piperidine linked to pyrimidine-thiophene sulfoxide with tetrahydropyran-4-yl-amino) | H | tetrahydropyran-4-yl | 4-chlorophenyl | CH₂OH | 87 |

TABLE C-continued
Chemical structures of the Example substances 164-332
| Ex. | Structure | R¹ | R² | R³ | R⁴ | % Inhibition PDE4B @ 1 µM |
|---|---|---|---|---|---|---|
| 282 | 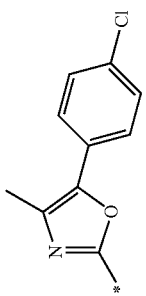 | H | tetrahydropyran-4-yl | 5-(4-chlorophenyl)-4-methyloxazol-2-yl | H | 87 |
| 283 | 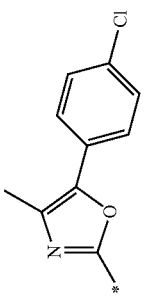 | H | 1-(hydroxymethyl)cyclopropyl | 5-(4-chlorophenyl)-4-methyloxazol-2-yl | H | 89 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 284 | 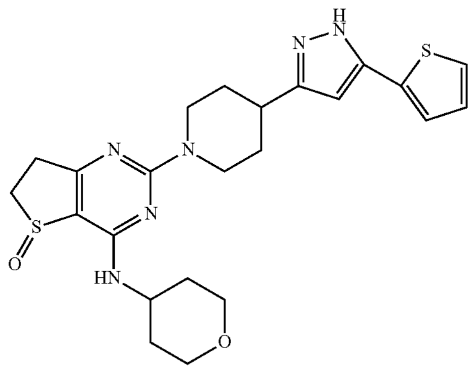 | H | tetrahydropyran-4-yl | 5-(thiophen-2-yl)-1H-pyrazol-3-yl | H | 83 |
| 285 | 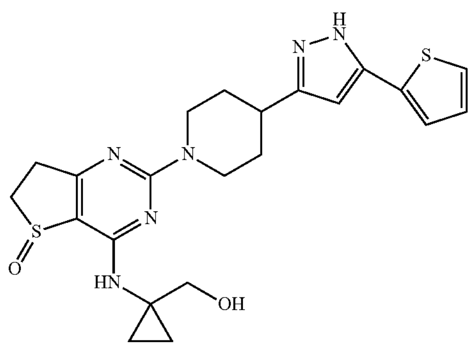 | H | (1-(hydroxymethyl)cyclopropyl) | 5-(thiophen-2-yl)-1H-pyrazol-3-yl | H | 90 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 286 | 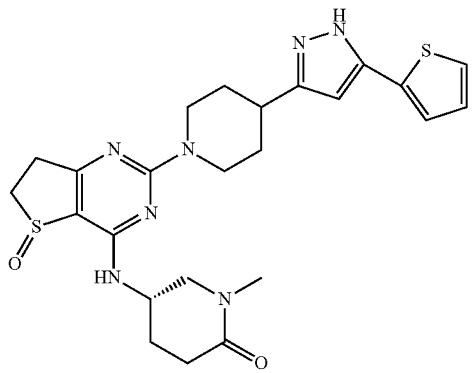 | H | N-methyl-2-oxopiperidin-5-yl | 5-(thiophen-2-yl)-1H-pyrazol-3-yl | H | 89 |
| 287 | 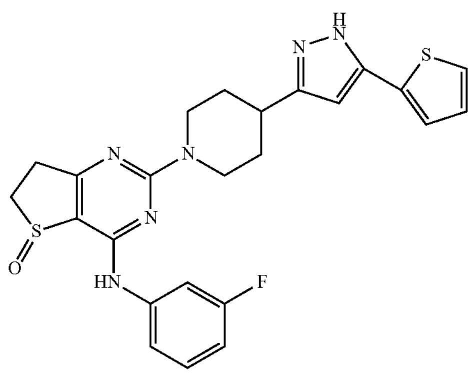 | H | 3-fluorophenyl | 5-(thiophen-2-yl)-1H-pyrazol-3-yl | H | 89 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 288 | (structure) | H | *-tetrahydropyran-4-yl | 4-Cl-phenyl* | OH | 89 |
| 289 | (structure) | H | *-1-(hydroxymethyl)cyclopropyl | 4-Cl-phenyl* | OH | 81 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 290 | (4-chlorophenyl, 4-hydroxypiperidine linked to pyrimidine-thiophene S-oxide with 3-fluoroanilino) | H | * —(3-F-phenyl) | * —(4-Cl-phenyl) | H | 86 |
| 291 | (4-chlorophenyl, 4-hydroxymethylpiperidine linked to pyrimidine-thiophene S-oxide with 3-fluoroanilino) | H | * —(3-F-phenyl) | * —(4-Cl-phenyl) | HOCH₂—* | 89 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 292 | 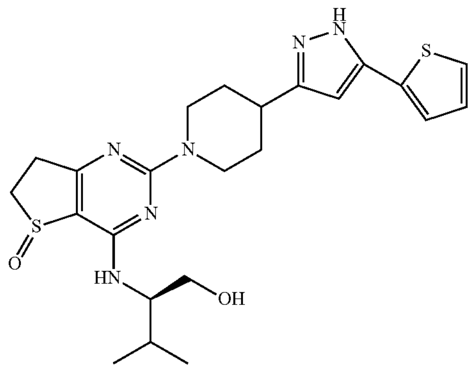 | H | (S)-CH(iPr)CH₂OH | 3-(thiophen-2-yl)-1H-pyrazol-5-yl | H | 83 |
| 293 | 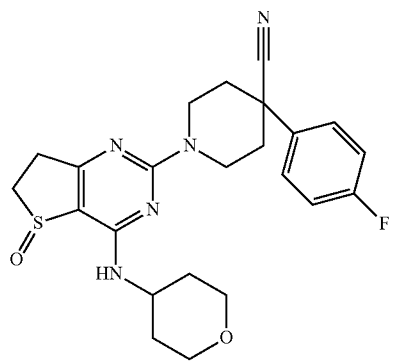 | H | tetrahydro-2H-pyran-4-yl | 4-fluorophenyl | CN | 86 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 294 | 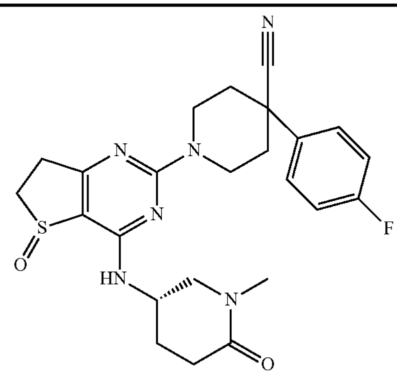 | H | *N-methyl-piperidinone (via 5-position) | 4-F-phenyl | CN | 88 |
| 295 | 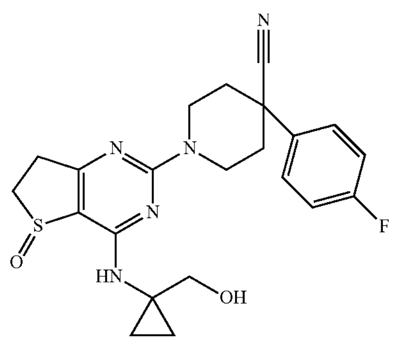 | H | 1-(hydroxymethyl)cyclopropyl | 4-F-phenyl | CN | 93 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 296 | 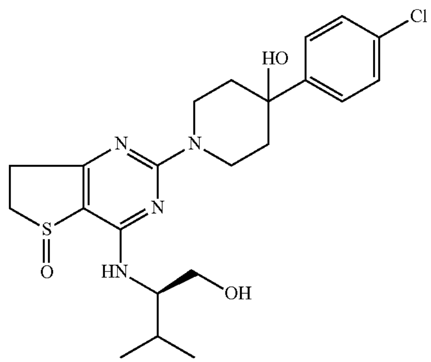 | H | *-CH(iPr)CH₂OH (S) | 4-Cl-C₆H₄- | OH | 81 |
| 297 | 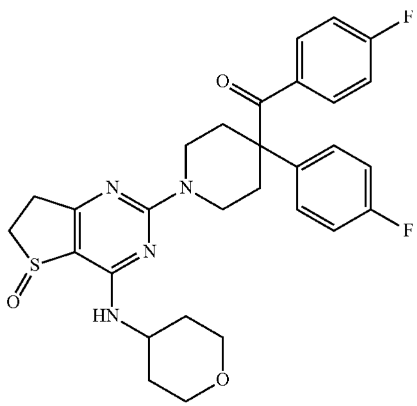 [SMILES: O=C(c1ccc(F)cc1)C1(c2ccc(F)cc2)CCN(c2nc3c(c(NC4CCOCC4)n2)S(=O)CC3)CC1] | H | 4-tetrahydropyranyl | 4-F-C₆H₄- | 4-F-C₆H₄-C(O)- | 73 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 298 | (structure) | H | *CH(iPr)CH2OH | 4-F-C6H4- | 4-F-C6H4-C(O)-* | 91 |
| 299 | (structure) | H | 3-F-C6H4-* | 4-F-C6H4- | 4-F-C6H4-C(O)-* | 90 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 300 | (structure) | H | *-CH(iPr)-CH₂OH | *-C₆H₄-Cl (4-Cl phenyl) | *-CH₂OH | 86 |
| 301 | (structure) | H | *-C(cyclopropyl)-CH₂OH | *-C₆H₄-Cl (4-Cl phenyl) | *-CH₂OH | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 302 | 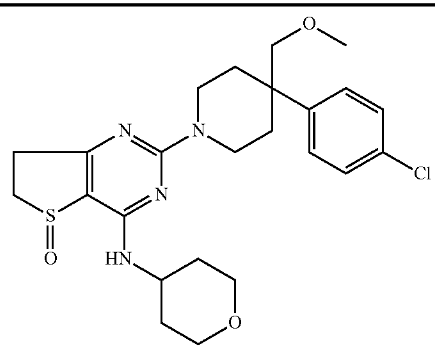 | H | tetrahydropyran-4-yl | 4-chlorophenyl | methoxymethyl | 91 |
| 303 | 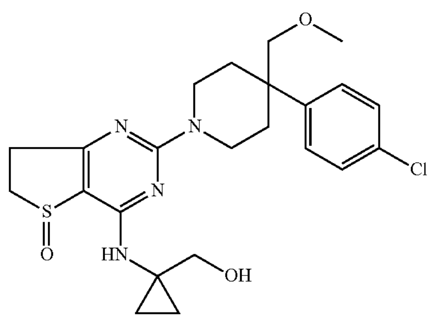 [SMILES: COCC1(c2ccc(Cl)cc2)CCN(c2nc3c(c(NC4(CO)CC4)n2)S(=O)CC3)CC1] | H | 1-(hydroxymethyl)cyclopropyl | 4-chlorophenyl | methoxymethyl | 89 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 304 | 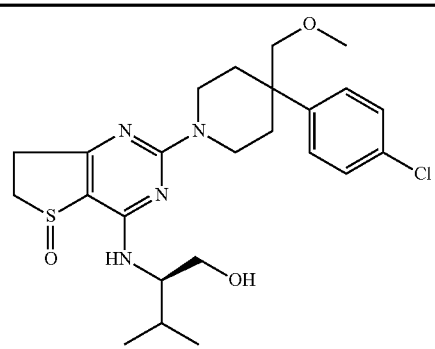 | H | *CH(iPr)CH2OH | 4-Cl-C6H4-* | *CH2OCH3 | 89 |
| 305 | 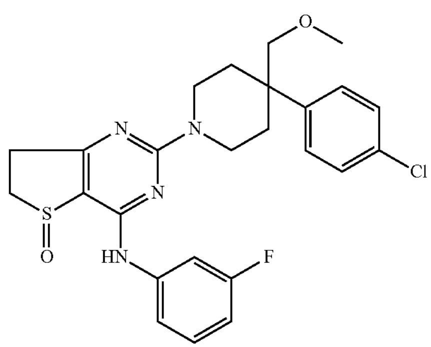 [SMILES: COCC1(c2ccc(Cl)cc2)CCN(c2nc3c(c(Nc4cccc(F)c4)n2)S(=O)CC3)CC1] | H | 3-F-C6H4-* | 4-Cl-C6H4-* | *CH2OCH3 | 91 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 306 | 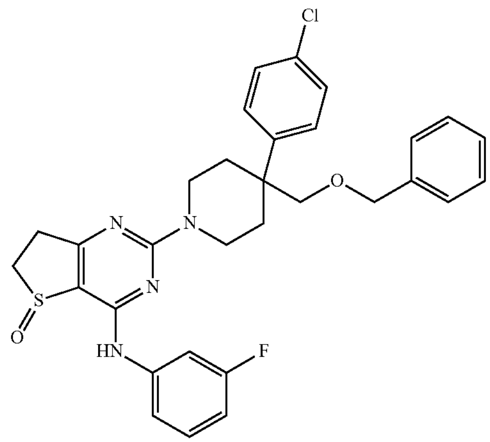 [SMILES: O=S1CCc2nc(N3CCC(COCc4ccccc4)(c4ccc(Cl)cc4)CC3)nc(Nc3cccc(F)c3)c21] | H | 3-fluorophenyl | 4-chlorophenyl | benzyloxymethyl | 89 |
| 307 | 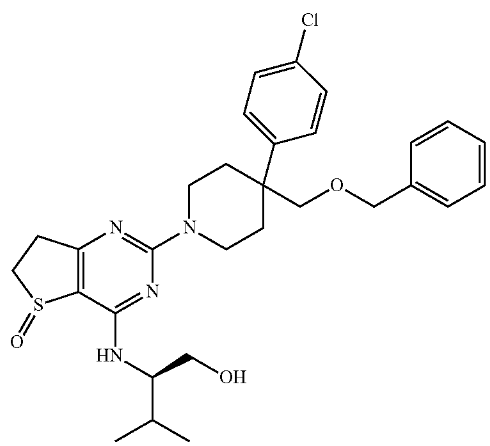 [SMILES: CC(C)[C@H](CO)Nc1nc(N2CCC(COCc3ccccc3)(c3ccc(Cl)cc3)CC2)nc2c1S(=O)CC2] | H | (S)-2-methyl-1-hydroxybut-3-yl | 4-chlorophenyl | benzyloxymethyl | 89 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 308 | 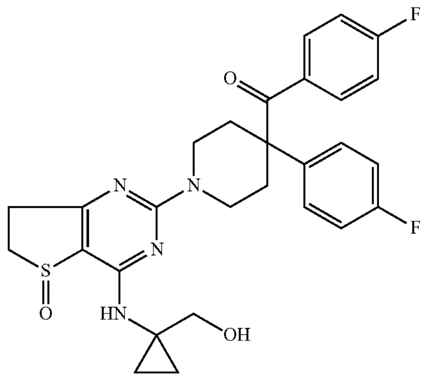 [SMILES: O=C(c1ccc(F)cc1)C1(c2ccc(F)cc2)CCN(c2nc3c(c(NC4(CO)CC4)n2)S(=O)CC3)CC1] | H | *-C(cyclopropyl)(CH₂OH) | 4-F-phenyl-* | 4-F-phenyl-C(=O)-* | 89 |
| 309 | 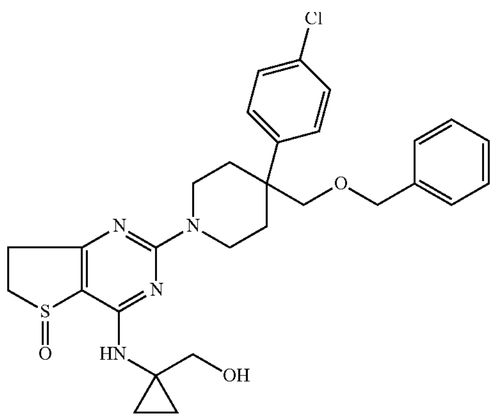 [SMILES: O=S1CCc2nc(N3CCC(COCc4ccccc4)(c4ccc(Cl)cc4)CC3)nc(NC3(CO)CC3)c21] | H | *-C(cyclopropyl)(CH₂OH) | 4-Cl-phenyl-* | PhCH₂-O-CH₂-* | 92 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 310 | (structure with 4-chlorophenyl, benzyloxymethyl piperidine, thienopyrimidine S-oxide, tetrahydropyran-4-ylamine) | H | 4-tetrahydropyranyl | 4-chlorophenyl | benzyloxymethyl | 92 |
| 311 | (structure with 3-phenyl-1,2,4-oxadiazole, piperidine, thienopyrimidine S-oxide, hydroxymethylcyclopropyl amine) | H | 1-(hydroxymethyl)cyclopropyl | 5-(3-phenyl-1,2,4-oxadiazolyl) | H | 91 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 312 | 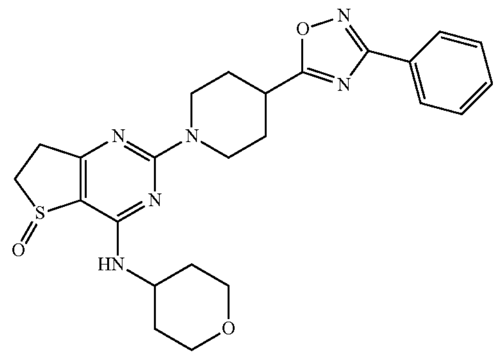 | H | tetrahydropyran-4-yl | 3-phenyl-1,2,4-oxadiazol-5-yl | H | 92 |
| 313 | 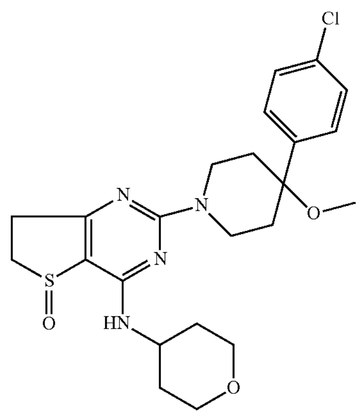 | H | tetrahydropyran-4-yl | 4-chlorophenyl | OCH₃ | 89 |

TABLE C-continued
Chemical structures of the Example substances 164-332
| Ex. | Structure | R¹ | R² | R³ | R⁴ | % Inhibition PDE4B @ 1 μM |
|---|---|---|---|---|---|---|
| 314 | 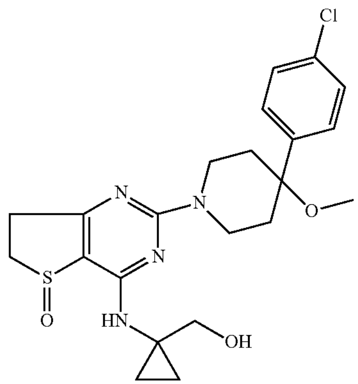 | H |  | 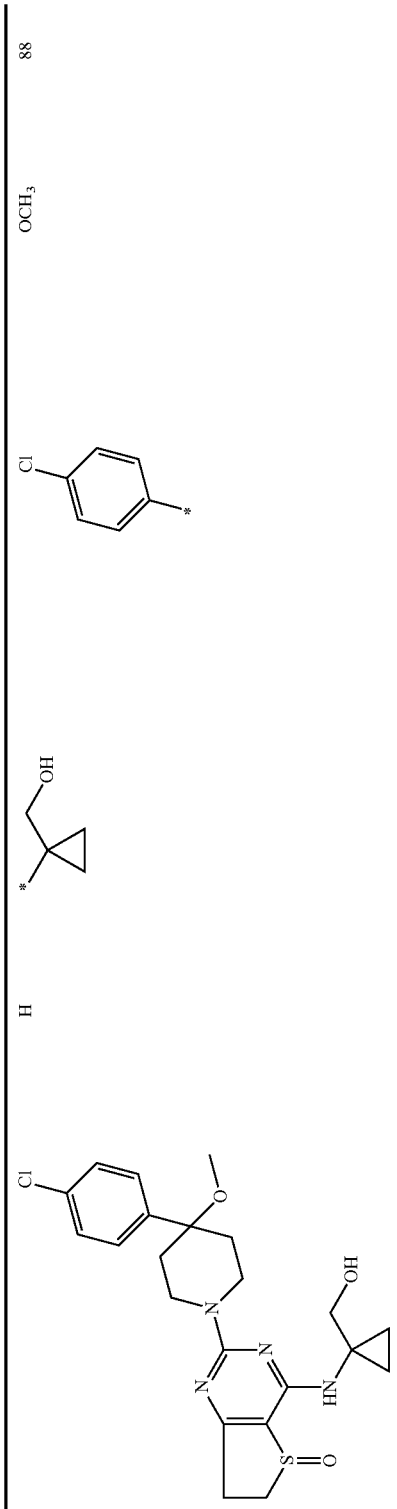 | OCH₃ | 88 |
| 315 | 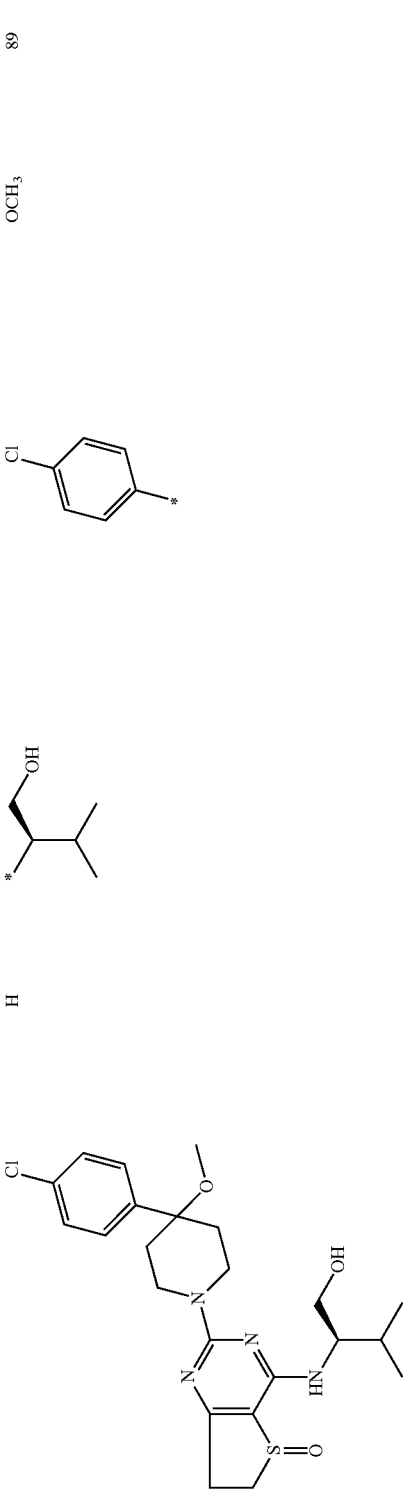 | H | 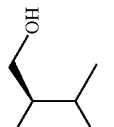 | 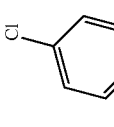 | OCH₃ | 89 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 316 | 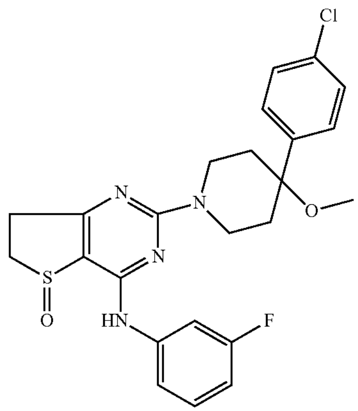 | H | 3-fluorophenyl | 4-chlorophenyl | OCH₃ | 92 |
| 317 | 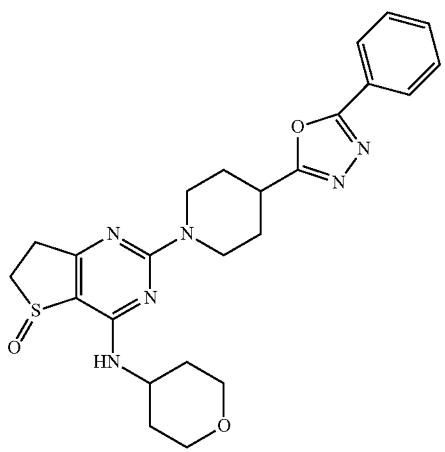 | H | tetrahydropyran-4-yl | 5-phenyl-1,3,4-oxadiazol-2-yl | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 318 | 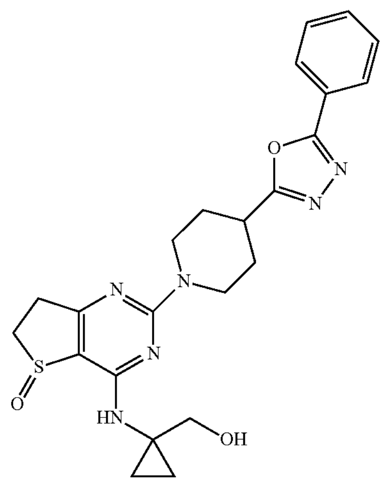 | H | cyclopropyl-CH₂OH (via *) | 2-phenyl-1,3,4-oxadiazol-5-yl | H | 91 |
| 319 | 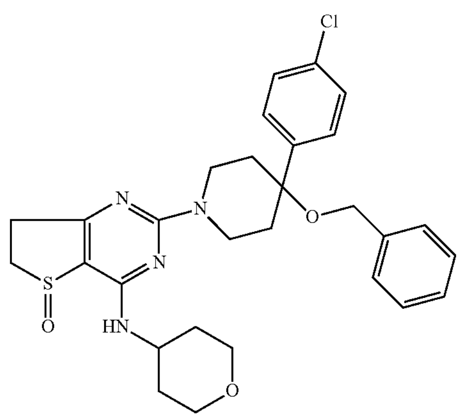 [SMILES: O=S1CCc2nc(N3CCC(OCc4ccccc4)(c4ccc(Cl)cc4)CC3)nc(NC3CCOCC3)c21] | H | tetrahydro-2H-pyran-4-yl | 4-chlorophenyl | benzyloxy (*O-CH₂-Ph) | 91 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 320 | 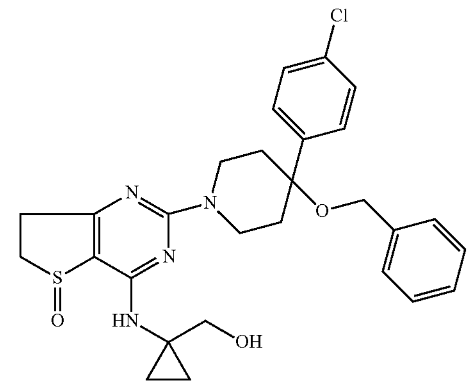 [SMILES: O=S1CCc2nc(N3CCC(OCc4ccccc4)(c4ccc(Cl)cc4)CC3)nc(NC3(CO)CC3)c21] | H | *−C(cyclopropyl)(CH₂OH) | 4-Cl-C₆H₄−* | *−O−CH₂−C₆H₅ | 92 |
| 321 | 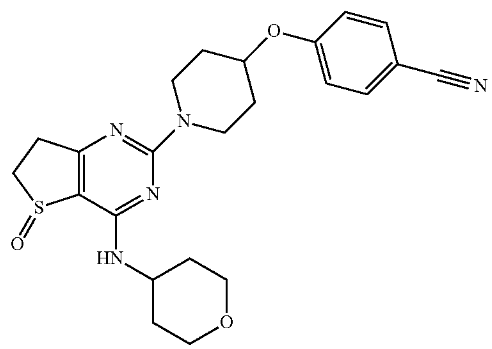 | H | *−(tetrahydropyran-4-yl) | 4-CN-C₆H₄−O−* | H | 93 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 322 | 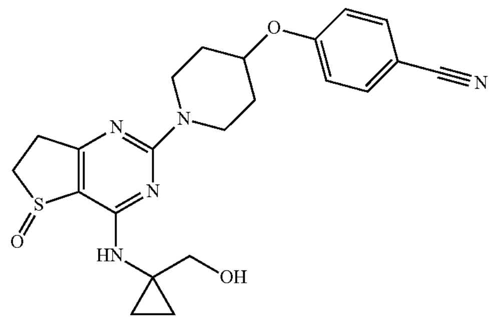 | H | (1-(hydroxymethyl)cyclopropyl) | 4-methoxyphenyl with CN | H | 91 |
| 323 | 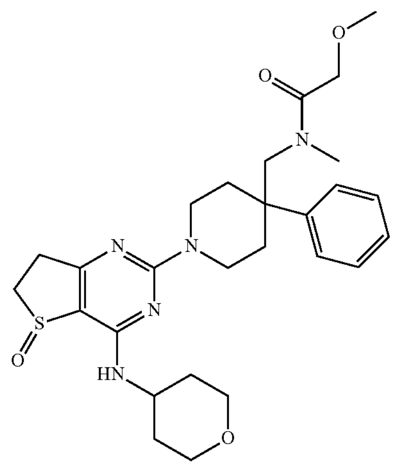 [SMILES: COCC(=O)N(C)CC1(c2ccccc2)CCN(c2nc3c(c(NC4CCOCC4)n2)S(=O)CC3)CC1] | H | tetrahydropyran-4-yl | phenyl | N-methyl-N-(methoxyacetyl)aminomethyl | 94 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 324 | 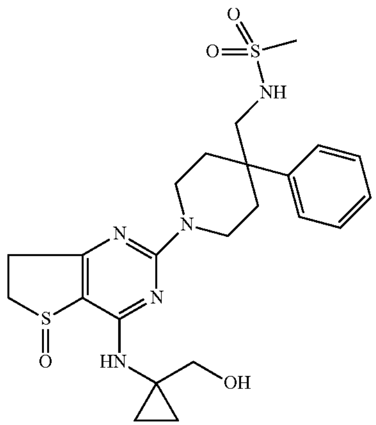 [SMILES: CS(=O)(=O)NCC1(c2ccccc2)CCN(c2nc3c(c(NC4(CO)CC4)n2)S(=O)CC3)CC1] | H | hydroxymethyl-cyclopropyl | phenyl | methanesulfonamidomethyl | 89 |
| 325 | 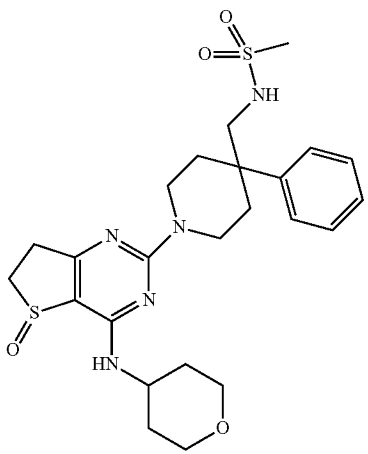 [SMILES: CS(=O)(=O)NCC1(c2ccccc2)CCN(c2nc3c(c(NC4CCOCC4)n2)S(=O)CC3)CC1] | H | tetrahydropyran-4-yl | phenyl | methanesulfonamidomethyl | 87 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 326 | 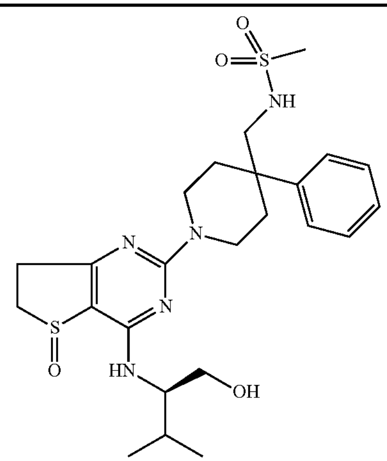 | H | *-CH(iPr)-CH₂OH | phenyl | -CH₂-NH-S(O)₂-CH₃ | 88 |
| 327 | 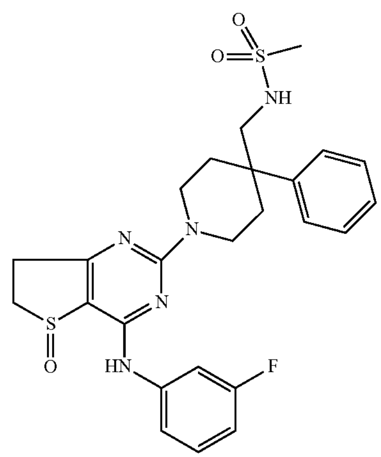 [SMILES: CS(=O)(=O)NCC1(c2ccccc2)CCN(c2nc3c(c(Nc4cccc(F)c4)n2)S(=O)CC3)CC1] | H | 3-fluorophenyl | phenyl | -CH₂-NH-S(O)₂-CH₃ | 83 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 328 | (structure) | H | cyclopropyl-CH₂OH | 4,5,6,7-tetrahydrobenzoxazol-2-yl | H | 93 |
| 329 | (structure) | H | tetrahydropyran-4-yl | 4,5,6,7-tetrahydrobenzoxazol-2-yl | H | 95 |

TABLE C-continued

Chemical structures of the Example substances 164-332

| Ex. | Structure | R¹ | R² | R³ | R⁴ | % Inhibition PDE4B @ 1 μM |
|---|---|---|---|---|---|---|
| 330 | 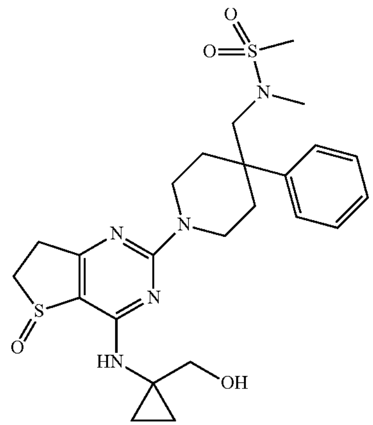 [SMILES: CN(CC1(c2ccccc2)CCN(c2nc3c(c(NC4(CO)CC4)n2)S(=O)CC3)CC1)S(C)(=O)=O] | H | hydroxymethyl-cyclopropyl* | phenyl* | methanesulfonyl-N-methyl-ethyl* | 92 |
| 331 | 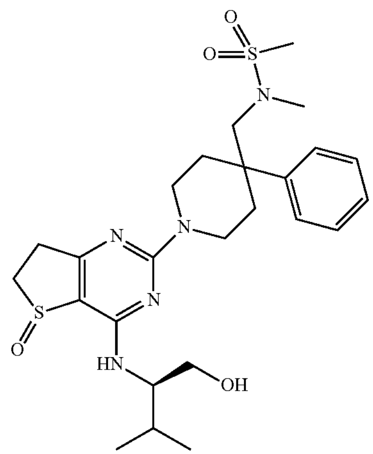 [SMILES: CC(C)[C@H](CO)Nc1nc(N2CCC(CN(C)S(C)(=O)=O)(c3ccccc3)CC2)nc2c1S(=O)CC2] | H | (S)-1-hydroxy-3-methylbutan-2-yl* | phenyl* | methanesulfonyl-N-methyl-ethyl* | 85 |

TABLE C-continued

Chemical structures of the Example substances 164-332

| Ex. | Structure | R¹ | R² | R³ | R⁴ | % Inhibition PDE4B @ 1 µM |
|---|---|---|---|---|---|---|
| 332 | (structure) | H | 3-F-phenyl | phenyl | CH₂N(CH₃)S(O)₂CH₃ | 93 |

1) This Example is diastereomeric to Example 245 (see experim. Section).
2) This Example is diastereomeric to Example 232 (see experim. Section)

Table D that follows gives detailed information on the chemical syntheses and the analysis of the individual Example substances 164-332.

TABLE D

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 164 | 89 | | | 1.13 method A |
| 165 | 73 | | | 1.39 method A |
| 166 | 90 | | | 1.20 method A |
| 167 | 89 | | | 1.16 method A |
| 168 | 14 | | | 1.17 method A |
| 169 | 100 | | | 1.15 method A |
| 170 | 90 | | | 0.94 method A |
| 172 | 90 | | | 1.15 method A |
| 173 | 90 | | | 0.97 method A |
| 174 | 90 | | | 1.15 method A |
| 175 | 90 | | | 1.21 method A |
| 176 | 90 | (structure: 4-(piperidin-4-yloxy)benzoic acid methyl ester) | J. Med. Chem. 2002, 3406 | 1.17 method A |
| 177 | 90 | | | 1.18 method A |
| 178 | see experim. Section | | | 1.01 method A |
| 179 | 90 | | | 1.22 method A |
| 180 | see experim. Section | | | 0.99 method A |
| 181 | 90 | | | 1.30 method A |
| 182 | see experim. Section | | | 1.27 method A |
| 183 | see experim. Section | | | 0.99 method A |
| 184 | see experim. Section | | | 1.19 method B |
| 185 | see experim. Section | | | 1.37 method B |
| 186 | see experim. Section | | | 1.10 method B |
| 187 | 100 | | | 1.33 method B |
| 188 | 100 | | | 1.03 method B |
| 189 | 100 | | | 1.18 method B |
| 190 | 100 | | | 1.14 method B |
| 191 | 90 | | | 1.18 method B |
| 192 | see experim. Section | | | 1.16 method B |
| 193 | 90 | (structure: 3-(piperidin-4-yl)-1-methyl-1H-indole) | WO2004/006922 | 1.23 method B |
| 194 | see experim. Section | | | 1.27 method B |
| 195 | see experim. Section | | | 1.21 method B |
| 196 | 100 | (structure: 4-(piperidin-4-yl)pyridine N-oxide) | WO03051868 | 0.96 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 197 | see experim. Section | | | 1.26 method B |
| 198 | see experim. Section | | | 1.21 method B |
| 199 | 100 | [structure: 4-(piperidin-4-yloxy)phenyl oxazoline] | (V-4) (see experim. Section, 37.3) | 1.07 method B |
| 200 | see experim. Section | | | 1.26 method B |
| 201 | see experim. Section | | | 1.36 method B |
| 202 | see experim. Section | | | 1.16 method B |
| 203 | see experim. Section | | | 1.38 method B |
| 204 | see experim. Section | | | 1.11 method B |
| 205 | see experim. Section | | | 1.23 method B |
| 206 | see experim. Section | | | 1.08 method B |
| 207 | 90 | | | 0.83 method D |
| 208 | 90 | [structure: 2-(piperidin-4-yl)-imidazo-purine] | Bioorg. Med. Chem. Lett. 2004, 695 | method D 0.76 |
| 209 | 90 | | | 0.95 method D |
| 210 | see experim. Section | | | 0.86 method D |
| 211 | see experim. Section | | | 1.45 method B |
| 212 | 90 | | | 0.99 method D |
| 213 | 90 | | | 1.00 method B |
| 214 | see experim. Section | | | 1.10 method D |
| 215 | 90 | [structure: piperidinyloxy-benzazepine with isobutyryl group] | Prepared analogously to (V-18) (see experim. Section 57.3)* | 1.11 method D |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 216 | 89 | (structure) | (V-12) (see experim. Section 50.2) | 1.20 method B |
| 217 | 90 | (structure) | (V-12) (see experim. Section 50.2) | 1.21 method B |
| 218 | 90 | (structure) | Prepared analogously to (V-19) (see experim. Section 59.2)* | 1.17 method B |
| 219 | 100 | | | 1.18 method B |
| 220 | 89 | | | 1.19 method B |
| 221 | 90 | | | 1.22 method B |
| 222 | see experim. Section | | | 1.46 method B |
| 223 | 90 | (structure) | Prepared analogously to (V-19) (see experim. Section 59.2)* | 1.03 method D |
| 224 | 90 | (structure) | Prepared analogously to (V-19) (see experim. Section 59.2)* | 0.99 method D |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 225 | 90 | | Prepared analogously to (V-19) (see experim. Section 59.2)* | 1.06 method D |
| 226 | 90 | | Prepared analogously to (V-19) (see experim. Section 59.2)* | 0.98 method D |
| 227 | 90 | | Prepared analogously to (V-19) (see experim. Section 59.2)* | 0.98 method D |
| 228 | 90 | | Prepared analogously to (V-19) (see experim. Section 59.2)* | 0.96 method D |
| 229 | see experim. Section | | | 1.05 method D |
| 230 | 90 | | Prepared analogously to (V-19) (see experim. Section 59.2)* | 0.99 method D |
| 231 | see experim. Section | | | 1.48 method B |
| 232[1)] | see experim. Section | | | 2.73 method E |
| 233 | see experim. Section | | | 1.24 method B |
| 234 | 186 | | | 1.14 method D |
| 235 | 186 | | | 1.21 method D |
| 236 | 242 | | | 1.02 method D |
| 237 | 242 | | | 0.98 method D |
| 238 | 242 | | | 1.05 method D |
| 239 | 242 | | | 0.97 method D |
| 240 | 242 | | | 1.23 method B |
| 241 | 242 | | | 1.09 method B |
| 242 | see experim. Section | | | 1.03 method D |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 243 | 242 | | | 0.97 method D |
| 244 | 242 | | | 0.99 method D |
| 245[2)] | see experim. Section | | | 2.85 method E |
| 246 | see experim. Section | | | 1.21 method B |
| 247 | 90 | | | 1.00 method D |
| 248 | 90 | | | 0.99 method D |
| 249 | see experim. Section | | | 1.05 method D |
| 250 | 249 | | | 1.01 method D |
| 251 | 249 | | | 1.14 method D |
| 252 | see experim. Section | | | 1.18 method B |
| 253 | see experim. Section | | | 1.15 method B |
| 254 | 100 | | | 1.23 method B |
| 255 | 249 | | | 1.04 method D |
| 256 | 249 | | | 1.00 method D |
| 257 | 249 | | | 1.07 method D |
| 258 | 249 | | | 1.00 method D |
| 259 | 249 | | | 0.98 method D |
| 260 | see experim. Section | | | 1.30 method B |
| 261 | see experim. Section | | | 1.30 method B |
| 262 | 90 | (structure: 4-(piperidin-4-yl)-N-((1,3-dimethyl-1H-pyrazol-4-yl)methyl)benzamide) | Prepared analogously to (V-19) (see experim. Section 59.2)* | 1.15 method B |
| 263 | 242 | | | 1.15 method B |
| 264 | 100 | | | 0.94 method B |
| 265 | 100 | | | 1.32 method B |
| 266 | 100 | | | 1.39 method B |
| 267 | 100 | | | 1.39 method B |
| 268 | 90 | | | 0.99 method B |
| 269 | 90 | | | 1.45 method B |
| 270 | see experim. Section | | | 1.21 method B |
| 271 | 90 | | | 1.39 method B |
| 272 | 90 | | | 1.45 method B |
| 273 | see experim. Section | | | 1.23 method B |
| 274 | see experim. Section | | | 1.19 method D |
| 275 | see experim. Section | | | 1.08 method D |
| 276 | 90 | (structure: 4-(5-methyl-4-phenyloxazol-2-yl)piperidine) | (V-25) (see experim. Section 72.1) | 1.18 method D |
| 277 | 89 | (structure: 4-(5-methyl-4-phenyloxazol-2-yl)piperidine) | (V-25) (see experim. Section 72.1) | 1.33 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 278 | see experim. Section | | | 1.40 method B |
| 279 | 90 | 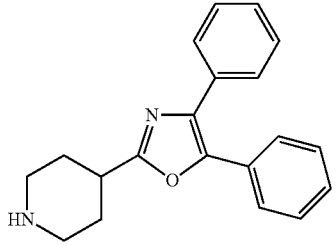 [SMILES: c1ccc(-c2nc(C3CCNCC3)oc2-c2ccccc2)cc1] | (V-26) (see experim. Section 73.2) | 1.50 method B |
| 280 | 89 | 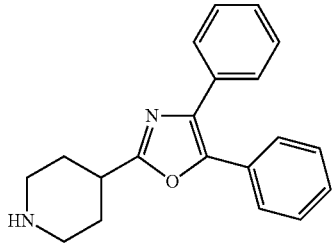 [SMILES: c1ccc(-c2nc(C3CCNCC3)oc2-c2ccccc2)cc1] | (V-26) (see experim. Section 73.2) | 1.43 method B |
| 281 | 90 | 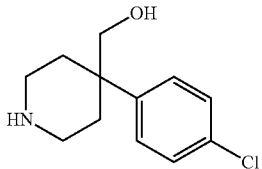 [SMILES: OCC1(c2ccc(Cl)cc2)CCNCC1] | J. Med. Chem. 2004, 497 | 1.24 method B |
| 282 | 90 | 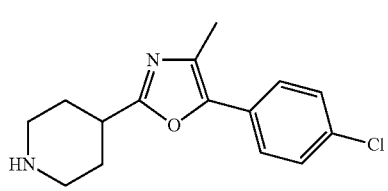 [SMILES: Cc1nc(C2CCNCC2)oc1-c1ccc(Cl)cc1] | (V-27) (see experim. Section 74.1) | 1.24 method B |
| 283 | see experim. Section | | | 1.37 method B |
| 284 | 90 | | | 1.23 method B |
| 285 | 89 | | | 1.0 method D |
| 286 | 100 | | | 1.19 method B |
| 287 | 73 | | | 1.17 method D |
| 288 | 90 | | | 1.25 method B |
| 289 | 89 | | | 1.23 method B |
| 290 | 73 | | | 1.42 method B |
| 291 | 73 | 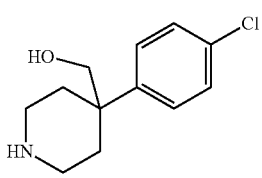 [SMILES: OCC1(c2ccc(Cl)cc2)CCNCC1] | J. Med. Chem. 2004, 497 | 1.41 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 292 | 14 | | | 1.03 method D |
| 293 | 90 | 4-(4-fluorophenyl)piperidine-4-carbonitrile | J. Med. Chem. 1999, 4778 | 1.11 method D |
| 294 | 100 | 4-(4-fluorophenyl)piperidine-4-carbonitrile | J. Med. Chem. 1999, 4778 | 1.03 method D |
| 295 | 89 | 4-(4-fluorophenyl)piperidine-4-carbonitrile | J. Med. Chem. 1999, 4778 | 1.08 method D |
| 296 | 14 | | | 1.27 method B |
| 297 | 90 | (4-fluorophenyl)(4-(4-fluorophenyl)piperidin-4-yl)methanone | (V-13) (see experim. Section 51.3) | 1.43 method B |
| 298 | 14 | (4-fluorophenyl)(4-(4-fluorophenyl)piperidin-4-yl)methanone | (V-13) (see experim. Section 51.3) | 1.45 method B |
| 299 | 73 | (4-fluorophenyl)(4-(4-fluorophenyl)piperidin-4-yl)methanone | (V-13) (see experim. Section 51.3) | 1.66 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 300 | 14 | | J. Med. Chem. 2004, 497 | 1.29 method B |
| 301 | 89 | | J. Med. Chem. 2004, 497 | 1.23 method B |
| 302 | 90 | | (V-20) (see experim. Section 67.3) | 1.48 method B |
| 303 | 89 | | (V-20) (see experim. Section 67.3) | 1.32 method B |
| 304 | 14 | | (V-20) (see experim. Section 67.3) | 1.37 method B |
| 305 | 73 | | (V-20) (see experim. Section 67.3) | 1.58 method B |
| 306 | see experim. Section | | | 1.75 method B |
| 307 | 14 | | (V-28) (see experim. Section 75.1) | 1.50 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 308 | 89 | 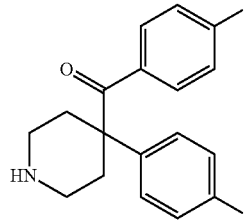 | (V-13) (see experim. Section 51.3) | 1.40 method B |
| 309 | 89 | 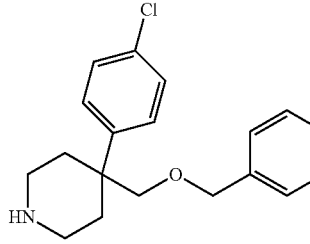 | (V-28) (see experim. Section 75.1) | 1.48 method B |
| 310 | 90 | 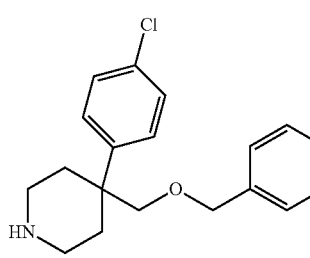 | (V-28) (see experim. Section 75.1) | 1.51 method B |
| 311 | 89 | | | 1.29 method B |
| 312 | 90 | | | 1.33 method B |
| 313 | 90 | 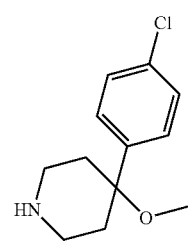 | (V-21) (see experim. Section 68.1) | 1.39 method B |
| 314 | 89 | 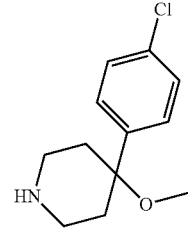 | (V-21) (see experim. Section 68.1) | 1.35 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 315 | 14 | 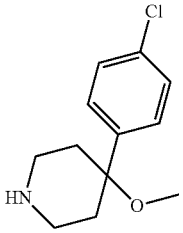 | (V-21) (see experim. Section 68.1) | 1.39 method B |
| 316 | 73 | 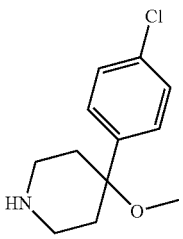 | (V-21) (see experim. Section 68.1) | 1.61 method B |
| 317 | 90 | | | 1.25 method B |
| 318 | 89 | | | 1.22 method B |
| 319 | 90 | 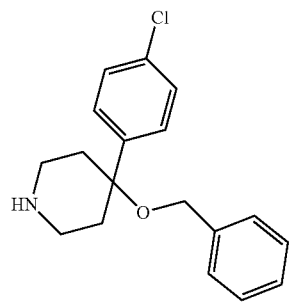 [SMILES: Clc1ccc(C2(OCc3ccccc3)CCNCC2)cc1] | (V-28) (see experim. Section 75.1) | 1.54 method B |
| 320 | 89 | 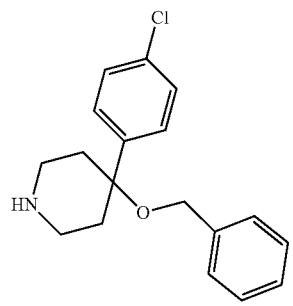 [SMILES: Clc1ccc(C2(OCc3ccccc3)CCNCC2)cc1] | (V-28) (see experim. Section 75.1) | 1.51 method B |
| 321 | 90 | 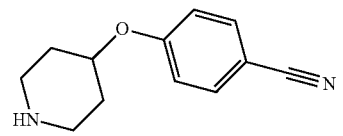 [SMILES: N#Cc1ccc(OC2CCNCC2)cc1] | WO2007/106705 | 1.29 method B |
| 322 | 89 | 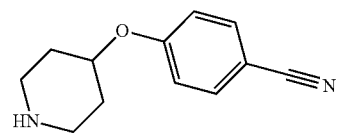 [SMILES: N#Cc1ccc(OC2CCNCC2)cc1] | WO2007/106705 | 1.24 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 323 | see experim. Section | | | 1.24 method B |
| 324 | 89 | *(structure)* | Bioorg. Med. Chem. Lett. 1998, 1851 | 1.21 method B |
| 325 | 90 | *(structure)* | Bioorg. Med. Chem. Lett. 1998, 1851 | 1.21 method B |
| 326 | 14 | *(structure)* | Bioorg. Med. Chem. Lett. 1998, 1851 | 1.24 method B |
| 327 | 73 | *(structure)* | Bioorg. Med. Chem. Lett. 1998, 1851 | 1.38 method B |
| 328 | 89 | *(structure)* | (V-30) (see experim. Section 77.2) | 1.23 method B |

TABLE D-continued

Detailed information on the preparation of the individual Example substances 164-332

| # | Prepared analogously to #* | non-commercial arylpiperidine component (V) | literature on the preparation of component (V) | analytical HPLC-MS, RT [min], method |
|---|---|---|---|---|
| 329 | see experim. Section | | | 1.23 method B |
| 330 | 89 | (structure: methanesulfonamide-CH₂-piperidine-phenyl) | (V-22) (see experim. Section 69.1) | 1.24 method B |
| 331 | 14 | (structure: methanesulfonamide-CH₂-piperidine-phenyl) | (V-22) (see experim. Section 69.1) | 1.30 method B |
| 332 | 73 | (structure: methanesulfonamide-CH₂-piperidine-phenyl) | (V-22) (see experim. Section 69.1) | 1.44 method B |

*the Example may be prepared and purified analogously.
[1] This Example is diastereomeric to Example 245 (see experim. Section).
[2] This Example is diastereomeric to Example 232 (see experim. Section)

TABLE E

Chemical structures and preparation of the Example substances 333-335

| # | Structure | R1 | R2 | R3 | R4 | preparation | analytical HPLC-MS, RT [min], method | % Inhibition PDE4B@1 µM |
|---|---|---|---|---|---|---|---|---|
| 333 | (thienopyrimidine S,S-dioxide structure with piperidine-phenyl-Cl and HN-CH₂-cyclopropyl-OH) | Cl | H | *⟨cyclopropyl⟩-CH₂OH | ⟨phenyl⟩-Cl | H | see experim. Section | 1.49 method B | 56 |

TABLE E-continued

Chemical structures and preparation of the Example substances 333-335

| # | Structure | R1 | R2 | R3 | R4 | preparation | analytical HPLC-MS, RT [min], method | % Inhibition PDE4B@1 μM |
|---|---|---|---|---|---|---|---|---|
| 334 | | Cl | H | * tetrahydropyran | Cl | H | see experim. Section | 1.55 method B | 65 |
| 335 | | Cl | H | * N-methyl piperidinone | Cl | H | see experim. Section | 1.48 method B | 85 |

Indications

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia as well as bone tumours such as e.g. osteosarcoma and all kinds of gliomas such as e.g. oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, MRP4-inhibitors, dopamine agonists, H1-antihistamines, PAF-antagonists and PI3-kinase inhibitors or double or triple combinations thereof, such as for example combinations of compounds of formula 1 with one or two compounds selected from among betamimetics, corticosteroids, PDE4-inhibitors, EGFR-inhibitors and LTD4-antagonists,
anticholinergics, betamimetics, corticosteroids, PDE4-inhibitors, EGFR-inhibitors and LTD4-antagonists,
PDE4-inhibitors, corticosteroids, EGFR-inhibitors and LTD4-antagonists
EGFR-inhibitors, PDE4-inhibitors and LTD4-antagonists
EGFR-inhibitors and LTD4-antagonists
CCR3-inhibitors, iNOS-inhibitors (inducible nitric oxide synthase-inhibitors), (6R)-L-erythro-5,6,7,8-tetrahydrobiopterin (hereinafter referred to as "BH4") and the derivatives thereof as mentioned in WO 2006/120176 and SYK-inhibitors (spleen tyrosine kinase inhibitors)
anticholinergics, betamimetics, corticosteroids, PDE4-inhibitors and MRP4-inhibitors.

The invention also relates to combinations of three active substances, each chosen from one of the above-mentioned categories of compounds.

Suitable betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5.6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1.4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid, 8-{2-[2-(3.4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers and optionally in the form of the pharmacologically acceptable acid addition salts, solvates or hydrates thereof.

Preferably the betamimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5.6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2- isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl-4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinoline-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers and optionally in the form of the pharmacologically acceptable acid addition salts, solvates or hydrates thereof.

Of these betamimetics the particularly preferred ones according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{(2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinoline-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, -cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl cyclopropyltropine 4,4'-difluorobenzil-ate methobromide, tropenol 9-hydroxy-xanthene-9-carboxylate-methobromide, -scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocort-propionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370, N-(3,5-dichloro-1-oxo-pyridin-4-yl)-4-difluoromethoxy-3-cyclopropyl-methoxybenzamide, (−)p-[(4aR*.10bS*)-9-ethoxy-1,2,3,4,4a,10b-hexahydro-8-methoxy-2-methylbenzo[s][1.6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, Cl-1018, CDC-801, D-22888, YM-58997, Z-15370, N-(3,5-dichloro-1-oxo-pyridin-4-yl)-4-difluoromethoxy-3-cyclopropylmethoxy-benzamide, cis [4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2.3-dichlorothieno[3,2-b]pyridin-5-yl)-(E)-ethenyl)phenyl)-3-(2-(1-hydroxy-1-methylethyl) phenyl)propyl)thio)methyl)cyclo-propane-acetic acid and [2-[[2-(4-tert-butyl-2-thiazolyl)-5-benzofuranyl]oxymethyl] phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl) amino]-6-{[4-(N,N-diethylamino)-1-oxo-2-buten-1-yl] amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl) oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl) amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl) methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d] pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)phenyl]amino}-6-(5-{[(2-methanesulphonyl-ethyl)amino] methyl}-furan-2-yl)quinazoline, 4-[(R)-(1-phenyl-ethyl) amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({-4-[N, N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl) methoxy]-quinazoline, 4-[(3-chloro-4-fluoro-phenyl) amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3- chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, cetuximab, trastuzumab, ABX-EGF and Mab ICR-62, optionally in the form of the racemates, enantiomers or diastereomers thereof, optionally in the form of the pharmacologically acceptable acid addition salts thereof, the solvates and/or hydrates thereof.

Preferred EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({-4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({-4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({-4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{((3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({-4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7- methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and cetuximab, optionally in the form of the racemates, enantiomers or diastereomers thereof, optionally in the form of the pharmacologically acceptable acid addition salts thereof, the solvates and/or hydrates thereof.

It is particularly preferable within the scope of the present invention to use those EGFR-inhibitors which are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxyquinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyl-dinitrophenyl-cysteine, dehydroepiandrosterone 3-sulphate, dilazep, dinitrophenyl-5-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the PDE4B-inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methylthiocitrullin, S-ethylthiocitrulline, L-NA (N$^\omega$-nitro-L-arginine), L-NAME (N$^\omega$-nitro-L-argininemethylester), L-NMMA (N$^G$-monomethyl-L-arginine), L-NIO (N$^\omega$-iminoethyl-L-ornithine), L-NIL (N$^\omega$-iminoethyl-lysine), (S)-6-acetimidoylamino-2-amino-hexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S.4R)-2-amino-4-(2-chloro-5-trifluoromethyl-phenylsulphanyl)-4-thiazol-5-yl-butan-1-01 (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. AR-C102222 (*J. Med. Chem.* 2003, 46, 913-916), (1S.5S.6R)-7-chloro-5-methyl-2-aza-bicyclo[4.1.0]hept-2-en-3-ylamine (ONO-1714) (*Biochem. Biophys. Res. Commun.* 2000, 270, 663-667), (4R, 5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[(benzo[1,3]dioxol-5-yl-methyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Compounds which may be used as SYK-inhibitors are preferably compounds selected from among:

2-[(2-aminoethyl)amino]-4-[(3-bromophenyl)amino]-5-pyrimidinecarboxamide;

2-[[7-(3,4-dimethoxyphenyl)imidazo[1,2-c]pyrimidin-5-yl]amino]-3-pyridinecarboxamide;

6-[[5-fluoro-2-[3,4,5-trimethoxyphenyl)amino]-4-pyrimidinyl]amino]-2,2-dimethyl-2H-pyrido[3,2-b]-1,4-oxazin-3 (4H)-one;
N-[3-bromo-7-(4-methoxyphenyl)-1,6-naphthyridin-5-yl]-1,3-propanediamine
7-(4-methoxyphenyl)-N-methyl-1,6-naphthyridin-5-amine;
N-[7-(4-methoxyphenyl)-1,6-naphthyridin-5-yl]-1,3-propanediamine;
N-[7-(2-thienyl)-1,6-naphthyridin-5-yl-1,3-propanediamine;
N-[7-[4-(dimethylamino)phenyl]-1,6-naphthyridin-5-yl]-1,2-ethanediamine;
N-[7-(4-methoxyphenyl)-2-(trifluoromethyl)-1,6-naphthyridin-5-yl]-1,3-propanediamine;
N-[7-(4-methoxyphenyl)-3-phenyl-1,6-naphthyridin-5-yl]-1,3-propanediamine;
N-(7-phenyl-1,6-naphthyridin-5-yl)-1,3-propanediamine;
N-[7-(3-fluorophenyl)-1,6-naphthyridin-5-yl]-1,3-propanediamine;
N-[7-(3-chlorophenyl)-1,6-naphthyridin-5-yl]-1,3-propanediamine;
N-[7-[3-(trifluoromethoxy)phenyl]-1,6-naphthyridin-5-yl]-1,3-propanediamine;
N-[7-(4-fluorophenyl)-1,6-naphthyridin-5-yl]-1,3-propanediamine;
N-[7-(4-fluorophenyl)-1,6-naphthyridin-5-yl]-1,3-propanediamine;
N-[7-(4-chlorophenyl)-1,6-naphthyridin-5-yl]-1,3-propanediamine;
N-[7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;
N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl]oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl]amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N'-methyl-1,3-propanediamine;
N-[7-[4-(dimethylamino)phenyl]-1,6-naphthyridin-5-yl]-N,N'-dimethyl-1,3-propanediamine;
1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine;
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;
N-[7-(3'-fluoro[1,1'-biphenyl]-3-yl)-1,6-naphthyridin-5-yl]-1,2-ethanediamine,
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridin-5-yl]-1,3-propanediamine;
N-[7-(2'-fluoro[1,1'-biphenyl]-4-yl)-1,6-naphthyridin-5-yl]-1,3-propanediamine;
N-[7-(3,4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;
1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1,1'-biphenyl]-4-yl)-1,6-naphthyridin-5-yl]amino]-2-propanol;
1-amino-3-[[7-(3,4,5-trimethoxyphenyl)-1,6-naphthyridin-5-yl]amino]-2-propanol;
1-amino-3-[[7-(4-bromophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]-benzenamine;
4-[5-(2-methoxyethoxy)-1,6-naphthyridin-7-yl]-N,N-dimethyl-benzenamine;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;

7-[4-(dimethylamino)phenyl]-N-[3-(1H-imidazol-1-yl)propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamide;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;
N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;
3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
N-[7-[4-(dimethylamino)phenyl]-1,6-naphthyridin-5-yl]-1,2-cyclohexanediamine, (1R.2S)-rel-.
N-[7-[4-(dimethylamino)phenyl]-1,6-naphthyridin-5-yl]-1,2-benzenedimethanamine;
N-[7-[4-(diethylamino)phenyl]-1,6-naphthyridin-5-yl]-1,4-butanediamine;
N-[7-[3'.5'-bis(trifluoromethyl)[1,1'-biphenyl]-4-yl]-1,6-naphthyridin-5-yl].3-propanediamine;
N-[7-(3'-methoxy[1,1'-biphenyl]-4-yl)-1,6-naphthyridin-5-yl]-1,3-propanediamine;
N-[7-(3'-fluoro[1,1'-biphenyl]-4-yl)-1,6-naphthyridin-5-yl]-1,3-propanediamine;
4-[[7-[4-(dimethylamino)phenyl]-1,6-naphthyridin-5-yl]oxy]-1-butanol;
N-[7-[4-(dimethylamino)phenyl]-1,6-naphthyridin-5-yl]-1,4-cyclohexanediamine;
7-[4-(dimethylamino)phenyl]-N-(2.2.6.6-tetramethyl-4-piperidinyl)-1,6-naphthyridin-5-amine;
N-[7-[3-bromo-4-(dimethylamino)phenyl]-1,6-naphthyridin-5-yl]-1,3-propanediamine;
N-[7-(1-methyl-1H-indol-5-yl)-1,6-naphthyridin-5-yl]-1,3-propanediamine;
N-[7-[3-(trifluoromethyl)phenyl]-1,6-naphthyridin-5-yl]-1,3-propanediamine;
N-[7-[4-(trifluoromethyl)phenyl]-1,6-naphthyridin-5-yl]-1,3-propanediamine;
N-[7-(3-bromo-4-methoxyphenyl)-1,6-naphthyridin-5-yl]-1,3-propanediamine;
N-[7-[4-[[3-(dimethylamino)propyl]methylamino]phenyl]-1,6-naphthyridin-5-yl]-1,4-cyclohexanediamine;
N-[7-[4-[[2-(dimethylamino)ethyl]methylamino]phenyl]-1,6-naphthyridin-5-yl]-1,4-cyclohexanediamine;
N-[7-[4-(dimethylamino)-3-methoxyphenyl]-1,6-naphthyridin-5-yl]-1,4-cyclohexanediamine;
N-[7-[4-(4-morpholinyl)phenyl]-1,6-naphthyridin-5-yl]-1,4-cyclohexanediamine;
N-[7-[3-bromo-4-(4-morpholinyl)phenyl]-1,6-naphthyridin-5-yl]-1,4-cyclohexanediamine;
4-[[7-[4-[[2-(dimethylamino)ethyl]methylamino]phenyl]-1,6-naphthyridin-5-yl]oxy]-cyclohexanol;
N-[7-[3-bromo-4-(4-morpholinyl)phenyl]-1,6-naphthyridin-5-yl]-1,3-propanediamine;
N,N-dimethyl-4-[5-(4-methyl-1-piperazinyl)-1,6-naphthyridin-7-yl]-benzenamine;
4-[[7-[4-[[3-(dimethylamino)propyl]methylamino]phenyl]-1,6-naphthyridin-5-yl]oxy]-cyclohexanol;
N-[7-[4-[[2-(dimethylamino)ethyl]methylamino]phenyl]-1,6-naphthyridin-5-yl]-1,4-butanediamine;
1,1-dimethylethyl[3-[[5-[(3-aminopropyl)amino]-7-(4-methoxyphenyl)-1,6-naphthyridin-2-yl]amino]propyl]-carbamate.

Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. Magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with dihydrothienopyrimidine and one or more combination partners selected from those described above.

The invention claimed is:
1. A compound of formula 1

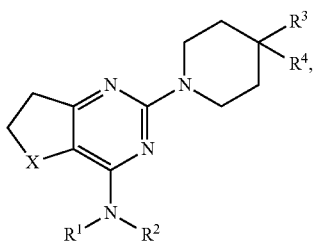

wherein:
X is SO or SO$_2$,
R$^1$ is H or C$_{1-6}$-alkyl,
R$^2$ is H or a group selected from C$_{1-10}$-alkyl and C$_{2-6}$-alkenyl, each optionally substituted by one or more groups selected from halogen and C$_{1-3}$-fluoroalkyl or optionally substituted by one or more groups selected from OR$^{2.1}$, COOR$^{2.1}$, CONR$^{2.2}$R$^{2.3}$, SR$^{2.1}$, SO—R$^{2.1}$, SO$_2$—R$^{2.1}$, C$_{6-10}$-aryl, -het, hetaryl, a mono- or bicyclic —C$_{3-10}$-cycloalkyl, CH$_2$—NR$^{2.2}$R$^{2.3}$, and NR$^{2.2}$R$^{2.3}$, which in turn are optionally substituted by one or more groups selected from OH, halogen, OR$^{2.1}$, oxo, CF$_3$, CHF$_2$, CH$_2$F, C$_{1-6}$-alkyl, C$_{1-6}$-alkanol, C$_{6-10}$-aryl, COOR$^{2.1}$, CH$_2$—NR$^{2.2}$R$^{2.3}$, and NR$^{2.2}$R$^{2.3}$,
R$^2$ is a mono- or polycyclic C$_{3-10}$ cycloalkyl, optionally bridged one or more times via C$_{1-3}$-alkyl groups and optionally substituted by a group selected from branched or unbranched C$_{1-6}$-alkanol, C$_{1-3}$-fluoroalkyl, C$_{1-3}$-alkylene-OR$^{2.1}$, OR$^{2.1}$, COOR$^{2.1}$, —SO$_2$—NR$^{2.2}$R$^{2.3}$, het, —NH—CO—O—(C$_{1-6}$-alkyl), —NH—CO—(C$_{1-6}$-alkyl), —NH—CO—O—(C$_{6-10}$-aryl), —NH—CO—(C$_{6-10}$-aryl), —NH—CO—O-hetaryl, —NH—CO-hetaryl, —NH—CO—O—(C$_{1-3}$-alkylene)-(C$_{6-10}$-aryl), —NH—CO—(C$_{1-3}$-alkylene)-(C$_{6-10}$-aryl), —N(C$_{1-3}$-alkyl)-CO—(C$_{1-6}$-alkyl), —N(C$_{1-3}$-alkyl)-CO—O—(C$_{6-10}$-aryl), —N(C$_{1-3}$-alkyl)-CO—(C$_{6-10}$-aryl), —N(C$_{1-3}$-alkyl)-CO—O-hetaryl, —N(C$_{1-3}$-alkyl)-CO-hetaryl, —N(C$_{1-3}$-alkyl)-CO—O—(C$_{1-3}$-alkylene)-(C$_{6-10}$-aryl), —N(C$_{1-3}$-alkyl)-CO—(C$_{1-3}$-alkylene)-(C$_{6-10}$-aryl), C$_{6-10}$-aryl, C$_{1-6}$-alkyl, C$_{6-10}$-aryl-C$_{1-6}$-alkylene, hetaryl-C$_{1-6}$-alkylene, mono- or bicyclic C$_{3-10}$ cycloalkyl, F, Cl, Br, and NR$^{2.2}$R$^{2.3}$, each optionally substituted by one or more groups selected from OH, OR$^{2.1}$, oxo, halogen, CF$_3$, CHF$_2$, CH$_2$F, C$_{1-6}$-alkyl, C$_{6-10}$-aryl, and NR$^{2.2}$R$^{2.3}$,
R$^2$ is a mono- or polycyclic C$_{6-10}$-aryl, optionally substituted by OH, SH, or halogen, or by one or more groups selected from OR$^{2.1}$, COOR$^{2.1}$, NR$^{2.2}$R$^{2.3}$, CH$_2$—NR$^{2.2}$R$^{2.3}$, C$_{3-10}$-cycloalkyl, het, C$_{1-6}$-alkyl, C$_{1-3}$-fluoroalkyl, CF$_3$, CHF$_2$, CH$_2$F, C$_{6-10}$-aryl-C$_{1-6}$-alkylene, het-C$_{1-6}$-alkylene, hetaryl-C$_{1-6}$-alkylene, C$_{6-10}$-aryl, SO$_2$—CH$_3$, SO$_2$—CH$_2$CH$_3$, and SO$_2$—NR$^{2.2}$R$^{2.3}$, each optionally substituted by one or more groups selected from OH, OR$^{2.1}$, CF$_3$, CHF$_2$, CH$_2$F, oxo, halogen, CF$_3$, CHF$_2$, CH$_2$F, C$_{1-6}$-alkyl, C$_{6-10}$-aryl, and NR$^{2.2}$R$^{2.3}$,
R$^2$ is a group selected from het and hetaryl, each optionally substituted by one or more groups selected from halogen, OH, oxo, CF$_3$, CHF$_2$, and CH$_2$F, or by one or more groups selected from OR$^{2.1}$, C$_{1-3}$-alkylene-OR$^{2.1}$, SR$^{2.1}$, SO—R$^{2.1}$, SO$_2$—R$^{2.1}$, COOR$^{2.1}$, COR$^{2.1}$, C$_{1-6}$-alkanol, mono- or bicyclic C$_{3-10}$-cycloalkyl, C$_{6-10}$-aryl, C$_{1-6}$-alkyl, C$_{6-10}$-aryl-C$_{1-6}$-alkylene, hetaryl-C$_{1-6}$-alkylene, het, hetaryl, C$_{1-3}$-alkylene-OR$^{2.1}$, and NR$^{2.2}$R$^{2.3}$, each optionally substituted by one or more groups selected from OH, OR$^{2.1}$, oxo, halogen, CF$_3$, CHF$_2$, CH$_2$F, C$_{1-6}$-alkyl, C$_{6-10}$-aryl, and NR$^{2.2}$R$^{2.3}$, or
NR$^1$R$^2$ together are a heterocyclic C$_{4-7}$ ring optionally bridged, which contains 1, 2, or 3 heteroatoms selected from N, O, and S and is optionally substituted by one or more groups selected from OH, OR$^{2.1}$, C$_{1-3}$-alkylene-OR$^{2.1}$, oxo, halogen, C$_{1-6}$-alkyl, C$_{6-10}$-aryl, COOR$^{2.1}$, CH$_2$—NR$^{2.2}$—COO—R$^{2.1}$, CH$_2$—NR$^{2.2}$—CO—R$^{2.1}$, CH$_2$—NR$^{2.2}$—CO—CH$_2$—NR$^{2.2}$R$^{2.3}$, CH$_2$—NR$^{2.2}$—SO$_2$—C$_{1-3}$-alkyl, CH$_2$—NR$^{2.2}$—SO$_2$—NR$^{2.2}$R$^{2.3}$, CH$_2$—NR$^{2.2}$—CO—NR$^{2.2}$R$^{2.3}$, CO—NR$^{2.2}$R$^{2.3}$, CH$_2$—NR$^{2.2}$R$^{2.3}$, and NR$^{2.2}$R$^{2.3}$,
R$^3$ is a C$_{6-10}$-aryl optionally substituted by in the ortho, para, or meta position by one, two, or three groups independently selected from fluorine, chlorine, bromine, hydroxy, CN, C$_{1-6}$-alkyl, C$_{1-3}$-fluoroalkyl, —C$_{1-3}$-alkylene-OR$^{2.1}$, —C$_{1-3}$-alkylene-NR$^{2.2}$R$^{2.3}$, NR$^{2.2}$R$^{2.3}$, O—R$^{2.1}$, SO—R$^{2.1}$, SO$_2$—R$^{2.1}$, COOR$^{2.1}$, —CO—NH—(C$_{1-6}$-alkylene)-hetaryl, —CO—NH-hetaryl, —CO—N(CH$_3$)-het, —CO—N(CH$_3$)—(C$_{1-3}$-alkylene)-het, —CO—N(CH$_3$)—(C$_{1-3}$-alkylene)-hetaryl, —CO—N(C$_{3-7}$-cycloalkyl)-het, —CO—NR$^{2.2}$R$^{2.3}$, —CO—NH—(C$_{1-6}$-alkylene)-het, NR$^{2.2}$—CO—R$^{2.1}$, C$_{6-10}$-aryl, C$_{6-10}$-aryl-C$_{1-2}$-alkylene, het-C$_{1-2}$-alkylene, -het, —CO-het, CO—N(CH$_3$)—C$_{3-7}$-cycloalkyl, C$_{3-7}$-cycloalkyl, C$_{3-7}$-cycloalkyl-C$_{1-2}$-alkylene, hetaryl-C$_{1-2}$-alkylene, and hetaryl, each optionally substituted by one or more groups selected from OH, halogen, —C$_{1-3}$-fluoroalkyl, oxo, methyl, and phenyl,
R$^3$ is a group selected from het and hetaryl, each optionally substituted by one or more groups selected from halogen, C$_{1-3}$-fluoroalkyl, CN, OH, oxo, —C$_{1-6}$-alkyl, —C$_{1-3}$-alkylene-NR$^{2.2}$R$^{2.3}$, —NR$^{2.2}$R$^{2.3}$, SO—R$^{2.1}$, SO$_2$—R$^{2.1}$, —O—R$^{2.1}$, —COOR$^{2.1}$, SO$_2$—(CH$_3$), SO$_2$—(CH$_2$—CH$_3$), C$_{6-10}$-aryl, het, C$_{3-7}$-cycloalkyl, and hetaryl, each optionally substituted by one or more groups selected from OH, halogen, —C$_{1-3}$-fluoroalkyl, C$_{1-6}$-alkyl, C$_{6-10}$-aryl, —COO(C$_{1-3}$-alkyl), and O—(C$_{1-3}$-alkyl), or
R$^3$ is —O—R$^{3.1}$, wherein R$^{3.1}$ is a group selected from —C$_{1-6}$-alkyl, —C$_{6-10}$-aryl, —C$_{1-3}$-alkylene-C$_{6-10}$-aryl, hetaryl, and het, each optionally substituted in the ortho, para, or meta position by one, two, or three groups independently selected from fluorine, chlorine, bromine, hydroxy, CN, C$_{1-6}$-alkyl, C$_{1-3}$-fluoroalkyl, CO—(C$_{1-5}$-alkyl), —CO—(C$_{1-3}$-fluoroalkyl), —CO—NH—(C$_{1-6}$-alkylene)-hetaryl, —CO—N(C$_{1-3}$-alkyl)-(C$_{1-6}$-alkylene)-hetaryl, —CO—N(C$_{1-3}$-alkyl)-het, —CO—N(C$_{3-7}$-cycloalkyl)-het, —C$_{1-3}$-alkylene-OR$^{2.1}$, —C$_{1-3}$-alkylene-NR$^{2.2}$R$^{2.3}$, —NR$^{2.2}$R$^{2.3}$, O—R$^{2.1}$; SO—R$^{2.1}$, SO$_2$—R$^{2.1}$, COOH, COO—(C$_{1-4}$-alkyl), —O—C$_{1-3}$-alkylene-N(C$_{1-3}$-alkyl)$_2$, CO—NR$^{2.2}$R$^{2.3}$, NR$^{2.2}$—CO—R$^{2.1}$, C$_{6-10}$-aryl, C$_{6-10}$-aryl-C$_{1-2}$-alkylene, het-C$_{1-2}$-alkylene, —CO-het, het, —CO—C$_{3-7}$- cycloalkyl, —CO—N($C_{1-3}$-alkyl)-$C_{3-7}$-cycloalkyl, $C_{3-7}$-cycloalkyl, $C_{3-7}$-cycloalkyl-$C_{1-2}$-alkylene, hetaryl-$C_{1-2}$-alkylene, and hetaryl, each optionally substituted by 1, 2, 3, or 4 groups independently selected from F, Cl, Br, methyl, O-methyl, ethyl, O-ethyl, OH, oxo, and $CF_3$, and $R^4$ is H, CN, OH, $CF_3$, $CHF_2$, $CH_2F$, F, methyl, ethyl, —O—($C_{1-3}$-alkyl), —$C_{1-3}$-alkylene-OH, —COO($C_{1-3}$-alkyl), —CO-het, —($C_{1-2}$-alkylene)-NH—$SO_2$—($C_{1-2}$-alkyl), —($C_{1-2}$-alkylene)-N ($C_{1-3}$-alkyl)-$SO_2$—($C_{1-2}$-alkyl), —($C_{1-2}$-alkylene)-O—($C_{1-2}$-alkylene)-$C_{6-10}$-aryl, —$C_{1-3}$-alkylene-O—$C_{1-3}$-alkyl, —($C_{1-2}$-alkylene)-N($C_{1-3}$-alkyl)-CO—($C_{1-2}$-alkyl), —NH—CO—($C_{1-3}$-alkylene)-O—($C_{1-3}$-alkyl), —$C_{1-3}$-alkylene-NH—CO—($C_{1-3}$-alkyl), —$C_{1-3}$-alkylene-NH—CO—($C_{1-3}$-alkylene)-N($C_{1-3}$-alkyl)$_2$, —O—($C_{1-2}$-alkylene)-($C_{6-10}$-aryl), —$C_{1-3}$-alkylene-NH—CO—($C_{1-3}$-alkylene)-O—($C_{1-3}$-alkyl), —CO—($C_{6-10}$-aryl), and —($C_{1-2}$-alkylene)-N($C_{1-3}$-alkyl)-CO—($C_{1-2}$-alkylene)-O—($C_{1-3}$-alkyl), wherein the aryl in the above groups of $R^4$ are optionally substituted by one or more other groups selected from F, Cl, Br, methyl, ethyl, propyl, isopropyl, cyclopropyl, —O-methyl, —O-ethyl, —O-propyl, —O-isopropyl, —O-cyclopropyl, —OH, and $CF_3$, or $R^3$ and $R^4$ together are a mono- or bicyclic, unsaturated, saturated, or partially saturated heterocycle, which contains 1, 2, or 3 heteroatoms selected from N, O and S, and optionally substituted by one or more groups selected from halogen, OH, oxo, $C_{1-3}$-fluoroalkyl, CN, $C_{1-6}$-alkyl, —O—$R^{2.1}$, —COOR$^{2.1}$, SO—$R^{2.1}$, $SO_2$—$R^{2.1}$, —$C_{1-3}$-alkylene-NR$^{2.2}$R$^{2.3}$, —NR$^{2.2}$R$^{2.3}$, $C_{6-10}$-aryl, $C_{3-7}$-cycloalkyl, het, and hetaryl, wherein:

$R^{2.1}$ is H or is a group selected from $C_{1-6}$-alkyl, $C_{1-6}$-alkanol, $C_{1-3}$-haloalkyl, mono- or bicyclic, —$C_{3-10}$-cycloalkyl, $C_{6-10}$-aryl-$C_{1-6}$-alkylene, hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, heteroaryl, and a -het, each optionally substituted by one or more groups selected from OH, O—($C_{1-3}$-alkyl), halogen, $C_{1-6}$-alkyl, and $C_{6-10}$-aryl, $R^{2.2}$ and $R^{2.3}$ are each independently H or a group selected from $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, CO—$NH_2$, CO—NHCH$_3$, —CO—N(CH$_3$)$_2$, $SO_2$—($C_1$-$C_2$-alkyl), CO—$R^{2.1}$, and COOR$^{2.1}$, each optionally substituted by one or more groups selected from OH, halogen, $C_{1-6}$-alkyl, $C_{6-10}$-aryl, and COOR$^{2.1}$, het is a three- to eleven-membered, mono- or bicyclic, saturated or partially saturated, optionally anellated or optionally bridged heterocycle which contains 1, 2, 3, or 4 heteroatoms independently selected from N, S, or O, hetaryl is a five- to eleven-membered, mono- or bicyclic, optionally anellated heteroaryl, which contains 1, 2, 3, or 4 heteroatoms independently selected from N, S, or O, and cycloalkyl is saturated or partially saturated, and pharmacologically acceptable salts thereof.

2. The compounds of formula 1 according to claim 1, wherein:

X is SO or $SO_2$, $R^1$ is H $R^2$ is H or $C_{1-10}$-alkyl optionally substituted by one or more groups selected from halogen and $C_{1-3}$-fluoroalkyl or optionally substituted by one or more groups selected from OR$^{2.1}$, COOR$^{2.1}$, CONR$^{2.2}$R$^{2.3}$, SR$^{2.1}$, SO—$R^{2.1}$, $SO_2$—$R^{2.1}$, phenyl, het, hetaryl, a monocyclic $C_{3-7}$-cycloalkyl, $CH_2$—NR$^{2.2}$R$^{2.3}$, and NR$^{2.2}$R$^{2.3}$, each optionally substituted by one or more groups selected from OH, F, Cl, Br, OR$^{2.1}$, oxo, $CF_3$, $CHF_2$, $CH_2F$, $C_{1-6}$-alkyl, $C_{1-6}$-alkanol, phenyl, COOR$^{2.1}$, $CH_2$—NR$^{2.2}$R$^{2.3}$, and NR$^{2.2}$R$^{2.3}$, $R^2$ is a monocyclic $C_{3-7}$ cycloalkyl optionally substituted by a group selected from branched or unbranched $C_{1-6}$-alkanol, $C_{1-3}$-fluoroalkyl, OR$^{2.1}$, $C_{1-3}$-alkylene-OR$^{2.1}$, OR$^{2.1}$, COOR$^{2.1}$, $SO_2$—NR$^{2.2}$R$^{2.3}$, -het, —NH—CO—O-(phenyl), phenyl, $C_{1-6}$-alkyl, phenyl-$C_{1-6}$-alkylene, -hetaryl-$C_{1-6}$-alkylene, monocyclic $C_{3-7}$ cycloalkyl, and NR$^{2.2}$R$^{2.3}$, each optionally substituted by one or more groups selected from OH, OR$^{2.1}$, oxo, F, Cl, $CF_3$, $CHF_2$, $CH_2F$, $C_{1-6}$-alkyl, phenyl, and —NR$^{2.2}$R$^{2.3}$, $R^2$ is a phenyl optionally substituted by OH, SH, or halogen, or by one or more groups selected from OR$^{2.1}$, COOR$^{2.1}$, NR$^{2.2}$R$^{2.3}$, $CH_2$—NR$^{2.2}$R$^{2.3}$, $C_{3-7}$-cycloalkyl, $C_{3-7}$ heterocycle, $C_{1-6}$-alkyl, $C_{1-3}$-fluoroalkyl, phenyl-$C_{1-6}$-alkylene, -het-$C_{1-6}$-alkylene, -hetaryl-$C_{1-6}$-alkylene, phenyl, $SO_2$—$CH_3$, $SO_2$—$CH_2CH_3$, and $SO_2$—NR$^{2.2}$R$^{2.3}$, each optionally substituted by one or more groups selected from OH, OR$^{2.1}$, oxo, F, Cl, $CF_3$, $CHF_2$, $CH_2F$, $C_{1-6}$-alkyl, phenyl, and NR$^{2.2}$R$^{2.3}$, $R^2$ is a group selected from het and hetaryl, each optionally substituted by one or more groups selected from F, Cl, OH, oxo, $CF_3$, $CHF_2$, and $CH_2F$, or by one or more groups selected from OR$^{2.1}$, —$C_{1-3}$-alkylene-OR$^{2.1}$, SR$^{2.1}$, SO—$R^{2.1}$, $SO_2$—$R^{2.1}$, COOR$^{2.1}$, COR$^{2.1}$, $C_{1-6}$-alkanol, monocyclic $C_{3-7}$-cycloalkyl, phenyl, $C_{1-6}$-alkyl, phenyl-$C_{1-6}$-alkylene, -hetaryl-$C_{1-6}$-alkylene, -het, -hetaryl, and NR$^{2.2}$R$^{2.3}$, each optionally substituted by one or more groups selected from OH, OR$^{2.1}$, oxo, F, Cl, $CF_3$, $CHF_2$, $CH_2F$, $C_{1-6}$-alkyl, phenyl, and NR$^{2.2}$R$^{2.3}$, or $NR^1R^2$ together are a heterocyclic $C_{4-7}$ ring optionally bridged, which contains 1, 2, or 3 heteroatoms selected from N, O, and S and is optionally substituted by one or more groups selected from OH, OR$^{2.1}$, $C_{1-3}$-alkylene-OR$^{2.1}$, oxo, F, Cl, $C_{1-6}$-alkyl, phenyl, COOR$^{2.1}$, $CH_2$—NR$^{2.2}$—COO—$R^{2.1}$, $CH_2$—NR$^{2.2}$—CO—$R^{2.1}$, $CH_2$—NR$^{2.2}$—CO—$CH_2$—NR$^{2.2}$R$^{2.3}$, $CH_2$—NR$^{2.2}$—$SO_2$—$C_{1-3}$-alkyl, $CH_2$—NR$^{2.2}$—$SO_2$—NR$^{2.2}$R$^{2.3}$, $CH_2$—NR$^{2.2}$—CO—NR$^{2.2}$R$^{2.3}$, CO—NR$^{2.2}$R$^{2.3}$, $CH_2$—NR$^{2.2}$R$^{2.3}$, and NR$^{2.2}$R$^{2.3}$, $R^3$ is a naphthalene or phenyl, each optionally substituted in the ortho, para, or meta position by one or two groups independently selected from fluorine, chlorine, bromine, hydroxy, CN, $C_{1-6}$-alkyl, $C_{1-3}$-fluoroalkyl, —$C_{1-3}$-alkylene-OR$^{2.1}$, —$C_{1-3}$-alkylene-NR$^{2.2}$R$^{2.3}$, —NR$^{2.2}$R$^{2.3}$, O—$R^{2.1}$; SO—$R^{2.1}$, $SO_2$—$R^{2.1}$, COOR$^{2.1}$, —CO—NH—($C_{1-6}$-alkylene)-hetaryl, —CO—NH-hetaryl, —CO—N(CH$_3$)-het, —CO—N(CH$_3$)—($C_{1-3}$-alkylene)-het, —CO—N(CH$_3$)—($C_{1-3}$-alkylene)-hetaryl, —CO—N($C_{3-7}$-cycloalkyl)-het, CO—NR$^{2.2}$R$^{2.3}$, —CO—NH—($C_{1-6}$-alkylene)-het, —NR$^{2.2}$—CO—$R^{2.1}$, phenyl, phenyl-$C_{1-2}$-alkylene, -het-$C_{1-2}$-alkylene, -het, —CO-het, CO—N(CH$_3$)—$C_{3-7}$-cycloalkyl, $C_{3-7}$-cycloalkyl, $C_{3-7}$-cycloalkyl-$C_{1-2}$-alkylene, -hetaryl-$C_{1-2}$-alkylene, and -hetaryl, each optionally substituted by one or more groups selected from OH, F, Cl, —$C_{1-3}$-fluoroalkyl, oxo, methyl, and phenyl, $R^3$ is a group selected from het and hetaryl, each optionally substituted by one or more groups selected from F, Cl, Br, $C_{1-3}$-fluoroalkyl, CN, OH, oxo, —$C_{1-6}$-alkyl, —$C_{1-3}$-alkylene-$NR^{2.2}R^{2.3}$, —$NR^{2.2}R^{2.3}$, SO—$R^{2.1}$, $SO_2$—$R^{2.1}$, —O—$R^{2.1}$, —$COOR^{2.1}$, $SO_2$—($CH_3$), $SO_2$—($CH_2$—$CH_3$), phenyl, het, $C_{3-7}$-cycloalkyl, and hetaryl, each optionally substituted by one or more groups selected from OH, F, Cl, Br, —$C_{1-3}$-fluoroalkyl, $C_{1-6}$-alkyl, phenyl, —COO($C_{1-3}$-alkyl), and O—($C_{1-3}$-alkyl), $R^3$ is —O—$R^{3.1}$, wherein $R^{3.1}$ is a group selected from —$C_{1-6}$-alkyl, -phenyl, —$C_{1-3}$-alkylene-phenyl, hetaryl and het, each optionally substituted in the ortho, para, or meta position by one, two, or three groups independently selected from fluorine, chlorine, bromine, hydroxy, CN, $C_{1-6}$-alkyl, $C_{1-3}$-fluoroalkyl, CO—($C_{1-5}$-alkyl), —CO—($C_{1-3}$-fluoroalkyl), —CO—NH—($C_{1-6}$-alkylene)-hetaryl, —CO—N($CH_3$)—($C_{1-6}$-alkylene)-hetaryl, —CO—N($CH_3$)-het, —CO—N($C_{3-7}$-cycloalkyl)-het, —$C_{1-3}$-alkylene-$OR^{2.1}$, —$C_{1-3}$-alkylene-$NR^{2.2}R^{2.3}$, —$NR^{2.2}R^{2.3}$, O—$R^{2.1}$; SO—$R^{2.1}$, $SO_2$—$R^{2.1}$, COOH, COO—($C_{1-4}$-alkyl), —O—$C_{1-3}$-alkylene-N($C_{1-3}$-alkyl)$_2$, CO—$NR^{2.2}R^{2.3}$, $NR^{2.2}$—CO—$R^{2.1}$, phenyl, phenyl-$C_{1-2}$-alkylene, het-$C_{1-2}$-alkylene, —CO-het, het, —CO—$C_{3-7}$-cycloalkyl, —CO—N($CH_3$)—$C_{3-7}$-cycloalkyl, $C_{3-7}$-cycloalkyl, $C_{3-7}$-cycloalkyl-$C_{1-2}$-alkylene, hetaryl-$C_{1-2}$-alkylene, and hetaryl, each optionally substituted by 1, 2, 3, or 4 groups independently selected from F, Cl, Br, methyl, O-methyl, ethyl, O-ethyl, OH, oxo, $CF_3$, and $R^4$ is H, CN, OH, $CF_3$, $CHF_2$, $CH_2F$, F, methyl, ethyl, O-methyl, O-ethyl, O-propyl, O-isopropyl, —$C_{1-3}$-alkylene-OH, —COO($C_{1-3}$-alkyl), —CO-het, —($C_{1-2}$-alkylene)-NH—$SO_2$—($C_{1-2}$-alkyl), —($C_{1-2}$-alkylene)-N($CH_3$)—$SO_2$—($C_{1-2}$-alkyl), —($C_{1-2}$-alkylene)-O—($C_{1-2}$-alkylene)-phenyl, —$C_{1-3}$-alkylene-O—$C_{1-3}$-alkyl, —($C_{1-2}$-alkylene)-N($CH_3$)—CO—($C_{1-2}$-alkyl), —NH—CO—($C_{1-3}$-alkylene)-O—($C_{1-3}$-alkyl), —$C_{1-3}$-alkylene-NH—CO—($C_{1-3}$-alkyl), —$C_{1-3}$-alkylene-NH—CO—($C_{1-3}$-alkylene)-N($C_{1-3}$-alkyl)$_2$, —O—($C_{1-2}$-alkylene)-phenyl-$C_{1-3}$-alkylene-NH—CO—($C_{1-3}$-alkylene)-O—($C_{1-3}$-alkyl), —CO-phenyl, and —($C_{1-2}$-alkylene)-N($CH_3$)—CO—($C_{1-2}$-alkylene)-O—($C_{1-3}$-alkyl), wherein the phenyl in the above groups of $R^4$ are optionally substituted by one or more other groups selected from F, Cl, Br, methyl, ethyl, propyl, —O-methyl, —O-ethyl, —O-propyl, —OH, and $CF_3$, or $R^3$ and $R^4$ together are a mono- or bicyclic, unsaturated, saturated or partially saturated heterocycle, which contains 1, 2, or 3 heteroatoms selected from N, O, and S, and optionally substituted by one or more groups selected from F, Cl, Br, OH, oxo, $C_{1-3}$-fluoroalkyl, CN, $C_{1-6}$-alkyl, —O—$R^{2.1}$, —$COOR^{2.1}$, SO—$R^{2.1}$, $SO_2$—$R^{2.1}$, —$C_{1-3}$-alkylene-$NR^{2.2}R^{2.3}$, —$NR^{2.2}R^{2.3}$, phenyl, $C_{3-7}$-cycloalkyl, het, and hetaryl, wherein:
$R^{2.1}$ is H or a group selected from $C_{1-6}$-alkyl, $C_{1-6}$-alkanol, $C_{1-3}$-haloalkyl, monocyclic $C_{3-7}$ cycloalkyl, phenyl-$C_{1-6}$-alkylene, hetaryl-$C_{1-6}$-alkylene, het-$C_{1-6}$-alkylene, —$C_{3-7}$-cycloalkyl-$C_{1-6}$-alkylene, phenyl, hetaryl, and a het, each optionally substituted by one or more groups selected from OH, F, Cl, $C_{1-6}$-alkyl, —O—($C_{1-3}$-alkyl), and phenyl,
wherein $R^{2.2}$ and $R^{2.3}$ are each independently H or a group selected from $C_{1-6}$-alkyl, monocyclic $C_{3-7}$ cycloalkyl, phenyl-$C_{1-3}$-alkylene, hetaryl-$C_{1-3}$-alkylene, phenyl, het, hetaryl, CO—$NH_2$, —CO—$NHCH_3$, —CON($CH_3$)$_2$, $SO_2$—($C_{1-3}$-alkyl), CO—$R^{2.1}$, and $COOR^{2.1}$, each optionally substituted by one or more groups selected from OH, F, Cl, $C_{1-6}$-alkyl, phenyl, and $COOR^{2.1}$,
het is a three- to seven-membered, monocyclic, saturated or partially saturated heterocycle or a seven- to eleven-membered, bicyclic, saturated or partially saturated heterocycle, which contains 1, 2, 3, or 4 heteroatoms independently selected from N, S, or O, and
hetaryl is a five- to six-membered, monocyclic, aromatic heteroaryl or a seven- to eleven-membered, bicyclic, aromatic heteroaryl, which contains in each case 1, 2, 3, or 4 heteroatoms independently selected from N, S, or O, and pharmacologically acceptable salts thereof.

3. The compounds of formula 1 according to claim 1, wherein:
X is SO,
$R^1$ is H,
$R^2$ is H or $C_{1-6}$-alkyl optionally substituted by one or more groups selected from F, Cl, $CF_3$, $CHF_2$, or $CH_2F$, or optionally substituted by one or more groups selected from $OR^{2.1}$, $COOR^{2.1}$, $CONR^{2.2}R^{2.3}$, $SR^{2.1}$, SO—$R^{2.1}$, $SO_2$—$R^{2.1}$, phenyl, het, hetaryl, a monocyclic $C_{3-7}$-cycloalkyl, $CH_2$—$NR^{2.2}R^{2.3}$, and $NR^{2.2}R^{2.3}$, each optionally substituted by one or more groups selected from OH, F, Cl, Br, $CF_3$, $CHF_2$, $CH_2F$, $OR^{2.1}$, oxo, methyl, ethyl, propyl, isopropyl, methanol, ethanol, phenyl, $COOR^{2.1}$, $CH_2$—$NR^{2.2}R^{2.3}$, and $NR^{2.2}R^{2.3}$,
$R^2$ is a monocyclic $C_{3-7}$ cycloalkyl optionally substituted by a group selected from $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, -het, —NH—CO—O-(phenyl), methyl, ethyl, propyl, isopropyl, phenyl, phenyl-$C_{1-2}$-alkylene, -hetaryl-$C_{1-2}$-alkylene, monocyclic $C_{3-7}$ cycloalkyl, and $NR^{2.2}R^{2.3}$, each optionally substituted by one or more groups selected from OH, $OR^{2.1}$, oxo, F, Cl, $CF_3$, $CHF_2$, $CH_2F$, methyl, ethyl, propyl, isopropyl, phenyl, and $NR^{2.2}R^{2.3}$,
$R^2$ is a phenyl optionally substituted by OH, SH, F, Cl, or Br, or by one or more groups selected from $OR^{2.1}$, $COOR^{2.1}$, $NR^{2.2}R^{2.3}$, $CH_2$—$NR^{2.2}R^{2.3}$, monocyclic $C_{3-7}$-cycloalkyl, -het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$, and $SO_2$—$NR^{2.2}R^{2.3}$, each optionally substituted by one or more groups selected from OH, $OR^{2.1}$, oxo, F, Cl, $CF_3$, $CHF_2$, $CH_2F$, methyl, ethyl, propyl, isopropyl, phenyl, and $NR^{2.2}R^{2.3}$,
$R^2$ is a group selected from het and hetaryl, each optionally substituted by one or more groups selected from F, Cl, OH, oxo, $CF_3$, $CHF_2$, and $CH_2F$, or by one or more groups selected from $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, methanol, ethanol, monocyclic $C_{3-7}$-cycloalkyl, phenyl, methyl, ethyl, propyl, isopropyl, phenyl-$C_{1-2}$-alkylene, hetaryl-$C_{1-2}$-alkylene, -het, -hetaryl, and $NR^{2.2}R^{2.3}$, each optionally substituted by one or more groups selected from OH, $OR^{2.1}$, oxo, F, Cl, $CF_3$, $CHF_2$, $CH_2F$, methyl, ethyl, propyl, isopropyl, butyl, isobutyl, phenyl, and $NR^{2.2}R^{2.3}$,
$R^3$ is a naphthalene or phenyl, each optionally substituted in the ortho, para, or meta position by one or two groups independently selected from fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, SO—$CH_3$, $COOCH_3$, $COOCH_2CH_3$, —CO—NH-(methylene)-hetaryl, —CO—NH-(ethylene)-hetaryl, —CO—NH-hetaryl, —CO—N($CH_3$)-het, —CO—N(CH₃)-(methylene)-het, —CO—N(CH₃)-(ethylene)-het, —CO—N(CH₃)-(methylene)-hetaryl, —CO—N(CH₃)-(ethylene)-hetaryl, —CO—N (cyclopropyl)-het, CO—NH₂, CONH(CH₃), CON(CH₃)₂, —CO—NH-(methylene)-het, —CO—NH-(ethylene)-het, —NH—CO-methyl, NCH₃—CO-methyl, —NH—CO-ethyl, NCH₃—CO-ethyl, —NH—CO-propyl, NCH₃—CO-propyl, —NH—CO-isopropyl, NCH₃—CO—isopropyl, phenyl, phenyl-methylene, phenyl-ethylene, het-methylene, het-ethylene, -het, —CO-het, CO—N(CH₃)-cyclopropyl, $C_{3-7}$-cycloalkyl, $C_{3-7}$-cycloalkyl-methylene, $C_{3-7}$-cycloalkyl-ethylene, hetaryl-methylene, hetaryl-ethylene, -hetaryl, CH₂—NH₂, CH₂—NH(CH₃), CH₂—N(CH₃)₂, —NH₂, —NH(CH₃), and —N(CH₃)₂, each optionally substituted by one or more groups selected from OH, F, Cl, —CF₃, CHF₂, CH₂F, oxo, methyl, and phenyl, $R^3$ is a group selected from a het and hetaryl, each optionally substituted by one or more groups selected from F, Cl, Br, CF₃, CHF₂, CH₂F, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, SO—(CH₃), SO—(CH₂—CH₃), SO₂—(CH₃), SO₂—(CH₂—CH₃), phenyl, CH₂—NH₂, CH₂—NH(CH₃), CH₂—N(CH₃)₂, —NH₂, —NH(CH₃), —N(CH₃)₂, het, and hetaryl, each optionally substituted by one or more groups selected from OH, F, Cl, CF₃, CHF₂, CH₂F, methyl, ethyl, propyl, isopropyl, phenyl, —COO-methyl, —COO-ethyl, O-methyl, and O-ethyl, $R^3$ is —O—$R^{3.1}$, wherein $R^{3.1}$ is a group selected from $C_{1-3}$-alkyl, -phenyl, —$C_{1-3}$-alkylene-phenyl, hetaryl and het, each optionally substituted in the ortho, para, or meta position by one, two, or three groups independently selected from fluorine, chlorine, bromine, hydroxy, CN, methyl, ethyl, propyl, isopropyl, butyl, isobutyl, CF₃, CHF₂, CH₂F, CO-(methyl), CO-(ethyl), CO-(propyl), CO-(isopropyl), —CO—(CF₃), —CO—NH-(methylene)-hetaryl, —CO—NH-(ethylene)-hetaryl, —CO—N(CH₃)-(methylene)-hetaryl, —CO—N(CH₃)-(ethylene)-hetaryl, —CO—N(CH₃)-(propylene)-hetaryl, —CO—N(CH₃)-(isopropylene)-hetaryl, —CO—N(CH₃)-het, —CO—N(cyclopropyl)-het, —CO—N($C_{5-7}$-cycloalkyl)-het, -methylene-O-methyl, -ethylene-O-methyl, -propylene-O-methyl, -methylene-O-ethyl, -ethylene-O-ethyl, -propylene-O-ethyl, -methylene-NH₂, -methylene-NHCH₃, -methylene-N(CH₃)₂, -ethylene-NH₂, -ethylene-NHCH₃, -ethylene-N(CH₃)₂, NH₂, N(CH₃)₂, NHCH₃, —O-methyl, O-ethyl, O-propyl, O-isopropyl, O-butyl, O-isobutyl, —SO—CH₃, SO-ethyl, —SO-propyl, —SO-isopropyl, SO₂-methyl, —SO₂-ethyl, SO₂-propyl, SO₂-isopropyl, COOH, COO-(methyl), COO-(ethyl), COO-(propyl), COO-(isopropyl), —O-methylene-N(methyl)₂, —O-ethylene-N(methyl)₂, —O-methylene-N(ethyl)₂, —O—ethylene-N(ethyl)₂, CO—NH₂, CO—NH(CH₃), CO—N(CH₃)₂, —NH—CO-methyl, —NCH₃—CO-methyl, —NH—CO-ethyl, NCH₃—CO—ethyl, phenyl, phenyl-methylene, phenyl-ethylene, het-methylene, het-ethylene, —CO-het, het, —CO—$C_{5-7}$-cycloalkyl, —CO-cyclopropyl, —CO—N(CH₃)—$C_{5-7}$-cycloalkyl, —CO—N(CH₃)-cyclopropyl, $C_{5-7}$-cycloalkyl, cyclopropyl, $C_{5-7}$-cycloalkyl-methylene, $C_{5-7}$-cycloalkyl-ethylene, cyclopropyl-methylene, cyclopropyl-ethylene, hetaryl-methylene, hetaryl-ethylene, and hetaryl, each optionally substituted by 1, 2, 3, or 4 groups independently selected from F, Cl, Br, methyl, O-methyl, ethyl, O-ethyl, OH, oxo, and CF₃, and $R^4$ is H, CN, OH, CF₃, CHF₂, CH₂F, F, methyl, ethyl, O-methyl, O-ethyl, -methylene-OH, -ethylene-OH, -propylene-OH, isopropylene-OH, —COO(methyl), —COO(ethyl), —COO(propyl), —COO(isopropyl), —CO-het, -(methylene)-NH—SO₂-(methyl), -(methylene)-NH—SO₂-(ethyl), -(ethylene)-NH—SO₂-(methyl), -(ethylene)-NH —SO₂-(ethyl), -(methylene)-N(CH₃)—SO₂-(methyl), -(methylene)-N(CH₃)—SO₂-(ethyl), -(ethylene)-N (CH₃)—SO₂-(methyl), -(ethylene)-N(CH₃)—SO₂-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl, -ethylene-O-ethyl, -(methylene)-N(CH₃)—CO—(methyl), -(methylene)-N (CH₃)—CO-(ethyl), -(ethylene)-N(CH₃)—CO-(methyl), -(ethylene)-N (CH₃)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO -(methyl), -methylene-NH—CO-(ethyl), -ethylene-NH—CO-(methyl), -ethylene-NH—CO-(ethyl), -methylene-NH—CO-(methylene)-N(methyl)₂, -methylene-NH—CO-(ethylene)-N(methyl)₂, -ethylene-NH—CO-(methylene)-N(methyl)₂, -ethylene-NH—CO-(ethylene)-N(methyl)₂, -methylene-NH—CO-(methylene)-O-(methyl), -methylene-NH —CO-(ethylene)-O-(methyl), -ethylene-NH—CO-(methylene)-O-(methyl), -methylene-NH—CO-(methylene)-O-(ethyl), -methylene-NH—CO-(ethylene)-O-(ethyl), -ethylene-NH —CO-(methylene)-O-(ethyl), -(methylene)-N(CH₃)—CO-(methylene)-O-(methyl), -(methylene)-N(CH₃) -CO-(ethylene)-O-(methyl), -(ethylene)-N(CH₃)—CO-(methylene)-O-(methyl), -(methylene)-N(CH₃)—CO-(methylene)-O-(ethyl), -(methylene)-N(CH₃)—CO-(ethylene)-O-(ethyl), -(methylene)-N(CH₃)—CO-(ethylene)-O-(ethyl), —O-(methylene)-phenyl, —O-(ethylene)-phenyl, and —CO-phenyl, wherein the phenyl in the above groups of $R^4$ are optionally substituted by one or more other groups selected from F, Cl, Br, methyl, ethyl, propyl, —O-methyl, —O-ethyl, —O-propyl, —OH, and CF₃, or $R^3$ and $R^4$ together are a mono- or bicyclic, unsaturated, saturated or partially saturated heterocycle, which contains 1, 2, or 3 heteroatoms selected from N, O, and S, and optionally substituted by one or more groups selected from F, Cl, Br, OH, oxo, CF₃, CHF₂, CH₂F, CN, methyl, ethyl, propyl, isopropyl, cyclopropyl, COO-methyl, —COO-ethyl, O-methyl, O-ethyl, SO₂—(CH₃), SO₂—(CH₂CH₃), SO —(CH₃), SO—(CH₂CH₃), CH₂—NH₂, CH₂—NH(CH₃), CH₂—N(CH₃)₂, —NH₂, —NH(CH₃), —N(CH₃)₂, phenyl, $C_{5-7}$-cycloalkyl, het, and hetaryl, wherein:

$R^{2.1}$ is H or a group selected from methyl, ethyl, propyl, isopropyl, methanol, ethanol, monocyclic $C_{3-7}$ cycloalkyl, phenyl-$C_{1-2}$-alkylene, -hetaryl-$C_{1-2}$-alkylene, -het-$C_{1-2}$-alkylene, $C_{3-7}$-cycloalkyl-$C_{1-2}$-alkylene, phenyl, hetaryl, and a het, each optionally substituted by one or more groups selected from OH, F, Cl, methyl, ethyl, propyl, isopropyl, O-methyl, O-ethyl, O-propyl, O-isopropyl, and phenyl, $R^{2.2}$ and $R^{2.3}$ are each independently H or a group selected from methyl, ethyl, propyl, isopropyl, monocyclic $C_{3-7}$ cycloalkyl, phenyl-$C_{1-3}$-alkylene, hetaryl-$C_{1-3}$-alkylene, phenyl, -het, -hetaryl, CO—$NH_2$, CO—$NHCH_3$, $CON(CH_3)_2$, $SO_2$—($C_{1-2}$-alkly), CO—$R^{2.1}$, and $COOR^{2.1}$, each optionally substituted by one or more groups selected from OH, F, Cl, methyl, ethyl, propyl, isopropyl, phenyl, and $COOR^{2.1}$, or het is a three- to seven-membered, monocyclic, saturated or partially saturated heterocycle, which contains 1, 2, or 3 heteroatoms independently selected from N, S, or O, and hetaryl is a five- to six-membered, monocyclic, aromatic heteroaryl which contains 1, 2, or 3 heteroatoms independently selected from N, S, or O, and pharmacologically acceptable salts thereof.

4. The compounds of formula 1 according to claim 1, wherein:

$R^2$ is a group according to formula 2

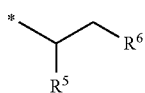

wherein:

$R^6$ is OH or $NH_2$, and $R^5$ is a group selected from $C_{1-4}$-alkyl, a five- to six-membered heteroaryl with 1, 2, or 3 heteroatoms selected from S, O, and N, and phenyl optionally substituted by one or more groups selected from OH, F, Br, $OR^{2.1}$, oxo, methyl, ethyl, methanol, ethanol, phenyl, $COOR^{2.1}$, $CH_2$—$NR^{2.2}R^{2.3}$, and $NR^{2.2}R^{2.3}$, and pharmacologically acceptable salts thereof.

5. The compounds of formula 1 according to claim 4, wherein:

$R^6$ is OH or $NH_2$, and $R^5$ is methyl, ethyl, propyl, or isopropyl, and pharmacologically acceptable salts thereof.

6. The compound of formula 1 according to claim 1, wherein:

$R^2$ is a monocyclic three-, four-, five-, six-, or seven-membered cycloalkyl ring optionally substituted in the spiro position by a group selected from —$CH_2$—, $OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$, and $C_{2-4}$-fluoroalkyl, wherein $R^{2.1}$ is selected from methyl, ethyl, propyl, isopropyl, butyl, and isobutyl, and pharmacologically acceptable salts thereof.

7. The compound of formula 1 according to claim 1, wherein:

$R^2$ is a cyclopropyl optionally substituted by another group selected from —$NH_2$, $CH2$—$NH_2$, —$NH(CH_3)$, —$N(CH_3)_2$, methyl, ethyl, propyl, isopropyl, —NH—CO -(tert-butyl), —NH—CO—O-(tert-butyl), —$N(CH_3)$—CO-(tert-butyl), —$N(CH_3)$—CO—O-(tert-butyl), —$CF_3$, —$CHF_2$, $CH_2F$, F, Cl, and Br, and pharmacologically acceptable salts thereof.

8. The compound of formula 1 according to claim 1, wherein:

$R^2$ is a phenyl optionally substituted in one or both meta positions by one or more groups selected from methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$, $NH(CH_3)$, and $N(CH_3)_2$, wherein $R^{2.1}$ is H, methyl, or ethyl, and pharmacologically acceptable salts thereof.

9. The compound of formula 1 according to claim 1, wherein:

$R^2$ is a group selected from monocyclic, saturated three-, four-, five-, six-, or seven-membered heterocycles with 1, 2, or 3 heteroatoms selected in each case from N, O, and S, each optionally substituted by one or more groups selected from fluorine, chlorine, bromine, $CF_3$, $CHF_2$, $CH_2F$, OH, and oxo or by one or more groups selected from $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, $C_{5-10}$-heteroaryl-$C_{1-6}$-alkylene, $C_{5-10}$ heterocycle, $C_{5-10}$-heteroaryl, and $NR^{2.2}R^{2.3}$, each optionally substituted by one or more groups selected from OH, $OR^{2.1}$, oxo, F, Cl, $CF_3$, $CHF_2$, $CH_2F$, $C_{1-6}$-alkyl, phenyl, and $NR^{2.2}R^{2.3}$, and pharmacologically acceptable salts thereof.

10. The compound of formula 1 according to claim 9, wherein:

$R^2$ is a group selected from a monocyclic, saturated six-membered heterocycle with a heteroatom selected from N, O, and S, each optionally substituted by one or more groups selected from F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy, and ethoxy, and pharmacologically acceptable salts thereof.

11. The compound of formula 1 according to claim 9, wherein:

$R^2$ is piperidine or tetrahydropyran, each optionally substituted by one or more groups selected from F, Cl, Br, OH, $CF_3$, $CHF_2$, $CH_2F$, $NH_2$, $NHCH_3$, $N(CH_3)_2$, oxo, methyl, and methoxy, and pharmacologically acceptable salts thereof.

12. The compounds of formula 1 according to claim 1, wherein:

$R^3$ is a naphthalene or phenyl, each optionally substituted in any position by one, two, or three groups independently selected from fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, $SO_2$—$CH_2CH_3$, $COOCH_3$, and CO—O—$CH_2CH_3$, and pharmacologically acceptable salts thereof.

13. The compound of formula 1 according to claim 1, wherein:

$R^3$ is a group selected from het and hetaryl, each optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, $C_{5-7}$-cycloalkyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, het, and hetaryl, each optionally substituted by one or more groups selected from OH, F, Cl, Br, $CF_3$, $CHF_2$, $CH_2F$, methyl, ethyl, propyl, isopropyl, phenyl, —COO-methyl, —COO-ethyl, —COO-propyl, —COO-isopropyl, O-methyl, O-ethyl, O-propyl, and O-isopropyl, $R^4$ is H, CN, OH, $CF_3$, $CHF_2$, $CH_2F$, F, methyl, ethyl, O-methyl, or O-ethyl, wherein:

het is a three- to seven-membered, monocyclic, saturated or partially saturated heterocycle or a seven- to eleven-membered, bicyclic, anellated, saturated or partially saturated heterocycle which contains 1, 2, or 3 heteroatoms independently selected from N, S, or O, and hetaryl is a five- to six-membered, monocyclic, aromatic heteroaryl or a seven- to eleven-membered, bicyclic, anellated, aromatic heteroaryl, which contains 1, 2, or 3 heteroatoms independently selected from N, S, or O, and pharmacologically acceptable salts thereof.

14. The compound of formula 1 according to claim 13, wherein:

$R^3$ is indole, dihydroindole, quinazoline, dihydroquinazoline, tetrahydroquinazoline, benzoisoxazole, dihydrobenzoisoxazole, benzoxazine, dihydrobenzoxazine, benzothiazole, dihydrobenzothiazole, triazolopyridine, dihydrotriazolopyridine, benzofuran, dihydrobenzofuran, isobenzofuran, or dihydroisobenzofuran, each optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, furanyl, and pyridinyl, each optionally substituted by one or more groups selected from OH, F, Cl, Br, $CF_3$, $CHF_2$, $CH_2F$, methyl, ethyl, propyl, isopropyl, phenyl, —COO-methyl, —COO-ethyl, O-methyl, and O-ethyl, and pharmacologically acceptable salts thereof.

15. The compound of formula 1 according to claim 13, wherein:

$R^3$ is imidazole, dihydroimidazole, oxadiazole, oxadiazolidine, pyrazole, pyridine, or dihydropyrazole, each optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, furanyl, and pyridinyl, each optionally substituted by one or more groups selected from OH, F, Cl, Br, $CF_3$, $CHF_2$, $CH_2F$, methyl, ethyl, propyl, isopropyl, phenyl, —COO-methyl, —COO-ethyl, and O-methyl, O-ethyl, and pharmacologically acceptable salts thereof.

16. The compounds of formula 1 according to claim 1, wherein:

$R^3$ and $R^4$ together are a mono- or bicyclic, unsaturated or partially saturated, three- to eleven-membered heterocycle which contains 1, 2, or 3 heteroatoms selected from N, O, and S, and optionally substituted by one or more groups selected from F, Cl, Br, OH, oxo, $CF_3$, $CHF_2$, $CH_2F$, CN, methyl, ethyl, propyl, isopropyl, cyclopropyl, COO-methyl, —COO-ethyl, O-methyl, O-ethyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2NHCH_3$, —$CH_2$—$N(CH_3)_2$, $NH_2$, $NHCH_3$, $N(CH_3)_2$, a saturated or partially saturated, five- to six-membered heterocycle, and a five- to six-membered heteroaryl, as well as pharmacologically acceptable salts thereof.

17. The compounds of formula 1 according to claim 16, wherein:

$R^3$ and $R^4$ together are tetrahydroquinazoline, tetrahydrobenzoxazine, dihydroindole, or dihydroisobenzofuran, each optionally substituted by one or more groups selected from F, Cl, Br, OH, oxo, $CF_3$, $CHF_2$, $CH_2F$, CN, methyl, ethyl, propyl, isopropyl, cyclopropyl, COO-methyl, O-methyl, O-ethyl, $SO_2$—$(CH_3)$, $SO_2$—$(CH_2$—$CH_3)$, phenyl, —$CH_2$—$NH_2$, —$CH_2NHCH_3$, —$CH_2$—$N(CH_3)_2$, $NH_2$, $NHCH_3$, $N(CH_3)_2$, a saturated or partially saturated, five- to six-membered heterocycle, and a five- to six-membered heteroaryl, and pharmacologically acceptable salts thereof.

18. The compounds of formula 1 according to claim 1, wherein:

$R^3$ is —O—$R^{3.1}$, wherein $R^{3.1}$ is a group selected from methyl, ethyl, propyl, isopropyl, butyl, isobutyl, pentyl, isopentyl, -phenyl, -methylene-phenyl, -ethylene-phenyl, -propylene-phenyl, -isopropylene-phenyl, hetaryl, and het, each optionally substituted in the ortho, para, or meta position by one, two, or three groups independently selected from fluorine, chlorine, bromine, hydroxy, CN, methyl, ethyl, propyl, isopropyl, butyl, isobutyl, —$CF_3$, $CHF_2$, $CH_2F$, CO-(methyl), CO-(ethyl), CO-(propyl), CO-(isopropyl), CO-(butyl), CO-(isobutyl), —CO—$(CF_3)$, —CO—$(CH_2F)$, —CO—$(CHF_2)$, —CO—NH-(methylene)-hetaryl, —CO—NH-(ethylene)-hetaryl, —CO—NH-(propylene)-hetaryl, —CO—NH-(isopropylene)-hetaryl, —CO—N$(CH_3)$—(methylene)-hetaryl, —CO—N$(CH_3)$-(ethylene)-hetaryl, —CO—N$(CH_3)$-(propylene)-hetaryl, —CO—N$(CH_3)$-(isopropylene)-hetaryl, —CO—N$(CH_3)$-het, —CO—N$(C_{3-7}$-cycloalkyl)-het, -methylene-O-methyl, -ethylene-O-methyl, -methylene-O-ethyl, -ethylene-O-ethyl, -methylene-$NH_2$, -ethylene-$NH_2$, -methylene-$NHCH_3$, -ethylene-$NHCH_3$, -methylene-$N(CH_3)_2$, -ethylene-$N(CH_3)_2$, —$NH_2$, —$NHCH_3$, —$N(CH_3)_2$, —O-methyl, —O-ethyl, —O-propyl, —O-isopropyl, —SO—$CH_3$, —SO—$(CH_2CH_3)$, —$SO_2$—$CH_3$, —$SO_2$—$(CH_2CH_3)$, COOH, COO-(methyl), COO-(ethyl), COO-(propyl), COO-(isopropyl), —O-methylene-N(methyl)$_2$, —O-ethylene-N(methyl)$_2$, —O-methylene-N(ethyl)$_2$, —O-ethylene-N(ethyl)$_2$, CO—$NH_2$, CO—$NHCH_3$, CO—N$(CH_3)_2$, NH—CO-methyl, $NCH_3$—CO-methyl, NH—CO-ethyl, N$(CH_3)$—CO-ethyl, phenyl, phenyl-methylene, phenyl-ethylene, het-methylene, het-ethylene, —CO-het, het, —CO—$C_{4-7}$-cycloalkyl, —CO-cyclopropyl, —CO—N$(CH_3)$-cyclopropyl, —CO—N$(CH_3)$—$C_{4-7}$-cycloalkyl, $C_{4-7}$-cycloalkyl, cyclopropyl, $C_{4-7}$-cycloalkyl-methylene, cyclopropyl-methylene, $C_{4-7}$-cycloalkyl-ethylene, cyclopropyl-ethylene, hetaryl-methylene, hetaryl-ethylene, and hetaryl, each optionally substituted by 1, 2, 3, or 4 groups independently selected from F, Cl, Br, methyl, O-methyl, ethyl, O-ethyl, OH, oxo, and $CF_3$, and pharmacologically acceptable salts thereof.

19. The compounds of formula 1 according to claim 1, wherein:

$R^4$ is H, CN, OH, $CF_3$, $CHF_2$, $CH_2F$, F, methyl, ethyl, O-methyl, O-ethyl, -methylene-OH, -ethylene-OH, -propylene-OH, isopropylene-OH, —COO(methyl), —COO(ethyl), —COO(propyl), —COO(isopropyl), —CO-het, -(methylene)-NH—$SO_2$-(methyl), -(methylene)-NH—$SO_2$-(ethyl), -(ethylene)-NH—$SO_2$-(methyl), -(ethylene)-NH —$SO_2$-(ethyl), -(methylene)-N$(CH_3)$—$SO_2$-(methyl), -(methylene)-N$(CH_3)$—$SO_2$-(ethyl), -(ethylene)-N$(CH_3)$—$SO_2$-(methyl), -(ethylene)-N$(CH_3)$—$SO_2$-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl, -ethylene-O-ethyl, -(methylene)-N(CH$_3$)—CO-(methyl), -(methylene)-N(CH$_3$)—CO-(ethyl), -(ethylene)-N(CH$_3$)—CO-(methyl), -(ethylene) -N(CH$_3$)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO-(methyl), -methylene-NH—CO-(ethyl), -ethylene-NH—CO-(methyl), -ethylene-NH—CO-(ethyl), -methylene-NH—CO-(methylene)-N(methyl)$_2$, -methylene-NH—CO-(ethylene)-N(methyl)$_2$, -ethylene-NH—CO-(methylene)-N(methyl)$_2$, -ethylene-NH—CO-(ethylene)-N(methyl)$_2$, -methylene-NH—CO-(methylene)-O-(methyl), -methylene-NH—CO-(ethylene)-O-(methyl), -ethylene-NH—CO-(methylene)-O-(methyl), -methylene-NH—CO-(methylene)-O-(ethyl), -methylene-NH—CO-(ethylene)-O-(ethyl), -ethylene-NH—CO-(methylene)-O-(ethyl), -(methylene)-N(CH$_3$)—CO-(methylene)-O-(methyl), -(methylene)-N(CH$_3$)—CO-(ethylene)-O-(methyl), -(ethylene)-N(CH$_3$)—CO-(methylene)-O-(methyl), -(methylene)-N(CH$_3$)—CO-(methylene)-O-(ethyl), -(methylene)-N(CH$_3$)—CO-(ethylene)-O-(ethyl), -(ethylene)-N(CH$_3$)—CO-(methylene)-O-(ethyl), —O-(methylene)-phenyl, —O-(ethylene)-phenyl, and —CO-phenyl, wherein the phenyl in the above groups of R$^4$ are optionally substituted by one or more other groups selected from F, Cl, Br, methyl, ethyl, propyl, —O-methyl, —O-ethyl, —O-propyl, —OH, and CF$_3$, and pharmacologically acceptable salts thereof.

20. The compounds of formula 1 according to claim 1, wherein:

R$^3$ is oxazole, imidazole, or thiazole, each optionally substituted by one, two, or three further groups independently selected from methyl, ethyl, propyl, isopropyl, O-methyl, O-ethyl, O-propyl, O-isopropyl, OH, F, Cl, Br, CF$_3$, phenyl, hetaryl, and C$_{3-6}$-cycloalkyl, and pharmacologically acceptable salts thereof.

21. The compounds of formula 1 according to claim 1, wherein X is SO$_2$, and pharmacologically acceptable salts thereof.

22. The compounds of formula 1 according to claim 1, wherein the compounds are selected from:

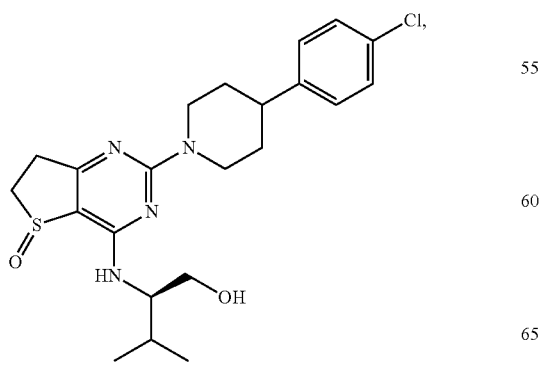

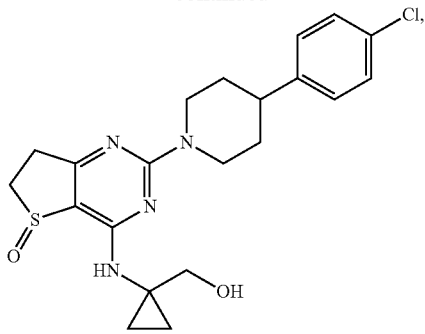

-continued

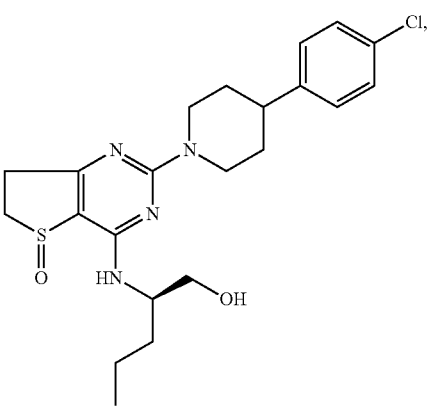

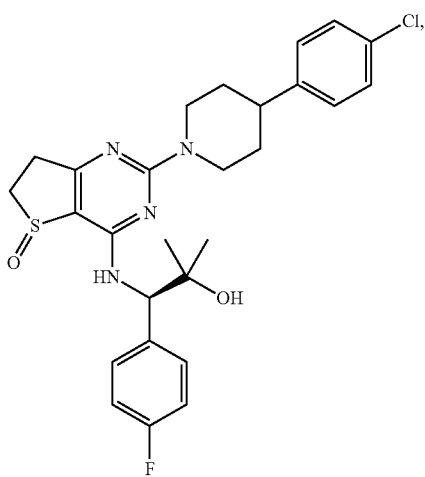

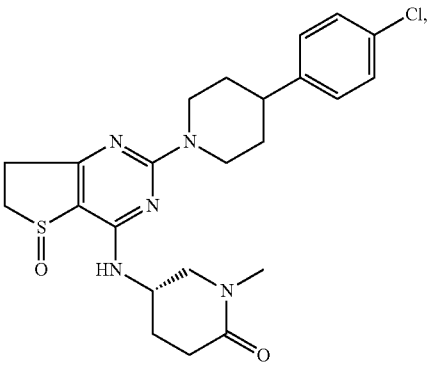

539
-continued
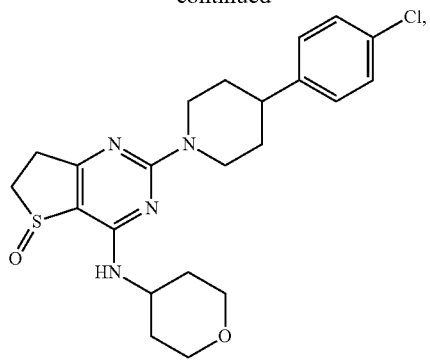
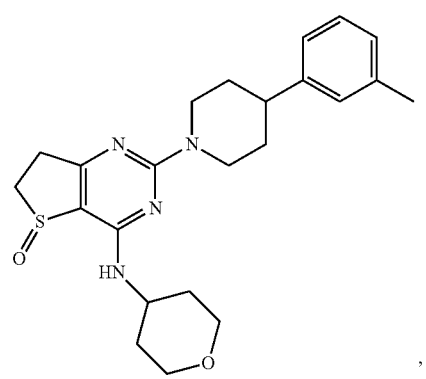
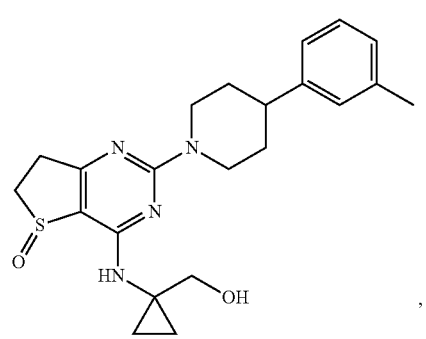
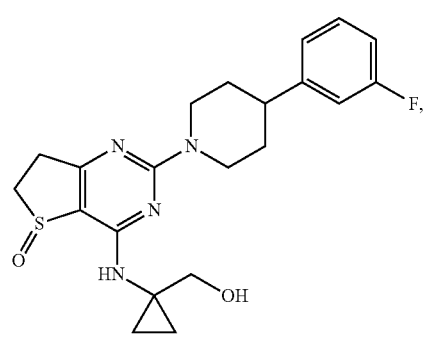
540
-continued
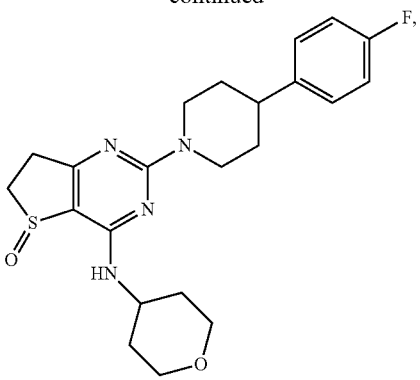
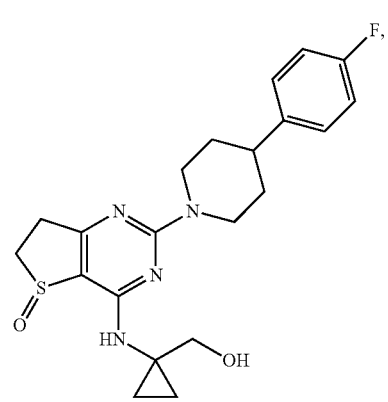
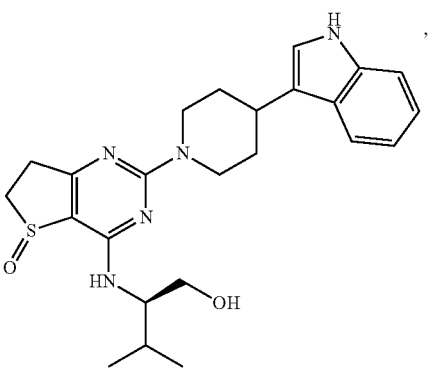
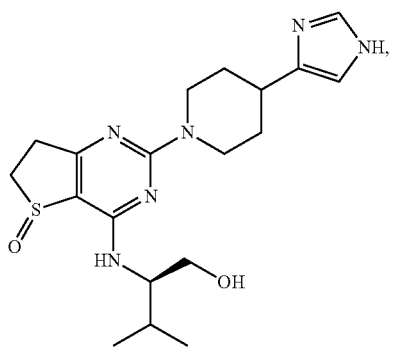

541
-continued
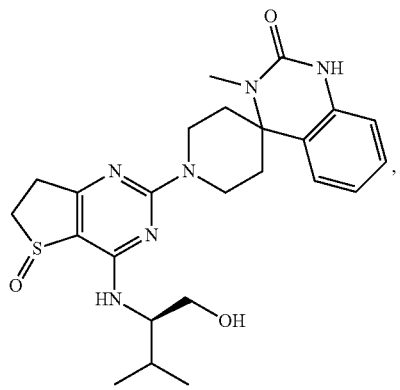
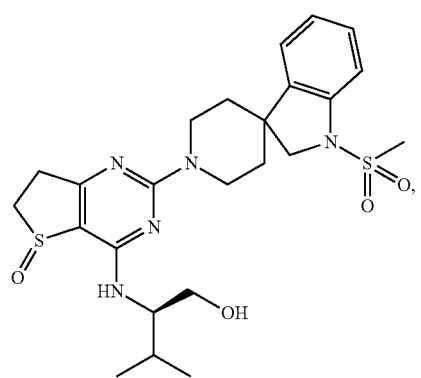
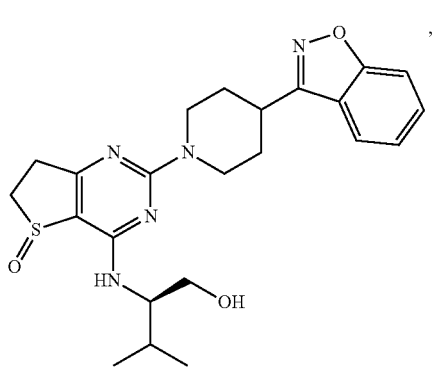
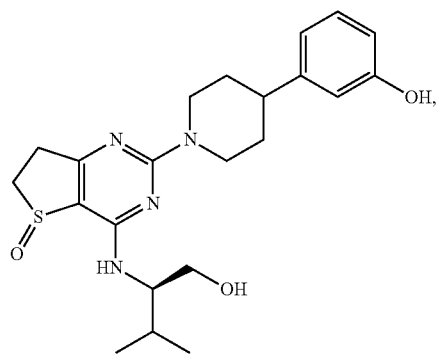
542
-continued
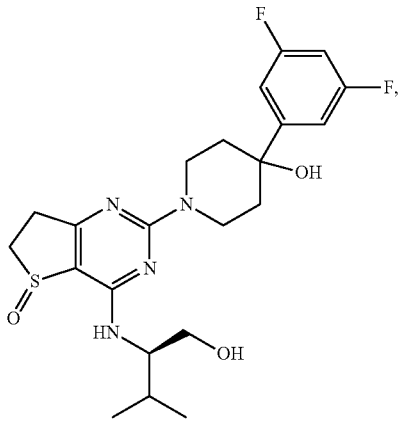
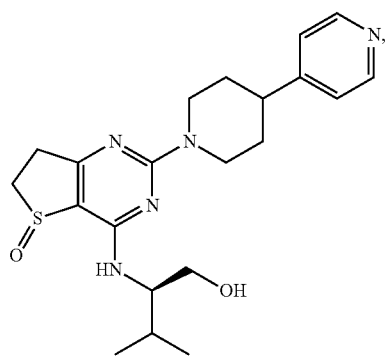
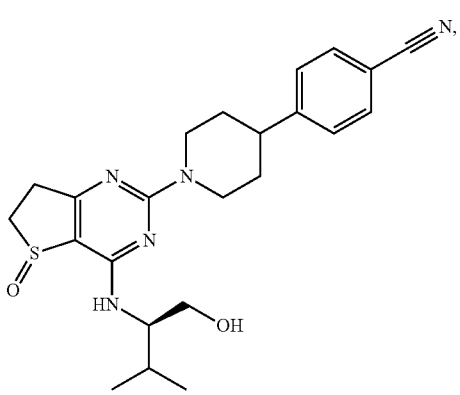
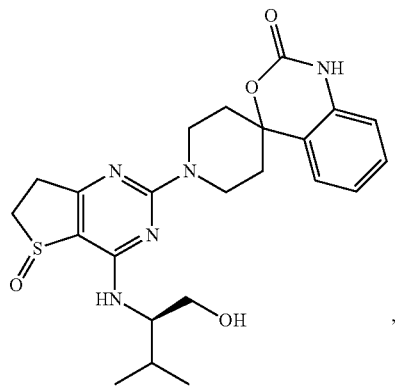

543
-continued
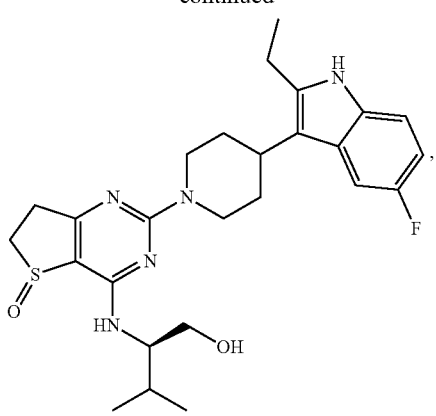
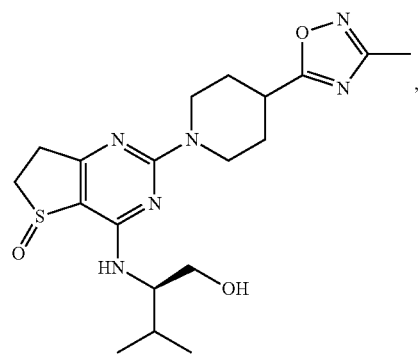
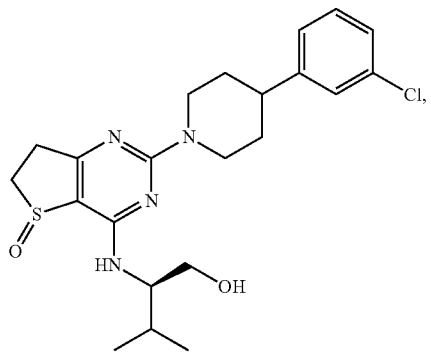
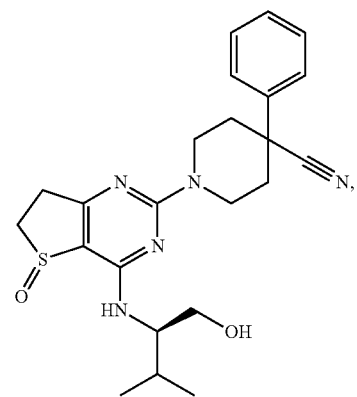
544
-continued
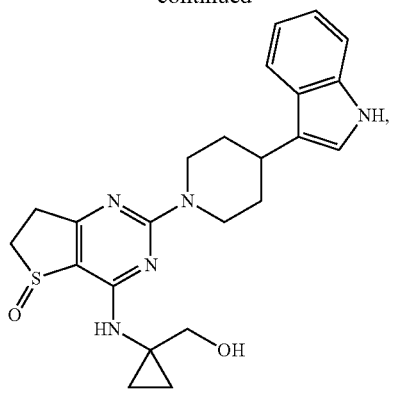
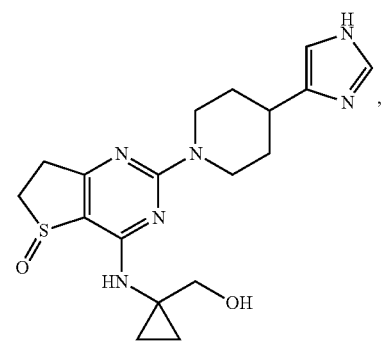
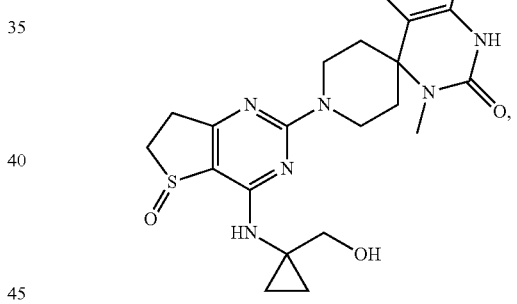
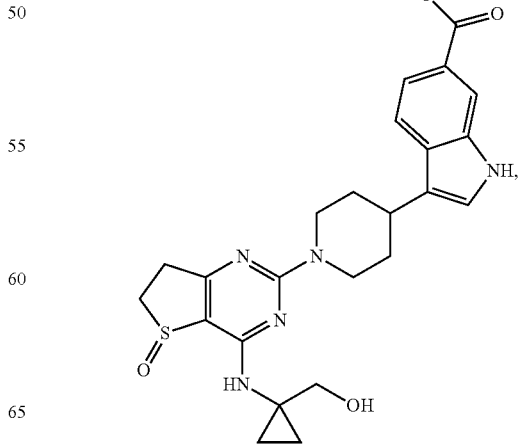

545
-continued
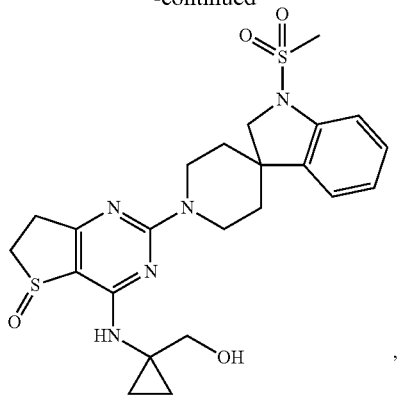
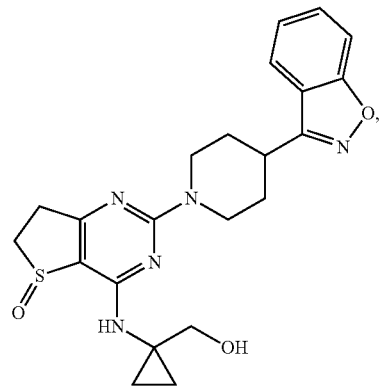
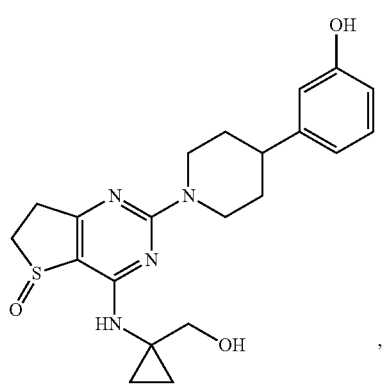
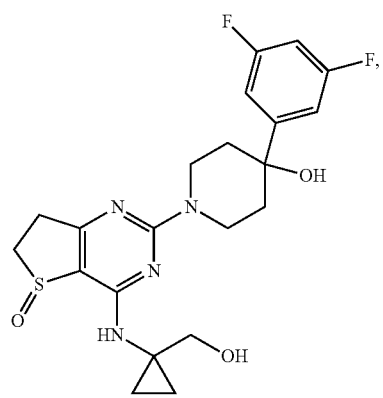
546
-continued
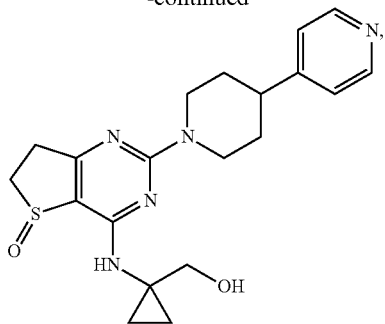
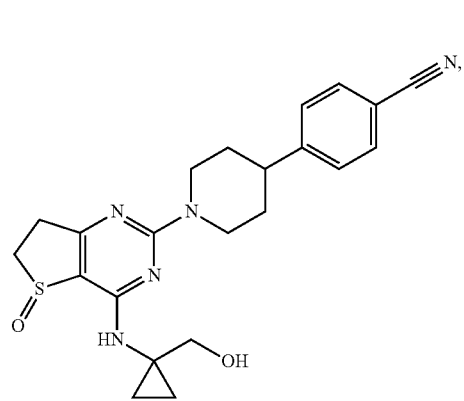
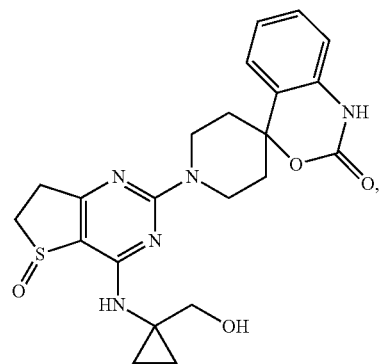
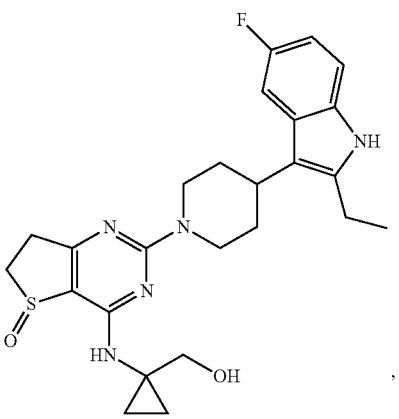

547
-continued
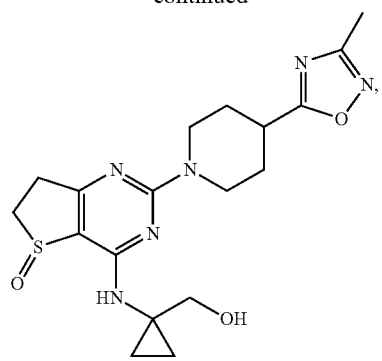
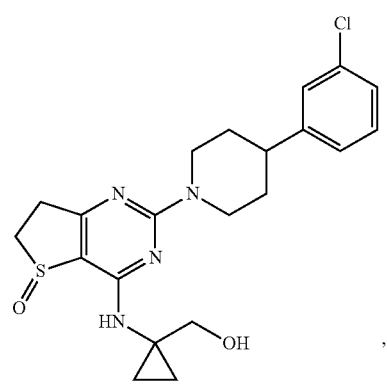
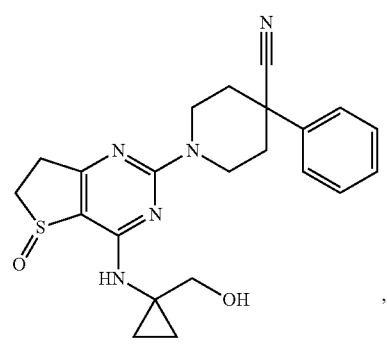
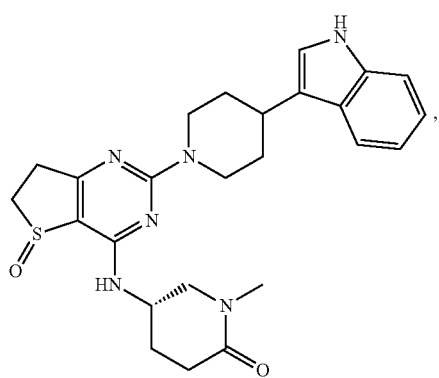
548
-continued
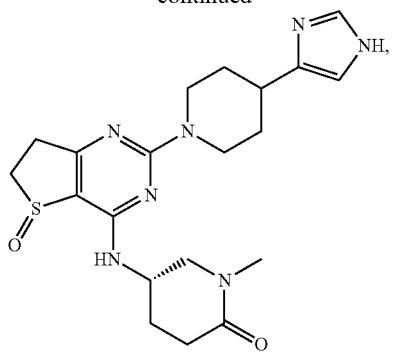
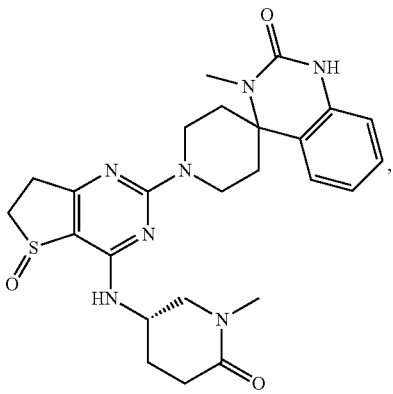
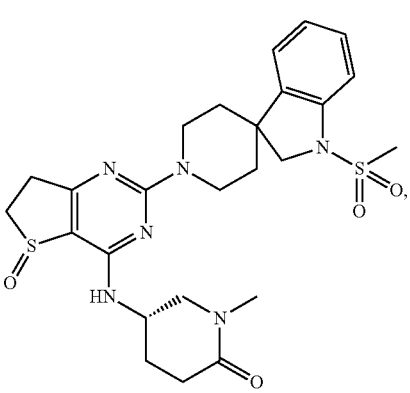
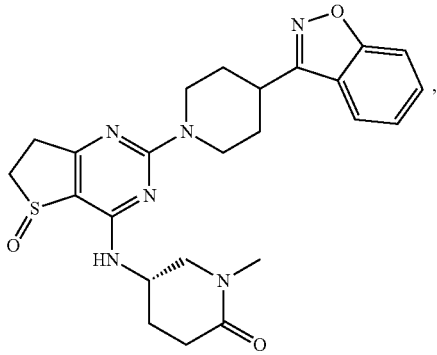

549
-continued

550
-continued

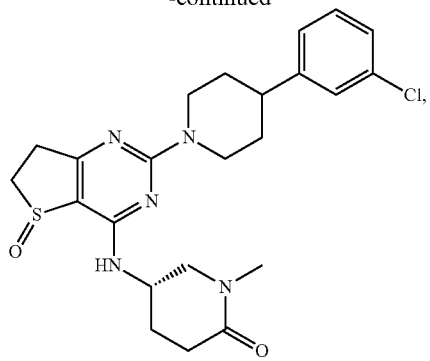
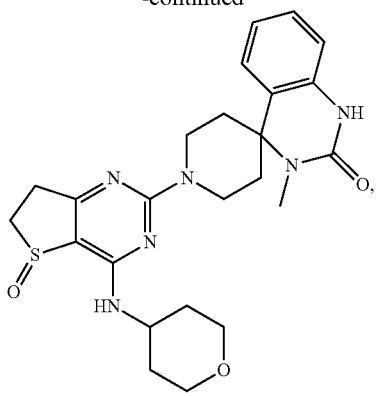
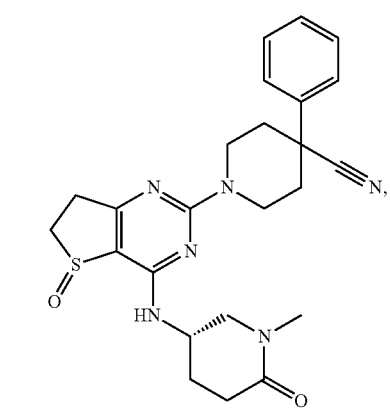
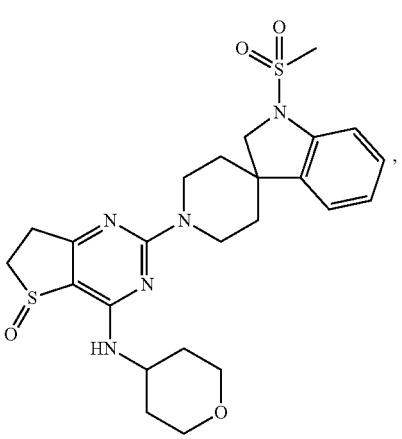
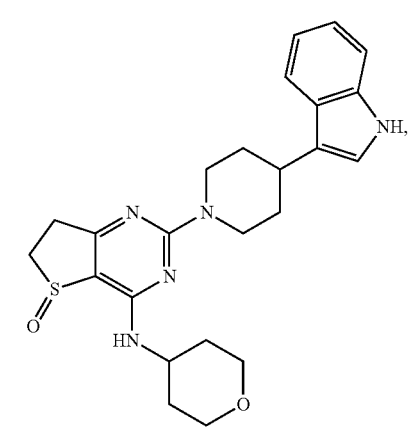
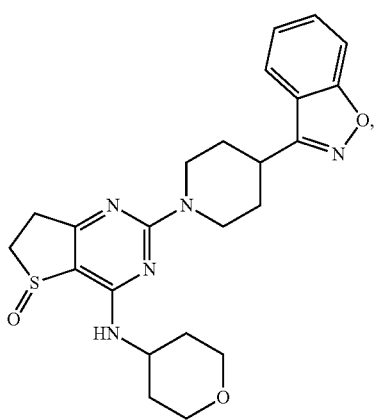
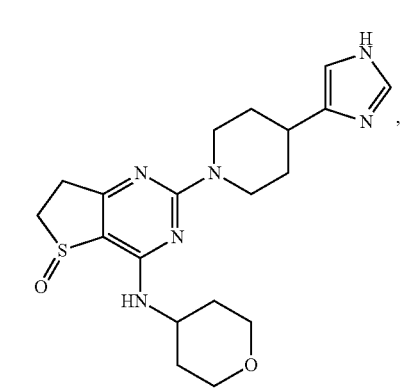
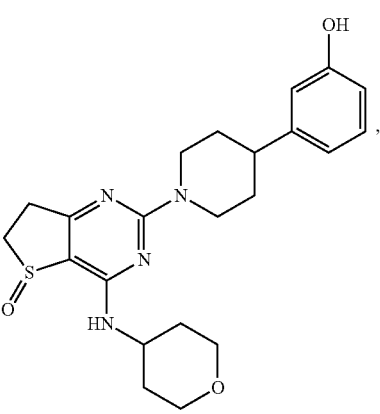

553
-continued
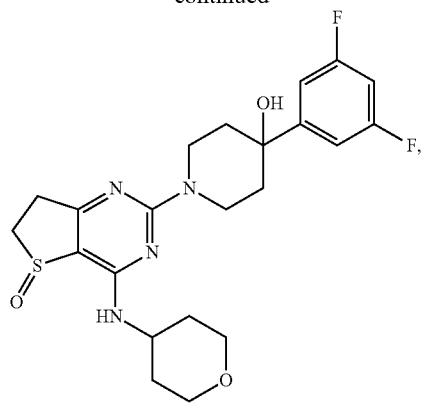
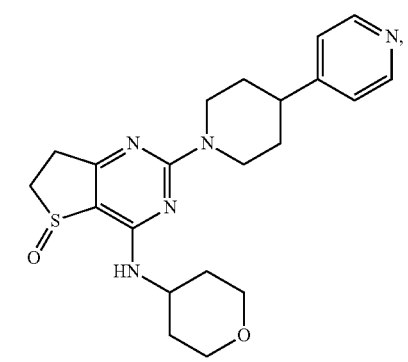
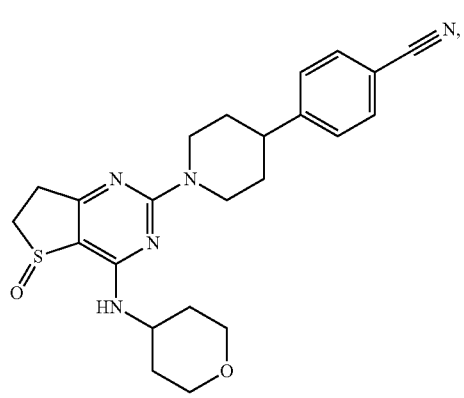
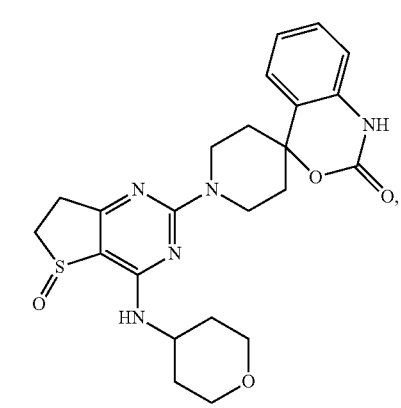
554
-continued
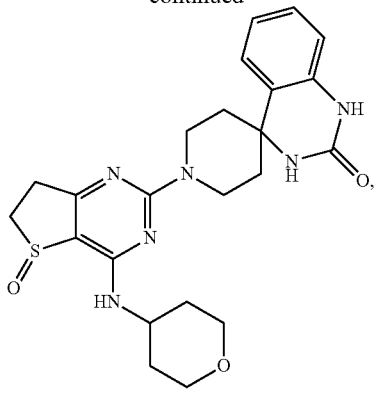
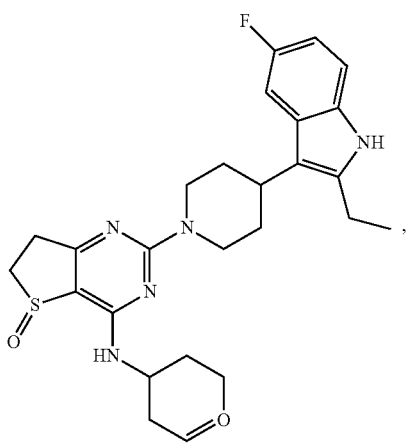
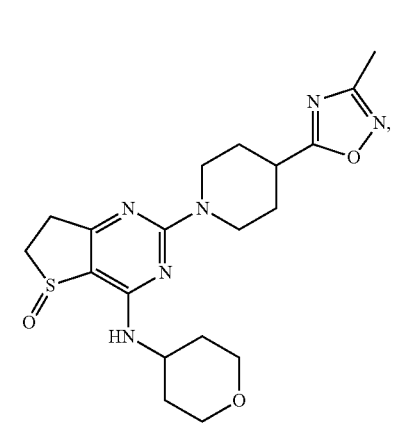
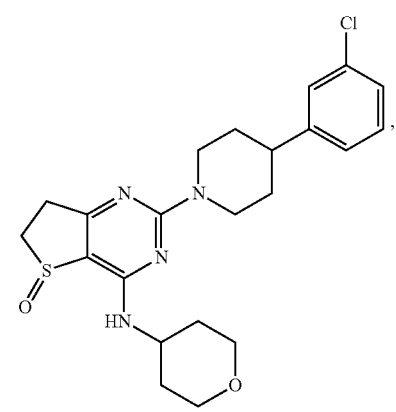

555
-continued
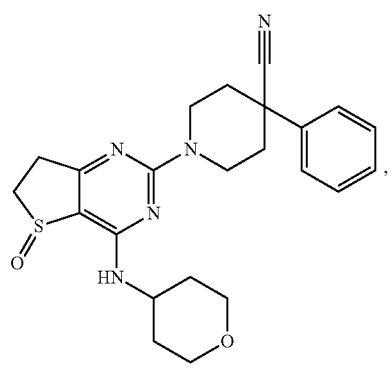
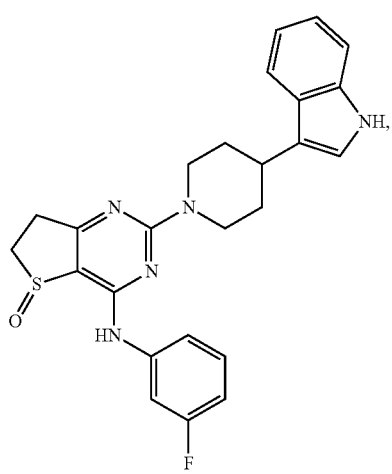
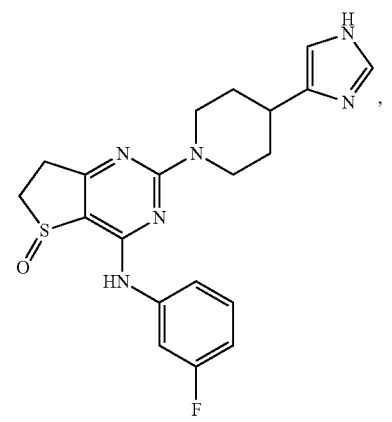
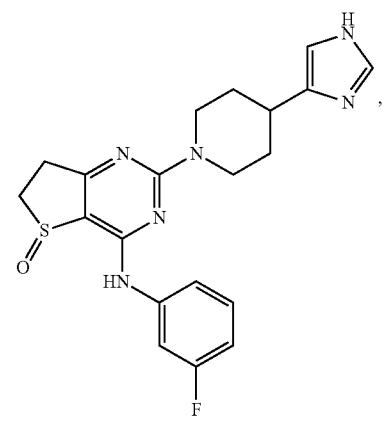
556
-continued
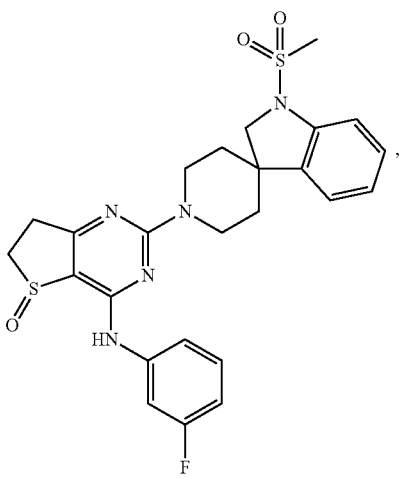
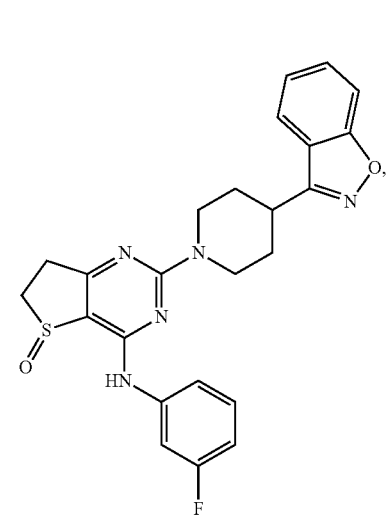
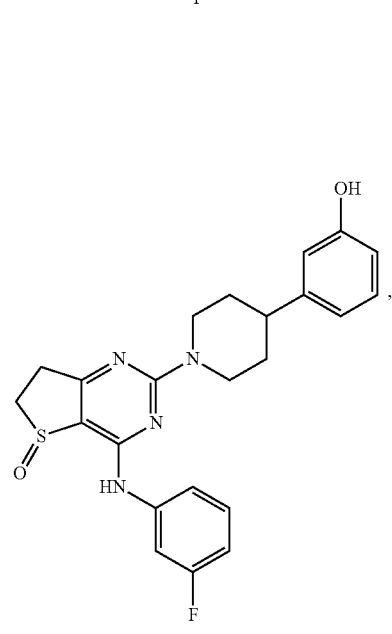

557
-continued
558
-continued
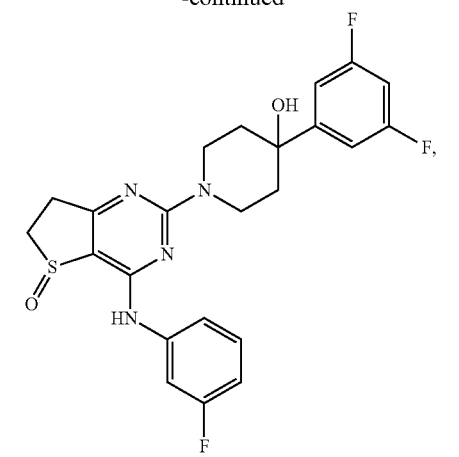
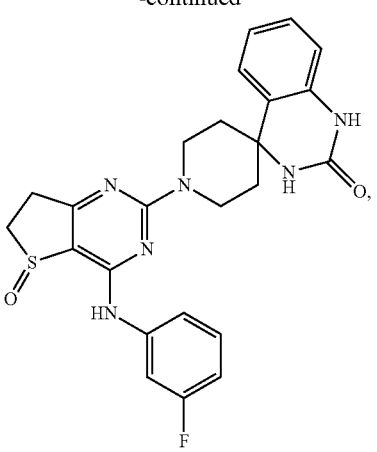
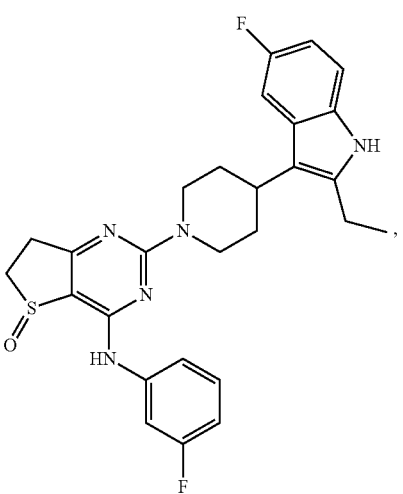
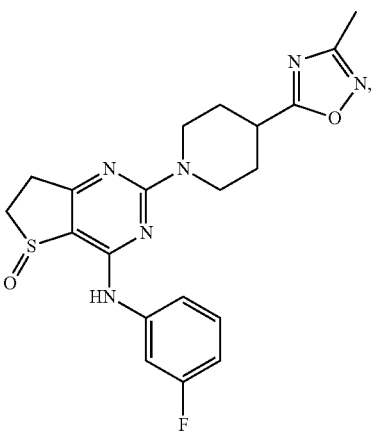

559
-continued
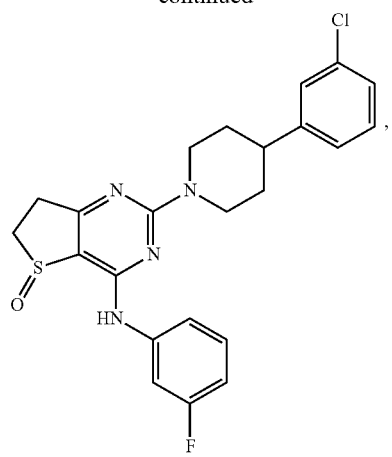
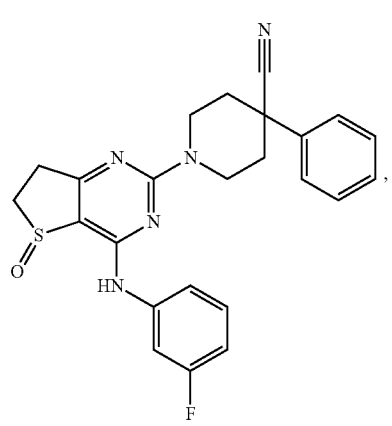
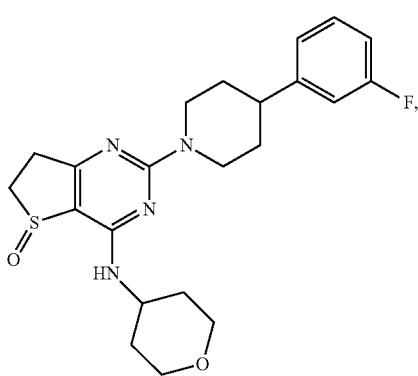
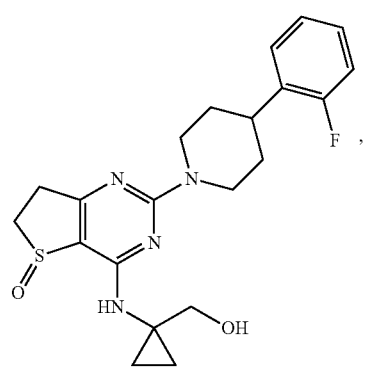
560
-continued
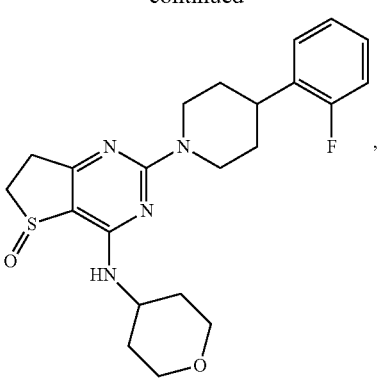
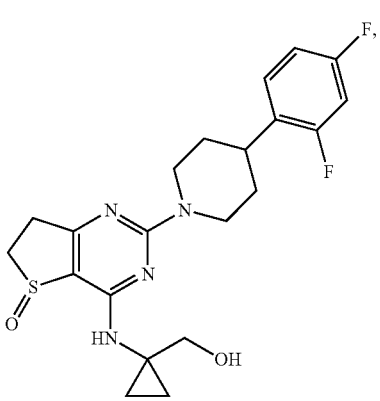
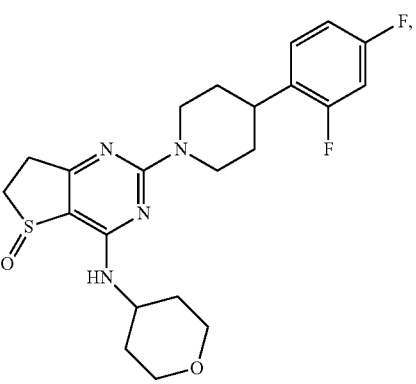
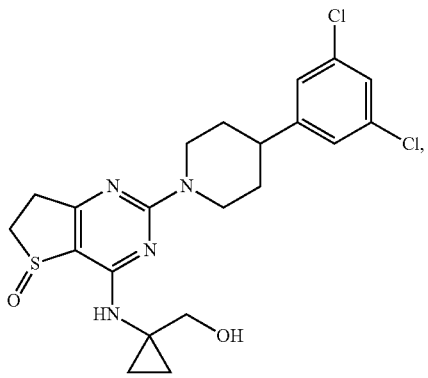

561
-continued
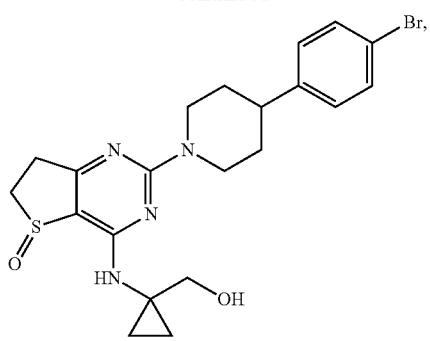
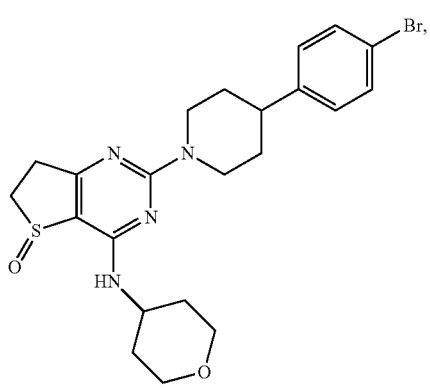
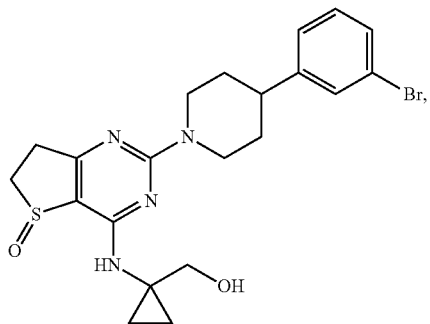
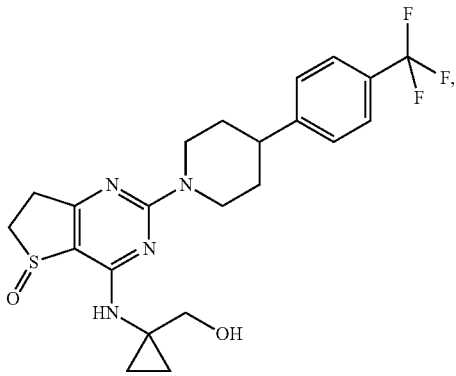
562
-continued
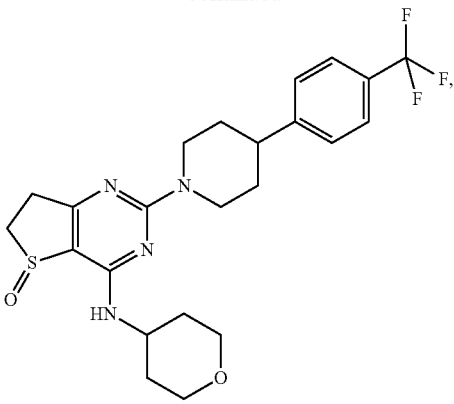
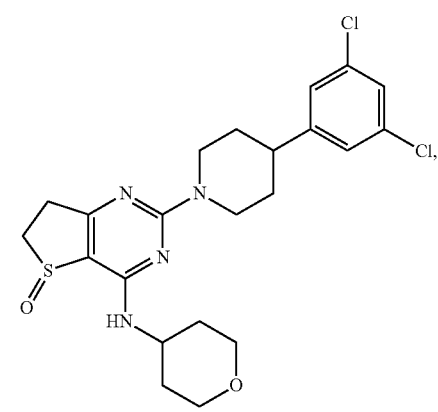
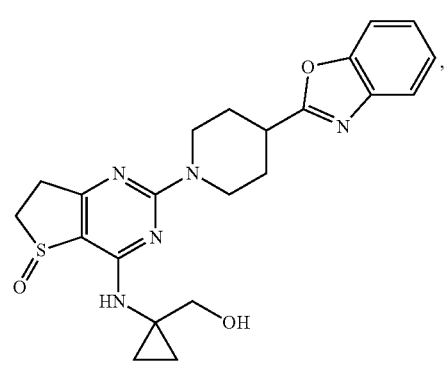
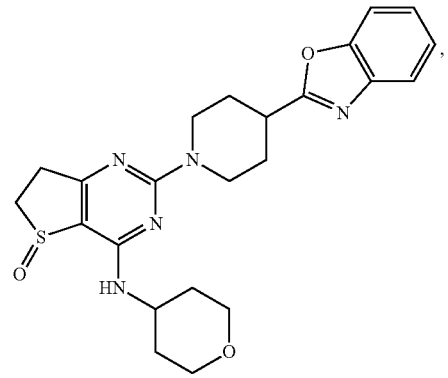

563
-continued
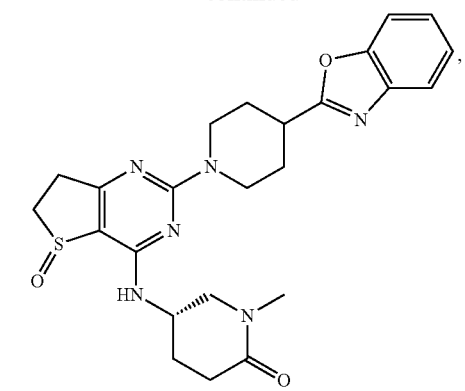
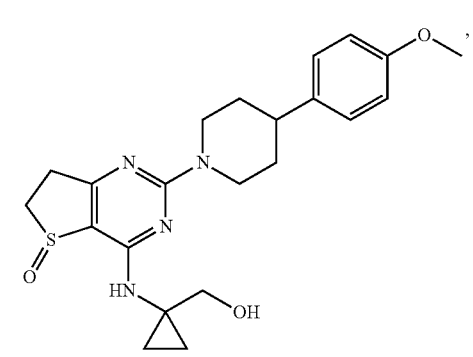
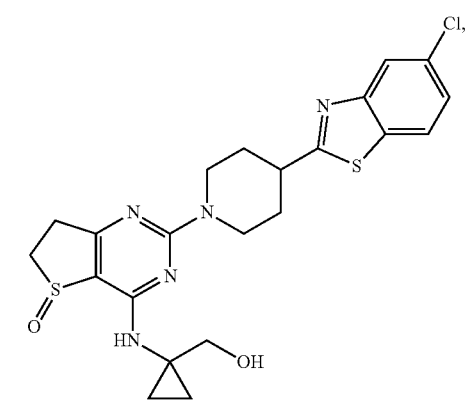
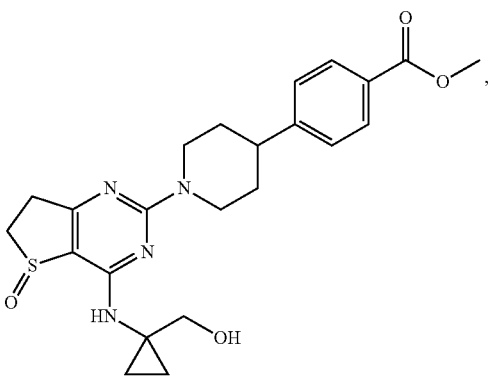
564
-continued
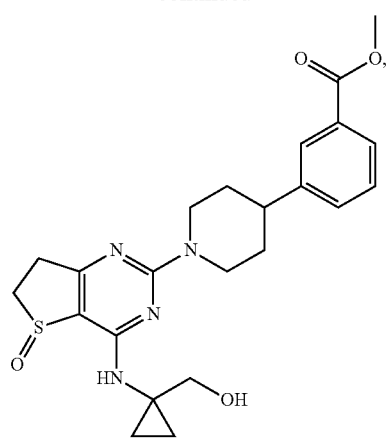
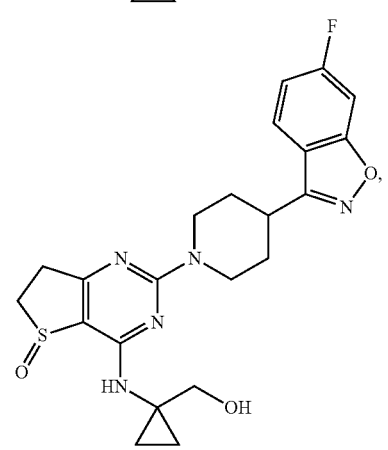
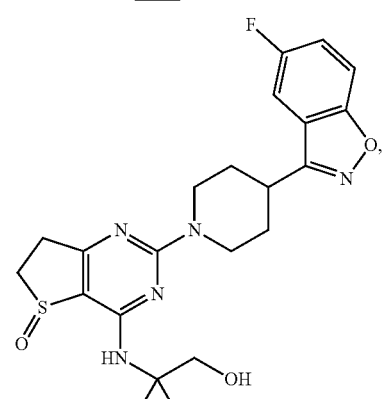
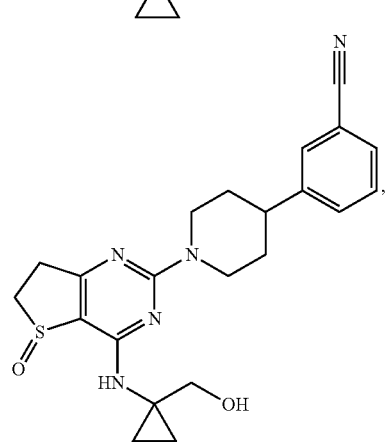

565
-continued
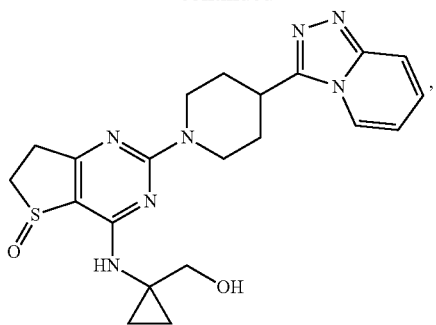
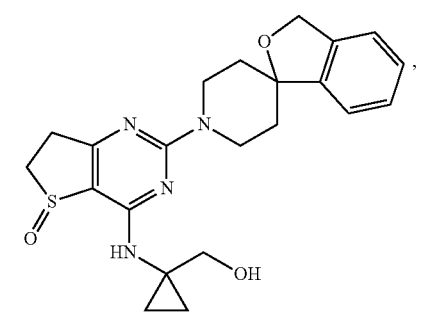
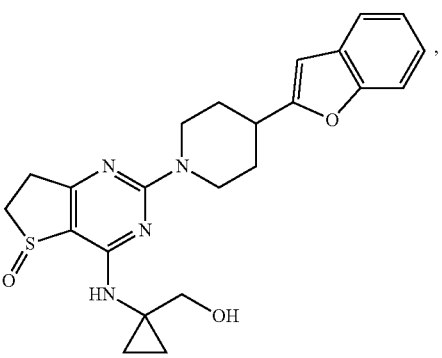
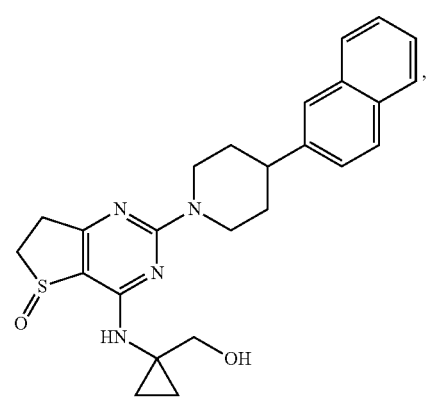
566
-continued
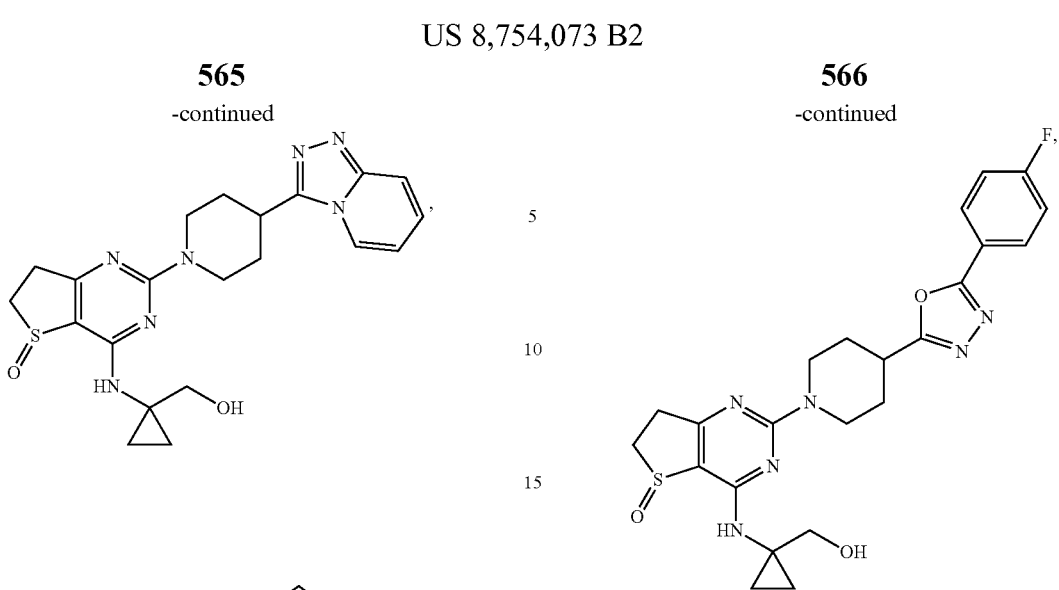
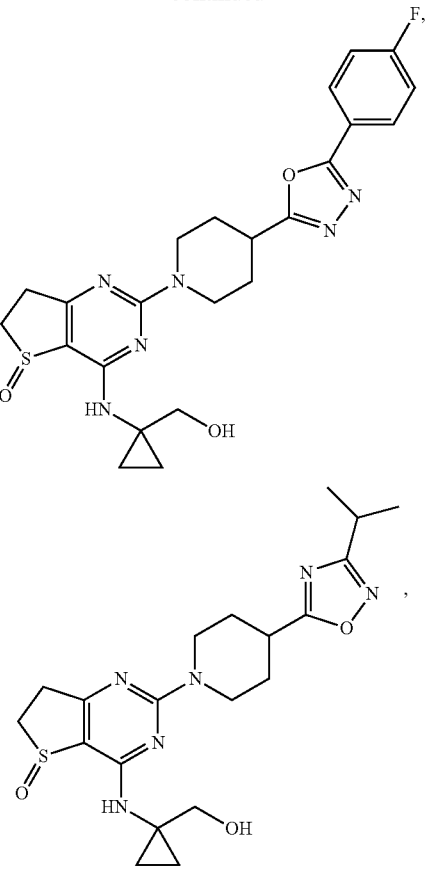
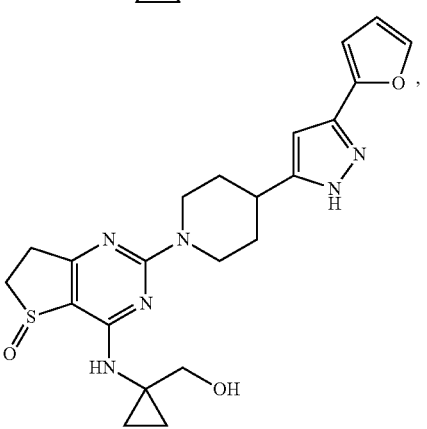
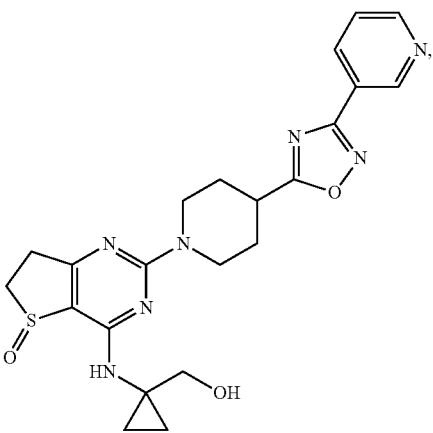

567
-continued
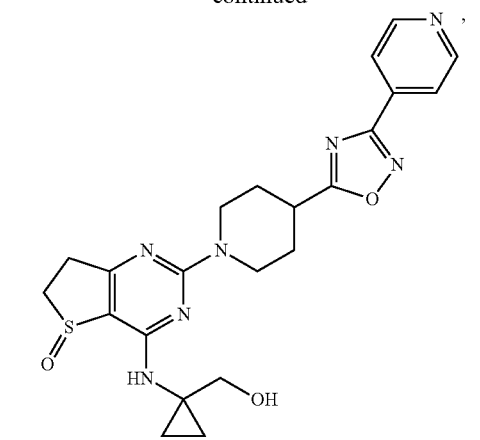
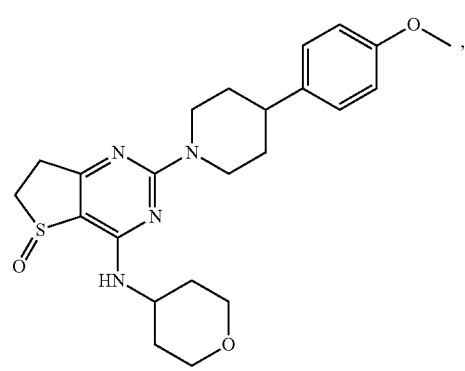
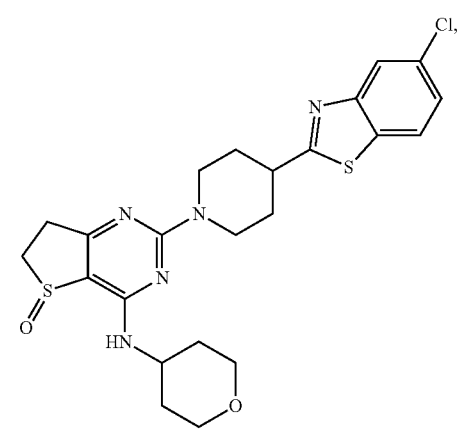
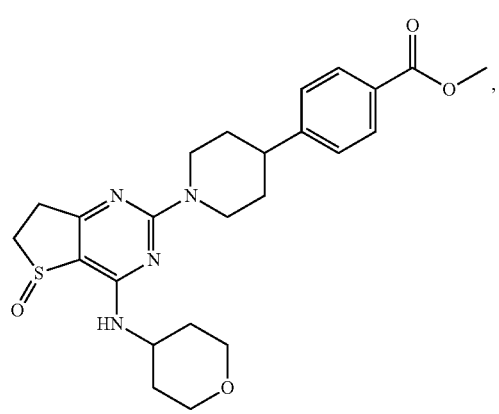
568
-continued
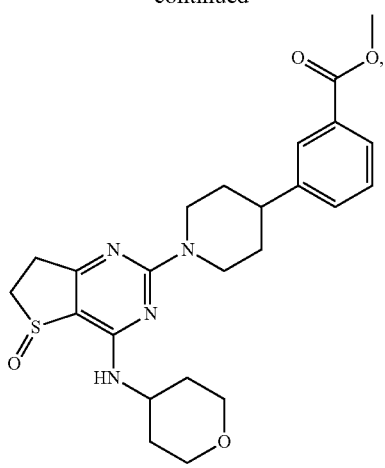
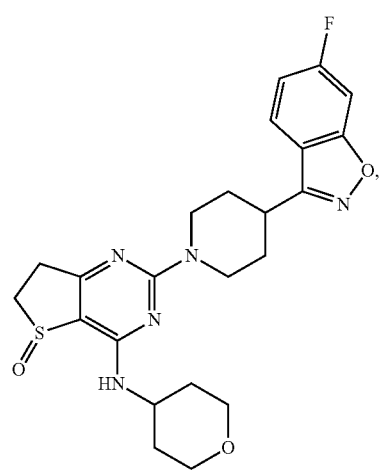
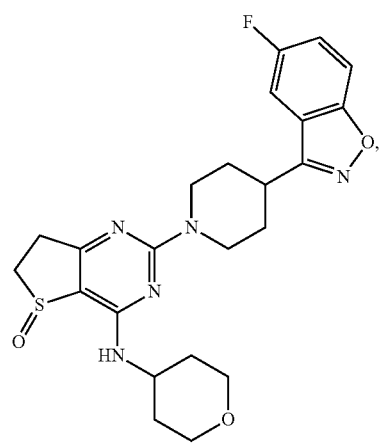

569
-continued
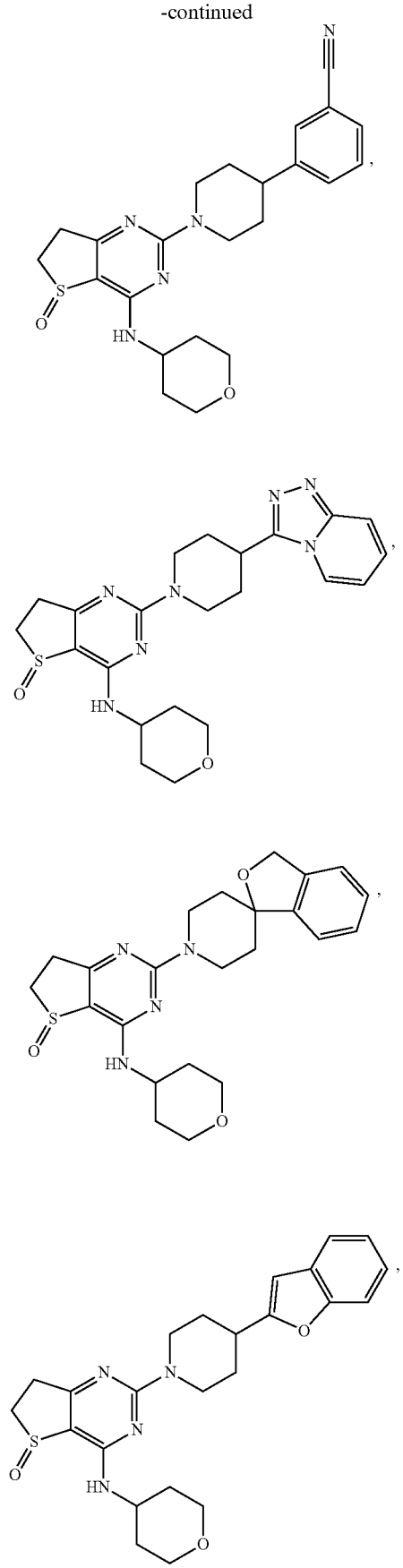
570
-continued
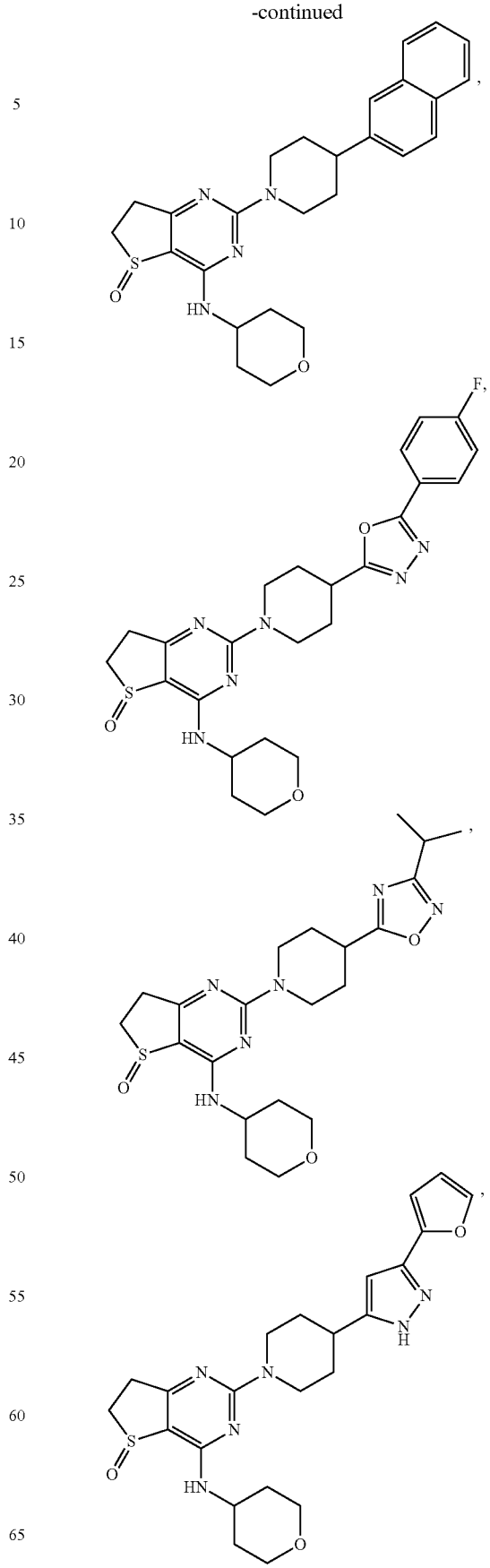

571
-continued
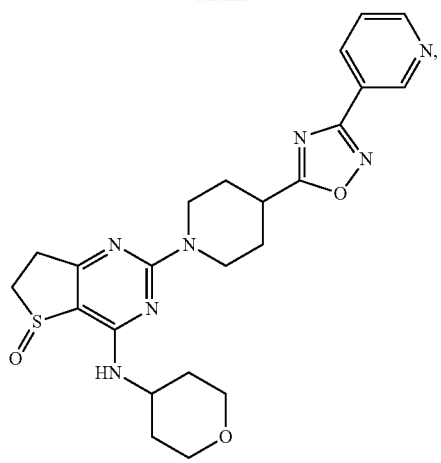
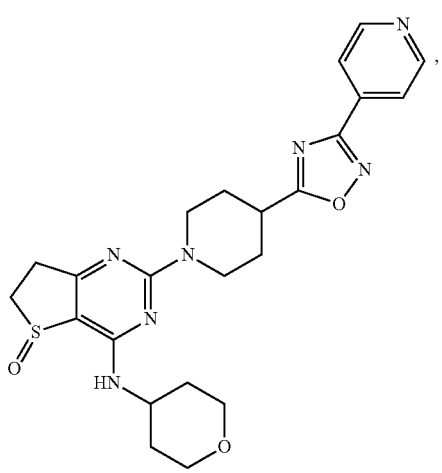
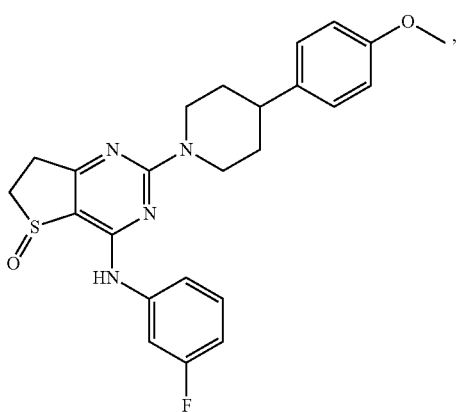
572
-continued
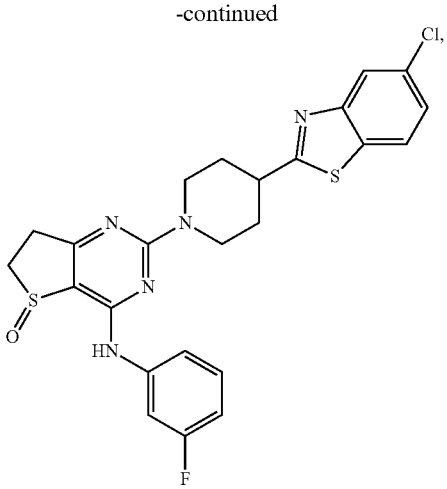
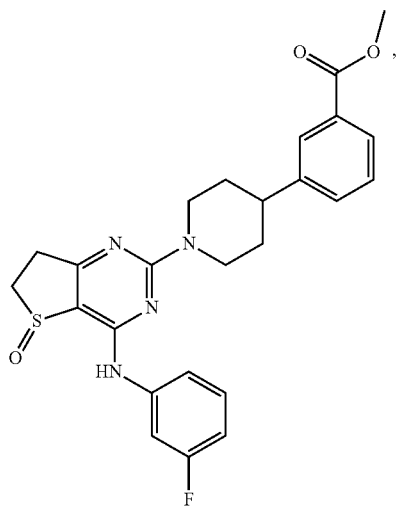
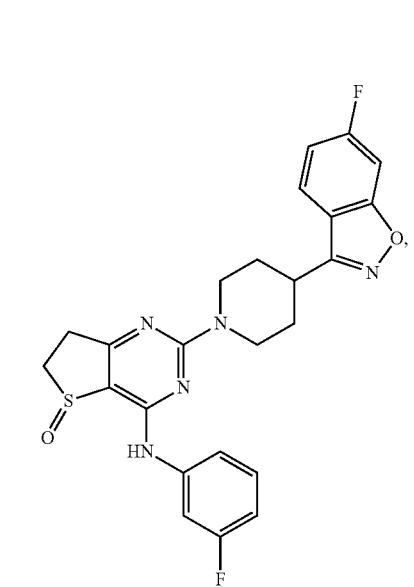

573
-continued
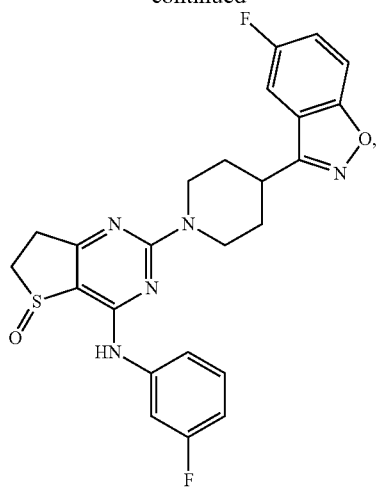
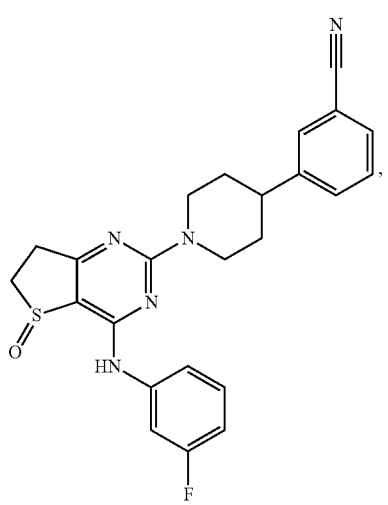
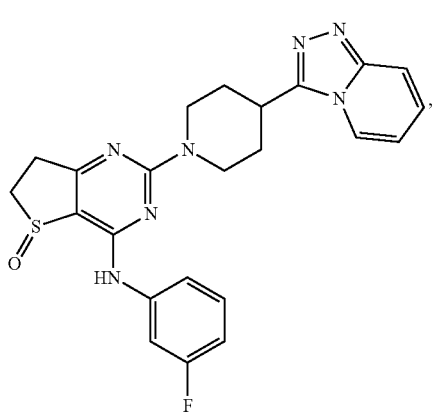
574
-continued
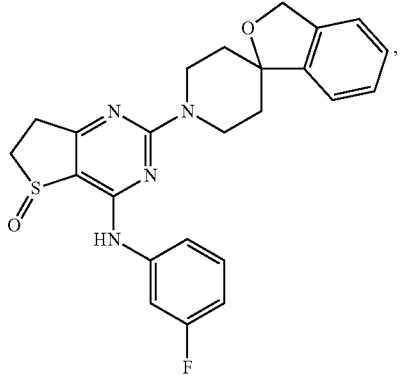
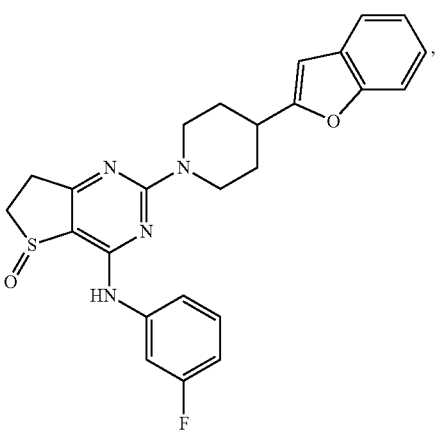
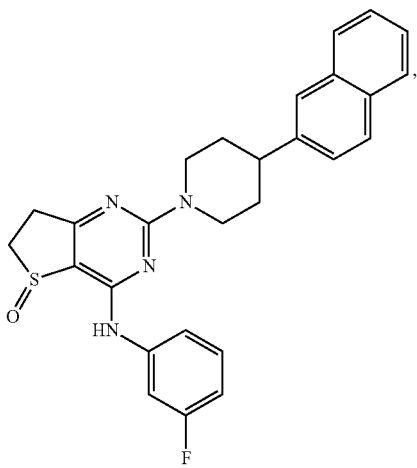

575
-continued
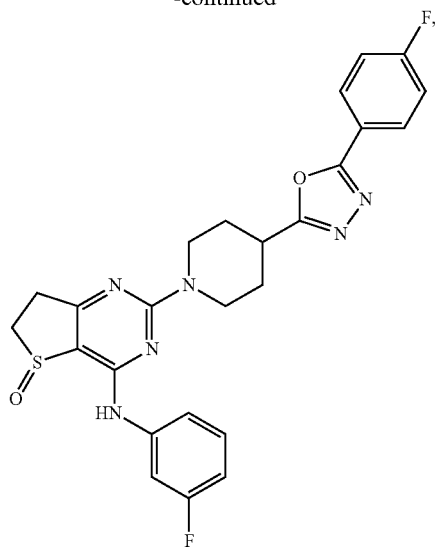
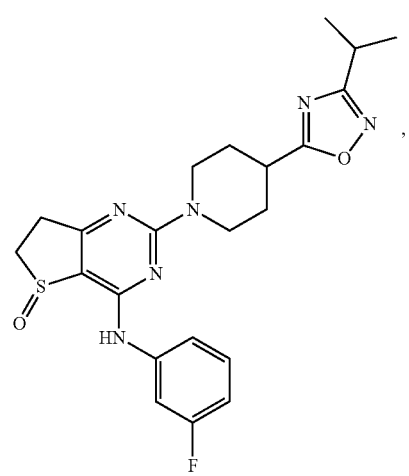
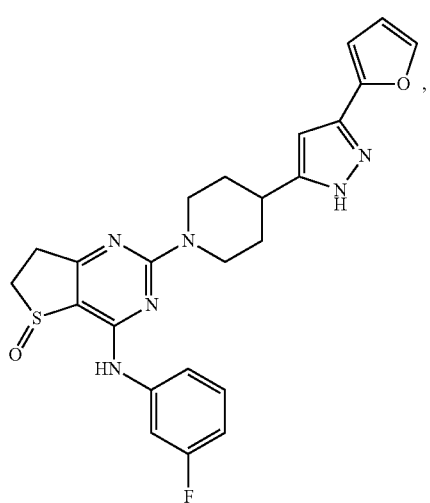
576
-continued
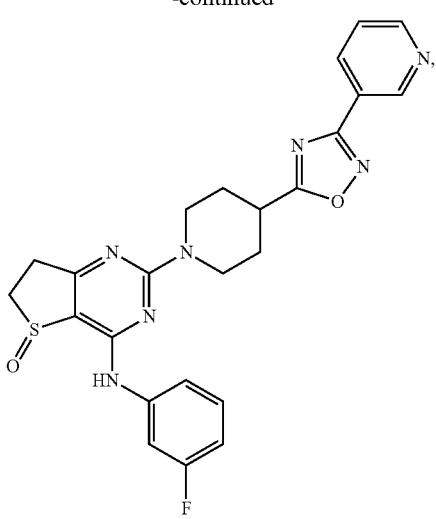
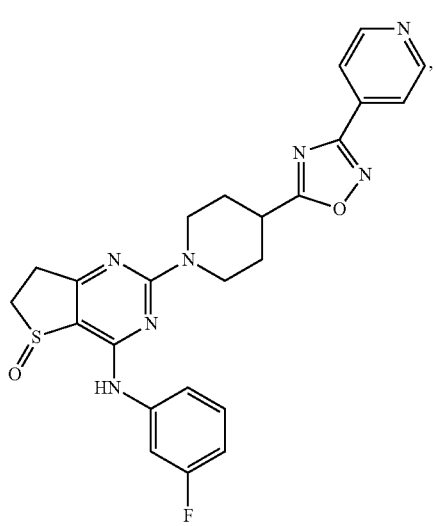
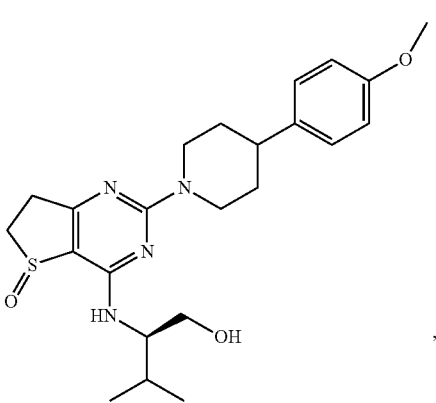

577
-continued
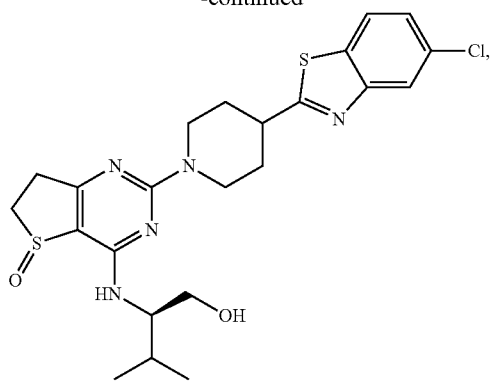
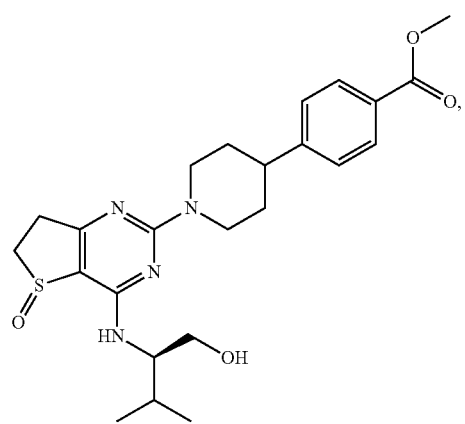
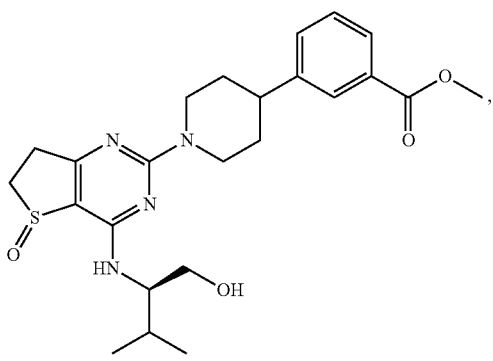
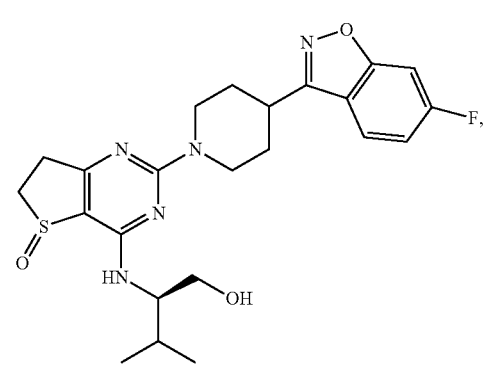
578
-continued
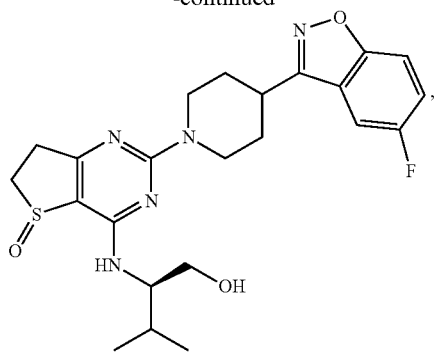
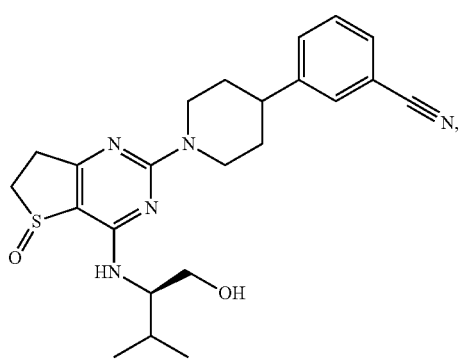
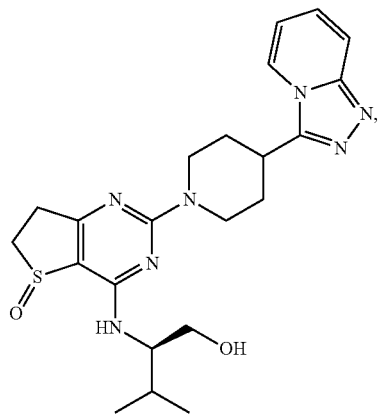
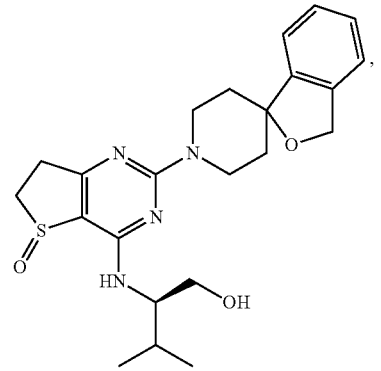

579
-continued
580
-continued
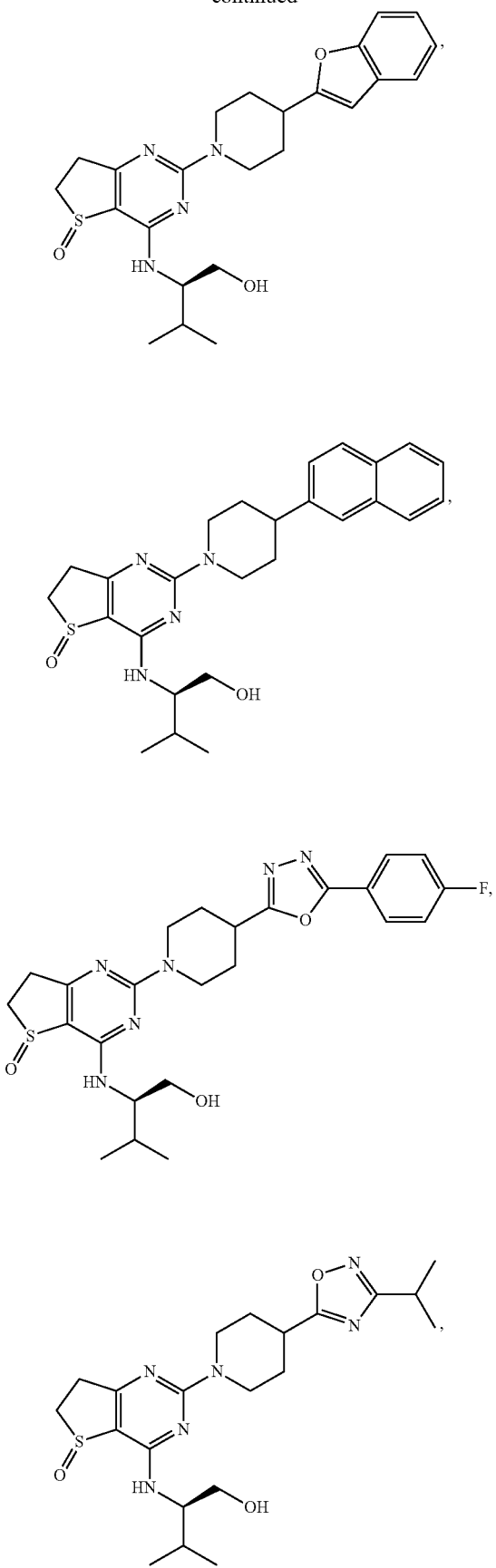
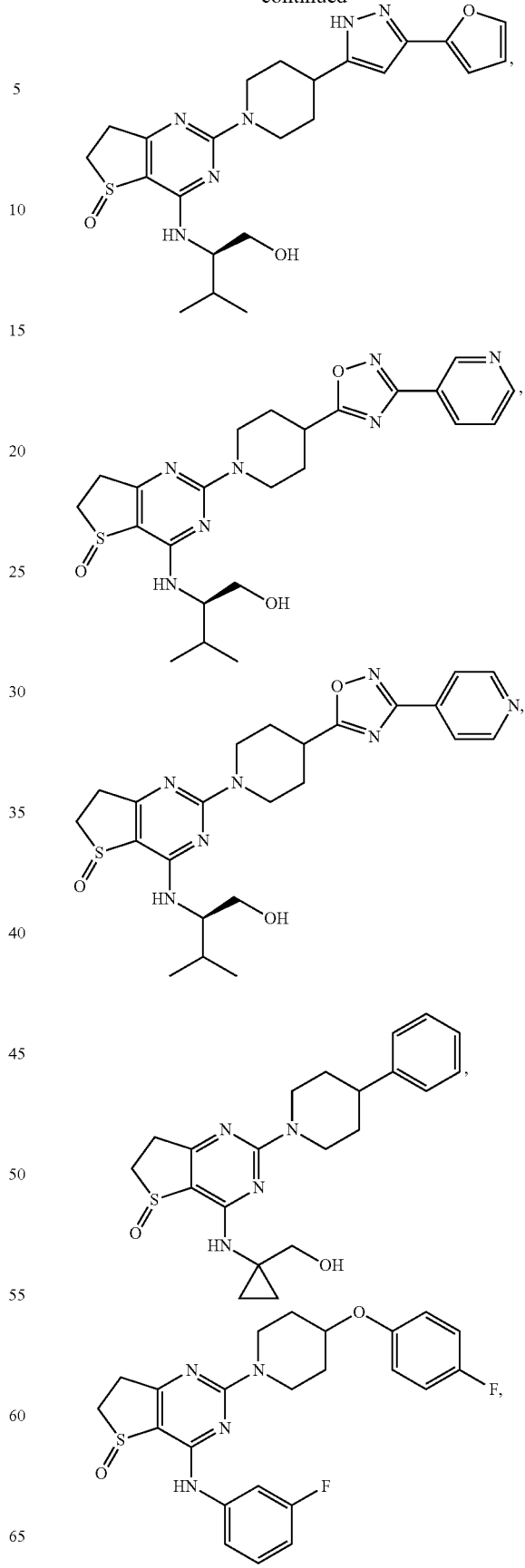

581
-continued
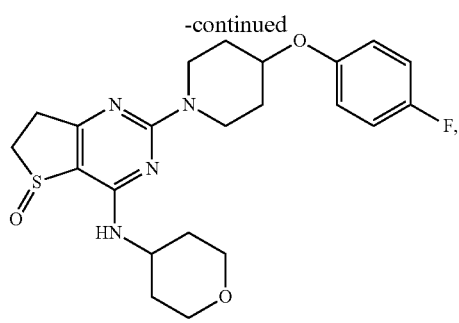
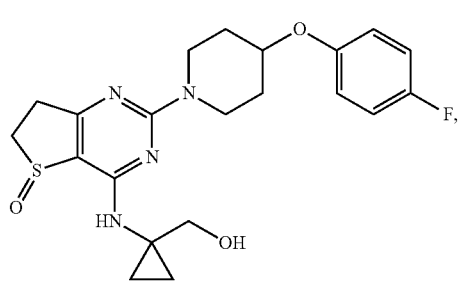
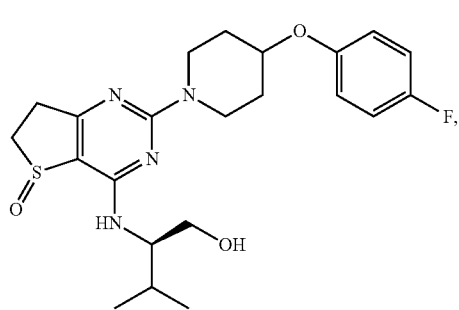
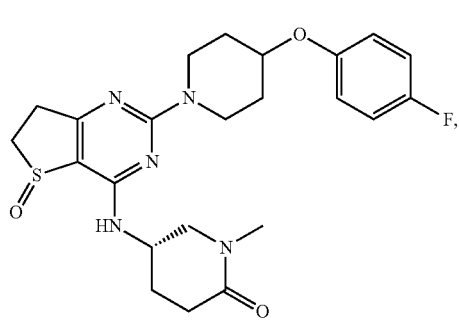
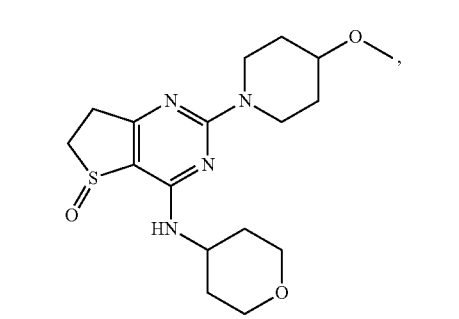
582
-continued
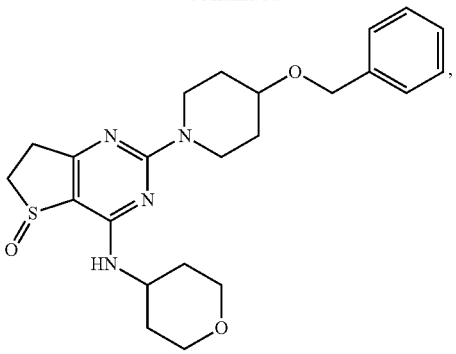
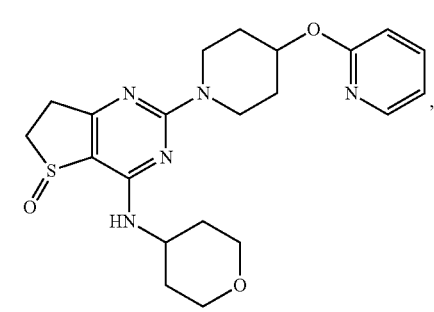
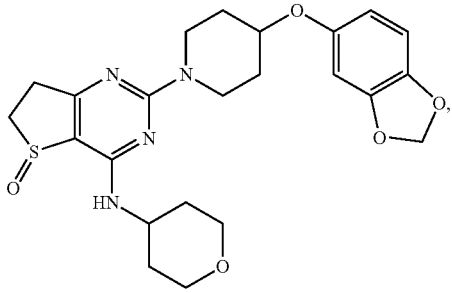
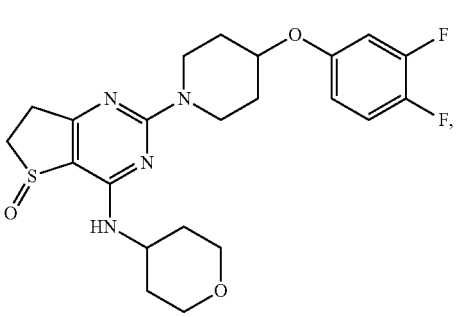
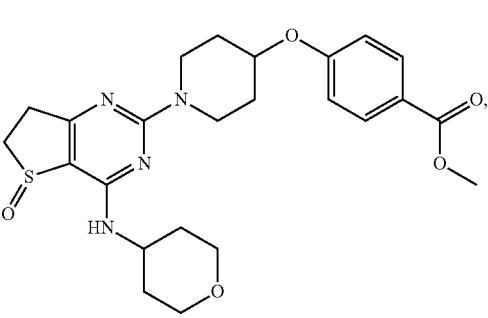

583
-continued
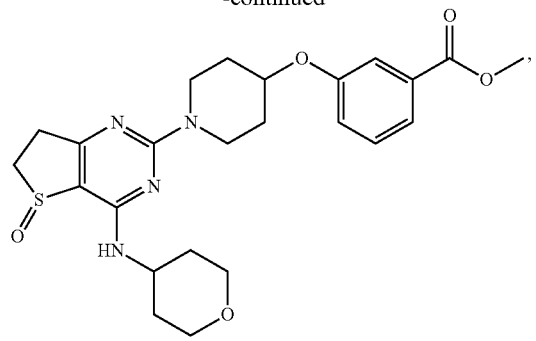
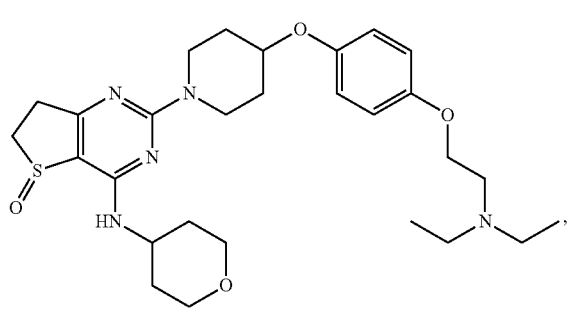
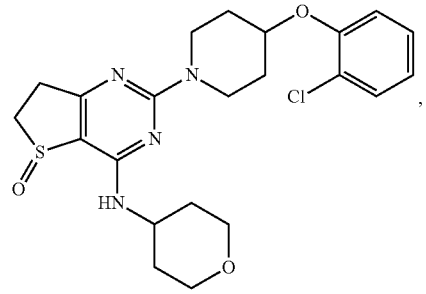
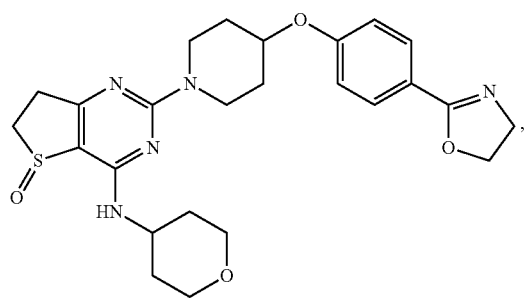
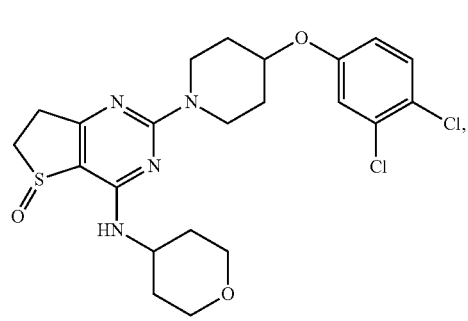
584
-continued
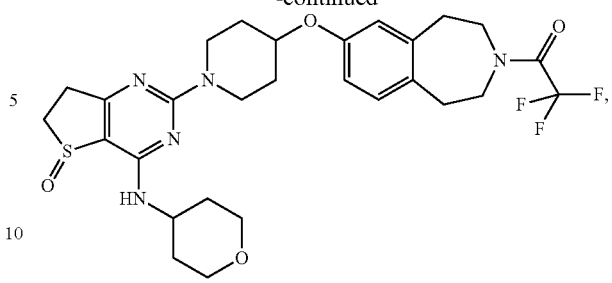
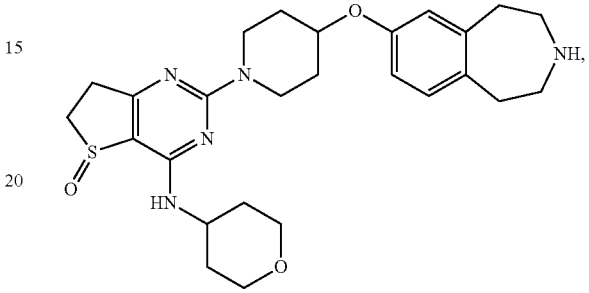
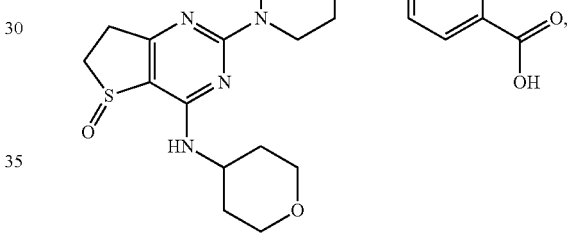
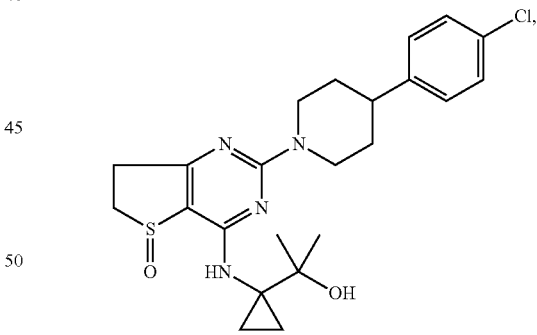
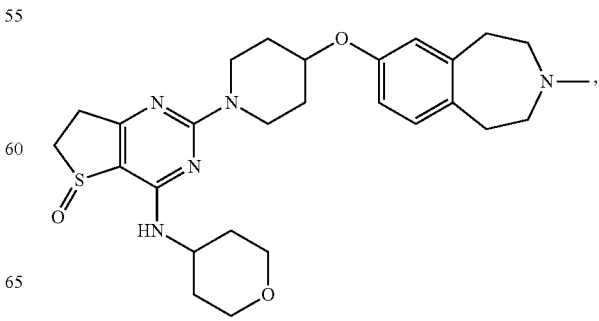

585
-continued
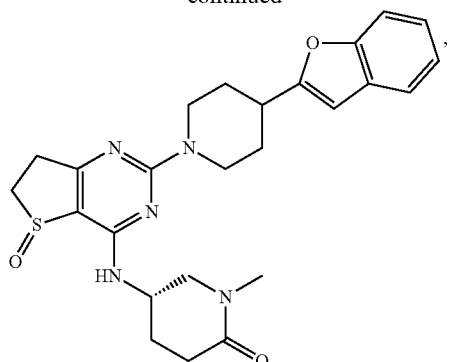
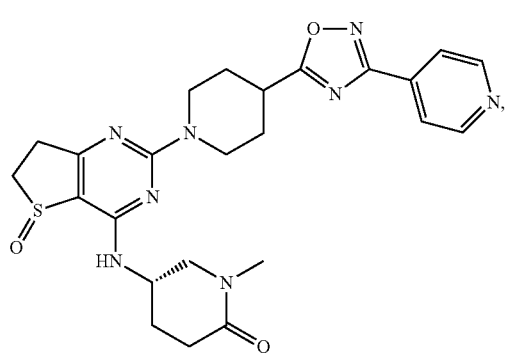
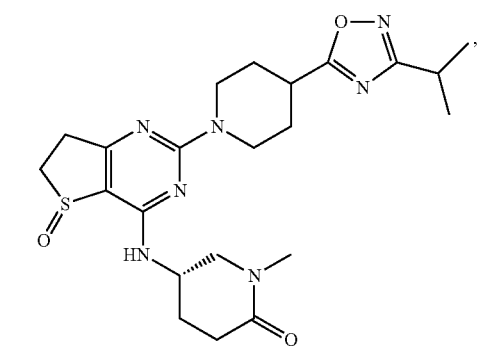
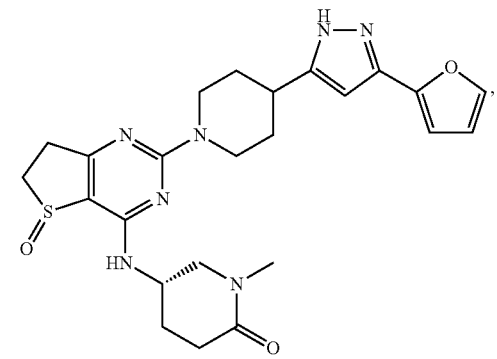
586
-continued
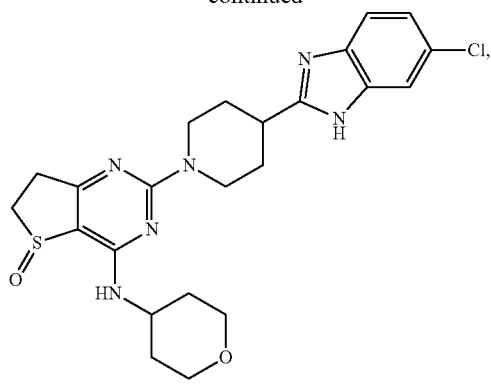
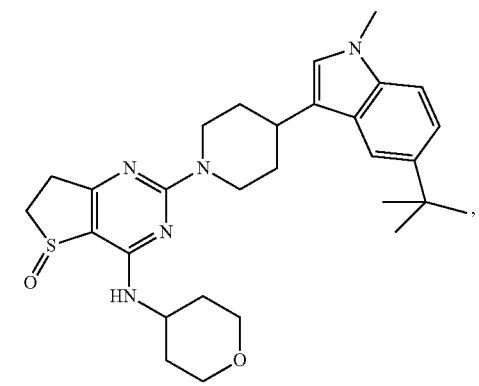
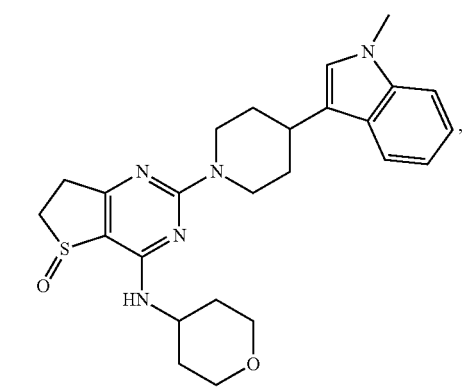
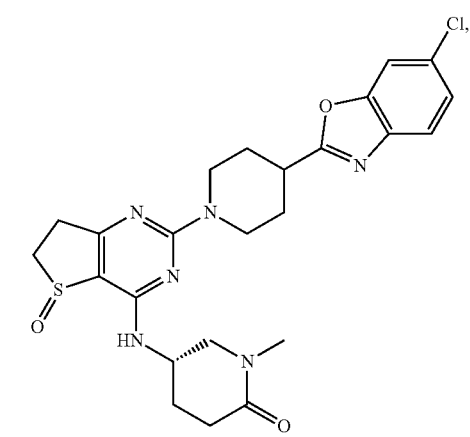

587
-continued
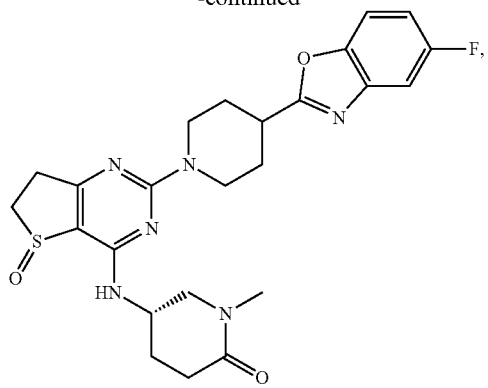
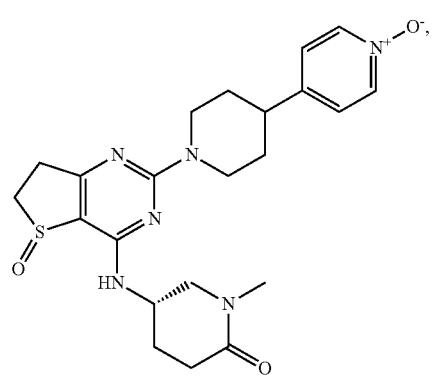
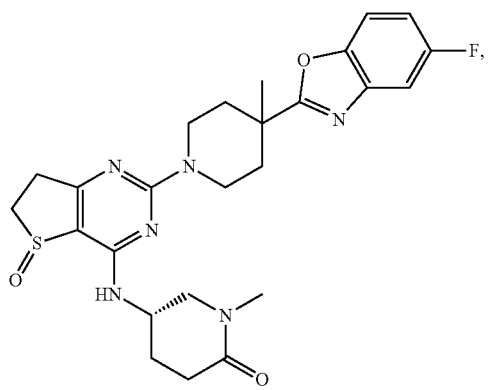
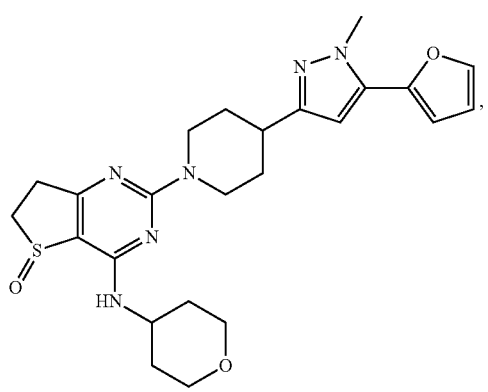
588
-continued
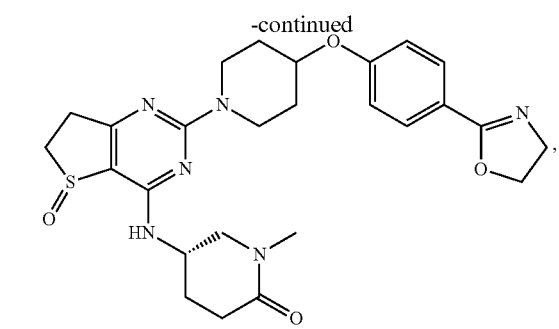
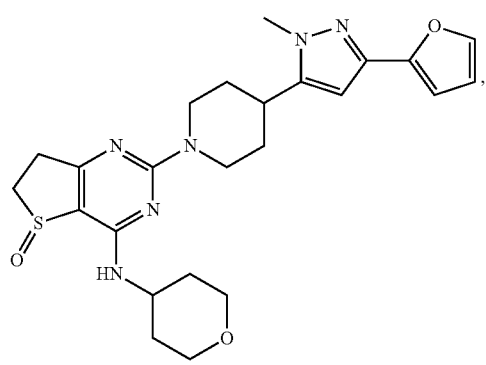
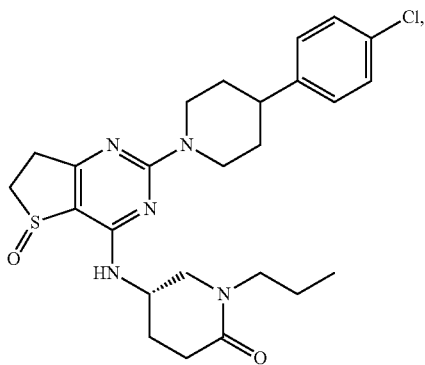
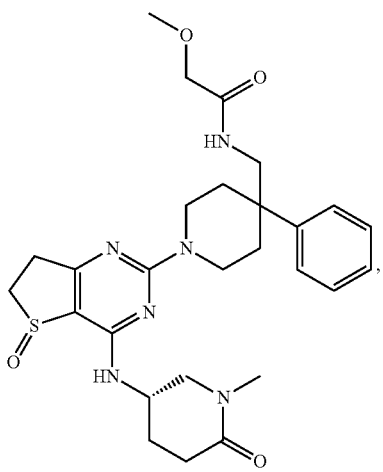

589
-continued
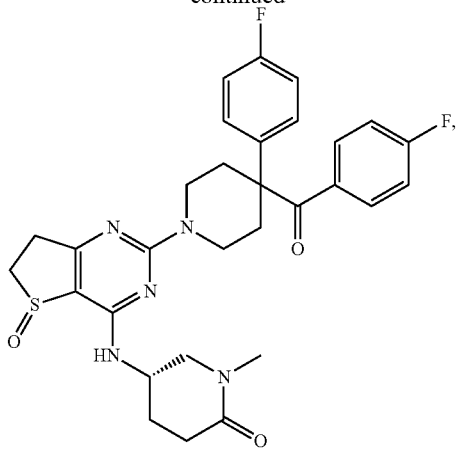
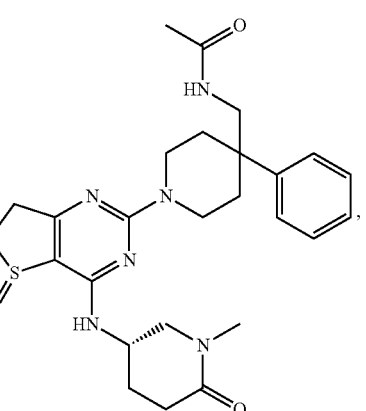
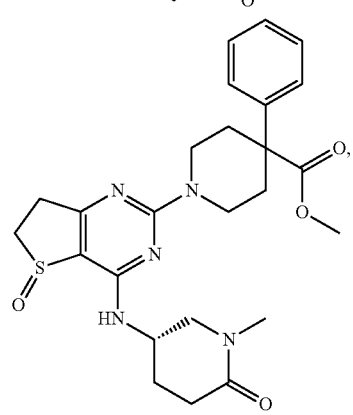
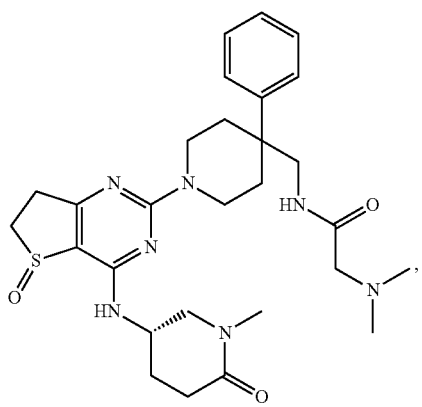
590
-continued
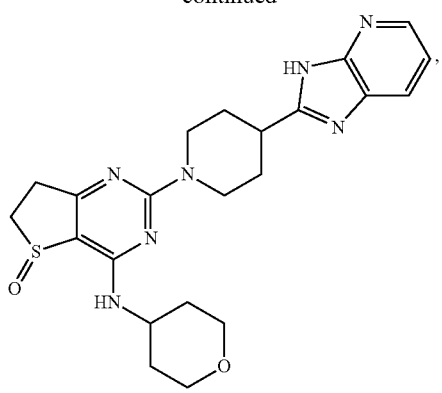
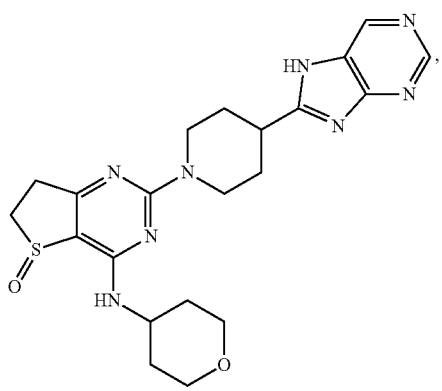
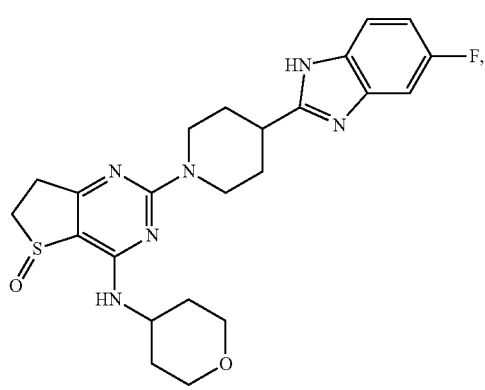
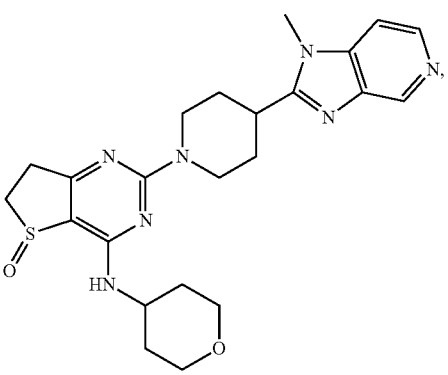

591
-continued
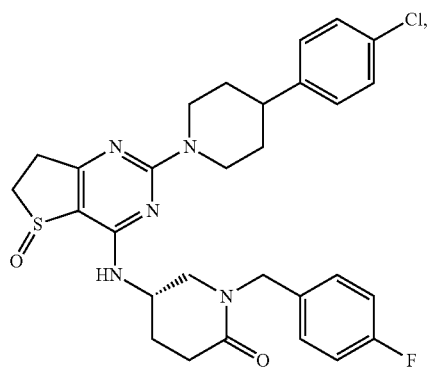
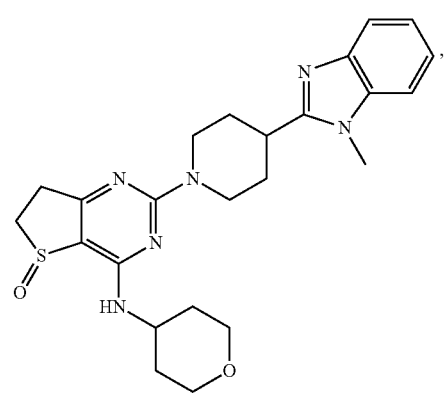
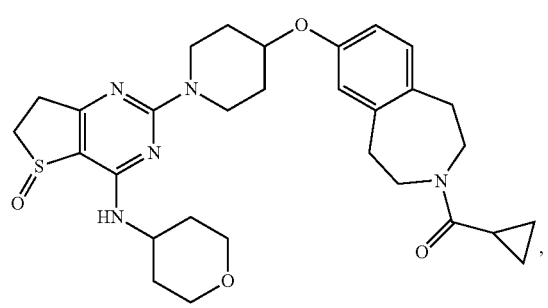
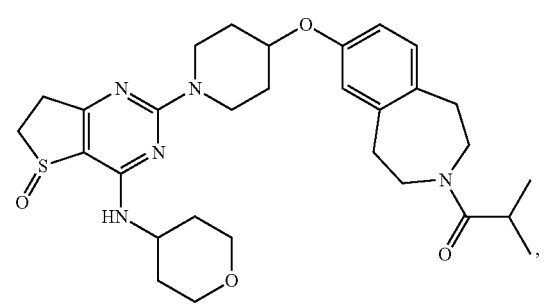
592
-continued
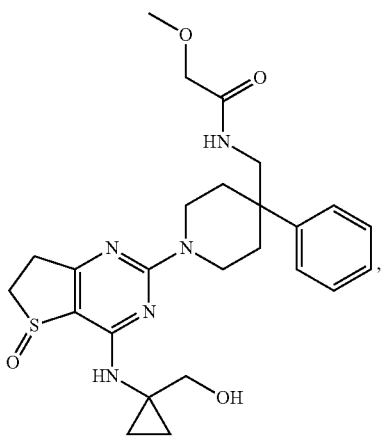
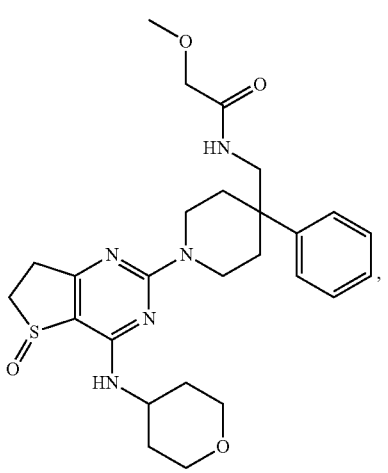
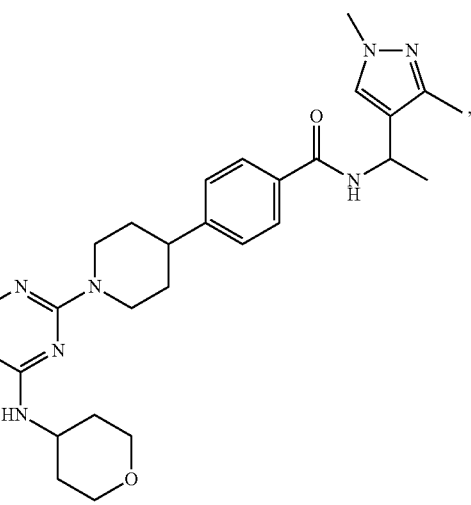

593
-continued
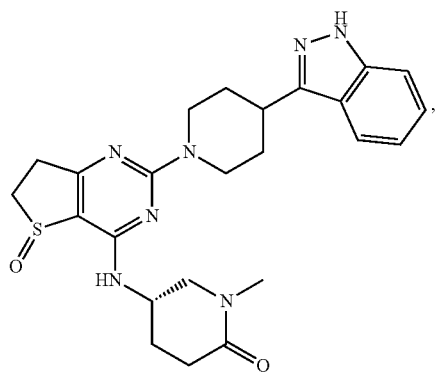
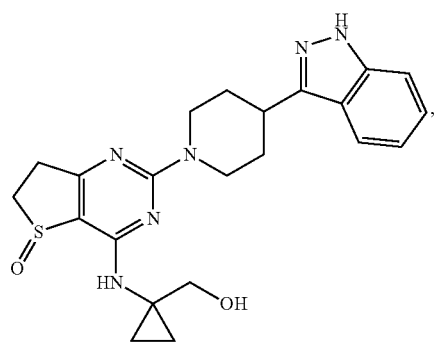
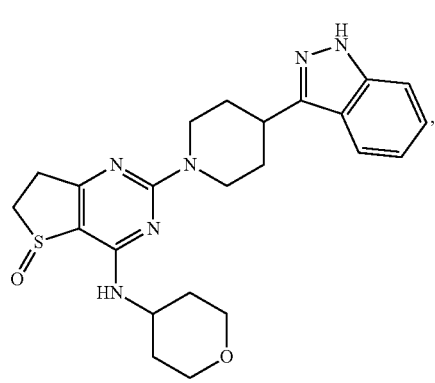
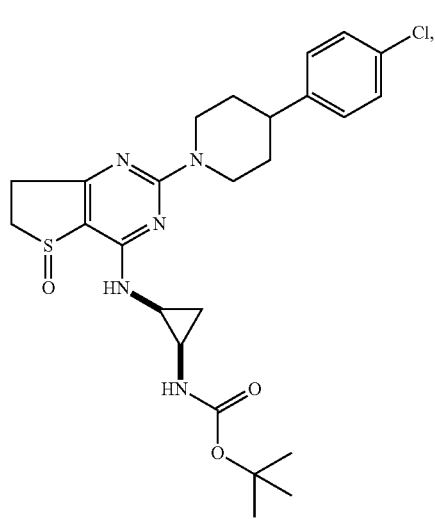
594
-continued
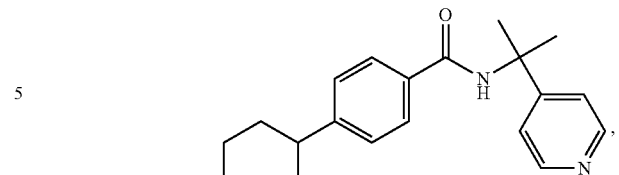
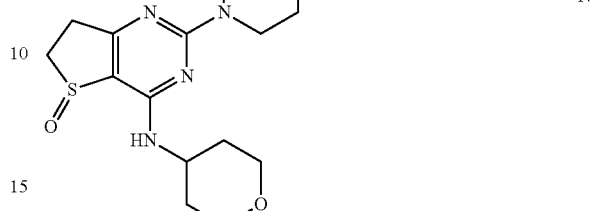
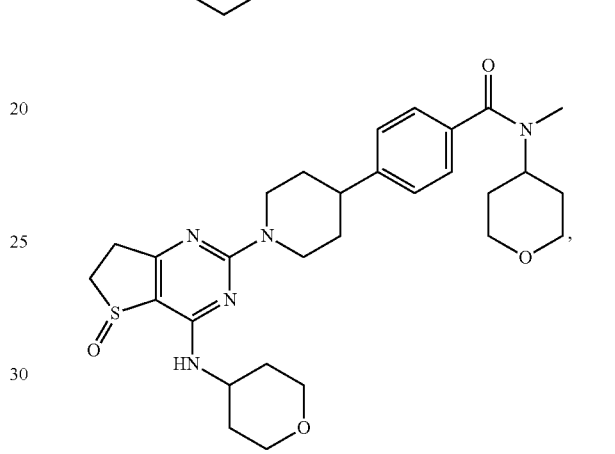
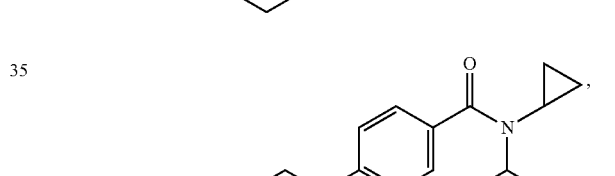
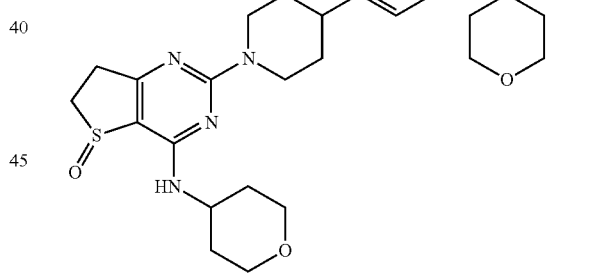
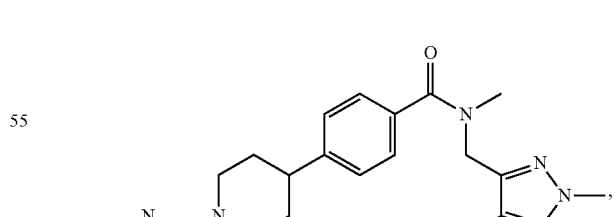
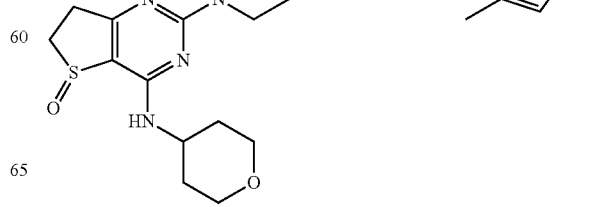

595
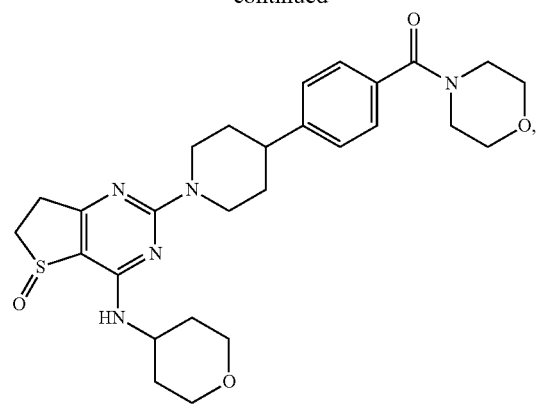
596
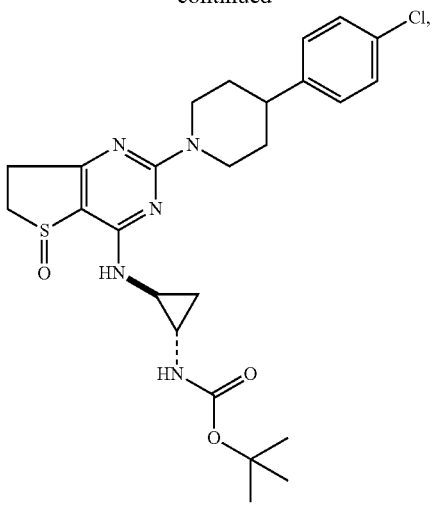

597
-continued
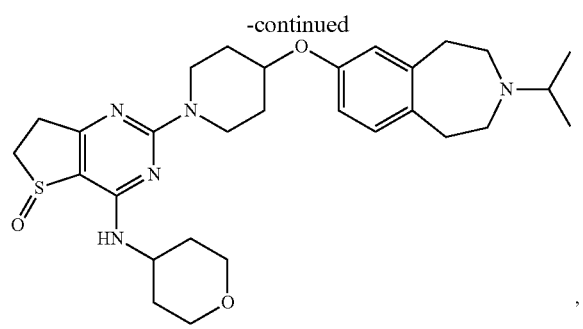
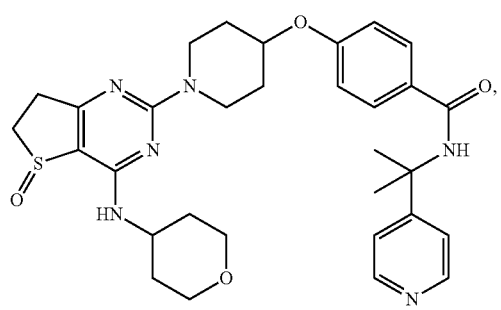
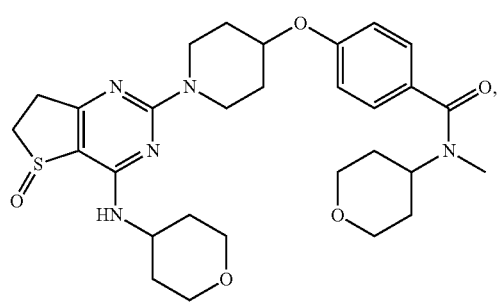
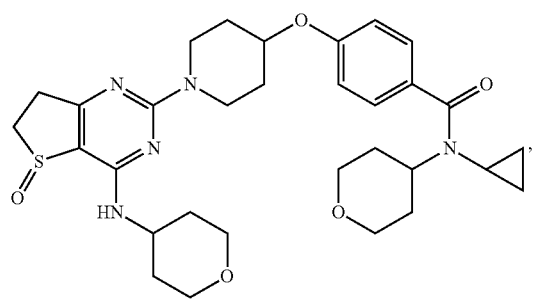
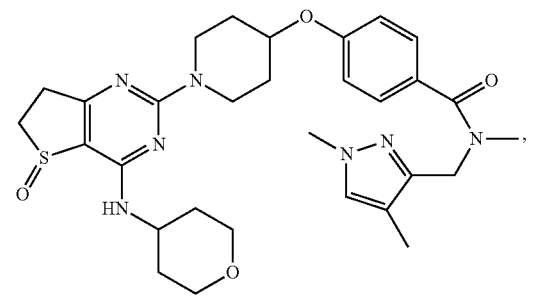
598
-continued
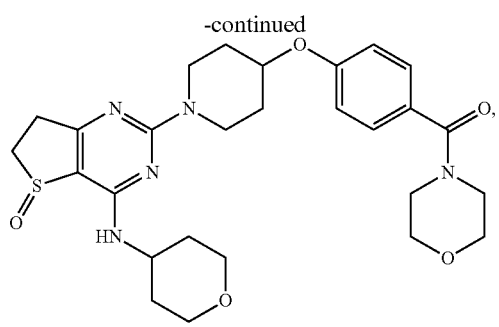
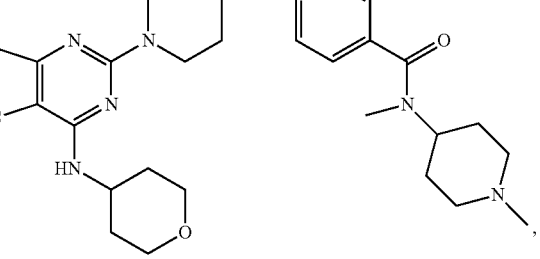
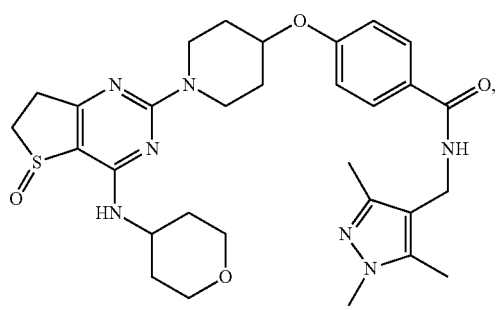
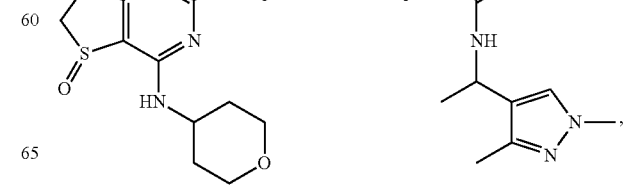

599
-continued
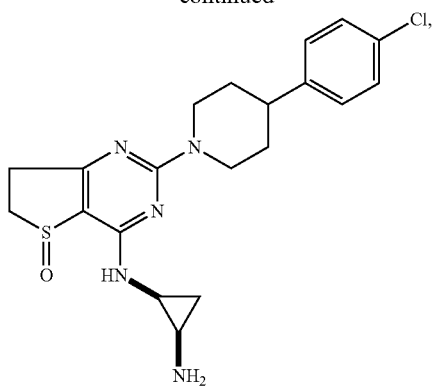
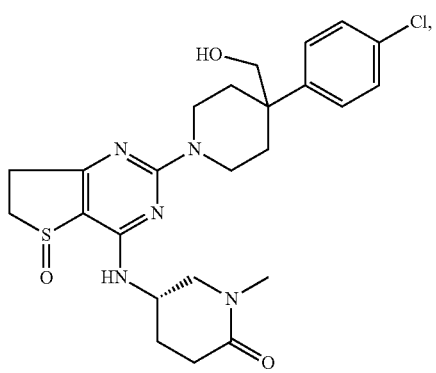
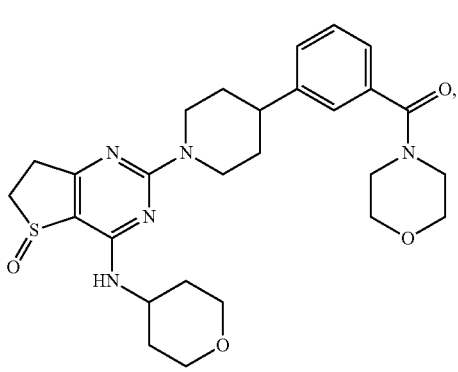
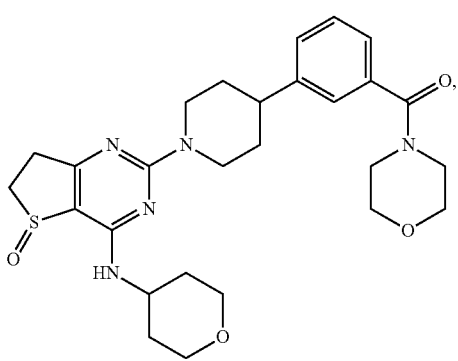
600
-continued
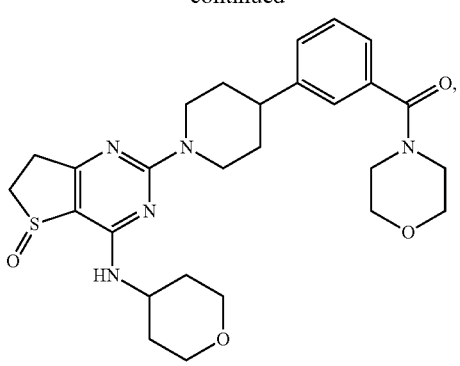
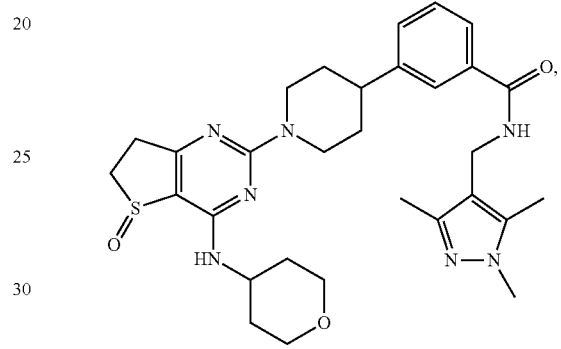
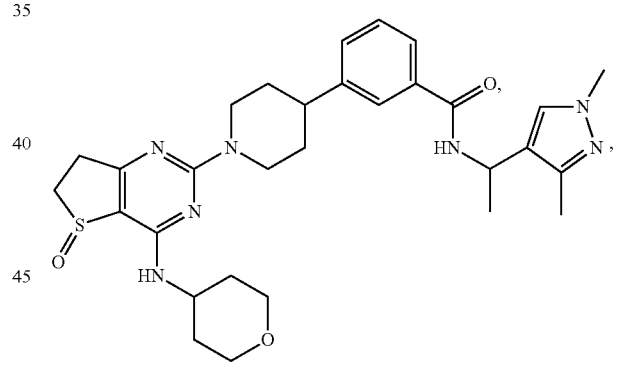
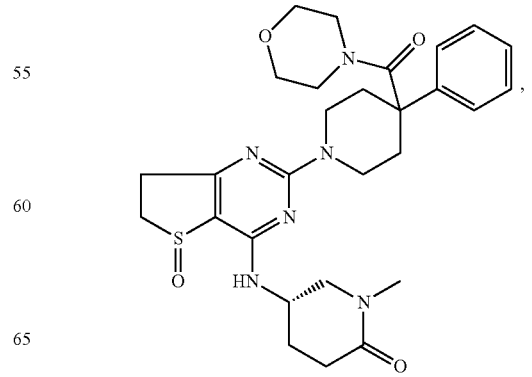

601
-continued
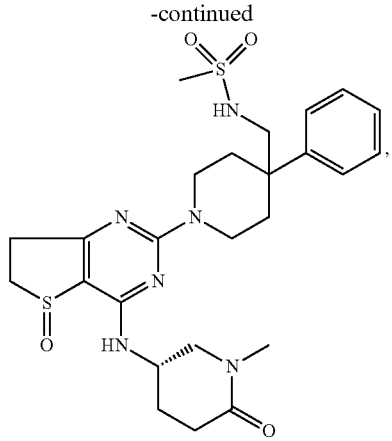
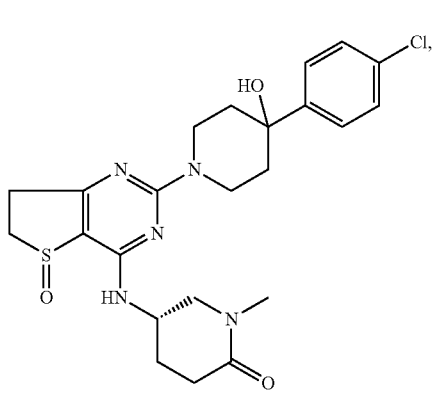
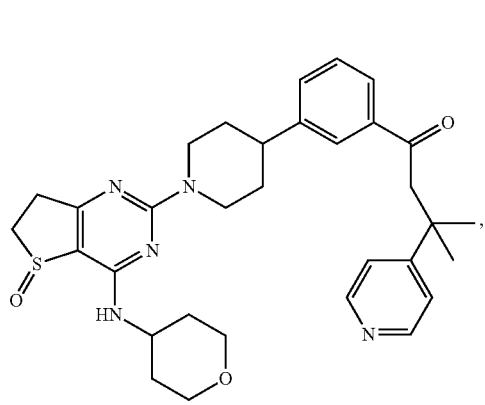
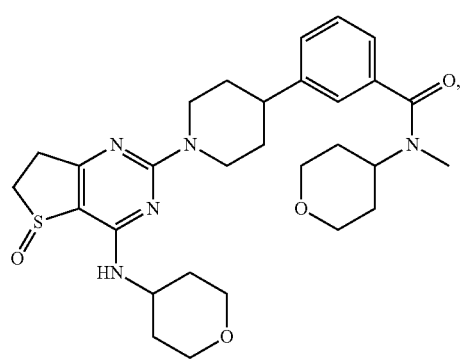
602
-continued
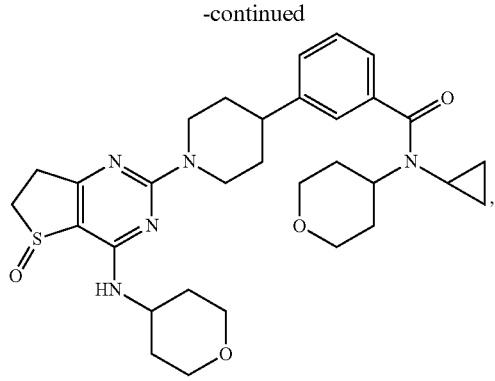
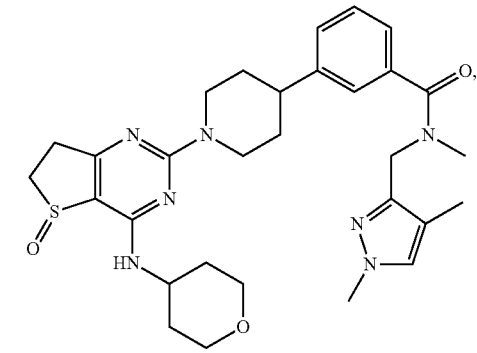
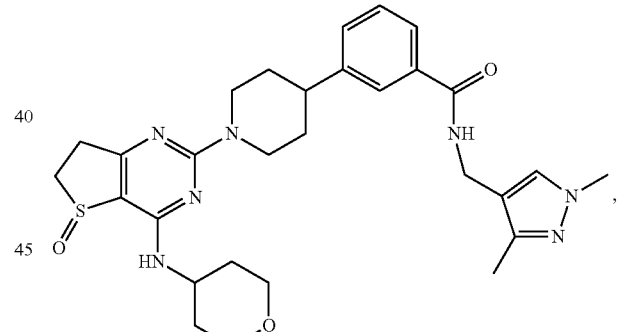
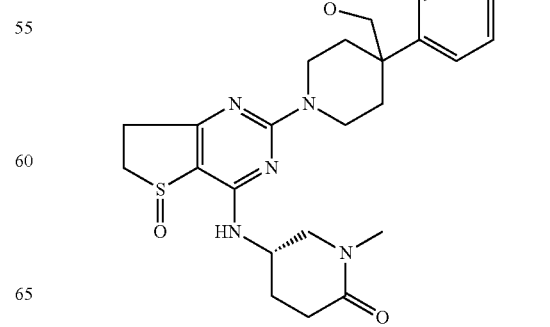

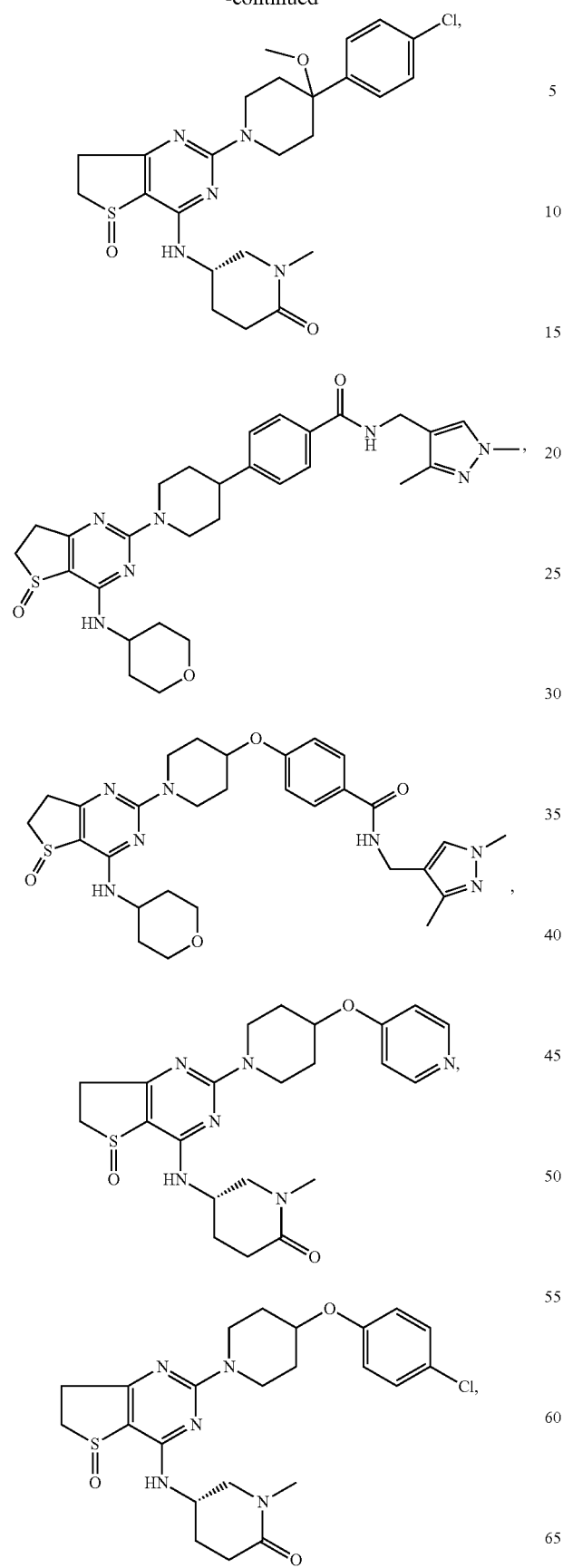
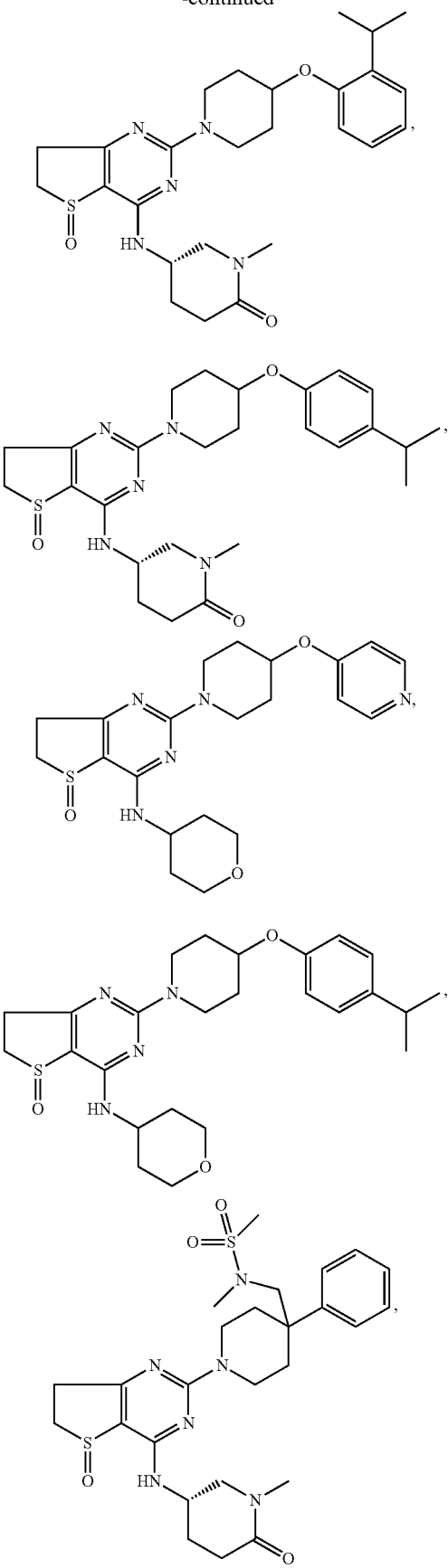

605
-continued
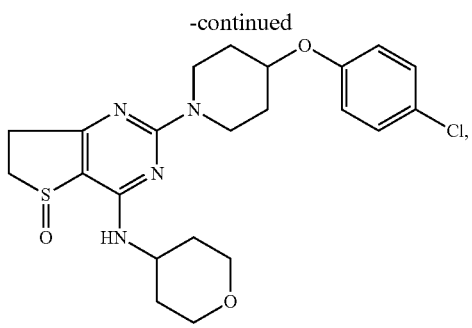
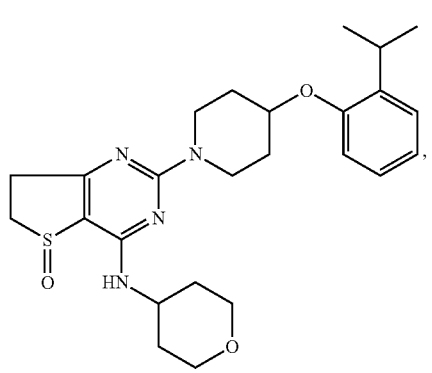
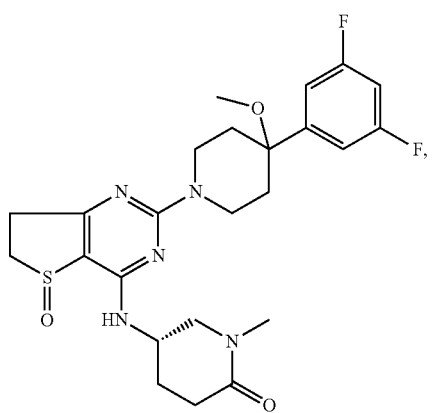
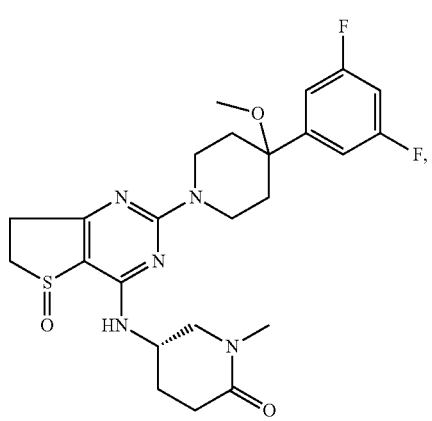
606
-continued
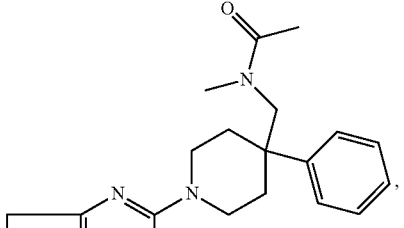
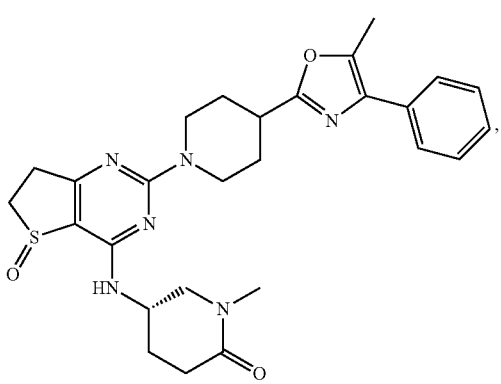
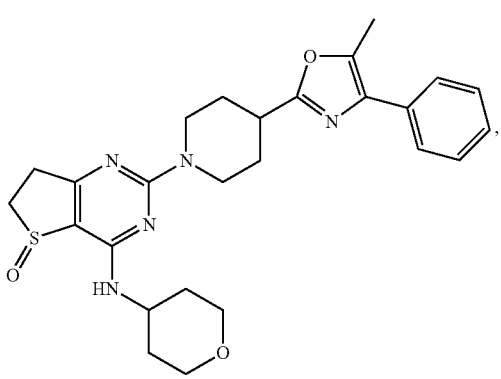
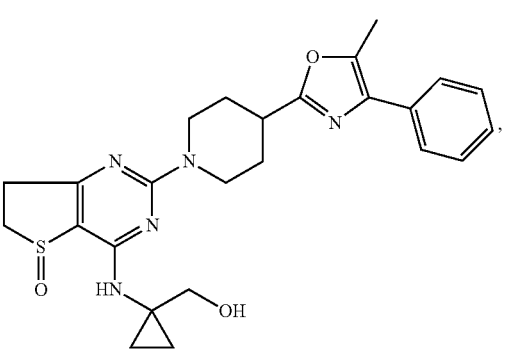

607
-continued
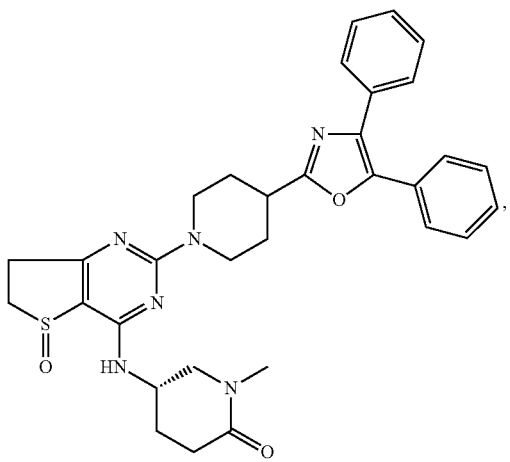
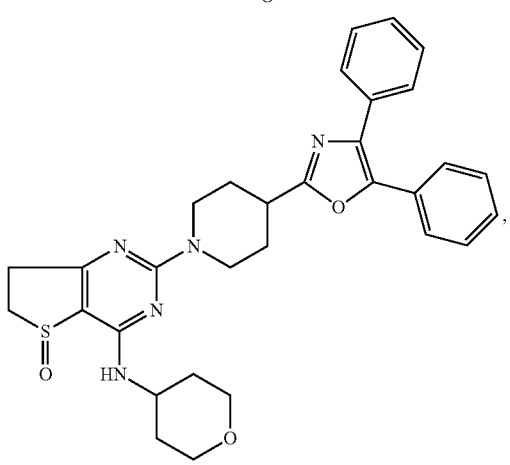
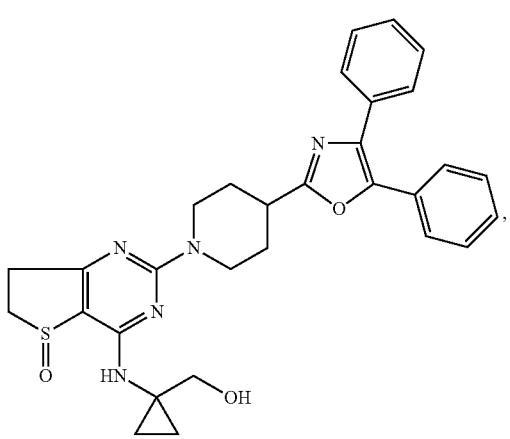
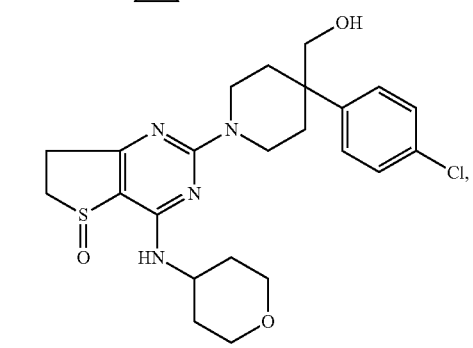
608
-continued
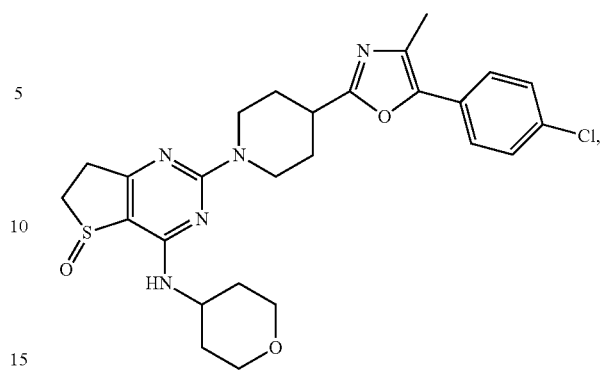
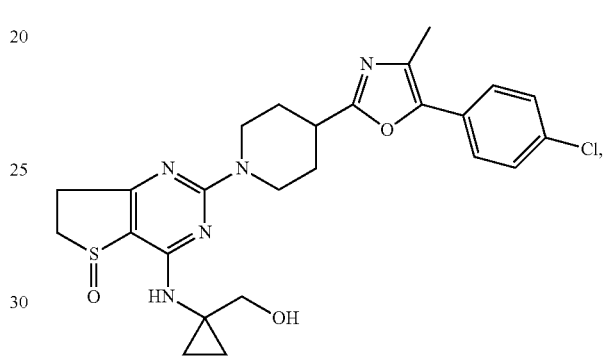
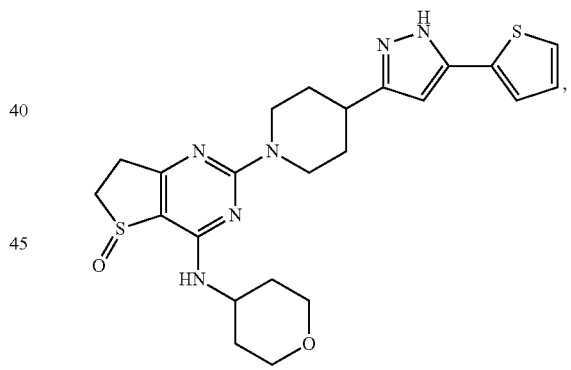
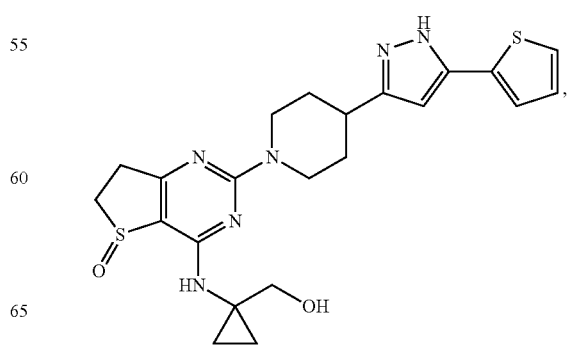

609 -continued

610 -continued

| 611 -continued | 612 -continued |
|---|---|
| 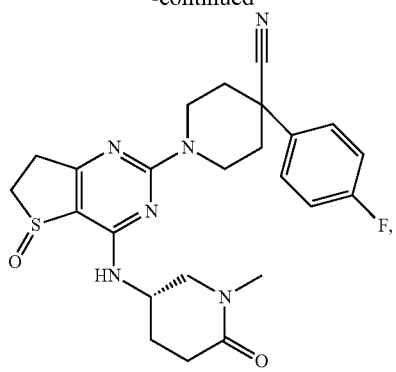 | 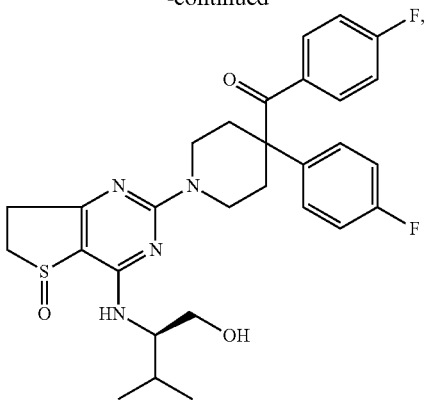 |
| 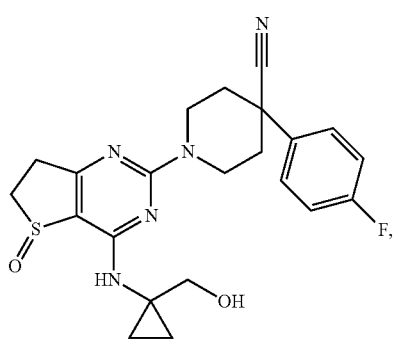 | 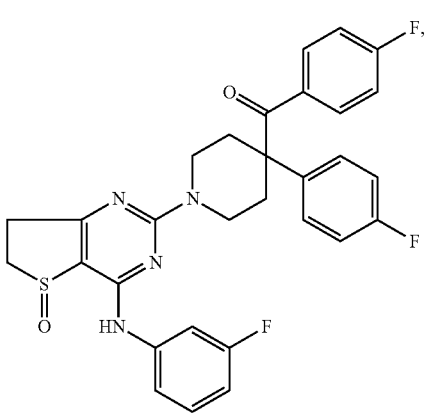 |
| 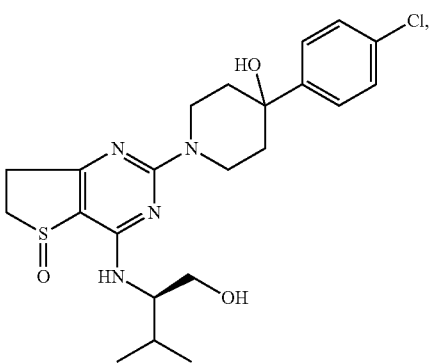 | 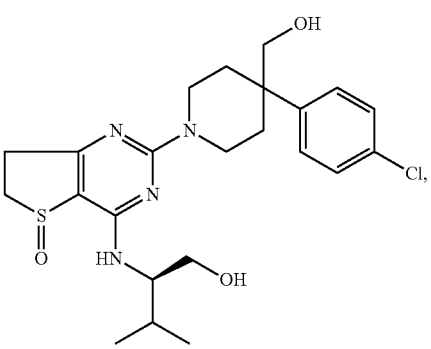 |
| 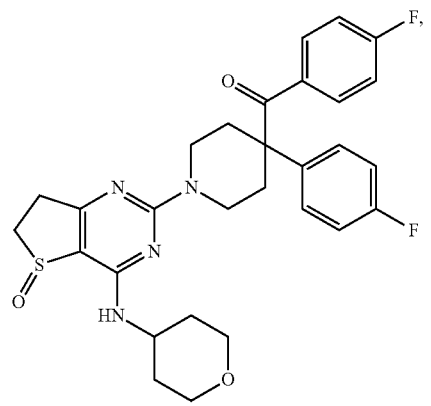 | 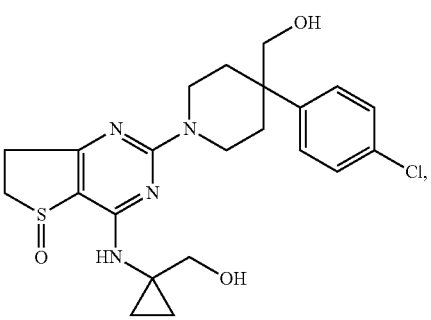 |

613
-continued
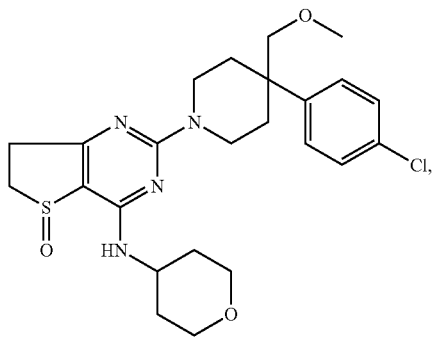
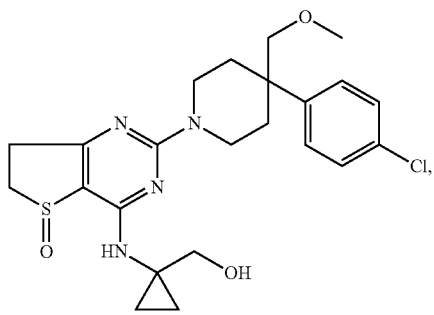
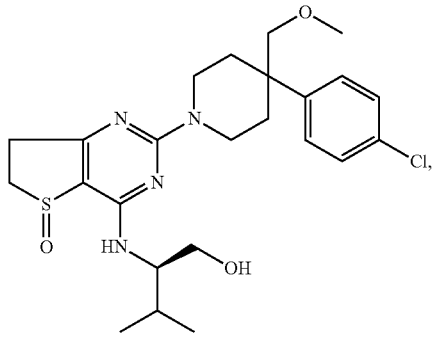
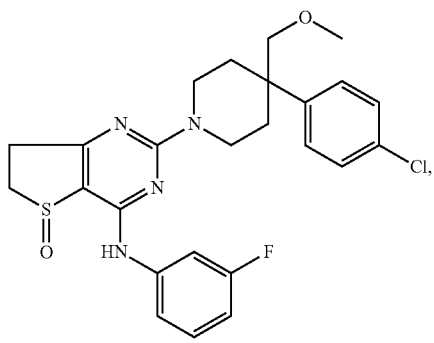
614
-continued
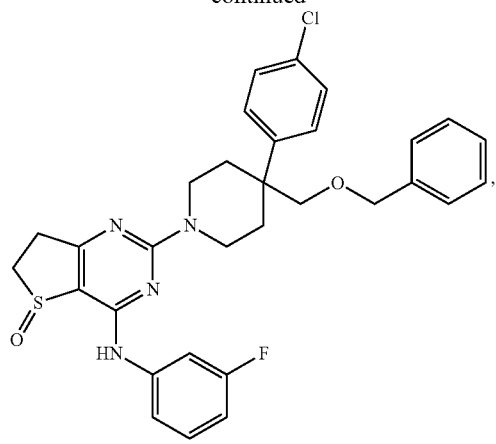
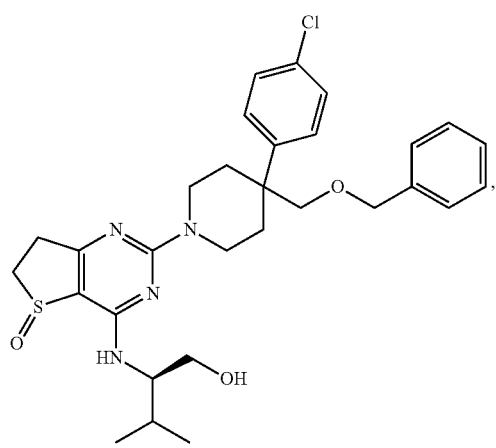
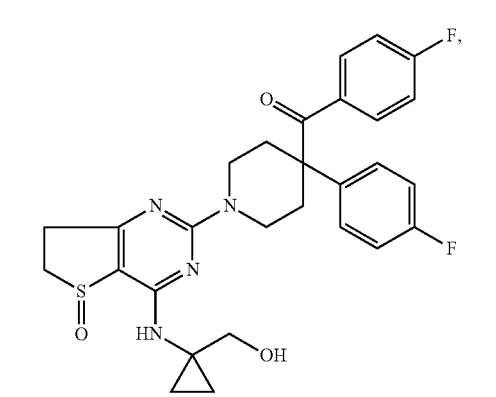
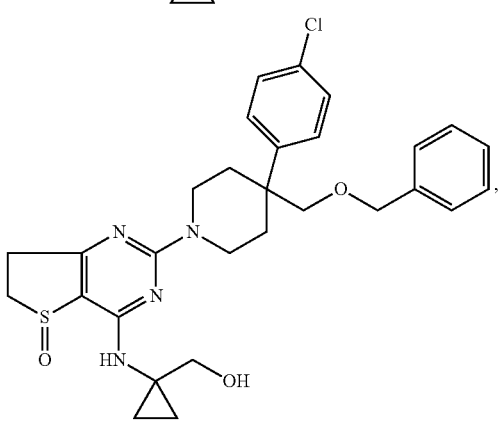

615
-continued
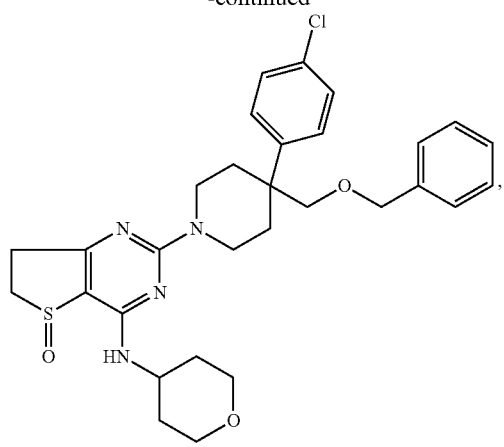
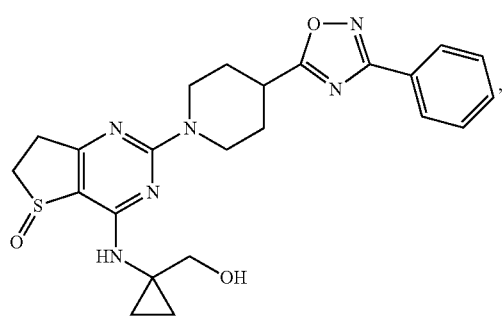
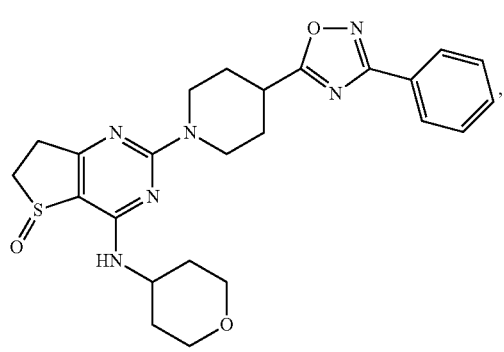
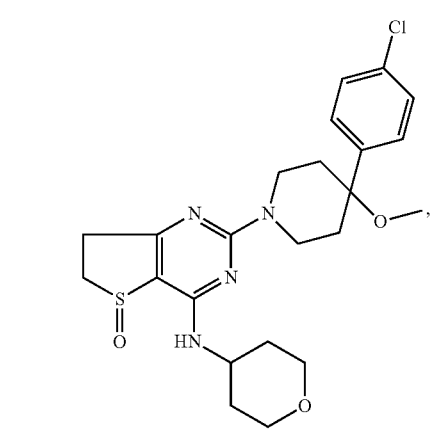
616
-continued
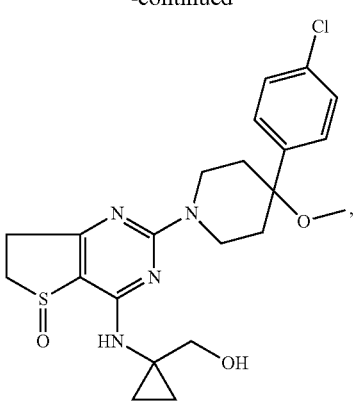
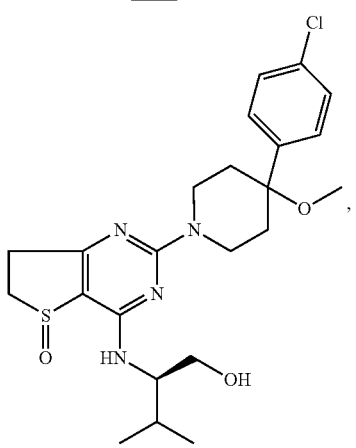
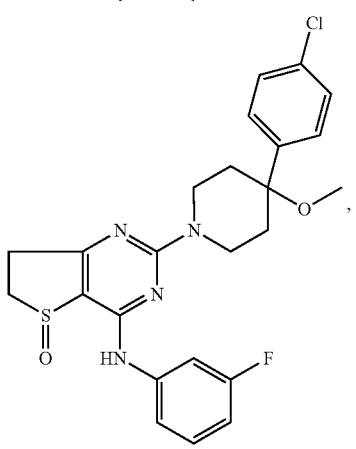
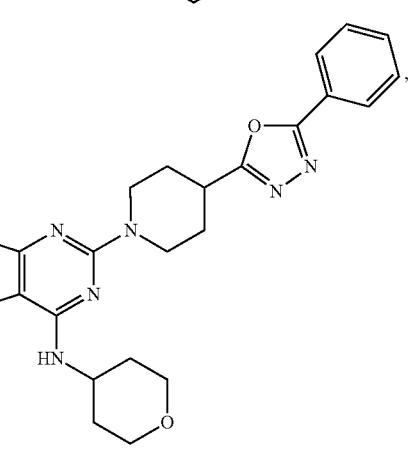

617
-continued
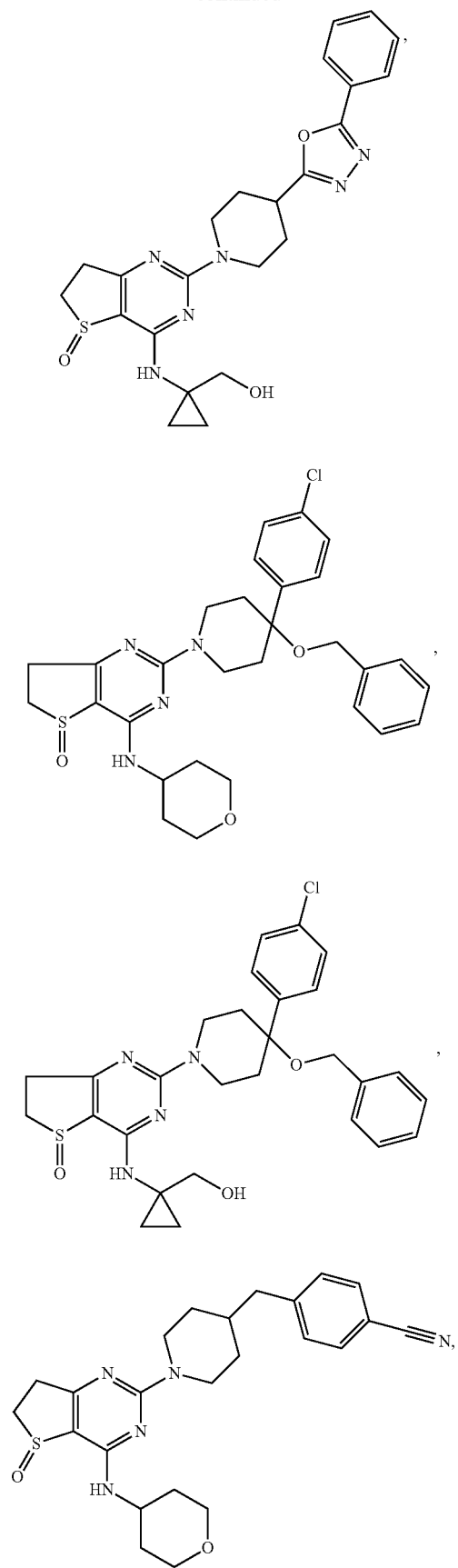
618
-continued
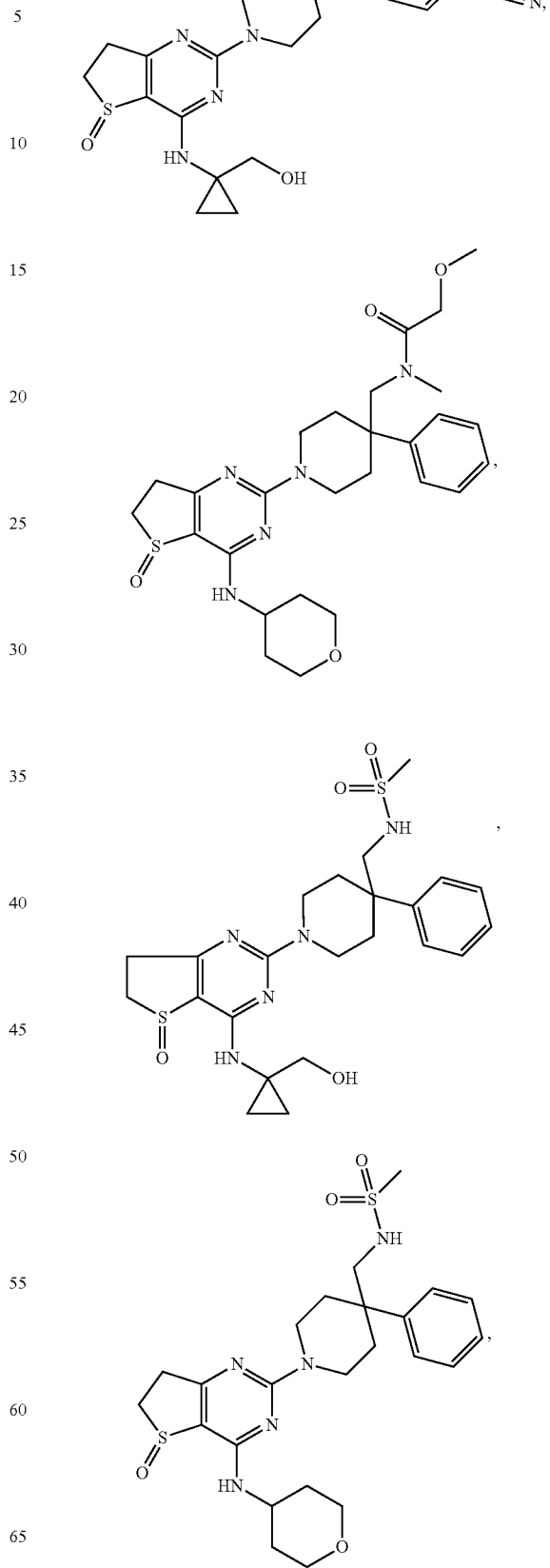

619
-continued
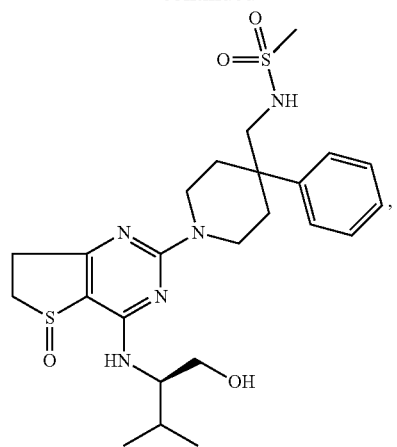
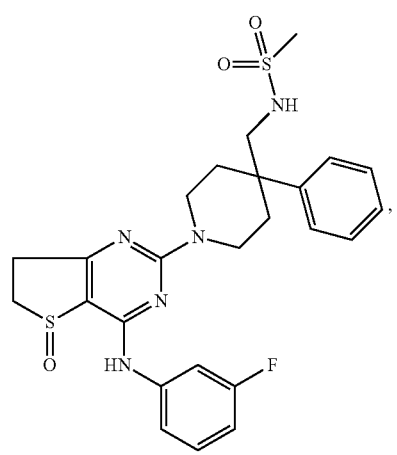
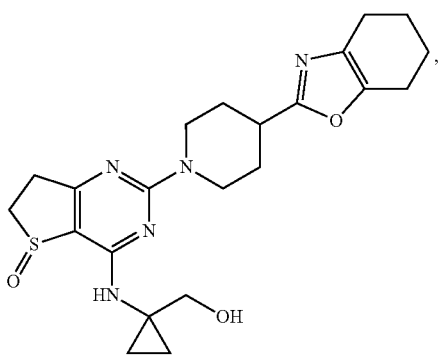
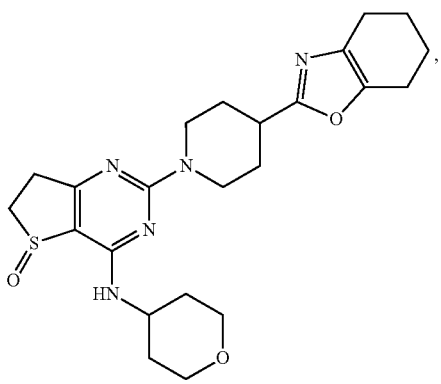
620
-continued
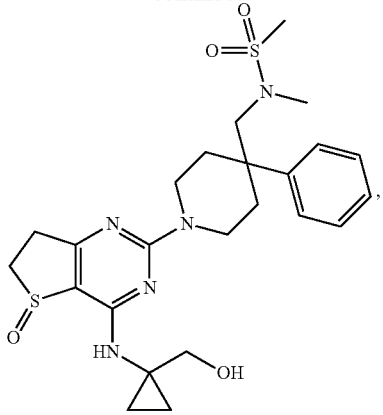
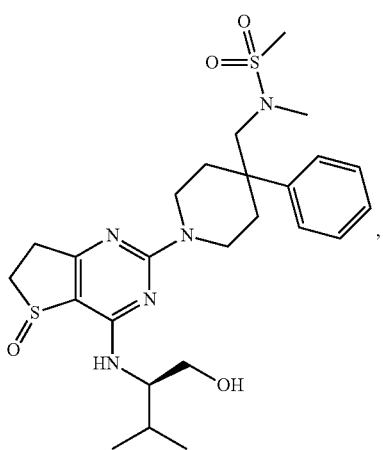
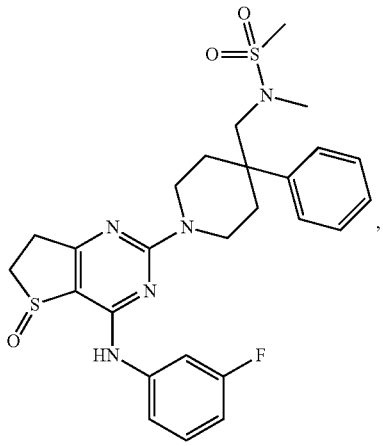
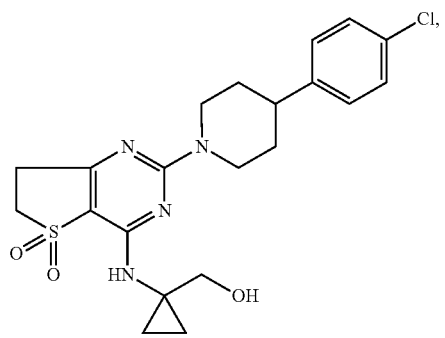

-continued

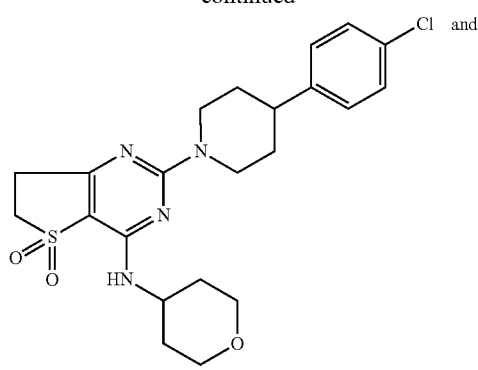

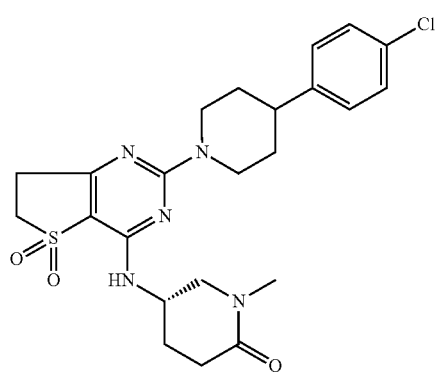 [SMILES: CN1C[C@@H](Nc2nc(N3CCC(c4ccc(Cl)cc4)CC3)nc3c2S(=O)(=O)CC3)CCC1=O]

and pharmacologically acceptable salts thereof.

23. A pharmaceutical formulation, comprising a compound according to formula 1 according to claim 1 and a pharmaceutical excipient.

24. A pharmaceutical formulation, comprising a compound of formula 1 according to claim 1 in combination with one or more active substances selected from betamimetics, corticosteroids, other phophodiesterase 4 inhibitors (PDE4-inhibitors), epidermal growth factor receptor inhibitors (EGFR-inhibitors), and leukotriene D4-antagonist (LTD4-antagonists), chemokine receptor 3-inhibitors (CCR3-inhibitors), inducible nitric oxide synthase inhibitors (iNOS-inhibitors), and spleen tyrosine kinase inhibitors (SYK-inhibitors).

25. The compound of formula 1 according to claim 1, wherein the compound is

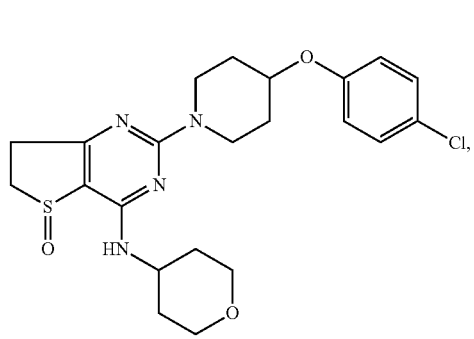 [SMILES: O=S1CCc2nc(N3CCC(Oc4ccc(Cl)cc4)CC3)nc(NC3CCOCC3)c21]

or a pharmaceutically acceptable salt thereof.

26. The compound of formula 1 according to claim 1, wherein the compound is

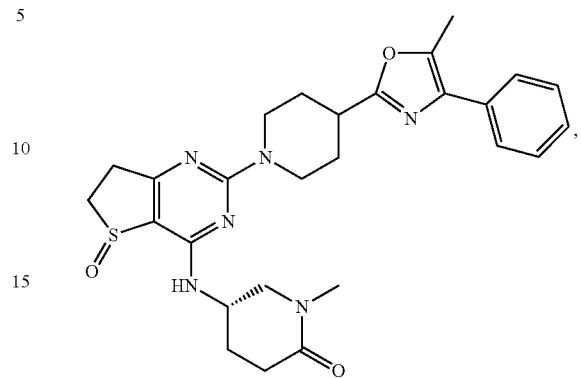

or a pharmaceutically acceptable salt thereof.

27. The compound of formula 1 according to claim 1, wherein the compound is

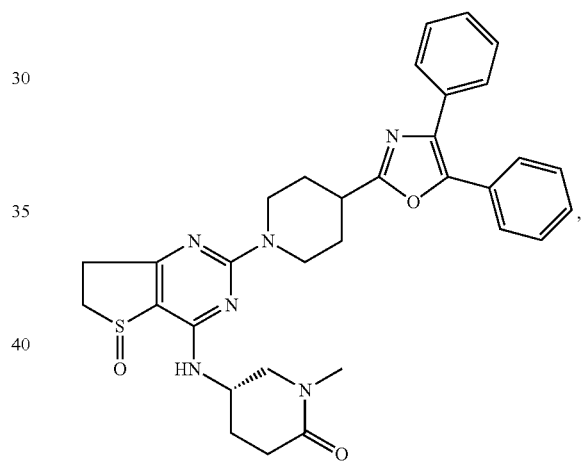

or a pharmaceutically acceptable salt thereof.

28. The compound of formula 1 according to claim 1, wherein the compound is

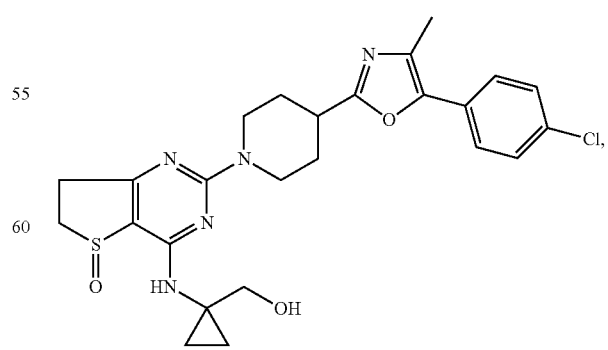

or a pharmaceutically acceptable salt thereof.

29. The compound of formula 1 according to claim 1, wherein the compound is

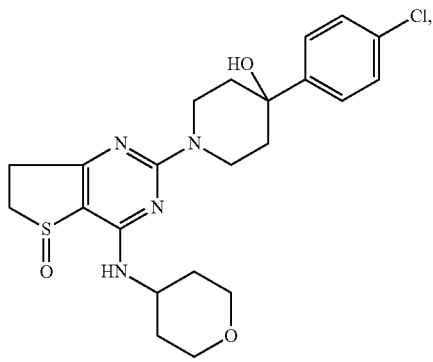 [SMILES: O=S1CCc2nc(N3CCC(O)(c4ccc(Cl)cc4)CC3)nc(NC3CCOCC3)c21]

or a pharmaceutically acceptable salt thereof.

30. The compound of formula 1 according to claim 1, wherein the compound is

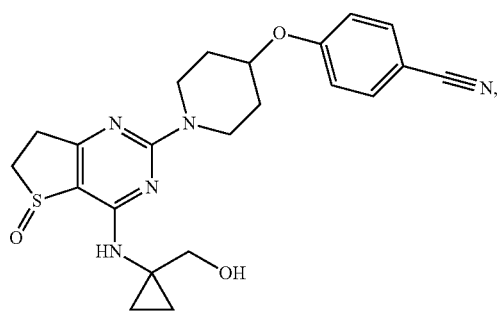 [SMILES: N#Cc1ccc(OC2CCN(c3nc4c(c(NC5(CO)CC5)n3)S(=O)CC4)CC2)cc1]

or a pharmaceutically acceptable salt thereof.

31. The compound of formula 1 according to claim 1, wherein the compound is

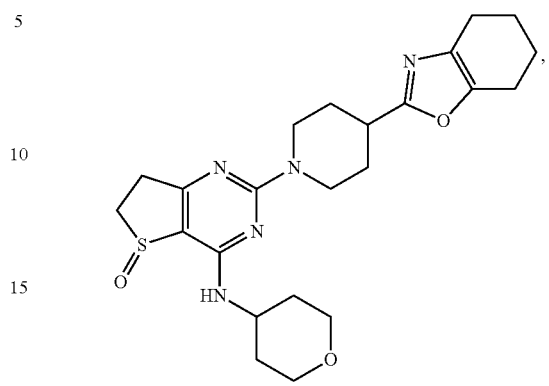

or a pharmaceutically acceptable salt thereof.

32. A method for treating idiopathic pulmonary fibrosis (IPF) in a patient comprising administering to the patient a therapeutically effective amount of the compound of formula 1 according to claim 1.

33. A method for treating chronic obstructive pulmonary disease (COPD), chronic sinusitis, asthma and ulcerative colitis in a patient comprising administering to the patient a therapeutically effective amount of the compound of formula 1 according to claim 1.

34. A method for treating depression and schizophrenia in a patient comprising administering to the patient a therapeutically effective amount of the compound of formula 1 according to claim 1.

* * * * *